(12) United States Patent
Fensholdt et al.

(10) Patent No.: US 8,034,811 B2
(45) Date of Patent: Oct. 11, 2011

(54) HYDROXAMIC ACID ESTERS AND PHARMACEUTICAL USE THEREOF

(75) Inventors: Jef Fensholdt, Stenløse (DK); Jacob Thorhauge, Ballerup (DK); Bjarne Nørremark, Stenløse (DK)

(73) Assignee: Leo Pharma A/S, Bellerup (DK)

( * ) Notice: Subject to any disclaimer, the term of this patent is extended or adjusted under 35 U.S.C. 154(b) by 846 days.

(21) Appl. No.: 10/580,967

(22) PCT Filed: Dec. 2, 2004

(86) PCT No.: PCT/DK2004/000840
§ 371 (c)(1),
(2), (4) Date: Mar. 12, 2007

(87) PCT Pub. No.: WO2005/054179
PCT Pub. Date: Jun. 16, 2005

(65) Prior Publication Data
US 2007/0244117 A1    Oct. 18, 2007

Related U.S. Application Data

(60) Provisional application No. 60/526,262, filed on Dec. 3, 2003.

(51) Int. Cl.
*A61K 31/5377* (2006.01)
*C07D 295/04* (2006.01)
(52) U.S. Cl. ..................................... 514/237.2; 544/109
(58) Field of Classification Search .................. 514/357, 514/237.2; 546/337; 544/109
See application file for complete search history.

(56) References Cited

U.S. PATENT DOCUMENTS

| 5,155,110 A | 10/1992 | Connor et al. |
| 6,147,107 A | 11/2000 | Dent et al. |

FOREIGN PATENT DOCUMENTS

| CA | 2092852 A1 | 10/1993 |
| EP | 0 475 206 A2 | 3/1992 |
| EP | 0 711 757 A | 5/1996 |
| EP | 1 321 518 A | 6/2003 |
| GB | 1126672 | 12/1965 |
| GB | 1 126 672 A | 9/1968 |
| GB | 1 126 672 A | 9/1968 |
| JP | 2000-281659 A | 10/2000 |
| JP | 2002-6453 A | 1/2002 |
| JP | 2004-075614 A | 3/2004 |
| NL | 6515475 | 11/1965 |
| WO | WO-95/25723 A | 9/1995 |
| WO | WO 97/10228 A1 | 3/1997 |
| WO | WO 97/30047 A1 | 8/1997 |
| WO | WO 98/14438 A1 | 4/1998 |
| WO | WO-99/01426 A | 1/1999 |
| WO | WO-99/01428 A | 1/1999 |
| WO | WO 00/15222 A1 | 3/2000 |
| WO | WO-00/35436 A | 6/2000 |
| WO | WO-00/40235 A | 7/2000 |
| WO | WO-00/41505 A | 7/2000 |
| WO | WO-01/68619 A | 9/2001 |
| WO | WO 01/70671 A2 | 9/2001 |
| WO | WO-02/06213 A | 1/2002 |
| WO | WO-02/18319 A | 3/2002 |
| WO | WO-02/055501 A | 7/2002 |
| WO | 02/066470 A1 | 8/2002 |
| WO | WO 02/066454 A1 | 8/2002 |
| WO | WO-02/068406 A | 9/2002 |
| WO | WO-02/076496 A | 10/2002 |
| WO | WO-03/024222 A | 3/2003 |
| WO | WO-03/062189 A | 7/2003 |
| WO | WO-03/062191 A | 7/2003 |
| WO | WO-2004/037853 A | 5/2004 |

OTHER PUBLICATIONS

King, Med Chem: Principle and Practice (1994), p. 206-208.*
Kalgutkar A S et al., Bioorganic & Medicinal Chemistry Letters, Oxford, GB, vol. 12, 2002, pp. 521-524.
Mamalis et al., Journal of the Chemical Society, Chemical Society, Letchworth, GB, 1965, pp. 6278-6287.
Wolf et al., Justus Liebigs Annalen Der Chemie, Verlag Chemie GMBH, Weinheim, DE, 1975, pp. 1245-1250.
Allais A et al., Chimie Therapeutique, Editions Dimeo, Arcueil, FR, vol. 8, 1973, pp. 154-168.
Scott A W et al., Journal of Organic Chemistry, American Chemical Society, Easton, US vol. 7, No. 6, 1942, pp. 508-516.
El-Khamry A M et al., Die Pharmazie, May 1989, vol. 44, No. 5, pp. 312-315.
Kohl H et al., Justus Liebigs Annalen Der Chemie, Verlag Chemie GMBH, Weinheim, DE, vol. 766, 1972, pp. 106-115.
Concalves et al, "Acetylation of o-Aminobenzamidoxime", Bulletin de la SocieteChimique de France 1970, 7, 2599-614.
Korbinits et al. "Ring Transformation of 1,2-Disubstituted 4(1H)-Quinazolone Oximes to 3,5-Disubstituted 1,2,4-Oxadiazoles", Chemische Berichte, 1989, 122(6), 1107-12.
Korbonits et al, "Recent Results on the Cyclization Tendency of Diacyl 2-aminobenzaidoximes", Acta Chimica Hungarica, 1990, 127(6), 795-802.

(Continued)

*Primary Examiner* — Taofiq A Solola
(74) *Attorney, Agent, or Firm* — Birch, Stewart, Kolasch & Birch, LLP

(57) ABSTRACT

The invention relates to compounds of general formula I

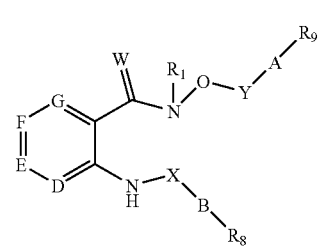

[I]

wherein D, E, F, G, W, Y, $R_1$, A, $R_9$, X, B, $R_8$ are as defined herein, and pharmaceutically acceptable salts, hydrates, or solvates thereof, for use—alone or in combination with one or more other pharmaceutically active compounds—in therapy, for treating diseases associated with deregulated angiogenesis, such as cancer.

24 Claims, 1 Drawing Sheet

OTHER PUBLICATIONS

CA Accession No. 1991:6034 & CAS RN 129858-49-0. (1991).
CA Accession No. 2000:715593. (2000).
CA Accession No. 2002:658103. (2002).
Napoleone Ferrara et al., "The Biology of VEGF and its Receptors", Nature Medicine, vol. 9, No. 6, Jun. 2003 pp. 669-676.
Peter Carmeliet, "Angiogenesis in Health and Disease", Nature Medicine, vol. 9, No. 6, Jun. 2003, pp. 653-660.
Carmeliet et al., "Angiogenesis in cancer and other diseases", Nature, vol. 407, Sep. 14, 2000, pp. 249-257.
Wolf et al., Cyclization Reactions of at the Amino Nitrogen Substituted O-Methyl o-Aminobenzohydroxamates, Liebigs Ann. Chem., 1975, pp. 1245-1251 w/translation.
Xuan et al,, "Effects of Crocin Analogs on Ocular Blood Flow and Retinal Function", Journal of Ocular Pharmacology and Therapeutics, vol. 15, No. 2, 1999, pp. 143-152.
Yancopoulous et al., Vascular-specific growth factors and blood vessel formation, Nature, vol. 407, Sep. 2000, pp. 242-248.

* cited by examiner

A

B

HYDROXAMIC ACID ESTERS AND PHARMACEUTICAL USE THEREOF

This application is the National Phase of PCT application PCT/DK2004/000840, filed Dec. 2, 2004 and claims priority under 35 U.S.C. 119(e) on U.S. Provisional Application Nos. 60/526,262 filed on Dec. 3, 2003 all of which are hereby incorporated by reference.

FIELD OF THE INVENTION

This invention relates to novel hydroxamic acid ester derivatives, intermediate compounds and processes for the preparation thereof, to said compounds for use in therapy, to pharmaceutical compositions comprising said compounds, to methods of treating diseases comprising administering to a patient in need thereof an effective amount of said compound, and to the use of said compounds in the manufacture of medicaments.

BACKGROUND OF THE INVENTION

This invention relates to novel compounds which can inhibit angiogenesis, i.e. which can inhibit the generation or maturation of new blood vessels. It is believed that said compounds may be beneficial in the treatment of a variety of diseases, such as neoplastic diseases and in particular cancer.

It is now widely accepted that blocking angiogenesis around tumours could be a viable way of treating cancer, possibly as an adjuvant treatment. This is also reflected in the large number of development projects and clinical trials with angiogenesis inhibitors with different inhibitory approaches. It is estimated that more than 300 drug candidates are currently in various stages of testing [Matter, *DDT*, 6, 1005-1024, 2001]. The formation of new blood vessels is a very complex process, which may be targeted in a number of different ways. The candidate drugs, hence, include metalloprotease inhibitors, inhibitors of vascular endothelial growth factor (VEGF) formation, inhibition of VEGF receptors, integrin antagonist, growth factor antibodies, etc.

Of particular interest for the present invention are VEGF receptor inhibitors, most particular VEGFR-2 (KDR) receptor inhibitors. The clinically most advanced VEGF receptor inhibitor is semaxanib from Sugen, which was recently discontinued in Phase III studies. Analogues of semaxanib, however, continue to be in development. Another VEGF receptor inhibitor in clinical trial is PTK-787 from Novartis which has recently entered Phase III studies. Bilodeau has reviewed such inhibitors in clinical trials in *Expert Opin. Investig. Drugs.*, 11, 737-745, 2002.

WO 01/29009 and WO 01/58899 describe pyridine derivatives as inhibitors of the VEGF receptor tyrosine kinase and the VEGF-dependent cell proliferation.

WO 02/090346 describes phthalazine derivatives as inhibitors of the VEGF receptor tyrosine kinase with angiogenesis inhibiting activity.

WO 04/056806 teaches 2-(1-H-indazol-6-ylamino)-benzamide compounds as protein kinases inhibitors which may be useful for the treatment of ophthalmic diseases.

PCT publications WO 00/27819, WO 00/27820, WO 01/55114, WO 01/81311, WO 01/85671, WO 01/85691, WO 01/85715, WO 02/055501, WO 02/066470, WO 02/090349, WO 02/090352, WO 03/000678, WO 02/068406, WO 03/040101, and WO 03/040102 all teach anthranilic acid amide derivatives which include compounds of general structure A, their preparation and their use as VEGF receptor tyrosine kinase inhibitors for the treatment of diseases associated with VEGF-dependent cell proliferation.

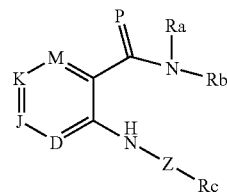

The use of anthranilic acid amide derivatives for other therapeutic purposes have previously been disclosed in, e.g. U.S. Pat. No. 3,409,688 (analgesic, anti-inflammatory, anti-ulcer), and in EP 564,356 (angiotensin II antagonist).

PCT publications WO 02/06213 and WO 99/01426 teach substituted phenylamino benzhydroxamic acid derivatives which include compounds of general structure B as MEK inhibitors, pharmaceutical compositions and methods of use thereof.

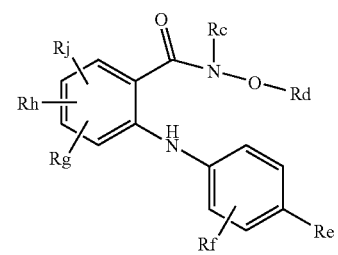

U.S. Pat. No. 5,155,110 teaches hydroxamic acid derivatives having cyclooxygenase and 5-lipoxygenase inhibiting properties and pharmaceutical compositions for treating conditions advantageously affected by the inhibition. The reference fails to describe tyrosine kinase inhibitory activity of the hydroxamic acid ester derivatives disclosed.

SUMMARY OF THE INVENTION

The present inventors have surprisingly found that a novel class of hydroxamic acid esters exhibit a high receptor tyrosine kinase inhibitory activity on a particular VEGF receptor, namely VEGFR-2, frequently referred to as the KDR receptor. The novel hydroxamic acid esters of the present invention may have a number of advantages in comparison to known structurally related anthranilic acid amides.

Compounds of the present invention may have improved pharmacokinetic and pharmacodynamic properties such as improved solubility, absorption and metabolic stability in comparison to known structurally related anthranilic acid amides.

Accordingly, the invention relates to compounds of general formula I

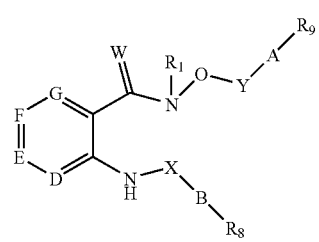

wherein $R_1$ represents hydrogen or a straight, branched and/or cyclic, saturated or unsaturated hydrocarbon radical, optionally substituted with one or more substituents selected from the group consisting of halogen, hydroxyl, amino, nitro, and cyano;

D represents nitrogen or C—$R_2$;
E represents nitrogen or C—$R_3$;
F represents nitrogen or C—$R_4$;
G represents nitrogen or C—$R_5$;

$R_2$, $R_3$, $R_4$, and $R_5$ are the same or different and individually represent hydrogen, halogen, hydroxyl, amino, nitro, carboxy, cyano, alkoxy, alkylthio, alkoxycarbonyl, alkylcarbonyloxy, alkoxycarbonyloxy, alkylcarbonyl, alkoxysulfonyloxy, aminosulfonyl, alkylsulfonylamino, formyl, aminocarbonyl, alkylcarbonylamino, or a straight or branched, saturated or unsaturated hydrocarbon radical, optionally substituted with one or more substituents independently selected from the group consisting of halogen, hydroxyl, amino, nitro, carboxy, cyano, alkoxy, alkylthio, alkoxycarbonyl, alkylcarbonyloxy, alkoxycarbonyloxy, alkylcarbonyl, alkoxysulfonyloxy, aminosulfonyl, alkylsulfonylamino, formyl, aminocarbonyl, and alkylcarbonylamino, or $R_2$ and $R_3$, or $R_3$ and $R_4$, or $R_4$ and $R_5$ together with the C atoms to which they are attached form a 5- or 6-membered carbocyclic or heterocyclic ring;

W represents oxygen, sulphur, two hydrogen atoms, =$CH_2$, =N—O—$R_6$ or the group =N($R_6$);

$R_6$ represents hydrogen, cycloalkyl, heterocycloalkyl, heterocycloalkenyl, cycloalkenyl, aryl, heteroaryl, alkenyl, alkynyl, or alkyl;

X and Y independently represents a radical of the formula —$(CH_2)_i$—NH—C(O)—$(CH_2)_j$—, —$(CH_2)_k$—C(O)—$(CH_2)_m$—, —$(CH_2)_n$—, —$(CH_2)_p$—CH=CH—$(CH_2)_q$—, —$(CH_2)_r$—O—$(CH_2)_s$—, —$(CH_2)_t$—NH—$(CH_2)_u$—, —$(CH_2)_w$—C(O)—NH—$(CH_2)_z$— where i, j, k, m, n, p, q, r, s, t, u, w, and z are integers from 0-6, wherein said radicals are optionally substituted by one or more substituents independently selected from the group consisting of $R_7$;

$R_7$ represents hydrogen, oxo, thioxo, halogen, hydroxyl, amino, imino, nitro, carboxy, carbamoyl, cyano, cycloalkyl, alkyl, aryl, heteroaryl, heterocycloalkyl, heterocycloalkenyl, heterocycloalkyl-heteroaryl, heterocycloalkylcarbonylamino, cycloalkenyl, alkenyl, alkynyl, alkoxy, alkoxyimino, alkylthio, alkoxycarbonyl, alkylcarbonyloxy, alkenylcarbonyloxy, alkoxycarbonyloxy, alkylureido, alkylthioureido, alkylcarbonyl, alkoxysulfonyloxy, aminosulfonyl, alkylsulfonylamino, alkylsulfonyl, arylsulfonyl, formyl, aminocarbonyl, and alkylcarbonylamino, wherein said amino, imino, cycloalkyl, alkyl, aryl, heteroaryl, heterocycloalkyl, heterocycloalkenyl, heterocycloalkyl-heteroaryl, heterocycloalkylcarbonylamino, cycloalkenyl, alkenyl, alkynyl, alkoxy, alkoxyimino, alkylthio, alkoxycarbonyl, alkylcarbonyloxy, alkenylcarbonyloxy, alkoxycarbonyloxy, alkylureido, alkylthioureido, alkylcarbonyl, alkoxysulfonyloxy, aminosulfonyl, alkylsulfonylamino, alkylsulfonyl, arylsulfonyl, aminocarbonyl, and alkylcarbonylamino are optionally substituted by one or more substituents independently selected from the group consisting of hydrogen, halogen, oxo, thioxo, hydroxyl, amino, imino, nitro, carboxy, cyano, alkoxy, alkylthio, alkoxycarbonyl, alkylcarbonyloxy, alkoxycarbonyloxy, alkylcarbonyl, alkoxysulfonyloxy, aminosulfonyl, alkylsulfonylamino, alkylsulfonyl, arylsulfonyl, aminocarbonyloxy, heteroarylsulfonylamino, formyl, aminocarbonyl, trifluoromethyl, alkylcarbonylamino, heterocycloalkyl, heterocycloalkenyl, aryl, alkylureido, alkylthioureido, heteroaryl, cycloalkyl, alkyl, cycloalkenyl, alkenyl, alkynyl, and alkylaminocarbonyl;

B represents aryl, heteroaryl, heterocycloalkyl, heterocycloalkenyl, cycloalkyl, or cycloalkenyl, all of which are optionally substituted with one or more substituents independently selected from the group consisting of $R_8$;

$R_8$ represents hydrogen, halogen, hydroxyl, amino, imino, oxo, thioxo, nitro, carboxy, cyano, alkoxy, phenoxy, alkylthio, alkoxycarbonyl, alkoxycarbamoyl, alkylcarbonyloxy, alkoxycarbonyloxy, alkylcarbonyl, alkoxysulfonyloxy, aminosulfonyl, arylsulfonyl, alkylsulfonylamino, formyl, aminocarbonyl, alkylureido, alkylthioureido, aminocarbonyloxy, alkylcarbonylamino, heterocycloalkylcarbonylamino, heterocycloalkyl, heterocycloalkenyl, aryl, heteroaryl, alkylaminocarbonyl, and a straight or branched, saturated or unsaturated hydrocarbon radical, wherein said amino, alkoxy, phenoxy, alkylthio, alkoxycarbonyl, alkoxycarbamoyl, alkylcarbonyloxy, alkoxycarbonyloxy, alkylcarbonyl, alkoxysulfonyloxy, aminosulfonyl, arylsulfonyl, alkylsulfonylamino, aminocarbonyl, alkylureido, alkylthioureido, aminocarbonyloxy, alkylcarbonylamino, heterocycloalkylcarbonylamino, heterocycloalkyl, heterocycloalkenyl, aryl, heteroaryl, alkylaminocarbonyl, and straight or branched, saturated or unsaturated hydrocarbon radical are optionally substituted with one or more substituents independently selected from the group consisting of $R_7$;

A represents a straight, branched and/or cyclic, saturated or unsaturated hydrocarbon radical, a heterocycloalkyl, a heterocycloalkenyl, or a heteroaryl, all of which are optionally substituted with one or more substituents independently selected from the group consisting of $R_9$;

$R_9$ represents hydrogen, oxo, halogen, trifluoromethyl, hydroxyl, amino, nitro, carboxy, cyano, alkoxy, alkylthio, alkoxycarbonyl, alkylcarbonyloxy, alkoxycarbonyloxy, alkylureido, alkylthioureido, alkylcarbonyl, alkoxysulfonyloxy, aminosulfonyl, arylsulfonyl, alkylsulfonylamino, arylsulfonylamino, heteroarylsulfonylamino, alkylsulfonyl, formyl, aminocarbonyl, alkylcarbonylamino, alkylaminocarbonyl, aminocarbonyloxy, heterocycloalkyl, heterocycloalkenyl, heteroaryl and a straight or branched, saturated or unsaturated hydrocarbon radical, wherein said amino, alkoxy, alkylthio, alkoxycarbonyl, alkylcarbonyloxy, alkoxycarbonyloxy, alkylureido, alkylthioureido, alkylcarbonyl, alkoxysulfonyloxy, aminosulfonyl, arylsulfonyl, alkylsulfonylamino, arylsulfonylamino, heteroarylsulfonylamino, alkylsulfonyl, aminocarbonyl, alkylcarbonylamino, alkylaminocarbonyl, aminocarbonyloxy, heterocycloalkyl, heterocycloalkenyl, heteroaryl and straight or branched, saturated or unsaturated hydrocarbon radical are optionally substituted by one or more substituents independently selected from the group consisting of $R_7$;

and pharmaceutically acceptable salts, hydrates, or solvates thereof;

provided that the compound is not

2-[(2-chloro-4-iodophenyl)amino]-4-fluoro-N-(2-hydroxyethoxy)-N-methyl-benzamide, 2-[(2,6-dichloro-3-methylphenyl)amino]-N-methoxy)-N-methyl-benzamide, 2-[(2,6-dichlorophenyl)amino]-N-hydroxy-N-methyl-benzamide, N-methoxy-2-[3-((E)-2-pyridin-2-yl-vinyl)-1H-indazol-6-ylamino]-benzamide, N-isopropoxy-2-[3-((E)-2-pyridin-2-yl-vinyl)-1H-indazol-6-ylamino]-benzamide, or N-allyloxy-2-[3-((E)-2-pyridin-2-yl-vinyl)-1H-indazol-6-ylamino]-benzamide.

In another aspect, the invention relates to pharmaceutical compositions comprising a compound of formula I or a pharmaceutically acceptable salt, hydrate, or solvate thereof together with a pharmaceutically acceptable vehicle or excipient.

In a further aspect, the invention relates to method of preventing, treating or ameliorating diseases or conditions associated with deregulated angiogenesis, the method comprising administering an effective amount of a compound according to formula I to a patient in need thereof.

In still a further aspect, the invention relates to the use of compounds according to formula I for the manufacture of a medicament for the prophylaxis, treatment or amelioration of diseases or conditions associated with deregulated angiogenesis, such as cancer.

In still a further aspect, the invention relates to intermediate compounds useful for the synthesis of compounds according to formula I, to and processes for the preparation of compounds of formula I and for said intermediates.

DETAILED DESCRIPTION OF THE INVENTION

Definitions

Figure 1:
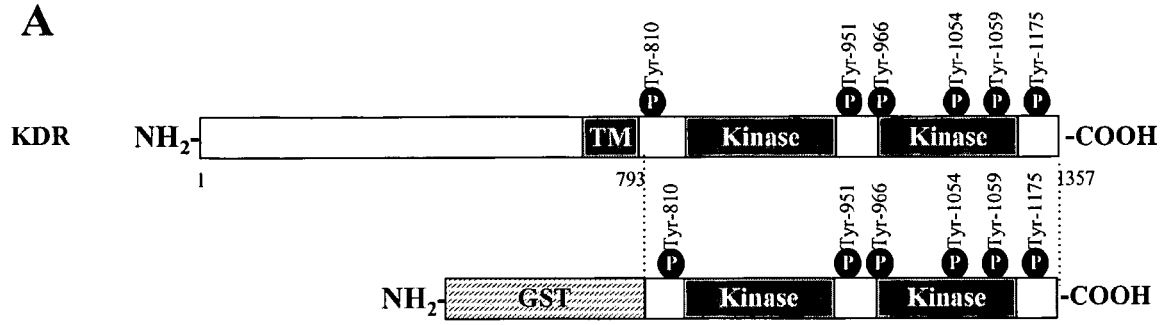
FIG. 1: The structure of the GST-KDR-cyt and the GST-PLCγ fusion protein.
A. A fusion protein containing the intracellular domain (amino acids 793 to 1357) of the KDR and N-terminally tagged to GST was constructed for expression in Sf9 insect cells.
B. A fusion protein containing the two SH2 domains and two phosphorylations sites (amino acids 541 to 797) and N-terminally tagged to GST was constructed and expressed in *E. coli*.
   TM: transmembrane domain, GST: glutathione-5-transferase; SH2: Src homology 2 domain; SH3: Src homology 3 domain.
Figure 1:
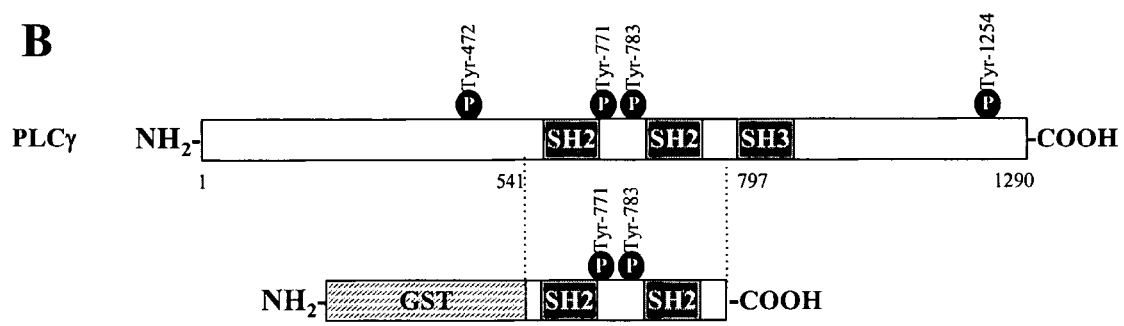

The term "hydrocarbon radical" is intended to indicate a radical containing only hydrogen and carbon atoms, it may contain one or more double and/or triple carbon-carbon bonds, and it may comprise cyclic moieties in combination with branched or linear moieties. Said hydrocarbon comprises 1-20 carbon atoms, and preferably comprises 1-12, e.g. 1-6, e.g. 1-4, e.g. 1-3, e.g. 1-2 carbon atoms. The term includes alkyl, alkenyl, cycloalkyl, cycloalkenyl, alkynyl and aryl, as indicated below.

In the present context, the term "alkyl" is intended to indicate the radical obtained when one hydrogen atom is removed from a hydrocarbon. Said alkyl comprises 1-20, preferably 1-12, such as 2-6, such as 3-4 carbon atoms. The term includes the subclasses normal alkyl (n-alkyl), secondary and tertiary alkyl, such as methyl, ethyl, n-propyl, isopropyl, n-butyl, isobutyl, sec.-butyl, tert.-butyl, pentyl, isopentyl, hexyl and isohexyl.

The term "cycloalkyl" is intended to indicate a saturated cycloalkane radical, including polycyclic radicals, such as bicyclic or tricyclic radicals, comprising 3-20 carbon atoms, preferably 3-10 carbon atoms, in particular 3-8 carbon atoms, such as 3-6 carbon atoms, such as 4-5 carbon atoms, e.g. cyclopropyl, cyclobutyl, cyclopentyl, cyclohexyl, cycloheptyl, cyclooctyl, bicyclo[2.2.1]heptyl and adamantyl.

The term "cycloalkenyl" is intended to indicate mono-, di-tri- or tetraunsaturated non-aromatic cyclic hydrocarbons radicals, including polycyclic radicals, comprising 3-20 carbon atoms, typically comprising 3-10 carbon atoms, such as 3-6 carbon atoms, such as 4-5-carbon atoms, e.g. cyclopropenyl, cyclobutenyl, cyclopentenyl, cyclohexenyl, bicyclo[2.2.1]heptenyl, or bicyclo[4.1.0]heptenyl.

The term "alkenyl" is intended to indicate a mono-, di-, tri-, tetra- or pentaunsaturated hydrocarbon radical comprising 2-10 carbon atoms, in particular 2-6 carbon atoms, such as 2-4 carbon atoms, e.g. ethenyl, allyl, propenyl, butenyl, pentenyl, nonenyl, or hexenyl.

The term "alkynyl" is intended to indicate an hydrocarbon radical comprising 1-5 C—C triple bonds and 2-20 carbon atoms, the alkane chain typically comprising 2-10 carbon atoms, in particular 2-6 carbon atoms, such as 2-4 carbon atoms, e.g. ethynyl, propynyl, butynyl, pentynyl or hexynyl.

The term "heteroaryl" is intended to include radicals of heterocyclic aromatic rings, optionally fused with carbocyclic rings or heterocyclic rings, comprising 1-6 heteroatoms (selected from O, S and N) and 1-20 carbon atoms, such as 1-5 heteroatoms and 1-10 carbon atoms, such as 1-5 heteroatoms and 1-6 carbon atoms, such as 1-5 heteroatoms and 1-3 carbon atoms, in particular 5- or 6-membered rings with 1-4 heteroatoms or 1-2 heteroatoms selected from O, S and N, or optionally fused bicyclic rings with 1-4 heteroatoms, and wherein at least one ring is aromatic, e.g. pyridyl, quinolyl, isoquinolyl, indolyl, tetrazolyl, thiazolyl, imidazolyl, imidazo[1,2-a]pyrimidinyl, pyrazolyl, oxazolyl, oxadiazolyl, thiophenyl, 1,2,4-triazolyl, isoxazolyl, pyrrolidinyl, thienyl, pyrazinyl, pyrimidinyl, [1,2,3]triazolyl, isothiazolyl, tetrahydrofuranyl, imidazo[2,1-b]thiazolyl, benzimidazolyl, benzofuranyl, 2H-chromenyl, or benzofuranyl.

The term "heterocycloalkyl" is intended to indicate a cycloalkyl radical as defined above, including polycyclic radicals, optionally fused with carbocyclic rings, comprising 1-6 heteroatoms, preferably 1-3 heteroatoms, selected from O, N, or S, e.g. tetrahydropyranyl, morpholine, imidazolidinyl, benzo[1,3]dioxolyl, or piperidinyl.

The term "heterocycloalkenyl" is intended to indicate a cycloalkenyl radical as defined above, including polycyclic radicals, optionally fused with carbocyclic rings, comprising 1-6 heteroatoms, preferably 1-3 heteroatoms, selected from O, N, or S, e.g. 1,6-dihydropyridinyl, 2,3-dihydrobenzofuranyl, 4,5-dihydro-1H-[1,2,4]-triazolyl, 4,5-dihydro-oxazolyl, 1H-indazolyl, 1-H-pyrazolyl, or 4,5-dihydro-isoxazolyl.

The term "aryl" is intended to indicate a radical of aromatic carbocyclic rings comprising 6-20 carbon atoms, such as 6-14 carbon atoms, preferably 6-10 carbon atoms, in particular 5- or 6-membered rings, optionally fused carbocyclic rings with at least one aromatic ring, such as phenyl, naphthyl, anthracenyl, indenyl or indanyl.

The term "carbocyclic" includes aryl, cycloalkanyl, and cycloalkenyl as indicated above.

The term "heterocyclic" includes heteroaryl, heterocycloalkyl, and heterocycloalkenyl as indicated above.

The term "halogen" is intended to indicate a substituent form the $7^{th}$ main group of the periodic table, preferably fluoro, chloro and bromo.

The term "alkenylcarbonyloxy" is intended to indicate a radical of the formula —O—C(O)—R, wherein R is alkenyl as indicated above, e.g. acryloyloxy.

The term "amino" is intended to indicate a radical of the formula —$NR_2$, wherein each R independently represents hydrogen, alkyl, alkenyl, cycloalkyl, or aryl as indicate above, e.g. —$NH_2$, aminophenyl, methylamino, diethylamino, cyclohexylamino, —NH-phenyl, tert-butylamino or ethylamino.

The term "imino" is intended to indicate a radical of the formula =N—R, wherein R represents hydrogen or alkyl as indicated above.

The term "alkoxy" is intended to indicate a radical of the formula —OR, wherein R is alkyl or alkenyl as indicated above, e.g. methoxy, ethoxy, n-propoxy, isopropoxy, butoxy, etc.

The term "alkylthio" is intended to indicate a radical of the formula —S—R, wherein R is alkyl as indicated above.

The term "alkoxycarbonyl" is intended to indicate a radical of the formula —C(O)—O—R, wherein R is alkyl as indicated above, e.g. methoxycarbonyl, ethoxycarbonyl, n-propoxycarbonyl, isopropoxycarbonyl, etc.

The term "alkylcarbonyloxy" is intended to indicate a radical of the formula —O—C(O)—R, wherein R is alkyl as indicated above, e.g. methylcarbonyloxy, or ethylcarbonyloxy.

The term "alkoxycarbonyloxy" is intended to indicate a radical of the formula —O—C(O)—O—R, wherein R is alkyl as indicated above.

The term "alkylcarbonyl" is intended to indicate a radical of the formula "—C(O)—R, wherein R is alkyl as indicated above, e.g. acetyl.

The term "alkylureido" is intended to indicate a radical of the formula "—NR'—C(O)—NH—R, wherein R' is hydrogen or alkyl as indicated above, and R is hydrogen, alkyl, or cycloalkyl as indicated above, e.g. —NH—C(O)—NH$_2$, methylureido, ethylureido, tert-butylureido, cyclohexylureido, methylthioureido, isopropylureido, or n-propylureido.

The term "alkylthioureido" is intended to indicate a radical of the formula "—NR'—C(S)—NH—R, wherein R' is hydrogen or alkyl as indicated above, and R is hydrogen, alkyl, or cycloalkyl as indicated above, e.g. —NH—C(S)—NH$_2$.

The term "alkoxysulfonyloxy" is intended to represent a radical of the formula —O—S(O)$_2$—O—R, wherein R is alkyl as indicated above.

The term "aminosulfonyl" is intended to indicate a radical of the formula —S(O)$_2$—NR$_2$, wherein each R independently represents hydrogen, alkyl or aryl as indicated above.

The term "aminocarbonyloxy" is intended to indicate a radical of the formula —NR'—C(O)—O—R, wherein R' is hydrogen or alkyl as indicated above, and R is alkyl as indicated above, e.g. aminocarbonyl-tert-butoxy.

The term "alkylsulfonylamino" is intended to indicate a radical of the formula —NR'—S(O)$_2$—R, wherein R is alkyl as indicated above, and R' is hydrogen or alkyl as indicated above, e.g. methylsulfonylamino.

The term "arylsulfonylamino" is intended to indicate a radical of the formula —NR'—S(O)$_2$—R, wherein R is aryl as indicated above, and R' is hydrogen or alkyl as indicated above, e.g. phenylsulfonylamino.

The term "heteroarylsulfonylamino" is intended to indicate a radical of the formula —NR'—S(O)$_2$—R, wherein R is heteroaryl as indicated above, and R' is hydrogen or alkyl as indicated above, e.g. thiazolesulfonylamino.

The term "alkoxyimino" intended to indicate a radical of the formula =N—O—R, wherein R is alkyl as indicated above, e.g. methoxyimino.

The term "alkoxycarbamoyl" intended to indicate a radical of the formula —C(O)NR'—O—R, wherein R' is hydrogen or alkyl as indicated above, and R is alkyl as indicated above.

The term "aminocarbonyl" is intended to indicate a radical of the formula —C(O)—NR$_{12}$, wherein each R' is independently hydrogen, alkyl, alkenyl, or aryl as indicated above, e.g. carbamoyl, methylaminocarbonyl, ethylaminocarbonyl, propylaminocarbonyl, or butylaminocarbonyl.

The term "alkylcarbonylamino" is intended to indicate a radical of the formula —NR'—C(O)—R, wherein R' is hydrogen or alkyl as indicated above, and R is alkyl as indicated above, e.g. acetylamino.

The term "heterocycloalkylcarbonylamino" is intended to indicate a radical of the formula —NR'—C(O)—R, wherein R' is hydrogen or alkyl as indicated above, and R is heterocycloalkyl as indicated above, e.g. pyrrolidinylcarbonylamino.

The term "arylsulfonylamino" is intended to indicate a radical of the formula —NR'—S(O)$_2$—R, wherein R' is hydrogen or alkyl as indicated above, and R is aryl as indicated above.

The term "arylsulfonyl" is intended to indicate a radical of the formula —S(O)$_2$—R, wherein R is aryl as indicated above.

The term "alkylsulfonyl" is intended to indicate a radical of the formula —S(O)$_2$—R, wherein R is alkyl as indicated above, e.g. methylsulfonyl.

The term "pharmaceutically acceptable salt" is intended to indicate salts prepared by reacting a compound of formula I with a suitable inorganic or organic acid, such as hydrochloric, hydrobromic, hydroiodic, sulfuric, nitric, phosphoric, formic, acetic, 2,2-dichloroaetic, adipic, ascorbic, L-aspartic, L-glutamic, galactaric, lactic, maleic, L-malic, phthalic, citric, propionic, benzoic, glutaric, gluconic, D-glucuronic, methanesulfonic, salicylic, succinic, malonic, tartaric, benzenesulfonic, ethane-1,2-disulfonic, 2-hydroxy ethanesulfonic acid, toluenesulfonic, sulfamic or fumaric acid. Pharmaceutically acceptable salts of compounds of formula I may also be prepared by reaction with a suitable base such as sodium hydroxide, potassium hydroxide, magnesium hydroxide, calcium hydroxide, silver hydroxide, ammonia or the like.

The term "solvate" is intended to indicate a species formed by interaction between a compound, e.g. a compound of formula I, and a solvent, e.g. alcohol, glycerol or water, wherein said species are in a solid form. When water is the solvent, said species is referred to as a hydrate.

Preferred Embodiments of Compounds of Formula I

In a currently preferred embodiment of the invention W represents oxygen.

In another preferred embodiment of the invention $R_1$ represents hydrogen.

In yet another preferred embodiment of the invention D is C—$R_2$, E is C—$R_3$, F is C—$R_4$, and G is C—$R_5$.

In yet another preferred embodiment of the invention $R_2$, $R_3$, $R_4$, and $R_5$ are hydrogen, chloro, bromo, fluoro, methoxy, or methyl.

In yet another preferred embodiment of the invention D is nitrogen, E is C—$R_3$, F is C—$R_4$, and G is C—$R_5$.

In yet another preferred embodiment of the invention $R_3$, $R_4$, and $R_5$ are hydrogen.

In yet another preferred embodiment of the invention D is C—$R_2$, E is nitrogen, F is C—$R_4$, and G is C—$R_5$.

In yet another preferred embodiment of the invention $R_2$, $R_4$ and $R_5$ are hydrogen.

In yet another preferred embodiment B represents phenyl or pyridyl, such as 2-pyridyl, 3-pyridyl, or 4-pyridyl, all of which are optionally substituted with one or more substituents independently selected from the group consisting of $R_8$.

In yet another embodiment B represents, naphthyl, 2,3-dihydrobenzofuranyl, benzofuranyl, 2H-chromenyl, thiazolyl, 4,5-dihydro-1H-[1,2,4]-triazolyl, tetrahydropyranyl, 1,6-dihydropyridinyl, imidazolyl, imidazolidinyl, imidazo[2,1-b]thiazolyl, imidazo[1,2-a]pyrimidinyl, 1,2,4-triazolyl, piperidinyl, pyrrolidinyl, 4,5-dihydro-oxazolyl, isoxazolyl, 4,5-dihydro-isoxazolyl, pyrimidinyl, 1-H-pyrazolyl, 1H-indazol-6-yl, quinolinyl or isoquinolinyl, all of which are optionally substituted with one or more substituents independently selected from the group consisting of $R_8$.

In yet another embodiment B represents 1H-indazol-6-yl substituted in the 3 position with one substituent independently selected from the group consisting of $R_8$, said 1H-indazol-6-yl optionally further substituted with one or more substituents independently selected from the group consisting of $R_8$.

In yet another preferred embodiment $R_8$ is hydrogen, halogen, alkoxy, phenoxy, alkoxycarbonyl, carboxy, aminocarbonyl, cyano, alkyl, oxo, hydroxy, amino, heterocycloalkyl, heterocycloalkenyl, alkylsulfonylamino, alkylsulfonyl, alkylureido, alkylthioureido, alkylcarbonylamino, heterocycloalkylcarbonylamino, or aminocarbonyloxy, wherein said alkoxy, phenoxy, alkoxycarbonyl, alkoxycarbamoyl, aminocarbonyl, alkyl, amino, heterocycloalkyl, alkylsulfonylamino, alkylsulfonyl, alkylureido, alkylthioureido, alkylcarbonylamino, heterocycloalkylcarbonylamino, or aminocarbonyloxy are optionally substituted with one or more substituents independently selected from the group consisting of $R_7$.

In yet another preferred embodiment $R_8$ is hydrogen, fluoro, chloro, bromo, cyano, carboxy, oxo, —$NH_2$, hydroxy, methoxy, phenoxy, methoxycarbonyl, ethoxycarbonyl, methoxycarbamoyl, methylaminocarbonyl, pyrrolidinylcarbonylamino, ethylaminocarbonyl, propylaminocarbonyl, butylaminocarbonyl, methyl, ethyl, propyl, morpholine, pyrrolidinyl, methylsulfonylamino, methylsulfonyl, methylureido, ethylureido, tert-butylureido, cyclohexylureido, methylthioureido, isopropylureido, n-propylureido, methylamino, or ethylamino, wherein said methoxy, phenoxy, methoxycarbonyl, ethoxycarbonyl, methoxycarbamoyl, tert-butoxycarbonyl, methylaminocarbonyl, pyrrolidinylcarbonylamino, ethylaminocarbonyl, propylaminocarbonyl, butylaminocarbonyl, methyl, ethyl, propyl, morpholine, pyrrolidinyl, methylsulfonylamino, methylsulfonyl, methylureido, ethylureido, tert-butylureido, cyclohexylureido, methylthioureido, isopropylureido, n-propylureido, methylamino, or ethylamino are optionally substituted with one or more substituents independently selected from the group consisting of $R_7$.

In yet another embodiment X and Y independently represents a radical of the formula —$(CH_2)_i$—NH—C(O)—$(CH_2)_j$—, —$(CH_2)_k$—C(O)—$(CH_2)_m$—, —$(CH_2)_n$—, —$(CH_2)_p$—CH=CH—$(CH_2)_q$—, —$(CH_2)_r$—O—$(CH_2)_s$—, —$(CH_2)_t$—NH—$(CH_2)_u$—, —$(CH_2)_w$—C(O)—NH—$(CH_2)_z$— where i, j, k, m, n, p, q, r, s, t, u, w, and z are integers from 1-5, such as 2-4 or 3, wherein said radicals are optionally substituted by one or more substituents independently selected from the group consisting of $R_7$;

In yet another preferred embodiment X is a bond, —$CH_2$—, —$(CH_2)_2$—, —CH($CH_3$)—, —C(O)—, —C(O)—$CH_2$—, —$(CH_2)_2$—O—$CH_2$—, or —CH=CH—.

In yet another preferred embodiment Y is radical of the formula —$(CH_2)_i$—NH—C(O)—$(CH_2)_j$—, where i is an integer from 1-4 and j is 0; or Y is radical of the formula —$(CH_2)_n$—, where n is an integer from 0-6; or Y is radical of the formula —$(CH_2)_p$—C(O)—NH—$(CH_2)_q$, where p is an integer from 0-6 and q is 0; or Y is radical of the formula —$(CH_2)_r$—O—$(CH_2)_s$, where r is an integer from 0-6 and s is an integer from 0-1; or Y is radical of the formula —$(CH_2)_t$—NH—$(CH_2)_u$—, where t is an integer from 0-4 and u is an integer from 0-1; wherein said radicals are optionally substituted by one or more substituents independently selected from the group consisting of $R_7$.

In particular, Y is a bond, —$CH_2$—, —$CH_2$—$CH_2$—, —CH($CH_3$)—, —$CH_2$—$CH_2$—O—, —$(CH_2)_2$—O—$CH_2$—, —$(CH_2)_3$—O—$CH_2$—, —$(CH_2)_3$—NH—C(O)—, —$(CH_2)_4$—NH—C(O)—, —$CH_2$—CH(OH)—$CH_2$—O—, —$(CH_2)_2$—NH—$CH_2$—, —$(CH_2)_4$—NH—$CH_2$—, —$CH_2$—$CH_2$—$CH_2$—, —$CH_2$—C(O)—, —$CH_2$—C(O)—NH—, or —CH($CH_2NHSO_2CH_3$)—.

In yet another preferred embodiment A represents ($C_6$-$C_{10}$)aryl, ($C_{3-10}$)heterocycloalkyl, ($C_3$-$C_{10}$)cycloalkyl, ($C_3$-$C_6$)cycloalkenyl, ($C_2$-$C_5$)alkenyl, ($C_1$-$C_6$)alkyl, ($C_2$-$C_{10}$)heteroaryl, heterocycloalkenyl, or toluoyl, all of which are optionally substituted with one or more substituents independently selected from the group consisting of $R_9$.

In another preferred embodiment A represents methyl, ethyl, ($C_6$)aryl, ($C_9$)aryl, ($C_{10}$)aryl, ($C_{14}$)aryl, ($C_3$)alkyl, ($C_4$)alkyl, ($C_5$)alkyl, ($C_2$)alkenyl, ($C_3$)alkenyl, ($C_4$)alkenyl, ($C_5$)alkenyl, ($C_3$)cycloalkyl, ($C_4$)cycloalkyl, ($C_5$)cycloalkyl, ($C_6$)cycloalkyl, ($C_7$)cycloalkyl, ($C_8$)cycloalkyl, ($C_{10}$)cycloalkyl, ($C_6$)cycloalkenyl, ($C_3$)heteroaryl, ($C_4$)heteroaryl, ($C_5$)heteroaryl, ($C_6$)heteroaryl, ($C_7$)heteroaryl, ($C_9$)heteroaryl, ($C_4$)heterocycloalkyl, ($C_5$)heterocycloalkyl, ($C_3$)heterocycloalkenyl, ($C_4$)heterocycloalkenyl, ($C_5$)heterocycloalkenyl, or toluoyl, all of which are optionally substituted with one or more substituents independently selected from the group consisting of $R_9$.

In particular, A represents methyl, ethyl, allyl, butenyl, phenyl, thiazolyl, pyridyl, tert-butyl, propyl, pentyl, isobutyl, benzo[1,3]dioxolyl, indanyl, naphthyl, anthracenyl, thiazolyl, thiophenyl, oxadiazolyl, isoxazolyl, cyclopropyl, cyclobutyl, [1,2,3]triazolyl, cyclopentyl, cyclohexyl, cyclohexenyl, adamantyl, bicyclo[2.2.1]heptenyl, bicyclo[2.2.1]heptyl, bicyclo[4.1.0]heptenyl, cycloheptyl, cyclooctyl, quinolinyl, tetrahydrofuranyl, 4,5-dihydrooxazolyl, or tetrahydropyranyl, all of which are optionally substituted with one or more substituents independently selected from the group consisting of $R_9$.

In yet another preferred embodiment $R_9$ is hydrogen, nitro, halogen, oxo, cyano, trifluoromethyl, carboxy, alkoxy, alkoxycarbonyl, alkyl, cycloalkyl, alkenyl, alkynyl, alkylthio, heterocycloalkyl, heterocycloalkenyl, heteroaryl, amino, arylsulfonylamino, alkylthioureido, alkylureido, heteroarylsulfonylamino, alkylsulfonylamino, aminocarbonyl, aminocarbonyloxy, aryl, wherein said alkoxycarbonyl, alkyl, cycloalkyl, alkenyl, alkynyl, alkylthio, heterocycloalkyl, heteroaryl, amino, arylsulfonylamino, alkylthioureido, alkylureido, heteroarylsulfonylamino, alkylsulfonylamino, aminocarbonyl, aminocarbonyloxy, or aryl, are optionally substituted by one or more substituents independently selected from the group consisting of $R_7$.

In particular $R_9$ is hydrogen, nitro, fluoro, chloro, bromo, iodo, oxo, cyano, carboxy, ethenyl, ethynyl, propynyl, butynyl, methoxy, aminomethyl, aminoethyl, aminophenyl, morpholine, carbomethoxy, cyano, trifluoromethyl, methyl, tert-butoxy, ethyl, propyl, butyl, pentyl, cyclopentyl, nonenyl, methylsulfanyl, aminocarbonyl-tert-butoxy, methylsulfonylamino, thiazolesulfonylamino, phenylsulfonylamino, —NH—C(S)—$NH_2$, —NH—C(O)—$NH_2$, morpholinyl, ethylaminocarbonyl, thiophene, amino, or phenyl, wherein said ethenyl, ethynyl, propynyl, butynyl, methoxy, ethoxy, aminomethyl, aminoethyl, morpholine, carbomethoxy, cyano, trifluoromethyl, methyl, ethyl, propyl, butyl, pentyl, cyclopentyl, nonenyl, methylsulfanyl, methylsulfonylamino, thiazolesulfonylamino, phenylsulfonylamino, —NH—C(S)—$NH_2$, —NH—C(O)—$NH_2$, morpholinyl, ethylaminocarbonyl, thiophene, amino, or phenyl are optionally substituted by one or more substituents independently selected from the group consisting of $R_7$.

In yet another embodiment B—$R_8$ represents 4-pyridyl, 4-fluorophenyl, or 4-methoxyphenyl.

In yet another embodiment A-R$_9$ represents 2-nitrophenyl, 4-nitrophenyl, 3-trifluoromethylphenyl, 2-trifluoromethylphenyl, 4-trifluoromethylphenyl, 3-methoxyphenyl, 3,4,5-trimethoxyphenyl, 2-chlorophenyl, 3-chlorophenyl, 4-chlorophenyl, 2-bromophenyl, 2,4-dichlorophenyl, 3,4-dichlorophenyl, 2,6-dichlorophenyl, 3,5-dichlorophenyl, 2,3-dichlorophenyl, 3,6-dichlorophenyl, 2-fluorophenyl, 3-fluorophenyl, 4-fluorophenyl, 6-fluoro-2-chlorophenyl, 4-fluoro-2-chlorophenyl, 2-fluoro-3-chlorophenyl, 4-carbomethoxyphenyl, 4-cyanophenyl, quinolin-2-yl, phenyl, 2-methylthiazol-4-yl, or 4-methoxyphenyl.

In yet another preferred embodiment R$_7$ is hydrogen, halogen, hydroxy, carboxy, carbamoyl, cyano, oxo, thioxo, aryl, alkyl, alkyl, alkoxy, arylsulfonyl, aminocarbonyl, heterocycloalkyl-heteroaryl, heterocycloalkyl, heteroaryl, heterocycloalkenyl, alkoxycarbonyl, alkoxy, imino, alkoxyimino, alkylcarbonyloxy, alkenylcarbonyloxy, cycloalkyl, or amino, wherein said aryl, alkyl, alkyl, alkoxy, alkoxyimino, arylsulfonyl, aminocarbonyl, heterocycloalkyl-heteroaryl, heterocycloalkyl, heteroaryl, heterocycloalkenyl, alkoxycarbonyl, alkoxy, imino, alkylcarbonyloxy, alkenylcarbonyloxy, cycloalkyl, or amino are optionally substituted by one or more substituents independently selected from the group consisting of halogen, alkenyloxy, hydroxy, cyano, amino, alkylcarbonyloxy, alkylcarbonylamino, alkyl, alkoxy, aryl, or oxo.

In particular R$_7$ is hydrogen, hydroxy, amino, —NH$_2$, diethylamino, cyclohexylamino, tert-butylamino, oxo, thioxo, phenyl, pyridyl, acetylamino, fluoro, methyl, ethyl, propyl, butyl, morpholine, methoxy, tert-butoxy, cyclopropyl, hydroxyethyl, methoxyimino, —NH-phenyl, trifluoroacetyl, acetyl, ethoxy, 2-acetylamino-4-methyl-thiazole, tert-butyl, methylpiperazine, 2-hydroxyethylpiperazinyl, methylthiazol, hydroxypyrrolidine, dimethylamino, toluoyl, trifluoromethyl, methylamino, pyrrolidine, methoxycarbonyl, ethoxycarbonyl, carboxy, carbamoyl, cyano, methylcarbonyloxy, ethylcarbonyloxy, acryloyloxy, cyclopropyl, or 2,5-dioxoimazolidinyl.

In yet another embodiment A-R$_9$ represents 2-nitrophenyl, 4-nitrophenyl, 3-trifluoromethylphenyl, 2-trifluoromethylphenyl, 4-trifluoromethylphenyl, 3-methoxyphenyl, 3,4,5-trimethoxyphenyl, 2-chlorophenyl, 3-chlorophenyl, 4-chlorophenyl, 2-bromophenyl, 2,4-dichlorophenyl, 3,4-dichlorophenyl, 2,6-dichlorophenyl, 3,5-dichlorophenyl, 2,3-dichlorophenyl, 3,6-dichlorophenyl, 2-fluorophenyl, 3-fluorophenyl, 4-fluorophenyl, 6-fluoro-2-chlorophenyl, 4-fluoro-2-chlorophenyl, 2-fluoro-3-chlorophenyl, 4-carbomethoxyphenyl, 4-cyanophenyl, quinolin-2-yl, phenyl, 2-methylthiazol-4-yl, or 4-methoxyphenyl.

In yet another preferred embodiment B represents 4-pyridyl optionally substituted in the 2-position with R$_8$ or B represents phenyl optionally substituted with up to two R$_8$, same or different.

In yet another preferred embodiment A represents 1-phenyl substituted in the 4 position with bromo, fluoro, methyl or chlorine, optionally further substituted with one or more substituents independently selected from the group consisting of R$_9$.

In yet another preferred embodiment A represents a hydrocarbon radical comprising a 5 or 6 membered carbocyclic ring, wherein said hydrocarbon radical is optionally substituted with one or more substituents independently selected from the group consisting of R$_9$.

In yet another preferred embodiment A represents phenyl substituted with at least one fluoro, optionally further substituted with one or more substituents independently selected from the group consisting of R$_9$.

In yet another presently preferred embodiment the compounds of general formula I have a molecular weight below 1300 Dalton, such as below 900 Dalton, e.g. below 800 Dalton, e.g. below 700 Dalton, e.g. below 600 Dalton, e.g. below 500 Dalton.

In yet another presently preferred embodiment A is substituted by no more than two substituents independently selected from the group consisting of R$_9$ other than hydrogen.

In yet another presently preferred embodiment B is substituted by no more than two substituents independently selected from the group consisting of R$_8$ other than hydrogen.

In particular compounds of formula I may be selected amongst the list consisting of N-Benzyloxy-2-[(pyridin-4-ylmethyl)-amino]-benzamide (compound 1),
N-(4-Nitro-benzyloxy)-2-[(pyridin-4-ylmethyl)-amino]-benzamide (compound 2),
N-(2-Nitro-benzyloxy)-2-[(pyridin-4-ylmethyl)-amino]-benzamide (compound 3),
2-[(Pyridin-4-ylmethyl)-amino]-N-(3-trifluoromethyl-benzyloxy)-benzamide (compound 4),
2-[(Pyridin-4-ylmethyl)-amino]-N-(2-trifluoromethyl-benzyloxy)-benzamide (compound 5),
N2-[(Pyridin-4-ylmethyl)-amino]-N-(4-trifluoromethyl-benzyloxy)-benzamide (compound 6),
N-(4-Methoxy-benzyloxy)-2-[(pyridin-4-ylmethyl)-amino]-benzamide (compound 7),
N-(3-Methoxy-benzyloxy)-2-[(pyridin-4-ylmethyl)-amino]-benzamide (compound 8),
2-[(pyridin-4-ylmethyl)-amino]-N-(3,4,5-trimethoxy-benzyloxy)-benzamide (compound 9),
N-(4-Chloro-benzyloxy)-2-[(pyridin-4-ylmethyl)-amino]-benzamide (compound 10),
N-(3-Chloro-benzyloxy)-2-[(pyridin-4-ylmethyl)-amino]-benzamide (compound 11),
N-(2-Chloro-benzyloxy)-2-[(pyridin-4-ylmethyl)-amino]-benzamide (compound 12),
N-(2-Bromo-benzyloxy)-2-[(pyridin-4-ylmethyl)-amino]-benzamide (compound 13),
N-(2,4-Dichloro-benzyloxy)-2-[(pyridin-4-ylmethyl)-amino]-benzamide (compound 14),
N-(3,4-Dichloro-benzyloxy)-2-[(pyridine-4-ylmethyl)-amino]-benzamide (compound 15),
N-(2,6-Dichloro-benzyloxy)-2-[(pyridin-4-ylmethyl)-amino]-benzamide (compound 16),
N-(3,5-Dichloro-benzyloxy)-2-[(pyridin-4-ylmethyl)-amino]-benzamide (compound 17),
N-(2,3-Dichloro-benzyloxy)-2-[(pyridin-4-ylmethyl)-amino]-benzamide (compound 18),
N-(2,5-Dichloro-benzyloxy)-2-[(pyridin-4-ylmethyl)-amino]-benzamide (compound 19),
N-(2-Fluoro-benzyloxy)-2-[(pyridin-4-ylmethyl)-amino]-benzamide (compound 20),
N-(3-Fluoro-benzyloxy)-2-[(pyridin-4-ylmethyl)-amino]-benzamide (compound 21),
N-(4-Fluoro-benzyloxy)-2-[(pyridin-4-ylmethyl)-amino]-benzamide (compound 22),
N-(2-Chloro-6-fluoro-benzyloxy)-2-[(pyridin-4-ylmethyl)-amino]-benzamide (compound 23),
N-(2-Chloro-4-fluoro-benzyloxy)-2-[(pyridin-4-ylmethyl)-amino]-benzamide (compound 24),
N-(3-Chloro-2-fluoro-benzyloxy)-2-[(pyridin-4-ylmethyl)-amino]-benzamide (compound 25),
4-{2-[(pyridin-4-ylmethyl)-amino]-benzoylaminooxymethyl}-benzoic acid methyl ester (compound 26),
N-(4-cyano-benzyloxy)-2-[(pyridin-4-ylmethyl)-amino]-benzamide (compound 27), 2-[(Pyridin-4-ylmethyl)-amino]-N-(quinolin-2-ylmethoxy)-benzamide (compound 28),
N-Phenoxy-2-[(pyridin-4-ylmethyl)-amino]-benzamide (compound 29),
N-(2-Phenoxy-ethoxy)-2-[(pyridin-4-ylmethyl)-amino]-benzamide (compound 30),
N-(3-Phenyl-propoxy)-2-[(pyridin-4-ylmethyl)-amino]-benzamide (compound 31),
N-(2-methyl-thiazol-4 ylmethoxy)-2-[(pyridin-4-ylmethyl)-amino]-benzamide (compound 32),
N-Benzyloxy-2-2-[(pyridin-4-ylmethyl)-amino]-nicotinamide (compound 33),
2-(4-Fluoro-benzylamino)-N-(4-methoxy-benzyloxy)-nicotinamide (compound 34),
2-(4-Methoxy-benzylamino)-N-(4-methoxy-benzyloxy)-nicotinamide (compound 35),
N-(4-Cyano-phenoxy)-2-[(pyridin-4-ylmethyl)-amino]-benzamide (compound 36),
N-(4-Bromo-phenoxy)-2-[(pyridin-4-ylmethyl)-amino]-benzamide (compound 37),
N-(4-Fluoro-2,6-dimethyl-benzyloxy)-2-[(pyridin-4-ylmethyl)-amino]-benzamide (compound 38),
N-(4-Fluoro-2-methoxy-benzyloxy)-2-[(pyridin-4-ylmethyl)-amino]-benzamide (compound 39),
N-(2,3-Difluoro-4-methyl-benzyloxy)-2-[(pyridin-4-ylmethyl)-amino]-benzamide (compound 40)
N-(3-Fluoro-4-methyl-benzyloxy)-2-[(pyridin-4-ylmethyl)-amino]-benzamide (compound 41),
N-(5-Fluoro-2-methyl-benzyloxy)-2-[(pyridin-4-ylmethyl)-amino]-benzamide (compound 42),
2-[(Pyridin-4-ylmethyl)-amino]-N-(2,3,5,6-tetrafluoro-4-methoxy-benzyloxy)benzamide (compound 43),
N-(4-Bromo-benzyloxy)-2-[(pyridin-4-ylmethyl)-amino]-benzamide (compound 44),
N-(2-Iodo-benzyloxy)-2-[(pyridin-4-ylmethyl)-amino]-benzamide (compound 45),
N-(3-Iodo-benzyloxy)-2-[(pyridin-4-ylmethyl)-amino]-benzamide (compound 46),
N-(4-Methyl-benzyloxy)-2-[(pyridin-4-ylmethyl)-amino]-benzamide (compound 47)
N-[2-(3,3-Dimethyl-but-1-enyl)-benzyloxy]-2-[(pyridin-4-ylmethyl)-amino]-benzamide (compound 48),
2-[(Pyridin-4-ylmethyl)-amino]-N-(2-styryl-benzyloxy)-benzamide (compound 49),
N-[3-(3-Hydroxy-prop-1-ynyl)-benzyloxy]-2-[(pyridin-4-ylmethyl)-amino]-benzamide (compound 50),
N-[3-(5-Cyano-pent-1-ynyl)-benzyloxy]-2-[(pyridin-4-ylmethyl)-amino]-benzamide (compound 51),
N-[2-(3-Hydroxy-prop-1-ynyl)-benzyloxy]-2-[(pyridin-4-ylmethyl)-amino]-benzamide (compound 52),
Acetic acid 2-[3-(2-{2-[(pyridin-4-ylmethyl)-amino]-benzoylaminooxymethyl}-phenyl)-prop-2-ynyloxy]-ethyl ester (compound 53),
N-[2-(3-Methyl-3H-imidazol-4-ylethynyl)-benzyloxy]-2-[(pyridin-4-ylmethyl)-amino]-benzamide (compound 54),
N-[3-(3-Methyl-3H-imidazol-4-ylethynyl)-benzyloxy]-2-[(pyridin-4-ylmethyl)-amino]-benzamide (compound 55),
N-(2-Cyanomethyl-benzyloxy)-2-[(pyridin-4-ylmethyl)-amino]-benzamide (compound 56),
N-(2-Benzenesulfonylmethyl-benzyloxy)-2-[(pyridin-4-ylmethyl)-amino]-benzamide (compound 57),
N-(4-Hydroxymethyl-benzyloxy)-2-[(pyridin-4-ylmethyl)-amino]-benzamide (compound 58),
N-(4-Fluoro-2-trifluoromethyl-benzyloxy)-2-[(pyridin-4-ylmethyl)-amino]-benzamide (compound 59),
N-(2-Fluoro-6-trifluoromethyl-benzyloxy)-2-[(Pyridin-4-ylmethyl)-amino]-benzamide (compound 60),
N-(4-Fluoro-3-trifluoromethyl-benzyloxy)-2-[(Pyridin-4-ylmethyl)-amino]-benzamide (compound 61),
N-(4-Methyl-3-trifluoromethyl-benzyloxy)-2-[(pyridin-4-ylmethyl)-amino]-benzamide (compound 62),
N-(4-Methoxy-3-trifluoromethyl-benzyloxy)-2-[(Pyridin-4-ylmethyl)-amino]-benzamide (compound 63),
N-(2-Methoxy-benzyloxy)-2-[(pyridin-4-ylmethyl)-amino]-benzamide (compound 64),
N-(4-Pentyloxy-benzyloxy)-2-[(pyridin-4-ylmethyl)-amino]-benzamide (compound 65),
2-[(Pyridin-4-ylmethyl)-amino]-N-(2-trifluoromethoxy-benzyloxy)-benzamide (compound 66),
2-[(Pyridin-4-ylmethyl)-amino]-N-(3-trifluoromethoxy-benzyloxy)-benzamide (compound 67),
2-[(Pyridin-4-ylmethyl)-amino]-N-(4-trifluoromethoxy-benzyloxy)-benzamide (compound 68),
N-(2-Difluoromethoxy-benzyloxy)-2-[(pyridin-4-ylmethyl)-amino]-benzamide (compound 69),
2-[(Pyridin-4-ylmethyl)-amino]-N-(2-trifluoromethylsulfanyl-benzyloxy)-benzamide (compound 70),
N-(6-Chloro-benzo[1,3]dioxol-5-ylmethoxy)-2-[(pyridin-4-ylmethyl)-amino]-benzamide (compound 71),
N-(Benzo[1,3]dioxol-5-ylmethoxy)-2-[(pyridin-4-ylmethyl)-amino]-benzamide (compound 72),
N-(Indan-5-ylmethoxy)-2-[(pyridin-4-ylmethyl)-amino]-benzamide (compound 73),
N-(3-Cyano-benzyloxy)-2-[(pyridin-4-ylmethyl)-amino]-benzamide (compound 74),
N-(2-Cyano-benzyloxy)-2-[(pyridin-4-ylmethyl)-amino]-benzamide (compound 75),
N-(4-Cyano-2-fluoro-benzyloxy)-2-[(pyridin-4-ylmethyl)-amino]-benzamide (compound 76),
N-(3-Bromo-4-cyano-benzyloxy)-2-[(pyridin-4-ylmethyl)-amino]-benzamide (compound 77),
N-(2-Chloro-4-cyano-benzyloxy)-2-[(pyridin-4-ylmethyl)-amino]-benzamide (compound 78),
N-(4-Cyano-2-methoxy-benzyloxy)-2-[(pyridin-4-ylmethyl)-amino]-benzamide (compound 79),
N-(4-Cyano-2-iodo-benzyloxy)-2-[(pyridin-4-ylmethyl)-amino]-benzamide (compound 80),
N-(2-Bromo-5-cyano-benzyloxy)-2-[(pyridin-4-ylmethyl)-amino]-benzamide (compound 81),
N-(4-Cyano-naphthalen-1-ylmethoxy)-2-[(pyridin-4-ylmethyl)-amino]-benzamide (compound 82),
N-(4-Morpholin-4-yl-benzyloxy)-2-[(pyridin-4-ylmethyl)-amino]-benzamide (compound 83),
N-(2-Morpholin-4-yl-benzyloxy)-2-[(pyridin-4-ylmethyl)-amino]-benzamide (compound 84),
N-(2-Amino-benzyloxy)-2-[(pyridin-4-ylmethyl)-amino]-benzamide (compound 85),
N-(2-Benzenesulfonylamino-benzyloxy)-2-[(pyridin-4-ylmethyl)-amino]-benzamide (compound 86),
3-{2-[(Pyridin-4-ylmethyl)-amino]-benzoylaminooxymethyl}-benzoic acid methyl ester (compound 87),
3-{2-[(Pyridin-4-ylmethyl)-amino]-benzoylaminooxymethyl}-benzoic acid (compound 88),
4-{2-[(Pyridin-4-ylmethyl)-amino]-benzoylaminooxymethyl}-benzoic acid (compound 89),
N-[4-(Morpholine-4-carbonyl)-benzyloxy]-2-[(pyridin-4-ylmethyl)-amino]-benzamide (compound 90),
N-{3-[4-(3-Cyano-pyridin-2-yl)-piperazine-1-carbonyl]-benzyloxy}-2-[(pyridin-4-ylmethyl)-amino]-benzamide (compound 91),
N-[3-(4-Methyl-piperazine-1-carbonyl)-benzyloxy]-2-[(pyridin-4-ylmethyl)-amino]-benzamide (compound 92),
N-[3-(Morpholine-4-carbonyl)-benzyloxy]-2-[(pyridin-4-ylmethyl)-amino]-benzamide (compound 93), N-[3-(3-Hydroxy-pyrrolidine-1-carbonyl)-benzyloxy]-2-[(pyridin-4-ylmethyl)-amino]-benzamide (compound 94),
N-[4-(4-Methyl-piperazine-1-carbonyl)-benzyloxy]-2-[(pyridin-4-ylmethyl)-amino]-benzamide (compound 95),
N-[3-(2-dimethylaminoethylcarbamoyl)-benzyloxy]-2-[(pyridin-4-ylmethyl)-amino]-benzamide (compound 96),
N-[3-(2-pyrrolidin-1-yl-ethylcarbamoyl)-benzyloxy]-2-[(pyridin-4-ylmethyl)-amino]-benzamide (compound 97),
2-[(Pyridin-4-ylmethyl)-amino]-N-(2-thiophen-2-yl-benzyloxy)-benzamide (compound 98),
N-(4'-Methoxy-biphenyl-2-ylmethoxy)-2-[(pyridin-4-ylmethyl)-amino]-benzamide (compound 99),
N-(Naphthalen-1-ylmethoxy)-2-[(pyridin-4-ylmethyl)-amino]-benzamide (compound 100),
N-(1-Phenyl-ethoxy)-2-[(pyridin-4-ylmethyl)-amino]-benzamide (compound 101),
2-[(Pyridin-4-ylmethyl)-amino]-N-[1-(2-trifluoromethyl-phenyl)-ethoxy]-benzamide (compound 102),
N-(Pyridin-2-ylmethoxy)-2-[(pyridin-4-ylmethyl)-amino]-benzamide (compound 103),
N-(2,6-Dichloro-pyridin-4-ylmethoxy)-2-[(pyridin-4-ylmethyl)-amino]-benzamide (compound 104),
2-[(Pyridin-4-ylmethyl)-amino]-N-(thiazol-4-ylmethoxy)-benzamide (compound 105),
N-(2-Chloro-thiazol-5-ylmethoxy)-2-[(pyridin-4-ylmethyl)-amino]-benzamide (compound 106),
N-(2-Phenyl-thiazol-4-ylmethoxy)-2-[(pyridin-4-ylmethyl)-amino]-benzamide (compound 107),
N-(5-Methyl-isoxazol-3-ylmethoxy)-2-[(pyridin-4-ylmethyl)-amino]-benzamide (compound 108),
N-(3,5-Dimethyl-isoxazol-4-ylmethoxy)-2-[(pyridin-4-ylmethyl)-amino]-benzamide (compound 109),
N-(3-Propyl-isoxazol-5-ylmethoxy)-2-[(pyridin-4-ylmethyl)-amino]-benzamide (compound 110),
N-(5-Chloro-thiophen-2-ylmethoxy)-2-[(pyridin-4-ylmethyl)-amino]-benzamide (compound 111),
N-[2-(4-Cyano-phenyl)-ethoxy]-2-[(pyridin-4-ylmethyl)-amino]-benzamide (compound 112),
N-Cyclopentylmethoxy-2-[(pyridin-4-ylmethyl)-amino]-benzamide (compound 113),
N-Cyclopropylmethoxy-2-[(pyridin-4-ylmethyl)-amino]-benzamide (compound 114),
N-Methoxy-2-[(pyridin-4-ylmethyl)-amino]-benzamide (compound 115),
N-(2,2-Dimethyl-propoxy)-2-[(pyridin-4-ylmethyl)-amino]-benzamide (compound 116),
N-(2-Ethyl-butoxy)-2-[(pyridin-4-ylmethyl)-amino]-benzamide (compound 117),
N-(3-Methyl-butoxy)-2-[(pyridin-4-ylmethyl)-amino]-benzamide (compound 118),
N-Cyclobutylmethoxy-2-[(pyridin-4-ylmethyl)-amino]-benzamide (compound 119),
N-Cyclohexylmethoxy-2-[(pyridin-4-ylmethyl)-amino]-benzamide (compound 120),
N-Cycloheptylmethoxy-2-[(pyridin-4-ylmethyl)-amino]-benzamide (compound 121),
N-Cyclooctylmethoxy-2-[(pyridin-4-ylmethyl)-amino]-benzamide (compound 122),
N-(1-Cyclopentyl-ethoxy)-2-[(pyridin-4-ylmethyl)-amino]-benzamide (compound 123),
N-Cyclohexyloxy-2-[(pyridin-4-ylmethyl)-amino]-benzamide (compound 124),
N-(2-Cyclopropyl-ethoxy)-2-[(pyridin-4-ylmethyl)-amino]-benzamide (compound 125),
N-(2-Cyclopentyl-ethoxy)-2-[(pyridin-4-ylmethyl)-amino]-benzamide (compound 126),
N-(3-Cyclopentyl-propoxy)-2-[(pyridin-4-ylmethyl)-amino]-benzamide (compound 127),
N-(Cyclohex-3-enylmethoxy)-2-[(pyridin-4-ylmethyl)-amino]-benzamide (compound 128),
N-(6-Methyl-cyclohex-3-enylmethoxy)-2-[(pyridin-4-ylmethyl)-amino]-benzamide (compound 129),
N-(trans-4-Hydroxymethyl-cyclohexylmethoxy)-2-[(pyridin-4-ylmethyl)-amino]-benzamide (compound 130),
N-(3-Methoxy-cyclohexylmethoxy)-2-[(pyridin-4-ylmethyl)-amino]-benzamide (compound 131),
N-(Adamantan-1-ylmethoxy)-2-[(pyridin-4-ylmethyl)-amino]-benzamide (compound 132)
N-(Bicyclo[2.2.1]hept-2-ylmethoxy)-2-[(pyridin-4-ylmethyl)-amino]-benzamide (compound 133),
N-(6,6-Dimethyl-bicyclo[3.1.1]hept-2-ylmethoxy)-2-[(pyridin-4-ylmethyl)-amino]-benzamide (compound 134),
2-[(Pyridin-4-ylmethyl)-amino]-N-(tetrahydro-furan-2-ylmethoxy)-benzamide (compound 135),
2-[(Pyridin-4-ylmethyl)-amino]-N-(tetrahydro-furan-3-ylmethoxy)-benzamide (compound 136)
N-(3-Methyl-4,5-dihydro-isoxazol-5-ylmethoxy)-2-[(pyridin-4-ylmethyl)-amino]-benzamide (compound 137),
N-(3-Ethyl-4,5-dihydro-isoxazol-5-ylmethoxy)-2-[(pyridin-4-ylmethyl)-amino]-benzamide (compound 138),
N-(3-Butyl-4,5-dihydro-isoxazol-5-ylmethoxy)-2-[(pyridin-4-ylmethyl)-amino]-benzamide (compound 139),
2-[(Pyridin-4-ylmethyl)-amino]-N-(tetrahydro-pyran-2-yloxy)-benzamide (compound 140),
2-[(Pyridin-4-ylmethyl)-amino]-N-(tetrahydro-pyran-4-ylmethoxy)-benzamide (compound 141),
2-[(Pyridin-4-ylmethyl)-amino]-N-(tetrahydro-pyran-2-ylmethoxy)-benzamide (compound 142),
4-Fluoro-N-(2-methyl-thiazol-4-ylmethoxy)-2-[(pyridin-4-ylmethyl)-amino]-benzamide (compound 143),
2-Fluoro-N-(2-methyl-thiazol-4-ylmethoxy)-6-[(pyridin-4-ylmethyl)-amino]-benzamide (compound 144),
5-Fluoro-N-(2-methyl-thiazol-4-ylmethoxy)-2-[(pyridin-4-ylmethyl)-amino]-benzamide (compound 145),
3-Methoxy-N-(2-methyl-thiazol-4-ylmethoxy)-2-[(pyridin-4-ylmethyl)-amino]-benzamide (compound 146),
N-(4-Chloro-benzyloxy)-3-methoxy-2-[(pyridin-4-ylmethyl)-amino]-benzamide (compound 147),
4,5-Dimethoxy-N-(2-methyl-thiazol-4-ylmethoxy)-2-[(pyridin-4-ylmethyl)-amino]-benzamide (compound 148),
N-Benzyloxy-4,5-dimethoxy-2-[(pyridin-4-ylmethyl)-amino]-benzamide (compound 149),
2-Methyl-N-(2-methyl-thiazol-4-ylmethoxy)-6-[(pyridin-4-ylmethyl)-amino]-benzamide (compound 150),
N-Benzyloxy-2-methyl-6-[(pyridin-4-ylmethyl)-amino]-benzamide (compound 151),
5-Methyl-N-(2-methyl-thiazol-4-ylmethoxy)-2-[(pyridin-4-ylmethyl)-amino]-benzamide (compound 152),
N-Benzyloxy-5-methyl-2-[(pyridin-4-ylmethyl)-amino]-benzamide (compound 153),
5-Bromo-N-(4-cyano-2-methoxy-benzyloxy)-2-[(pyridin-4-ylmethyl)-amino]-benzamide (compound 154).
N-Benzyloxy-5-bromo-2-[(pyridin-4-ylmethyl)-amino]-benzamide (compound 155),
N-(4-Cyano-benzyloxy)-2-[(pyridin-4-ylmethyl)-amino]-nicotinamide (compound 156),
N-(2-Chloro-4-cyano-benzyloxy)-2-[(pyridin-4-ylmethyl)-amino]-nicotinamide (compound 157),
N-(4-Cyano-2-fluoro-benzyloxy)-2-[(pyridin-4-ylmethyl)-amino]-nicotinamide (compound 158).
N-(3-Bromo-4-cyano-benzyloxy)-2-[(pyridin-4-ylmethyl)-amino]-nicotinamide (compound 159), N-(2-Iodo-benzyloxy)-2-[(pyridin-4-ylmethyl)-amino]-nicotinamide (compound 160),
N-(2-Bromo-benzyloxy)-2-[(pyridin-4-ylmethyl)-amino]-nicotinamide (compound 161),
N-(4-Cyano-2-methoxy-benzyloxy)-2-[(pyridin-4-ylmethyl)-amino]-nicotinamide (compound 162),
N-(2-Methyl-thiazol-4-ylmethoxy)-2-[(pyridin-4-ylmethyl)-amino]-nicotinamide (compound 163),
N-Cyclopentylmethoxy-2-[(pyridin-4-ylmethyl)-amino]-nicotinamide (compound 164),
N-Benzyloxy-2-(4-fluoro-benzylamino)-nicotinamide (compound 165),
N-Benzyloxy-2-(4-chloro-benzylamino)-nicotinamide (compound 166).
N-Benzyloxy-2-(4-methoxy-benzylamino)-nicotinamide (compound 167),
N-Benzyloxy-2-(isoquinolin-5-ylamino)-nicotinamide (compound 168),
N-(4-Cyano-2-methoxy-benzyloxy)-3-[(pyridin-4-ylmethyl)-amino]-isonicotinamide (compound 169),
N-Benzyloxy-3-[(pyridin-4-ylmethyl)-amino]-isonicotinamide (compound 170),
N-(2-Methyl-thiazol-4-ylmethoxy)-3-[(pyridin-4-ylmethyl)-amino]-isonicotinamide (compound 171).
N-Benzyloxy-2-(4-fluoro-benzylamino)-benzamide (compound 172),
N-(4-Cyano-benzyloxy)-2-(4-fluoro-benzylamino)-benzamide (compound 173).
2-(4-Fluoro-benzylamino)-N-(2-methyl-thiazol-4-ylmethoxy)-benzamide (compound 174),
N-Benzyloxy-2-(3-cyano-4-fluoro-benzylamino)-benzamide (compound 175),
N-(2-Bromo-benzyloxy)-2-(3-cyano-4-fluoro-benzylamino)-benzamide (compound 176),
5-[(2-Benzyloxycarbamoyl-phenylamino)-methyl]-2-fluoro-benzoic acid methyl ester (compound 177),
5-[(2-Cyclopentylmethoxycarbamoyl-phenylamino)-methyl]-2-fluoro-benzoic acid methyl ester (compound 178).
2-Fluoro-5-{[2-(4-fluoro-benzyloxycarbamoyl)-phenylamino]-methyl}-benzoic acid methyl ester (compound 179).
5-{[2-(4-Cyano-benzyloxycarbamoyl)-phenylamino]-methyl}-2-fluoro-benzoic acid methyl ester (compound 180).
5-[(2-Cyclopentylmethoxycarbamoyl-phenylamino)-methyl]-2-fluoro-benzoic acid (compound 181).
2-Fluoro-5-{[2-(4-fluoro-benzyloxycarbamoyl)-phenylamino]-methyl}-benzoic acid (compound 182),
5-[(2-Benzyloxycarbamoyl-phenylamino)-methyl]-2-fluoro-benzoic acid (compound 183).
5-[(2-Benzyloxycarbamoyl-phenylamino)-methyl]-2-fluoro-N-(2-hydroxy-ethyl)benzamide (compound 184),
5-[(2-Benzyloxycarbamoyl-phenylamino)-methyl]-2-fluoro-N-(3-hydroxy-propyl)benzamide (compound 185),
5-[(2-Benzyloxycarbamoyl-phenylamino)-methyl]-2-fluoro-N-(4-hydroxy-butyl)benzamide (compound 186),
5-[(2-Benzyloxycarbamoyl-phenylamino)-methyl]-N-(3-dimethylamino-propyl)-2-fluoro-benzamide (compound 187).
5-[(2-Cyclopentylmethoxycarbamoyl-phenylamino)-methyl]-2-fluoro-N-(3-hydroxypropyl)-benzamide (compound 188),
N-Cyclopentylmethoxy-2-[4-fluoro-3-(4-methyl-piperazine-1-carbonyl)-benzylamino]-benzamide (compound 189),
N-Cyclopentylmethoxy-2-[4-fluoro-3-(morpholine-4-carbonyl)-benzylamino]-benzamide (compound 190),
N-Benzyloxy-2-(4-methoxy-benzylamino)-benzamide (compound 191),
2-(4-Methoxy-benzylamino)-N-(2-methyl-thiazol-4-ylmethoxy)-benzamide (compound 192),
N-Benzyloxy-2-[(4-methoxy-naphthalen-1-ylmethyl)-amino]-benzamide (compound 193),
N-(4-Cyano-benzyloxy)-2-[(4-methoxy-naphthalen-1-ylmethyl)-amino]-benzamide (compound 194),
2-[(2,3-Dihydro-benzofuran-5-ylmethyl)-amino]-N-(4-fluoro-benzyloxy)-benzamide (compound 195),
N-(4-Cyano-benzyloxy)-2-[(2,3-dihydro-benzofuran-5-ylmethyl)-amino]-benzamide (compound 196),
2-[(Benzofuran-5-ylmethyl)-amino]-N-(4-cyano-benzyloxy)-benzamide (compound 197),
2-[(Benzofuran-5-ylmethyl)-amino]-N-benzyloxy-benzamide (compound 198),
2-[(Benzofuran-5-ylmethyl)-amino]-N-(4-fluoro-benzyloxy)-benzamide (compound 199).
N-(4-Cyano-benzyloxy)-2-[(2-oxo-2H-chromen-6-ylmethyl)-amino]-benzamide (compound 200),
N-(4-Chloro-benzyloxy)-2-(4-cyano-benzylamino)-benzamide (compound 201),
2-[(3,5-Dichloro-pyridin-4-ylmethyl)-amino]-N-(2-methyl-thiazol-4-ylmethoxy)benzamide (compound 202),
N-Benzyloxy-2-[(3,5-dichloro-pyridin-4-ylmethyl)-amino]-benzamide (compound 203),
2-[(2-Bromo-pyridin-4-ylmethyl)-amino]-N-(4-fluoro-benzyloxy)-benzamide (compound 204),
N-(4-Cyano-2-methoxy-benzyloxy)-2-[(2-hydroxy-pyridin-4-ylmethyl)-amino]-benzamide (compound 205),
2-[(2-Amino-pyridin-4-ylmethyl)-amino]-N-(4-cyano-benzyloxy)-benzamide (compound 206),
N-(4-Fluoro-benzyloxy)-2-[(2-morpholin-4-yl-pyridin-4-ylmethyl)-amino]-benzamide (compound 207),
N-Cyclopentylmethoxy-2-[(2-methanesulfonylamino-pyridin-4-ylmethyl)-amino]-benzamide (compound 208),
N-(4-Cyano-benzyloxy)-2-[(2-methanesulfonylamino-pyridin-4-ylmethyl)-amino]-benzamide (compound 209),
N-(4-Cyano-benzyloxy)-2-{[2-(3-methyl-ureido)-pyridin-4-ylmethyl]-amino}-benzamide (compound 210),
N-(4-Cyano-2-methoxy-benzyloxy)-2-{[2-(3-methyl-ureido)-pyridin-4-ylmethyl]-amino}-benzamide (compound 211),
N-Cyclopentylmethoxy-2-{[2-(3-methyl-ureido)-pyridin-4-ylmethyl]-amino}-benzamide (compound 212),
N-(2,3-Difluoro-4-methyl-benzyloxy)-2-{[2-(3-methyl-ureido)-pyridin-4-ylmethyl]-amino}-benzamide (compound 213)
[3-(4-{[2-(4-Cyano-benzyloxycarbamoyl)-phenylamino]-methyl}-pyridin-2-yl)-ureido]-acetic acid ethyl ester (compound 214),
(3-{4-[(2-Cyclopentylmethoxycarbamoyl-phenylamino)-methyl]-pyridin-2-yl}-ureido)acetic acid ethyl ester (compound 215),
[3-(4-{[2-(4-Cyano-benzyloxycarbamoyl)-phenylamino]-methyl}-pyridin-2-yl)-ureido]-acetic acid (compound 216),
(3-{4-[(2-Cyclopentylmethoxycarbamoyl-phenylamino)-methyl]-pyridin-2-yl}-ureido)acetic acid (compound 217),
2-Methyl-acrylic acid 2-[3-(4-{[2-(4-cyano-benzyloxycarbamoyl)-phenylamino]-methyl}-pyridin-2-yl)-ureido]-ethyl ester (compound 218),
2-Methyl-acrylic acid 2-(3-{4-[(2-cyclopentylmethoxycarbamoyl-phenylamino)methyl]-pyridin-2-yl}-ureido)-ethyl ester (compound 219), N-(4-Cyano-benzyloxy)-2-({2-[3-(2-hydroxy-ethyl)-ureido]-pyridin-4-ylmethyl}-amino)-benzamide (compound 220), N-Cyclopentylmethoxy-2-({2-[3-(2-hydroxy-ethyl)-ureido]-pyridin-4-ylmethyl}-amino)-benzamide (compound 221), Acetic acid (4-{[2-(4-cyano-benzyloxycarbamoyl)-phenylamino]-methyl}-pyridin-2-ylcarbamoyl)-methyl ester (compound 222), Acetic acid {4-[(2-cyclopentylmethoxycarbamoyl-phenylamino)-methyl]-pyridin-2-ylcarbamoyl}-methyl ester (compound 223), N-(4-Cyano-benzyloxy)-2-{[2-(2-hydroxy-acetylamino)-pyridin-4-ylmethyl]-amino}-benzamide (compound 224), 4-{[2-(4-Cyano-benzyloxycarbamoyl)-phenylamino]-methyl}-pyridin-2-yl)-carbamic acid ethyl ester (compound 225), N-(4-Cyano-benzyloxy)-2-{[2-(cyclopropanecarbonyl-amino)-pyridin-4-ylmethyl]-amino}-benzamide (compound 226), N-Cyclopentylmethoxy-2-{[2-(cyclopropanecarbonyl-amino)-pyridin-4-ylmethyl]-amino}-benzamide (compound 227), N-Cyclopentylmethoxy-2-({2-[2-(2,5-dioxo-imidazolidin-4-yl)-acetylamino]-pyridin-4-ylmethyl}-amino)-benzamide (compound 228), 2-[(2-Amino-pyridin-4-ylmethyl)-amino]-N-cyclopentylmethoxy-benzamide (compound 229), N-Benzyloxy-2-[(quinolin-4-ylmethyl)-amino]-benzamide (compound 230), N-(4-Cyano-benzyloxy)-2-[(quinolin-4-ylmethyl)-amino]-benzamide (compound 231), N-(2-Methyl-thiazol-4-ylmethoxy)-2-[(quinolin-4-ylmethyl)-amino]-benzamide (compound 232), N-Cyclopentylmethoxy-2-[(quinolin-4-ylmethyl)-amino]-benzamide (compound 233), 2-[(Quinolin-4-ylmethyl)-amino]-N-(tetrahydro-pyran-4-ylmethoxy)-benzamide (compound 234), N-(4-Cyano-2-methoxy-benzyloxy)-2-[(6-methoxy-pyridin-3-ylmethyl)-amino]-benzamide (compound 235), N-Benzyloxy-2-[(6-methoxy-pyridin-3-ylmethyl)-amino]-benzamide (compound 236), N-(4-Cyano-benzyloxy)-2-[(6-methoxy-pyridin-3-ylmethyl)-amino]-benzamide (compound 237), N-Benzyloxy-2-[(thiazol-5-ylmethyl)-amino]-benzamide (compound 238), N-(2,4-Dichloro-benzyloxy)-2-[(thiazol-5-ylmethyl)-amino]-benzamide (compound 239), N-(2-Methyl-thiazol-4-ylmethoxy)-2-[(5-oxo-4,5-dihydro-1H-[1,2,4]triazol-3-ylmethyl)amino]-benzamide (compound 240), N-Benzyloxy-2-[(5-oxo-4,5-dihydro-1H-[1,2,4]triazol-3-ylmethyl)-amino]-benzamide (compound 241), N-Benzyloxy-2-(2-imidazol-1-yl-ethylamino)-benzamide (compound 242), N-Cyclopentylmethoxy-2-(2-imidazol-1-yl-ethylamino)-benzamide (compound 243), N-(4-Cyano-benzyloxy)-2-(1-pyridin-4-yl-ethylamino)-benzamide (compound 244), 2-{[2-(3-Methyl-ureido)-pyridin-4-ylmethyl]-amino}-N-(tetrahydro-pyran-2-ylmethoxy)-benzamide (compound 245), N-Cyclopentylmethoxy-2-{[2-(2-methoxy-acetylamino)-pyridin-4-ylmethyl]-amino}-benzamide (compound 246), N-(4-Cyano-benzyloxy)-2-[(6-oxo-1,6-dihydro-pyridin-3-ylmethyl)-amino]-benzamide (compound 247), N-Cyclopentylmethoxy-2-[(tetrahydro-pyran-4-ylmethyl)-amino]-benzamide (compound 248), N-(3-Iodo-4-methyl-benzyloxy)-2-[(pyridin-4-ylmethyl)-amino]-benzamide (compound 250), N-(4-Ethyl-benzyloxy)-2-[(pyridin-4-ylmethyl)-amino]-benzamide (compound 251), N-(4-Isopropyl-benzyloxy)-2-[(pyridin-4-ylmethyl)-amino]-benzamide (compound 252), N-(4-tert-Butyl-benzyloxy)-2-[(pyridin-4-ylmethyl)-amino]-benzamide (compound 253), N-(2-Ethyl-benzyloxy)-2-[(pyridin-4-ylmethyl)-amino]-benzamide (compound 254), N-(2-Non-1-enyl-benzyloxy)-2-[(pyridin-4-ylmethyl)-amino]-benzamide (compound 255), N-(4-Phenylaminomethyl-benzyloxy)-2-[(pyridin-4-ylmethyl)-amino]-benzamide (compound 256), N-(4-Diethylaminomethyl-benzyloxy)-2-[(pyridin-4-ylmethyl)-amino]-benzamide (compound 257), N-(2-Carbamoylmethyl-benzyloxy)-2-[(pyridin-4-ylmethyl)-amino]-benzamide (compound 258), N-[4-Cyano-2-(2-methoxy-ethoxy)-benzyloxy]-2-[(pyridin-4-ylmethyl)-amino]-benzamide (compound 259), N-(4-Cyanomethyl-2-methoxy-benzyloxy)-2-[(pyridin-4-ylmethyl)-amino]-benzamide (compound 260), N-(5-Cyano-2-methoxy-benzyloxy)-2-[(pyridin-4-ylmethyl)-amino]-benzamide (compound 261), 2-{2-[(Pyridin-4-ylmethyl)-amino]-benzoylaminooxymethyl}-phenyl)-carbamic acid tert-butyl ester (compound 262), N-(2-Acetylamino-benzyloxy)-2-[(pyridin-4-ylmethyl)-amino]-benzamide (compound 263), N-(2-Benzoylamino-benzyloxy)-2-[(pyridin-4-ylmethyl)-amino]-benzamide (compound 264), N-(2-Methanesulfonylamino-benzyloxy)-2-[(pyridin-4-ylmethyl)-amino]-benzamide (compound 265), N-(4-Acetylamino-benzyloxy)-2-[(pyridin-4-ylmethyl)-amino]-benzamide (compound 266), N-(Biphenyl-4-ylmethoxy)-2-[(pyridin-4-ylmethyl)-amino]-benzamide (compound 267), N-(Biphenyl-2-ylmethoxy)-2-[(pyridin-4-ylmethyl)-amino]-benzamide (compound 268), N-(3'-Methoxy-biphenyl-2-ylmethoxy)-2-[(pyridin-4-ylmethyl)-amino]-benzamide (compound 269), N-(2'-Methoxy-biphenyl-2-ylmethoxy)-2-[(pyridin-4-ylmethyl)-amino]-benzamide (compound 270), N-(3'-Hydroxymethyl-biphenyl-2-ylmethoxy)-2-[(pyridin-4-ylmethyl)-amino]-benzamide (compound 271), N-(3-Phenoxy-benzyloxy)-2-[(pyridin-4-ylmethyl)-amino]-benzamide (compound 272), N-(Anthracen-9-ylmethoxy)-2-[(pyridin-4-ylmethyl)-amino]-benzamide (compound 273), N-[4-(2-Methyl-thiazol-4-yl)-benzyloxy]-2-[(pyridin-4-ylmethyl)-amino]-benzamide (compound 274), N-(2-Methanesulfonylamino-1-phenyl-ethoxy)-2-[(pyridin-4-ylmethyl)-amino]-benzamide (compound 275), 2-[(Pyridin-4-ylmethyl)-amino]-N-[2-(4-trifluoromethyl-phenyl)-thiazol-4-ylmethoxy]-benzamide (compound 276), 2-[(Pyridin-4-ylmethyl)-amino]-N-(3-p-tolyl-isoxazol-5-ylmethoxy)-benzamide (compound 277), N-(3-Methyl-isoxazol-5-ylmethoxy)-2-[(pyridin-4-ylmethyl)-amino]-benzamide (compound 278), N-(3-Ethyl-isoxazol-5-ylmethoxy)-2-[(pyridin-4-ylmethyl)-amino]-benzamide (compound 279), N-(3-Butyl-isoxazol-5-ylmethoxy)-2-[(pyridin-4-ylmethyl)-amino]-benzamide (compound 280), N-(3-Pentyl-isoxazol-5-ylmethoxy)-2-[(pyridin-4-ylm-
ethyl)-amino]-benzamide (compound 281),
2-[(Pyridin-4-ylmethyl)-amino]-N-[5-(3-trifluoromethyl-
phenyl)-[1,2,4]oxadiazol-3-ylmethoxy]-benzamide (compound 282),
N-(1-Benzyl-1H-[1,2,3]triazol-4-ylmethoxy)-2-[(pyridin-4-
ylmethyl)-amino]-benzamide (compound 283),
N-(1-Cyclopentyl-1H-[1,2,3]triazol-4-ylmethoxy)-2-[(pyridin-4-ylmethyl)-amino]-benzamide (compound 284),
N-(5-Oxo-4,5-dihydro-1H-[1,2,4]triazol-3-ylmethoxy)-2-
[(pyridin-4-ylmethyl)-amino]-benzamide (compound 285),
N-(3-Phenoxy-propoxy)-2-[(pyridin-4-ylmethyl)-amino]-
benzamide (compound 286),
N-(3-Benzyloxy-propoxy)-2-[(pyridin-4-ylmethyl)-amino]-
benzamide (compound 287),
N-(2-Benzyloxy-ethoxy)-2-[(pyridin-4-ylmethyl)-amino]-
benzamide (compound 288),
N-[2-Hydroxy-3-(4-methoxy-phenoxy)-propoxy]-2-[(pyridin-4-ylmethyl)-amino]-benzamide (compound 289),
N-(3-Benzoylamino-propoxy)-2-[(pyridin-4-ylmethyl)-
amino]-benzamide (compound 290),
N-(4-Benzoylamino-butoxy)-2-[(pyridin-4-ylmethyl)-
amino]-benzamide (compound 291),
N-(2-Methanesulfonylamino-ethoxy)-2-[(pyridin-4-ylm-
ethyl)-amino]-benzamide (compound 292),
N-(4-Benzenesulfonylamino-butoxy)-2-[(pyridin-4-ylm-
ethyl)-amino]-benzamide (compound 293),
N-(3-Benzenesulfonylamino-propoxy)-2-[(pyridin-4-ylm-
ethyl)-amino]-benzamide (compound 294),
N-[2-(4-Cyano-benzenesulfonylamino)-ethoxy]-2-[(pyridin-4-ylmethyl)-amino]-benzamide (compound 295),
N-[3-(4-Cyano-benzenesulfonylamino)-propoxy]-2-[(pyridin-4-ylmethyl)-amino]-benzamide (compound 296),
N-(3-Phenylmethanesulfonylamino-propoxy)-2-[(pyridin-
4-ylmethyl)-amino]-benzamide (compound 297),
N-(2-Phenylmethanesulfonylamino-ethoxy)-2-[(pyridin-4-
ylmethyl)-amino]-benzamide (compound 298),
N-[3-(2-Acetylamino-4-methyl-thiazole-5-sulfonylamino)-
propoxy]-2-[(pyridin-4-ylmethyl)-amino]-benzamide
(compound 299),
N-[2-(2-Acetylamino-4-methyl-thiazole-5-sulfonylamino)-
ethoxy]-2-[(pyridin-4-ylmethyl)-amino]-benzamide
(compound 300),
N-(2-Benzylamino-ethoxy)-2-[(pyridin-4-ylmethyl)-
amino]-benzamide (compound 301),
N-(4-Benzylamino-butoxy)-2-[(pyridin-4-ylmethyl)-
amino]-benzamide (compound 302),
(2-{2-[(Pyridin-4-ylmethyl)-amino]-benzoylaminooxy}-
ethyl)-carbamic acid tert-butyl ester (compound 303),
(3-{2-[(Pyridin-4-ylmethyl)-amino]-benzoylaminooxy}-
propyl)-carbamic acid tert-butyl ester (compound 304),
(4-{2-[(Pyridin-4-ylmethyl)-amino]-benzoylaminooxy}-butyl)-carbamic acid tert-butyl ester (compound 305),
N-[2-(3-Phenyl-thioureido)-ethoxy]-2-[(pyridin-4-ylm-
ethyl)-amino]-benzamide (compound 306),
N-[4-(3-Phenyl-thioureido)-butoxy]-2-[(pyridin-4-ylm-
ethyl)-amino]-benzamide (compound 307),
N-[2-(3-Phenyl-ureido)-ethoxy]-2-[(pyridin-4-ylmethyl)-
amino]-benzamide (compound 308),
N-[3-(3-Phenyl-ureido)-propoxy]-2-[(pyridin-4-ylmethyl)-
amino]-benzamide (compound 309),
N-[4-(3-Phenyl-ureido)-butoxy]-2-[(pyridin-4-ylmethyl)-
amino]-benzamide (compound 310),
N-(2-Amino-ethoxy)-2-[(pyridin-4-ylmethyl)-amino]-ben-
zamide (compound 311),
N-(3-Amino-propoxy)-2-[(pyridin-4-ylmethyl)-amino]-
benzamide (compound 312),
N-(4-Amino-butoxy)-2-[(pyridin-4-ylmethyl)-amino]-ben-
zamide (compound 313),
N-(2-Morpholin-4-yl-2-oxo-ethoxy)-2-[(pyridin-4-ylm-
ethyl)-amino]-benzamide (compound 314),
N-[(2-Methoxy-phenylcarbamoyl)-methoxy]-2-[(pyridin-4-
ylmethyl)-amino]-benzamide (compound 315),
N-tert-Butoxy-2-[(pyridin-4-ylmethyl)-amino]-benzamide
(compound 316),
N-Isobutoxy-2-[(pyridin-4-ylmethyl)-amino]-benzamide
(compound 317),
N-(2-Methyl-allyloxy)-2-[(pyridin-4-ylmethyl)-amino]-
benzamide (compound 318),
N-(3-Methyl-but-2-enyloxy)-2-[(pyridin-4-ylmethyl)-
amino]-benzamide (compound 319),
N-(4-Hydroxy-pent-2-enyloxy)-2-[(pyridin-4-ylmethyl)-
amino]-benzamide (compound 320),
N-Cyclopentyloxy-2-[(pyridin-4-ylmethyl)-amino]-benza-
mide (compound 321),
N-Cyclooctyloxy-2-[(pyridin-4-ylmethyl)-amino]-benza-
mide (compound 322),
N-(2-Cyclohexyl-ethoxy)-2-[(pyridin-4-ylmethyl)-amino]-
benzamide (compound 323),
N-(2-Methyl-cyclohexylmethoxy)-2-[(pyridin-4-ylmethyl)-
amino]-benzamide (compound 324),
N-(4-Methyl-cyclohexylmethoxy)-2-[(pyridin-4-ylmethyl)-
amino]-benzamide (compound 325),
N-(4-Methoxy-cyclohexylmethoxy)-2-[(pyridin-4-ylm-
ethyl)-amino]-benzamide (compound 326),
N-(3-Methyl-bicyclo[2.2.1]hept-2-ylmethoxy)-2-[(pyridin-
4-ylmethyl)-amino]-benzamide (compound 327),
N-(Bicyclo[2.2.1]hept-5-en-2-ylmethoxy)-2-[(pyridin-4-yl-
methyl)-amino]-benzamide (compound 328),
Benzyl-(2-{2-[(pyridin-4-ylmethyl)-amino]-benzoylami-
nooxymethyl}-cyclohexyl)carbamic acid tert-butyl ester
(compound 329),
N-(2-Benzylamino-cyclohexylmethoxy)-2-[(pyridin-4-ylm-
ethyl)-amino]-benzamide (compound 330),
N-(3-Propyl-4,5-dihydro-isoxazol-5-ylmethoxy)-2-[(pyri-
din-4-ylmethyl)-amino]-benzamide (compound 331),
N-(3-Pentyl-4,5-dihydro-isoxazol-5-ylmethoxy)-2-[(pyri-
din-4-ylmethyl)-amino]-benzamide (compound 332),
4-Methyl-N-(2-methyl-thiazol-4-ylmethoxy)-2-[(pyridin-4-
ylmethyl)-amino]-benzamide (compound 333),
N-(5-Cyano-2-methoxy-benzyloxy)-2-[(pyridin-4-ylm-
ethyl)-amino]-nicotinamide (compound 334),
2-Benzylamino-N-benzyloxy-nicotinamide (compound
335),
2-Benzylamino-N-(4-methoxy-benzyloxy)-nicotinamide
(compound 336),
N-Benzyloxy-2-(2-chloro-benzylamino)-nicotinamide
(compound 337),
2-(2-Chloro-benzylamino)-N-(4-methoxy-benzyloxy)-nico-
tinamide (compound 338),
N-Benzyloxy-2-(2,4-dichloro-benzylamino)-nicotinamide
(compound 339),
2-(3,5-Dichloro-benzylamino)-N-(4-methoxy-benzyloxy)-
nicotinamide (compound 340),
N-Benzyloxy-2-(2-methoxy-benzylamino)-nicotinamide
(compound 341),
2-(2-Methoxy-benzylamino)-N-(4-methoxy-benzyloxy)-
nicotinamide (compound 342),
N-Benzyloxy-2-(2-pyridin-4-yl-ethylamino)-nicotinamide
(compound 343),
N-(2-Bromo-benzyloxy)-2-([1,2,4]triazol-4-ylamino)-nico-
tinamide (compound 344), 4-{[3-(4-Methoxy-benzyloxycarbamoyl)-pyridin-2-ylamino]-methyl}-piperidine-1-carboxylic acid tert-butyl ester (compound 345),
N-Benzyloxy-5-[(2-benzyloxycarbamoyl-phenylamino)-methyl]-2-fluoro-benzamide (compound 346),
N-(2-Bromo-benzyloxy)-2-(3-cyano-4-methoxy-benzylamino)-benzamide (compound 347),
N-(2-Bromo-benzyloxy)-2-(4-methanesulfonyl-benzylamino)-benzamide (compound 348),
2-[4-(Methoxyimino-methyl)-benzylamino]-N-(2-methyl-thiazol-4-ylmethoxy)benzamide (compound 349),
N-(2-Bromo-benzyloxy)-2-[(2,6-dichloro-pyridin-4-ylmethyl)-amino]-benzamide (compound 350),
N-Benzyloxy-2-[(pyridin-3-ylmethyl)-amino]-benzamide (compound 351),
N-(2-Methyl-thiazol-4-ylmethoxy)-2-[(pyridin-3-ylmethyl)-amino]-benzamide (compound 352),
N-(2-Methyl-thiazol-4-ylmethoxy)-2-[(pyridin-2-ylmethyl)-amino]-benzamide (compound 353),
N-Benzyloxy-2-[(pyridin-2-ylmethyl)-amino]-benzamide (compound 354),
N-Benzyloxy-2-[(3-bromo-pyridin-2-ylmethyl)-amino]-benzamide (compound 355),
2-[(3-Bromo-pyridin-2-ylmethyl)-amino]-N-(2-methyl-thiazol-4-ylmethoxy)-benzamide (compound 356),
N-(2,4-Dichloro-benzyloxy)-2-[(2,6-dimethoxy-pyrimidin-4-ylmethyl)-amino]-benzamide (compound 357),
N-Benzyloxy-2-[(1,3,5-trimethyl-1H-pyrazol-4-ylmethyl)-amino]-benzamide (compound 358),
N-(2,4-Dichloro-benzyl)-2-[(1,3,5-trimethyl-1H-pyrazol-4-ylmethyl)-amino]-benzamide (compound 359),
N-Benzyloxy-2-[(1-methyl-1H-imidazol-2-ylmethyl)-amino]-benzamide (compound 360),
2-[(1-Methyl-1H-imidazol-2-ylmethyl)-amino]-N-(2-methyl-thiazol-4-ylmethoxy)benzamide (compound 361),
N-Benzyloxy-2-[(3-methyl-3H-imidazol-4-ylmethyl)-amino]-benzamide (compound 362),
2-[(3-Methyl-3H-imidazol-4-ylmethyl)-amino]-N-(2-methyl-thiazol-4-ylmethoxy)benzamide (compound 363),
N-Benzyloxy-2-[(5-methyl-3H-imidazol-4-ylmethyl)-amino]-benzamide (compound 364),
2-[(5-Methyl-3H-imidazol-4-ylmethyl)-amino]-N-(2-methyl-thiazol-4-ylmethoxy)benzamide (compound 365),
2-[(2-Ethyl-3H-imidazol-4-ylmethyl)-amino]-N-(2-methyl-thiazol-4-ylmethoxy)benzamide (compound 366),
N-Benzyloxy-2-[(2-ethyl-3H-imidazol-4-ylmethyl)-amino]-benzamide (compound 367),
N-(2,5-Dichloro-benzyloxy)-2-[(5-oxo-pyrrolidin-2-ylmethyl)-amino]-benzamide (compound 368),
N-Benzyloxy-2-[(3-ethyl-4,5-dihydro-isoxazol-5-ylmethyl)-amino]-benzamide (compound 369),
N-Benzyloxy-2-[(3-propyl-4,5-dihydro-isoxazol-5-ylmethyl)-amino]-benzamide (compound 370),
5-[(2-Benzyloxycarbamoyl-phenylamino)-methyl]-3-methyl-4,5-dihydro-isoxazole-5-carboxylic acid ethyl ester (compound 371),
5-[(2-Benzyloxycarbamoyl-phenylamino)-methyl]-3-ethyl-4,5-dihydro-isoxazole-5-carboxylic acid ethyl ester (compound 372),
5-[(2-Benzyloxycarbamoyl-phenylamino)-methyl]-3-propyl-4,5-dihydro-isoxazole-5-carboxylic acid ethyl ester (compound 373),
N-(4-Cyano-benzyloxy)-2-[(3-methyl-4,5-dihydro-isoxazol-5-ylmethyl)-amino]-benzamide (compound 374),
N-(4-Cyano-benzyloxy)-2-[(3-ethyl-4,5-dihydro-isoxazol-5-ylmethyl)-amino]-benzamide (compound 375),
N-(4-Cyano-benzyloxy)-2-[(3-propyl-4,5-dihydro-isoxazol-5-ylmethyl)-amino]-benzamide (compound 376),
5-{[2-(4-Cyano-benzyloxycarbamoyl)-phenylamino]-methyl}-3-methyl-4,5-dihydro-isoxazole-5-carboxylic acid ethyl ester (compound 377),
5-{[2-(4-Cyano-benzyloxycarbamoyl)-phenylamino]-methyl}-3-ethyl-4,5-dihydro-isoxazole-5-carboxylic acid ethyl ester (compound 378),
5-{[2-(4-Cyano-benzyloxycarbamoyl)phenylamino]-methyl}-3-propyl-4,5-dihydro-isoxazole-5-carboxylic acid ethyl ester (compound 379),
N-(4-Cyano-benzyloxy)-2-[(3-methyl-isoxazol-5-ylmethyl)-amino]-benzamide (compound 380),
N-(4-Cyano-benzyloxy)-2-[(3-ethyl-isoxazol-5-ylmethyl)-amino]-benzamide (compound 381),
N-(4-Cyano-benzyloxy)-2-[(3-propyl-isoxazol-5-ylmethyl)-amino]-benzamide (compound 382),
N-(4-Cyano-benzyloxy)-2-[(3,5-dimethyl-4,5-dihydro-isoxazol-5-ylmethyl)-amino]-benzamide (compound 383),
N-(4-Cyano-benzyloxy)-2-[(3-ethyl-5-methyl-4,5-dihydro-isoxazol-5-ylmethyl)-amino]-benzamide (compound 384),
N-(4-Cyano-benzyloxy)-2-[(5-methyl-3-propyl-4,5-dihydro-isoxazol-5-ylmethyl)amino]-benzamide (compound 385),
N-Benzyloxy-2-[(3-methyl-4,5-dihydro-isoxazol-5-ylmethyl)-amino]-benzamide (compound 386),
N-(4-Cyano-benzyloxy)-2-[2-(3-methyl-4,5-dihydro-isoxazol-5-yl)-ethylamino]-benzamide (compound 387),
N-Cyclopentylmethoxy-2-[2-(3-methyl-4,5-dihydro-isoxazol-5-yl)-ethylamino]-benzamide (compound 388),
N-(4-Cyano-benzyloxy)-2-[2-(3-ethyl-4,5-dihydro-isoxazol-5-yl)-ethylamino]-benzamide (compound 389),
N-Cyclopentylmethoxy-2-[2-(3-ethyl-4,5-dihydro-isoxazol-5-yl)-ethylamino]-benzamide (compound 390),
N-(4-Cyano-benzyloxy)-2-[2-(3-propyl-4,5-dihydro-isoxazol-5-yl)-ethylamino]-benzamide (compound 391),
N-Cyclopentylmethoxy-2-[2-(3-propyl-4,5-dihydro-isoxazol-5-yl)-ethylamino]-benzamide (compound 392),
N-Benzyloxy-2-[2-(2,4-dioxo-imidazolidin-1-yl)-ethylamino]-benzamide (compound 393),
N-Benzyloxy-2-[(6-chloro-imidazo[2,1-b]thiazol-5-ylmethyl)-amino]-benzamide (compound 395),
N-Benzyloxy-2-[(2-methyl-imidazo[1,2-a]pyrimidin-3-ylmethyl)-amino]-benzamide (compound 396),
N-Benzyloxy-2-(2-benzyloxy-ethylamino)-benzamide (compound 397),
N-(2-Benzyloxycarbamoyl-phenyl)-isonicotinamide (compound 398),
N-Benzyloxy-2-(2-pyridin-4-yl-acetylamino)-benzamide (compound 399),
N-Benzyloxy-N-methyl-2-[(pyridin-4-ylmethyl)-amino]-benzamide (compound 400),
N-(5-Oxo-pyrrolidin-2-ylmethoxy)-2-[(pyridin-4-ylmethyl)-amino]-benzamide (compound 402),
4-{2-[(Pyridin-4-ylmethyl)-amino]-benzoylaminooxymethyl}-piperidine-1-carboxylic acid tert-butyl ester (compound 403),
N-Cyclopentylmethoxy-2-{[6-(cyclopropanecarbonyl-amino)-pyridin-3-ylmethyl]-amino}-benzamide (compound 404),
N-Cyclopentylmethoxy-2-[(6-pyrrolidin-1-yl-pyridin-3-ylmethyl)-amino]-benzamide (compound 405),
2-[(6-Amino-pyridin-3-ylmethyl)-amino]-N-(4-cyano-benzyloxy)-benzamide (compound 406),
N-(4-Cyano-benzyloxy)-2-[(6-pyrrolidin-1-yl-pyridin-3-ylmethyl)-amino]-benzamide (compound 407), N-Cyclopentylmethoxy-2-{[2-(cyclopropanecarbonyl-amino)-4-methyl-thiazol-5-ylmethyl]-amino}-benzamide (compound 408),
2-[(6-Amino-pyridin-3-ylmethyl)-amino]-N-cyclopentylmethoxy-benzamide (compound 409),
N-[3-(2,2-Dibromo-vinyl)-cyclopentylmethoxy]-2-[(pyridin-4-ylmethyl)-amino]-benzamide (compound 410),
N-(3-Hydroxymethyl-cyclopentylmethoxy)-2-[(pyridin-4-ylmethyl)-amino]-benzamide (compound 411),
N-(2-Hydroxymethyl-cyclohexylmethoxy)-2-[(pyridin-4-ylmethyl)-amino]-benzamide (compound 412),
N-[4-(4-Methyl-piperazin-1-ylmethyl)-benzyloxy]-2-[(pyridin-4-ylmethyl)-amino]-benzamide (compound 413),
N-{4-[4-(2-Hydroxy-ethyl)-piperazin-1-ylmethyl]-benzyloxy}-2-[(pyridin-4-ylmethyl)amino]-benzamide (compound 414),
N-(4-Cyano-benzyloxy)-2-{[2-(3-isopropyl-ureido)-pyridin-4-ylmethyl]-amino}-benzamide (compound 415),
N-(4-Cyano-benzyloxy)-2-{[2-(3-ethyl-ureido)-pyridin-4-ylmethyl]-amino}-benzamide (compound 416),
N-Cyclopentylmethoxy-2-{[2-(3-isopropyl-ureido)-pyridin-4-ylmethyl]-amino}-benzamide (compound 417),
N-Cyclopentylmethoxy-2-{[2-(3-propyl-ureido)-pyridin-4-ylmethyl]-amino}-benzamide (compound 418),
N-Cyclopentylmethoxy-2-{[2-(3-ethyl-ureido)-pyridin-4-ylmethyl]-amino}-benzamide (compound 419),
N-(3-Hydroxy-cyclopentylmethoxy)-2-[(pyridin-4-ylmethyl)-amino]-benzamide (compound 420),
N-Cyclopentylmethoxy-2-{[2-(3-methyl-thioureido)-pyridin-4-ylmethyl]-amino}-benzamide (compound 421),
2-{[2-(3-tert-Butyl-ureido)-pyridin-4-ylmethyl]-amino}-N-cyclopentylmethoxy-benzamide (compound 422),
N-(4-Cyano-benzyloxy)-2-{[2-(3-cyclohexyl-ureido)-pyridin-4-ylmethyl]-amino}-benzamide (compound 423),
2-{[2-(3-Cyclohexyl-ureido)-pyridin-4-ylmethyl]-amino}-N-cyclopentylmethoxy-benzamide (compound 424),
N-{4-[(2-Cyclopentylmethoxycarbamoyl-phenylamino)-methyl]-pyridin-2-yl}-isonicotinamide (compound 425),
1-(2,2,2-Trifluoro-acetyl)-pyrrolidine-2-carboxylic acid {4-[(2-cyclopentylmethoxycarbamoyl-phenylamino)-methyl]-pyridin-2-yl}-amide (compound 426),
1-(2,2,2-Trifluoro-acetyl)-pyrrolidine-2-carboxylic acid (4-{[2-(4-cyano-benzyloxycarbamoyl)-phenylamino]-methyl}-pyridin-2-yl)-amide (compound 427),
1-Acetyl-piperidine-4-carboxylic acid {4-[(2-cyclopentylmethoxycarbamoyl-phenylamino)-methyl]-pyridin-2-yl}-amide (compound 428),
1-Acetyl-piperidine-4-carboxylic acid (4-{[2-(4-cyano-benzyloxycarbamoyl)phenylamino]-methyl}-pyridin-2-yl)-amide (compound 429),
N-Cyclopentylmethoxy-2-[(2,4-dihydroxy-pyrimidin-5-ylmethyl)-amino]-benzamide (compound 430),
Pyrrolidine-2-carboxylic acid (4-{[2-(4-cyano-benzyloxycarbamoyl)-phenylamino]-methyl}-pyridin-2-yl)-amide (compound 431),
Pyrrolidine-2-carboxylic acid {4-[(2-cyclopentylmethoxycarbamoyl-phenylamino)methyl]-pyridin-2-yl}-amide (compound 432), and
2-[(Pyridin-4-ylmethyl)-amino]-N-(4-vinylbenzyloxy)benzamide (compound 433).

The compounds of formula I may be obtained in crystalline form either directly by concentration from an organic solvent or by crystallisation or recrystallisation from an organic solvent or mixture of said solvent and a cosolvent that may be organic or inorganic, such as water. The crystals may be isolated in essentially solvent-free form or as a solvate, such as a hydrate. The invention covers all crystalline modifications and forms and also mixtures thereof.

Compounds of formula I may comprise asymmetrically substituted (chiral) carbon atoms and carbon-carbon double bonds which may give rise to the existence of isomeric forms, e.g. enantiomers, diastereomers and geometric isomers. The present invention relates to all such isomers, either in pure form or as mixtures thereof. The invention also relates to all possible tautomers of the compounds of formula I.

Compounds useful as intermediates for the synthesis of compounds according to formula I, may in particular be selected amongst the list consisting of
O-(3,4,5-Trimethoxy-benzyl)-hydroxylamine (preparation 8),
O-(4-Chloro-benzyl)-hydroxylamine (preparation 9),
4-Aminooxymethyl-benzonitrile (preparation 10),
O-Quinolin-2-ylmethyl-hydroxylamine (preparation 11),
O-(2-Methyl-thiazol-4-ylmethyl)-hydroxylamine (preparation 12),
O-(4-Fluoro-2,6-dimethyl-benzyl)-hydroxylamine (preparation 13),
O-(4-Fluoro-2-methoxy-benzyl)-hydroxylamine (preparation 14),
O-(2,3-Difluoro-4-methyl-benzyl)-hydroxylamine (preparation 15),
O-(3-Fluoro-4-methyl-benzyl)-hydroxylamine (preparation 16),
O-(5-Fluoro-2-methyl-benzyl)-hydroxylamine (preparation 17),
O-(2,3,5,6-Tetrafluoro-4-methoxy-benzyl)-hydroxylamine (preparation 18),
O-(4-Bromo-benzyl)-hydroxylamine (preparation 19),
O-(2-Iodo-benzyl)-hydroxylamine (preparation 20),
O-(3-Iodo-benzyl)-hydroxylamine (preparation 21),
(2-Aminooxymethyl-phenyl)-acetonitrile (preparation 22),
O-(2-Benzenesulfonylmethyl-benzyl)-hydroxylamine (preparation 23),
(4-Aminooxymethyl-phenyl)-methanol (preparation 24),
O-(4-Fluoro-2-trifluoromethyl-benzyl)-hydroxylamine (preparation 25),
O-(2-Fluoro-6-trifluoromethyl-benzyl)-hydroxylamine (preparation 26),
O-(4-Fluoro-3-trifluoromethyl-benzyl)-hydroxylamine (preparation 27),
O-(4-Methyl-3-trifluoromethyl-benzyl)-hydroxylamine (preparation 28),
O-(4-Methoxy-3-trifluoromethyl-benzyl)-hydroxylamine (preparation 29),
O-(2-Methoxy-benzyl)-hydroxylamine (preparation 30),
O-(4-Pentyloxy-benzyl)-hydroxylamine (preparation 31),
O-(2-Trifluoromethoxy-benzyl)-hydroxylamine (preparation 32),
O-(3-Trifluoromethoxy-benzyl)-hydroxylamine (preparation 33),
O-(4-Trifluoromethoxy-benzyl)-hydroxylamine (preparation 34),
O-(2-Difluoromethoxy-benzyl)-hydroxylamine (preparation 35),
O-(2-Trifluoromethylsulfanyl-benzyl)-hydroxylamine (preparation 36),
O-(6-Chloro-benzo[1,3]dioxol-5-ylmethyl)-hydroxylamine (preparation 37),
O-Benzo[1,3]dioxol-5-ylmethyl-hydroxylamine (preparation 38),
O-Indan-5-ylmethyl-hydroxylamine (preparation 39),
3-Aminooxymethyl-benzonitrile (preparation 40),
2-Aminooxymethyl-benzonitrile (preparation 41), 4-Aminooxymethyl-3-fluoro-benzonitrile (preparation 42),
4-Aminooxymethyl-2-bromo-benzonitrile (preparation 43),
4-Aminooxymethyl-3-chloro-benzonitrile (preparation 44),
4-Aminooxymethyl-3-methoxy-benzonitrile (preparation 45),
4-Aminooxymethyl-3-iodo-benzonitrile (preparation 46),
3-Aminooxymethyl-4-bromo-benzonitrile (preparation 47),
4-Aminooxymethyl-naphthalene-1-carbonitrile (preparation 48),
O-(4-Morpholin-4-yl-benzyl)-hydroxylamine (preparation 49),
O-(2-Morpholin-4-yl-benzyl)-hydroxylamine (preparation 50),
O-(2-Amino-benzyl)-hydroxylamine (preparation 51),
3-Aminooxymethyl-benzoic acid methyl ester (preparation 52),
O-Naphthalen-1-ylmethyl-hydroxylamine (preparation 53),
O-(1-Phenyl-ethyl)-hydroxylamine (preparation 54),
O-[1-(2-Trifluoromethyl-phenyl)-ethyl]-hydroxylamine (preparation 55),
O-Pyridin-2-ylmethyl-hydroxylamine (preparation 56),
O-(2,6-Dichloro-pyridin-4-ylmethyl)-hydroxylamine (preparation 57),
O-Thiazol-4-ylmethyl-hydroxylamine (preparation 58),
O-(2-Chloro-thiazol-5-ylmethyl)-hydroxylamine (preparation 59),
O-(2-Phenyl-thiazol-4-ylmethyl)-hydroxylamine (preparation 60),
O-(5-Methyl-isoxazol-3-ylmethyl)-hydroxylamine (preparation 61),
O-(3,5-Dimethyl-isoxazol-4-ylmethyl)-hydroxylamine (preparation 62),
O-(3-Propyl-isoxazol-5-ylmethyl)-hydroxylamine (preparation 63),
O-(5-Chloro-thiophen-2-ylmethyl)-hydroxylamine (preparation 64),
4-(2-Aminooxy-ethyl)-benzonitrile (preparation 65),
O-Cyclopentylmethyl-hydroxylamine (preparation 66),
O-Cyclopropylmethyl-hydroxylamine (preparation 67),
O-(2,2-Dimethyl-propyl)-hydroxylamine (preparation 68),
O-(2-Ethyl-butyl)-hydroxylamine (preparation 69),
O-Isobutyl-hydroxylamine (preparation 70),
O-Cyclobutylmethyl-hydroxylamine (preparation 71),
O-Cyclohexylmethyl-hydroxylamine (preparation 72),
O-Cycloheptylmethyl-hydroxylamine (preparation 73),
O-Cyclooctylmethyl-hydroxylamine (preparation 74),
O-(1-Cyclopentyl-ethyl)-hydroxylamine (preparation 75),
O-Cyclohexyl-hydroxylamine (preparation 76),
O-(2-Cyclopropyl-ethyl)-hydroxylamine (preparation 77),
O-(2-Cyclopentyl-ethyl)-hydroxylamine (preparation 78),
O-(3-Cyclopentyl-propyl)-hydroxylamine (preparation 79),
O-Cyclohex-3-enylmethyl-hydroxylamine (preparation 80),
O-(6-Methyl-cyclohex-3-enylmethyl)-hydroxylamine (preparation 81),
(4-Aminooxymethyl-cyclohexyl)-methanol (preparation 82),
O-(3-Methoxy-cyclohexylmethyl)-hydroxylamine (preparation 83),
O-Adamantan-1-ylmethyl-hydroxylamine (preparation 84),
O-Bicyclo[2.2.1]hept-2-ylmethyl-hydroxylamine (preparation 85),
O-(6,6-Dimethyl-bicyclo[3.1.1]hept-2-ylmethyl)-hydroxylamine (preparation 86),
O-(Tetrahydro-furan-2-ylmethyl)-hydroxylamine (preparation 87),
O-(Tetrahydro-furan-3-ylmethyl)-hydroxylamine (preparation 88),
O-(3-Methyl-4,5-dihydro-isoxazol-5-ylmethyl)-hydroxylamine (preparation 89),
O-(3-Ethyl-4,5-dihydro-isoxazol-5-ylmethyl)-hydroxylamine (preparation 90),
O-(3-Butyl-4,5-dihydro-isoxazol-5-ylmethyl)-hydroxylamine (preparation 91),
O-(Tetrahydro-pyran-4-ylmethyl)-hydroxylamine (preparation 92),
O-(Tetrahydro-pyran-2-ylmethyl)-hydroxylamine (preparation 93),
O-(3-Iodo-4-methyl-benzyl)-hydroxylamine (preparation 94),
O-(4-Ethyl-benzyl)-hydroxylamine (preparation 95),
O-(4-Isopropyl-benzyl)-hydroxylamine (preparation 96),
O-(4-tert-Butyl-benzyl)-hydroxylamine (preparation 97),
O-(2-Ethyl-benzyl)-hydroxylamine (preparation 98),
O-(2-Non-1-enyl-benzyl)-hydroxylamine (preparation 99),
O-(4-Phenylaminomethyl-benzyl)-hydroxylamine (preparation 100),
O-(4-Diethylaminomethyl-benzyl)-hydroxylamine (preparation 101),
2-(2-Aminooxymethyl-phenyl)-acetamide (preparation 102),
4-Aminooxymethyl-3-(2-methoxy-ethoxy)-benzonitrile (preparation 103),
(4-Aminooxymethyl-3-methoxy-phenyl)-acetonitrile (preparation 104),
3-Aminooxymethyl-4-methoxy-benzonitrile (preparation 105),
(2-Aminooxymethyl-phenyl)-carbamic acid tert-butyl ester (preparation 106),
N-(2-Aminooxymethyl-phenyl)-acetamide (preparation 107),
N-(2-Aminooxymethyl-phenyl)-benzamide (preparation 108),
N-(2-Aminooxymethyl-phenyl)-methanesulfonamide (preparation 109),
N-(2-Aminooxymethyl-phenyl)-acetamide (preparation 110),
O-Biphenyl-4-ylmethyl-hydroxylamine (preparation 111),
O-Biphenyl-2-ylmethyl-hydroxylamine (preparation 112),
O-(3'-Methoxy-biphenyl-2-ylmethyl)-hydroxylamine (preparation 113),
O-(2'-Methoxy-biphenyl-2-ylmethyl)-hydroxylamine (preparation 114),
(2'-Aminooxymethyl-biphenyl-3-yl)-methanol (preparation 115),
O-(3-Phenoxy-benzyl)-hydroxylamine (preparation 116),
O-Anthracen-9-ylmethyl-hydroxylamine (preparation 117),
O-[4-(2-Methyl-thiazol-4-yl)-benzyl]-hydroxylamine (preparation 118),
N-(2-Aminooxy-2-phenyl-ethyl)-methanesulfonamide (preparation 119),
O-[2-(4-Trifluoromethyl-phenyl)-thiazol-4-ylmethyl]-hydroxylamine (preparation 120),
O-(3-p-Tolyl-isoxazol-5-ylmethyl)-hydroxylamine (preparation 121),
O-(3-Methyl-isoxazol-5-ylmethyl)-hydroxylamine (preparation 122),
O-(3-Ethyl-isoxazol-5-ylmethyl)-hydroxylamine (preparation 123),
O-(3-Butyl-isoxazol-5-ylmethyl)-hydroxylamine (preparation 124),
O-(3-Pentyl-isoxazol-5-ylmethyl)-hydroxylamine (preparation 125),
O-[5-(3-Trifluoromethyl-phenyl)-[1,2,4]oxadiazol-3-ylmethyl]-hydroxylamine (preparation 126), O-(1-Benzyl-1H-[1,2,3]triazol-4-ylmethyl)-hydroxylamine (preparation 127),
O-(1-Cyclopentyl-1H-[1,2,3]triazol-4-ylmethyl)-hydroxylamine (preparation 128),
5-Aminooxymethyl-2,4-dihydro-[1,2,4]triazol-3-one (preparation 129),
O-(3-Phenoxy-propyl)-hydroxylamine (preparation 130),
O-(3-Benzyloxy-propyl)-hydroxylamine (preparation 131),
O-(2-Benzyloxy-ethyl)-hydroxylamine (preparation 132),
N-(3-Aminooxy-propyl)-benzamide (preparation 133),
N-(4-Aminooxy-butyl)-benzamide (preparation 134),
N-(2-Aminooxy-ethyl)-methanesulfonamide (preparation 135),
N-(4-Aminooxy-butyl)-benzenesulfonamide (preparation 136),
N-(3-Aminooxy-propyl)-benzenesulfonamide (preparation 137),
N-(2-Aminooxy-ethyl)-4-cyano-benzenesulfonamide (preparation 138),
N-(3-Aminooxy-propyl)-4-cyano-benzenesulfonamide (preparation 139),
N-(3-Aminooxy-propyl)-C-phenyl-methanesulfonamide (preparation 140),
N-(2-Aminooxy-ethyl)-C-phenyl-methanesulfonamide (preparation 141),
N-[5-(3-Aminooxy-propylsulfamoyl)-4-methyl-thiazol-2-yl]-acetamide (preparation 142),
N-[5-(2-Aminooxy-ethylsulfamoyl)-4-methyl-thiazol-2-yl]-acetamide (preparation 143),
O-(2-Benzylamino-ethyl)-hydroxylamine (preparation 144),
O-(4-Benzylamino-butyl)-hydroxylamine (preparation 145),
(2-Aminooxy-ethyl)-carbamic acid tert-butyl ester (preparation 146),
(3-Aminooxy-propyl)-carbamic acid tert-butyl ester (preparation 147),
(4-Aminooxy-butyl)-carbamic acid tert-butyl ester (preparation 148),
O-Isobutyl-hydroxylamine (preparation 149),
O-(2-Methyl-allyl)-hydroxylamine (preparation 150),
5-Aminooxy-pent-3-en-2-ol (preparation 151),
O-Cyclopentyl-hydroxylamine (preparation 152),
O-Cyclooctyl-hydroxylamine (preparation 153),
O-(2-Cyclohexyl-ethyl)-hydroxylamine (preparation 154),
O-(2-Methyl-cyclohexylmethyl)-hydroxylamine (preparation 155),
O-(4-Methyl-cyclohexylmethyl)-hydroxylamine (preparation 156),
O-(4-Methoxy-cyclohexylmethyl)-hydroxylamine (preparation 157),
O-(3-Methyl-bicyclo[2.2.1]hept-2-ylmethyl)-hydroxylamine (preparation 158),
O-Bicyclo[2.2.1]hept-5-en-2-ylmethyl-hydroxylamine (preparation 159),
(2-Aminooxymethyl-cyclohexyl)-benzyl-carbamic acid tert-butyl ester (preparation 160),
O-(3-Propyl-4,5-dihydro-isoxazol-5-ylmethyl)-hydroxylamine (preparation 161),
O-(3-Pentyl-4,5-dihydro-isoxazol-5-ylmethyl)-hydroxylamine (preparation 162),
5-Aminooxymethyl-pyrrolidin-2-one (preparation 163),
4-Aminooxymethyl-piperidine-1-carboxylic acid tert-butyl ester (preparation 164),
O-[3-(2,2-Dibromo-vinyl)-cyclopentylmethyl]-hydroxylamine (preparation 165),
(3-Aminooxymethyl-cyclopentyl)-methanol (preparation 166),
(2-Aminooxymethyl-cyclohexyl)-methanol (preparation 167),
O-[4-(4-Methyl-piperazin-1-ylmethyl)-benzyl]-hydroxylamine (preparation 168),
2-[4-(4-Aminooxymethyl-benzyl)-piperazin-1-yl]-ethanol (preparation 169), and
3-Aminooxymethyl-cyclopentanol (preparation 170);
and salts with hydrochloric acid, hydrobromic acid, or sulphuric acids thereof.

Yet other compounds useful as intermediates for the synthesis of compounds according to formula I, may in particular be selected amongst the list consisting of
4-Fluoro-2-[(pyridin-4-ylmethyl)-amino]-benzoic acid (preparation 1A),
2-Fluoro-6-[(pyridin-4-ylmethyl)-amino]-benzoic acid (preparation 1B),
5-Fluoro-2-[(pyridin-4-ylmethyl)-amino]-benzoic acid (preparation 1C),
3-Methoxy-2-[(pyridin-4-ylmethyl)-amino]-benzoic acid (preparation 1D),
4,5-Dimethoxy-2-[(pyridin-4-ylmethyl)-amino]-benzoic acid (preparation 1E),
2-Methyl-6-[(pyridin-4-ylmethyl)-amino]-benzoic acid (preparation 1F),
5-Methyl-2-[(pyridin-4-ylmethyl)-amino]-benzoic acid (preparation 1G),
5-Bromo-2-[(pyridin-4-ylmethyl)-amino]-benzoic acid (preparation 1H),
3-[(Pyridin-4-ylmethyl)-amino]-isonicotinic acid (preparation 1I),
2-(4-Fluoro-benzylamino)-benzoic acid (preparation 1J),
2-(3-Cyano-4-fluoro-benzylamino)-benzoic acid (preparation 1K),
5-[(2-Carboxy-phenylamino)-methyl]-2-fluoro-benzoic acid methyl ester (preparation 1L),
2-(4-Methoxy-benzylamino)-benzoic acid (preparation 1M),
2-[(4-Methoxy-naphthalen-1-ylmethyl)-amino]-benzoic acid (preparation 1N),
2-[(2,3-Dihydro-benzofuran-5-ylmethyl)-amino]-benzoic acid (preparation 1O),
2-[(Benzofuran-5-ylmethyl)-amino]-benzoic acid (preparation 1P),
2-[(2-Oxo-2H-chromen-6-ylmethyl)-amino]-benzoic acid (preparation 1Q),
2-[(3,5-Dichloro-pyridin-4-ylmethyl)-amino]-benzoic acid (preparation 1R),
2-[(2-Bromo-pyridin-4-ylmethyl)-amino]-benzoic acid (preparation 1S),
2-[(2-Hydroxy-pyridin-4-ylmethyl)-amino]-benzoic acid (preparation 1T),
2-[(2-Morpholin-4-yl-pyridin-4-ylmethyl)-amino]-benzoic acid (preparation 1U),
2-[(Quinolin-4-ylmethyl)-amino]-benzoic acid (preparation 1V),
2-[(6-Methoxy-pyridin-3-ylmethyl)-amino]-benzoic acid (preparation 1W),
2-[(Thiazol-5-ylmethyl)-amino]-benzoic acid (preparation 1X),
2-[(Tetrahydro-pyran-4-ylmethyl)-amino]-benzoic acid (preparation 1Y),
2-[(pyridin-4-ylmethyl)-amino]-nicotinic acid (preparation 2),
2-(4-Fluoro-benzylamino)-nicotinic acid (preparation 3),
2-(4-Chloro-benzylamino)-nicotinic acid (preparation 3A),
2-(Isoquinolin-5-ylamino)-nicotinic acid (preparation 3B),
2-(4-Methoxy-benzylamino)-nicotinic acid (preparation 4), 2-[(Pyridin-4-ylmethyl-amino]-nicotinonitrile (preparation 5),
2-(4-Fluoro-benzylamino)-nicotinonitrile (preparation 6),
2-(4-Methoxy-benzylamino)-nicotinonitrile (preparation 7),
2-(isoquinolin-5-ylamino)-nicotinonitrile (preparation 3B),
1-Pyridin-4-ylmethyl-1H-benzo[d][1,3]oxazine-2,4-dione (preparation 7A),
1-(2-Amino-pyridin-4-ylmethyl)-1H-benzo[d][1,3]oxazine-2,4-dione (preparation 7B),
2-[(Pyridin-4-ylmethyl)-amino]-benzoic acid pentafluorophenyl ester (preparation 7C),
4-(2,4-Dioxo-4H-benzo[d][1,3]oxazin-1-ylmethyl)-benzonitrile (preparation 7D),
1-(5-Oxo-4,5-dihydro-1H-[1,2,4]triazol-3-ylmethyl)-1H-benzo[d][1,3]oxazine-2,4-dione (preparation 7E),
1-(2-Imidazol-1-yl-ethyl)-1H-benzo[d][1,3]oxazine-2,4-dione (preparation 7F),
1-(1-Pyridin-4-yl-ethyl)-1H-benzo[d][1,3]oxazine-2,4-dione (preparation 7G),
1-(6-Oxo-1,6-dihydro-pyridin-3-ylmethyl)-1H-benzo[d][1,3]oxazine-2,4-dione (preparation 7H), and
1-(6-Oxo-1,6-dihydro-pyridin-3-ylmethyl)-1H-pyrido[2,3-d][1,3]oxazine-2,4-dione (preparation 7I).

Formation of new blood vessels takes place in a balance between factors working for and against this formation, i.e. in a balance between pro-angiogenic and anti-angiogenic compounds. Early in development, proliferating and differentiating endothelial cells form vessels in previously avascular tissue. This first stage is a leaky network which has to be remodelled to reach a mature vessel. This process is referred to as vasculogenesis. Formation of a new blood vessel may also occur from an already existing blood vessel in a process referred to as angiogenic sprouting. Here, the "old" vessel is initially destabilised at a located site, and the new vessel is formed from there and is subsequently matured.

The processes above commonly involve the vascular endothelial, which is a particular type of endothelium composed by a single layer of smooth cells that cover the lumen of blood vessels. A number of specific growth factors acting on said endothelial have been identified, and they include five members of the vascular endothelial growth factor (VEGF) family, four members of the angiopoietin family, and one member of the large ephrin family. VEGF, however, holds the position as the most critical driver of vascular formation as it is required to initiate the formation of immature vessels both by vasculogenesis and angiogenic sprouting [Yancopoulos, Nature, 407, 242-248, 2000]. VEGF, originally termed "Vascular Permeability Factor" (VPF) is the angiogenic factor which lies at the centre of the network regulating the growth and differentiation of the vascular system and its components during embryonic development, normal growth and in a wide number of pathological anomalies along with its cellular receptors [G. Breier et al., Trends in Cell Biology 6, 454-6, 1996].

VEGF is a dimeric, disulfide-linked 46-kDa glycoprotein related to "Platelet-Derived Growth Factor" (PDGF); it is produced by normal cell lines and tumour cell lines; it is an endothelial cell-specific mitogen; shows angiogenic activity in in vivo test systems (e.g. rabbit cornea); is chemotactic for endothelial cells and monocytes; and induces plasminogen activators in endothelial cells, which are involved in the proteolytic degradation of extracellular matrix during the formation of capillaries. A number of isoforms of VEGF are known, which show comparable biological activity, but differ in the type of cells that secrete them and in their heparin-binding capacity. In addition, there are other members of the VEGF family, such as "Placenta Growth Factor" (PlGF) and VEGF-C.

VEGF's are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF-mediated responses, Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features. As such, regulators of angiogenesis have become an important therapeutic agent.

Three VEGF receptors are known, VEGFR-1 (or fms-like tyrosine kinase receptor (Flt-1)), VEGFR-2 and VEGFR-3, and they are expressed almost exclusive on endothelial cells. VEGFR-2 was previously referred to as KDR (kinase insert domain-containing receptor), and this receptor appears to play a crucial role in the induction of cell proliferation by VEGF [Ellis, Seminars in Oncology, 28, 94-104, 2001]. The VEGF receptors belong to the group of tyrosine kinease receptors, and they are composed of seven extracellular Ig-like domains, harbouring the VEGF binding site, and an intracellular tyrosine kinase domain. The intra- and extracellular domains are connected by a short transmembrane segment [Shawver, DDT, 2, 50-63, 1997]. Like other receptor tyrosine kinases, VEGFR-2 dimerise upon binding to VEGF, and the tyrosine kinase domain becomes autophosphorylated. This activated form, in turn, binds to other molecules which are activated, e.g. by yet another phosphorylation. This cascade eventually triggers the proliferation of endothelial cells, and thus the formation of new blood vessels.

Tumour cells require oxygen to grow and to metastasize. Oxygen has a very limited diffusion range, so for the tumour to grow beyond a very limited size, they cannot rely on passive oxygen transport, but rather they have to establish an active oxygen transport, i.e. they have to attract blood vessels from the host. Nutrients, required by the tumour, are also supplied through the blood vessels. A tumour will start in or eventually expand into an avascular area resulting in low $pO_2$ and pH, and these factors trigger an upregulation of, e.g. VEGF in the tumour cells. Without sufficient oxygen and nutrient supply, the tumour cells become necrotic or apoptotic, and the tumour will thus cease to grow, and may even regress. Angiogenesis is regarded as an absolute prerequisite for tumours which grow beyond a diameter of about 1-2-mm; up to this limit, oxygen and nutrients may be supplied to the tumour cells by diffusion. Every tumour, regardless of its origin and its cause, is thus dependent on angiogenesis for its growth after it has reached a certain size. A large number of human tumours, especially gliomas and carcinomas, express high levels of VEGF. This has led to the hypothesis that the VEGF released by tumor cells stimulates the growth of blood capillaries and the proliferation of tumour endothelium in a paracrine manner and through improved blood supply, accelerate tumour growth. Increased VEGF expression could explain the occurrence of cerebral edema in patients with glioma. Direct evidence of the role of VEGF as a tumour angiogenesis factor in vivo is shown in studies in which VEGF expression or VEGF activity was inhibited. This was achieved with anti-VEGF antibodies, with dominant-negative VEGFR-2 mutants which inhibited signal transduction, and with antisense-VEGF RNA techniques. All approaches led to a reduction in the growth of glioma cell lines or other tumour cell lines in vivo as a result of inhibited tumour angiogenesis. Already in 1971 Folkman suggested that inhibition of angiogenesis could be a strategy for treating cancers which are manifested by solid tumours [Folkman, in Cancer Medicine, (Eds Holland et al), 132-152, Decker Ontario, Canada, 2000]. This notion was based on even earlier observations that angiogenesis occurs around tumours, and on hypotheses that an "angiogenic" principle was produced by the tumours.

Three principal mechanisms play an important part in the activity of angiogenesis inhibitors against tumours: 1) inhibition of the growth of vessels, especially capillaries, into vascular resting tumours, with the result that there is no net tumour growth owing to the balance that is achieved between apoptosis and proliferation; 2) prevention of the migration of tumour cells owing to the absence of blood flow to and from tumours; and 3) inhibition of endothelial cell proliferation, thus avoiding the paracrine growth-stimulating effect exerted on the surrounding tissue by the endothelial cells which normally line the vessels [R. Connell et al., Exp. Opin. Ther. Patents, 11, 77-114, 2001]. As mentioned above, the compounds of the present invention inhibit VEGFR-2 (KDR), and therefore prevent angiogenesis, i.e. the formation of new blood vessels, and they will thus cause the tumour to cease growing and perhaps even to regress.

Compounds of the invention would be useful for the prophylaxis, treatment or amelioration of a disease or condition associated with deregulated angiogenesis, such as the prophylaxis, treatment or amelioration of tumours or neoplastic diseases including cancer and metastasis, including, but not limited to: carcinoma such as cancer of the bladder, urinary tract, breast, intestine, colon, kidney, liver, small or non-small cell lung carcinoma, esophagus, gall-bladder, ovary, pancreas, stomach, cervix, thyroid, prostate, head, brain, neck, uterus, and skin (including squamous cell carcinoma); hematopoietic tumours of lymphoid lineage (including leukaemia, acute lymphocitic leukaemia, acute lymphoblastic leukaemia, B-cell lymphoma, T-cell-lymphoma, Hodgkin's disease lymphoma, non-Hodgkin's lymphoma, hairy cell lymphoma and Burkett's lymphoma); hematopoietic tumours of myeloid lineage (including acute and chronic myelogenous leukemias, myelodysplastic syndrome and promyelocytic leukaemia); tumours of mesenchymal origin (including fibrosarcoma and rhabdomyosarcoma, and other sarcomas, e.g. soft tissue and bone); tumours of the central and peripheral nervous system (including astrocytoma, neuroblastoma, glioma and schwannomas); and other tumours (including melanoma, seminoma, teratocarcinoma, osteosarcoma, xenoderoma pigmentosum, keratoctanthoma, thyroid follicular cancer and Kaposi's sarcoma).

Preferably, the compounds may be useful for the treatment of neoplasia selected from lung cancer, colon cancer, renal cancer and breast cancer.

The blood vessels are also of major importance when the tumours metastasize, as the metastases are transported in the blood stream. A reduced number of blood vessels in and around the tumour reduces the metastatic potential of a tumour. The invention thus also provides a method of reducing the metastatic potential of a tumour.

Very small tumours may survive even in lack of adequate vasculature, and such tumours may start to grow and induce angiogenesis if the anti-angiogenic treatment is stopped. It therefore believed that treatment with compounds of the present invention may beneficially include co-administration or combination therapy of other therapeutically active compounds typically used in the treatment of tumours or cancer, such as chemotherapeutic agents, cytotoxic agents, and anticancer agents. The other therapeutically active compounds also include other inhibitors of protein kinases, such as tyrosine kinases useful in the treatment of tumours or cancer. The other therapeutically active compounds may be administered concomitantly or sequentially, and it lies within the capabilities of a skilled physician or veterinary to decide a dosing regime which fits best to the needs of the patient. The therapeutic agents may also be given as a single composition, such as in a single capsule or tablet having a fixed ratio of the active agents. The invention is not limited in the sequence of administration; compounds of the invention may be administered either prior to, simultaneous with or after administration of the known chemotherapeutic, cytotoxic, or anticancer agent. Therapeutically active compounds typically used in the treatment of tumours or cancer include S-triazine derivatives such as altretamine; enzymes such as asparaginase; antibiotic agents such as bleomycin, dactinomycin, daunorubicin, doxorubicin, idarubicin, mitomycin, epirubicin and plicamycin; alkylating agents such as busulfan, carboplatin, carmustine, chlorambucil, cisplatin, cyclophosphamide, dacarbazine, ifosfamide, lomustine, mechlorethamine, melphalan, procarbazine and thiotepa; antimetabolites such as cladribine, cytarabine, floxuridine, fludarabine, fluorouracil, hydroxyurea, mercaptopurine, methotrexate, gemcitabin, pentostatin and thioguanine; antimitotic agents such as etoposide, paclitaxel, teniposide, vinblastine, vinorelbin and vincristine; hormonal agents, e.g. aromatase inhibitors such as aminoglutethimide, corticosteroids, such as dexamethasone and prednisone, and luteinizing hormone releasing hormone (LH-RH); antiestrogens such as tamoxifen, formestan and letrozol; antiandrogens such as flutamide; biological response modifiers, e.g. lymphokines such as aldesleukin and other interleukines; interferon such as interferon-α; growth factors such as erythropoietin, filgrastim and sagramostim; differentiating agents such as vitamin D derivatives and all-trans retinoic acid; immunoregulators such as levamisole; and monoclonal antibodies, tumour necrosis factor α and angiogenesis inhibitors. Finally, ionising radiation (radiation therapy), although not readily defined as a compound, is often used in the treatment of tumours, and may be combined with the compounds of the present invention. Due to the severe side effects often experienced by patients receiving anti-tumour treatment it is often desirable also to administer therapeutica which do not themselves treat the tumour, but rather help relieving the side effects. Such compounds include amifostin, leucovorin and mesna.

Pathological or deregulated angiogenesis is not only connected to tumours, but has also been implicated in a number of other pathological conditions or diseases (see P. Carmeliet & R. K. Jain, Nature, Vol. 407, 2000, pp. 249-257; A. H. Vagnucci & W. W. Li, The Lancet, Vol. 361, 2003, 605-608; B. Xuan et al., J. Ocular Pharmacology & Therapeutics, Vol. 15(2), 1999, pp. 143-152) associated with deregulated angiogenesis. Compounds of the present invention would be useful for, but are not limited to the prevention, prophylaxis, treatment or amelioration of a disease or condition associated or related with deregulated angiogenesis. These conditions or diseases include conditions or diseases characterized by abnormal angiogenesis or vascular malfunction, rosacea, atherosclerosis, haemangioma, haemangioendothelioma, warts, pyogenic granulomas, hair growth, scar keloids, allergic oedema, dysfunctional uterine bleeding, follicular cysts, ovarian hyperstimulation, endometriosis, obesity, arthritis, rheumatoid arthritis, synovitis, bone and cartilage destruction, osteomyelitis, pannus growth, osteophyte formation, inflammatory and infectious diseases (hepatitis, pneumonia, glomerulonephritis), asthma, nasal polyps, transplantation, liver regeneration, retinopathy, diabetic retinopathy, neovascular glaucoma, endometriosis, psoriasis, lymphoproliferative disorders, thyroiditis, thyroid enlargement, obstructive lung disease, or cerebral ischaemia reperfusion injury, Alzheimer's disease, and eye diseases such as acute macular degeneration, age-related macular degeneration, choroidal neovascularisation, retinitis, cytomegalovirus retinitis, macular edema and ischemic retinopathy.

Besides being useful for human treatment, the compounds of the present invention may also be useful for veterinary treatment of animals including mammals such as horses, cattle, sheep, pigs, dogs, and cats.

For use in therapy, compounds of the present invention are typically in the form of a pharmaceutical composition or pharmaceutical formulation. The invention therefore relates to a pharmaceutical composition comprising a compound of formula I, optionally together with one or more other therapeutically active compounds, such as chemotherapeutic agents, anticancer agents, cytotoxic agents, together with a pharmaceutically acceptable excipient or vehicle. Examples of such other therapeutically active compounds include those typically used in the treatment of tumours or cancer listed above. The excipient must be "acceptable" in the sense of being compatible with the other ingredients of the composition and not deleterious to the recipient thereof.

If the treatment involves administration of another therapeutically active compound it is recommended to consult *Goodman & Gilman's The Pharmacological Basis of Therapeutics*, 9$^{th}$ Ed., J. G. Hardman and L. E. Limbird (Eds.), McGraw-Hill 1995, for useful dosages of said compounds.

Conveniently, the active ingredient comprises from 0.1-99.9% by weight of the composition.

By the term "dosage unit" is meant a unitary, i.e. a single dose which is capable of being administered to a patient, and which may be readily handled and packed, remaining as a physically and chemically stable unit dose comprising either the active material as such or a mixture of it with solid or liquid pharmaceutical diluents or carriers. In the form of a dosage unit, the compound may be administered one or more times a day at appropriate intervals, always depending, however, on the condition of the patient, and in accordance with the prescription made by the medical practitioner. It is also envisaged that in certain treatment regimes, administration with longer intervals e.g. every other day, every week, or even with longer intervals may be beneficial.

Conveniently, dosage unit of a formulation contains between 0.01 mg and 10000 mg, preferably between 100 mg and 3000 mg, such as between 200 mg and 1000 mg of a compound of formula I.

The formulations include e.g. those in a form suitable for oral (including sustained or timed release), rectal, parenteral (including subcutaneous, intraperitoneal, intramuscular, intraarticular and intravenous), transdermal, ophthalmic, topical, nasal or buccal administration.

The formulations may conveniently be presented in dosage unit form and may be prepared by any of the methods well known in the art of pharmacy, e.g. as disclosed in Remington, *The Science and Practice of Pharmacy*, 20$^{th}$ ed., 2000. All methods include the step of bringing the active ingredient into association with the carrier, which constitutes one or more accessory ingredients. In general, the formulations are prepared by uniformly and intimately bringing the active ingredient into association with a liquid carrier or a finely divided solid carrier or both, and then, if necessary, shaping the product into the desired formulation.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid, such as ethanol or glycerol; or in the form of an oil-in-water emulsion or a water-in-oil emulsion. Such oils may be edible oils, such as e.g. cottonseed oil, sesame oil, coconut oil or peanut oil. Suitable dispersing or suspending agents for aqueous suspensions include synthetic or natural gums such as tragacanth, alginate, acacia, dextran, sodium carboxymethylcellulose, gelatin, methylcellulose, hydroxypropylmethylcellulose, hydroxypropylcellulose, carbomers and polyvinylpyrrolidone. The active ingredients may also be administered in the form of a bolus, electuary or paste.

A tablet may be made by compressing or moulding the active ingredient optionally with one or more accessory ingredients. Compressed tablets may be prepared by compressing, in a suitable machine, the active ingredient(s) in a free-flowing form such as a powder or granules, optionally mixed by a binder, such as e.g. lactose, glucose, starch, gelatine, acacia gum, tragacanth gum, sodium alginate, carboxymethylcellulose, methylcellulose, hydroxypropylmethylcellulose, polyethylene glycol, waxes or the like; a lubricant such as e.g. sodium oleate, sodium stearate, magnesium stearate, sodium benzoate, sodium acetate, sodium chloride or the like; a disintegrating agent such as e.g. starch, methylcellulose, agar, bentonite, croscarmellose sodium, sodium starch glycollate, crospovidone or the like or a dispersing agent, such as polysorbate 80. Moulded tablets may be made by moulding, in a suitable machine, a mixture of the powdered active ingredient and suitable carrier moistened with an inert liquid diluent.

Formulations for rectal administration may be in the form of suppositories in which the compound of the present invention is admixed with low melting water soluble or insoluble solids such as cocoa butter, hydrogenated vegetable oils, polyethylene glycol or fatty acids esters of polyethylene glycols, while elixirs may be prepared using myristyl palmitate.

Formulations suitable for parenteral administration conveniently comprise a sterile oily or aqueous preparation of the active ingredients, which is preferably isotonic with the blood of the recipient, e.g. isotonic saline, isotonic glucose solution or buffer solution. The formulation may be conveniently sterilised by for instance filtration through a bacteria retaining filter, addition of sterilising agent to the formulation, irradiation of the formulation or heating of the formulation. Liposomal formulations as disclosed in e.g. Encyclopedia of Pharmaceutical Technology, vol. 9, 1994, are also suitable for parenteral administration.

Alternatively, the compound of formula I may be presented as a sterile, solid preparation, e.g. a freeze-dried powder, which is readily dissolved in a sterile solvent immediately prior to use.

Transdermal formulations may be in the form of a plaster or a patch.

Formulations suitable for ophthalmic administration may be in the form of a sterile aqueous preparation of the active ingredients, which may be in microcrystalline form, for example, in the form of an aqueous microcrystalline suspension. Liposomal formulations or biodegradable polymer systems e.g. as disclosed in Encyclopedia of Pharmaceutical Technology, vol. 2, 1989, may also be used to present the active ingredient for ophthalmic administration.

Formulations suitable for topical or ophthalmic administration include liquid or semi-liquid preparations such as liniments, lotions, gels, applicants, oil-in-water or water-in-oil emulsions such as creams, ointments or pastes; or solutions or suspensions such as drops.

Formulations suitable for nasal or buccal administration include powder, self-propelling and spray formulations, such as aerosols and atomisers. Such formulations are disclosed in greater detail in e.g. Modern Pharmaceutics, 2$^{nd}$ ed., G. S. Banker and C. T. Rhodes (Eds.), page 427-432, Marcel Dekker, New York; Modern Pharmaceutics, 3$^{th}$ ed., G. S. Banker and C. T. Rhodes (Eds.), page 618-619 and 718-721, Marcel Dekker, New York and Encyclopedia of Pharmaceutical Technology vol. 10. J Swarbrick and J. C. Boylan (Eds), page 191-221, Marcel Dekker, New York In addition to the aforementioned ingredients, the formulations of a compound of formula I may include one or more additional ingredients such as diluents, buffers, flavouring agents, colourant, surface active agents, thickeners, preservatives, e.g. methyl hydroxybenzoate (including anti-oxidants), emulsifying agents and the like.

When the active ingredient is administered in the form of salts with pharmaceutically acceptable non-toxic acids or bases, preferred salts are for instance easily water-soluble or slightly soluble in water, in order to obtain a particular and appropriate rate of absorption.

Methods of Preparation

The compounds of the present invention can be prepared in a number of ways well known to those skilled in the art of organic synthesis. The compounds of the present invention can be synthesised using the methods outlined below, together with methods known in the art of synthetic organic chemistry, or variations thereof as appreciated by those skilled in the art. Preferred methods include, but are not limited to, those described below.

The novel compounds of formula (I) may be prepared using the reactions and techniques described in this section. The reactions are performed in solvents appropriate to the reagents and materials employed and suitable for the transformations being effected. Also, in the synthetic methods described below, it is to be understood that all proposed reaction conditions, including choice of solvent, reaction atmosphere, reaction temperature, duration of experiment and work-up procedures, are chosen to be conditions of standard for that reaction, which should be readily recognised by one skilled in the art. It is understood by one skilled in the art of organic synthesis that the functionality present on various portions of the starting molecule in a reaction must be compatible with the reagents and reactions proposed. Not all compounds of formula (I) falling into a given class may be compatible with some of the reaction conditions required in some of the methods described. Such restrictions to the substituents which are compatible with the reaction conditions will be readily apparent to one skilled in the art and alternative methods can be used.

The compounds of formula (I) can be prepared by techniques and procedures readily available to one skilled in the art, for example by following the procedures as set forth in the following Schemes. These Schemes are not intended to limit the scope of the invention in any way. All substituents, unless otherwise indicated, are previously defined. The reagents and starting materials are readily available to one skilled in the art.

The compounds of formula (I) are generally obtained by condensation of acids of general formula (II) and O-substituted (Y-A-R$_9$) hydroxylamines of general formula (III) by action of coupling agent, such as a peptide coupling agent, optionally in the presence of a base, in an appropriate solvent as shown in Scheme 1. Preferred coupling agents include N,N'-carbonyldiimidazole (CDI), diphenylphoshinic chloride (DPP-Cl), benzotriazol-yloxy-tripyrrolidinophosphonium hexafluorophosphate (PyBOP), benzotriazol-1-yloxy-tris(dimethylamino)phosphonium hexafluorophosphate (BOP), N,N'-dicyclohexylcarbodiimide (DCC), or 1-ethyl-3-(3-dimethylaminopropyl)carbodiimide hydrochloride (EDCl). Preferred bases include diisopropylethylamine, triethylamine, 4-methylmorpholine, 1,8-diazabicyclo[5.4.0]undec-7-ene (DBU), or pyridine or a substituted pyridine, for example 4-dimethylaminopyridine or 2,6-dimethylpyridine. Preferred solvents are polar aprotic solvents such as dichloromethane, tetrahydrofuran, 1-methyl-2-pyrrolidinone, or dimethylformamide. The reactions are generally carried out at a temperature between about −78° C. to about 60° C., and are normally complete within about 2 hours to about 5 days. The product hydroxamic acid esters of general structure (I) can be isolated by extraction with a suitable organic solvent, preferably a non-water miscible solvent such as ethyl acetate after dilution of the reaction mixture with water. Evaporation of the solvent under reduced pressure affords the products that may be further purified, if desired, by standard methods such as chromatography, crystallisation, or distillation. Alternatively, the products can be isolated by removing the solvent used to perform the reaction in, for example by evaporation under reduced pressure and further purified as mentioned above.

Scheme 1: General method for the preparation of benzamides of general formula (I) from acids of general formula (II)

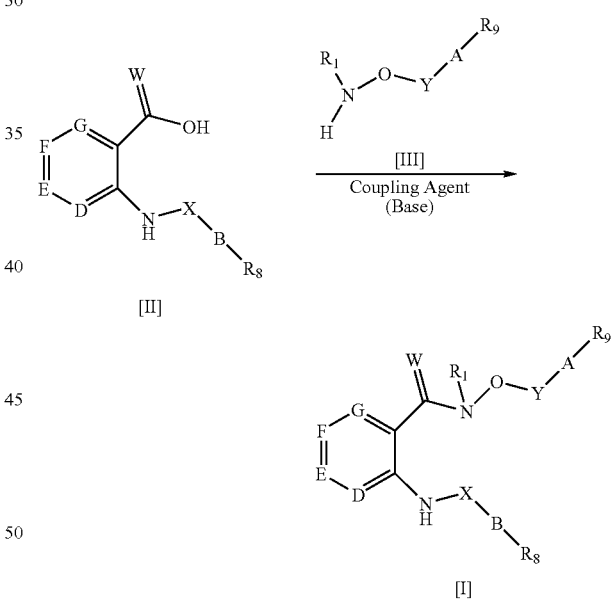

The disclosed compounds may also generally be prepared as shown in Scheme 2 by the reaction of O-substituted (Y-A-R$_9$) hydroxylamines of general formula (III) with "activated" acids of general formula IV, wherein "LG" is a leaving group. Compounds of general structure IV include, but are not limited to, acid halides, anhydrides, mixed anhydrides, or an activated esters, e.g. pentafluorophenyl esters, nitrophenyl esters or thioesters. The reaction is preferably carried out in the presence of base such as diisopropylethylamine, triethylamine, 4-methylmorpholine, or pyridine or a substituted pyridine, for example 4-dimethylaminopyridine or 2,6-dimethylpyridine. Preferred solvents include polar aprotic solvents such as dichloromethane, tetrahydrofuran, 1-methyl-2-pyrrolidinone, or dimethylformamide. The synthesis of hydroxamic acid esters from pentafluorophenyl esters of benzoic acid derivatives has been previously described in WO 02/06213.

Scheme 2: General method for the preparation of benzamides of general formula (I) from "activated" acids of general formula (IV)

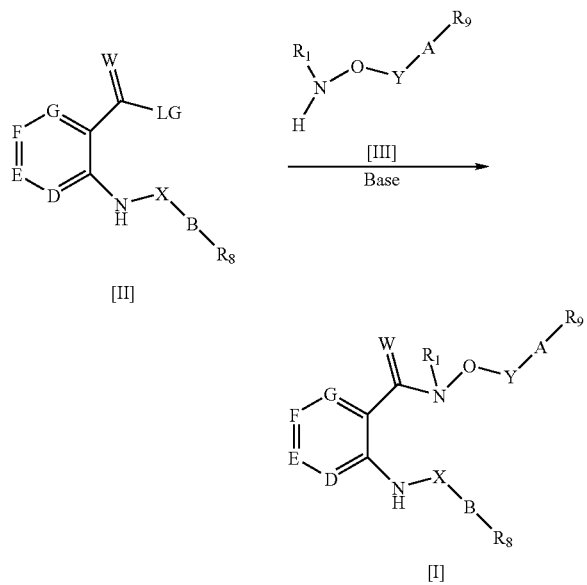

Furthermore, the disclosed compounds may generally be prepared as shown in Scheme 2a by the reaction of O-substituted (Y-A-R$_9$) hydroxylamines of general formula (III) with anhydrides of general formula (XV). The reaction is generally carried out in solvents such as dichloromethane, tetrahydrofuran, 1-methyl-2-pyrrolidinone, dimethylformamide or pyridine. Reactions are generally carried out at a temperature between about 20° C. to about 100° C., and are normally complete within about 2 hours to about 5 days. The product hydroxamic acid esters of general structure (I) can be isolated by extraction with a suitable organic solvent, preferably a non-water miscible solvent such as ethyl acetate after dilution of the reaction mixture with water. Evaporation of the solvent under reduced pressure affords the products that may be further purified, if desired, by standard methods such as chromatography, crystallisation, or distillation. Alternatively, the products can be isolated by removing the solvent used to perform the reaction in, for example by evaporation under reduced pressure and further purified as mentioned above.

Scheme 2a: General method for the preparation of benzamides of general formula (I) from anhydrides of general formula (XV).

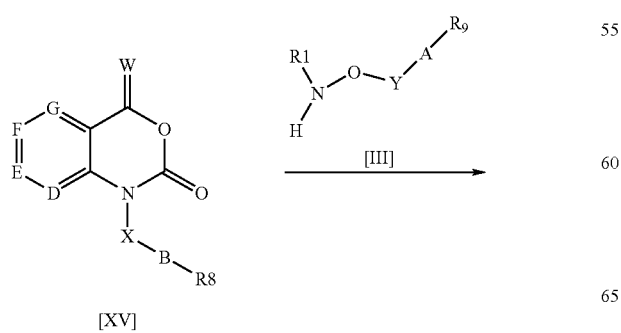

Nitrogen substituted anhydrides of general formula XV can be prepared from anhydrides of general formula X1 as depicted in Scheme 2b. Treatment of anhydrides of general formula XIII with alcohols (LG-X—B—R$_8$, LG=OH) in a Mitsunobu-like reaction, such as with triphenylphosphine and diethyl azodicarboxylate (DEAD) or diisopropyl azodicarboxylate in a suitable solvent not limited to but such as tetrahydrofuran or diethylether. Alternatively N-alkylated anhydrides of general formula XV can be prepared by treatment of XIII with a suitable base such as sodium carbonate or sodium hydride followed by alkylation with an appropriate alkyl halide (LG-X—B—R$_8$, LG=Cl, Br, I). Non-limiting examples of such preparations have been described by e.g. G. M. Coppola: Synthetic Communications (2002), 32, 1009-1013 and references herein and in WO 00/27819.

The anhydrides of general formula XIII are either commercially available or can be readily prepared using procedures well-known to a person skilled in the art. Non-limiting examples of such preparations have been described by G. M. Coppola: Synthesis (1980), 505-536; S. Jonsson et. al.: J. Med. Chem. (2004), 47, 2075-2088; J. Clews et al.: Tetrahedron (2000), 56, 8735-8746 and U.S. Pat. No. 3,887,550.

Scheme 2b: General method for the preparation of Nitrogen substituted anhydrides of general formula XV from anhydrides of general formula XIIII.

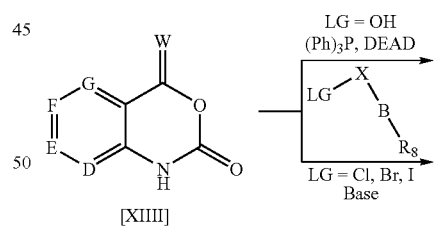

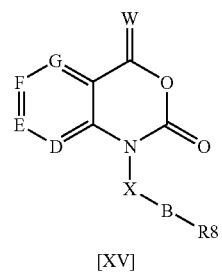

The starting materials O-substituted (Y-A-R$_9$) hydroxylamines of general formula (III) are either commercially available or can be readily prepared using procedures well-known to a person skilled in the art. Non-limiting examples of such preparations have been described by e.g. J. N. Kim et al.: *Synthetic Communications*, (1992) 22, 1427-1432, M. Arimoto et al.: *The Journal of Antibiotics* (1988) XLI, 12, 1795-1811, H. M. Petrassi et al.: *Organic Letters* (2001), 3, 139-142, E. Grochowski, J. Jurczak: *Synthesis* (1976), 682-684, and WO 02/06213. Typical but non-limiting synthetic routes to obtain O-substituted Y-A-$R_9$) hydroxylamines of general formula (III) is illustrated in Scheme 3: Reaction of N-hydroxyphthalimide or tert-butyl-N-hydroxycarbamate with an alkylating agent, e.g. an alkyl halide (LG-Y-A-$R_9$), in a suitable solvent in the presence of a base such as triethylamine, 1,8-diazabicyclo[5,4,0]-undec-7-ene (DBU), potassium carbonate, or caesium carbonate, afford intermediates of general formula V or VI respectively. Alternatively an alcohol (LG in LG-Y-A-$R_9$=OH) can be reacted with N-hydroxyphthalimide in a Mitsunobu-like reaction in the presence of triphenylphosphine and diethyl azodicarboxylate (DEAD) or diisopropyl azodicarboxylate in a suitable solvent such as tetrahydrofuran or diethylether, affording compounds of general formula V. Reaction of V with hydrazine affords the desired O-substituted (Y-A-$R_9$) hydroxylamines of general formula (III). Treatment of VI with acid, e.g. trifluoroacetic acid or hydrochloric acid also yields the desired O-substituted (Y-A-$R_9$) hydroxylamines of general formula (III). The O-substituted (Y-A-$R_9$) hydroxylamines of general formula (III) may be isolated and used either as free amines or as the corresponding salts, e.g. hydrochloric acid salts, hydrobromic acid salts, or sulphuric acids salts.

The acids of formula (II) (in which W is oxygen) may be prepared from esters of general formula (VII) (in which Q e.g. represents alkyl or substituted alkyl) by hydrolysis, such as base catalysed hydrolysis, acid catalysed, or enzyme mediated hydrolysis, as shown in Scheme 4. Non-limiting examples of bases which can be used are lithium hydroxide, sodium hydroxide or potassium hydroxide.

Scheme 4: General method for the preparation of acids of general formula II from esters of general formula (VII)

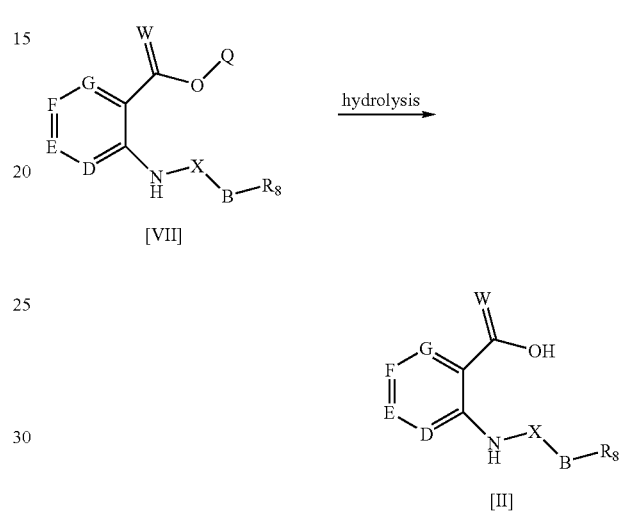

Scheme 3: Methods for preparation of O-substituted (Y-A) hydroxylamines of general formula (III) (R1 = H).

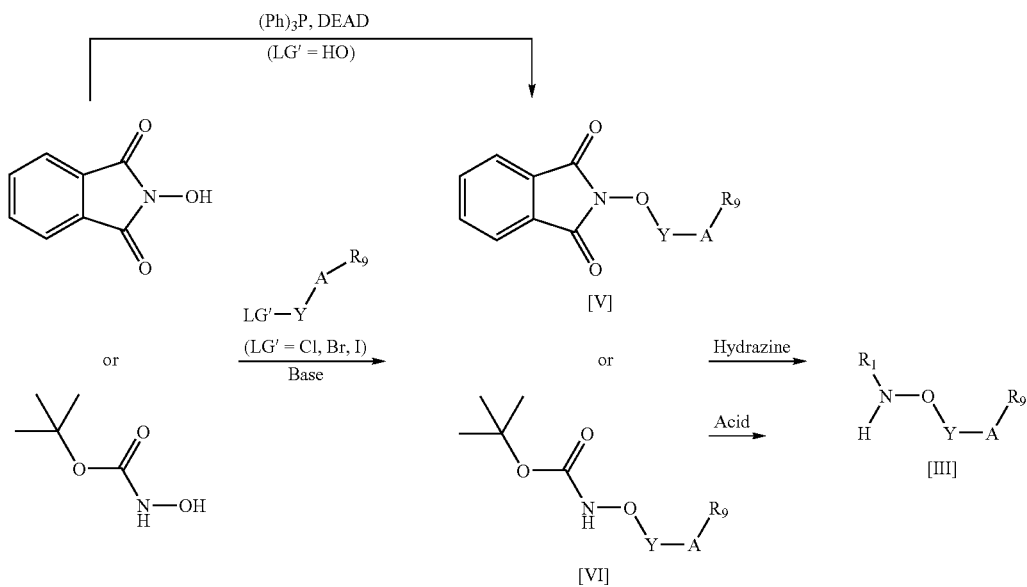

Alternatively, the acids of general formula (II) (in which W is oxygen) may be prepared by hydrolysis of nitriles of general formula (VIII) as shown in Scheme 5, such as by basic, acidic, or enzymatic hydrolysis.

Scheme 5: General method for the preparation of acids of general formula II from nitiles of general formula (VIII)

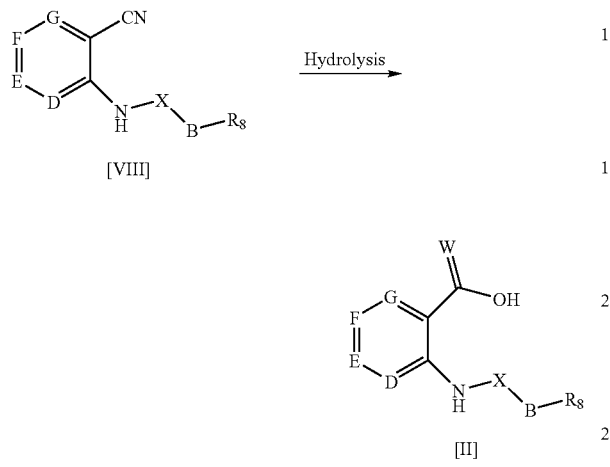

Esters of general formula (VII) may be prepared from the corresponding amines of general formula (IX) and aldehydes of general formula (X) (obtainable from commercial sources or prepared as e.g. described in WO 02/090352) e.g. by reductive amination, (see for example: A. F. Abdel-Magid et al.: *J. Org. Chem.* (1996), 61, 3849-3862, WO 00/27819, and WO 02/090352) as shown in Scheme 6. Suitable reducing agents are e.g. sodium cyanoborohydride, sodium borohydride, or sodium triacetoxyborohydride. Amines of general formula IX are either readily prepared by a person skilled in the art or are commercially available.

Scheme 6: General method for the preparation of esters of general formula (VII) from amines of general formula (IX)

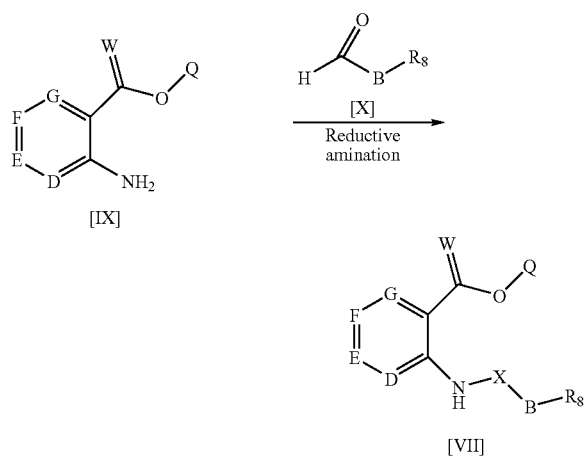

Nitriles of formula (VIII) (e.g. in which D represents nitrogen) can for example be prepared by reaction of compounds of general formula (XI) (in which LG" represents a suitable leaving group such as halogen, e.g. fluorine or chlorine) with amines of general formula (XII) (for examples see R. Kwok. *J. Heterocyclic Chem.* (1978) 15, 877-880; S. Brunel et al. *J. Heterocyclic Chem.* (1980) 17, 235-240) as shown in Scheme 7. Compounds of general formula XI are either readily prepared by a person skilled in the art or are commercially available.

Scheme 7: General preparation of nitriles of general formula (VIII) from nitriles of general formula (XI)

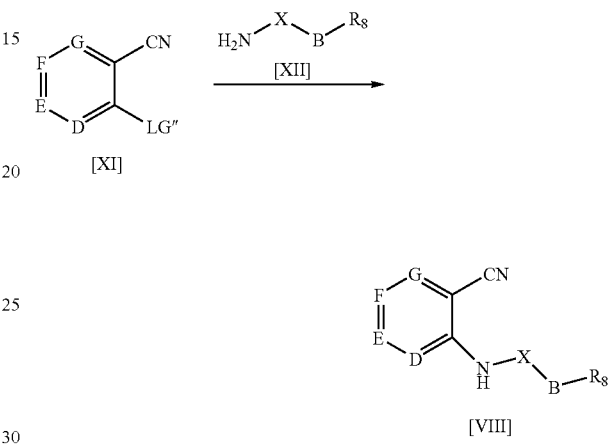

GENERAL PROCEDURES, PREPARATIONS AND EXAMPLES

The exemplified compounds of general formula (I) are listed in Table 1. For $^1$H nuclear magnetic resonance (NMR) spectra (300 MHz) and $^{13}$C NMR (75.6 MHz) chemical shift values (δ) (in ppm) are quoted for dimethyl-$d_6$ sulfoxide (DMSO-$d_6$) solutions relative to internal tetramethylsilan (δ=0) standard. The value of a multiplet, either defined (doublet (d), triplet (t), quartet (q)) or not (m) at the approximate mid point is given unless a range is quoted, (bs) indicates a broad singlet. The organic solvents used were anhydrous unless otherwise specified. The reactions were preferably carried out under an inert atmosphere such as under nitrogen or argon. Chromatography was performed on silica gel (from Merck, 0.040-0.063 mm). Selected compounds or intermediates were commercially available from e.g. Aldrich, SPECS, Bionet research intermediates, Matrix, or Lancaster.

The following abbreviations have been used throughout:
Brine saturated aqueous sodium chloride
Boc tert-Butoxycarbonyl
DMF N,N'-Dimethylformamide
EtOAc Ethyl acetate
eq. equivalent
M Molar (mol/L)
NMP 1-Methyl-2-pyrrolidinone
NMR Nuclear magnetic resonance
THF Tetrahydrofuran

TABLE 1

Compounds of general formula (I) (W = oxygen; compound 1-399 and 402-432 $R_1$ = hydrogen, compound 400 $R_1$ = methyl)

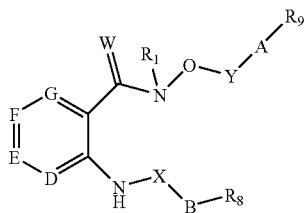

[I]

| Compound | Example | D | E | F | G | X | B-R$_8$ | Y |
|---|---|---|---|---|---|---|---|---|
| 1 | 1 | CH | CH | CH | CH | —CH$_2$— | 4-pyridyl | —CH$_2$— |
| 2 | 2 | CH | CH | CH | CH | —CH$_2$— | 4-pyridyl | —CH$_2$— |
| 3 | 3 | CH | CH | CH | CH | —CH$_2$— | 4-pyridyl | —CH$_2$— |
| 4 | 4 | CH | CH | CH | CH | —CH$_2$— | 4-pyridyl | —CH$_2$— |
| 5 | 5 | CH | CH | CH | CH | —CH$_2$— | 4-pyridyl | —CH$_2$— |
| 6 | 6 | CH | CH | CH | CH | —CH$_2$— | 4-pyridyl | —CH$_2$— |
| 7 | 7 | CH | CH | CH | CH | —CH$_2$— | 4-pyridyl | —CH$_2$— |
| 8 | 8 | CH | CH | CH | CH | —CH$_2$— | 4-pyridyl | —CH$_2$— |
| 9 | 9 | CH | CH | CH | CH | —CH$_2$— | 4-pyridyl | —CH$_2$— |
| 10 | 10 | CH | CH | CH | CH | —CH$_2$— | 4-pyridyl | —CH$_2$— |
| 11 | 11 | CH | CH | CH | CH | —CH$_2$— | 4-pyridyl | —CH$_2$— |
| 12 | 12 | CH | CH | CH | CH | —CH$_2$— | 4-pyridyl | —CH$_2$— |
| 13 | 13 | CH | CH | CH | CH | —CH$_2$— | 4-pyridyl | —CH$_2$— |
| 14 | 14 | CH | CH | CH | CH | —CH$_2$— | 4-pyridyl | —CH$_2$— |
| 15 | 15 | CH | CH | CH | CH | —CH$_2$— | 4-pyridyl | —CH$_2$— |
| 16 | 16 | CH | CH | CH | CH | —CH$_2$— | 4-pyridyl | —CH$_2$— |
| 17 | 17 | CH | CH | CH | CH | —CH$_2$— | 4-pyridyl | —CH$_2$— |
| 18 | 18 | CH | CH | CH | CH | —CH$_2$— | 4-pyridyl | —CH$_2$— |
| 19 | 19 | CH | CH | CH | CH | —CH$_2$— | 4-pyridyl | —CH$_2$— |
| 20 | 20 | CH | CH | CH | CH | —CH$_2$— | 4-pyridyl | —CH$_2$— |
| 21 | 21 | CH | CH | CH | CH | —CH$_2$— | 4-pyridyl | —CH$_2$— |
| 22 | 22 | CH | CH | CH | CH | —CH$_2$— | 4-pyridyl | —CH$_2$— |
| 23 | 23 | CH | CH | CH | CH | —CH$_2$— | 4-pyridyl | —CH$_2$— |
| 24 | 24 | CH | CH | CH | CH | —CH$_2$— | 4-pyridyl | —CH$_2$— |
| 25 | 25 | CH | CH | CH | CH | —CH$_2$— | 4-pyridyl | —CH$_2$— |
| 26 | 26 | CH | CH | CH | CH | —CH$_2$— | 4-pyridyl | —CH$_2$— |
| 27 | 27 | CH | CH | CH | CH | —CH$_2$— | 4-pyridyl | —CH$_2$— |
| 28 | 28 | CH | CH | CH | CH | —CH$_2$— | 4-pyridyl | —CH$_2$— |
| 29 | 29 | CH | CH | CH | CH | —CH$_2$— | 4-pyridyl | bond |
| 30 | 30 | CH | CH | CH | CH | —CH$_2$— | 4-pyridyl | —(CH$_2$)$_2$—O— |
| 31 | 31 | CH | CH | CH | CH | —CH$_2$— | 4-pyridyl | —(CH$_2$)$_3$— |
| 32 | 32 | CH | CH | CH | CH | —CH$_2$— | 4-pyridyl | —(CH$_2$)$_3$— |
| 33 | 33 | N | CH | CH | CH | —CH$_2$— | 4-pyridyl | —CH$_2$— |
| 34 | 34 | N | CH | CH | CH | —CH$_2$— | 4-fluorophenyl | —CH$_2$— |
| 35 | 35 | N | CH | CH | CH | —CH$_2$— | 4-methoxy | —CH$_2$— |
| 36 | 351 | CH | CH | CH | CH | —CH$_2$— | 4-pyridyl | bond |
| 37 | 352 | CH | CH | CH | CH | —CH$_2$— | 4-pyridyl | bond |
| 38 | 353 | CH | CH | CH | CH | —CH$_2$— | 4-pyridyl | —CH$_2$— |
| 39 | 354 | CH | CH | CH | CH | —CH$_2$— | 4-pyridyl | —CH$_2$— |
| 40 | 355 | CH | CH | CH | CH | —CH$_2$— | 4-pyridyl | —CH$_2$— |
| 41 | 356 | CH | CH | CH | CH | —CH$_2$— | 4-pyridyl | —CH$_2$— |
| 42 | 357 | CH | CH | CH | CH | —CH$_2$— | 4-pyridyl | —CH$_2$— |
| 43 | 358 | CH | CH | CH | CH | —CH$_2$— | 4-pyridyl | —CH$_2$— |
| 44 | 359 | CH | CH | CH | CH | —CH$_2$— | 4-pyridyl | —CH$_2$— |
| 45 | 360 | CH | CH | CH | CH | —CH$_2$— | 4-pyridyl | —CH$_2$— |
| 46 | 361 | CH | CH | CH | CH | —CH$_2$— | 4-pyridyl | —CH$_2$— |
| 47 | 362 | CH | CH | CH | CH | —CH$_2$— | 4-pyridyl | —CH$_2$— |
| 48 | 363 | CH | CH | CH | CH | —CH$_2$— | 4-pyridyl | —CH$_2$— |
| 49 | 364 | CH | CH | CH | CH | —CH$_2$— | 4-pyridyl | —CH$_2$— |
| 50 | 365 | CH | CH | CH | CH | —CH$_2$— | 4-pyridyl | —CH$_2$— |
| 51 | 366 | CH | CH | CH | CH | —CH$_2$— | 4-pyridyl | —CH$_2$— |
| 52 | 367 | CH | CH | CH | CH | —CH$_2$— | 4-pyridyl | —CH$_2$— |
| 53 | 368 | CH | CH | CH | CH | —CH$_2$— | 4-pyridyl | —CH$_2$— |
| 54 | 369 | CH | CH | CH | CH | —CH$_2$— | 4-pyridyl | —CH$_2$— |
| 55 | 370 | CH | CH | CH | CH | —CH$_2$— | 4-pyridyl | —CH$_2$— |
| 56 | 371 | CH | CH | CH | CH | —CH$_2$— | 4-pyridyl | —CH$_2$— |
| 57 | 372 | CH | CH | CH | CH | —CH$_2$— | 4-pyridyl | —CH$_2$— |
| 58 | 373 | CH | CH | CH | CH | —CH$_2$— | 4-pyridyl | —CH$_2$— |
| 59 | 374 | CH | CH | CH | CH | —CH$_2$— | 4-pyridyl | —CH$_2$— |
| 60 | 375 | CH | CH | CH | CH | —CH$_2$— | 4-pyridyl | —CH$_2$— |
| 61 | 376 | CH | CH | CH | CH | —CH$_2$— | 4-pyridyl | —CH$_2$— |
| 62 | 377 | CH | CH | CH | CH | —CH$_2$— | 4-pyridyl | —CH$_2$— |

TABLE 1-continued

Compounds of general formula (I) (W = oxygen; compound 1-399 and 402-432 $R_1$ = hydrogen, compound 400 $R_1$ = methyl)

[I]

| | | D | E | F | G | Y | A-R$_9$ | X-B |
|---|---|---|---|---|---|---|---|---|
| 63 | 378 | CH | CH | CH | CH | —CH$_2$— | 4-pyridyl | —CH$_2$— |
| 64 | 379 | CH | CH | CH | CH | —CH$_2$— | 4-pyridyl | —CH$_2$— |
| 65 | 380 | CH | CH | CH | CH | —CH$_2$— | 4-pyridyl | —CH$_2$— |
| 66 | 381 | CH | CH | CH | CH | —CH$_2$— | 4-pyridyl | —CH$_2$— |
| 67 | 382 | CH | CH | CH | CH | —CH$_2$— | 4-pyridyl | —CH$_2$— |
| 68 | 383 | CH | CH | CH | CH | —CH$_2$— | 4-pyridyl | —CH$_2$— |
| 69 | 384 | CH | CH | CH | CH | —CH$_2$— | 4-pyridyl | —CH$_2$— |
| 70 | 385 | CH | CH | CH | CH | —CH$_2$— | 4-pyridyl | —CH$_2$— |
| 71 | 386 | CH | CH | CH | CH | —CH$_2$— | 4-pyridyl | —CH$_2$— |
| 72 | 387 | CH | CH | CH | CH | —CH$_2$— | 4-pyridyl | —CH$_2$— |
| 73 | 388 | CH | CH | CH | CH | —CH$_2$— | 4-pyridyl | —CH$_2$— |
| 74 | 389 | CH | CH | CH | CH | —CH$_2$— | 4-pyridyl | —CH$_2$— |
| 75 | 390 | CH | CH | CH | CH | —CH$_2$— | 4-pyridyl | —CH$_2$— |
| 76 | 391 | CH | CH | CH | CH | —CH$_2$— | 4-pyridyl | —CH$_2$— |
| 77 | 392 | CH | CH | CH | CH | —CH$_2$— | 4-pyridyl | —CH$_2$— |
| 78 | 393 | CH | CH | CH | CH | —CH$_2$— | 4-pyridyl | —CH$_2$— |
| 79 | 394 | CH | CH | CH | CH | —CH$_2$— | 4-pyridyl | —CH$_2$— |
| 80 | 395 | CH | CH | CH | CH | —CH$_2$— | 4-pyridyl | —CH$_2$— |
| 81 | 396 | CH | CH | CH | CH | —CH$_2$— | 4-pyridyl | —CH$_2$— |
| 82 | 397 | CH | CH | CH | CH | —CH$_2$— | 4-pyridyl | —CH$_2$— |
| 83 | 398 | CH | CH | CH | CH | —CH$_2$— | 4-pyridyl | —CH$_2$— |
| 84 | 399 | CH | CH | CH | CH | —CH$_2$— | 4-pyridyl | —CH$_2$— |
| 85 | 400 | CH | CH | CH | CH | —CH$_2$— | 4-pyridyl | —CH$_2$— |
| 86 | 401 | CH | CH | CH | CH | —CH$_2$— | 4-pyridyl | —CH$_2$— |
| 87 | 402 | CH | CH | CH | CH | —CH$_2$— | 4-pyridyl | —CH$_2$— |
| 88 | 403 | CH | CH | CH | CH | —CH$_2$— | 4-pyridyl | —CH$_2$— |
| 89 | 404 | CH | CH | CH | CH | —CH$_2$— | 4-pyridyl | —CH$_2$— |
| 90 | 405 | CH | CH | CH | CH | —CH$_2$— | 4-pyridyl | —CH$_2$— |
| 91 | 406 | CH | CH | CH | CH | —CH$_2$— | 4-pyridyl | —CH$_2$— |
| 92 | 407 | CH | CH | CH | CH | —CH$_2$— | 4-pyridyl | —CH$_2$— |
| 93 | 408 | CH | CH | CH | CH | —CH$_2$— | 4-pyridyl | —CH$_2$— |
| 94 | 409 | CH | CH | CH | CH | —CH$_2$— | 4-pyridyl | —CH$_2$— |
| 95 | 410 | CH | CH | CH | CH | —CH$_2$— | 4-pyridyl | —CH$_2$— |
| 96 | 411 | CH | CH | CH | CH | —CH$_2$— | 4-pyridyl | —CH$_2$— |
| 97 | 412 | CH | CH | CH | CH | —CH$_2$— | 4-pyridyl | —CH$_2$— |
| 98 | 413 | CH | CH | CH | CH | —CH$_2$— | 4-pyridyl | —CH$_2$— |
| 99 | 414 | CH | CH | CH | CH | —CH$_2$— | 4-pyridyl | —CH$_2$— |
| 100 | 415 | CH | CH | CH | CH | —CH$_2$— | 4-pyridyl | —CH$_2$— |
| 101 | 416 | CH | CH | CH | CH | —CH$_2$— | 4-pyridyl | —CH(CH$_3$)— |
| 102 | 417 | CH | CH | CH | CH | —CH$_2$— | 4-pyridyl | —CH(CH$_3$)— |
| 103 | 418 | CH | CH | CH | CH | —CH$_2$— | 4-pyridyl | —CH$_2$— |
| 104 | 419 | CH | CH | CH | CH | —CH$_2$— | 4-pyridyl | —CH$_2$— |
| 105 | 420 | CH | CH | CH | CH | —CH$_2$— | 4-pyridyl | —CH$_2$— |
| 106 | 421 | CH | CH | CH | CH | —CH$_2$— | 4-pyridyl | —CH$_2$— |
| 107 | 422 | CH | CH | CH | CH | —CH$_2$— | 4-pyridyl | —CH$_2$— |
| 108 | 423 | CH | CH | CH | CH | —CH$_2$— | 4-pyridyl | —CH$_2$— |
| 109 | 424 | CH | CH | CH | CH | —CH$_2$— | 4-pyridyl | —CH$_2$— |
| 110 | 425 | CH | CH | CH | CH | —CH$_2$— | 4-pyridyl | —CH$_2$— |
| 111 | 426 | CH | CH | CH | CH | —CH$_2$— | 4-pyridyl | —CH$_2$— |
| 112 | 427 | CH | CH | CH | CH | —CH$_2$— | 4-pyridyl | —(CH$_2$)$_2$— |
| 113 | 428 | CH | CH | CH | CH | —CH$_2$— | 4-pyridyl | —CH$_2$— |
| 114 | 429 | CH | CH | CH | CH | —CH$_2$— | 4-pyridyl | —CH$_2$— |
| 115 | 430 | CH | CH | CH | CH | —CH$_2$— | 4-pyridyl | bond |
| 116 | 431 | CH | CH | CH | CH | —CH$_2$— | 4-pyridyl | —CH$_2$— |
| 117 | 432 | CH | CH | CH | CH | —CH$_2$— | 4-pyridyl | —CH$_2$— |
| 118 | 433 | CH | CH | CH | CH | —CH$_2$— | 4-pyridyl | —CH$_2$— |

TABLE 1-continued

Compounds of general formula (I) (W = oxygen; compound 1-399 and 402-432 R₁ = hydrogen, compound 400 R₁ = methyl)

[I]

| | | D | E | F | G | Y | R₉ | A |
|---|---|---|---|---|---|---|---|---|
| 119 | 434 | CH | CH | CH | CH | —CH₂— | 4-pyridyl | —CH₂— |
| 120 | 435 | CH | CH | CH | CH | —CH₂— | 4-pyridyl | —CH₂— |
| 121 | 436 | CH | CH | CH | CH | —CH₂— | 4-pyridyl | —CH₂— |
| 122 | 437 | CH | CH | CH | CH | —CH₂— | 4-pyridyl | —CH₂— |
| 123 | 438 | CH | CH | CH | CH | —CH₂— | 4-pyridyl | >CH—CH₃ |
| 124 | 439 | CH | CH | CH | CH | —CH₂— | 4-pyridyl | bond |
| 125 | 440 | CH | CH | CH | CH | —CH₂— | 4-pyridyl | —(CH₂)₂— |
| 126 | 441 | CH | CH | CH | CH | —CH₂— | 4-pyridyl | —(CH₂)₂— |
| 127 | 442 | CH | CH | CH | CH | —CH₂— | 4-pyridyl | —(CH₂)₃— |
| 128 | 443 | CH | CH | CH | CH | —CH₂— | 4-pyridyl | —CH₂— |
| 129 | 444 | CH | CH | CH | CH | —CH₂— | 4-pyridyl | —CH₂— |
| 130 | 445 | CH | CH | CH | CH | —CH₂— | 4-pyridyl | —CH₂— |
| 131 | 446 | CH | CH | CH | CH | —CH₂— | 4-pyridyl | —CH₂— |
| 132 | 447 | CH | CH | CH | CH | —CH₂— | 4-pyridyl | —CH₂— |
| 133 | 448 | CH | CH | CH | CH | —CH₂— | 4-pyridyl | —CH₂— |
| 134 | 449 | CH | CH | CH | CH | —CH₂— | 4-pyridyl | —CH₂— |
| 135 | 450 | CH | CH | CH | CH | —CH₂— | 4-pyridyl | —CH₂— |
| 136 | 451 | CH | CH | CH | CH | —CH₂— | 4-pyridyl | —CH₂— |
| 137 | 452 | CH | CH | CH | CH | —CH₂— | 4-pyridyl | —CH₂— |
| 138 | 453 | CH | CH | CH | CH | —CH₂— | 4-pyridyl | —CH₂— |
| 139 | 454 | CH | CH | CH | CH | —CH₂— | 4-pyridyl | —CH₂— |
| 140 | 455 | CH | CH | CH | CH | —CH₂— | 4-pyridyl | bond |
| 141 | 456 | CH | CH | CH | CH | —CH₂— | 4-pyridyl | —CH₂— |
| 142 | 457 | CH | CH | CH | CH | —CH₂— | 4-pyridyl | —CH₂— |
| 143 | 458 | CH | CH | CF | CH | —CH₂— | 4-pyridyl | —CH₂— |
| 144 | 459 | CH | CH | CH | CF | —CH₂— | 4-pyridyl | —CH₂— |
| 145 | 460 | CH | CH | CF | CH | —CH₂— | 4-pyridyl | —CH₂— |
| 146 | 461 | CO CH₃ | CH | CH | CH | —CH₂— | 4-pyridyl | —CH₂— |
| 147 | 462 | CO CH₃ | CH | CH | CH | —CH₂— | 4-pyridyl | —CH₂— |
| 148 | 463 | CH | CO CH₃ | CO CH₃ | CH | —CH₂— | 4-pyridyl | —CH₂— |
| 149 | 464 | CH | CO CH₃ | CO CH₃ | CH | —CH₂— | 4-pyridyl | —CH₂— |
| 150 | 465 | CH | CH | CH | CCH₃ | —CH₂— | 4-pyridyl | —CH₂— |
| 151 | 466 | CH | CH | CH | CCH₃ | —CH₂— | 4-pyridyl | —CH₂— |
| 152 | 467 | CH | CH | C—CH₃ | CH | —CH₂— | 4-pyridyl | —CH₂— |
| 153 | 468 | CH | CH | C—CH₃ | CH | —CH₂— | 4-pyridyl | —CH₂— |
| 154 | 469 | CH | CH | CBr | CH | —CH₂— | 4-pyridyl | —CH₂— |
| 155 | 470 | CH | CH | CBr | CH | —CH₂— | 4-pyridyl | —CH₂— |
| 156 | 471 | N | CH | CH | CH | —CH₂— | 4-pyridyl | —CH₂— |
| 157 | 472 | N | CH | CH | CH | —CH₂— | 4-pyridyl | —CH₂— |
| 158 | 473 | N | CH | CH | CH | —CH₂— | 4-pyridyl | —CH₂— |
| 159 | 474 | N | CH | CH | CH | —CH₂— | 4-pyridyl | —CH₂— |
| 160 | 475 | N | CH | CH | CH | —CH₂— | 4-pyridyl | —CH₂— |
| 161 | 476 | N | CH | CH | CH | —CH₂— | 4-pyridyl | —CH₂— |
| 162 | 477 | N | CH | CH | CH | —CH₂— | 4-pyridyl | —CH₂— |
| 163 | 478 | N | CH | CH | CH | —CH₂— | 4-pyridyl | —CH₂— |
| 164 | 479 | N | CH | CH | CH | —CH₂— | 4-pyridyl | —CH₂— |

TABLE 1-continued

Compounds of general formula (I) (W = oxygen; compound 1-399 and 402-432 R₁ = hydrogen, compound 400 R₁ = methyl)

[I]

| | | G | F | E | D | Y | A-R₉ | X-B |
|---|---|---|---|---|---|---|---|---|
| 165 | 480 | N | CH | CH | CH | —CH₂— | 4-fluorophenyl | —CH₂— |
| 166 | 481 | N | CH | CH | CH | —CH₂— | 4-chlorophenyl | —CH₂— |
| 167 | 482 | N | CH | CH | CH | —CH₂— | 4-methoxyphenyl | —CH₂— |
| 168 | 483 | N | CH | CH | CH | | 5-isoquinolinyl | —CH₂— |
| 169 | 484 | CH | N | CH | CH | —CH₂— | 4-pyridyl | —CH₂— |
| 170 | 485 | CH | N | CH | CH | —CH₂— | 4-pyridyl | —CH₂— |
| 171 | 486 | CH | N | CH | CH | —CH₂— | 4-pyridyl | —CH₂— |
| 172 | 487 | CH | CH | CH | CH | —CH₂— | 4-fluorophenyl | —CH₂— |

TABLE 1-continued
Compounds of general formula (I) (W = oxygen; compound 1-399 and 402-432 R₁ = hydrogen, compound 400 R₁ = methyl)
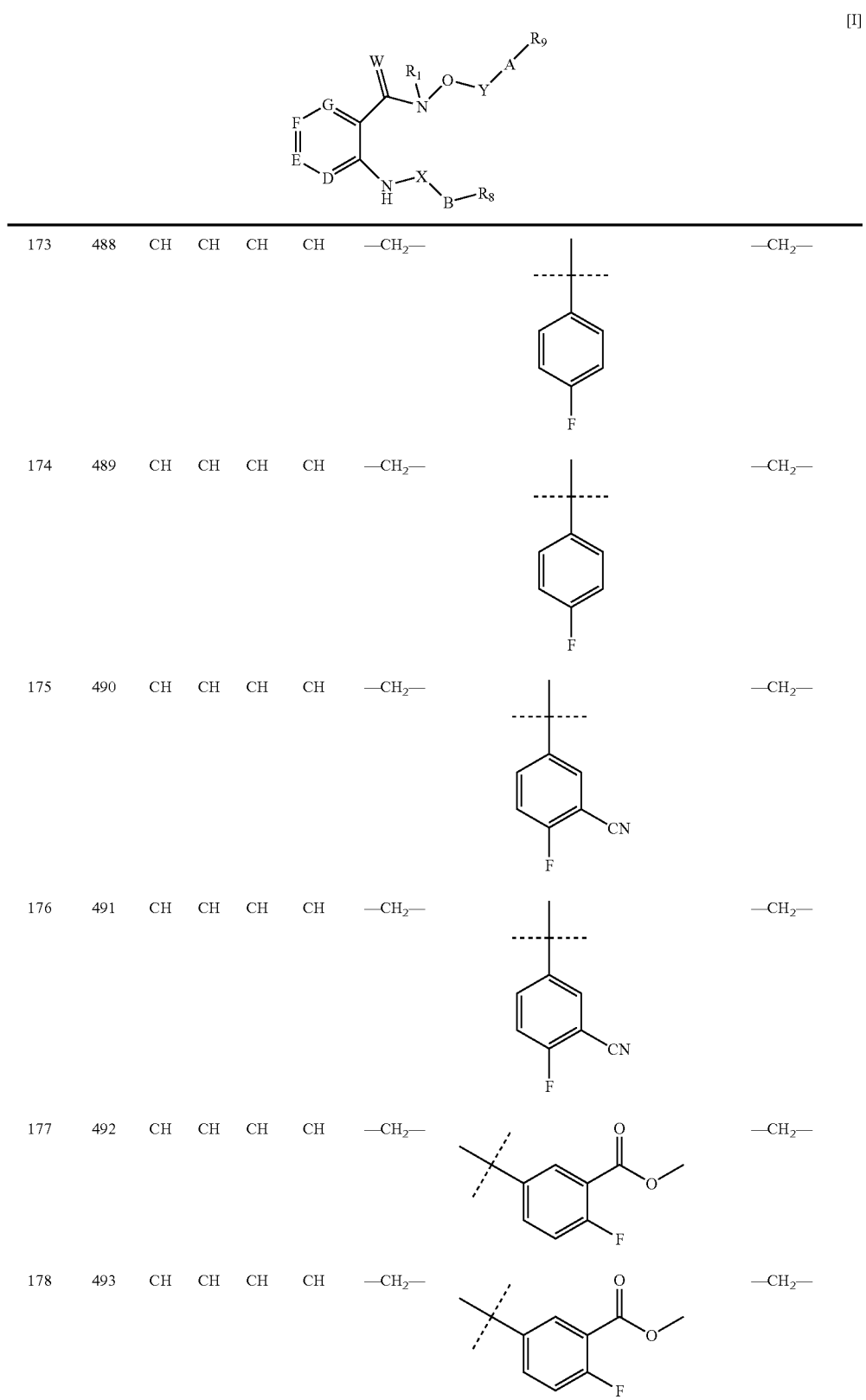
[I]
| | | D | E | F | G | X | B-R₈ | Y |
|---|---|---|---|---|---|---|---|---|
| 173 | 488 | CH | CH | CH | CH | —CH₂— | 4-F-C₆H₄ | —CH₂— |
| 174 | 489 | CH | CH | CH | CH | —CH₂— | 4-F-C₆H₄ | —CH₂— |
| 175 | 490 | CH | CH | CH | CH | —CH₂— | 3-CN-4-F-C₆H₃ | —CH₂— |
| 176 | 491 | CH | CH | CH | CH | —CH₂— | 3-CN-4-F-C₆H₃ | —CH₂— |
| 177 | 492 | CH | CH | CH | CH | —CH₂— | 3-CO₂Me-4-F-C₆H₃ | —CH₂— |
| 178 | 493 | CH | CH | CH | CH | —CH₂— | 3-CO₂Me-4-F-C₆H₃ | —CH₂— |

TABLE 1-continued

Compounds of general formula (I) (W = oxygen; compound 1-399 and 402-432 $R_1$ = hydrogen, compound 400 $R_1$ = methyl)

| | | D | E | F | G | X | B-R8 | Y |
|---|---|---|---|---|---|---|---|---|
| 179 | 494 | CH | CH | CH | CH | —CH$_2$— | methyl 2-fluoro-5-substituted benzoate | —CH$_2$— |
| 180 | 495 | CH | CH | CH | CH | —CH$_2$— | methyl 2-fluoro-5-substituted benzoate | —CH$_2$— |
| 181 | 496 | CH | CH | CH | CH | —CH$_2$— | 2-fluoro-5-substituted benzoic acid | —CH$_2$— |
| 182 | 497 | CH | CH | CH | CH | —CH$_2$— | 2-fluoro-5-substituted benzoic acid | —CH$_2$— |
| 183 | 498 | CH | CH | CH | CH | —CH$_2$— | 2-fluoro-5-substituted benzoic acid | —CH$_2$— |
| 184 | 499 | CH | CH | CH | CH | —CH$_2$— | N-(2-hydroxyethyl)-2-fluoro-5-substituted benzamide | —CH$_2$— |
| 185 | 500 | CH | CH | CH | CH | —CH$_2$— | N-(3-hydroxypropyl)-2-fluoro-5-substituted benzamide | —CH$_2$— |

TABLE 1-continued
Compounds of general formula (I) (W = oxygen; compound 1-399 and 402-432 R$_1$ = hydrogen, compound 400 R$_1$ = methyl)
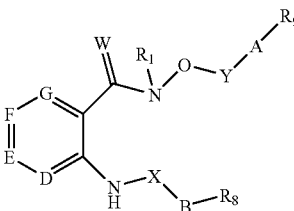
[I]
| 186 | 501 | CH | CH | CH | CH | —CH$_2$— | 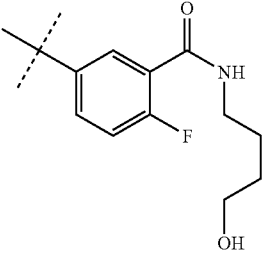 | —CH$_2$— |
| 187 | 502 | CH | CH | CH | CH | —CH$_2$— | 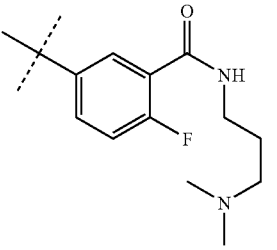 | —CH$_2$— |
| 188 | 503 | CH | CH | CH | CH | —CH$_2$— | 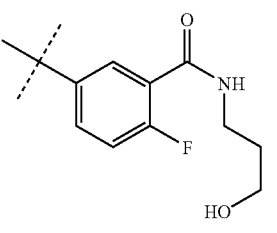 | —CH$_2$— |
| 189 | 504 | CH | CH | CH | CH | —CH$_2$— | 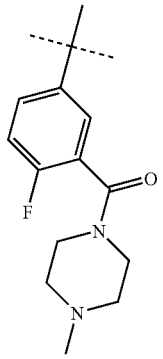 | —CH$_2$— |

TABLE 1-continued
Compounds of general formula (I) (W = oxygen; compound 1-399 and
402-432 R$_1$ = hydrogen, compound 400 R$_1$ = methyl)
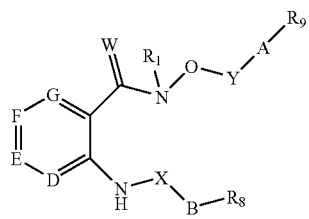
[I]
| | | D | E | F | G | X | B-R$_8$ | Y |
|---|---|---|---|---|---|---|---|---|
| 190 | 505 | CH | CH | CH | CH | —CH$_2$— | 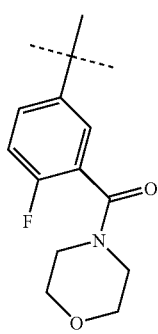 | —CH$_2$— |
| 191 | 506 | CH | CH | CH | CH | —CH$_2$— | 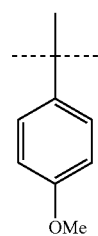 | —CH$_2$— |
| 192 | 507 | CH | CH | CH | CH | —CH$_2$— | 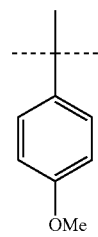 | —CH$_2$— |
| 193 | 508 | CH | CH | CH | CH | —CH$_2$— | 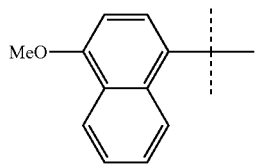 | —CH$_2$— |
| 194 | 509 | CH | CH | CH | CH | —CH$_2$— | 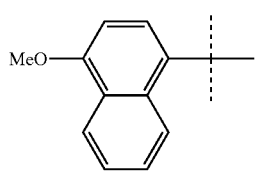 | —CH$_2$— |

TABLE 1-continued
Compounds of general formula (I) (W = oxygen; compound 1-399 and 402-432 $R_1$ = hydrogen, compound 400 $R_1$ = methyl)
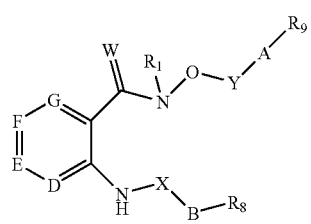
[I]
| | | | | | | | | |
|---|---|---|---|---|---|---|---|---|
| 195 | 510 | CH | CH | CH | CH | —CH$_2$— | 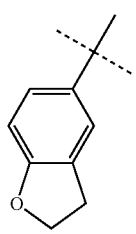 | —CH$_2$— |
| 196 | 511 | CH | CH | CH | CH | —CH$_2$— | 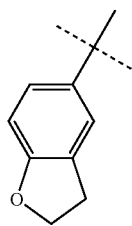 | —CH$_2$— |
| 197 | 512 | CH | CH | CH | CH | —CH$_2$— | 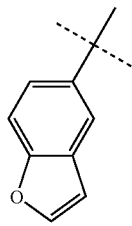 | —CH$_2$— |
| 198 | 513 | CH | CH | CH | CH | —CH$_2$— | 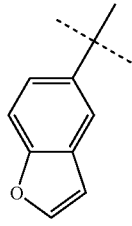 | —CH$_2$— |
| 199 | 514 | CH | CH | CH | CH | —CH$_2$— | 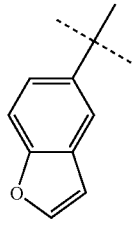 | —CH$_2$— |

TABLE 1-continued

Compounds of general formula (I) (W = oxygen; compound 1-399 and
402-432 R₁ = hydrogen, compound 400 R₁ = methyl)

[I]

| | | D | E | F | G | Y | A-R₉ | X |
|---|---|---|---|---|---|---|---|---|
| 200 | 515 | CH | CH | CH | CH | —CH₂— | 6-tert-butyl-coumarin | —CH₂— |
| 201 | 516 | CH | CH | CH | CH | —CH₂— | 4-cyanophenyl | —CH₂— |
| 202 | 517 | CH | CH | CH | CH | —CH₂— | 3,5-dichloropyridin-4-yl | —CH₂— |
| 203 | 518 | CH | CH | CH | CH | —CH₂— | 3,5-dichloropyridin-4-yl | —CH₂— |
| 204 | 519 | CH | CH | CH | CH | —CH₂— | 2-bromopyridin-4-yl | —CH₂— |
| 205 | 520 | CH | CH | CH | CH | —CH₂— | 2-hydroxypyridin-4-yl | —CH₂— |

TABLE 1-continued

Compounds of general formula (I) (W = oxygen; compound 1-399 and 402-432 R₁ = hydrogen, compound 400 R₁ = methyl)

[I]

| 206 | 521 | CH | CH | CH | CH | —CH₂— | 4-(2-aminopyridyl) | —CH₂— |
| 207 | 522 | CH | CH | CH | CH | —CH₂— | 4-(2-morpholinopyridyl) | —CH₂— |
| 208 | 523 | CH | CH | CH | CH | —CH₂— | 4-(2-methanesulfonamidopyridyl) | —CH₂— |
| 209 | 524 | CH | CH | CH | CH | —CH₂— | 4-(2-methanesulfonamidopyridyl) | —CH₂— |
| 210 | 525 | CH | CH | CH | CH | —CH₂— | 4-(2-(3-methylureido)pyridyl) | —CH₂— |

TABLE 1-continued
Compounds of general formula (I) (W = oxygen; compound 1-399 and 402-432 $R_1$ = hydrogen, compound 400 $R_1$ = methyl)
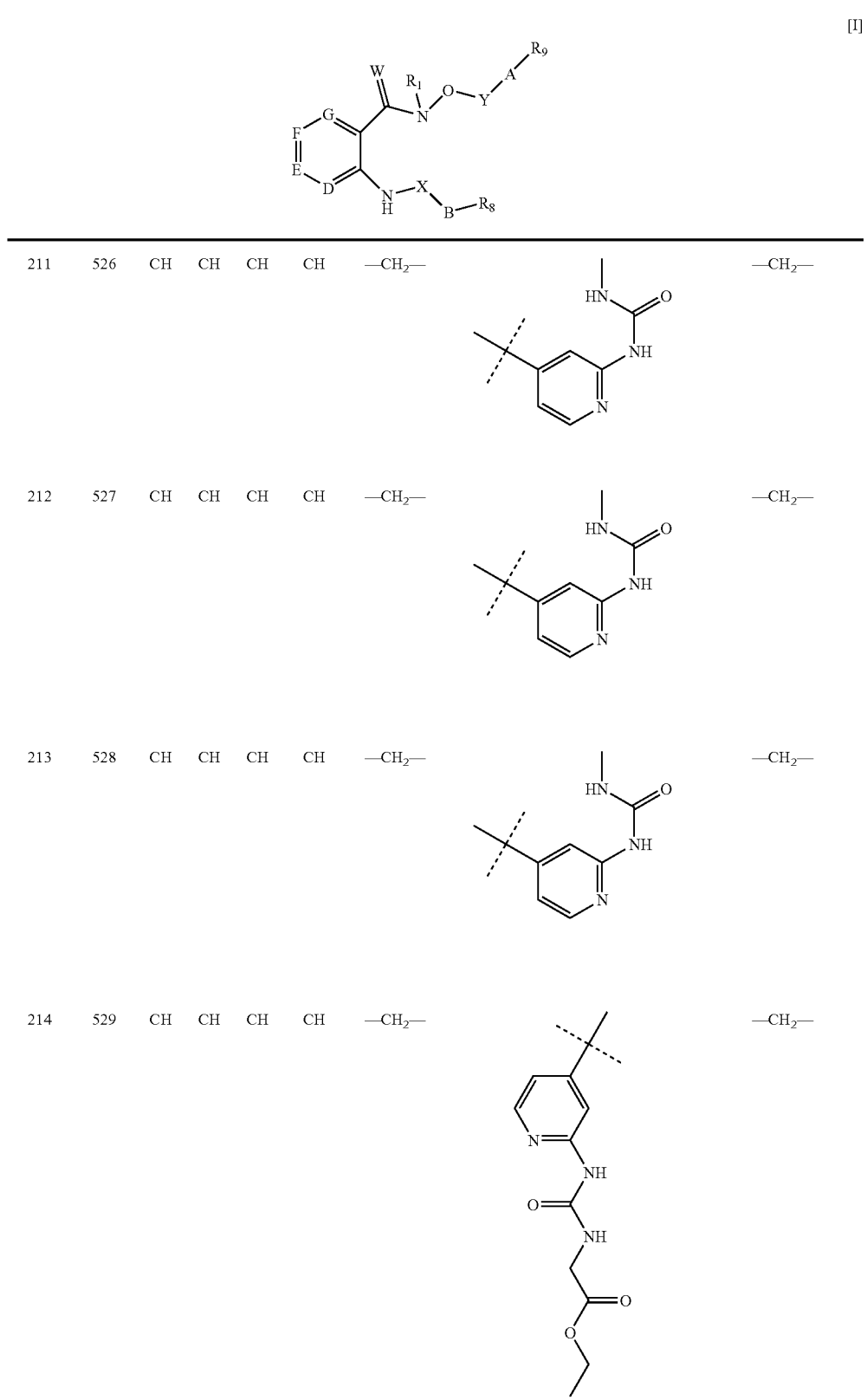
| 211 | 526 | CH | CH | CH | CH | —CH$_2$— | | —CH$_2$— |
| 212 | 527 | CH | CH | CH | CH | —CH$_2$— | | —CH$_2$— |
| 213 | 528 | CH | CH | CH | CH | —CH$_2$— | | —CH$_2$— |
| 214 | 529 | CH | CH | CH | CH | —CH$_2$— | | —CH$_2$— |

TABLE 1-continued

Compounds of general formula (I) (W = oxygen; compound 1-399 and 402-432 $R_1$ = hydrogen, compound 400 $R_1$ = methyl)

[I]

| | | | | | | | | |
|---|---|---|---|---|---|---|---|---|
| 215 | 530 | CH | CH | CH | CH | —CH$_2$— | (4-pyridyl-NH-C(O)-NH-CH$_2$-C(O)-O-ethyl) | —CH$_2$— |
| 216 | 531 | CH | CH | CH | CH | —CH$_2$— | (4-pyridyl-NH-C(O)-NH-CH$_2$-COOH) | —CH$_2$— |
| 217 | 532 | CH | CH | CH | CH | —CH$_2$— | (4-pyridyl-NH-C(O)-NH-CH$_2$-COOH) | —CH$_2$— |

TABLE 1-continued
Compounds of general formula (I) (W = oxygen; compound 1-399 and
402-432 R₁ = hydrogen, compound 400 R₁ = methyl)
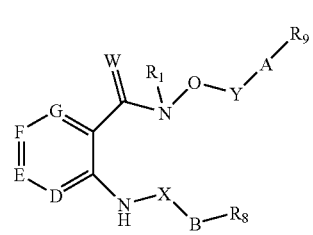
[I]
| 218 | 533 | CH | CH | CH | CH | —CH₂— | 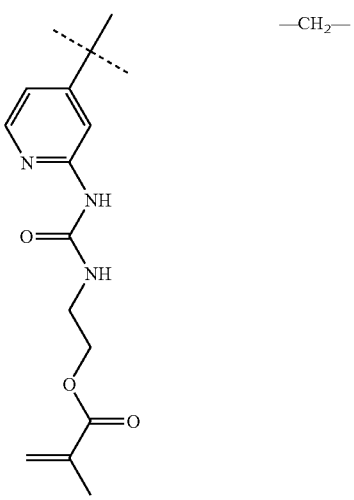 | —CH₂— |
| 219 | 534 | CH | CH | CH | CH | —CH₂— | 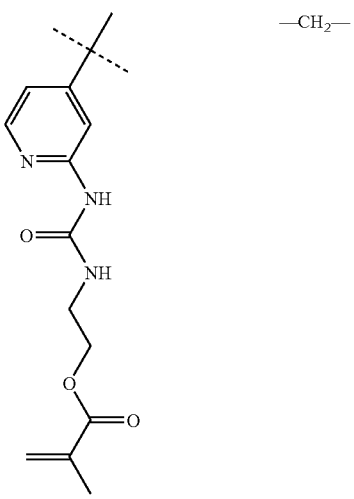 | —CH₂— |

TABLE 1-continued
Compounds of general formula (I) (W = oxygen; compound 1-399 and 402-432 $R_1$ = hydrogen, compound 400 $R_1$ = methyl)
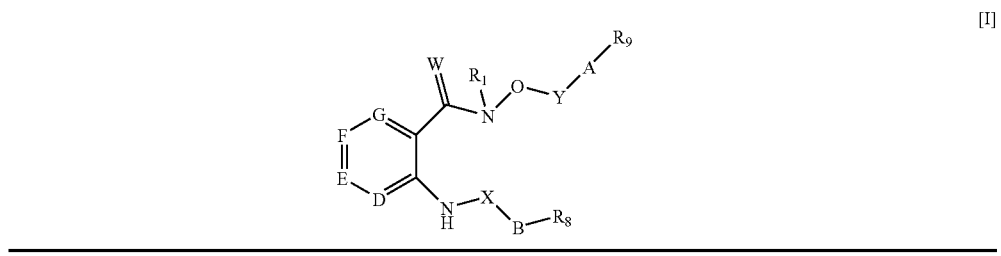
[I]
| | | | | | | | | |
|---|---|---|---|---|---|---|---|---|
| 220 | 535 | CH | CH | CH | CH | —CH$_2$— | 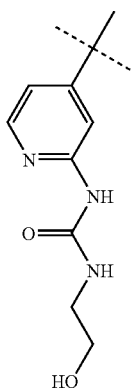 | —CH$_2$— |
| 221 | 536 | CH | CH | CH | CH | —CH$_2$— | 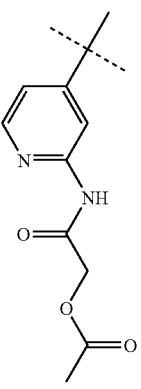 | —CH$_2$— |
| 222 | 537 | CH | CH | CH | CH | —CH$_2$— | | —CH$_2$— |

TABLE 1-continued
Compounds of general formula (I) (W = oxygen; compound 1-399 and 402-432 R₁ = hydrogen, compound 400 R₁ = methyl)
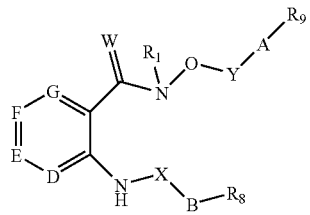
[I]
| | | D | E | F | G | X | B-R₈ | Y |
|---|---|---|---|---|---|---|---|---|
| 223 | 538 | CH | CH | CH | CH | —CH₂— | 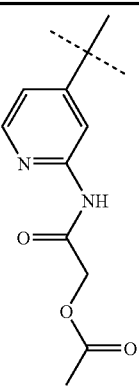 | —CH₂— |
| 224 | 539 | CH | CH | CH | CH | —CH₂— | 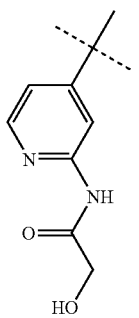 | —CH₂— |
| 225 | 540 | CH | CH | CH | CH | —CH₂— | 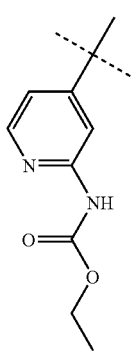 | —CH₂— |
| 226 | 541 | CH | CH | CH | CH | —CH₂— | 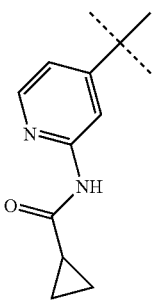 | —CH₂— |

TABLE 1-continued
Compounds of general formula (I) (W = oxygen; compound 1-399 and 402-432 R$_1$ = hydrogen, compound 400 R$_1$ = methyl)
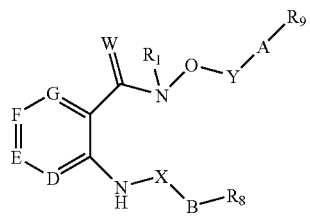
[I]
| | | | | | | | | |
|---|---|---|---|---|---|---|---|---|
| 227 | 542 | CH | CH | CH | CH | —CH$_2$— | 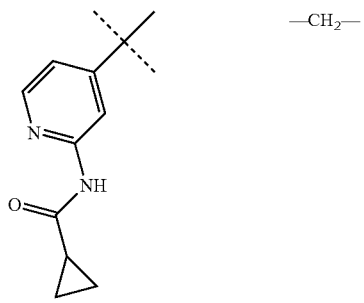 | —CH$_2$— |
| 228 | 543 | CH | CH | CH | CH | —CH$_2$— | 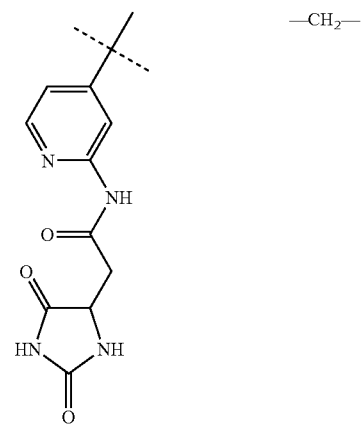 | —CH$_2$— |
| 229 | 544 | CH | CH | CH | CH | —CH$_2$— | 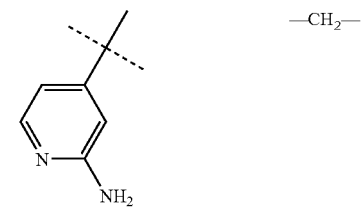 | —CH$_2$— |
| 230 | 545 | CH | CH | CH | CH | —CH$_2$— | 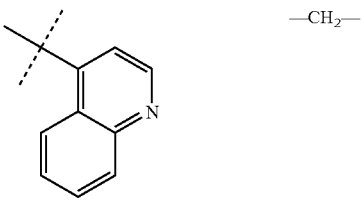 | —CH$_2$— |

TABLE 1-continued
Compounds of general formula (I) (W = oxygen; compound 1-399 and 402-432 $R_1$ = hydrogen, compound 400 $R_1$ = methyl)
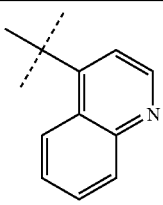
[I]
| 231 | 546 | CH | CH | CH | CH | —CH$_2$— | 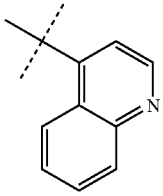 | —CH$_2$— |
| --- | --- | --- | --- | --- | --- | --- | --- | --- |
| 232 | 547 | CH | CH | CH | CH | —CH$_2$— | 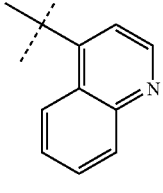 | —CH$_2$— |
| 233 | 548 | CH | CH | CH | CH | —CH$_2$— | 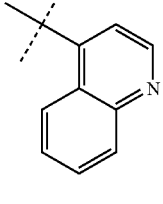 | —CH$_2$— |
| 234 | 549 | CH | CH | CH | CH | —CH$_2$— | 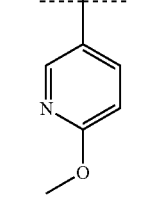 | —CH$_2$— |
| 235 | 550 | CH | CH | CH | CH | —CH$_2$— | 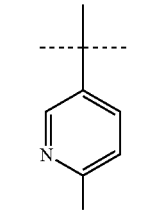 | —CH$_2$— |
| 236 | 551 | CH | CH | CH | CH | —CH$_2$— |  | —CH$_2$— |

TABLE 1-continued
Compounds of general formula (I) (W = oxygen; compound 1-399 and 402-432 R₁ = hydrogen, compound 400 R₁ = methyl)
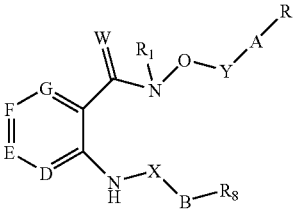
[I]
| | | D | E | F | G | X | B-R₈ | Y |
|---|---|---|---|---|---|---|---|---|
| 237 | 552 | CH | CH | CH | CH | —CH₂— | 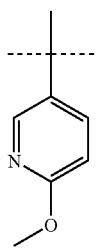 | —CH₂— |
| 238 | 553 | CH | CH | CH | CH | —CH₂— | 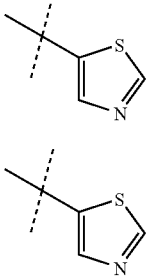 | —CH₂— |
| 239 | 554 | CH | CH | CH | CH | —CH₂— | 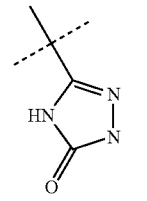 | —CH₂— |
| 240 | 555 | CH | CH | CH | CH | —CH₂— | 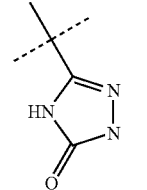 | —CH₂— |
| 241 | 556 | CH | CH | CH | CH | —CH₂— | 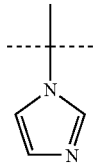 | —CH₂— |
| 242 | 557 | CH | CH | CH | CH | —(CH₂)₂— | 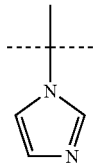 | —CH₂— |
| 243 | 558 | CH | CH | CH | CH | —(CH₂)₂— |  | —CH₂— |

TABLE 1-continued

Compounds of general formula (I) (W = oxygen; compound 1-399 and 402-432 R₁ = hydrogen, compound 400 R₁ = methyl)

[I]

| | | D | E | F | G | X | B-R₈ | Y |
|---|---|---|---|---|---|---|---|---|
| 244 | 559 | CH | CH | CH | CH | CH(CH₃)- | 4-pyridyl | —CH₂— |
| 245 | 560 | CH | CH | CH | CH | —CH₂— | 4-(t-Bu)-2-(3-methylureido)pyridyl | —CH₂— |
| 246 | 561 | CH | CH | CH | CH | —CH₂— | 4-(t-Bu)-2-(methoxyacetamido)pyridyl | —CH₂— |
| 247 | 562 | CH | CH | CH | CH | —CH₂— | 5-(t-Bu)-2-oxo-1H-pyridyl | —CH₂— |
| 248 | 563 | CH | CH | CH | CH | —CH₂— | 4-(tetrahydropyran-4-yl)methyl | |
| 250 | 564 | CH | CH | CH | CH | —CH₂— | 4-pyridyl | —CH₂— |
| 251 | 565 | CH | CH | CH | CH | —CH₂— | 4-pyridyl | —CH₂— |
| 252 | 566 | CH | CH | CH | CH | —CH₂— | 4-pyridyl | —CH₂— |
| 253 | 567 | CH | CH | CH | CH | —CH₂— | 4-pyridyl | —CH₂— |
| 254 | 568 | CH | CH | CH | CH | —CH₂— | 4-pyridyl | —CH₂— |
| 255 | 569 | CH | CH | CH | CH | —CH₂— | 4-pyridyl | —CH₂— |
| 256 | 570 | CH | CH | CH | CH | —CH₂— | 4-pyridyl | —CH₂— |
| 257 | 571 | CH | CH | CH | CH | —CH₂— | 4-pyridyl | —CH₂— |
| 258 | 572 | CH | CH | CH | CH | —CH₂— | 4-pyridyl | —CH₂— |
| 259 | 573 | CH | CH | CH | CH | —CH₂— | 4-pyridyl | —CH₂— |
| 260 | 574 | CH | CH | CH | CH | —CH₂— | 4-pyridyl | —CH₂— |

TABLE 1-continued

Compounds of general formula (I) (W = oxygen; compound 1-399 and 402-432 $R_1$ = hydrogen, compound 400 $R_1$ = methyl)

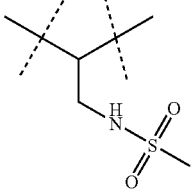

[I]

| | | | | | | | | |
|---|---|---|---|---|---|---|---|---|
| 261 | 575 | CH | CH | CH | CH | —CH$_2$— | 4-pyridyl | —CH$_2$— |
| 262 | 576 | CH | CH | CH | CH | —CH$_2$— | 4-pyridyl | —CH$_2$— |
| 263 | 577 | CH | CH | CH | CH | —CH$_2$— | 4-pyridyl | —CH$_2$— |
| 264 | 578 | CH | CH | CH | CH | —CH$_2$— | 4-pyridyl | —CH$_2$— |
| 265 | 579 | CH | CH | CH | CH | —CH$_2$— | 4-pyridyl | —CH$_2$— |
| 266 | 580 | CH | CH | CH | CH | —CH$_2$— | 4-pyridyl | —CH$_2$— |
| 267 | 581 | CH | CH | CH | CH | —CH$_2$— | 4-pyridyl | —CH$_2$— |
| 268 | 582 | CH | CH | CH | CH | —CH$_2$— | 4-pyridyl | —CH$_2$— |
| 269 | 583 | CH | CH | CH | CH | —CH$_2$— | 4-pyridyl | —CH$_2$— |
| 270 | 584 | CH | CH | CH | CH | —CH$_2$— | 4-pyridyl | —CH$_2$— |
| 271 | 585 | CH | CH | CH | CH | —CH$_2$— | 4-pyridyl | —CH$_2$— |
| 272 | 586 | CH | CH | CH | CH | —CH$_2$— | 4-pyridyl | —CH$_2$— |
| 273 | 587 | CH | CH | CH | CH | —CH$_2$— | 4-pyridyl | —CH$_2$— |
| 274 | 588 | CH | CH | CH | CH | —CH$_2$— | 4-pyridyl | —CH$_2$— |
| 275 | 589 | CH | CH | CH | CH | —CH$_2$— | 4-pyridyl | (neopentyl-CH$_2$-NH-S(O)$_2$-CH$_3$) |
| 276 | 590 | CH | CH | CH | CH | —CH$_2$— | 4-pyridyl | —CH$_2$— |
| 277 | 591 | CH | CH | CH | CH | —CH$_2$— | 4-pyridyl | —CH$_2$— |
| 278 | 592 | CH | CH | CH | CH | —CH$_2$— | 4-pyridyl | —CH$_2$— |
| 279 | 593 | CH | CH | CH | CH | —CH$_2$— | 4-pyridyl | —CH$_2$— |
| 280 | 594 | CH | CH | CH | CH | —CH$_2$— | 4-pyridyl | —CH$_2$— |
| 281 | 595 | CH | CH | CH | CH | —CH$_2$— | 4-pyridyl | —CH$_2$— |
| 282 | 596 | CH | CH | CH | CH | —CH$_2$— | 4-pyridyl | —CH$_2$— |
| 283 | 597 | CH | CH | CH | CH | —CH$_2$— | 4-pyridyl | —CH$_2$— |
| 284 | 598 | CH | CH | CH | CH | —CH$_2$— | 4-pyridyl | —CH$_2$— |
| 285 | 599 | CH | CH | CH | CH | —CH$_2$— | 4-pyridyl | —CH$_2$— |
| 286 | 600 | CH | CH | CH | CH | —CH$_2$— | 4-pyridyl | —(CH$_2$)$_2$—O— |
| 287 | 601 | CH | CH | CH | CH | —CH$_2$— | 4-pyridyl | —(CH$_2$)$_3$—O—CH$_2$— |
| 288 | 602 | CH | CH | CH | CH | —CH$_2$— | 4-pyridyl | —(CH$_2$)$_2$—O—CH$_2$— |
| 289 | 603 | CH | CH | CH | CH | —CH$_2$— | 4-pyridyl | —CH$_2$—CH(OH)—CH$_2$—O— |
| 290 | 604 | CH | CH | CH | CH | —CH$_2$— | 4-pyridyl | —(CH$_2$)$_3$—NH—C(O)— |
| 291 | 605 | CH | CH | CH | CH | —CH$_2$— | 4-pyridyl | —(CH$_2$)$_4$—NH—C(O)— |
| 292 | 606 | CH | CH | CH | CH | —CH$_2$— | 4-pyridyl | —CH$_2$— |
| 293 | 607 | CH | CH | CH | CH | —CH$_2$— | 4-pyridyl | —CH$_2$— |
| 294 | 608 | CH | CH | CH | CH | —CH$_2$— | 4-pyridyl | —CH$_2$— |
| 295 | 609 | CH | CH | CH | CH | —CH$_2$— | 4-pyridyl | —CH$_2$— |
| 296 | 610 | CH | CH | CH | CH | —CH$_2$— | 4-pyridyl | —CH$_2$— |
| 297 | 611 | CH | CH | CH | CH | —CH$_2$— | 4-pyridyl | —CH$_2$— |
| 298 | 612 | CH | CH | CH | CH | —CH$_2$— | 4-pyridyl | —CH$_2$— |
| 299 | 613 | CH | CH | CH | CH | —CH$_2$— | 4-pyridyl | —CH$_2$— |
| 300 | 614 | CH | CH | CH | CH | —CH$_2$— | 4-pyridyl | —CH$_2$— |
| 301 | 615 | CH | CH | CH | CH | —CH$_2$— | 4-pyridyl | —(CH$_2$)$_2$—NH—CH$_2$— |
| 302 | 616 | CH | CH | CH | CH | —CH$_2$— | 4-pyridyl | —(CH$_2$)$_4$—NH—CH$_2$— |
| 303 | 617 | CH | CH | CH | CH | —CH$_2$— | 4-pyridyl | —CH$_2$— |
| 304 | 618 | CH | CH | CH | CH | —CH$_2$— | 4-pyridyl | —CH$_2$— |
| 305 | 619 | CH | CH | CH | CH | —CH$_2$— | 4-pyridyl | —CH$_2$— |
| 306 | 620 | CH | CH | CH | CH | —CH$_2$— | 4-pyridyl | —CH$_2$— |
| 307 | 621 | CH | CH | CH | CH | —CH$_2$— | 4-pyridyl | —CH$_2$— |
| 308 | 622 | CH | CH | CH | CH | —CH$_2$— | 4-pyridyl | —CH$_2$— |
| 309 | 623 | CH | CH | CH | CH | —CH$_2$— | 4-pyridyl | —CH$_2$— |

TABLE 1-continued

Compounds of general formula (I) (W = oxygen; compound 1-399 and 402-432 $R_1$ = hydrogen, compound 400 $R_1$ = methyl)

[I]

|     |     | D   | E   | F   | G   | X    | B-R8             | Y    |
| --- | --- | --- | --- | --- | --- | ---- | ---------------- | ---- |
| 310 | 624 | CH  | CH  | CH  | CH  | —CH₂— | 4-pyridyl       | —CH₂— |
| 311 | 625 | CH  | CH  | CH  | CH  | —CH₂— | 4-pyridyl       | —CH₂— |
| 312 | 626 | CH  | CH  | CH  | CH  | —CH₂— | 4-pyridyl       | —CH₂— |
| 313 | 627 | CH  | CH  | CH  | CH  | —CH₂— | 4-pyridyl       | —CH₂— |
| 314 | 628 | CH  | CH  | CH  | CH  | —CH₂— | 4-pyridyl       | —CH₂— |
| 315 | 629 | CH  | CH  | CH  | CH  | —CH₂— | 4-pyridyl       | —CH₂— |
| 316 | 630 | CH  | CH  | CH  | CH  | —CH₂— | 4-pyridyl       | bond |
| 317 | 631 | CH  | CH  | CH  | CH  | —CH₂— | 4-pyridyl       | —CH₂— |
| 318 | 632 | CH  | CH  | CH  | CH  | —CH₂— | 4-pyridyl       | —CH₂— |
| 319 | 633 | CH  | CH  | CH  | CH  | —CH₂— | 4-pyridyl       | —CH₂— |
| 320 | 634 | CH  | CH  | CH  | CH  | —CH₂— | 4-pyridyl       | —CH₂— |
| 321 | 635 | CH  | CH  | CH  | CH  | —CH₂— | 4-pyridyl       | bond |
| 322 | 636 | CH  | CH  | CH  | CH  | —CH₂— | 4-pyridyl       | bond |
| 323 | 637 | CH  | CH  | CH  | CH  | —CH₂— | 4-pyridyl       | —CH₂— |
| 324 | 638 | CH  | CH  | CH  | CH  | —CH₂— | 4-pyridyl       | —CH₂— |
| 325 | 639 | CH  | CH  | CH  | CH  | —CH₂— | 4-pyridyl       | —CH₂— |
| 326 | 640 | CH  | CH  | CH  | CH  | —CH₂— | 4-pyridyl       | —CH₂— |
| 327 | 641 | CH  | CH  | CH  | CH  | —CH₂— | 4-pyridyl       | —CH₂— |
| 328 | 642 | CH  | CH  | CH  | CH  | —CH₂— | 4-pyridyl       | —CH₂— |
| 329 | 643 | CH  | CH  | CH  | CH  | —CH₂— | 4-pyridyl       | —CH₂— |
| 330 | 644 | CH  | CH  | CH  | CH  | —CH₂— | 4-pyridyl       | —CH₂— |
| 331 | 645 | CH  | CH  | CH  | CH  | —CH₂— | 4-pyridyl       | —CH₂— |
| 332 | 646 | CH  | CH  | CH  | CH  | —CH₂— | 4-pyridyl       | —CH₂— |
| 333 | 647 | CH  | CMe | CH  | CH  | —CH₂— | 4-pyridyl       | —CH₂— |
| 334 | 648 | N   | CH  | CH  | CH  | —CH₂— | 4-pyridyl       | —CH₂— |
| 335 | 649 | N   | CH  | CH  | CH  | —CH₂— | 4-pyridyl       | —CH₂— |
| 336 | 650 | N   | CH  | CH  | CH  | —CH₂— | 4-pyridyl       | —CH₂— |
| 337 | 651 | N   | CH  | CH  | CH  | —CH₂— | 2-chlorophenyl  | —CH₂— |
| 338 | 652 | N   | CH  | CH  | CH  | —CH₂— | 2-chlorophenyl  | —CH₂— |
| 339 | 653 | N   | CH  | CH  | CH  | —CH₂— | 2,4-dichlorophenyl | —CH₂— |
| 340 | 654 | N   | CH  | CH  | CH  | —CH₂— | 3,5-dichlorophenyl | —CH₂— |

TABLE 1-continued

Compounds of general formula (I) (W = oxygen; compound 1-399 and 402-432 $R_1$ = hydrogen, compound 400 $R_1$ = methyl)

[I]

| | | | | | | | | |
|---|---|---|---|---|---|---|---|---|
| 341 | 655 | N | CH | CH | CH | —CH$_2$— | 2-methoxyphenyl (iPr) | —CH$_2$— |
| 342 | 656 | N | CH | CH | CH | —CH$_2$— | 2-methoxyphenyl (iPr) | —CH$_2$— |
| 343 | 567 | N | CH | CH | CH | —(CH$_2$)$_2$— | 4-pyridyl | —CH$_2$— |
| 344 | 658 | N | CH | CH | CH | bond | 1,2,4-triazol-4-yl | —CH$_2$— |
| 345 | 659 | N | CH | CH | CH | —CH$_2$— | 1-Boc-piperidin-4-yl | —CH$_2$— |
| 346 | 660 | CH | CH | CH | CH | —CH$_2$— | 2-fluoro-5-(benzyloxyaminocarbonyl)phenyl | —CH$_2$— |

TABLE 1-continued

Compounds of general formula (I) (W = oxygen; compound 1-399 and 402-432 R₁ = hydrogen, compound 400 R₁ = methyl)

[I]

| | | | | | | | | | |
|---|---|---|---|---|---|---|---|---|---|
| 347 | 661 | CH | CH | CH | CH | —CH₂— | 3-cyano-4-methoxyphenyl (tert-butyl) | | —CH₂— |
| 348 | 662 | CH | CH | CH | CH | —CH₂— | 4-(methylsulfonyl)phenyl | | —CH₂— |
| 349 | 663 | CH | CH | CH | CH | —CH₂— | 4-((methoxyimino)methyl)phenyl | | —CH₂— |
| 350 | 664 | CH | CH | CH | CH | —CH₂— | 2,6-dichloropyridin-4-yl | | —CH₂— |
| 351 | 665 | CH | CH | CH | CH | —CH₂— | 3-pyridyl | | —CH₂— |
| 352 | 666 | CH | CH | CH | CH | —CH₂— | 3-pyridyl | | —CH₂— |
| 353 | 667 | CH | CH | CH | CH | —CH₂— | 2-pyridyl | | —CH₂— |
| 354 | 668 | CH | CH | CH | CH | —CH₂— | 2-pyridyl | | —CH₂— |
| 355 | 669 | CH | CH | CH | CH | —CH₂— | 3-bromopyridin-2-yl | | —CH₂— |

TABLE 1-continued
Compounds of general formula (I) (W = oxygen; compound 1-399 and 402-432 R₁ = hydrogen, compound 400 R₁ = methyl)
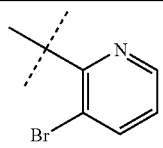
| | | | | | | | | |
|---|---|---|---|---|---|---|---|---|
| 356 | 670 | CH | CH | CH | CH | —CH₂— | 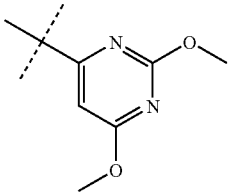 | —CH₂— |
| 357 | 671 | CH | CH | CH | CH | —CH₂— | 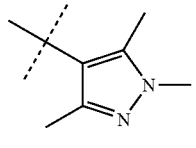 | —CH₂— |
| 358 | 672 | CH | CH | CH | CH | —CH₂— | 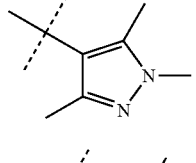 | —CH₂— |
| 359 | 673 | CH | CH | CH | CH | —CH₂— | 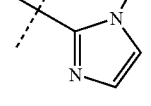 | —CH₂— |
| 360 | 674 | CH | CH | CH | CH | —CH₂— | 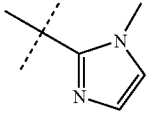 | —CH₂— |
| 361 | 675 | CH | CH | CH | CH | —CH₂— | 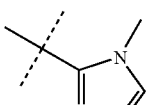 | —CH₂— |
| 362 | 676 | CH | CH | CH | CH | —CH₂— | 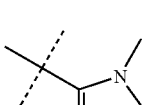 | —CH₂— |
| 363 | 677 | CH | CH | CH | CH | —CH₂— | 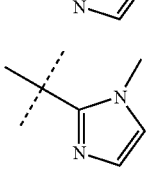 | —CH₂— |
| 364 | 678 | CH | CH | CH | CH | —CH₂— |  | —CH₂— |

TABLE 1-continued

Compounds of general formula (I) (W = oxygen; compound 1-399 and 402-432 $R_1$ = hydrogen, compound 400 $R_1$ = methyl)

| | | D | E | F | G | X | B-R$_8$ | Y |
|---|---|---|---|---|---|---|---|---|
| 365 | 679 | CH | CH | CH | CH | —CH$_2$— | 1-methylimidazol-2-yl | —CH$_2$— |
| 366 | 680 | CH | CH | CH | CH | —CH$_2$— | 2-ethylimidazol-5-yl | —CH$_2$— |
| 367 | 681 | CH | CH | CH | CH | —CH$_2$— | 2-ethylimidazol-5-yl | —CH$_2$— |
| 368 | 682 | CH | CH | CH | CH | —CH$_2$— | (S)-5-oxopyrrolidin-2-yl | —CH$_2$— |
| 369 | 683 | CH | CH | CH | CH | —CH$_2$— | 3-ethyl-4,5-dihydroisoxazol-5-yl | —CH$_2$— |
| 370 | 684 | CH | CH | CH | CH | —CH$_2$— | 3-propyl-4,5-dihydroisoxazol-5-yl | —CH$_2$— |
| 371 | 685 | CH | CH | CH | CH | —CH$_2$— | 5-(ethoxycarbonyl)-3-methyl-4,5-dihydroisoxazol-5-yl | —CH$_2$— |

TABLE 1-continued

Compounds of general formula (I) (W = oxygen; compound 1-399 and 402-432 $R_1$ = hydrogen, compound 400 $R_1$ = methyl)

| | | | | | | | | |
|---|---|---|---|---|---|---|---|---|
| 372 | 686 | CH | CH | CH | CH | —CH$_2$— | ethyl ester, ethyl-isoxazoline | —CH$_2$— |
| 373 | 687 | CH | CH | CH | CH | —CH$_2$— | ethyl ester, propyl-isoxazoline | —CH$_2$— |
| 374 | 688 | CH | CH | CH | CH | —CH$_2$— | methyl-isoxazoline | —CH$_2$— |
| 375 | 689 | CH | CH | CH | CH | —CH$_2$— | ethyl-isoxazoline | —CH$_2$— |
| 376 | 690 | CH | CH | CH | CH | —CH$_2$— | propyl-isoxazoline | —CH$_2$— |
| 377 | 691 | CH | CH | CH | CH | —CH$_2$— | ethyl ester, methyl-isoxazoline | —CH$_2$— |

TABLE 1-continued

Compounds of general formula (I) (W = oxygen; compound 1-399 and 402-432 R₁ = hydrogen, compound 400 R₁ = methyl)

| | | | | | | | | |
|---|---|---|---|---|---|---|---|---|
| 378 | 692 | CH | CH | CH | CH | —CH₂— | (ethyl ester, ethyl-isoxazoline) | —CH₂— |
| 379 | 693 | CH | CH | CH | CH | —CH₂— | (ethyl ester, propyl-isoxazole) | —CH₂— |
| 380 | 694 | CH | CH | CH | CH | —CH₂— | (methyl-isoxazole) | —CH₂— |
| 381 | 695 | CH | CH | CH | CH | —CH₂— | (ethyl-isoxazole) | —CH₂— |
| 382 | 696 | CH | CH | CH | CH | —CH₂— | (propyl-isoxazole) | —CH₂— |
| 383 | 697 | CH | CH | CH | CH | —CH₂— | (dimethyl-isoxazoline) | —CH₂— |

TABLE 1-continued

Compounds of general formula (I) (W = oxygen; compound 1-399 and 402-432 R$_1$ = hydrogen, compound 400 R$_1$ = methyl)

| | | | | | | | | |
|---|---|---|---|---|---|---|---|---|
| 384 | 698 | CH | CH | CH | CH | —CH$_2$— | (5-methyl-3-ethyl-4,5-dihydroisoxazol-5-yl) | —CH$_2$— |
| 385 | 699 | CH | CH | CH | CH | —CH$_2$— | (5-methyl-3-propyl-4,5-dihydroisoxazol-5-yl) | —CH$_2$— |
| 386 | 700 | CH | CH | CH | CH | —CH$_2$— | (3-methyl-4,5-dihydroisoxazol-5-yl) | —CH$_2$— |
| 387 | 701 | CH | CH | CH | CH | —(CH$_2$)$_2$— | (5-tert-butyl-3-methyl-4,5-dihydroisoxazol-5-yl) | —CH$_2$— |
| 388 | 702 | CH | CH | CH | CH | —(CH$_2$)$_2$— | (5-tert-butyl-3-methyl-4,5-dihydroisoxazol-5-yl) | —CH$_2$— |
| 389 | 703 | CH | CH | CH | CH | —(CH$_2$)$_2$— | (5-methyl-3-ethyl-4,5-dihydroisoxazol-5-yl) | —CH$_2$— |

TABLE 1-continued
Compounds of general formula (I) (W = oxygen; compound 1-399 and 402-432 R$_1$ = hydrogen, compound 400 R$_1$ = methyl)
[I]
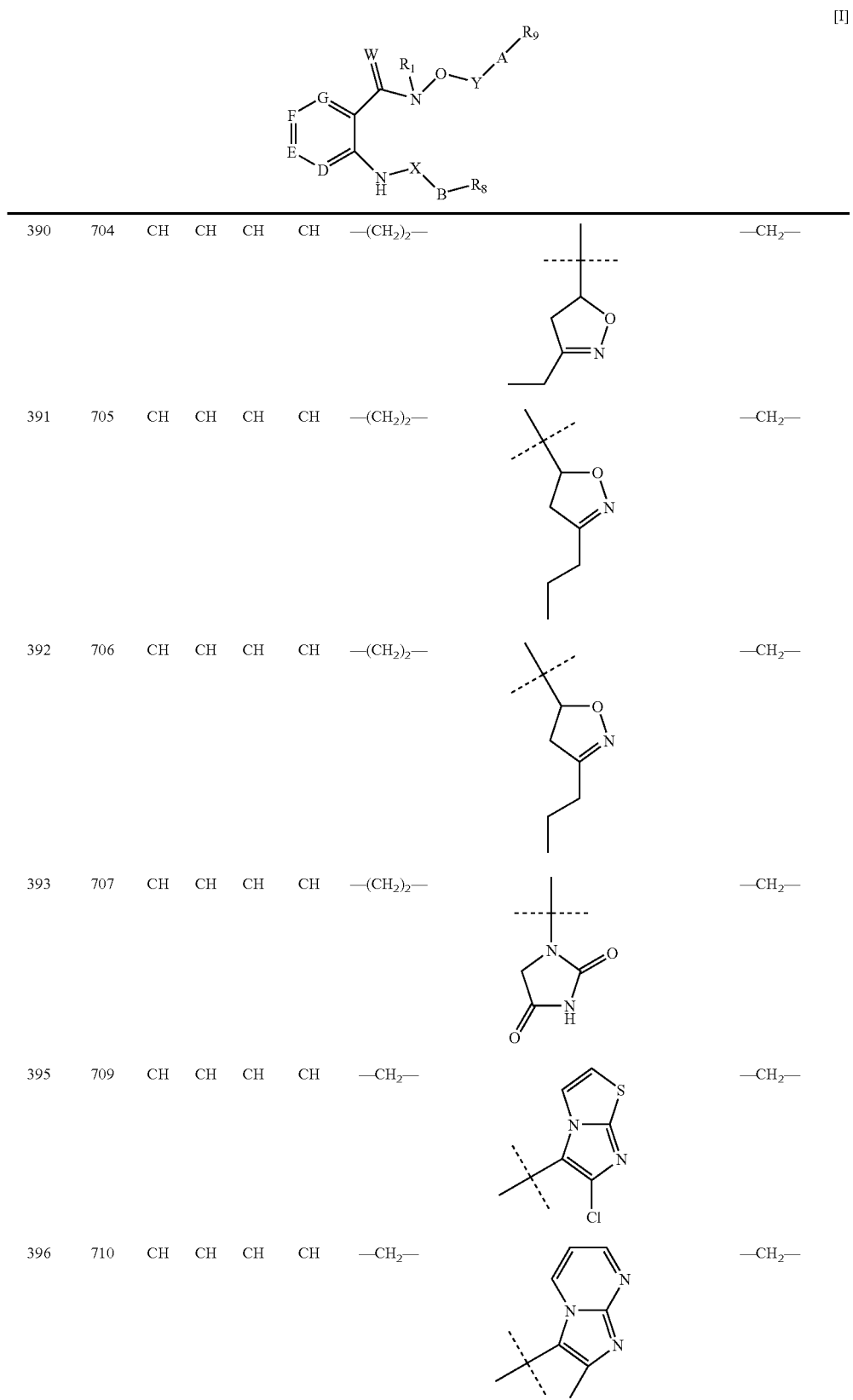
| | | D | E | F | G | X | B—R$_8$ | Y |
|---|---|---|---|---|---|---|---|---|
| 390 | 704 | CH | CH | CH | CH | —(CH$_2$)$_2$— | | —CH$_2$— |
| 391 | 705 | CH | CH | CH | CH | —(CH$_2$)$_2$— | | —CH$_2$— |
| 392 | 706 | CH | CH | CH | CH | —(CH$_2$)$_2$— | | —CH$_2$— |
| 393 | 707 | CH | CH | CH | CH | —(CH$_2$)$_2$— | | —CH$_2$— |
| 395 | 709 | CH | CH | CH | CH | —CH$_2$— | | —CH$_2$— |
| 396 | 710 | CH | CH | CH | CH | —CH$_2$— | | —CH$_2$— |

TABLE 1-continued
Compounds of general formula (I) (W = oxygen; compound 1-399 and 402-432 $R_1$ = hydrogen, compound 400 $R_1$ = methyl)
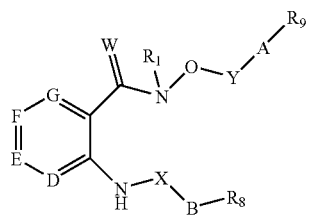
[I]
| | | | | | | | | |
|---|---|---|---|---|---|---|---|---|
| 397 | 711 | CH | CH | CH | CH | —(CH$_2$)$_2$—O—CH$_2$— | phenyl | —CH$_2$— |
| 398 | 712 | CH | CH | CH | CH | —C=O | 4-pyridyl | —CH$_2$— |
| 399 | 713 | CH | CH | CH | CH | —C=O—(CH$_2$)— | 4-pyridyl | —CH$_2$— |
| 400 | 714 | CH | CH | CH | CH | —CH$_2$— | 4-pyridyl | —CH$_2$— |
| 402 | 715 | CH | CH | CH | CH | —CH$_2$— | 4-pyridyl | —CH$_2$— |
| 403 | 716 | CH | CH | CH | CH | —CH$_2$— | 4-pyridyl | —CH$_2$— |
| 404 | 717 | CH | CH | CH | CH | —CH$_2$— | 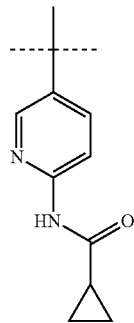 | —CH$_2$— |
| 405 | 718 | CH | CH | CH | CH | —CH$_2$— | 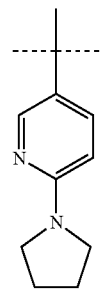 | —CH$_2$— |
| 406 | 719 | CH | CH | CH | CH | —CH$_2$— | 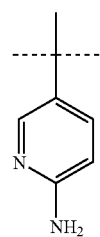 | —CH$_2$— |

TABLE 1-continued
Compounds of general formula (I) (W = oxygen; compound 1-399 and 402-432 R₁ = hydrogen, compound 400 R₁ = methyl)
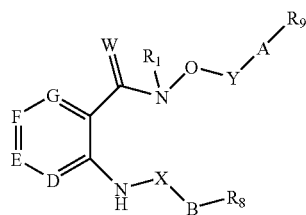
[I]
| | | | | | | | | |
|---|---|---|---|---|---|---|---|---|
| 407 | 720 | CH | CH | CH | CH | —CH₂— | 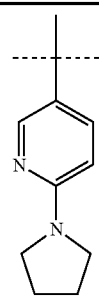 | —CH₂— |
| 408 | 721 | CH | CH | CH | CH | —CH₂— | 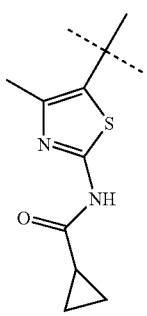 | —CH₂— |
| 409 | 722 | CH | CH | CH | CH | —CH₂— | 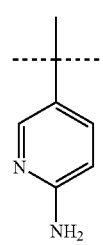 | —CH₂— |
| 410 | 723 | CH | CH | CH | CH | —CH₂— | 4-pyridyl | —CH₂— |
| 411 | 724 | CH | CH | CH | CH | —CH₂— | 4-pyridyl | —CH₂— |
| 412 | 725 | CH | CH | CH | CH | —CH₂— | 4-pyridyl | —CH₂— |
| 413 | 726 | CH | CH | CH | CH | —CH₂— | 4-pyridyl | —CH₂— |
| 414 | 727 | CH | CH | CH | CH | —CH₂— | 4-pyridyl | —CH₂— |
| 415 | 728 | CH | CH | CH | CH | —CH₂— | 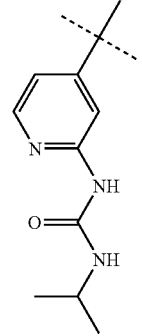 | —CH₂— |

TABLE 1-continued
Compounds of general formula (I) (W = oxygen; compound 1-399 and 402-432 $R_1$ = hydrogen, compound 400 $R_1$ = methyl)
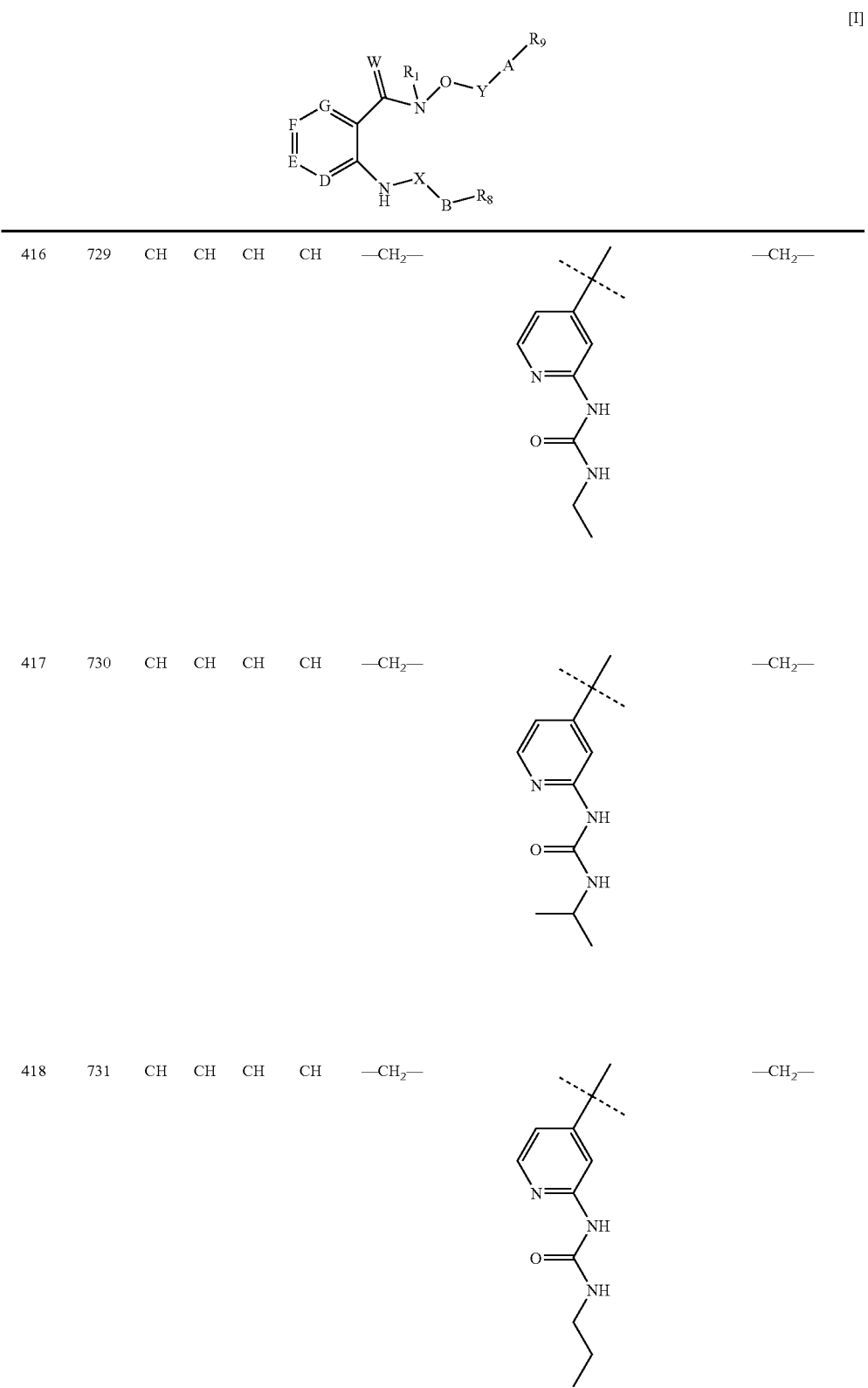
| | | | | | | | | |
|---|---|---|---|---|---|---|---|---|
| 416 | 729 | CH | CH | CH | CH | —CH$_2$— | | —CH$_2$— |
| 417 | 730 | CH | CH | CH | CH | —CH$_2$— | | —CH$_2$— |
| 418 | 731 | CH | CH | CH | CH | —CH$_2$— | | —CH$_2$— |

TABLE 1-continued
Compounds of general formula (I) (W = oxygen; compound 1-399 and 402-432 R₁ = hydrogen, compound 400 R₁ = methyl)
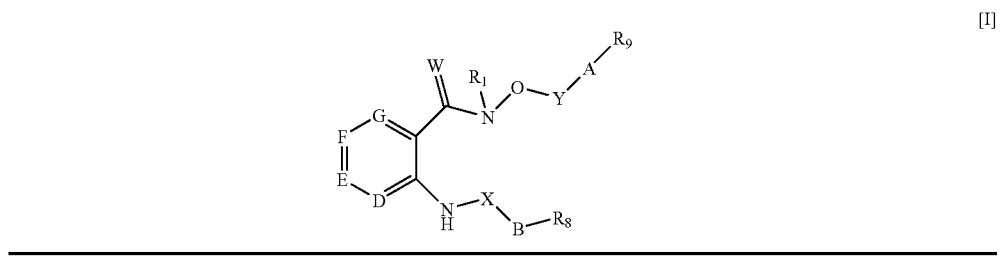
[I]
| 419 | 732 | CH | CH | CH | CH | —CH₂— | 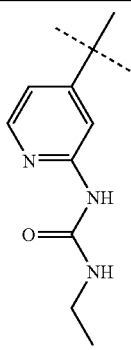 | —CH₂— |
| 420 | 733 | CH | CH | CH | CH | —CH₂— | 4-pyridyl | —CH₂— |
| 421 | 734 | CH | CH | CH | CH | —CH₂— | 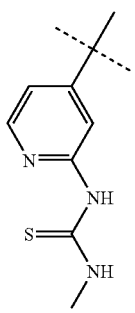 | —CH₂— |
| 422 | 735 | CH | CH | CH | CH | —CH₂— | 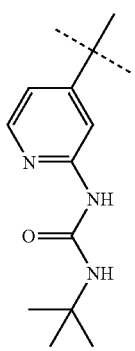 | —CH₂— |

TABLE 1-continued
Compounds of general formula (I) (W = oxygen; compound 1-399 and 402-432 R₁ = hydrogen, compound 400 R₁ = methyl)
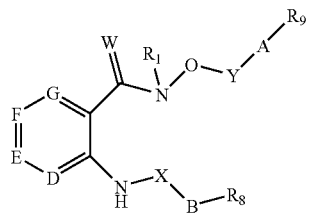
[I]
| | | D | E | F | G | X | B-R₈ | Y-A-R₉ |
|---|---|---|---|---|---|---|---|---|
| 423 | 736 | CH | CH | CH | CH | —CH₂— | 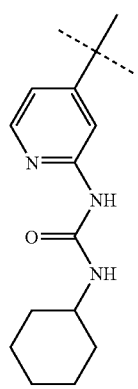 | —CH₂— |
| 424 | 737 | CH | CH | CH | CH | —CH₂— | 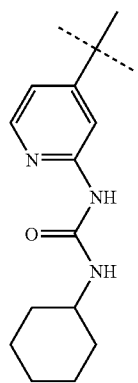 | —CH₂— |
| 425 | 738 | CH | CH | CH | CH | —CH₂— | 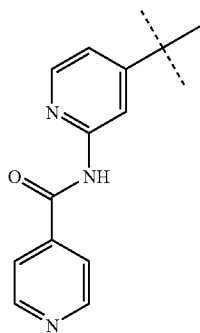 | —CH₂— |

TABLE 1-continued
Compounds of general formula (I) (W = oxygen; compound 1-399 and 402-432 $R_1$ = hydrogen, compound 400 $R_1$ = methyl)
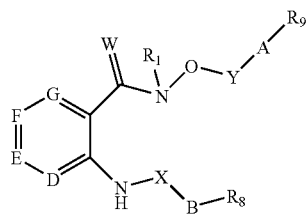
[I]
| | | | | | | | | |
|---|---|---|---|---|---|---|---|---|
| 426 | 739 | CH | CH | CH | CH | —CH$_2$— | 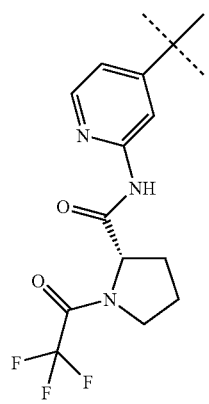 | —CH$_2$— |
| 427 | 740 | CH | CH | CH | CH | —CH$_2$— | 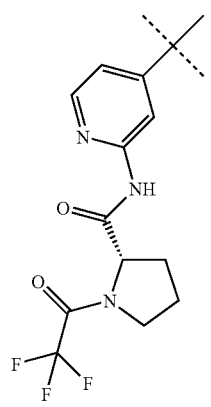 | —CH$_2$— |
| 428 | 741 | CH | CH | CH | CH | —CH$_2$— | 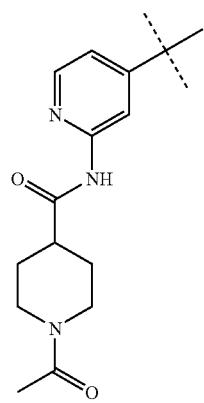 | —CH$_2$— |

TABLE 1-continued
Compounds of general formula (I) (W = oxygen; compound 1-399 and
402-432 R₁ = hydrogen, compound 400 R₁ = methyl)
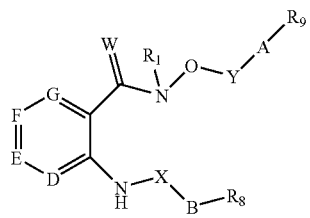
[I]
| | | | | | | | | |
|---|---|---|---|---|---|---|---|---|
| 429 | 742 | CH | CH | CH | CH | —CH₂— | 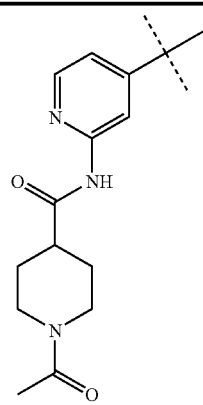 | —CH₂— |
| 430 | 743 | CH | CH | CH | CH | —CH₂— | 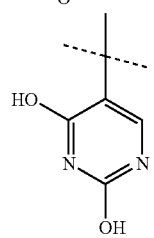 | —CH₂— |
| 431 | 744 | CH | CH | CH | CH | —CH₂— | 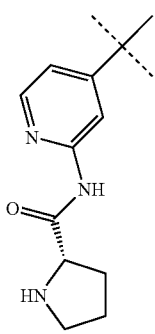 | —CH₂— |
| 432 | 745 | CH | CH | CH | CH | —CH₂— | 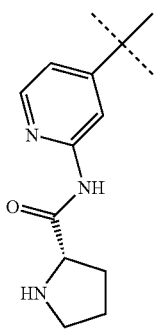 | —CH₂— |
| 433 | 746 | CH | CH | CH | CH | —CH₂— | 4-pyridyl | —CH₂— |

TABLE 1-continued

Compounds of general formula (I) (W = oxygen; compound 1-399 and 402-432 $R_1$ = hydrogen, compound 400 $R_1$ = methyl)

[I]

![Structure of formula I]

| Compound | Example | A-R$_9$ |
|---|---|---|
| 1 | 1 | phenyl |
| 2 | 2 | 4-nitrophenyl |
| 3 | 3 | 2-nitrophenyl |
| 4 | 4 | 3-trifluoromethylphenyl |
| 5 | 5 | 2-trifluoromethylphenyl |
| 6 | 6 | 4-trifluoromethylphenyl |
| 7 | 7 | 4-methoxyphenyl |
| 8 | 8 | 3-methoxyphenyl |
| 9 | 9 | 3,4,5-trimethoxyphenyl |
| 10 | 10 | 4-chlorophenyl |
| 11 | 11 | 3-chlorophenyl |
| 12 | 12 | 2-chlorophenyl |
| 13 | 13 | 2-bromophenyl |
| 14 | 14 | 2,4-dichlorophenyl |
| 15 | 15 | 3,4-dichlorophenyl |
| 16 | 16 | 2,6-dichlorophenyl |
| 17 | 17 | 3,5-dichlorophenyl |
| 18 | 18 | 2,3-dichlorophenyl |
| 19 | 19 | 3,6-dichlorophenyl |
| 20 | 20 | 2-fluorophenyl |
| 21 | 21 | 3-fluorophenyl |
| 22 | 22 | 4-fluorophenyl |
| 23 | 23 | 6-fluoro-2-chlorophenyl |
| 24 | 24 | 4-fluoro-2-chlorophenyl |
| 25 | 25 | 2-fluoro-3-chlorophenyl |
| 26 | 26 | 4-carbomethoxyphenyl |
| 27 | 27 | 4-cyanophenyl |
| 28 | 28 | quinolin-2-yl |
| 29 | 29 | phenyl |
| 30 | 30 | phenyl |
| 31 | 31 | phenyl |
| 32 | 32 | 2-methylthiazol-4-yl |
| 33 | 33 | phenyl |
| 34 | 34 | 4-methoxyphenyl |
| 35 | 35 | 4-methoxyphenyl |
| 36 | 351 | 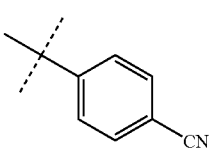 |
| 37 | 352 | 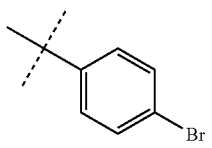 |
| 38 | 353 | 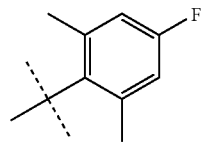 |

TABLE 1-continued
Compounds of general formula (I) (W = oxygen; compound 1-399 and 402-432 $R_1$ = hydrogen, compound 400 $R_1$ = methyl)
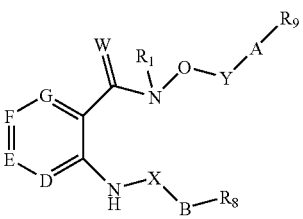
[I]
| | | |
|---|---|---|
| 39 | 354 | 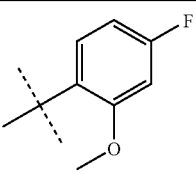 |
| 40 | 355 | 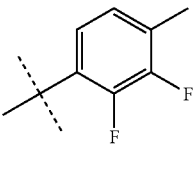 |
| 41 | 356 | 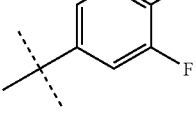 |
| 42 | 357 | 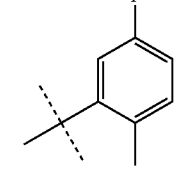 |
| 43 | 358 | 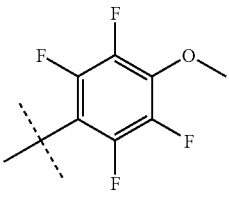 |
| 44 | 359 | 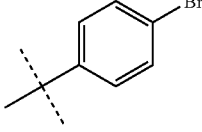 |
| 45 | 360 | 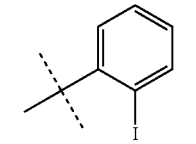 |
| 46 | 361 | 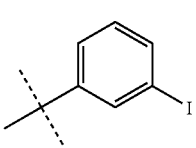 |

TABLE 1-continued
Compounds of general formula (I) (W = oxygen; compound 1-399 and 402-432 R$_1$ = hydrogen, compound 400 R$_1$ = methyl)
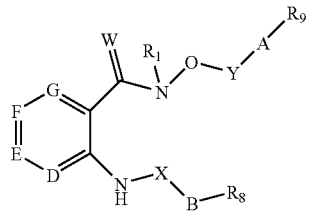
[I]
| | | |
|---|---|---|
| 47 | 362 | 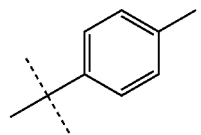 |
| 48 | 363 | 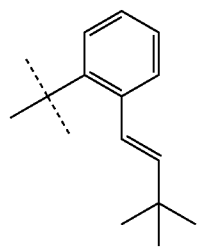 |
| 49 | 364 | 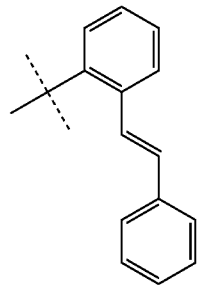 |
| 50 | 365 | 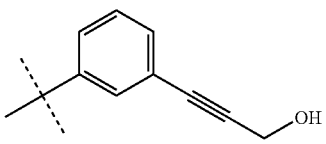 |
| 51 | 366 | 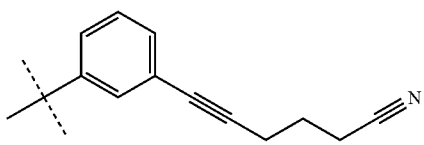 |
| 52 | 367 | 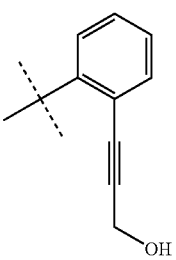 |

TABLE 1-continued
Compounds of general formula (I) (W = oxygen; compound 1-399 and 402-432 $R_1$ = hydrogen, compound 400 $R_1$ = methyl)
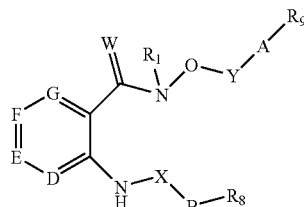
[I]
| | | |
|---|---|---|
| 53 | 368 | 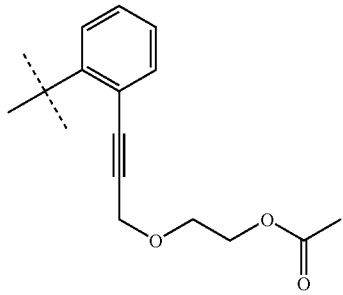 |
| 54 | 369 | 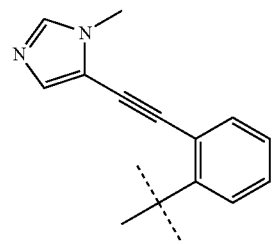 |
| 55 | 370 | 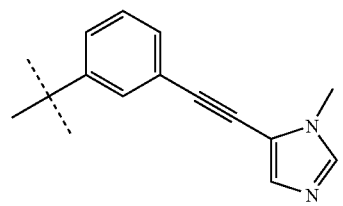 |
| 56 | 371 | 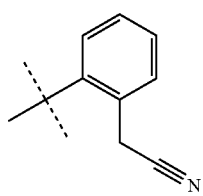 |
| 57 | 372 | 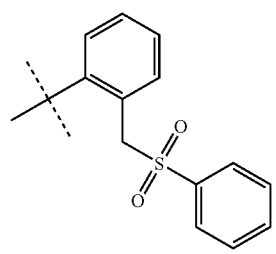 |

TABLE 1-continued
Compounds of general formula (I) (W = oxygen; compound 1-399 and 402-432 $R_1$ = hydrogen, compound 400 $R_1$ = methyl)
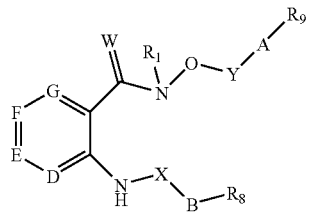
[I]
| 58 | 373 | 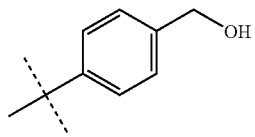 |
| 59 | 374 | 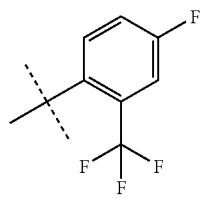 |
| 60 | 375 | 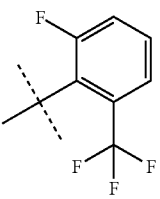 |
| 61 | 376 | 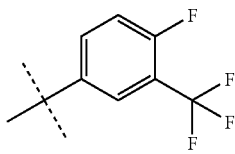 |
| 62 | 377 | 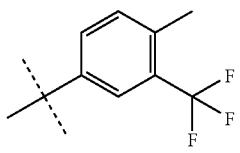 |
| 63 | 378 | 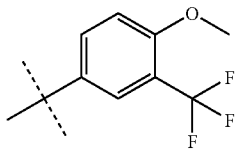 |
| 64 | 379 | 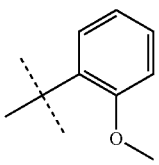 |

TABLE 1-continued
Compounds of general formula (I) (W = oxygen; compound 1-399 and 402-432 R₁ = hydrogen, compound 400 R₁ = methyl)
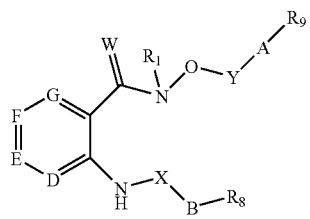
[I]
| | | |
|---|---|---|
| 65 | 380 | 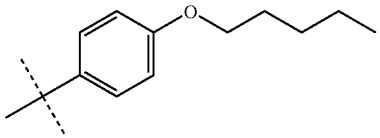 |
| 66 | 381 | 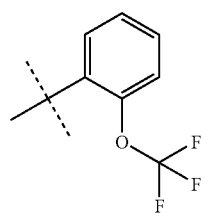 |
| 67 | 382 | 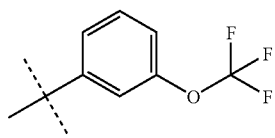 |
| 68 | 383 | 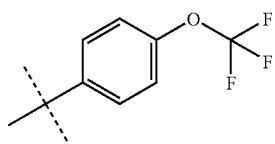 |
| 69 | 384 | 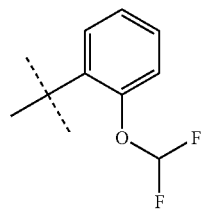 |
| 70 | 385 | 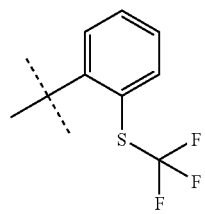 |
| 71 | 386 | 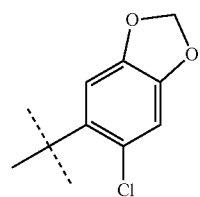 |

TABLE 1-continued
Compounds of general formula (I) (W = oxygen; compound 1-399 and 402-432 $R_1$ = hydrogen, compound 400 $R_1$ = methyl)
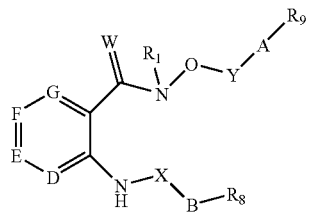
[I]
| | | |
|---|---|---|
| 72 | 387 | 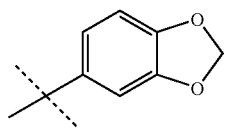 |
| 73 | 388 | 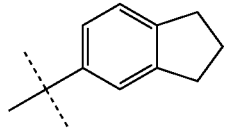 |
| 74 | 389 | 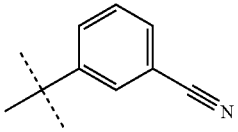 |
| 75 | 390 | 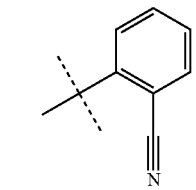 |
| 76 | 391 | 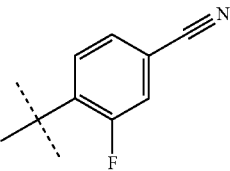 |
| 77 | 392 | 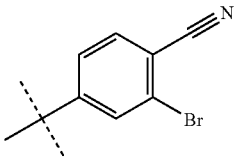 |
| 78 | 393 | 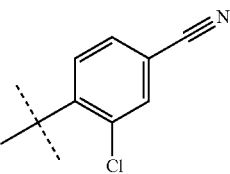 |

TABLE 1-continued
Compounds of general formula (I) (W = oxygen; compound 1-399 and
402-432 R$_1$ = hydrogen, compound 400 R$_1$ = methyl)
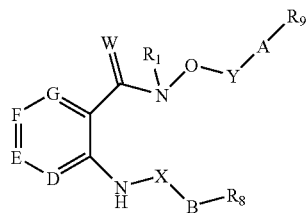
[I]
| | | |
|---|---|---|
| 79 | 394 | 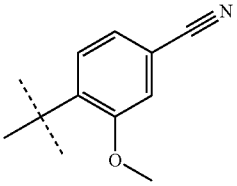 |
| 80 | 395 | 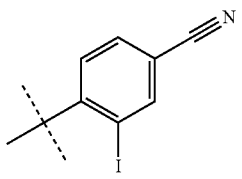 |
| 81 | 396 | 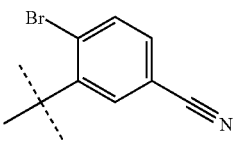 |
| 82 | 397 | 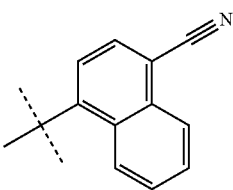 |
| 83 | 398 | 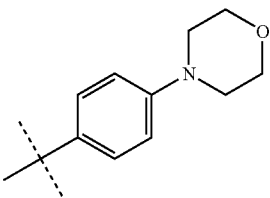 |
| 84 | 399 | 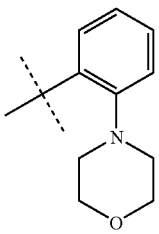 |
| 85 | 400 | 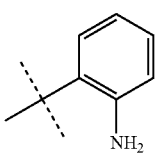 |

TABLE 1-continued
Compounds of general formula (I) (W = oxygen; compound 1-399 and 402-432 $R_1$ = hydrogen, compound 400 $R_1$ = methyl)
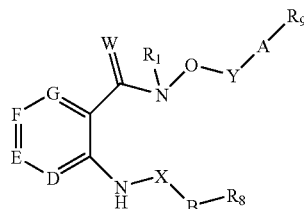
[I]
| | | |
|---|---|---|
| 86 | 401 | 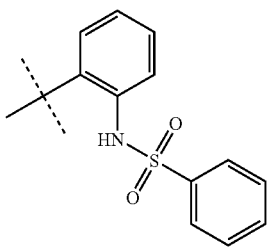 |
| 87 | 402 | 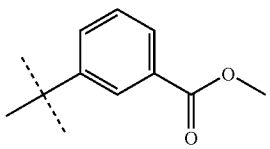 |
| 88 | 403 | 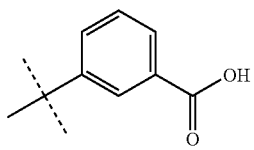 |
| 89 | 404 | 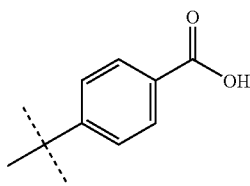 |
| 90 | 405 | 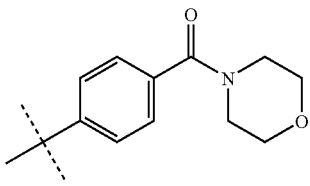 |
| 91 | 406 | 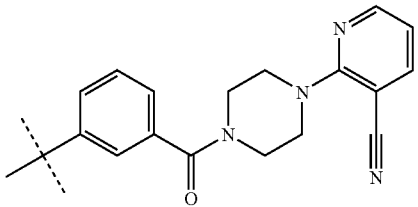 |

US 8,034,811 B2
137 138
TABLE 1-continued
Compounds of general formula (I) (W = oxygen; compound 1-399 and 402-432 R$_1$ = hydrogen, compound 400 R$_1$ = methyl)
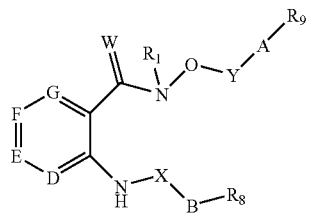
[I]
| | | |
|---|---|---|
| 92 | 407 | 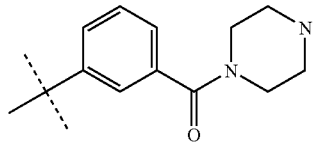 |
| 93 | 408 | 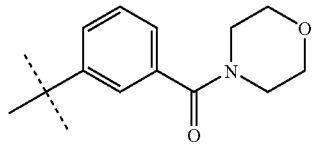 |
| 94 | 409 | 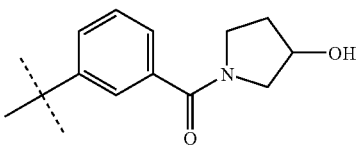 |
| 95 | 410 | 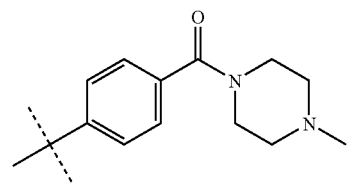 |
| 96 | 411 | 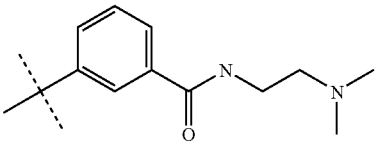 |
| 97 | 412 | 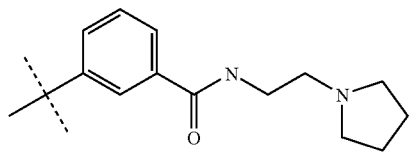 |
| 98 | 413 | 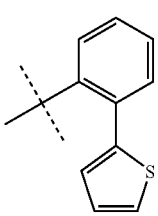 |

TABLE 1-continued
Compounds of general formula (I) (W = oxygen; compound 1-399 and 402-432 $R_1$ = hydrogen, compound 400 $R_1$ = methyl)
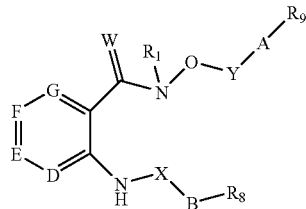
[I]
| | | |
|---|---|---|
| 99 | 414 | 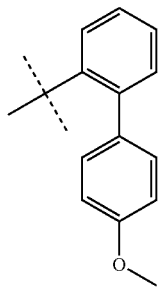 |
| 100 | 415 | 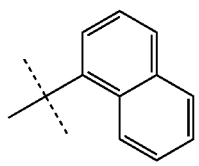 |
| 101 | 416 | 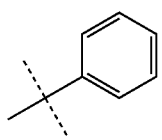 |
| 102 | 417 | 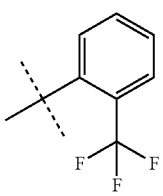 |
| 103 | 418 | 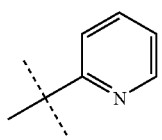 |
| 104 | 419 | 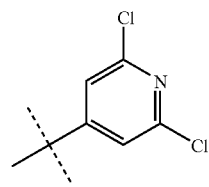 |
| 105 | 420 | 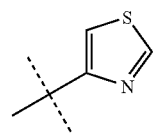 |

TABLE 1-continued

Compounds of general formula (I) (W = oxygen; compound 1-399 and 402-432 $R_1$ = hydrogen, compound 400 $R_1$ = methyl)

[I]

| | | |
|---|---|---|
| 106 | 421 | 2-chloro-thiazol-5-yl |
| 107 | 422 | 2-phenyl-thiazol-4-yl |
| 108 | 423 | 5-methyl-isoxazol-3-yl |
| 109 | 424 | 3,5-dimethyl-isoxazol-4-yl |
| 110 | 425 | 3-propyl-isoxazol-5-yl |
| 111 | 426 | 5-chloro-thiophen-2-yl |
| 112 | 427 | 4-cyanophenyl |
| 113 | 428 | cyclopentyl |

TABLE 1-continued

Compounds of general formula (I) (W = oxygen; compound 1-399 and 402-432 $R_1$ = hydrogen, compound 400 $R_1$ = methyl)

[I]

| | | |
|---|---|---|
| 114 | 429 | cyclopropyl |
| 115 | 430 | —CH$_3$ |
| 116 | 431 | tert-butyl |
| 117 | 432 | 3-pentyl |
| 118 | 433 | isobutyl |
| 119 | 434 | cyclobutyl |
| 120 | 435 | cyclohexyl |
| 121 | 436 | cycloheptyl |
| 122 | 437 | cyclooctyl |
| 123 | 438 | cyclopentyl |

TABLE 1-continued
Compounds of general formula (I) (W = oxygen; compound 1-399 and 402-432 R$_1$ = hydrogen, compound 400 R$_1$ = methyl)
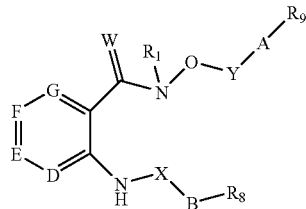
[I]
| | | |
|---|---|---|
| 124 | 439 | 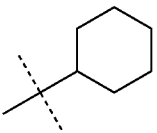 |
| 125 | 440 | 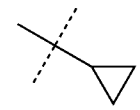 |
| 126 | 441 | 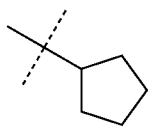 |
| 127 | 442 | 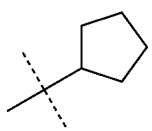 |
| 128 | 443 | 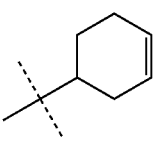 |
| 129 | 444 | 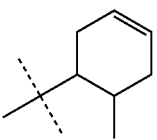 |
| 130 | 445 | 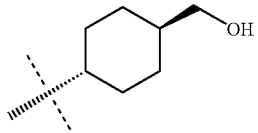 |
| 131 | 446 | 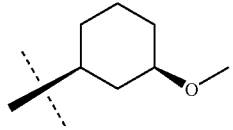 |
| 132 | 447 | 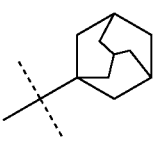 |

147
148
TABLE 1-continued
Compounds of general formula (I) (W = oxygen; compound 1-399 and 402-432 R₁ = hydrogen, compound 400 R₁ = methyl)
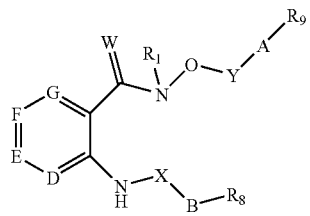
[I]
| | | |
|---|---|---|
| 133 | 448 | 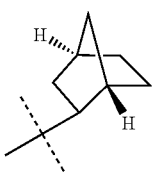 |
| 134 | 449 | 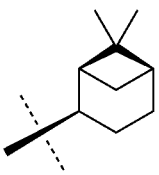 |
| 135 | 450 | 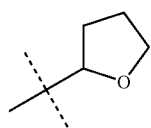 |
| 136 | 451 | 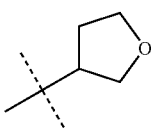 |
| 137 | 452 | 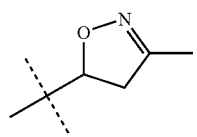 |
| 138 | 453 | 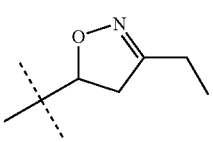 |
| 139 | 454 | 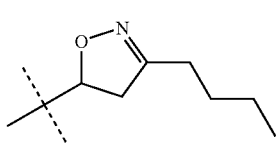 |
| 140 | 455 | 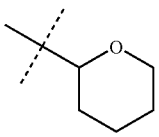 |

US 8,034,811 B2
TABLE 1-continued
Compounds of general formula (I) (W = oxygen; compound 1-399 and 402-432 R₁ = hydrogen, compound 400 R₁ = methyl)
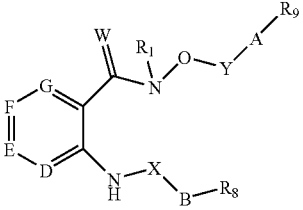
[I]
| | | |
|---|---|---|
| 141 | 456 | 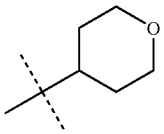 |
| 142 | 457 | 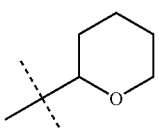 |
| 143 | 458 | 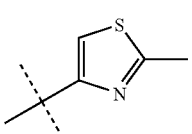 |
| 144 | 459 | 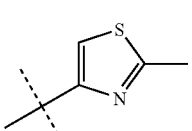 |
| 145 | 460 | 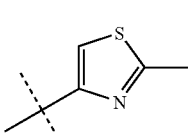 |
| 146 | 461 | 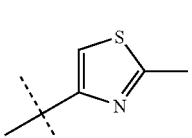 |
| 147 | 462 | 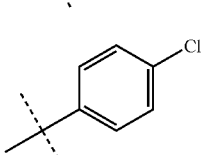 |
| 148 | 463 | 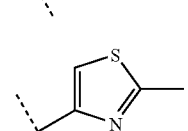 |
| 149 | 464 | 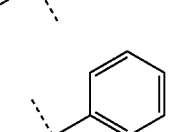 |

151 152
TABLE 1-continued
Compounds of general formula (I) (W = oxygen; compound 1-399 and
402-432 $R_1$ = hydrogen, compound 400 $R_1$ = methyl)
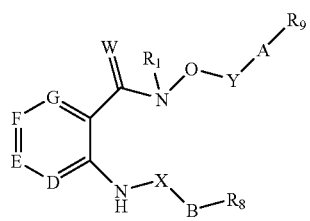
[I]
| | | |
|---|---|---|
| 150 | 465 | 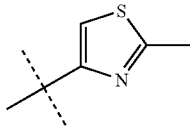 |
| 151 | 466 | 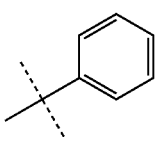 |
| 152 | 467 | 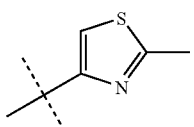 |
| 153 | 468 | 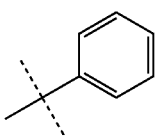 |
| 154 | 469 | 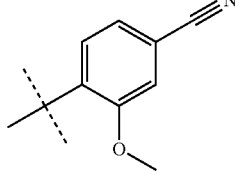 |
| 155 | 470 | 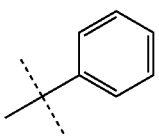 |
| 156 | 471 | 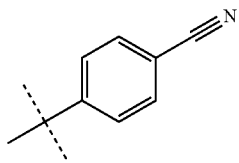 |
| 157 | 472 | 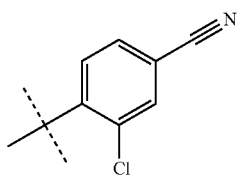 |

TABLE 1-continued
Compounds of general formula (I) (W = oxygen; compound 1-399 and 402-432 $R_1$ = hydrogen, compound 400 $R_1$ = methyl)
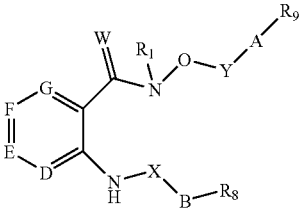
| | | |
|---|---|---|
| 158 | 473 | 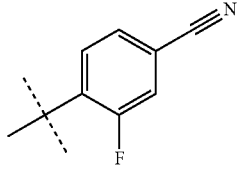 |
| 159 | 474 | 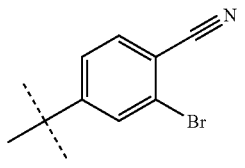 |
| 160 | 475 | 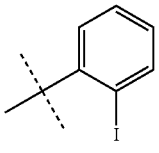 |
| 161 | 476 | 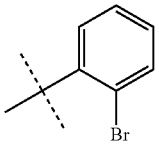 |
| 162 | 477 | 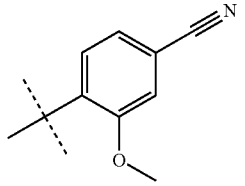 |
| 163 | 478 | 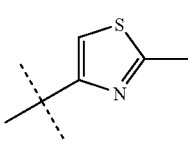 |
| 164 | 479 | 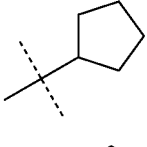 |
| 165 | 480 | 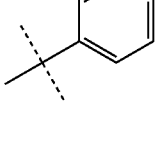 |

TABLE 1-continued

Compounds of general formula (I) (W = oxygen; compound 1-399 and 402-432 R₁ = hydrogen, compound 400 R₁ = methyl)

| | | |
|---|---|---|
| 166 | 481 | phenyl |
| 167 | 482 | phenyl |
| 168 | 483 | phenyl |
| 169 | 484 | 4-substituted-3-methoxy-benzonitrile |
| 170 | 485 | phenyl |
| 171 | 486 | 2-methyl-thiazol-4-yl |
| 172 | 487 | phenyl |
| 173 | 488 | 4-cyanophenyl |

TABLE 1-continued
Compounds of general formula (I) (W = oxygen; compound 1-399 and 402-432 R₁ = hydrogen, compound 400 R₁ = methyl)
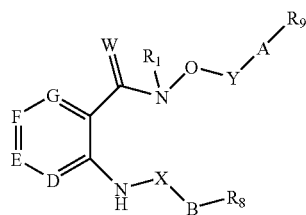
[I]
| | | |
|---|---|---|
| 174 | 489 | 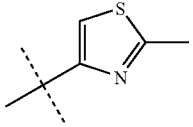 |
| 175 | 490 | 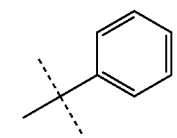 |
| 176 | 491 | 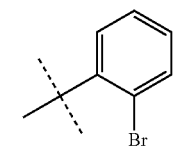 |
| 177 | 492 | 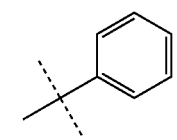 |
| 178 | 493 | 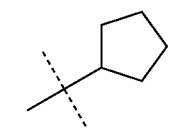 |
| 179 | 494 | 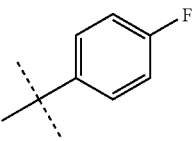 |
| 180 | 495 | 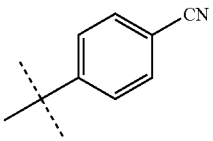 |
| 181 | 496 | 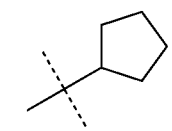 |
| 182 | 497 | 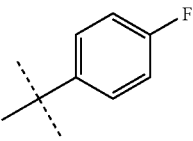 |

TABLE 1-continued
Compounds of general formula (I) (W = oxygen; compound 1-399 and
402-432 R₁ = hydrogen, compound 400 R₁ = methyl)
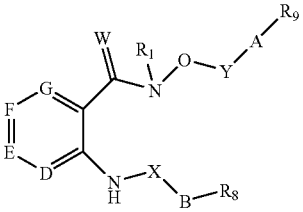
[I]
| | | |
|---|---|---|
| 183 | 498 | 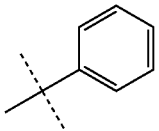 |
| 184 | 499 | 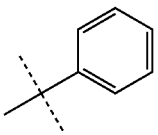 |
| 185 | 500 | 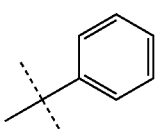 |
| 186 | 501 | 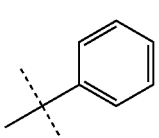 |
| 187 | 502 | 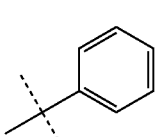 |
| 188 | 503 | 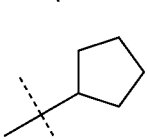 |
| 189 | 504 | 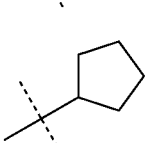 |
| 190 | 505 | 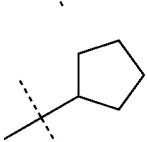 |
| 191 | 506 | 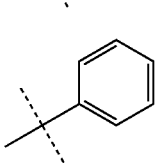 |

TABLE 1-continued
Compounds of general formula (I) (W = oxygen; compound 1-399 and 402-432 R₁ = hydrogen, compound 400 R₁ = methyl)
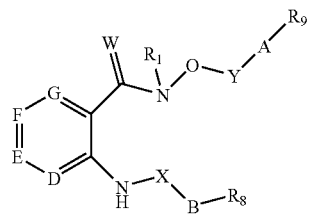
[I]
| | | |
|---|---|---|
| 192 | 507 | 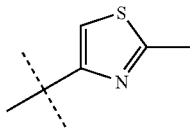 |
| 193 | 508 | 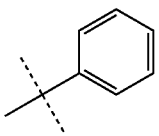 |
| 194 | 509 | 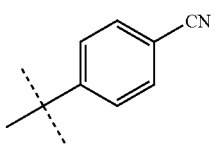 |
| 195 | 510 | 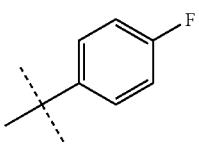 |
| 196 | 511 | 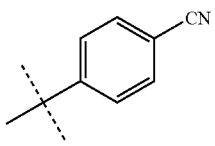 |
| 197 | 512 | 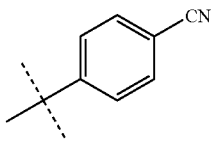 |
| 198 | 513 | 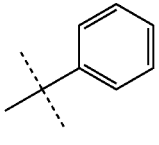 |
| 199 | 514 | 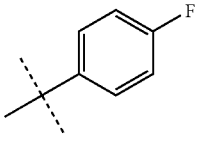 |

TABLE 1-continued

Compounds of general formula (I) (W = oxygen; compound 1-399 and 402-432 $R_1$ = hydrogen, compound 400 $R_1$ = methyl)

[I]

| | | |
|---|---|---|
| 200 | 515 | 4-cyanophenyl |
| 201 | 516 | 4-chlorophenyl |
| 202 | 517 | 2-methylthiazol-4-yl |
| 203 | 518 | phenyl |
| 204 | 519 | 4-fluorophenyl |
| 205 | 520 | 4-cyano-2-methoxyphenyl |
| 206 | 521 | 4-cyanophenyl |
| 207 | 522 | 4-fluorophenyl |

TABLE 1-continued

Compounds of general formula (I) (W = oxygen; compound 1-399 and 402-432 R$_1$ = hydrogen, compound 400 R$_1$ = methyl)

[I]

| | | |
|---|---|---|
| 208 | 523 | cyclopentylmethyl |
| 209 | 524 | 4-cyanobenzyl |
| 210 | 525 | 4-cyanobenzyl |
| 211 | 526 | 4-methyl-3-methoxy-benzonitrile substituent |
| 212 | 527 | cyclopentylmethyl |
| 213 | 528 | 2,3-difluoro-6-methylbenzyl |
| 214 | 529 | 4-cyanobenzyl |
| 215 | 530 | cyclopentylmethyl |

TABLE 1-continued

Compounds of general formula (I) (W = oxygen; compound 1-399 and 402-432 R₁ = hydrogen, compound 400 R₁ = methyl)

[I]

| | | |
|---|---|---|
| 216 | 531 | 4-cyanophenyl |
| 217 | 532 | cyclopentyl |
| 218 | 533 | 4-cyanophenyl |
| 219 | 534 | cyclopentyl |
| 220 | 535 | 4-cyanophenyl |
| 221 | 536 | cyclopentyl |
| 222 | 537 | 4-cyanophenyl |
| 223 | 538 | cyclopentyl |
| 224 | 539 | 4-cyanophenyl |

TABLE 1-continued
Compounds of general formula (I) (W = oxygen; compound 1-399 and 402-432 $R_1$ = hydrogen, compound 400 $R_1$ = methyl)
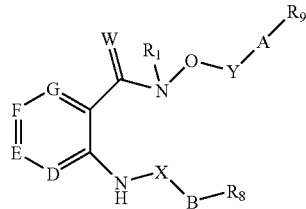
[I]
| | | |
|---|---|---|
| 225 | 540 | 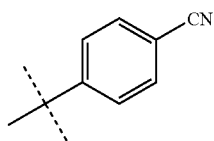 |
| 226 | 541 | 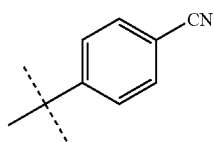 |
| 227 | 542 | 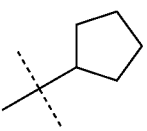 |
| 228 | 543 | 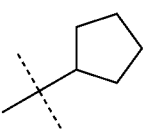 |
| 229 | 544 | 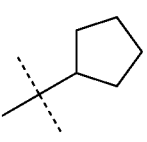 |
| 230 | 545 | 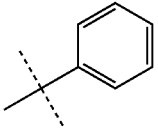 |
| 231 | 546 | 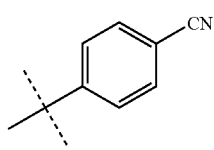 |
| 232 | 547 | 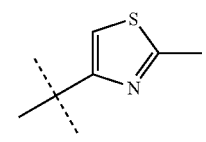 |
| 233 | 548 | 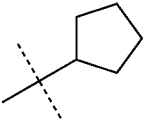 |

TABLE 1-continued
Compounds of general formula (I) (W = oxygen; compound 1-399 and 402-432 $R_1$ = hydrogen, compound 400 $R_1$ = methyl)
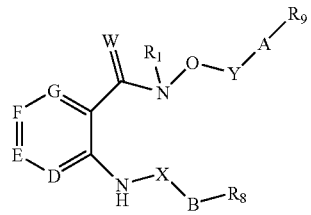
[I]
| | | |
|---|---|---|
| 234 | 549 | 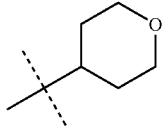 |
| 235 | 550 | 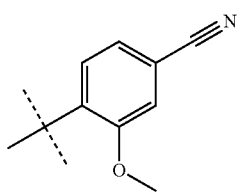 |
| 236 | 551 | 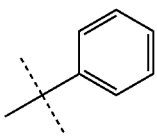 |
| 237 | 552 | 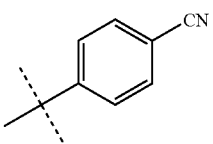 |
| 238 | 553 | 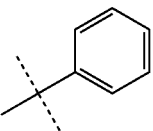 |
| 239 | 554 | 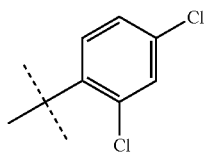 |
| 240 | 555 | 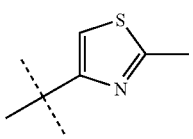 |
| 241 | 556 | 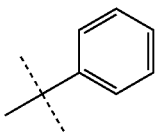 |

TABLE 1-continued
Compounds of general formula (I) (W = oxygen; compound 1-399 and 402-432 $R_1$ = hydrogen, compound 400 $R_1$ = methyl)
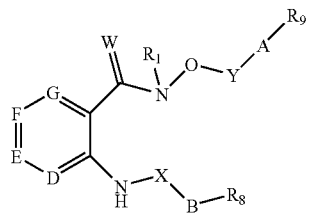
[I]
| 242 | 557 | 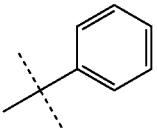 |
| 243 | 558 | 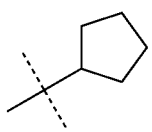 |
| 244 | 559 | 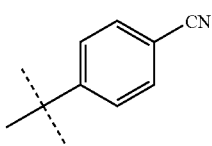 |
| 245 | 560 | 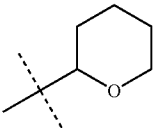 |
| 246 | 561 | 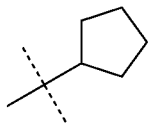 |
| 247 | 562 | 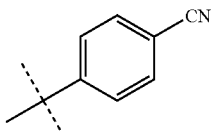 |
| 248 | 563 | 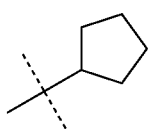 |
| 250 | 564 | 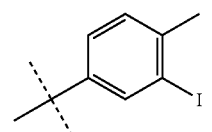 |
| 251 | 565 | 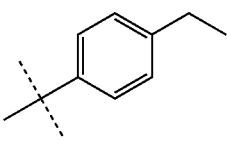 |

TABLE 1-continued

Compounds of general formula (I) (W = oxygen; compound 1-399 and 402-432 R₁ = hydrogen, compound 400 R₁ = methyl)

[I]

| | | |
|---|---|---|
| 252 | 566 | 4-isopropyl-phenyl (with t-butyl) |
| 253 | 567 | 4-tert-butyl-phenyl (with t-butyl) |
| 254 | 568 | 2-ethyl-phenyl (with methyl) |
| 255 | 569 | 2-substituted phenyl with long alkenyl chain |
| 256 | 570 | 4-(phenylaminomethyl)phenyl |

TABLE 1-continued
Compounds of general formula (I) (W = oxygen; compound 1-399 and 402-432 $R_1$ = hydrogen, compound 400 $R_1$ = methyl)
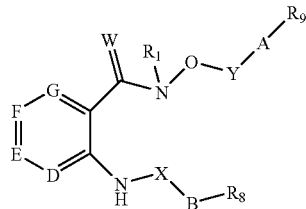
[I]
| | | |
|---|---|---|
| 257 | 571 | 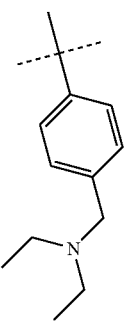 |
| 258 | 572 | 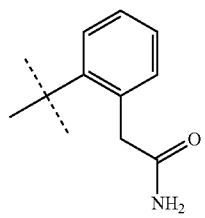 |
| 259 | 573 | 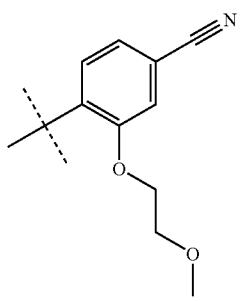 |
| 260 | 574 | 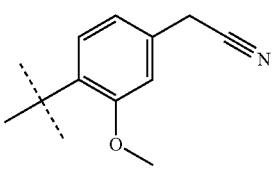 |
| 261 | 575 | 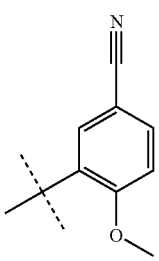 |

TABLE 1-continued
Compounds of general formula (I) (W = oxygen; compound 1-399 and 402-432 R$_1$ = hydrogen, compound 400 R$_1$ = methyl)
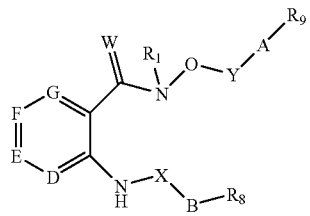
[I]
| | | |
|---|---|---|
| 262 | 576 | 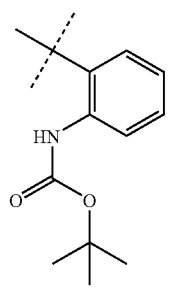 |
| 263 | 577 | 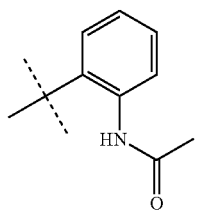 |
| 264 | 578 | 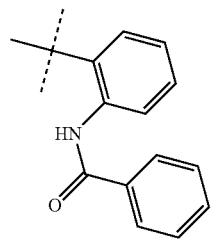 |
| 265 | 579 | 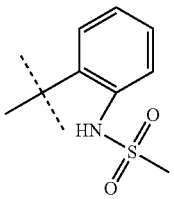 |
| 266 | 580 | 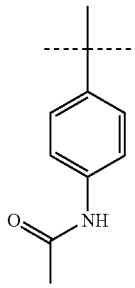 |

TABLE 1-continued

Compounds of general formula (I) (W = oxygen; compound 1-399 and 402-432 R₁ = hydrogen, compound 400 R₁ = methyl)

$$[I]$$

| | | |
|---|---|---|
| 267 | 581 | 4'-biphenyl (para-biphenyl) |
| 268 | 582 | 2'-biphenyl (ortho-biphenyl) |
| 269 | 583 | 2-(3-methoxyphenyl)phenyl |
| 270 | 584 | 2-(2-methoxyphenyl)phenyl |
| 271 | 585 | 2-[3-(hydroxymethyl)phenyl]phenyl |

TABLE 1-continued

Compounds of general formula (I) (W = oxygen; compound 1-399 and 402-432 R₁ = hydrogen, compound 400 R₁ = methyl)

[I]

| | | |
|---|---|---|
| 272 | 586 | 3-phenoxyphenyl group |
| 273 | 587 | anthracen-9-yl group |
| 274 | 588 | 4-(2-methylthiazol-4-yl)phenyl group |
| 275 | 589 | phenyl |
| 276 | 590 | 2-(4-trifluoromethylphenyl)thiazol-4-yl group |

TABLE 1-continued

Compounds of general formula (I) (W = oxygen; compound 1-399 and 402-432 R₁ = hydrogen, compound 400 R₁ = methyl)

[I]

| | | |
|---|---|---|
| 277 | 591 | 5-tert-butyl-3-(4-methylphenyl)isoxazole |
| 278 | 592 | 5-tert-butyl-3-methylisoxazole |
| 279 | 593 | 5-(propan-2-yl)-3-ethylisoxazole |
| 280 | 594 | 5-(propan-2-yl)-3-butylisoxazole |
| 281 | 595 | 5-(propan-2-yl)-3-pentylisoxazole |

TABLE 1-continued
Compounds of general formula (I) (W = oxygen; compound 1-399 and 402-432 R₁ = hydrogen, compound 400 R₁ = methyl)
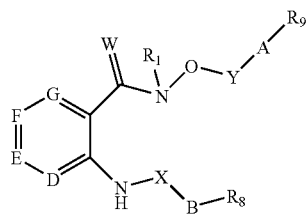
[I]
| | | |
|---|---|---|
| 282 | 596 | 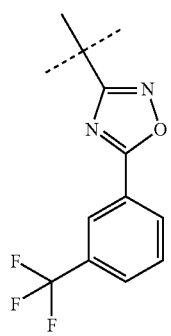 |
| 283 | 597 | 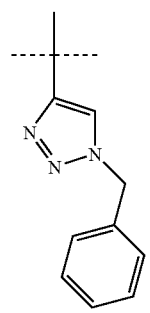 |
| 284 | 598 | 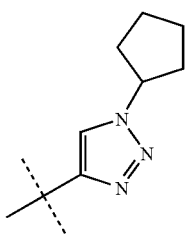 |
| 285 | 599 | 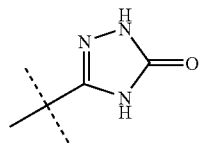 |
| 286 | 600 | phenyl |
| 287 | 601 | phenyl |
| 288 | 602 | phenyl |

TABLE 1-continued
Compounds of general formula (I) (W = oxygen; compound 1-399 and 402-432 R₁ = hydrogen, compound 400 R₁ = methyl)
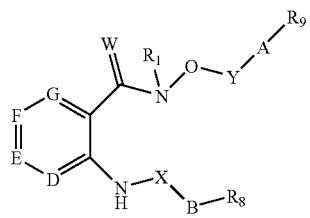
[I]
| | | |
|---|---|---|
| 289 | 603 | 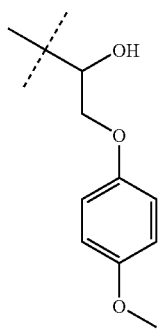 |
| 290 | 604 | phenyl |
| 291 | 605 | phenyl |
| 292 | 606 | 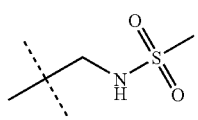 |
| 293 | 607 | 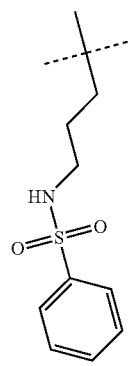 |
| 294 | 608 | 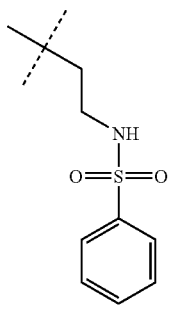 |

TABLE 1-continued
Compounds of general formula (I) (W = oxygen; compound 1-399 and 402-432 R₁ = hydrogen, compound 400 R₁ = methyl)
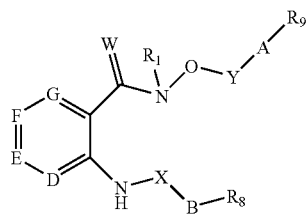
[I]
| | | |
|---|---|---|
| 295 | 609 | 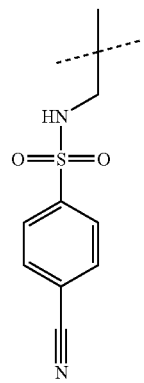 |
| 296 | 610 | 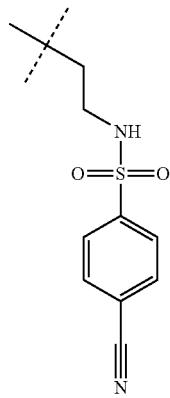 |
| 297 | 611 | 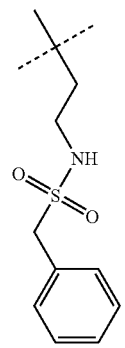 |

TABLE 1-continued
Compounds of general formula (I) (W = oxygen; compound 1-399 and 402-432 $R_1$ = hydrogen, compound 400 $R_1$ = methyl)
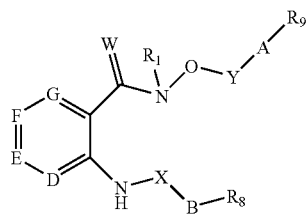
[I]
| | | |
|---|---|---|
| 298 | 612 | 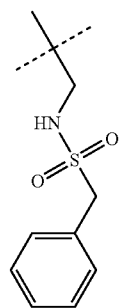 |
| 299 | 613 | 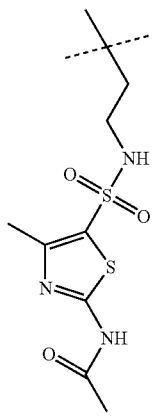 |
| 300 | 614 | 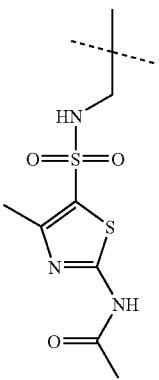 |
| 301 | 615 | phenyl |
| 302 | 616 | phenyl |

TABLE 1-continued

Compounds of general formula (I) (W = oxygen; compound 1-399 and 402-432 R₁ = hydrogen, compound 400 R₁ = methyl)

[I]

| 303 | 617 | |
| 304 | 618 | |
| 305 | 619 | |
| 306 | 620 | |

TABLE 1-continued
Compounds of general formula (I) (W = oxygen; compound 1-399 and 402-432 R$_1$ = hydrogen, compound 400 R$_1$ = methyl)
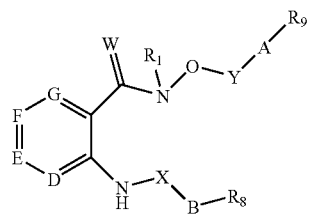
[I]
| | | |
|---|---|---|
| 307 | 621 | 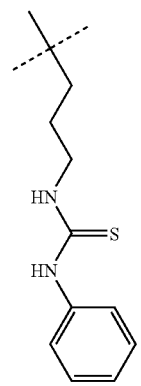 |
| 308 | 622 | 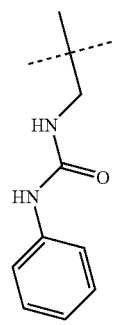 |
| 309 | 623 | 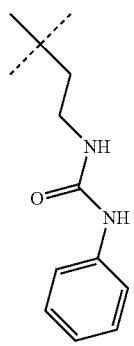 |

TABLE 1-continued
Compounds of general formula (I) (W = oxygen; compound 1-399 and 402-432 $R_1$ = hydrogen, compound 400 $R_1$ = methyl)
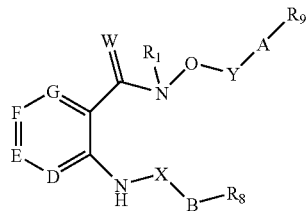
[I]
| 310 | 624 | 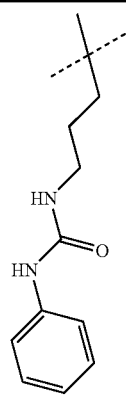 |
| --- | --- | --- |
| 311 | 625 | 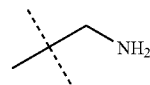 |
| 312 | 626 | 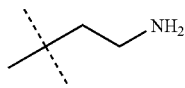 |
| 313 | 627 |  |
| 314 | 628 | 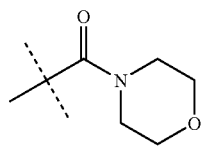 |
| 315 | 629 | 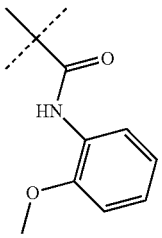 |
| 316 | 630 | 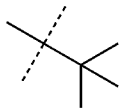 |

TABLE 1-continued
Compounds of general formula (I) (W = oxygen; compound 1-399 and
402-432 $R_1$ = hydrogen, compound 400 $R_1$ = methyl)
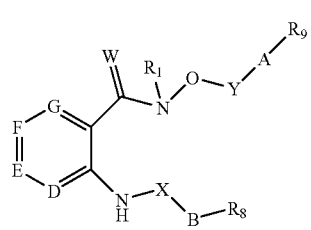
[I]
| | | |
|---|---|---|
| 317 | 631 | |
| 318 | 632 | |
| 319 | 633 | |
| 320 | 634 | |
| 321 | 635 | |
| 322 | 636 | |
| 323 | 637 | |
| 324 | 638 | |
| 325 | 639 | |

TABLE 1-continued

Compounds of general formula (I) (W = oxygen; compound 1-399 and 402-432 R₁ = hydrogen, compound 400 R₁ = methyl)

| | | |
|---|---|---|
| 326 | 640 | |
| 327 | 641 | |
| 328 | 642 | |
| 329 | 643 | |
| 330 | 644 | |
| 331 | 645 | |

TABLE 1-continued
Compounds of general formula (I) (W = oxygen; compound 1-399 and 402-432 R₁ = hydrogen, compound 400 R₁ = methyl)
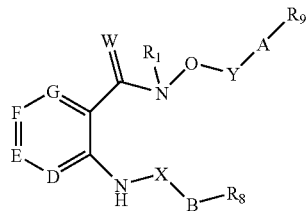
[I]
| | | |
|---|---|---|
| 332 | 646 | 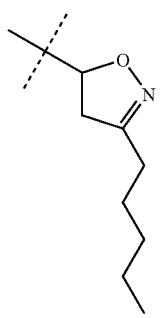 |
| 333 | 647 | 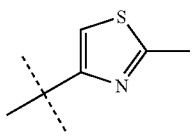 |
| 334 | 648 | 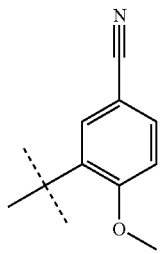 |
| 335 | 649 | phenyl |
| 336 | 650 | 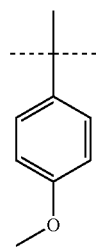 |
| 337 | 651 | phenyl |
| 338 | 652 | 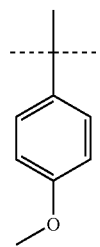 |

TABLE 1-continued
Compounds of general formula (I) (W = oxygen; compound 1-399 and 402-432 R$_1$ = hydrogen, compound 400 R$_1$ = methyl)
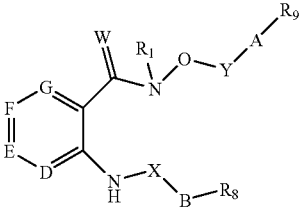
[I]
| | | |
|---|---|---|
| 339 | 653 | phenyl |
| 340 | 654 | 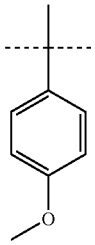 |
| 341 | 655 | phenyl |
| 342 | 656 | 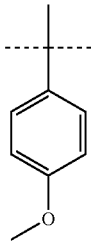 |
| 343 | 567 | phenyl |
| 344 | 658 | 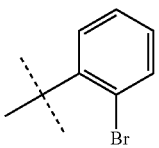 |
| 345 | 659 | 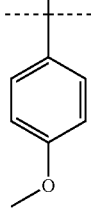 |
| 346 | 660 | phenyl |
| 347 | 661 | 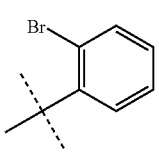 |

TABLE 1-continued

Compounds of general formula (I) (W = oxygen; compound 1-399 and
402-432 R$_1$ = hydrogen, compound 400 R$_1$ = methyl)

[I]

| 348 | 662 | 2-bromophenyl |
| 349 | 663 | 2-methylthiazol-4-yl |
| 350 | 664 | 2-bromophenyl |
| 351 | 665 | phenyl |
| 352 | 666 | 2-methylthiazol-4-yl |
| 353 | 667 | 2-methylthiazol-4-yl |
| 354 | 668 | phenyl |
| 355 | 669 | phenyl |
| 356 | 670 | 2-methylthiazol-4-yl |
| 357 | 671 | 2,4-dichlorophenyl |
| 358 | 672 | phenyl |

TABLE 1-continued

Compounds of general formula (I) (W = oxygen; compound 1-399 and 402-432 $R_1$ = hydrogen, compound 400 $R_1$ = methyl)

[I]

| | | | |
|---|---|---|---|
| 359 | 673 | | 2,4-dichlorophenyl |
| 360 | 674 | | phenyl |
| 361 | 675 | | 2-methylthiazol-4-yl |
| 362 | 676 | | phenyl |
| 363 | 677 | | 2-methylthiazol-4-yl |
| 364 | 678 | | phenyl |
| 365 | 679 | | 2-methylthiazol-4-yl |
| 366 | 680 | | 2-methylthiazol-4-yl |
| 367 | 681 | | phenyl |
| 368 | 682 | | 2,5-dichlorophenyl |
| 369 | 683 | | phenyl |
| 370 | 684 | | phenyl |
| 371 | 685 | | phenyl |
| 372 | 686 | | phenyl |
| 373 | 687 | | phenyl |

TABLE 1-continued
Compounds of general formula (I) (W = oxygen; compound 1-399 and 402-432 R₁ = hydrogen, compound 400 R₁ = methyl)
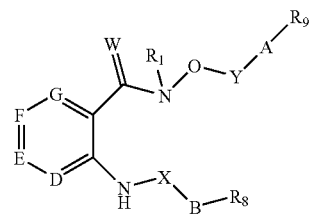
[I]
| | | |
|---|---|---|
| 374 | 688 | 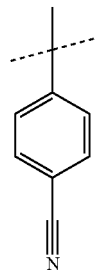 |
| 375 | 689 | 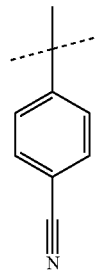 |
| 376 | 690 | 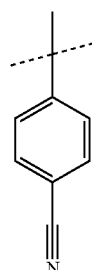 |
| 377 | 691 | 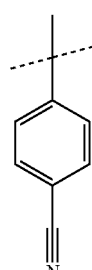 |

TABLE 1-continued
Compounds of general formula (I) (W = oxygen; compound 1-399 and 402-432 $R_1$ = hydrogen, compound 400 $R_1$ = methyl)
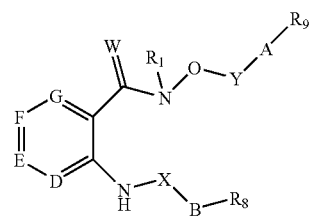
[I]
| 378 | 692 | 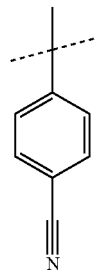 |
| 379 | 693 | 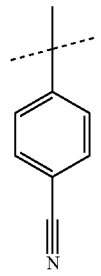 |
| 380 | 694 | 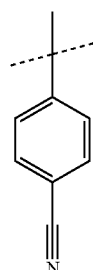 |
| 381 | 695 | 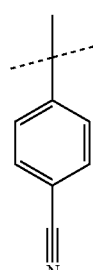 |

TABLE 1-continued
Compounds of general formula (I) (W = oxygen; compound 1-399 and 402-432 R₁ = hydrogen, compound 400 R₁ = methyl)
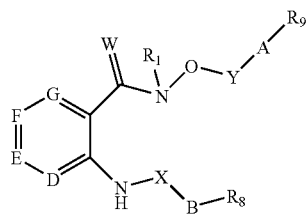
[I]
| 382 | 696 | 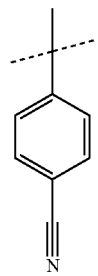 |
| 383 | 697 | 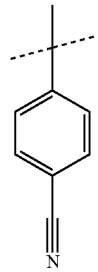 |
| 384 | 698 | 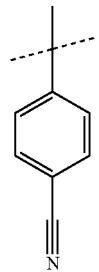 |
| 385 | 699 | 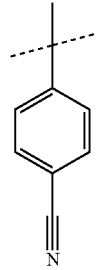 |
| 386 | 700 | phenyl |

TABLE 1-continued
Compounds of general formula (I) (W = oxygen; compound 1-399 and 402-432 R₁ = hydrogen, compound 400 R₁ = methyl)
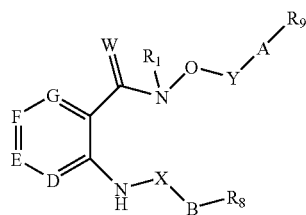
[I]
| | | |
|---|---|---|
| 387 | 701 | 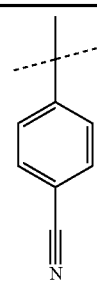 |
| 388 | 702 | 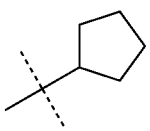 |
| 389 | 703 | 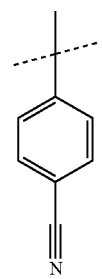 |
| 390 | 704 | 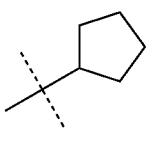 |
| 391 | 705 | 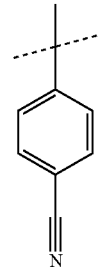 |
| 392 | 706 | 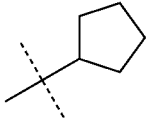 |
| 393 | 707 | phenyl |
| 395 | 709 | phenyl |
| 396 | 710 | phenyl |
| 397 | 711 | phenyl |

US 8,034,811 B2
TABLE 1-continued
Compounds of general formula (I) (W = oxygen; compound 1-399 and 402-432 $R_1$ = hydrogen, compound 400 $R_1$ = methyl)
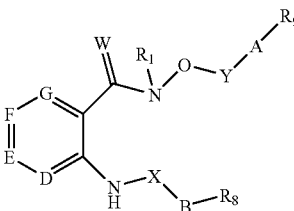
[I]
| 398 | 712 | phenyl |
| 399 | 713 | phenyl |
| 400 | 714 | phenyl |
| 402 | 715 | 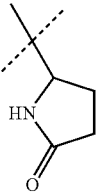 |
| 403 | 716 | 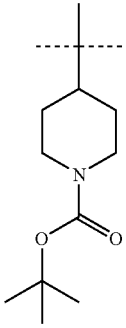 |
| 404 | 717 | 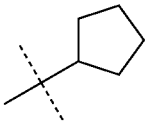 |
| 405 | 718 | 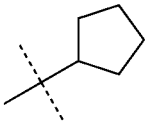 |
| 406 | 719 |  |

TABLE 1-continued
Compounds of general formula (I) (W = oxygen; compound 1-399 and 402-432 R$_1$ = hydrogen, compound 400 R$_1$ = methyl)
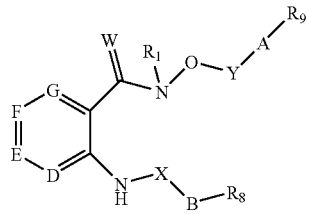
[I]
| | | |
|---|---|---|
| 407 | 720 | 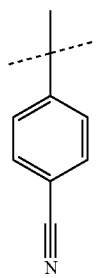 |
| 408 | 721 | 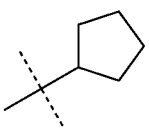 |
| 409 | 722 | 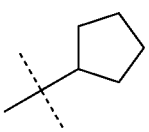 |
| 410 | 723 | 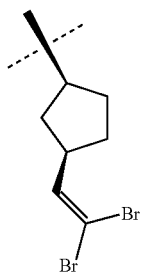 |
| 411 | 724 | 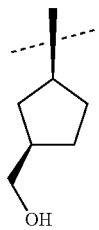 |
| 412 | 725 | 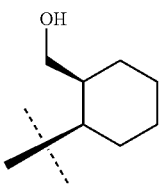 |

TABLE 1-continued
Compounds of general formula (I) (W = oxygen; compound 1-399 and 402-432 R₁ = hydrogen, compound 400 R₁ = methyl)
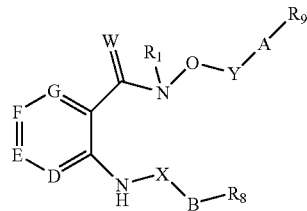
[I]
| | | |
|---|---|---|
| 413 | 726 | 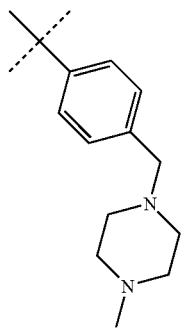 |
| 414 | 727 | 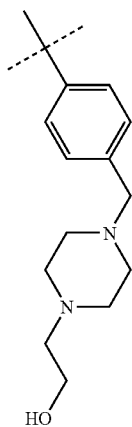 |
| 415 | 728 | 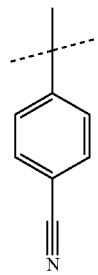 |
| 416 | 729 | 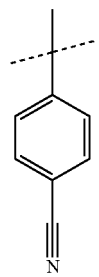 |

TABLE 1-continued
Compounds of general formula (I) (W = oxygen; compound 1-399 and 402-432 R₁ = hydrogen, compound 400 R₁ = methyl)
[I]
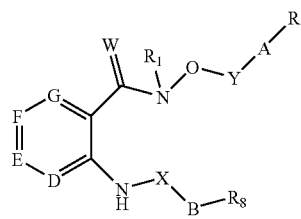
| | | |
|---|---|---|
| 417 | 730 | 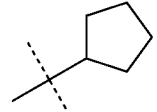 |
| 418 | 731 | 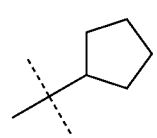 |
| 419 | 732 | 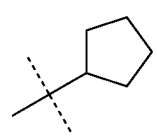 |
| 420 | 733 | 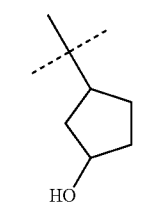 |
| 421 | 734 | 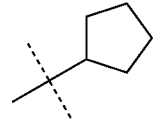 |
| 422 | 735 | 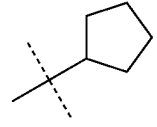 |
| 423 | 736 | 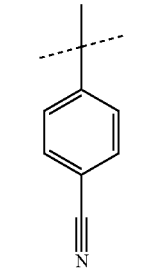 |
| 424 | 737 | 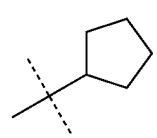 |

TABLE 1-continued
Compounds of general formula (I) (W = oxygen; compound 1-399 and 402-432 $R_1$ = hydrogen, compound 400 $R_1$ = methyl)
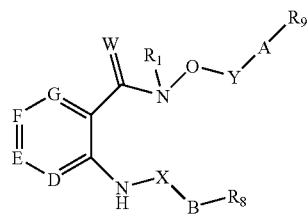
[I]
| | | |
|---|---|---|
| 425 | 738 | 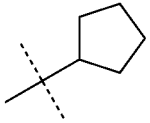 |
| 426 | 739 | 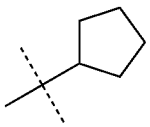 |
| 427 | 740 | 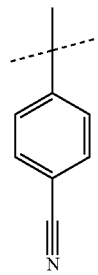 |
| 428 | 741 | 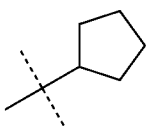 |
| 429 | 742 | 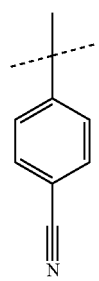 |
| 430 | 743 | 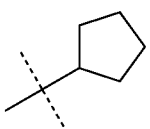 |

TABLE 1-continued

Compounds of general formula (I) (W = oxygen; compound 1-399 and 402-432 $R_1$ = hydrogen, compound 400 $R_1$ = methyl)

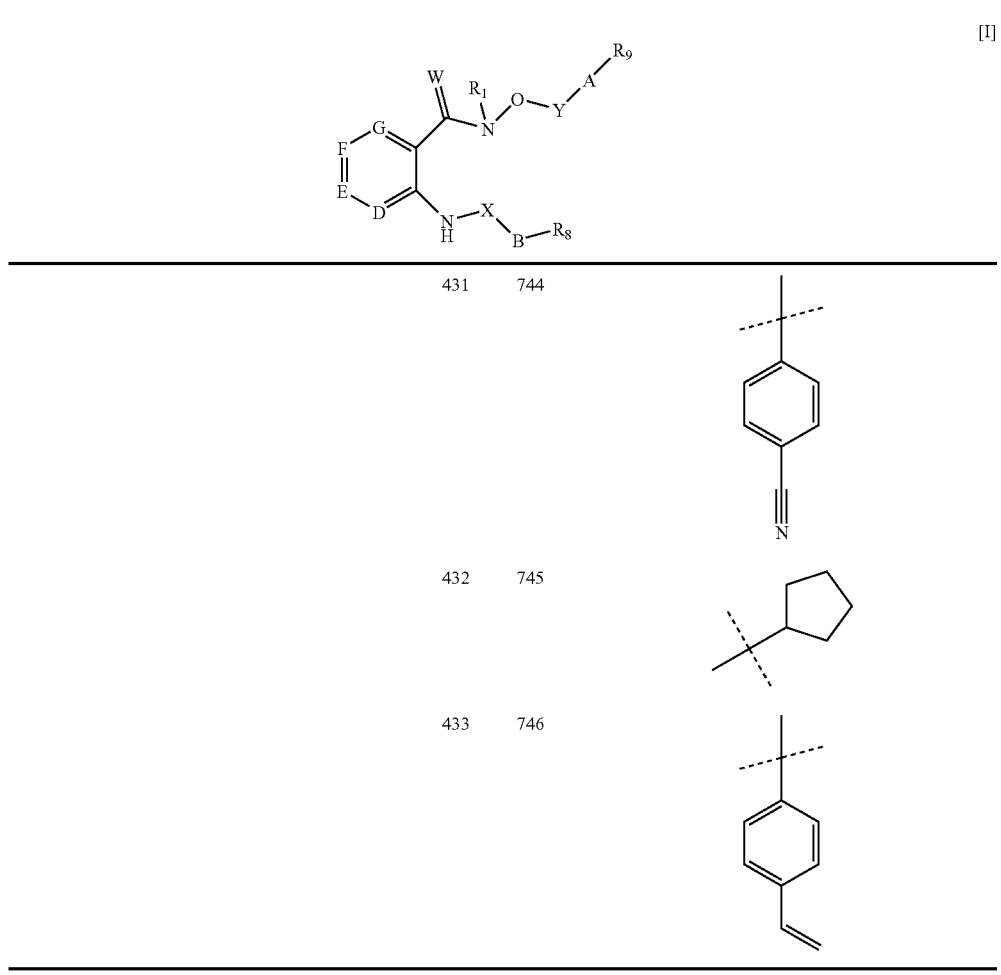

[I]

| | | |
|---|---|---|
| 431 | 744 | (4-cyanophenyl) |
| 432 | 745 | (cyclopentylmethyl) |
| 433 | 746 | (4-vinylphenyl) |

TABLE 2

Exemplified intermediates of general formula II

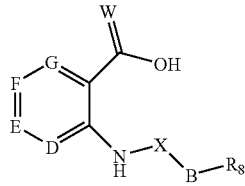

[II]

| Preparation | D | E | F | G | W | X | B-$R_8$ |
|---|---|---|---|---|---|---|---|
| 1 | CH | CH | CH | CH | O | —CH$_2$— | 4-pyridyl |
| 1A | CH | CF | CH | CH | O | —CH$_2$— | 4-pyridyl |
| 1B | CH | CH | CH | CF | O | —CH$_2$— | 4-pyridyl |
| 1C | CH | CH | CF | CH | O | —CH$_2$— | 4-pyridyl |
| 1D | COCH$_3$ | CH | CH | CH | O | —CH$_2$— | 4-pyridyl |
| 1E | CH | COCH$_3$ | COCH$_3$ | CH | O | —CH$_2$— | 4-pyridyl |
| 1F | CH | CH | CH | CCH$_3$ | O | —CH$_2$— | 4-pyridyl |
| 1G | CH | CH | CCH$_3$ | CH | O | —CH$_2$— | 4-pyridyl |
| 1H | CH | CH | CBr | CH | O | —CH$_2$— | 4-pyridyl |
| 1I | CH | N | CH | CH | O | —CH$_2$— | 4-pyridyl |
| 1J | CH | CH | CH | CH | O | —CH$_2$— | 4-fluorophenyl |

TABLE 2-continued

Exemplified intermediates of general formula II

[II]

| Preparation | D | E | F | G | W | X | B-R$_8$ |
|---|---|---|---|---|---|---|---|
| 1K | CH | CH | CH | CH | O | —CH$_2$— | 4-fluoro-3-cyano-phenyl |
| 1L | CH | CH | CH | CH | O | —CH$_2$— | 4-fluoro-3-(methoxycarbonyl)phenyl |
| 1M | CH | CH | CH | CH | O | —CH$_2$— | 4-methoxy-phenyl |
| 1N | CH | CH | CH | CH | O | —CH$_2$— | 4-methoxy-naphthalen-1-yl |
| 1O | CH | CH | CH | CH | O | —CH$_2$— | 2,3-dihydrobenzofuran-5-yl |
| 1P | CH | CH | CH | CH | O | —CH$_2$— | benzofuran-5-yl |

TABLE 2-continued
Exemplified intermediates of general formula II
[II]
| Preparation | D | E | F | G | W | X | B-R₈ |
|---|---|---|---|---|---|---|---|
| 1Q | CH | CH | CH | CH | O | —CH₂— |  |
| 1R | CH | CH | CH | CH | O | —CH₂— | 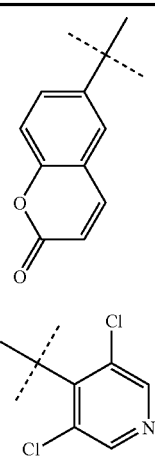 |
| 1S | CH | CH | CH | CH | O | —CH₂— | 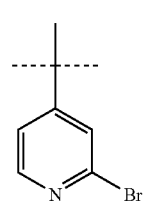 |
| 1T | CH | CH | CH | CH | O | —CH₂— | 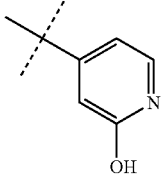 |
| 1U | CH | CH | CH | CH | O | —CH₂— | 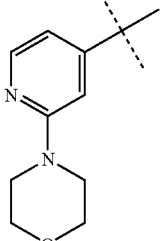 |
| 1V | CH | CH | CH | CH | O | —CH₂— | 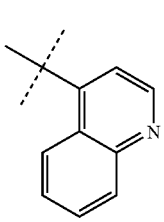 |

TABLE 2-continued

Exemplified intermediates of general formula II

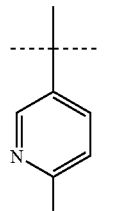

[II]

| Preparation | D | E | F | G | W | X | B-R$_8$ |
|---|---|---|---|---|---|---|---|
| 1W | CH | CH | CH | CH | O | —CH$_2$— | 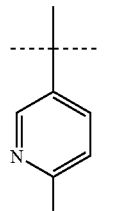 |
| 1X | CH | CH | CH | CH | O | —CH$_2$— | 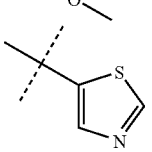 |
| 1Y | CH | CH | CH | CH | O | —CH$_2$— | 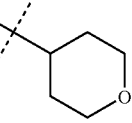 |
| 2 | N | CH | CH | CH | O | —CH$_2$— | 4-pyridyl |
| 3 | N | CH | CH | CH | O | —CH$_2$— | 4-fluorophenyl |
| 3A | N | CH | CH | CH | O | —CH$_2$— | 4-chlorophenyl |
| 3B | N | CH | CH | CH | O |  | 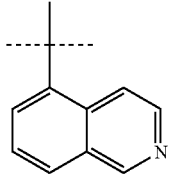 |
| 4 | N | CH | CH | CH | O | —CH$_2$— | 4-methoxy-phenyl |

TABLE 3

Exemplified intermediates of general formula VIII

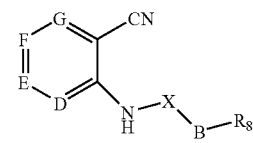

[VIII]

| Preparation | D | E | F | G | X | B-R$_8$ |
|---|---|---|---|---|---|---|
| 5 | N | CH | CH | CH | —CH$_2$— | 4-pyridyl |
| 6 | N | CH | CH | CH | —CH$_2$— | 4-fluorophenyl |
| 7 | N | CH | CH | CH | —CH$_2$— | 4-methoxy-phenyl |

TABLE 3-continued

Exemplified intermediates of general formula VIII

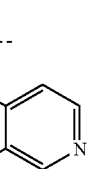

[VIII]

| Preparation | D | E | F | G | X | B-R$_8$ |
|---|---|---|---|---|---|---|
| 3B | N | CH | CH | CH | bond | 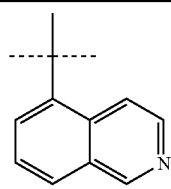 |

TABLE 4

Exemplified nitrogen substituted anhydrides of general formula XV

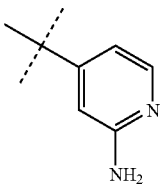

[XV]

| Preparation | D | E | F | G | W | X | B-R8 |
|---|---|---|---|---|---|---|---|
| 7A | CH | CH | CH | CH | O | —CH2— | 4-pyridyl |
| 7B | CH | CH | CH | CH | O | —CH2— | 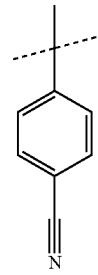 |
| 7D | CH | CH | CH | CH | O | —CH2— | 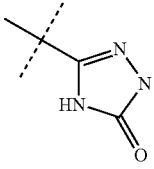 |
| 7E | CH | CH | CH | CH | O | —CH2— | 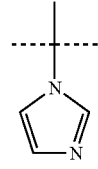 |
| 7F | CH | CH | CH | CH | O | —(CH2)2— | 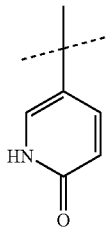 |
| 7G | CH | CH | CH | CH | O | 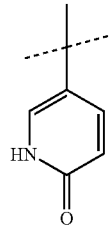 | 4-pyridyl |
| 7H | CH | CH | CH | CH | O | —CH2— | 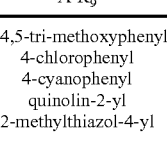 |

TABLE 4-continued

Exemplified nitrogen substituted anhydrides of general formula XV

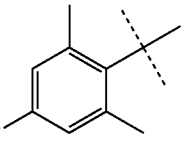

[XV]

| Preparation | D | E | F | G | W | X | B-R8 |
|---|---|---|---|---|---|---|---|
| 7I | N | CH | CH | CH | O | —CH2— | 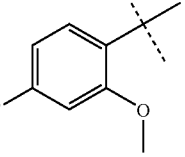 |

TABLE 5

Exemplified O-substituted (Y-A) hydroxylamines of general formula III

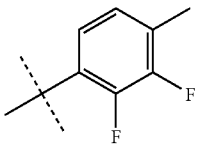

[III]

| Preparation | R1 | Y | A-R9 |
|---|---|---|---|
| 8 | H | —CH2— | 3,4,5-tri-methoxyphenyl |
| 9 | H | —CH2— | 4-chlorophenyl |
| 10 | H | —CH2— | 4-cyanophenyl |
| 11 | H | —CH2— | quinolin-2-yl |
| 12 | H | —CH2— | 2-methylthiazol-4-yl |
| 13 | H | —CH2— |  |
| 14 | H | —CH2— | 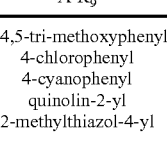 |
| 15 | H | —CH2— | 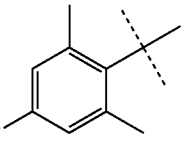 |

TABLE 5-continued
Exemplified O-substituted (Y-A) hydroxylamines of general formula III
[III]
| Preparation | R1 | Y | A-R9 |
|---|---|---|---|
| 16 | H | —CH2— | 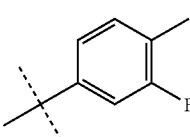 |
| 17 | H | —CH2— | 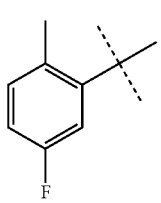 |
| 18 | H | —CH2— | 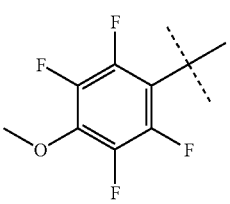 |
| 19 | H | —CH2— | 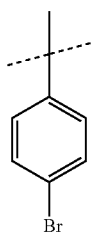 |
| 20 | H | —CH2— | 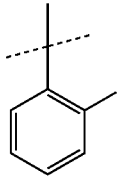 |
| 21 | H | —CH2— | 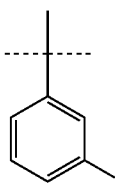 |
| 22 | H | —CH2— | 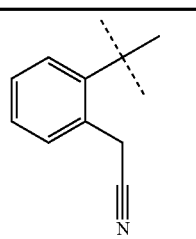 |
| 23 | H | —CH2— | 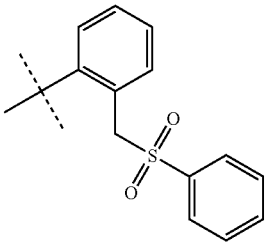 |
| 24 | H | —CH2— | 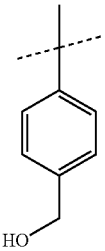 |
| 25 | H | —CH2— | 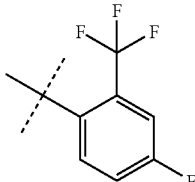 |
| 26 | H | —CH2— | 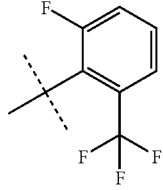 |
| 27 | H | —CH2— | 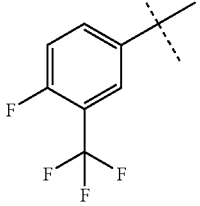 |

TABLE 5-continued

Exemplified O-substituted (Y-A) hydroxylamines of general formula III

[III]

R1-N(H)-O-Y-A-R9

| Preparation | R1 | Y | A-R9 |
|---|---|---|---|
| 28 | H | —CH₂— | 4-tert-butyl-2-(trifluoromethyl)phenyl |
| 29 | H | —CH₂— | 4-tert-butyl-2-(trifluoromethyl)-1-methoxyphenyl |
| 30 | H | —CH₂— | 2-methoxyphenyl (isopropyl) |
| 31 | H | —CH₂— | 4-tert-butylphenoxy-pentyl |
| 32 | H | —CH₂— | 2-(trifluoromethoxy)phenyl (isopropyl) |
| 33 | H | —CH₂— | 3-tert-butyl-phenoxy-OCF₃ |
| 34 | H | —CH₂— | 4-tert-butyl-phenyl-OCF₃ |
| 35 | H | —CH₂— | 2-tert-butyl-phenyl-OCHF₂ |
| 36 | H | —CH₂— | 2-tert-butyl-phenyl-SCF₃ |
| 37 | H | —CH₂— | 6-chloro-benzo[1,3]dioxol-5-yl (tert-butyl) |
| 38 | H | —CH₂— | benzo[1,3]dioxol-5-yl (tert-butyl) |

TABLE 5-continued
Exemplified O-substituted (Y-A) hydroxylamines of general formula III
[III] R1\N(H)\O\Y\A\R9
| Preparation | R1 | Y | A-R9 |
|---|---|---|---|
| 39 | H | —CH2— | 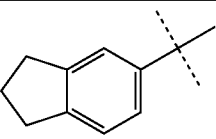 |
| 40 | H | —CH2— | 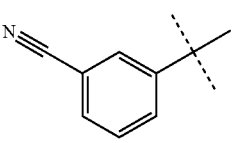 |
| 41 | H | —CH2— | 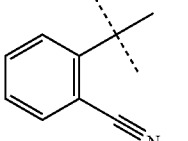 |
| 42 | H | —CH2— | 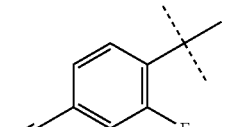 |
| 43 | H | —CH2— | 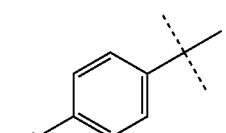 |
| 44 | H | —CH2— | 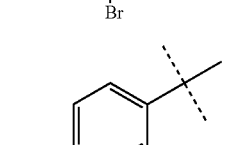 |
| 45 | H | —CH2— | 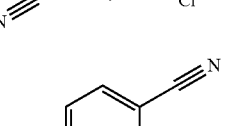 |
| 46 | H | —CH2— | 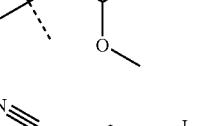 |
| 47 | H | —CH2— | 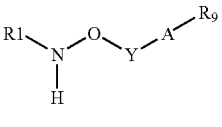 |
| 48 | H | —CH2— | 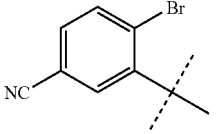 |
| 49 | H | —CH2— | 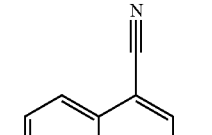 |
| 50 | H | —CH2— | 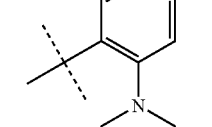 |
| 51 | H | —CH2— | 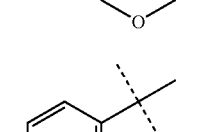 |
| 52 | H | —CH2— | 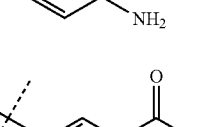 |

TABLE 5-continued
Exemplified O-substituted (Y-A) hydroxylamines of general formula III
[III]
| Preparation | R1 | Y | A-R9 |
|---|---|---|---|
| 53 | H | —CH2— | 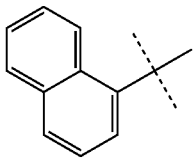 |
| 54 | H | 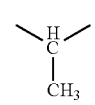 | Phenyl |
| 55 | H | 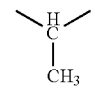 | 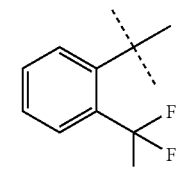 |
| 56 | H | —CH2— | 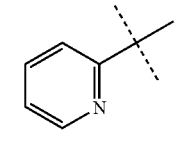 |
| 57 | H | —CH2— | 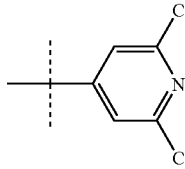 |
| 58 | H | —CH2— | 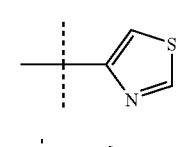 |
| 59 | H | —CH2— | 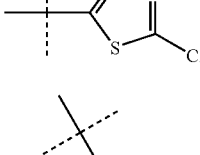 |
| 60 | H | —CH2— | 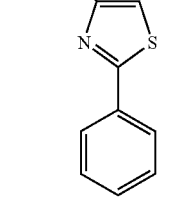 |
| 61 | H | —CH2— | 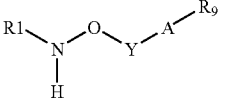 |
| 62 | H | —CH2— | 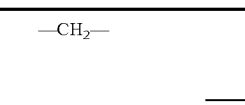 |
| 63 | H | —CH2— | 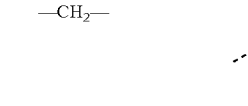 |
| 64 | H | —CH2— | 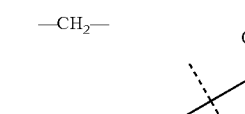 |
| 65 | H | —(CH2)2— | 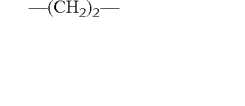 |
| 66 | H | —CH2— |  |
| 67 | H | —CH2— | |
| 68 | H | —CH2— | |
| 69 | H | —CH2— | |

TABLE 5-continued

Exemplified O-substituted (Y-A) hydroxylamines of general formula III $$R_1\text{-}N(H)\text{-}O\text{-}Y\text{-}A\text{-}R_9 \quad [III]$$

| Preparation | R1 | Y | A-R9 |
|---|---|---|---|
| 70 | H | —(CH$_2$)$_2$— | isobutyl |
| 71 | H | —CH$_2$— | cyclobutyl (quaternary C) |
| 72 | H | —CH$_2$— | cyclohexyl (quaternary C) |
| 73 | H | —CH$_2$— | cycloheptyl (quaternary C) |
| 74 | H | —CH$_2$— | cyclooctyl (quaternary C) |
| 75 | H | —CH(CH$_3$)— | cyclopentyl (quaternary C) |
| 76 | H | bond | cyclohexyl (quaternary C) |
| 77 | H | —(CH$_2$)$_2$— | cyclopropyl (quaternary C) |
| 78 | H | —(CH$_2$)$_2$— | cyclopentyl (quaternary C) |
| 79 | H | —(CH$_2$)$_3$— | cyclopentyl (quaternary C) |
| 80 | H | —CH$_2$— | cyclohex-3-enyl (quaternary C) |
| 81 | H | —CH$_2$— | 2-methylcyclohex-3-enyl (quaternary C) |
| 82 | H | —CH$_2$— | trans-4-(hydroxymethyl)cyclohexyl |
| 83 | H | —CH$_2$— | 3-methoxycyclohexyl (with methyl) |
| 84 | H | —CH$_2$— | adamantyl |
| 85 | H | —CH$_2$— | norbornyl derivative |
| 86 | H | —CH$_2$— | pinanyl |
| 87 | H | —CH$_2$— | tetrahydrofuran-2-yl |

TABLE 5-continued
Exemplified O-substituted (Y-A) hydroxylamines of general formula III
[III]
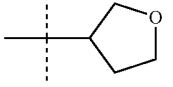
| Preparation | R1 | Y | A-R9 |
|---|---|---|---|
| 88 | H | —CH$_2$— | 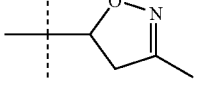 |
| 89 | H | —CH$_2$— | 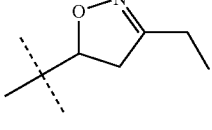 |
| 90 | H | —CH$_2$— | 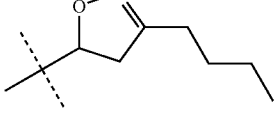 |
| 91 | H | —CH$_2$— | 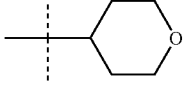 |
| 92 | H | —CH$_2$— | 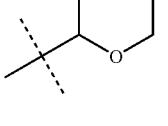 |
| 93 | H | —CH$_2$— | 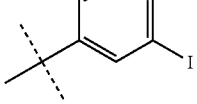 |
| 94 | H | —CH$_2$— | 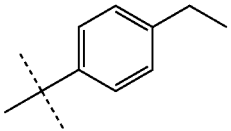 |
| 95 | H | —CH$_2$— | 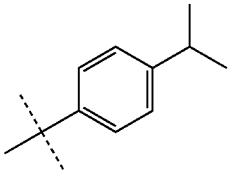 |
| 96 | H | —CH$_2$— | 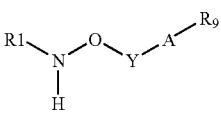 |
| 97 | H | —CH$_2$— | 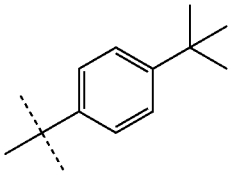 |
| 98 | H | —CH$_2$— | 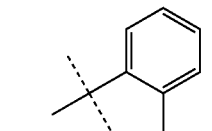 |
| 99 | H | —CH$_2$— | 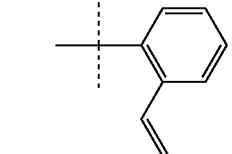 |
| 100 | H | —CH$_2$— | 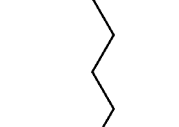 |

TABLE 5-continued
Exemplified O-substituted (Y-A) hydroxylamines of general formula III
[III]
R1—N(H)—O—Y—A—R9
| Preparation | R1 | Y | A-R9 |
|---|---|---|---|
| 101 | H | —CH₂— | 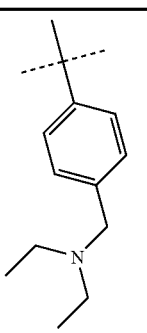 |
| 102 | H | —CH₂— | 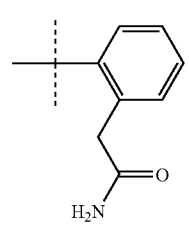 |
| 103 | H | —CH₂— | 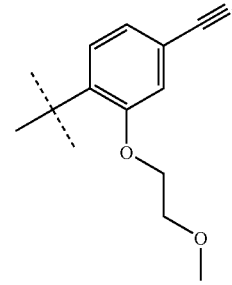 |
| 104 | H | —CH₂— | 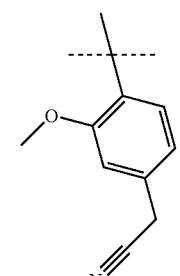 |
| 105 | H | —CH₂— | 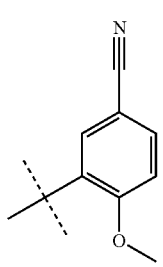 |
| 106 | H | —CH₂— | 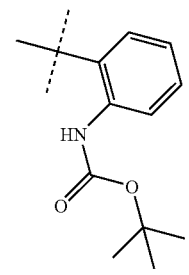 |
| 107 | H | —CH₂— | 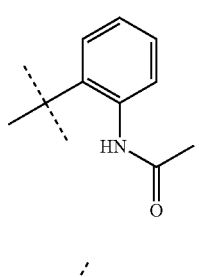 |
| 108 | H | —CH₂— | 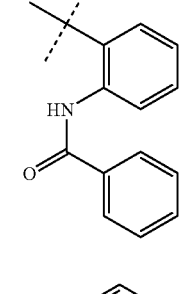 |
| 109 | H | —CH₂— | 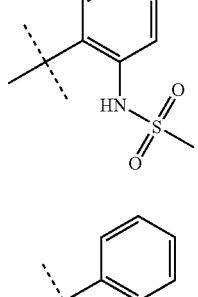 |
| 110 | H | —CH₂— | 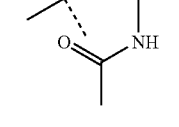 |

TABLE 5-continued

Exemplified O-substituted (Y-A) hydroxylamines of general formula III $$\text{R1}\diagdown\underset{H}{N}\diagdown O\diagdown Y\diagdown A\diagdown R_9 \quad [III]$$

| Preparation | R1 | Y | A-R9 |
|---|---|---|---|
| 111 | H | —CH₂— | 4-biphenylyl |
| 112 | H | —CH₂— | 2-biphenylyl |
| 113 | H | —CH₂— | 3'-methoxy-2-biphenylyl |
| 114 | H | —CH₂— | 2'-methoxy-2-biphenylyl |
| 115 | H | —CH₂— | 3'-(hydroxymethyl)-2-biphenylyl |
| 116 | H | —CH₂— | 3-phenoxyphenyl |
| 117 | H | —CH₂— | anthracen-9-yl |
| 118 | H | —CH₂— | 4-(2-methylthiazol-4-yl)phenyl |
| 119 | H | (2,2-dimethyl-1-(methylsulfonamidomethyl)propyl) | phenyl |

TABLE 5-continued

Exemplified O-substituted (Y-A) hydroxylamines of general formula III $$R1\text{-}N(H)\text{-}O\text{-}Y\text{-}A\text{-}R_9 \quad [III]$$

| Preparation | R1 | Y | A-R9 |
|---|---|---|---|
| 120 | H | —CH2— | 4-(4-(trifluoromethyl)phenyl)thiazol-2-yl |
| 121 | H | —CH2— | 3-(p-tolyl)isoxazol-5-yl |
| 122 | H | —CH2— | 3-methylisoxazol-5-yl |
| 123 | H | —CH2— | 3-ethylisoxazol-5-yl |
| 124 | H | —CH2— | 3-butylisoxazol-5-yl |
| 125 | H | —CH2— | 3-pentylisoxazol-5-yl |
| 126 | H | —CH2— | 5-(3-(trifluoromethyl)phenyl)-1,2,4-oxadiazol-3-yl |
| 127 | H | —CH2— | 1-benzyl-1H-1,2,3-triazol-4-yl |
| 128 | H | —CH2— | 1-cyclopentyl-1H-1,2,3-triazol-4-yl |
| 129 | H | —CH2— | 5-oxo-4,5-dihydro-1H-1,2,4-triazol-3-yl |

TABLE 5-continued
Exemplified O-substituted (Y-A) hydroxylamines of general formula III
[III]
R1—N(H)—O—Y—A—R9
| Preparation | R1 | Y | A-R9 |
|---|---|---|---|
| 130 | H | —CH2— | 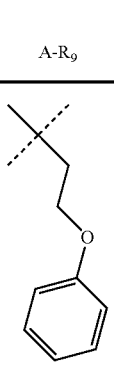 |
| 131 | H | —CH2— | 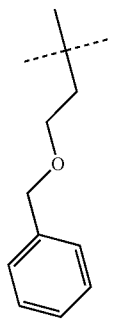 |
| 132 | H | —CH2— | 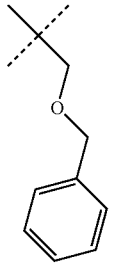 |
| 133 | H | —CH2— | 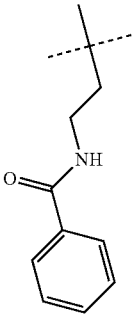 |
| 134 | H | —CH2— |  |
| 135 | H | —CH2— | 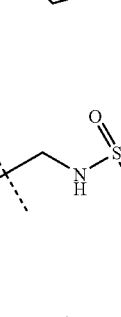 |
| 136 | H | —CH2— | 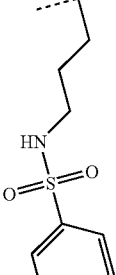 |
| 137 | H | —CH2— | 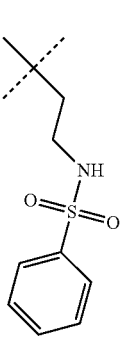 |

TABLE 5-continued

Exemplified O-substituted (Y-A) hydroxylamines of general formula III $$R_1\text{-NH-O-Y-A-}R_9 \quad [III]$$

| Preparation | R1 | Y | A-R9 |
|---|---|---|---|
| 138 | H | —CH2— | (CH2)-NH-SO2-C6H4-CN |
| 139 | H | —CH2— | (CH2)2-NH-SO2-C6H4-CN |
| 140 | H | —CH2— | (CH2)2-NH-SO2-CH2-C6H5 |
| 141 | H | —CH2— | (CH2)-NH-SO2-CH2-C6H5 |
| 142 | H | —CH2— | (CH2)2-NH-SO2-(4-methylthiazol-5-yl with 2-NHC(O)CH3) |
| 143 | H | —CH2— | (CH2)-NH-SO2-(4-methylthiazol-5-yl with 2-NHC(O)CH3) |
| 144 | H | —CH2— | (CH2)2-NH-CH2-C6H5 |

TABLE 5-continued

Exemplified O-substituted (Y-A) hydroxylamines of general formula III $$R_1\text{-NH-O-Y-A-}R_9 \quad [III]$$

| Preparation | R1 | Y | A-R9 |
|---|---|---|---|
| 145 | H | —CH2— | 4-(benzylamino)butyl |
| 146 | H | —CH2— | 2-(Boc-amino)ethyl |
| 147 | H | —CH2— | 3-(Boc-amino)propyl |
| 148 | H | —CH2— | 4-(Boc-amino)butyl |
| 149 | H | —CH2— | isobutyl |
| 150 | H | —CH2— | 2-methylallyl |
| 151 | H | —CH2— | 4-hydroxy-2-pentenyl |
| 152 | H | bond | cyclopentyl |
| 153 | H | bond | cyclooctyl |
| 154 | H | —CH2— | cyclohexylmethyl |
| 155 | H | —CH2— | 2-methylcyclohexyl |
| 156 | H | —CH2— | 4-methylcyclohexyl |
| 157 | H | —CH2— | trans-4-methoxycyclohexyl |
| 158 | H | —CH2— | bornyl |

TABLE 5-continued
Exemplified O-substituted (Y-A) hydroxylamines of general formula III
[III]
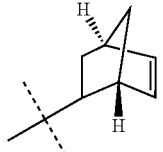
| Preparation | R1 | Y | A-R9 |
|---|---|---|---|
| 159 | H | —CH2— | 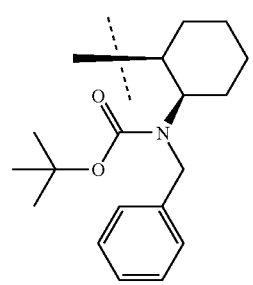 |
| 160 | H | —CH2— | 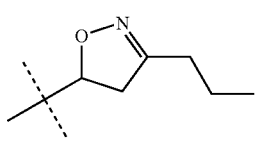 |
| 161 | H | —CH2— | 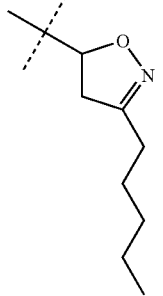 |
| 162 | H | —CH2— | 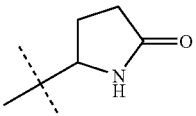 |
| 163 | H | —CH2— | 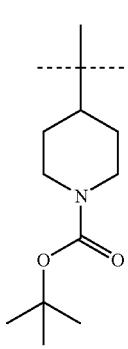 |
| 164 | H | —CH2— | 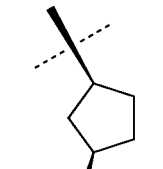 |
TABLE 5-continued
Exemplified O-substituted (Y-A) hydroxylamines of general formula III
[III]
| Preparation | R1 | Y | A-R9 |
|---|---|---|---|
| 165 | H | —CH2— | 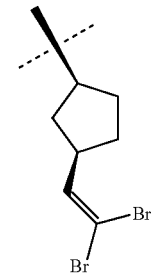 |
| 166 | H | —CH2— | 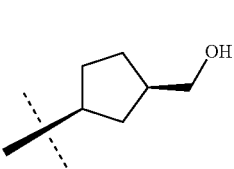 |
| 167 | H | —CH2— | 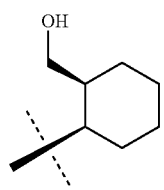 |
| 168 | H | —CH2— | 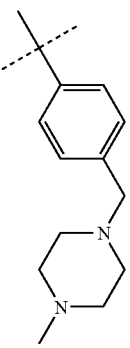 |

TABLE 5-continued

Exemplified O-substituted (Y-A) hydroxylamines of general formula III

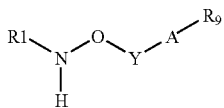

[III]

| Preparation | R1 | Y | A-R9 |
|---|---|---|---|
| 169 | H | —CH$_2$— | ![structure with piperazine linked to benzyl and ethanol] |
| 170 | H | —CH$_2$— | ![cyclopentane-OH structure] |

General Procedure 1

Synthesis of Hydroxamic Acid Esters of General Formula (I) from Carboxylic Acids of General Formula (II)

Method 1: A carboxylic acid of general formula (II) (1.0 eq.) was dissolved in dry DMF or dry NMP under argon to obtain a 0.2M solution or suspension. N,N'-Carbonyldiimidazole (1.0 eq.) was added in one portion and the resulting reaction mixture was stirred at room temperature for 45-60 min. O-Substituted hydroxylamine (III) or the corresponding hydrochloride (1.0 eq.) was added and stirring continued at room temperature for 20 hours. Water was added and if the product precipitated, it was isolated by filtration and recrystallised (typically from ethanol). If the crude product did not precipitate as a solid material, the mixture was extracted with EtOAc. The combined organic layers were washed with water and brine, dried (MgSO$_4$) and evaporated under reduced pressure. The residue was either purified by crystallisation or chromatography on silica gel (EtOAc/petroleum ether) to afford hydroxamic acid esters of general formula (I).

Method 2: carboxylic acid of general formula (II) (1.0 eq.) was dissolved in dry DMF or dry NMP under argon to obtain a 0.1M to 0.2M solution or suspension. O-Substituted hydroxylamine (III) or the corresponding hydrochloride (1.0-1.05 eq.), 1-hydroxybenzotriazole hydrate (1.0-1.05 eq.), N-methylmorpholine (2.0 eq.) and 1-ethyl-3-(3-dimethylaminopropyl)carbodiimide hydrochloride (1.0-1.3 eq.) was added in that order. The reaction mixture was stirred at room temperature for 15-20 hours. Water was added to the mixture and the product was extracted several times with EtOAc. The combined organic layers were washed with water and brine, dried (MgSO$_4$ or Na$_2$SO$_4$) and evaporated under reduced pressure. The crude product was either purified by chromatography on silica gel (typically using EtOAc/petroleum ether as the eluent) or by crystallisation and re-crystallisation from a suitable solvent such as ethanol or EtOAc, to obtain hydroxamic acid esters of general formula (I).

General Procedure 1A

Synthesis of Hydroxamic Acid Esters of General Formula (I) from N-Alkylated Anhydrides of General Formula (XV)

A mixture of anhydride of general formula (XV) (1.0 eq.) and O-Substituted hydroxylamine (III) or the corresponding amine hydrochloride (1.1 eq.) in pyridine (1 to 2 ml/mmol anhydride) was stirred at room temperature for 1 to 20 hours or until LC/MS or TLC indicated complete conversion of the starting material. The solvent was evaporated under reduced pressure and the residue was dissolved in EtOAc. The mixture washed with water and brine, dried (MgSO$_4$ or Na$_2$SO$_4$) and evaporated under reduced pressure. The crude product was purified by either chromatography on silica gel (using EtOAc/petroleum ether as solvent typically) or by crystallisation and re-crystallisation from a suitable solvent such as ethanol or EtOAc, to obtain hydroxamic acid esters of general formula (I).

General Procedure 2

Synthesis of Carboxylic Acids of General Formula (II) from the Corresponding Esters of General Formula (VII)

To a stirred 0.25 M solution of ester with the general formula (VII) (1.0 eq.) in THF/water (3:1, v/v) was added lithium hydroxide (6-8 eq.). The reaction mixture was stirred at room temperature for 60 min. then heated to 60° C. and stirring continued at this temperature for 20 hours. The mixture was cooled to room temperature and most of the THF solvent was evaporated under reduced pressure. The residue was diluted with water and the pH of the mixture was adjusted to 5-6 by addition of 4 M hydrochloric acid. The resulting precipitated material was isolated by filtration and washed with water. Crystallisation from ethanol afforded the carboxylic acid of general formula (II).

General Procedure 3

Synthesis of Carboxylic Acids of General Formula (II) from the Corresponding Nitriles of General Formula (VIII)

A suspension of nitrile of general formula (VIII) in 27.65% sodium hydroxide (2.5 ml/mmol nitrile) and methanol (1 ml/mmol of nitrile) was heated to reflux and stirred at this temperature for 3 hours. The mixture was cooled to room temperature and diluted with water. The pH of the mixture was adjusted to 5-6 by addition of 4M hydrochloric acid. If a precipitate formed, it was isolated by filtration washed with water and dried under high vacuum, affording carboxylic acid of general formula (II). If the product acid did not precipitate the neutralised aqueous mixture was concentrated under reduced pressure and extracted thoroughly with ethyl acetate. The combined organic layers were dried (MgSO$_4$) and evaporated under reduced pressure. The residue was recrystallised from ethanol or methanol and gave the carboxylic acid of general formula (II).

Preparation 1

2-[(Pyridin-4-ylmethyl)-amino]-benzoic acid

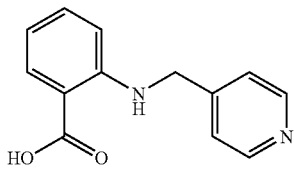

General procedure 2. (alternative preparation is described in WO 00/27819). Starting material: 2-[(pyridin-4-ylmethyl)-amino]-benzoic acid methyl ester (Manley P. W. et al. *J. Med. Chem.* (2002), 45, 5687-5693). $^{13}$C-NMR (DMSO-d$_6$) δ 169.69, 150.05, 149.35, 148.64, 134.03, 131.47, 121.70, 114.54, 111.30, 110.45, 44.41.

Preparation 1A

4-Fluoro-2-[(pyridin-4-ylmethyl)-amino]-benzoic acid

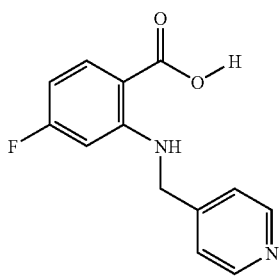

To a stirred mixture of 2-amino-4-fluorobenzoic acid (Aldrich, 2.0 g) and pyridine-4-carbaldehyde (1.21 ml) in 1,2-dichloroethane (20 ml) was added sodium triacetoxy-borohydride (4.1 g). The reaction mixture was stirred at room temperature for 18 hours. Silica gel was added and the solvent was evaporated under reduced pressure. The residue was subjected to column chromatography on silica gel (elution with EtOAc/methanol 19/1, v/v) and gave the title compound (1.04 g). $^{13}$C-NMR (DMSO-d$_6$) δ 169.1, 166.2, 152.5, 149.6, 148.2, 134.6, 121.9, 107.6, 102.1, 97.7, 44.6.

Preparation 1B

2-Fluoro-6-[(pyridin-4-ylmethyl)-amino]-benzoic acid

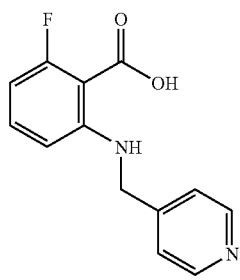

Prepared by a similar procedure as described for preparation 1A, starting from 2-amino-6-fluorobenzoic acid (Aldrich) and pyridine-4-carbaldehyde. $^{13}$C-NMR (DMSO-d$_6$) δ 167.7, 162.7, 150.6, 149.5, 148.6, 133.8, 121.9, 107.3, 102.6, 101.9, 45.0.

Preparation 1C

5-Fluoro-2-[(pyridin-4-ylmethyl)-amino]-benzoic acid

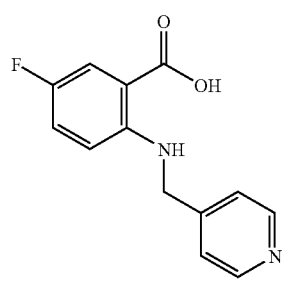

Prepared by a similar procedure as described for preparation 1A, starting from 2-amino-5-fluorobenzoic acid (Aldrich) and pyridine-4-carbaldehyde. $^{13}$C-NMR (DMSO-d$_6$) δ 168.9, 152.4, 149.6, 148.8, 147.2, 121.9, 121.6, 116.6, 113.0, 110.7, 44.9.

Preparation 1D

3-Methoxy-2-[(pyridin-4-ylmethyl)-amino]-benzoic acid

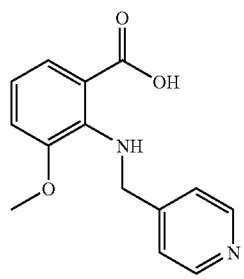

Step 1: To a stirred solution of 3-methoxy-2-nitro-benzoic acid (11.50 g) in DMF (100 ml) was added N,N'-carbonyldiimidazole (11.35 g) and the reaction mixture was stirred at room temperature for 45 minutes. Methanol (18.6 ml) was added and the mixture was stirred at room temperature for 60 minutes. The mixture was poured into water (800 ml) containing some ice and the precipitated material was isolated by filtration and crystallised from hot ethanol and gave 3-Methoxy-2-nitro-benzoic acid methyl ester. Step 2: The above obtained methyl ester (11.81 g) was suspended in water (45 ml) and ethanol (60 ml). Ammonium chloride (12.26 g) was added followed by addition of iron powder (11.86 g). The reaction mixture was heated to reflux and stirred for 1 hour. The mixture was cooled on an ice bath and was then filtrated though a pad of Celite. The filtrate was evaporated under reduced pressure. The residue was re-dissolved in a minimum amount of EtOAc and was filtrated through a pad of silica gel, washing with EtOAc. The combined filtrates were evaporated under reduced pressure. The remaining oil was dissolved in EtOAc (40 ml) and hexane was added until a precipitate formed. The solid material was isolated by filtration and dried under high vacuum and gave 2-amino-3-methoxy-benzoic acid methyl ester. Step 3: The above obtained amine (7.5 g) was dissolved in 1,2-dichloroethane (125 ml) and pyridine- 4-carbaldehyde (6.65 g) was added followed by addition of sodium triacetoxy-borohydride (17.5 g). The reaction mixture was heated to 50° C. and stirred for 2.5 hours. More and pyridine-4-carbaldehyde (1.5 ml) and sodium triacetoxy-borohydride (5.0 g) was added and stirring was continued at 50° C. for 15 hours. Saturated aqueous sodium bicarbonate was carefully added and the mixture was extracted with dichloromethane. The organic layer washed with saturated aqueous sodium bicarbonate, water and brine, dried (MgSO$_4$) and evaporated under reduced pressure. The residue was subjected to column chromatography on silica gel (elution with 0 to 50% EtOAc in dichloromethane) and gave 3-methoxy-2-[(pyridin-4-ylmethyl)-amino]-benzoic acid methyl ester as a pale yellow oil. Step 4: The compound obtained in step 3 (8 g) was dissolved in methanol (100 ml) and 2M sodium hydroxide (50 ml) was added. The reaction mixture was heated to 45° C. and stirred for 1 hour. The mixture was cooled to room temperature and stirring continued for 18 hours. The mixture was concentrated to ca. 50 ml under reduced pressure. Water (200 ml) was added and the pH of the mixture was adjusted to 6 with 4M HCl. The precipitated material was isolated by filtration and dried in vacuo and gave the title compound. $^{13}$C-NMR (DMSO-d$_6$) δ 170.1, 150.3, 149.8, 149.3, 141.8, 123.4, 122.0, 117.0, 116.4, 114.8, 55.6, 48.4.

Preparation 1E 4,5-Dimethoxy-2-[(pyridin-4-ylmethyl)-amino]-benzoic acid

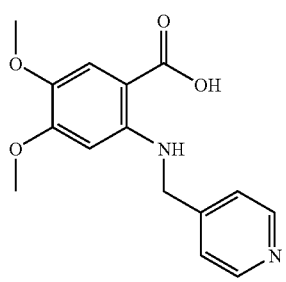

Prepared by a similar procedure as described for preparation 1A, starting from 2-amino-4,5-dimethoxybenzoic acid (Aldrich) and pyridine-4-carbaldehyde. $^{13}$C-NMR (DMSO-d$_6$) δ 169.4, 154.8, 149.6, 149.0, 147.5, 138.9, 122.1, 114.6, 101.4, 95.5, 56.1, 55.2, 45.0.

Preparation 1F

2-Methyl-6-[(pyridin-4-ylmethyl)-amino]-benzoic acid

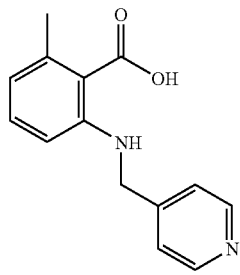

Prepared by a similar procedure as described for preparation 1A, starting from 2-amino-6-methylbenzoic acid (Fluka) and pyridine-4-carbaldehyde. $^{13}$C-NMR (DMSO-d$_6$) δ 170.4, 149.5, 149.3, 147.8, 138.5, 131.2, 121.9, 118.7, 115.8, 109.1, 45.1, 22.1.

Preparation 1G

5-Methyl-2-[(pyridin-4-ylmethyl)-amino]-benzoic acid

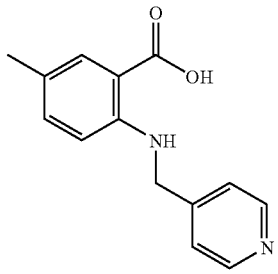

Prepared by a similar procedure as described for preparation 1A, starting from 2-amino-5-methylbenzoic acid (Aldrich) and pyridine-4-carbaldehyde. $^{13}$C-NMR (DMSO-d$_6$) δ 169.9, 149.5, 149.1, 148.3, 135.1, 131.5, 123.2, 121.9, 111.7, 110.5, 44.7, 19.6.

Preparation 1H

5-Bromo-2-[(pyridin-4-ylmethyl)-amino]-benzoic acid

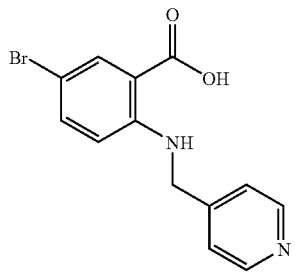

Prepared by a similar procedure as described for preparation 1A, starting from 2-amino-5-bromobenzoic acid (Aldrich) and pyridine-4-carbaldehyde. $^{13}$C-NMR (DMSO-d$_6$) δ 170.4, 149.4, 149.4, 148.7, 133.9, 132.3, 123.2, 122.0, 112.2, 104.9, 44.9.

Preparation 1I

3-[(Pyridin-4-ylmethyl)-amino]-isonicotinic acid

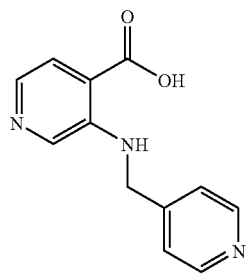

Step 1: To a stirred solution of potassium tert-butoxide (29.8 g) in DMSO (100 ml) was added 3-amino-pyridin (10.0 g). The dark red reaction mixture was stirred at room temperature for 45 minutes. A solution of di-tert-butyl-dicarbonate (30.14 g) in DMSO (50 ml) was added and the reaction mixture was stirred at room temperature for 90 minutes. The mixture was poured into ice-water and the pH of the mixture was adjusted to 6-7 by addition of glacial acetic acid. The mixture was extracted with EtOAc. The organic layer washed with water and brine and evaporated under reduced pressure. The remaining oil was passed through a pad of silica gel, first washing with dichloromethane then with EtOAc/dichloromethane 1/1. Fractions containing compound were evaporated under reduced pressure. The remaining oil was dissolved in diethyl ether (10 ml) and on addition of hexane (100-150 ml) a solid material resulted, that was isolated by filtration and gave pyridin-3-yl-carbamic acid tert-butyl ester. Step 2: The carbamate obtained in step 1 (6.71 g) was dissolved in THF (70 ml) and the mixture was cooled to −77° C. tert-Butyllithium (45 ml of a 1.7 M solution in pentane) was added drop-wise, and stirring was continued at −75° C. for 2.5 hours. Dry $CO_2$ gas was bobbled though the mixture at −75° C. for 30 minutes. The mixture was then allowed to warm to room temperature and poured into ice-water. The mixture was extracted with EtOAc and the pH of the aqueous layer was adjusted to 7-8 and another extraction with EtOAc was performed. The pH of the aqueous layer was then adjusted to 5-6 with glacial acetic acid and the resulting precipitated material was isolated by filtration and dried under high vacuum, affording 3-tert-butoxycarbonylamino-isonicotinic acid (4.96 g). Step 3: The acid (4.96 g) obtained in step 2 was dissolved in DMF (70 ml) and N,N'-carbonyldiimidazole (4.04 g) was added. The reaction mixture was stirred at room temperature for 45 minutes and methanol (9.5 ml) and 4-dimethylaminopyridine (catalytic amount) was added. The mixture was stirred at room temperature for 2 hours. Water was added and the precipitated material was isolated by filtration and gave 3-tert-butoxy-carbonylamino-isonicotinic acid methyl ester (5.1 g). Step 4: The methyl ester (5.1 g) obtained in step 3 was heated to 185° C. for 5 minutes. The resulting brown material was suspended in EtOAc and filtrated through a pad of silica gel, washing with EtOAc. Silica gel was added to the combined filtrates and the solvent was evaporated under reduced pressure. The silica containing compound was heated to 160° C. for 10 minutes. The mixture was cooled to room temperature then re-heated to 160° C. for another 10 minutes. The silica was then washed with 5% methanol in EtOAc. The combined washings were evaporated under reduced pressure and the resulting oil was treated with diethyl ether (10 ml) and hexane (70 ml) and gave 3-amino-isonicotinic acid methyl ester as a solid material. Step 5: The amine (2.27 g) obtained in step 4 was dissolved in 1,2-dichloroethane (100 ml) and pyridine-4-carbaldehyde (1.92 g) was added followed by addition of sodium triacetoxy-borohydride (6.32 g). The reaction mixture was stirred at room temperature for 4 hours and saturated aqueous sodium bicarbonate was added. The mixture was extracted with dichloromethane and the organic layer was dried ($MgSO_4$) and evaporated under reduced pressure. The residue was subjected to column chromatography on silica gel (elution with 5% methanol in EtOAc) and gave 3-[(pyridin-4-ylmethyl)-amino]-isonicotinic acid methyl ester. Step 6: The compound (577 mg) obtained in step 5 was dissolved in methanol (10 ml) and 2M sodium hydroxide (10 ml) was added. The mixture was stirred at room temperature for 15 minutes. The pH of the mixture was adjusted to 6 and the precipitated material was isolated by centrifugation and removing the solvent by suction. After drying under high vacuum the title compound was obtained as a white fine powder. $^1$H-NMR (DMSO-$d_6$) δ 8.54 (d, 2H), 8.08 (s, 1H), 7.88 (d, 1H), 7.64 (d, 1H), 7.36 (d, 2H), 4.68 (s, 2H).

Preparation 1J 2-(4-Fluoro-benzylamino)-benzoic acid

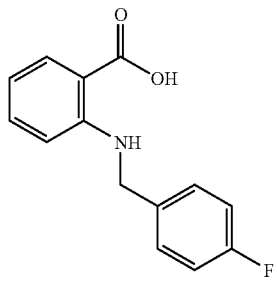

To a stirred mixture of anthranilic acid methyl ester (5.0 g) and 4-fluorobenzaldehyde (3.55 ml) in 1,2-dichloroethane (50 ml) was added sodium triacetoxy-borohydride (10.5 g). The reaction mixture was stirred at room temperature for 15 hours. Saturated aqueous sodium bicarbonate was added. Layers were separated and the aqueous layer was extracted with 1,2-dichloroethane. The combined organic layers were washed with water and brine, dried ($Na_2SO_4$) and evaporated under reduced pressure. The residue was subjected to column chromatography on silica gel (elution with EtOAc/petroleum ether 1/9) and gave 2-(4-fluoro-benzylamino)-benzoic acid methyl ester (6.22 g). The obtained ester was converted into the title compound using general procedure 2. $^{13}$C-NMR (DMSO-$d_6$) δ 169.9, 161.1, 150.4, 135.5, 134.3, 131.6, 128.9, 115.2, 114.5, 111.6, 110.4, 45.0.

Preparation 1K 2-(3-Cyano-4-fluoro-benzylamino)-benzoic acid

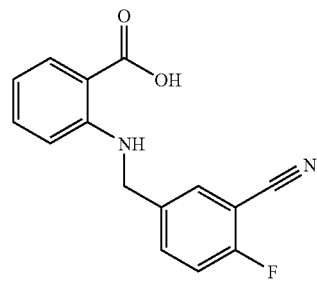

Prepared by a similar procedure as described for preparation 1A, starting from anthranilic acid and 2-fluoro-5-formyl-benzonitrile (Aldrich). $^{13}$C-NMR (DMSO-$d_6$) δ 172.1, 161.3, 149.5, 138.7, 134.6, 131.9, 130.2, 121.4, 116.6, 114.2, 114.0, 110.0, 99.8, 44.8.

Preparation 1L

5-[(2-Carboxy-phenylamino)-methyl]-2-fluoro-benzoic acid methyl ester

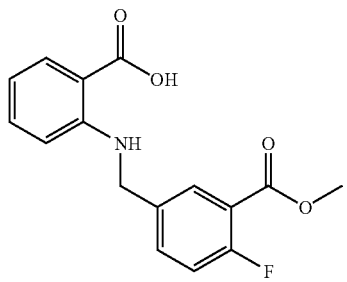

2-Fluoro-5-formylbenzoic acid (ABCR, 1.0 g) was dissolved in benzene (10 ml) and methanol (5 ml) and cooled to 0-5° C.

(Trimethylsilyl)diazomethane (6.0 ml of a 2M sol. in hexane) was added drop-wise over 20 minutes. The reaction mixture was stirred for 30 minutes at 5° C. and the solvent was evaporated under reduced pressure, affording 2-fluoro-5-formyl-benzoic acid methyl ester that was used without further purification. The obtained crude ester was converted into the title compound, using a similar procedure as described for preparation 1A, by reductive amination with anthranilic acid. $^{13}$C-NMR (DMSO-$d_6$) δ 169.9, 163.9, 159.8, 150.3, 136.1, 134.3, 133.5, 131.7, 129.9, 117.9, 117.1, 114.7, 111.6, 110.5, 52.3, 44.6.

Preparation 1M 2-(4-Methoxy-benzylamino)-benzoic acid

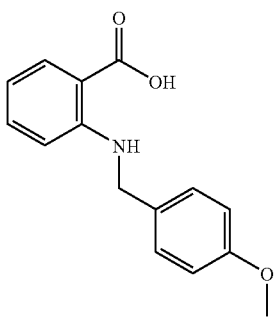

Prepared by a similar procedure as described for preparation 1J, starting from anthranilic acid methyl ester and 4-methoxybenzaldehyde. $^{13}$C-NMR (DMSO-$d_6$) δ 169.9, 158.2, 150.6, 134.2, 131.6, 131.0, 128.3, 114.3, 113.9, 111.6, 110.2, 54.9, 45.3.

Preparation 1N

2-[(4-Methoxy-naphthalen-1-ylmethyl)-amino]-benzoic acid

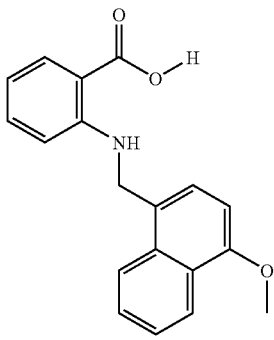

Prepared by a similar procedure as described for preparation 1A, starting from anthranilic acid and 4-methoxy-1-naphthaldehyde (Aldrich). $^{13}$C-NMR (DMSO-$d_6$) δ 169.9, 154.4, 150.7, 134.4, 131.8, 131.6, 126.7, 125.8, 125.7, 125.2, 125.1, 123.3, 122.0, 114.4, 111.6, 110.1, 103.7, 55.4, 43.9.

Preparation 1O

2-[(2,3-Dihydro-benzofuran-5-ylmethyl)-amino]-benzoic acid

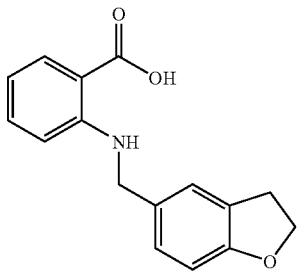

Prepared by a similar procedure as described for preparation 1A, starting from anthranilic acid and 2,3-dihydrobenzo[b]furan-5-carboxaldehyde (Matrix). $^{13}$C-NMR (DMSO-$d_6$) δ 169.9, 158.7, 150.6, 134.3, 131.6, 130.9, 127.5, 126.8, 124.0, 114.3, 111.5, 110.1, 108.6, 70.8, 45.6, 29.0.

Preparation 1P

2-[(Benzofuran-5-ylmethyl)-amino]-benzoic acid

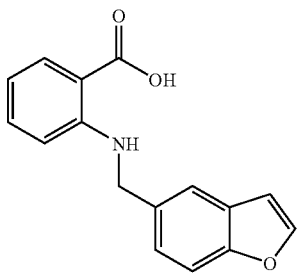

Prepared by a similar procedure as described for preparation 1A, starting from anthranilic acid and 1-benzofuran-5-carbaldehyde (Maybridge). $^{13}$C-NMR (DMSO-$d_6$) δ 169.9, 153.5, 150.6, 146.3, 134.3, 133.9, 131.6, 127.3, 123.6, 119.5, 114.4, 111.6, 111.2, 110.2, 106.6, 45.8.

Preparation 1Q

2-[(2-Oxo-2H-chromen-6-ylmethyl)-amino]-benzoic acid

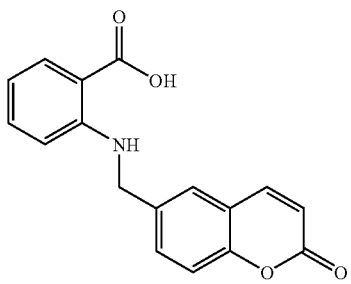

Prepared by a similar procedure as described for preparation 1A, starting from anthranilic acid and coumarin-6-carboxaldehyde (Matrix). $^{13}$C-NMR (DMSO-$d_6$) δ 169.9, 159.9, 152.5, 150.4, 144.1, 135.8, 134.3, 131.7, 130.7, 126.4, 118.6, 116.4, 116.3, 114.6, 111.6, 110.5, 45.0.

Preparation 1R

2-[(3,5-Dichloro-pyridin-4-ylmethyl)-amino]-benzoic acid

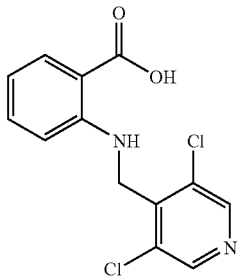

Prepared by a similar procedure as described for preparation 1J, starting from anthranilic acid methyl ester and 3,5-dichloro-4-pyridinecarboxaldehyde (Aldrich). $^{13}$C-NMR (DMSO-$d_6$) δ 170.1, 149.7, 147.9, 142.6, 133.5, 132.2, 131.7, 115.1, 113.2, 110.9, 41.4.

Preparation 1S

2-[(2-Bromo-pyridin-4-ylmethyl)-amino]-benzoic acid

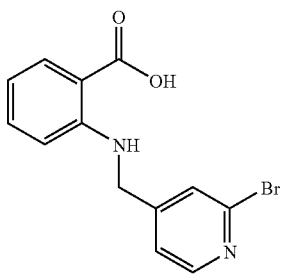

Prepared by a similar procedure as described for preparation 1A, starting from anthranilic acid and 2-bromo-pyridine-4-carbaldehyde (prepared as described in WO 2004/013102 A1).
$^{13}$C-NMR (DMSO-$d_6$) δ 169.8, 153.3, 150.4, 149.9, 141.5, 134.3, 131.7, 125.8, 121.6, 115.0, 111.5, 110.8, 44.1.

Preparation 1T

2-[(2-Hydroxy-pyridin-4-ylmethyl)-amino]-benzoic acid

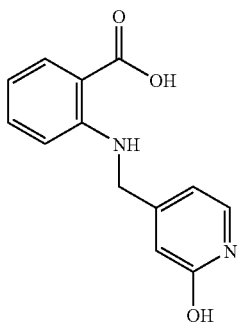

Prepared by a similar procedure as described for preparation 1A, starting from anthranilic acid and 2-hydroxy-4-pyridinecarboxaldehyde (Tyger). $^{13}$C-NMR (DMSO-$d_6$) δ 169.8, 162.4, 153.6, 150.2, 135.0, 134.2, 131.6, 115.8, 114.7, 111.5, 110.5, 104.0, 44.7.

Preparation 1U

2-[(2-Morpholin-4-yl-pyridin-4-ylmethyl)-amino]-benzoic acid

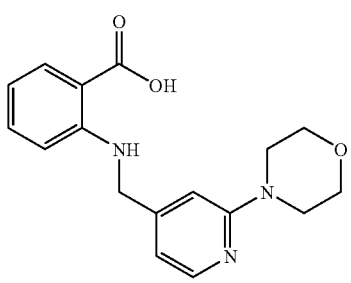

Step 1: Palladium(II) acetate (324 mg) and racemic 2,2'-bis(diphenylphosphino)-1,1'-binaphthalene (899 mg) was suspended in toluene (100 ml) and the mixture was deoxygenated. Morpholine (3.77 ml) and sodium tert-butoxide (4.85 g) was added and the mixture was heated to 50° C. 2-Chloro-isonicotinonitrile (5.0 g) was added portion-wise over 15 minutes and the resulting reaction mixture was stirred at 50° C. for 24 hours. The mixture was cooled to room temperature and filtrated through a thin pad of Celite, washing with plenty of EtOAc. The combined filtrates were evaporated under reduced pressure and the remaining solid was re-crystallised from ethanol, and gave 2-morpholin-4-yl-isonicotino-nitrile as an yellow crystalline material (3.91 g). Step 2: The compound obtained in step 1 (379 mg) was dissolved in toluene and cooled to −30° C. Diisobutylaluminum hydride (1.7 ml of a 1.2M solution in toluene) was added drop-wise and the reaction mixture was allowed slowly to warm to −15° C. and stirred at this temperature 60 minutes. Glacial acetic acid (1.0 ml) was added and the cooling bath was removed. Water was added and the mixture was stirred at room temperature for 2.5 hours. The mixture was diluted with EtOAc and basified by addition of 2 M sodium hydroxide. Sodium/potassium tartrate solution was added and layers were separated. The organic layer washed with brine, dried (Na$_2$SO$_4$) and evaporated under reduced pressure and gave 2-Morpholin-4-yl-pyridine-4-carbaldehyde that was used without further purification. Step 3: The crude aldehyde product obtained in step 2 was converted into the title compound by reaction with anthranilic acid, using a similar procedure as described for preparation 1A. $^{13}$C-NMR (DMSO-$d_6$) δ 169.9, 159.3, 150.5, 150.3, 147.5, 134.3, 131.6, 114.7, 112.0, 111.6, 110.4, 104.9, 65.8, 45.3, 45.1.

Preparation 1V

2-[(Quinolin-4-ylmethyl)-amino]-benzoic acid

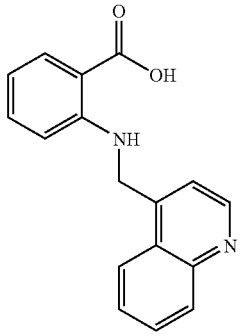

A solution of anthranilic acid (5.46 g) in methanol was added to a melt of quinoline-4-carbaldehyde (6.26 g) and the mixture was heated on a water bath for 6 hours. The mixture was cooled to room temperature and the solid material was isolated by filtration and washed with methanol, affording 2-[(quinolin-4-ylmethylene)-amino]-benzoic acid (10.33 g). This intermediate (10.3 g) was dissolved in THF and ethanol, and sodium borohydride (1.41 g) was added portion-wise. The reaction mixture was stirred at room temperature for 3 hours. More sodium borohydride (1.41 g) and a small amount of methanol were added and stirring continued at room temperature for 4 hours. The mixture was evaporated under reduced pressure and transferred to a separatory funnel with EtOAc and water. Layers were separated and the aqueous layer was neutralised by addition of 4M hydrochloric acid. The resulting precipitated material was isolated by filtration, washed with water and dried in vacuo, affording the title compound (7.1 g). $^{13}$C-NMR (DMSO-$d_6$) δ 170.4, 150.3, 150.3, 147.6, 144.8, 133.4, 131.7, 129.6, 129.2, 126.5, 126.1, 123.5, 118.5, 114.6, 112.9, 111.2, 42.7.

Preparation 1W

2-[(6-Methoxy-pyridin-3-ylmethyl)-amino]-benzoic acid

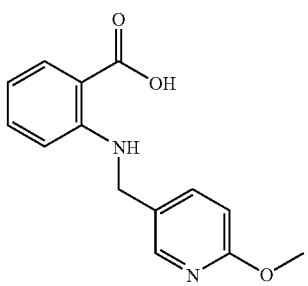

Prepared by a similar procedure as described for preparation 1A, starting from anthranilic acid and 2-methoxypyridine-5-carboxaldehyde (Aldrich). $^{13}$C-NMR (DMSO-$d_6$) δ 169.9, 162.9, 150.4, 145.7, 138.6, 134.4, 131.7, 127.7, 114.7, 111.7, 110.5, 110.5, 53.1, 42.8.

Preparation 1X

2-[(Thiazol-5-ylmethyl)-amino]-benzoic acid

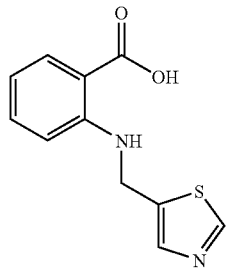

Prepared by a similar procedure as described for preparation 1J, starting from anthranilic acid methyl ester and thiazole-5-carboxaldehyde (Combi-Blocks). $^{13}$C-NMR (DMSO-$d_6$) δ 169.8, 153.6, 149.9, 140.8, 137.9, 134.3, 131.6, 115.0, 111.6, 110.7, 38.3.

Preparation 1Y

2-[(Tetrahydro-pyran-4-ylmethyl)-amino]-benzoic acid

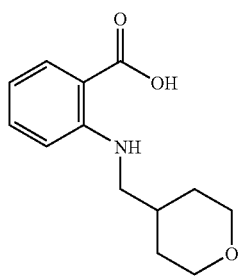

To a stirred mixture of isatoic anhydride (2.5 g) and triphenylphosphine (4.0 g) in THF (100 ml) at 0° C. was added drop-wise diisopropyl azodicarboxylate (3.0 ml), followed by addition (tetrahydro-pyran-4-yl)-methanol (1.78 g). The reaction mixture was stirred at room temperature for 15 hours, and the solvent was evaporated under reduced pressure. The residue was subjected to column chromatography on silica gel (EtOAc/petroleum ether, 9/1) affording impure 1-(tetrahydro-pyran-4-ylmethyl)-1H-benzo[d][1,3]oxazine-2,4-dione. This material was treated with 27% sodium hydroxide (20 ml) at 50° C. for 48 hours. The mixture was cooled to room temperature and 37% hydrochloric acid (15 ml) was added. The mixture was extracted several times with EtOAc and the combined organic layers were washed with water, dried (Na$_2$SO$_4$) and evaporated under reduced pressure. The residue was purified by column chromatography on silica (EtOAc/petroleum ether, 2/8) and gave the title compound. $^{13}$C-NMR (DMSO-$d_6$) δ 170.0, 151.0, 134.4, 131.6, 113.9, 111.2, 109.7, 66.7, 47.8, 34.1, 30.4.

Preparation 2

2-[(pyridin-4-ylmethyl)-amino]-nicotinic acid

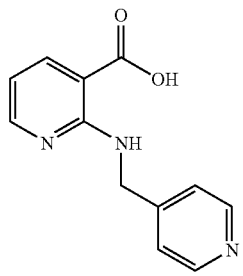

General procedure 3. Starting material: 2-[(Pyridin-4-yl-methyl-amino]-benzoic acid (see preparation 5). $^{13}$C-NMR (DMSO-$d_6$) δ 168.75, 157.91, 153.01, 149.64, 149.27, 140.13, 121.94, 111.67, 106.50, 42.69.

Preparation 3

2-(4-Fluoro-benzylamino)-nicotinic acid

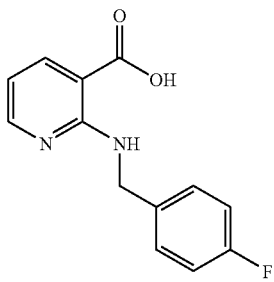

General procedure 3. Starting material: 2-(4-Fluoro-benzylamino)nicotinonitrile (see preparation 6). $^1$H-NMR (DMSO-$d_6$) δ 13.07 (bs, 1H), 8.47 (bs, 1H), 8.25 (dd, 1H), 8.10 (dd, 1H), 7.34-7.39 (m, 2H), 7.10-7.16 (m, 2H), 6.63 (dd, 1H), 4.67 (d, 2H).

Preparation 3A 2-(4-Chloro-benzylamino)-nicotinic acid

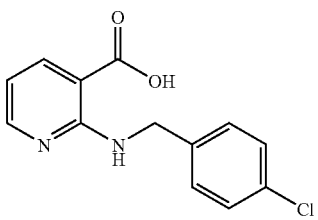

Prepared by a similar procedure as described for preparation 3, starting from 2-(4-Chloro-benzylamino)-nicotinonitrile (prepared from 2-chloro-nicotinonitrile and 4-chloro-benzylamine using the same procedure as described for preparation 6). $^1$H-NMR (DMSO-$d_6$) δ 13.09 (br, 1H), 8.51 (br, 1H), 8.23 (dd, 1H), 8.09 (dd, 1H), 7.40-7.30 (m, 4H), 6.63 (dd, 1H), 4.68 (d, 2H).

Preparation 3B 2-(Isoquinolin-5-ylamino)-nicotinic acid

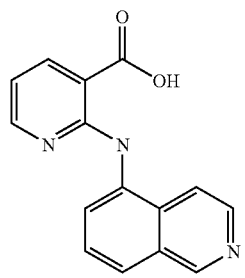

To a stirred solution of 5-amino-isoquinoline (526 mg) in DMF (20 ml) at 0-5° C. was added sodium hydride (400 mg of a 55 to 65% dispersion in mineral oil). The cooling bath was removed and the dark green reaction mixture was stirred at room temperature for 30 minutes. 2-Chloro-nicotinonitrile (506 mg) was added and the mixture was stirred at room temperature for 12 hours. The reaction was quenched by addition of water and the products were extracted several times with EtOAc. The combined organic layers were washed with water and 3M CaCl$_2$, dried (MgSO$_4$) and evaporated under reduced pressure. The remaining red-brown solid material was re-crystallised from ethanol and gave 2-(iso-quinolin-5-ylamino)-nicotinonitrile (306 mg): $^{13}$C-NMR (DMSO-$d_6$) δ 157.6, 152.4, 152.4, 143.1, 142.5, 135.0, 132.1, 129.0, 127.2, 126.9, 125.1, 116.5, 116.3, 114.3, 92.5.

The above obtained nitrile compound was converted into the title compound using general procedure 3.

Preparation 4

2-(4-Methoxy-benzylamino)-nicotinic acid

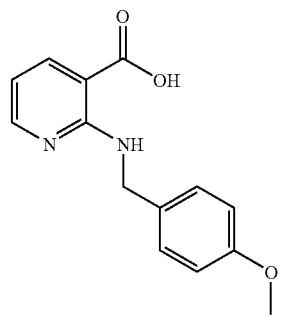

General procedure 3. Starting material: 2-(4-Methoxy-benzylamino)nicotinonitrile (see preparation 7). $^{13}$C-NMR (DMSO-$d_6$) δ 168.83, 158.11, 157.96, 153.19, 140.06, 131.74, 128.55, 113.69, 111.21, 105.95, 54.92, 43.16.

Preparation 5

2-[(Pyridin-4-ylmethyl-amino]-nicotinonitrile

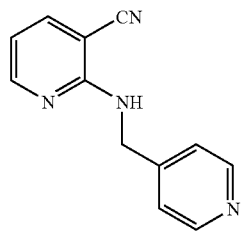

To a stirred solution of 2-chloro-nicotinonitrile (Aldrich, 10.4 g, 75.06 mmol) in dry NMP (40 ml) was added 4-(aminomethyl)pyridin (15.2 ml, 150.26 mmol). The reaction mixture was heated to 130° C., and stirred at this temperature for 20 hours. The mixture was cooled to room temperature and diluted with EtOAc (500 ml) and washed with saturated aqueous NaHCO$_3$, water and brine. The organic layer was dried (Na$_2$SO$_4$) and evaporated under reduced pressure. The remaining red-brown solid material was recrystallised from ethanol affording the title compound (7.73 g) as an off-white solid. The filtrate was evaporated under reduced pressure, redissolved in 2% methanol/EtOAc (v/v) and filtrated through a pad of silica gel. The filtrate was evaporated under reduced pressure and the residue was recrystallised from ethanol and gave an additional amount of the title compound (2.44 g).

$^{13}$C-NMR (DMSO-d$_6$) δ 157.80, 152.65, 149.30, 149.10, 142.49, 121.94, 116.65, 112.09, 90.62, 43.00.

Preparation 6

2-(4-Fluoro-benzylamino)-nicotinonitrile

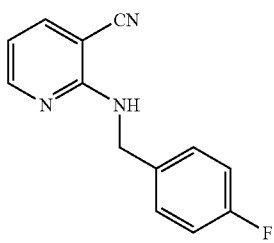

To a stirred suspension of 2-chloro-nicotinonitrile (Aldrich, 3.30 g, 23.82 mmol) in 2-propanol (30 ml) was added 4-fluoro-benzylamine (3.00 ml, 26.25 mmol) and N,N-diisopropylethylamine (8.30 ml, 47.65 mmol). The reaction mixture was heated to 80° C. for 24 hours. More 4-fluoro-benzylamine (0.55 ml, 4.81 mmol) was added and stirring was continued at 80° C. for another 24 hours. The reaction mixture was cooled to room temperature and the precipitated material was isolated by filtration and washed with 2-propanol. Residual 2-propanol was removed in vacuo affording the title compound (3.04 g) as a white crystalline material. $^1$H-NMR (DMSO-d$_6$) δ 8.23-8.25 (m, 1H), 7.91 (dd, 1H), 7.73 (t, 1H), 7.34-7.38 (m, 2H), 7.08-7.14 (m, 2H), 6.63-6.67 (m, 1H), 4.57 (d, 2H).

Preparation 7

2-(4-Methoxy-benzylamino)-nicotinonitrile

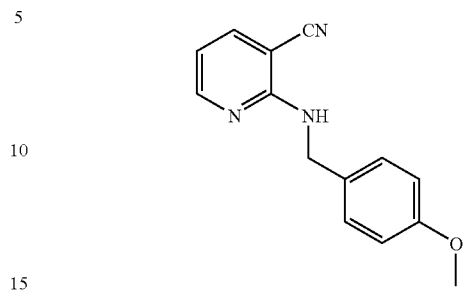

To a stirred mixture of 2-chloro-nicotinonitrile (Aldrich, 2.20 g, 15.88 mmol) and 4-methoxy-benzylamine (2.27 ml, 17.49 mmol) in 2-propanol (20 ml) was added N,N-diisopropylethylamine (5.53 ml, 31.75 mmol). The reaction mixture was heated to 80° C. and stirred at this temperature for 24 hours. More 4-methoxybenzylamine (0.50 ml, 3.85 mmol) was added and stirring continued at 70° C. for 48 hours. The mixture was cooled to room temperature and the resulting solid material (4-methoxy-benzylamine hydrochloride) removed by filtration. On standing a crystalline product formed in the filtrate, which was isolated by filtration, washed with 2-propanol and dried under reduced pressure affording the title compound as pale yellow crystals (1.27 g). $^1$H-NMR (DMSO-d$_6$) δ 8.21-8.30 (m, 1H), 7.90 (d, 1H), 7.65 (t, 1H), 7.25 (d, 2H), 6.85 (d, 2H), 6.59-6.68 (m, 1H), 4.50 (d, 2H), 3.75 (s, 3H).

Preparation 7A

1-Pyridin-4-ylmethyl-1H-benzo[d][1,3]oxazine-2,4-dione

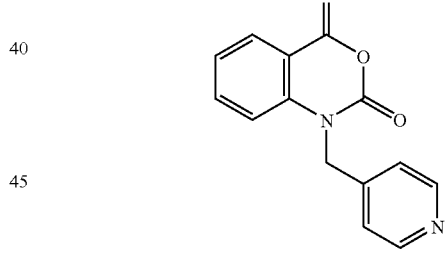

To a stirred mixture of isatoic anhydride (72.60 g/445.0 mmol) and triphenylphosphine (116.74 g/445.1 mmol) in THF (1 L) at 0° C. was added diisopropyl azodicarboxylate drop-wise over ca. 50 min. The resulting pale yellow reaction mixture was stirred for 10 min. before drop-wise addition of a solution of 4-hydroxmethyl pyridine (48.57 g, 445.1 mmol) in THF (250 ml). The reaction mixture was stirred at room temperature for 2 hours. The resulting red solution was filtrated through a pad of silica gel, and the filtrate was evaporated under reduced pressure. The residue was treated with EtOAc and the resulting precipitated material was isolated by filtration and re-crystallised from EtOAc affording the title compound as a white solid material (37.5 g). The filtrate from this crystallisation was extracted with 0.1M HCl aq. The pH of the aqueous layer was adjusted to 7-8 with saturated aqueous sodium bicarbonate. The precipitated material was isolated by filtration and washed with water to yield more of the title compound (9.8 g). The combined aqueous filtrates were extracted several times with EtOAc. The combined organic layers were evaporated under reduced pressure. The residue was re-crystallised from EtOAc affording an additional amount of the title compound (20.3 g). $^{13}$C-NMR (DMSO-d$_6$) δ 158.7, 149.7, 148.2, 144.5, 141.1, 136.9, 129.5, 123.8, 121.5, 114.8, 112.1, 46.7.

Preparation 7B 1-(2-Amino-pyridin-4-ylmethyl)-1H-benzo[d][1,3]oxazine-2,4-dione

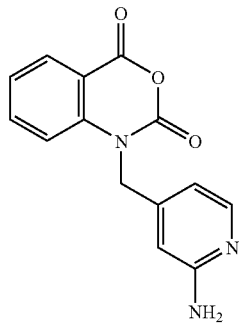

To a stirred mixture of 2-aminopyridine-4-methanol (commercially available from CB Research, 25.05 g, 201.79 mmol), isatoic anhydride (32.91 g/201.74 mmol), and triphenylphosphine (52.92 g/201.76 mmol) in THF (400 ml) at 20° C. was added diisopropyl azodicarboxylate (40.8 g/201.77 mmol) drop-wise. The reaction mixture was stirred at room temperature for 1 hour. The mixture was cooled to 0° C. and the precipitated material was isolated by filtration and washed with a small amount of THF, to afford the title compound as a yellow solid material (18.93 g). The filtrate was evaporated under reduced pressure. To the residual oil was added dichloromethane. The resulting precipitate was isolated by filtration affording more product (1.21 g). The filtrate was extracted with 0.1M HClaq., and the pH of the aqueous layer was adjusted to ca. 7-8 with aqueous sodium bicarbonate, then extracted with EtOAc. The organic layer was evaporated under reduced pressure, and the resulting solid material was suspended in THF (100 ml). The solid material was isolated by filtration to yield more product (9.10 g). The filtrate was concentrated to ca. 45 ml, affording more precipitate and an additional amount of the title compound (1.77 g) after filtration and drying under vacuum. $^{13}$C-NMR (DMSO-d$_6$) δ 160.0, 158.7, 148.1, 148.0, 145.0, 141.2, 137.1, 129.5, 123.8, 115.0, 111.7, 109.9, 104.5, 46.8.

Preparation 7C

2-[(Pyridin-4-ylmethyl)-amino]-benzoic acid pentafluorophenyl ester

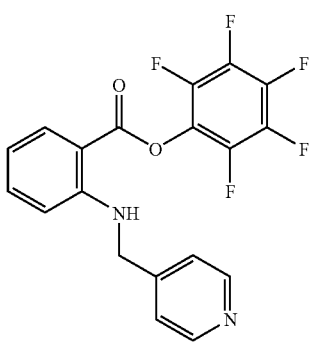

To a stirred suspension of 2-[(Pyridin-4-ylmethyl)-amino]-benzoic acid (preparation 1, 300 mg) in EtOAC (10 ml) was added 2,3,4,5,6-pentafluorophenol (413 mg) followed by drop-wise addition of a solution of N,N-dicyclohexyl-carbodiimide (461 mg) in EtOAc (5 ml). The reaction mixture was stirred at room temperature for 15 hours. The formed precipitate was removed by filtration and the filtrate was evaporated under reduced pressure. The remaining material was subjected to column chromatography on silica gel (petroleum ether/EtOAc as eluent) and gave the title compound (352 mg). $^{13}$C-NMR (DMSO-d$_6$) δ 163.2, 151.4, 149.7, 148.1, 140.9, 138.9, 137.6, 136.9, 131.9, 124.7, 121.9, 115.6, 112.5, 105.5, 44.7.

Preparation 7D 4-(2,4-Dioxo-4H-benzo[d][1,3]oxazin-1-ylmethyl)-benzonitrile

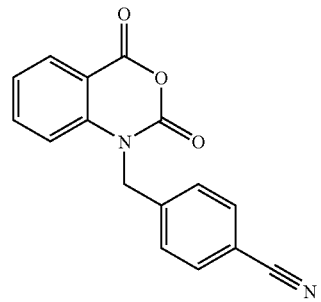

To a stirred mixture of isatoic anhydride (2.0 g) and 4-cyano-benzyl bromide (2.40 g) in DMF (20 ml) was added drop-wise 1,8-diazabicyclo[5,4,0]-undec-7-ene (2.20 ml). The reaction mixture was stirred at room temperature for 22 hours, cooled in an ice-bath and water (75 ml) was added. The resulting precipitated material was isolated by filtration and re-crystallised from hot toluene and gave the title compound (1.65 g) as an off-white solid. $^{13}$C-NMR (DMSO-d$_6$) δ 158.7, 148.2, 141.2, 141.1, 136.9, 132.4, 129.5, 128.8, 128.1, 127.5, 123.7, 118.6, 114.8, 112.2, 110.2, 47.3.

Preparation 7E 1-(5-Oxo-4,5-dihydro-1H-[1,2,4]triazol-3-ylmethyl)-1H-benzo[d][1,3]oxazine-2,4-dione

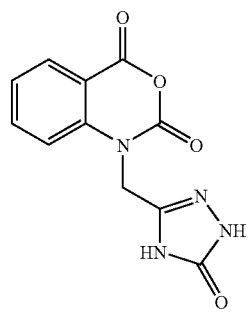

To a stirred suspension of semicarbazid hydrochloride (5.69 g) in methanol (100 ml) was added 2-chloro-1,1,1-trimethoxyethane (13.75 ml). The reaction mixture was stirred at room temperature for 3 days. The resulting almost clear solution was filtrated and the filtrate was evaporated under reduced pressure. The residue was suspended in toluene and the undisclosed material was isolated by filtration and washed with toluene, affording 5-chloromethyl-2,4-dihydro-[1,2,4]triazol-3-one (6.1 g). This compound was converted into the title compound by reaction with isatoic anhydride, using the same procedure as described for preparation 7D.

$^{13}$C-NMR (DMSO-d$_6$) δ 158.7, 156.0, 147.9, 142.5, 141.1, 137.4, 129.6, 124.2, 114.7, 111.8, 40.6.

Preparation 7F 1-(2-Imidazol-1-yl-ethyl)-1H-benzo[d][1,3]oxazine-2,4-dione

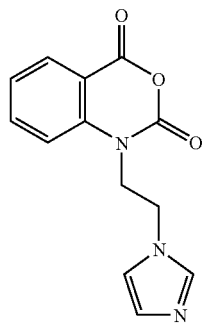

Prepared by a similar procedure as described for preparation 7B, starting from isatoic anhydride and 1-(2-hydroxyethyl)-imidazole (Fluorochem). $^{13}$C-NMR (DMSO-d$_6$) δ 158.7, 147.5, 141.3, 137.6, 136.9, 129.4, 128.5, 123.6, 119.7, 114.0, 111.3, 45.1, 43.3.

Preparation 7G 1-(1-Pyridin-4-yl-ethyl)-1H-benzo[d][1,3]oxazine-2,4-dione

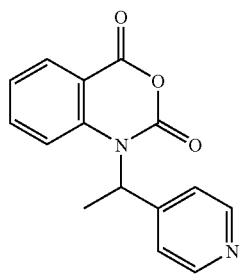

Prepared by a similar procedure as described for preparation 7A, starting from isatoic anhydride and (+/−)-1-(4-pyridyl)ethanol (Fluka). $^{13}$C-NMR (DMSO-d$_6$) δ 159.0, 149.8, 148.6, 140.6, 136.5, 129.8, 123.6, 121.2, 115.7, 112.9, 53.1, 15.4.

Preparation 7H 1-(6-Oxo-1,6-dihydro-pyridin-3-ylmethyl)-1H-benzo[d][1,3]oxazine-2,4-dione

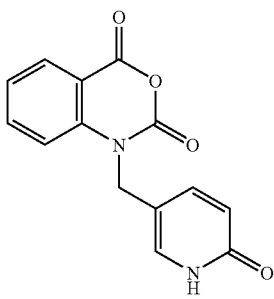

Prepared by a similar procedure as described for preparation 7B, starting from isatoic anhydride and 5-hydroxymethyl-1H-pyridin-2-one (prepared as described in WO 01/77078 A1).

$^{13}$C-NMR (DMSO-d$_6$) δ 162.0, 158.9, 148.4, 141.2, 140.9, 137.0, 134.1, 129.5, 123.7, 120.1, 115.0, 112.3, 112.0, 44.3.

Preparation 7I 1-(6-Oxo-1,6-dihydro-pyridin-3-ylmethyl)-1H-pyrido[2,3-d][1,3]oxazine-2,4-dione

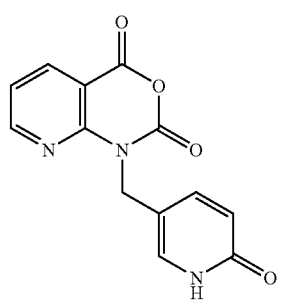

May be prepared by a similar procedure as described for preparation 7B, starting from 1H-pyrido[2,3-d][1,3]oxazine-2,4-dione (can be prepared as described by Beckwith and Hickman in J. Chem. Soc. (C), 1968 pp 2756-2759) and 5-hydroxymethyl-1H-pyridin-2-one (prepared as described in WO 01/77078 A1).

Preparation 8

O-(3,4,5-Trimethoxy-benzyl)-hydroxylamine hydrochloride

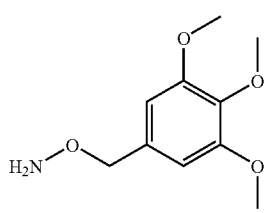

To a stirred solution of 3,4,5-trimethoxybenzyl chloride (1.00 g, 4.6 mmol) and tert-butyl-N-hydroxycarbamate (0.62 g, 4.6 mmol) in acetonitrile (20 ml) was added Cs$_2$CO$_3$ (4.51 g, 13.8 mmol). The reaction mixture was stirred at room temperature for 24 hours. Water was added and the products extracted twice with EtOAc. The combined organic extracts were washed with water and brine, dried (MgSO$_4$) and evaporated under reduced pressure. The crude product was purified by chromatography on silica using a gradient of EtOAc in petroleum ether (0-40%, v/v) affording 411 mg of Boc-protected O-(3,4,5-trimethoxy-benzyl)-hydroxylamine. This intermediate (383 mg/1.22 mmol) was treated with 37% hydrochloric acid (2.5 ml) in EtOAc (7.5 ml) for 30 min. at room temperature. The mixture was concentrated under reduced pressure and diethyl ether was added. The resulting precipitated material was isolated by filtration and dried under high vacuum affording the title compound (211 mg) as white shiny crystals.

$^1$H-NMR (DMSO-d$_6$) δ 11.10 (bs, 3H), 6.76 (s, 2H), 4.98 (s, 2H), 3.79 (s, 6H), 3.67 (s, 3H).

Preparation 9

O-(4-Chloro-benzyl)-hydroxylamine hydrochloride

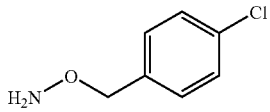

Same procedure as described for preparation 8. Starting materials: 4-Chlorobenzyl bromide and tert-butyl-N-hydroxycarbamate. $^1$H-NMR (DMSO-$d_6$) δ 11.18 (bs, 3H), 7.44-7.51 (m, 4H), 5.06 (s, 2H).

Preparation 10

O-(4-cyanobenzyl)hydroxylamine hydrochloride

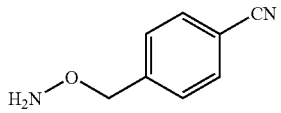

N-Hydroxyphthalimide (3.30 g, 20.2 mmol) was dissolved in NMP (50 ml) and 4-cyanobenzyl bromide (4.35 g, 22.2 mmol) was added followed by drop-wise addition of 1,8-diazabicyclo[5,4,0]-undec-7-ene (DBU) (3.0 ml, 20.1 mmol). After complete addition of DBU (ca. 15 min.) the reaction mixture was stirred at room temperature for 65 min. The mixture was poured into ice cooled 1M aqueous hydrochloric acid (500 ml) and the precipitated material was collected by filtration and washed with water and dried under high vacuum. This phthalimide derivative (5.31 g, 19.1 mmol) was suspended in ethanol (40 ml) and a solution of hydrazine monohydrate (0.93 ml, 19.1 mmol) in ethanol (10 ml) was added drop wise. The reaction mixture was heated to reflux and stirred for 2.5 hours. The mixture was cooled to room temperature and the solid material removed by filtration and washed with ethanol. The combined filtrates were evaporated under reduced pressure. The residue was resuspended in EtOAc and the undissolved material was removed by filtration. The EtOAc filtrate washed with saturated aqueous NaHCO$_3$, and water, dried (MgSO$_4$) and evaporated under reduced pressure. The residue was suspended in diethyl ether (150 ml) and concentrated hydrochloric acid (50 ml) was added and the resulting slurry was stirred at room temperature for 30 min. The precipitated product was isolated by filtration, washed with diethyl ether and dried in vacuo, affording the title compound (2.24 g) as a white powder. $^1$H-NMR (DMSO-$d_6$) δ 11.26 (bs, 3H), 7.90 (d, 2H), 7.63 (d, 2H), 5.17 (s, 2H).

Preparation 11

O-Quinolin-2-ylmethyl-hydroxylamine

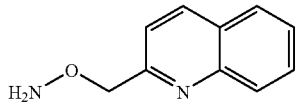

tert-Butyl-N-hydroxycarbamate (1.00 g, 7.51 mmol) was dissolved in DMF (25 ml) and the mixture was cooled in an ice bath. Sodium hydride (655 mg of a 55-65% dispersion in mineral oil) was added and after 20 min. 2-chloromethyl-quinolin hydrochloride (1.6 g, 7.50 mmol) was added portion wise. The cooling bath was removed and the reaction mixture was stirred at room temperature for 20 hours. The reaction was quenched by addition of water and the product was extracted with EtOAc. The combined organic layers were washed with water and brine, dried (MgSO$_4$) and evaporated under reduced pressure. The resulting yellow oil was decanted with petroleum ether and the product was crystallised from EtOAc/petroleum ether, affording N-Boc protected O-quinolin-2-ylmethyl-hydroxylamine (881 mg) as a pale yellow solid. $^{13}$C-NMR (DMSO-$d_6$) δ 157.12, 156.19, 146.78, 136.44, 129.60, 128.53, 127.78, 127.18, 126.48, 120.31, 79.81, 78.38, 27.89. This material (860 mg, 3.14 mmol) was dissolved in CH$_2$Cl$_2$ (10 ml) and trifluoroacetic acid (4.4 ml) was added. The reaction mixture was stirred at room temperature for 60 min. and the solvents were evaporated under reduced pressure. The residue was dissolved in EtOAc and washed with saturated aqueous NaHCO$_3$, dried (MgSO$_4$) and evaporated under reduced pressure. This gave the title compound (376 mg) as a yellow oil, which was used without further purification.

Preparation 12

O-(2-Methyl-thiazol-4-ylmethyl)-hydroxylamine hydrochloride

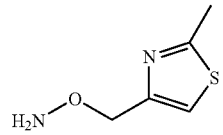

N-Hydroxyphthalimide (15.2 g) was dissolved in DMF (120 ml) and 4-chloromethyl-2-methyl-thiazole (18.4 g) was added. The mixture was cooled in an ice bath and a solution of triethylamine (28.6 ml) in DMF (30 ml) was added drop-wise. The cooling bath was removed and the reaction mixture was stirred at room temperature for 3 days. The mixture was poured into water (600 ml) and the precipitated material was isolated by filtration washed with water and dried in vacuo. This phthalimide intermediate (21.4 g) was refluxed in ethanol (150 ml) containing n-butylamine (7.7 ml) for 2.5 hours. The mixture was cooled to room temperature and 4M hydrochloric acid in diethyl ether (25 ml) was added. The mixture was placed at 0-5° C. over night at the resulting precipitated material was isolated by filtration and washed with cold ethanol and diethyl ether, affording the title compound (11.2 g) as a white crystalline material. $^{13}$C-NMR (DMSO-$d_6$) δ 166.85, 147.15, 121.35, 70.03, 18.37.

Preparation 13

O-(4-Fluoro-2,6-dimethyl-benzyl)-hydroxylamine hydrochloride

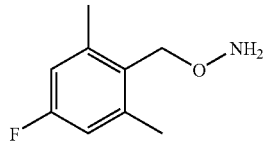

To a stirred solution of 2,6-dimethyl-4-fluorobenzyl bromide (4.89 g, 22.5 mmol) in DMF (100 ml) was added N-hydroxyphthalimide (3.67 g, 22.5 mmol) followed by drop-wise addition of triethylamine (3.5 ml, 25.1 mmol). The reaction mixture was stirred at room temperature for 2 hours. The mixture was poured into 1M HCl$_{aq}$. and the resulting white precipitate was isolated by filtration, washed with water and dried in vacuo. This phthalimide intermediate (6.51 g, 21.9 mmol) was treated with hydrazine monohydrate (1.06 ml, 21.8 mmol) in ethanol (60 ml) at reflux for 3 hours. The mixture was cooled to room temperature and ether was added. The precipitated material was removed by filtration, and the filtrate was evaporated under reduced pressure. The residue was suspended in EtOAc and filtrated. 4M HCl in dioxane (22 mmol) was added to the filtrate and the resulting precipitate was isolated by filtration and dried under vacuum, and gave the title compound (3.92 g) as a white powder. $^{13}$C-NMR (DMSO-d$_6$) δ 161.9, 141.8, 126.5, 114.3, 69.3, 19.2. Alternatively, the phthalimide intermediate can be treated with hydrazine monohydrate (1 eq.) in dichloromethane at room temperature for 20 to 24 hours, remove the formed solids by filtration and evaporate the filtrate to obtain the free hydroxylamine.

Preparation 14

O-(4-Fluoro-2-methoxy-benzyl)-hydroxylamine hydrochloride

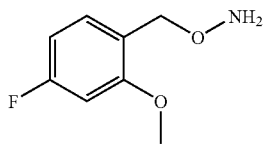

4-Fluoro-2-methoxybenzaldehyde (Fluorochem, 4.5 g) was dissolved in methanol (40 ml) and cooled to 0° C. Sodium borohydride (1.1 g) was added and the mixture was stirred for 1 hour. Water (200 ml) was added and the mixture was concentrated under reduced pressure (ca. 100 ml). The resulting precipitate was isolated by filtration, washed with water and dried under vacuum and gave 4-fluoro-2-methoxy-phenyl)-methanol (3.76 g). This alcohol (3.76 g) was dissolved in THF (100 ml) and N-Hydroxyphthalimide (3.93 g) and triphenylphosphine (6.32 g) was added followed by drop-wise addition of diisopropyl azodicarboxylate (4.87 g). The resulting turbid red reaction mixture was stirred at room temperature for 30 min. The mixture was filtrated through a pad of silica gel and the filtrate was evaporated under reduced pressure. Ethanol (70 ml) was added to the residue which dissolved on heating. On cooling a crystalline material formed that was isolated by filtration and dried under vacuum. This phthalimide intermediate (6.15 g) was suspended in ethanol (50 ml) and hydrazine monohydrate (1.0 ml) dissolved in ethanol (10 ml) was added. The reaction mixture was heated to reflux and stirred for ca. 3 hours. The mixture was cooled to room temperature and the solid material was removed by filtration. The filtrate was evaporated under reduced pressure and the residue was treated with EtOAc and filtrated. 4 M HCl in dioxane (1.0 eq.) was added to the filtrate and the resulting precipitated material was isolated by filtration and gave the title compound (3.26 g) as a white solid material. $^{13}$C-NMR (DMSO-d$_6$) δ 163.7, 159.2, 132.6, 117.8, 106.6, 99.7, 70.2, 56.0.

Preparation 15

O-(2,3-Difluoro-4-methyl-benzyl)-hydroxylamine and hydrochloride

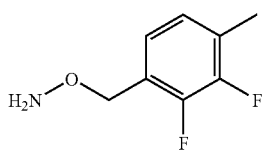

To a stirred solution of 2,3-difluoro-4-methylbenzyl bromide (Matrix, 10.47 g) and N-hydroxyphthalimide (7.73 g) in DMF (100 ml) was added drop-wise triethylamine (Et$_3$N) (7.3 ml) (DBU may be used as an alternative to Et$_3$N). The red reaction mixture was stirred at room temperature for 2 hours. On addition of 1 M HCl$_{aq}$. a white precipitate formed, that was isolated by filtration and washed with water and dried in vacuo affording a phthalimide intermediate (12.55 g, white shiny material). This compound (6.07 g) was dissolved in dichloromethane and methyl-hydrazine (1.16 ml) was added drop-wise. The reaction mixture was stirred at room temperature for 30 min. and the solid material was removed by filtration. The filtrate was evaporated under reduced pressure and purified by chromatography on silica gel (EtOAc/petroleum ether as eluent) and gave the title amine as a clear colourless oil (3.34 g). Alternatively the phthalimide intermediate can be treated with hydrazine monohydrate (1.0 eq.) in refluxing ethanol for 2-3 hours and the title compound obtained as the hydrochloride salt by treatment with 4M HCl in dioxane as described above for preparation 14. HCl salt: $^{13}$C-NMR (DMSO-d$_6$) δ 150.0, 146.8, 128.4, 126.2, 126.1, 120.3, 68.9, 13.9. Free amine: $^{13}$C-NMR (CDCl$_3$) δ149.2, 149.3, 127.0, 125.4, 124.5, 124.0, 70.9, 14.3

Preparation 16

O-(3-Fluoro-4-methyl-benzyl)-hydroxylamine hydrochloride

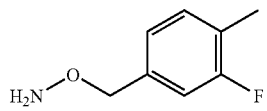

Prepared analogous to the procedure described in preparation 13, starting from 3-fluoro-4-methylbenzyl bromide (Fluorochem) and N-hydroxyphthalimide. $^{13}$C-NMR (DMSO-d$_6$) δ 160.4, 133.5, 131.7, 124.9, 115.5, 74.6, 13.9.

Preparation 17

O-(5-Fluoro-2-methyl-benzyl)-hydroxylamine hydrochloride

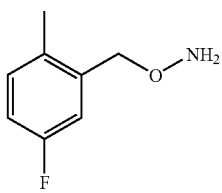

Prepared analogous to the procedure described in preparation 13, starting from 5-fluoro-2-methylbenzyl bromide (Apollo) and N-hydroxyphthalimide. $^{13}$C-NMR (DMSO-d$_6$) δ 160.1, 133.8, 133.7, 131.9, 116.6, 115.7, 73.2, 17.6

Preparation 18

O-(2,3,5,6-Tetrafluoro-4-methoxy-benzyl)-hydroxylamine hydrochloride

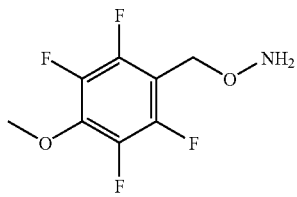

To a stirred solution of N-hydroxyphthalimide (2.15 g) and 2,3,5,6-tetrafluoro-4-methoxybenzyl bromide (Apollo, 3.96 g) in NMP (30 ml) was added drop-wise 1,8-diazabicyclo[5,4,0]-undec-7-ene (1.97 ml). The resulting clear pale yellow reaction mixture was stirred at room temperature for 2 hours. After ca. 1.5 hours precipitation was observed. The mixture was poured into 1M HCl aq. (300 ml) and the white solid material was isolated by filtration, washed with water (200 ml) and dried under high vacuum. This phthalimide intermediate (4.40 g) was suspended in ethanol and hydrazine monohydrate (0.62 g) was added. The mixture was heated to reflux and stirred for 4 hours. The mixture was cooled to room temperature and the solid material was removed by filtration. The filtrate was evaporated under reduced pressure and the residue was re-suspended in diethyl ether (200 ml). 4M HCl in dioxane (3.075 ml) was added and the precipitated material was isolated by filtration and gave the title compound as a white solid material. $^{13}$C-NMR (DMSO-$d_6$) δ 145.7, 140.1, 139.2, 105.5, 62.7, 62.2.

Preparation 19

O-(4-Bromo-benzyl)-hydroxylamine hydrochloride

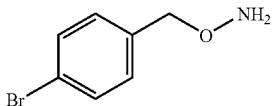

Synthesised as described for preparation 18, starting from 4-bromobenzyl bromide and N-hydroxyphthalimide. $^{13}$C-NMR (DMSO-$d_6$) δ 133.1, 131.5, 131.3, 122.3, 74.7.

Preparation 20

O-(2-Iodo-benzyl)-hydroxylamine hydrochloride

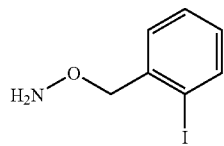

Synthesised according to the procedure described in preparation 18, starting from 2-iodobenzyl chloride (Aldrich) and N-hydroxyphthalimide. The reaction time of 2-iodobenzyl chloride and N-hydroxyphthalimide to afford the phthalimide intermediate was 20 hours.

Preparation 21

O-(3-Iodo-benzyl)-hydroxylamine hydrochloride

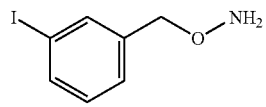

Synthesised according to the procedure described in preparation 18, starting from 3-iodobenzyl bromide (Lancaster) and N-hydroxyphthalimide. $^{13}$C-NMR (DMSO-$d_6$) δ 137.5, 137.4, 136.2, 130.7, 128.4, 94.8, 74.5.

Preparation 22

(2-Aminooxymethyl-phenyl)-acetonitrile

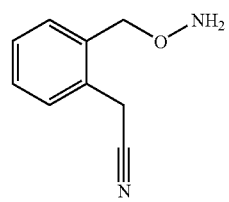

To a stirred solution of 2-methylbenzyl cyamide (3.11 ml) in CCl$_4$ (100 ml) was added N-bromosuccinimide (4.89 g) and a catalytic amount of benzoyl peroxide. The mixtures was heated to reflux and stirred for 1.5 hours. The mixture was cooled to room temperature and was filtrated. The filtrate was evaporated under reduced pressure and the residue was dissolved in a minimum amount of EtOAc and petroleum ether was added. The resulting solid material was isolated by filtration and washed with petroleum ether and gave (2-bromomethyl-phenyl)-acetonitrile (926 mg). The filtrate was evaporated under reduced pressure and the residue was subjected to chromatography on silica gel (elution petroleum ether/EtOAc 10/1, v/v) affording an additional amount of (2-bromomethyl-phenyl)-acetonitrile (1.45 g). This benzyl bromide (2.27 g) was dissolved in NMP and N-hydroxyphthalimide (1.53 g) was added followed by drop-wise addition of 1,8-diazabicyclo[5,4,0]-undec-7-ene (1.40 ml). The reaction mixture was stirred at room temperature for 5 hours. 1M HCl aq. (173 ml) was added and the resulting precipitated material was isolated by filtration and washed with water and dried under high vacuum and gave [2-(1,3-Dioxo-1,3-dihydro-isoindol-2-yloxymethyl)-phenyl]-acetonitrile (2.25 g). This phthalimide intermediate (2.23 g) was dissolved in dichloromethane and methyl-hydrazine (1.1 eq.) was added. The reaction mixture was stirred at room temperature for 30 minutes and the formed solid material was removed by filtration. The filtrate was evaporated under reduced pressure and the residue was subjected to column chromatography on silica gel (petroleum ether/EtOAc 3/1, v/v) and gave the title compound. $^{13}$C-NMR (CDCl$_3$) δ 135.0, 130.9, 129.7, 129.2, 129.2, 128.3, 118.0, 75.8, 21.1.

Preparation 23

O-(2-Benzenesulfonylmethyl-benzyl)-hydroxylamine

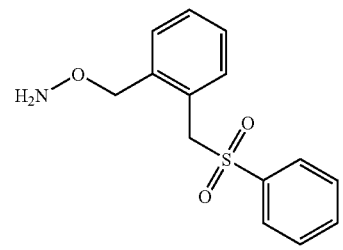

Prepared by the same procedure as described for preparation 15, starting from N-hydroxyphthalimide and 1-(bromomethyl)-2-[(phenylsulfonyl)methyl]benzene (Aldrich). $^{13}$C-NMR (CDCl$_3$) δ 138.6, 137.5, 133.8, 132.3, 130.8, 129.0, 128.6, 128.4, 127.4, 75.6, 59.3.

Preparation 24

(4-Aminooxymethyl-phenyl)-methanol hydrochloride

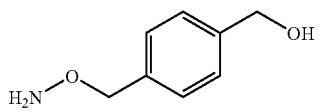

Prepared by a similar procedure as described for preparation 18, starting from N-hydroxyphthalimide and 4-(chloromethyl)benzyl alcohol (Aldrich). $^{13}$C-NMR (DMSO-d$_6$) δ 143.6, 131.8, 129.0, 126.4, 75.5, 62.4.

Preparation 25

O-(4-Fluoro-2-trifluoromethyl-benzyl)-hydroxylamine hydrochloride

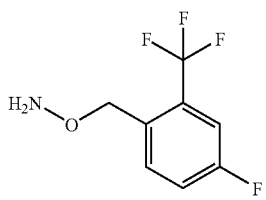

Prepared by the same procedure as described for preparation 13, starting from N-hydroxyphthalimide and 4-fluoro-2-(trifluoromethyl)benzyl bromide (Matrix). $^{13}$C-NMR (DMSO-d$_6$) δ 161.8, 135.0, 128.0, 122.9, 119.8, 114.0, 71.0.

Preparation 26

O-(2-Fluoro-6-trifluoromethyl-benzyl)-hydroxylamine hydrochloride

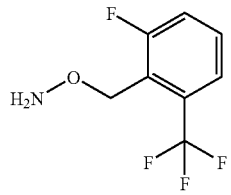

Prepared by the same procedure as described for preparation 13, starting from N-hydroxyphthalimide and 2-fluoro-6-(trifluoromethyl)benzyl bromide (Aldrich). $^{13}$C-NMR (DMSO-d$_6$) δ 161.9, 132.8, 130.3, 123.1, 122.4, 120.4, 118.6, 65.2.

Preparation 27

O-(4-Fluoro-3-trifluoromethyl-benzyl)-hydroxylamine hydrochloride

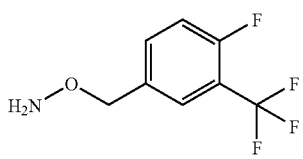

Prepared by the same procedure as described for preparation 13, starting from N-hydroxyphthalimide and 4-fluoro-3-(trifluoromethyl)benzyl bromide (Matrix). $^{13}$C-NMR (DMSO-d$_6$) δ 159.1, 136.3, 131.2, 128.2, 122.4, 117.5, 116.7, 73.9.

Preparation 28

O-(4-Methyl-3-trifluoromethyl-benzyl)-hydroxylamine

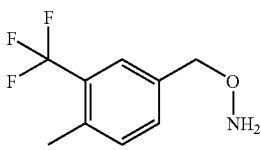

Prepared by a similar procedure as described for preparation 15, starting from N-hydroxyphthalimide and 4-methyl-3-(trifluoromethyl)benzyl bromide (JRD fluorochemicals). $^{13}$C-NMR (CDCl$_3$) δ 136.4, 135.5, 132.1, 131.5, 129.0, 125.8, 124.5, 77.0, 19.1.

Preparation 29

O-(4-Methoxy-3-trifluoromethyl-benzyl)-hydroxylamine hydrochloride

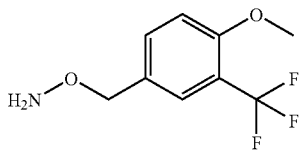

Prepared by a similar procedure as described for preparation 13, starting from N-hydroxyphthalimide and 4-methoxy-3-(trifluoromethyl)benzyl bromide (Fluorochem). $^{13}$C-NMR (DMSO-d$_6$) δ 157.5, 135.6, 128.0, 125.7, 123.4, 116.8, 113.0, 74.5, 56.3.

Preparation 30

O-(2-Methoxy-benzyl)-hydroxylamine hydrochloride

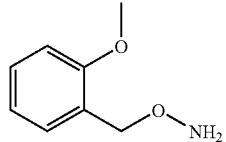

Prepared by a similar procedure as described for preparation 18, starting from N-hydroxyphthalimide and 2-methoxybenzyl chloride (Aldrich). $^{13}$C-NMR (DMSO-d$_6$) δ 157.5, 130.8, 130.7, 121.5, 120.3, 111.1, 70.8, 55.4.

Preparation 31

O-(4-Pentyloxy-benzyl)-hydroxylamine

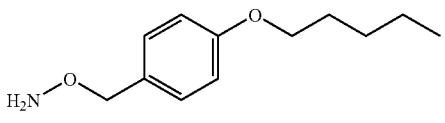

To a stirred solution N-hydroxyphthalimide (2.45 g), 4-pentyloxybenzyl alcohol (Aldrich, 2.92 g) and triphenylphosphine (4.72 g) in THF was added drop-wise diethyl azodicarboxylate (1.2 eq.). The reaction mixture was stirred at room temperature for 2 hours. The solvent was evaporated under reduced pressure and the residue was subjected to column chromatography on silica gel (petroleum ether/EtOAc, 1/2, v/v) and gave 2-(4-pentyloxy-benzyloxy)-isoindole-1,3-dione. This phthalimide intermediate (4.35 g) was dissolved in dichloromethane and methyl-hydrazine (1.1 eq.) was added. The reaction mixture stirred at room temperature for 60 minutes and the formed solid material was removed by filtration. The filtrate was evaporated under reduced pressure and the residue was subjected to column chromatography on silica gel (petroleum ether/EtOAc, 5/1, v/v), and gave the title compound (2.55 g). $^{13}$C-NMR (CDCl$_3$) δ 159.1, 130.1, 129.2, 114.5, 77.7, 68.0, 29.0, 28.2, 22.5, 14.0.

Preparation 32

O-(2-Trifluoromethoxy-benzyl)-hydroxylamine hydrochloride

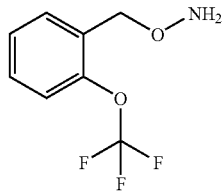

Prepared by the same procedure as described for preparation 13, starting from N-hydroxyphthalimide and 2-(trifluoromethoxy)benzyl bromide (Matrix). $^{13}$C-NMR (DMSO-d$_6$) δ 146.9, 132.0, 131.3, 127.7, 126.3, 120.7, 120.0, 69.7.

Preparation 33

O-(3-Trifluoromethoxy-benzyl)-hydroxylamine hydrochloride

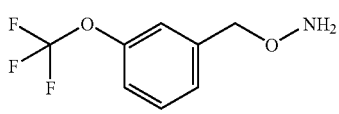

Prepared by the same procedure as described for preparation 18, starting from N-hydroxyphthalimide and 3-(trifluoromethoxy)benzyl bromide (Yarsley). $^{13}$C-NMR (DMSO-d$_6$) δ 148.3, 136.5, 130.6, 128.0, 121.4, 121.3, 120.0, 74.5.

Preparation 34

O-(4-Trifluoromethoxy-benzyl)-hydroxylamine hydrochloride

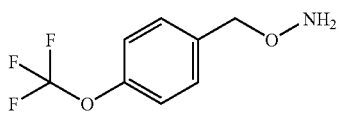

Prepared by the same procedure as described for preparation 18, starting from N-hydroxyphthalimide and 4-(trifluoromethoxy)benzyl bromide (Aldrich). $^{13}$C-NMR (DMSO-d$_6$) δ 148.7, 133.2, 131.2, 121.1, 120.0, 74.5.

Preparation 35

O-(2-Difluoromethoxy-benzyl)-hydroxylamine hydrochloride

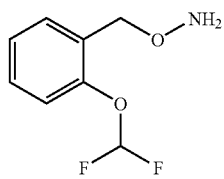

Prepared by a similar procedure as described for preparation 13, starting from N-hydroxyphthalimide and 2-(difluoromethoxy)benzyl bromide (Matrix). $^{13}$C-NMR (DMSO-d$_6$) δ 149.4, 131.5, 130.9, 125.4, 124.7, 118.3, 116.4, 70.1.

Preparation 36

O-(2-Trifluoromethylsulfanyl-benzyl)-hydroxylamine hydrochloride

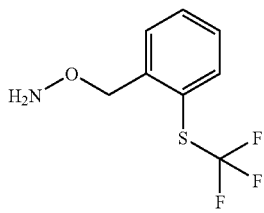

Prepared by a similar procedure as described for preparation 13, starting from N-hydroxyphthalimide and 2-(trifluoromethylthio)benzyl bromide (Matrix). $^{13}$C-NMR (DMSO-d$_6$) δ 138.6, 137.9, 132.1, 131.4, 130.5, 123.3, 73.1.

Preparation 37

O-(6-Chloro-benzo[1,3]-dioxol-5-ylmethyl)-hydroxylamine hydrochloride

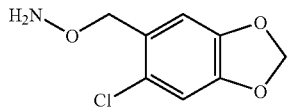

Prepared by a similar procedure as described for preparation 18, starting from N-hydroxyphthalimide and 6-chloropiperonyl chloride (Aldrich). $^{13}$C-NMR (DMSO-d$_6$) δ 148.9, 146.5, 126.2, 124.2, 111.1, 109.8, 102.3, 72.7.

Preparation 38

O-Benzo[1,3]-dioxol-5-ylmethyl-hydroxylamine

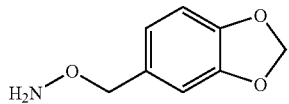

Prepared by a similar procedure as described for preparation 15, starting from N-hydroxyphthalimide and 3,4-methylenedioxybenzyl chloride (Fluorochem). $^{13}$C-NMR (CDCl$_3$) δ 147.5, 147.2, 131.0, 121.9, 108.7, 107.9, 100.8, 77.5.

Preparation 39

O-Indan-5-ylmethyl-hydroxylamine hydrochloride

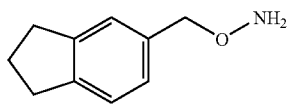

Prepared by a similar procedure as described for preparation 31, starting from N-hydroxyphthalimide and 5-hydroxymethyl-indane (Tyger). The hydrochloride salt was formed by addition of 4 M HCl in dioxane (1.0 eq.) to the initially prepared hydroxylamine. $^{13}$C-NMR (DMSO-d$_6$) δ 144.8, 144.1, 131.3, 127.4, 125.3, 124.2, 75.8, 32.0, 24.9.

Preparation 40

3-Aminooxymethyl-benzonitrile

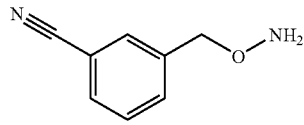

Prepared by a similar procedure as described for preparation 15, starting from N-hydroxyphthalimide and 3-bromomethyl-benzonitrile. $^{13}$C-NMR (CDCl$_3$) δ 139.5, 132.5, 131.7, 131.5, 129.2, 118.7, 112.6, 76.5.

Preparation 41

2-Aminooxymethyl-benzonitrile

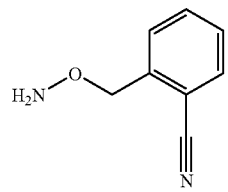

Prepared by a similar procedure as described for preparation 15, starting from N-hydroxyphthalimide and 2-bromomethyl-benzonitrile. $^{13}$C-NMR (CDCl$_3$) δ 141.3, 132.9, 132.8, 129.5, 128.4, 117.5, 112.4, 75.3

Preparation 42

4-Aminooxymethyl-3-fluoro-benzonitrile hydrochloride

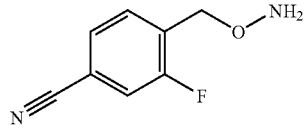

Prepared by a similar procedure as described for preparation 22, starting from 3-fluoro-4-methylbenzonitrile (Apollo). $^{13}$C-NMR (DMSO-d$_6$) δ 160.0, 132.6, 128.9, 126.9, 119.5, 117.3, 113.5, 68.7.

Preparation 43

4-Aminooxymethyl-2-bromo-benzonitrile hydrochloride

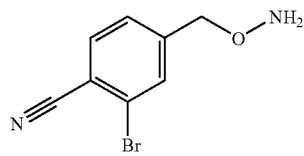

Prepared by a similar procedure as described for preparation 22, starting from 2-bromo-4-methylbenzonitrile (Chemie Brunschwig). $^{13}$C-NMR (DMSO-d$_6$) δ 141.5, 135.0, 132.8, 128.3, 124.4, 116.9, 114.4, 73.7.

Preparation 44

4-Aminooxymethyl-3-chloro-benzonitrile hydrochloride

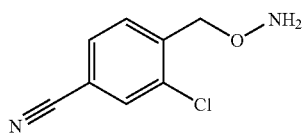

Prepared by a similar procedure as described for preparation 22, starting from 3-chloro-4-methylbenzonitrile (Aldrich). $^{13}$C-NMR (DMSO-d$_6$) δ 137.3, 133.7, 132.8, 131.4, 131.4, 117.2, 113.1, 72.0.

Preparation 45

4-Aminooxymethyl-3-methoxy-benzonitrile hydrochloride

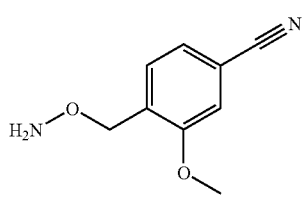

Prepared by a similar procedure as described for preparation 22, starting from 3-methoxy-4-methylbenzonitrile (Apin). $^{13}$C-NMR (DMSO-d$_6$) δ 157.2, 130.7, 127.5, 124.5, 118.4, 114.4, 112.7, 69.9, 56.2.

Preparation 46

4-Aminooxymethyl-3-iodo-benzonitrile hydrochloride

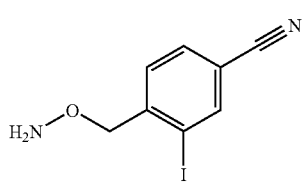

Prepared by a similar procedure as described for preparation 22, starting from 3-iodo-4-methyl-benzonitrile. $^{13}$C-NMR (DMSO-d$_6$) δ 141.9, 132.1, 129.9, 116.9, 113.0, 99.3, 78.1.

Preparation 47

3-Aminooxymethyl-4-bromo-benzonitrile

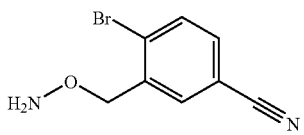

Prepared by a similar procedure as described for preparation 22, starting from 4-bromo-3-methylbenzonitrile (Lancaster).

Preparation 48

4-Aminooxymethyl-naphthalene-1-carbonitrile hydrochloride

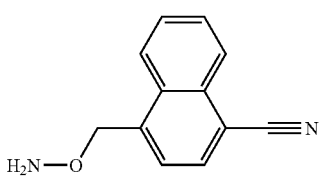

Prepared by a similar procedure as described for preparation 22, starting from 1-cyano-4-methylnaphthalene (Aldrich). $^{13}$C-NMR (DMSO-d$_6$) δ 135.6, 132.8, 131.6, 131.1, 129.1, 128.3, 128.0, 125.3, 124.8, 117.2, 110.5, 73.0.

Preparation 49

O-(4-Morpholin-4-yl-benzyl)-hydroxylamine hydrochloride

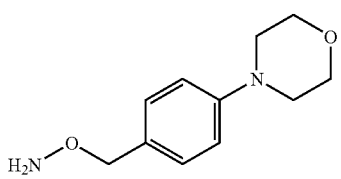

Prepared by a similar procedure as described for preparation 31 starting from (4-morpholinophenyl)methanol (Maybridge) and N-hydroxyphthalimide. The initial formed free hydroxylamine was treated with 4M HCl in dioxane (1.0 eq.) to afford the corresponding hydrochloride salt.

Preparation 50

O-(2-Morpholin-4-yl-benzyl)-hydroxylamine hydrochloride

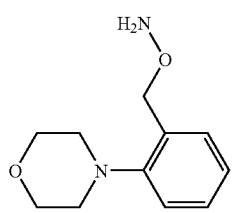

Prepared by a similar procedure as described for preparation 31 starting from (2-morpholinophenyl)methanol (Maybridge) and N-hydroxyphthalimide. The initial formed free hydroxylamine was treated with 4M HCl in dioxane (1.0 eq.) to afford the corresponding hydrochloride salt. $^1$H-NMR (DMSO-$d_6$) δ 11.3 (s, 3H), 7.45-7.35 (m, 2H), 7.25-7.1 (m, 2H), 5.19 (s, 2H), 3.79 (m, 4H), 2.88 (m, 4H).

Preparation 51

O-(2-Amino-benzyl)-hydroxylamine

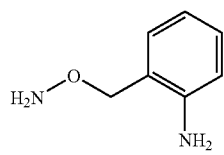

Prepared by a similar procedure as described for preparation 31 starting from 2-amino-benzylalcohol and N-hydroxyphthalimide. $^{13}$C-NMR (CDCl$_3$) δ 146.4, 131.2, 129.7, 121.4, 118.1, 115.9, 76.6.

Preparation 52

3-Aminooxymethyl-benzoic acid methyl ester hydrochloride

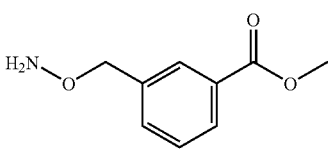

Methyl 3-(bromomethyl)benzoate (Lancaster, 5.0 g), tert-butyl-n-hydroxycarbamate (4.35 g) was dissolved in acetonitrile (40 ml). Potassium carbonate (3.77 g) was added and the mixture was stirred at room temperature for 3 hours. The mixture was diluted with EtOAc and washed with water and brine. The organic layer was dried (MgSO$_4$) and the mixture was filtrated through a pad of silica gel, washing with EtOAc (100 ml). The combined filtrates were evaporated under reduced pressure. The remaining oil was dissolved in EtOAc (40 ml) and 4M HCl in dioxane (5.5 ml) was added followed by addition of water (0.4 ml). The mixture was stirred at room temperature for 3 hours and the resulting solid material was isolated by filtration and dried under high vacuum, affording the title compound. $^{13}$C-NMR (DMSO-$d_6$) δ 165.8, 134.5, 133.8, 129.9, 129.6, 129.1, 74.9, 52.2.

Preparation 53

O-Naphthalen-1-ylmethyl-hydroxylamine

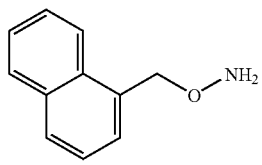

Prepared by a similar procedure as described for preparation 13. Starting materials: N-Hydroxyphthalimide and 1-chloromethyl-naphthalen. $^{13}$C-NMR (DMSO-$d_6$) δ 133.5, 133.2, 131.4, 128.2, 126.8, 126.7, 126.0, 125.6, 125.2, 124.1, 75.4.

Preparation 54

O-(1-Phenyl-ethyl)-hydroxylamine hydrochloride

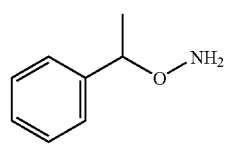

Prepared by a similar procedure as described for preparation 18. Starting materials: N-Hydroxyphthalimide and 1-phenylethyl bromide (Aldrich). $^{13}$C-NMR (DMSO-$d_6$) δ 138.9, 128.7, 128.6, 126.8, 81.4, 20.6.

Preparation 55

O-[1-(2-Trifluoromethyl-phenyl)-ethyl]-hydroxylamine hydrochloride

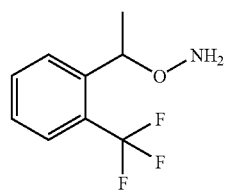

Prepared by the same procedure as described for preparation 13, starting from N-hydroxyphthalimide and alpha-methyl-2-(trifluoromethyl)benzyl bromide (Matrix). $^{13}$C-NMR (DMSO-$d_6$) δ 138.5, 133.3, 129.0, 127.5, 126.1, 125.6, 124.0, 77.1, 21.9.

Preparation 56

O-Pyridin-2-ylmethyl-hydroxylamine hydrochloride

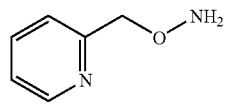

Prepared by a similar procedure as described for preparation 12, starting from and N-hydroxyphthalimide 2-chloromethyl-pyridine.

Preparation 57

O-(2,6-Dichloro-pyridin-4-ylmethyl)-hydroxylamine hydrochloride

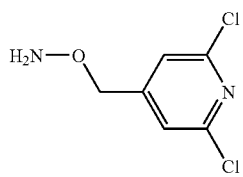

Prepared by a similar procedure as described for preparation 18. Starting materials: N-hydroxyphthalimide and 4-bromomethyl-2,6-dichloropyridin (Maybridge). $^1$H-NMR (DMSO-d$_6$) δ 11.2 (br, 3H), 7.62 (s, 2H), 5.18 (s, 2H).

Preparation 58

O-Thiazol-4-ylmethyl-hydroxylamine hydrochloride

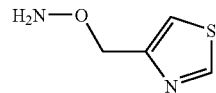

Prepared by a similar procedure as described for preparation 18. Starting materials: N-hydroxyphthalimide and 4-(chloromethyl)thiazole hydrochloride (TCl). $^{13}$C-NMR (DMSO-d$_6$) δ 155.1, 149.2, 121.4, 70.3.

Preparation 59

O-(2-Chloro-thiazol-5-ylmethyl)-hydroxylamine

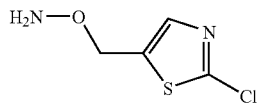

2-[(2-Chloro-1,3-thiazol-5-yl)methoxy]-1H-isoindole-1,3 (2H)-dione (Bionet, 5.0 g), was suspended in ethanol (120 ml) and hydrazine monohydrate (0.83 ml) was added. The mixture was heated to reflux and stirred at this temperature for 4 hours. The mixture was cooled to room temperature and the solid material was removed by filtration. The filtrate was evaporated under reduced pressure. The residue was re-suspended in diethyl ether (400 ml) and 4M HCl in dioxane (4.25 ml) was added. The solid material was isolated by filtration and dried under vacuum, and gave the title compound (3.3 g). $^{13}$C-NMR (DMSO-d$_6$) δ 152.5, 143.3, 133.5, 66.9.

Preparation 60

O-(2-Phenyl-thiazol-4-ylmethyl)-hydroxylamine hydrochloride

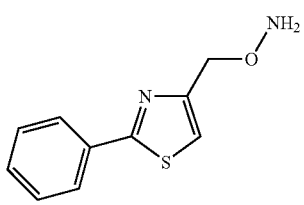

Prepared by a similar procedure as described for preparation 12, starting from N-hydroxyphthalimide and 4-chloromethyl-2-phenyl-thiazole hydrochloride.

Preparation 61

O-(5-Methyl-isoxazol-3-ylmethyl)-hydroxylamine

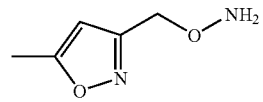

Prepared by a similar procedure as described for preparation 15. Starting materials: N-hydroxyphthalimide and 3-chloromethyl-5-methylisoxazole (Maybridge). $^{13}$C-NMR (DMSO-d$_6$) δ 169.1, 161.5, 101.4, 68.0, 11.7.

Preparation 62

O-(3,5-Dimethyl-isoxazol-4-ylmethyl)-hydroxylamine hydrochloride

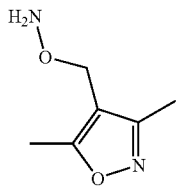

Prepared by a similar procedure as described for preparation 13. Starting materials: N-hydroxyphthalimide and 4-(chloromethyl)-3,5-dimethylisoxazole (Aldrich). $^{13}$C-NMR (DMSO-d$_6$) δ 169.7, 159.6, 108.2, 64.4, 10.8, 9.5.

Preparation 63

O-(3-Propyl-isoxazol-5-ylmethyl)-hydroxylamine

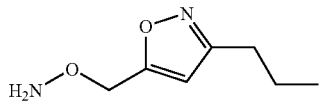

Step 1: To a stirred solution of N-hydroxyphthalimide (50.5 g) and propargyl bromide (37.0 g) in DMF (250 ml) at 0° C. was added drop-wise triethylamine (50 ml). The cooling bath was removed and the reaction mixture was stirred at room temperature for 4 hours. The mixture was poured into water containing some ice and the precipitated material was isolated by filtration. The crude product was recrystallised from ethanol and gave 2-prop-2-ynyloxy-isoindole-1,3-dione (47.5 g). Step 2: The above obtained phthalimide intermediate (1 mmol) was mixed with p-tolyl isocyanate (2.8 mmol), triethylamine (0.05 mmol) and 1-nitrobutane (1.44 mmol) in toluene (3 ml). The reaction mixture was stirred at room temperature for 48 hours, filtrated and subjected to column chromatography on silica, affording 2-(3-propyl-isoxazol-5-ylmethoxy)-isoindole-1,3-dione. Step 3: The above cycloaddition product was dissolved in methanol+ dichloromethane and hydrazine monohydrate (1 eq.) was added. The reaction mixture was stirred at room temperature for 20 hours and placed at 5° C. for 3 hours. The solid material was removed by filtration and the filtrate was evaporated under reduced pressure and gave the title compound. $^{13}$C-NMR (DMSO-$d_6$) δ 169.0, 163.2, 103.0, 67.4, 27.2, 21.0, 13.5.

Preparation 64

O-(5-Chloro-thiophen-2-ylmethyl)-hydroxylamine

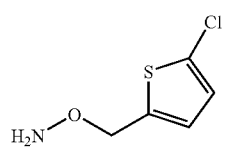

Prepared by a similar procedure as described for preparation 15. Starting materials: N-hydroxyphthalimide and 2-chloro-5-(chloromethyl)thiophene (Aldrich). $^{13}$C-NMR (DMSO-$d_6$) δ 140.2, 127.9, 126.3, 126.0, 71.1.

Preparation 65

4-(2-Aminooxy-ethyl)-benzonitrile

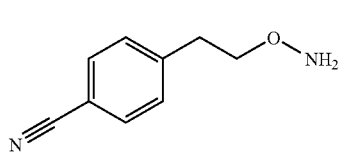

Prepared by a similar procedure as described for preparation 31. Starting materials: N-hydroxyphthalimide and 4-(2-hydroxyethyl)benzonitrile (Maybridge). $^{13}$C-NMR (DMSO-$d_6$) δ 145.6, 131.9, 129.9, 118.9, 108.7, 74.6, 34.3.

Preparation 66

O-Cyclopentylmethyl-hydroxylamine hydrochloride

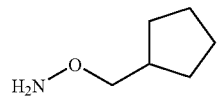

Prepared by a similar procedure as described for preparation 31. Starting materials: N-Hydroxyphthalimide and (hydroxymethyl)cyclopentane (Aldrich). Diisopropyl azodicarboxylate was used instead of dietyl azodicarboxylate and the initial formed free hydroxylamine was treated with 4M HCl in dioxane (1.0 eq.) to obtain the corresponding hydrochloride salt. $^{13}$C-NMR (DMSO-$d_6$) δ 77.9, 37.1, 28.8, 24.9.

Preparation 67

O-Cyclopropylmethyl-hydroxylamine hydrochloride

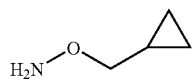

Prepared by a similar procedure as described for preparation 13. Starting materials: N-hydroxyphthalimide and bromomethyl-cyclopropane. $^{13}$C-NMR (DMSO-$d_6$) δ 78.4, 8.5, 3.0.

Preparation 68

O-(2,2-Dimethyl-propyl)-hydroxylamine hydrochloride

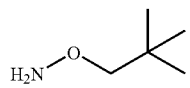

Prepared by a similar procedure as described for preparation 66. Starting materials: N-hydroxyphthalimide and 2,2-dimethyl-1-propanol. $^{13}$C-NMR (DMSO-$d_6$) δ 82.9, 31.2, 26.1.

Preparation 69

O-(2-Ethyl-butyl)-hydroxylamine hydrochloride

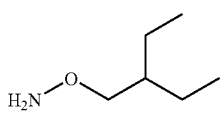

Prepared by a similar procedure as described for preparation 13. Starting materials: N-hydroxyphthalimide and 1-bromo-2-ethyl-butane. $^{13}$C-NMR (DMSO-$d_6$) δ 66.3, 39.2, 22.6, 10.7.

Preparation 70

O-(3-Methyl-butyl)-hydroxylamine hydrochloride

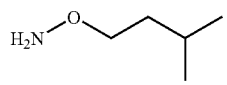

Prepared by a similar procedure as described for preparation 13. Starting materials: N-hydroxyphthalimide and isoamyl bromide. $^{13}$C-NMR (DMSO-d$_6$) δ 72.5, 35.8, 24.4, 22.3.

Preparation 71

O-Cyclobutylmethyl-hydroxylamine hydrochloride

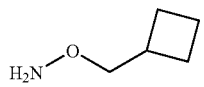

Prepared by a similar procedure as described for preparation 13. Starting materials: N-hydroxyphthalimide and cyclobutylmethyl bromide (Aldrich). $^{13}$C-NMR (DMSO-d$_6$) δ 77.6, 32.3, 24.1, 18.0.

Preparation 72

O-Cyclohexylmethyl-hydroxylamine hydrochloride

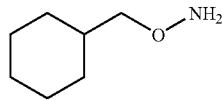

Prepared by a similar procedure as described for preparation 13. Starting materials: N-hydroxyphthalimide and cyclohexylmethyl bromide. $^{13}$C-NMR (DMSO-d$_6$) δ 78.8, 35.7, 28.8, 25.7, 24.9.

Preparation 73

O-Cycloheptylmethyl-hydroxylamine hydrochloride

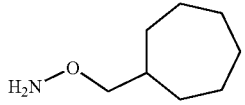

Methanol (20 ml) was cooled to 0° C. and acetyl chloride (2.0 ml) was added. The mixture was stirred for 10 minutes and cycloheptanecarboxylic acid (2.0 ml) was added. The cooling bath was removed and the mixture was heated to reflux and stirred for 8 hours. The mixture was cooled to room temperature and the solvent was evaporated under reduced pressure. The residue was extracted with EtOAc. The organic layer washed with saturated aqueous sodium bicarbonate, dried (Na$_2$SO$_4$) and evaporated under reduced pressure, affording cycloheptanecarboxylic acid methylester (1.82 g) as a pale yellow liquid. This methylester intermediate (1.8 g) was dissolved in THF (25 ml) and cooled to −40° C. Lithium aluminium hydride (11.5 ml of a 1.0 M sol. in THF) was added drop-wise. The reaction mixture was allowed slowly to warm to 0° C. and stirring was continued at this temperature for 3 hours. Aqueous sodium hydroxide (5 ml of a 1 M sol.) was added and the mixture was filtrated. The filtrate was evaporated under reduced pressure and re-dissolved in EtOAc (20 ml), dried (Na$_2$SO$_4$) and evaporated under reduced pressure, and gave cycloheptyl-methanol (1.37 g) as a clear colourless oil. This alcohol intermediate was converted into the title compound, as described for preparation 66, using N-hydroxyphthalimide. $^{13}$C-NMR (DMSO-d$_6$) δ 78.8, 37.1, 30.0, 27.9, 25.6.

Preparation 74

O-Cyclooctylmethyl-hydroxylamine

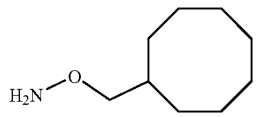

Prepared by a similar procedure as described for preparation 31. Starting materials: N-hydroxyphthalimide and cyclooctanemethanol (Acros). $^{13}$C-NMR (CDCl$_3$) δ 82.3, 36.4, 29.4, 27.0, 26.5, 25.5.

Preparation 75

O-(1-Cyclopentyl-ethyl)-hydroxylamine hydrochloride

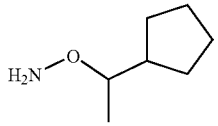

Prepared by a similar procedure as described for preparation 66. Starting materials: N-hydroxyphthalimide and 1-cyclopentylethanol (Aldrich). $^{13}$C-NMR (DMSO-d$_6$) δ 83.8, 43.4, 28.3, 28.1, 25.0, 25.0, 16.9.

Preparation 76

O-Cyclohexyl-hydroxylamine hydrochloride

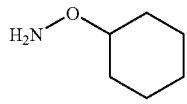

Prepared by a similar procedure as described for preparation 15. Starting materials: N-hydroxyphthalimide and cyclohexyl bromide (Fluka). $^{13}$C-NMR (DMSO-d$_6$) δ 81.2, 29.8, 24.6, 22.7.

Preparation 77

O-(2-Cyclopropyl-ethyl)-hydroxylamine hydrochloride

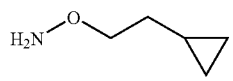

Prepared by a similar procedure as described for preparation 31. Starting materials: N-hydroxyphthalimide and 2-cyclopropylethanol (Lancaster). The initial formed free hydroxylamine was treated with 4M HCl in dioxane (1.0 eq.) to obtain the corresponding hydrochloride salt. $^{13}$C-NMR (DMSO-d$_6$) δ 74.2, 31.9, 7.2, 4.0.

Preparation 78

O-(2-Cyclopentyl-ethyl)-hydroxylamine

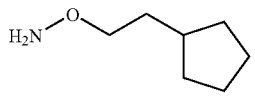

Prepared by a similar procedure as described for preparation 31. Starting materials: N-hydroxyphthalimide and 2-cyclopentylethanol (Lancaster). $^{13}$C-NMR (CDCl$_3$) δ 75.7, 37.0, 34.6, 32.8, 25.1.

Preparation 79

O-(3-Cyclopentyl-propyl)-hydroxylamine

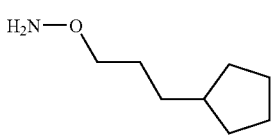

Prepared by a similar procedure as described for preparation 31. Starting materials: N-hydroxyphthalimide and 3-cyclopentyl-1-propanol (Aldrich). $^{13}$C-NMR (CDCl$_3$) δ 76.5, 40.0, 32.7, 32.4, 27.7, 25.2.

Preparation 80

O-Cyclohex-3-enylmethyl-hydroxylamine hydrochloride

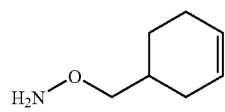

Prepared by a similar procedure as described for preparation 66. Starting materials: N-hydroxyphthalimide and 1,2,3,6-tetrahydrobenzylalcohol (Aldrich). $^{13}$C-NMR (DMSO-d$_6$) δ 126.9, 125.4, 78.1, 31.8, 27.4, 24.5, 23.7.

Preparation 81

O-(6-Methyl-cyclohex-3-enylmethyl)-hydroxylamine hydrochloride

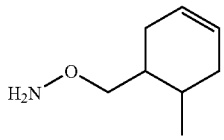

Prepared by a similar procedure as described for preparation 66. Starting materials: N-hydroxyphthalimide and 6-methyl-3-cyclohexene-1-methanol (Aldrich). The final product contained some impurities, but was used without further purification.

Preparation 82

(trans-4-Aminooxymethyl-cyclohexyl)-methanol

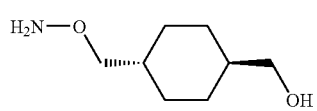

Prepared by a similar procedure as described for preparation 31. Starting materials: N-hydroxyphthalimide and trans-1,4-cyclohexanedimethanol (Acros). $^{13}$C-NMR (CDCl$_3$) δ 81.6, 68.2, 40.3, 36.8, 29.0, 28.7.

Preparation 83

O-(3-Methoxy-cyclohexylmethyl)-hydroxylamine hydrochloride

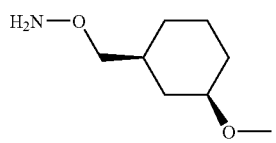

Prepared by a similar procedure as described for preparation 73, starting from 3-methoxycyclohexanecarboxylic acid (Aldrich). The title compound was not obtained in a pure form but used without further purification.

Preparation 84

O-Adamantan-1-ylmethyl-hydroxylamine hydrochloride

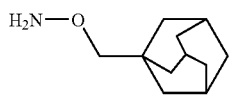

Prepared by a similar procedure as described for preparation 31. Starting materials: N-Hydroxyphthalimide and 1-adamantanemethanol (Aldrich). The initial formed free hydroxylamine was treated with 4M HCl in dioxane (1.0 eq.) to obtain the corresponding hydrochloride salt. $^{13}$C-NMR (DMSO-d$_6$) δ 83.2, 38.5, 36.3, 33.2, 27.2.

Preparation 85

O-Bicyclo[2.2.1]hept-2-ylmethyl-hydroxylamine hydrochloride

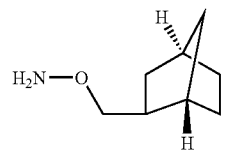

Prepared by a similar procedure as described for preparation 31. Starting materials: N-hydroxyphthalimide and 2-hydroxymethylbicyclo[2.2.1]heptane (Aldrich). The initial formed free hydroxylamine was treated with 4M HCl in dioxane (1.0 eq.) to obtain the corresponding hydrochloride salt. $^{13}$C-NMR (DMSO-d$_6$) δ 77.1, 75.7, 39.1, 37.7, 37.5, 37.2, 35.8, 35.4, 34.9, 33.3, 32.9, 29.1, 28.9, 28.2, 22.2.

Preparation 86

O-(6,6-Dimethyl-bicyclo[3.1.1]hept-2-ylmethyl)-hydroxylamine hydrochloride

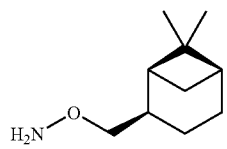

Prepared by a similar procedure as described for preparation 31. Starting materials: N-hydroxyphthalimide and (1S, 2R)-10-pinanol (Fluka). The initial formed free hydroxylamine was treated with 4M HCl in dioxane (1.0 eq.) to obtain the corresponding hydrochloride salt. $^{13}$C-NMR (DMSO-d$_6$) δ 78.3, 42.4, 40.5, 38.6, 37.9, 32.0, 27.5, 25.3, 22.8, 17.9.

Preparation 87

O-(Tetrahydro-furan-2-ylmethyl)-hydroxylamine hydrochloride

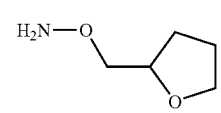

Prepared by a similar procedure as described for preparation 18. Starting materials: N-hydroxyphthalimide and tetrahydrofurfuryl bromide. $^1$H-NMR (DMSO-d$_6$) δ 11.08 (s, 3H), 4.1-3.9 (m, 3H), 3.8-3.6 (m, 2H), 2.0-1.7 (m, 3H), 1.6-1.45 (m, 1H).

Preparation 88

O-(Tetrahydro-furan-3-ylmethyl)-hydroxylamine hydrochloride

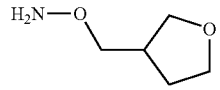

Prepared by a similar procedure as described for preparation 66. Starting materials: N-hydroxyphthalimide and (tetrahydro-furan-3-yl)-methanol (Aldrich). $^{13}$C-NMR (DMSO-d$_6$) δ 75.6, 69.3, 66.7, 36.7, 28.1.

Preparation 89

O-(3-Methyl-4,5-dihydro-isoxazol-5-ylmethyl)-hydroxylamine

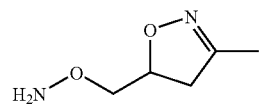

N-Hydroxyphthalimide (48.9 g) was dissolved in DMF (200 ml) and triethylamine (43.9 ml) was added followed by addition of allyl bromide. The reaction mixture was stirred at room temperature for 18 hours and the resulting precipitated material was removed by filtration. The filtrate was concentrated under reduced pressure. The residue was dissolved in dichloromethane and washed with saturated aqueous sodium bicarbonate, 4 M HCl aq. and brine. The organic layer was dried (MgSO$_4$) and evaporated under reduced pressure. The remaining material was crystallised from hexane/EtOAc, affording 2-allyloxy-isoindole-1,3-dione (43.6 g). This allyl intermediate (2.03 g) was dissolved in toluene (5 ml) and nitroethane (825 mg), phenylisocyanate (2.4 ml) and triethylamine (0.02 eq.) was added. The reaction mixture was stirred at room temperature for 48 hours, and the precipitated material was removed by filtration. The filtrate was evaporated onto silica gel and chromatographed (0 to 50% EtOAc/heptane) and gave 2-(3-methyl-4,5-dihydro-isoxazol-5-ylmethoxy)-isoindole-1,3-dione (2.4 g). $^{13}$C-NMR (DMSO-d$_6$) δ 162.9, 155.4, 134.7, 128.5, 123.2, 78.0, 76.9, 40.3, 12.4. This phthalimide intermediate (260 mg) was dissolved in methanol (1 ml) and dichloromethane (1 ml) and hydrazine monohydrate (1.0 eq.) was added. The mixture was stirred at room temperature for 20 hours. The formed solid material was removed by filtration. The filtrate was evaporated under reduced pressure and gave the title compound, which was used without further purification.

Preparation 90

O-(3-Ethyl-4,5-dihydro-isoxazol-5-ylmethyl)-hydroxylamine

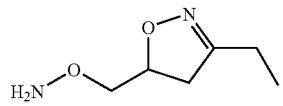

Prepared by a similar procedure as described for preparation 89, using 1-nitropropane instead of nitroethane. $^{13}$C-NMR (DMSO-d$_6$) δ 159.5, 76.9, 76.3, 38.7, 20.5, 10.6.

Preparation 91

O-(3-Butyl-4,5-dihydro-isoxazol-5-ylmethyl)-hydroxylamine

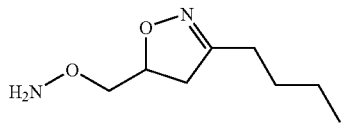

Prepared by a similar procedure as described for preparation 89, using 1-nitropentane instead of nitroethane. $^{13}$C-NMR (DMSO-$d_6$) δ 158.5, 76.8, 76.3, 38.8, 27.8, 26.5, 21.6, 13.5.

Preparation 92

O-(Tetrahydro-pyran-4-ylmethyl)-hydroxylamine hydrochloride

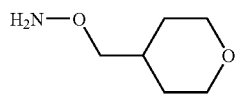

Methyl tetrahydropyran-4-carboxylate (Fluka) was reduced to the corresponding alcohol with lithium aluminium hydride and converted into the title compound as described for preparation 73. $^{13}$C-NMR (DMSO-$d_6$) δ 78.1, 66.3, 33.0, 28.7.

Preparation 93

O-(Tetrahydro-pyran-2-ylmethyl)-hydroxylamine hydrochloride

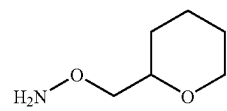

Prepared by a similar procedure as described for preparation 18. Starting materials: N-hydroxyphthalimide and 2-(bromomethyl)tetrahydro-2h-pyran (Aldrich). $^{13}$C-NMR (DMSO-$d_6$) δ 76.6, 74.5, 67.1, 26.9, 25.2, 22.3.

Preparation 94-170

These compounds were prepared by similar procedures as described above for preparation 8-93. $^{13}$C-NMR data were found in full accordance with their structures.

Example 1

N-Benzyloxy-2-[(pyridin-4-ylmethyl)-amino]-benzamide (compound 1)

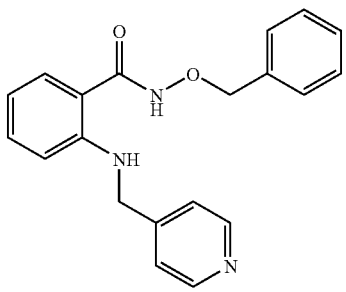

General procedure 1, method 1.

Starting materials: 2-[(Pyridin-4-ylmethyl)-amino]-benzoic acid (see preparation 1) and O-benzylhydroxylamine hydrochloride (Aldrich).

$^{13}$C-NMR (DMSO-$d_6$) δ 166.9, 149.7, 149.1, 148.3, 136.1, 132.5, 129.0, 128.4, 128.3, 128.2, 122.1, 114.9, 113.6, 111.6, 76.9, 44.9.

Example 2

N-(4-Nitro-benzyloxy)-2-[(pyridin-4-ylmethyl)-amino]-benzamide (compound 2)

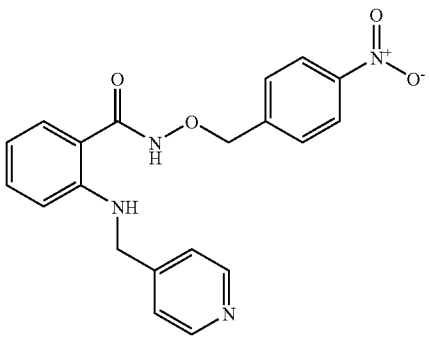

General procedure 1, method 1.

Starting materials: 2-[(Pyridin-4-ylmethyl)-amino]-benzoic acid (see preparation 1) and O-(4-nitrobenzyl)hydroxylamine hydrochloride (Aldrich).

$^1$H-NMR (DMSO-$d_6$) δ 11.69 (bs, 1H), 8.49 (d, 2H), 8.26 (d, 2H), 7.89 (bt, 1H), 7.77 (d, 2H), 7.38 (d, 1H), 7.30 (d, 2H), 7.20 (t, 1H), 6.55 (t, 1H), 6.51 (d, 1H), 5.10 (s, 2H), 4.46 (d, 1H).

Example 3

N-(2-Nitro-benzyloxy)-2-[(pyridin-4-ylmethyl)-amino]-benzamide (compound 3)

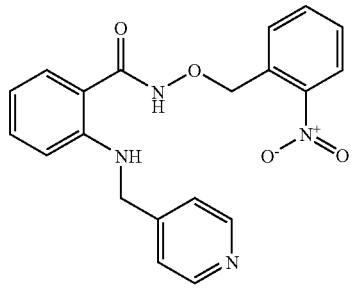

General procedure 1, method 1.

Starting materials: 2-[(Pyridine-4-ylmethyl)-amino]-benzoic acid (see preparation 1) and O-(2-nitrobenzyl)hydroxylamine hydrochloride (Bionet research intermediates).

$^{13}$C-NMR (DMSO-d$_6$) δ 167.5, 149.5, 148.9, 148.3, 147.8, 133.7, 132.6, 131.6, 130.4, 129.3, 128.1, 124.6, 122.0, 114.8, 113.0, 111.5, 73.2, 44.8.

Example 4

2-[(Pyridin-4-ylmethyl)-amino]-N-(3-trifluoromethyl-benzyloxy)-benzamide (compound 4)

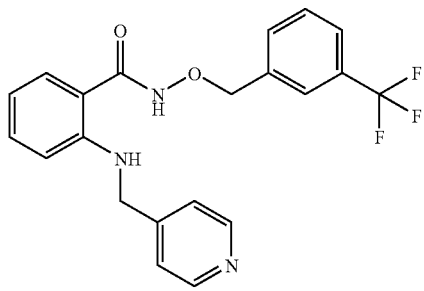

General procedure 1, method 1.

Starting materials: 2-[(Pyridine-4-ylmethyl)-amino]-benzoic acid (see preparation 1) and O-(3-trifluoromethylbenzyl)hydroxylamine hydrochloride (Bionet research intermediates). $^{13}$C-NMR (DMSO-d$_6$) δ 167.3, 149.5, 149.0, 148.3, 137.5, 132.7, 132.6, 129.3, 129.0, 128.0, 125.1, 124.8, 124.1, 122.0, 114.8, 113.3, 111.5, 76.0, 44.8.

Example 5

2-[(Pyridin-4-ylmethyl)-amino]-N-(2-trifluoromethyl-benzyloxy)-benzamide (compound 5)

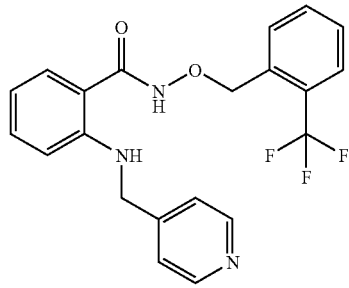

General procedure 1, method 1.

Starting materials: 2-[(Pyridin-4-ylmethyl)-amino]-benzoic acid (see preparation 1) and O-(2-trifluoromethylbenzyl) hydroxylamine hydrochloride (Bionet research intermediates).

$^{13}$C-NMR (DMSO-d$_6$) δ 167.5, 149.5, 149.0, 148.3, 134.3, 132.6, 132.5, 131.1, 128.7, 128.1, 126.9, 125.6, 124.2, 122.0, 114.8, 113.1, 111.5, 72.7, 44.8.

Example 6

N2-[(Pyridin-4-ylmethyl)-amino]-N-(4-trifluoromethyl-benzyloxy)-benzamide (compound 6)

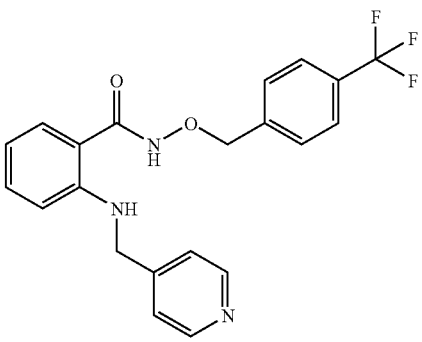

General procedure 1, method 1.

Starting materials: 2-[(Pyridin-4-ylmethyl)-amino]-benzoic acid (see preparation 1) and O-(4-trifluoromethylbenzyl) hydroxylamine hydrochloride (Bionet research intermediates).

$^{13}$C-NMR (DMSO-d$_6$) δ 167.4, 149.6, 149.0, 148.3, 140.9, 132.6, 129.2, 128.6, 128.1, 125.1, 124.2, 122.0, 114.8, 113.2, 111.5, 76.0, 44.8.

Example 7

N-(4-Methoxy-benzyloxy)-2-[(pyridin-4-ylmethyl)-amino]-benzamide (compound 7)

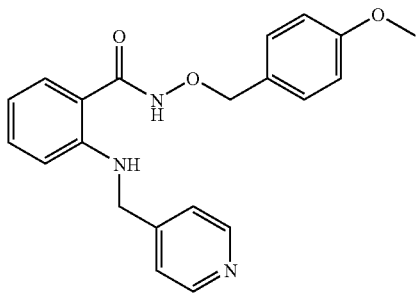

General procedure 1, method 1.

Starting materials: 2-[(Pyridin-4-ylmethyl)-amino]-benzoic acid (see preparation 1) and O-(4-methoxybenzyl)hydroxylamine hydrochloride (Bionet research intermediates).

$^{13}$C-NMR (DMSO-d$_6$) δ 167.1, 159.3, 149.5, 149.0, 148.3, 132.4, 130.6, 128.0, 127.8, 122.0, 114.8, 113.6, 113.5, 111.4, 76.6, 55.0, 44.8.

Example 8

N-(3-Methoxy-benzyloxy)-2-[(pyridin-4-ylmethyl)-amino]-benzamide (compound 8)

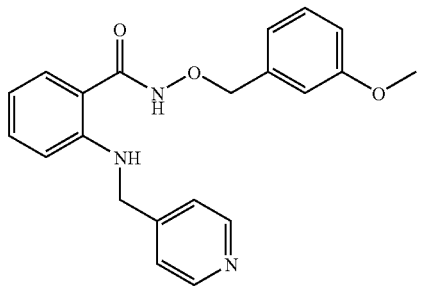

General procedure 1, method 1.

Starting materials: 2-[(Pyridin-4-ylmethyl)-amino]-benzoic acid (see preparation 1) and O-(3-methoxybenzyl)hydroxylamine hydrochloride (Bionet research intermediates).

$^{13}$C-NMR (DMSO-d$_6$) δ 167.1, 159.1, 149.5, 149.0, 148.3, 137.5, 132.4, 129.3, 128.0, 122.0, 120.8, 114.8, 114.0, 113.7, 113.4, 111.4, 76.7, 54.9, 44.8.

Example 9

2-[(pyridin-4-ylmethyl)-amino]-N-(3,4,5-trimethoxy-benzyloxy)-benzamide (compound 9)

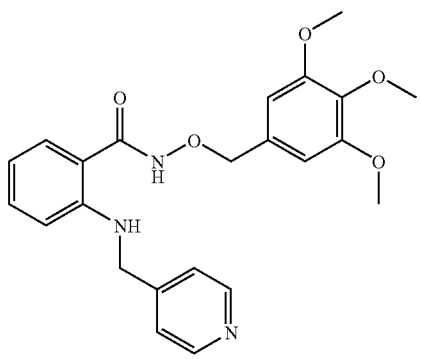

General procedure 1, method 1.

Starting materials: 2-[(Pyridin-4-ylmethyl)-amino]-benzoic acid (see preparation 1) and O-(3,4,5-trimethoxybenzyl) hydroxylamine hydrochloride (Se preparation 8).

$^{13}$C-NMR (DMSO-d$_6$) δ 167.1, 152.7, 149.5, 149.0, 148.2, 137.3, 132.5, 131.6, 128.1, 121.9, 114.8, 113.5, 111.4, 105.9, 76.9, 59.9, 55.8, 44.8

Example 10

N-(4-Chloro-benzyloxy)-2-[(pyridin-4-ylmethyl)-amino]-benzamide (compound 10)

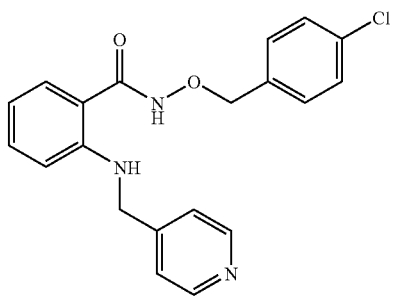

General procedure 1, method 1.

Starting materials: 2-[(Pyridin-4-ylmethyl)-amino]-benzoic acid (see preparation 1) and O-(4-chlorobenzyl)hydroxylamine hydrochloride (see preparation 9).

$^{13}$C-NMR (DMSO-d$_6$) δ 167.2, 149.5, 149.0, 148.3, 135.0, 132.8, 132.5, 130.7, 128.2, 128.0, 122.0, 114.8, 113.3, 111.5, 76.0, 44.8.

Example 11

N-(3-Chloro-benzyloxy)-2-[(pyridin-4-ylmethyl)-amino]-benzamide (compound 11)

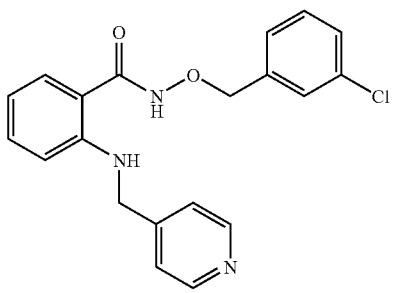

General procedure 1, method 1.

Starting materials: 2-[(Pyridin-4-ylmethyl)-amino]-benzoic acid (see preparation 1) and O-(3-chlorobenzyl)hydroxylamine hydrochloride (Bionet research intermediates).

$^{13}$C-NMR (DMSO-d$_6$) δ 167.3, 149.8, 149.5, 149.0, 148.3, 138.6, 132.9, 132.5, 130.1, 128.4, 128.1, 127.2, 122.0, 114.8, 113.3, 111.5, 76.0, 44.8.

Example 12

N-(2-Chloro-benzyloxy)-2-[(pyridin-4-ylmethyl)-amino]-benzamide (compound 12)

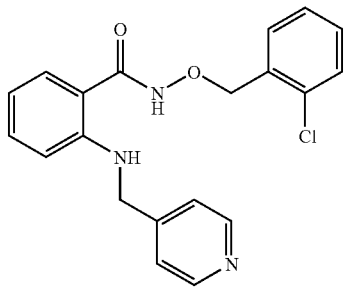

General procedure 1, method 1.

Starting materials: 2-[(Pyridin-4-ylmethyl)-amino]-benzoic acid (see preparation 1) and O-(2-chlorobenzyl)hydroxylamine hydrochloride (Bionet research intermediates).

$^{13}$C-NMR (DMSO-d$_6$) δ 167.3, 149.5, 149.0, 148.3, 133.5, 133.1, 132.5, 131.3, 130.0, 129.2, 128.1, 127.1, 122.0, 114.8, 113.3, 111.4, 73.7, 44.8.

Example 13

N-(2-Bromo-benzyloxy)-2-[(pyridin-4-ylmethyl)-amino]-benzamide (compound 13)

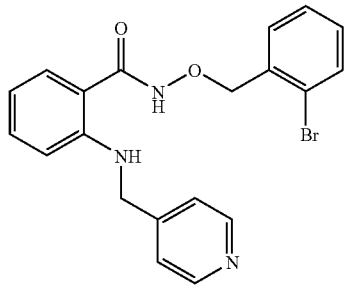

General procedure 1, method 1.
Starting materials: 2-[(Pyridin-4-ylmethyl)-amino]-benzoic acid (see preparation 1) and O-(2-bromobenzyl)hydroxylamine hydrochloride (Bionet research intermediates).
$^{13}$C-NMR (DMSO-d$_6$) δ 167.4, 149.5, 149.0, 148.3, 135.3, 132.5, 132.4, 131.1, 130.2, 128.2, 127.7, 123.2, 122.0, 114.8, 113.2, 111.4, 75.9, 44.8.

Example 14

N-(2,4-Dichloro-benzyloxy)-2-[(pyridin-4-ylmethyl)-amino]-benzamide (compound 14)

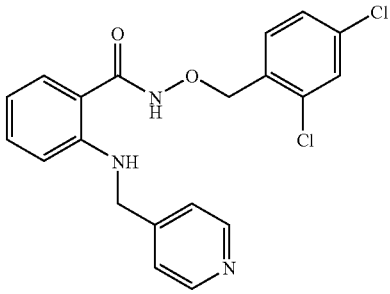

General procedure 1, method 1.
Starting materials: 2-[(Pyridin-4-ylmethyl)-amino]-benzoic acid (see preparation 1) and O-(2,4-dichlorobenzyl)hydroxylamine hydrochloride (Bionet research intermediates).
$^{13}$C-NMR (DMSO-d$_6$) δ 167.4, 149.5, 148.9, 148.3, 134.2, 133.7, 132.8, 132.6, 128.7, 128.1, 127.3, 121.9, 114.8, 113.2, 111.4, 73.0, 44.8.

Example 15

N-(3,4-Dichloro-benzyloxy)-2-[(pyridine-4-ylmethyl)-amino]-benzamide (compound 15)

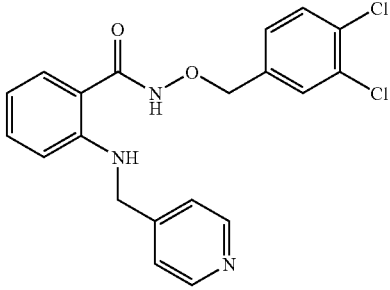

General procedure 1, method 1.
Starting materials: 2-[(Pyridin-4-ylmethyl)-amino]-benzoic acid (see preparation 1) and O-(3,4-dichlorobenzyl)hydroxylamine hydrochloride (Bionet research intermediates).
$^{13}$C-NMR (DMSO-d$_6$) δ 167.3, 149.5, 148.9, 148.3, 137.4, 132.6, 130.9, 130.7, 130.5, 130.4, 128.9, 128.1, 121.9, 114.8, 113.2, 111.5, 75.3, 44.8.

Example 16

N-(2,6-Dichloro-benzyloxy)-2-[(pyridin-4-ylmethyl)-amino]-benzamide (compound 16)

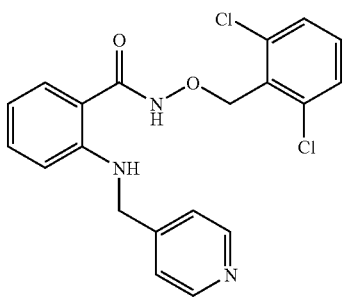

General procedure 1, method 1.
Starting materials: 2-[(Pyridin-4-ylmethyl)-amino]-benzoic acid (see preparation 1) and O-(2,6-dichlorobenzyl)hydroxylamine hydrochloride (Bionet research intermediates).
$^{13}$C-NMR (DMSO-d$_6$) δ 167.3, 149.5, 149.0, 148.3, 136.7, 132.4, 131.5, 131.3, 128.5, 128.3, 121.9, 114.7, 113.4, 111.3, 70.7, 44.8.

Example 17

N-(3,5-Dichloro-benzyloxy)-2-[(pyridin-4-ylmethyl)-amino]-benzamide (compound 17)

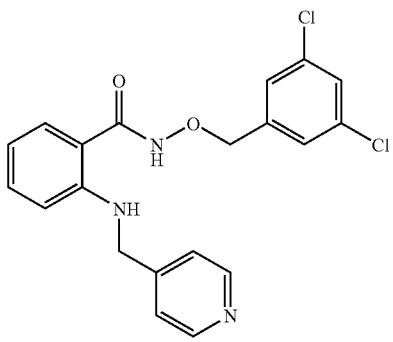

General procedure 1, method 1.
Starting materials: 2-[(Pyridin-4-ylmethyl)-amino]-benzoic acid (see preparation 1) and O-(3,5-dichlorobenzyl)hydroxylamine hydrochloride (Bionet research intermediates).
$^{13}$C-NMR (DMSO-d$_6$) δ 167.4, 149.5, 148.9, 148.3, 140.6, 133.8, 132.6, 128.0, 127.6, 127.1, 121.9, 114.8, 113.2, 111.5, 75.3, 44.8.

Example 18

N-(2,3-Dichloro-benzyloxy)-2-[(pyridin-4-ylmethyl)-amino]-benzamide (compound 18)

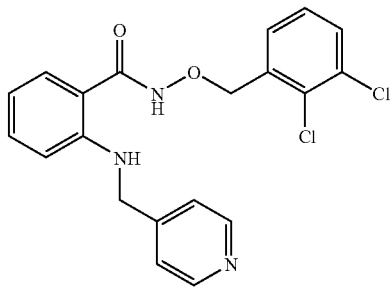

General procedure 1, method 1.
Starting materials: 2-[(Pyridin-4-ylmethyl)-amino]-benzoic acid (see preparation 1) and O-(2,3-dichlorobenzyl)hydroxylamine hydrochloride (Bionet research intermediates).
$^{13}$C-NMR (DMSO-d$_6$) δ 167.3, 149.5, 148.9, 148.3, 136.3, 132.6, 131.7, 131.1, 130.3, 129.7, 128.1, 128.0, 121.9, 114.8, 113.2, 111.4, 74.1, 44.8.

Example 19

N-(2,5-Dichloro-benzyloxy)-2-[(pyridin-4-ylmethyl)-amino]-benzamide (compound 19)

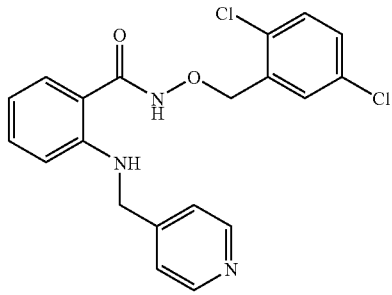

General procedure 1, method 1.
Starting materials: 2-[(Pyridin-4-ylmethyl)-amino]-benzoic acid (see preparation 1) and O-(2,5-dichlorobenzyl)hydroxylamine hydrochloride (Bionet research intermediates).
$^{13}$C-NMR (DMSO-d$_6$) δ 167.4, 149.5, 148.9, 148.3, 135.9, 132.5, 131.7, 131.5, 130.8, 130.4, 129.6, 128.1, 121.9, 114.8, 113.1, 111.5, 73.1, 44.8.

Example 20

N-(2-Fluoro-benzyloxy)-2-[(pyridin-4-ylmethyl)-amino]-benzamide (compound 20)

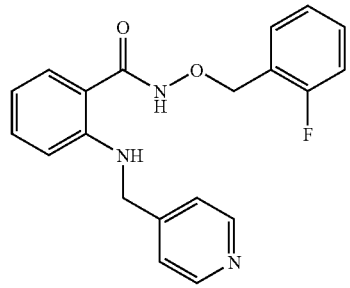

General procedure 1, method 1.
Starting materials: 2-[(Pyridin-4-ylmethyl)-amino]-benzoic acid (see preparation 1) and O-(2-fluorobenzyl)hydroxylamine hydrochloride (Bionet research intermediates).
$^{13}$C-NMR (DMSO-d$_6$) δ 167.2, 160.8, 149.5, 149.0, 148.3, 132.0, 130.7, 128.1, 124.3, 122.8, 122.0, 115.4, 115.1, 114.8, 113.3, 111.4, 70.2, 44.8.

Example 21

N-(3-Fluoro-benzyloxy)-2-[(pyridin-4-ylmethyl)-amino]-benzamide (compound 21)

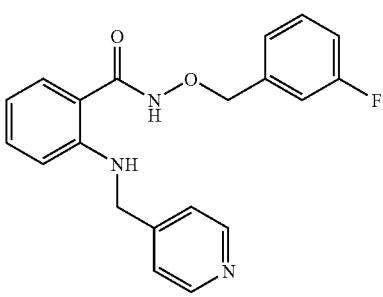

General procedure 1, method 1.
Starting materials: 2-[(Pyridin-4-ylmethyl)-amino]-benzoic acid (see preparation 1) and O-(3-fluorobenzyl)hydroxylamine hydrochloride (Bionet research intermediates).
$^{13}$C-NMR (DMSO-d$_6$) δ 167.3, 162.0, 149.5, 148.9, 148.3, 138.9, 132.5, 130.2, 128.0, 124.5, 122.0, 115.3, 114.9, 114.7, 113.3, 111.5, 76.0, 44.8.

Example 22

N-(4-Fluoro-benzyloxy)-2-[(pyridin-4-ylmethyl)-amino]-benzamide (compound 22)

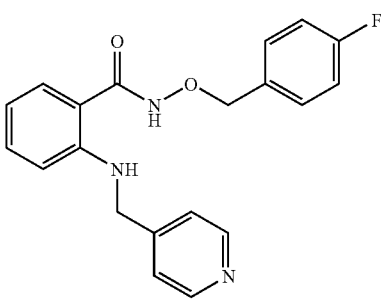

General procedure 1, method 1.
Starting materials: 2-[(Pyridin-4-ylmethyl)-amino]-benzoic acid (see preparation 1) and O-(4-fluorobenzyl)hydroxylamine hydrochloride (Bionet research intermediates).
$^{13}$C-NMR (DMSO-d$_6$) δ 167.2, 162.0, 149.5, 149.0, 148.3, 132.5, 132.2, 131.1, 128.0, 122.0, 115.2, 114.8, 113.3, 111.5, 76.1, 44.8.

Example 23

N-(2-Chloro-6-fluoro-benzyloxy)-2-[(pyridin-4-ylmethyl)-amino]-benzamide (compound 23)

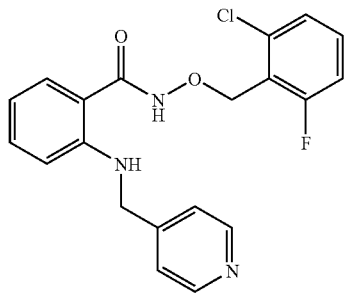

General procedure 1, method 1.

Starting materials: 2-[(Pyridin-4-ylmethyl)-amino]-benzoic acid (see preparation 1) and O-(2-chloro-6-fluorobenzyl)hydroxylamine hydrochloride (Bionet research intermediates).

$^{13}$C-NMR (DMSO-$d_6$) δ 167.3, 162.0, 149.5, 149.0, 148.3, 135.9, 132.4, 131.7, 128.1, 125.4, 121.9, 121.7, 114.7, 114.5, 113.3, 111.4, 66.9, 44.7.

Example 24

N-(2-Chloro-4-fluoro-benzyloxy)-2-[(pyridin-4-ylmethyl)-amino]-benzamide (compound 24)

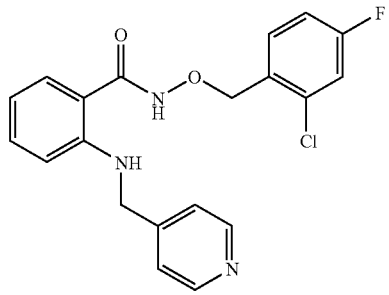

General procedure 1, method 1.

Starting materials: 2-[(Pyridin-4-ylmethyl)-amino]-benzoic acid (see preparation 1) and O-(2-chloro-4-fluorobenzyl)hydroxylamine hydrochloride (Bionet research intermediates).

$^{13}$C-NMR (DMSO-$d_6$) δ 167.3, 161.8, 149.5, 149.0, 148.3, 134.3, 133.1, 132.5, 130.1, 128.1, 122.0, 116.5, 114.8, 114.3, 113.2, 111.5, 73.0, 44.8.

Example 25

N-(3-Chloro-2-fluoro-benzyloxy)-2-[(pyridin-4-ylmethyl)-amino]-benzamide (compound 25)

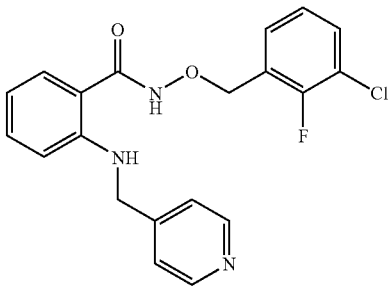

General procedure 1, method 1.

Starting materials: 2-[(Pyridin-4-ylmethyl)-amino]-benzoic acid (see preparation 1) and O-(3-chloro-2-fluorobenzyl)hydroxylamine hydrochloride (Bionet research intermediates).

$^{13}$C-NMR (DMSO-$d_6$) δ 167.2, 156.0, 149.5, 148.9, 148.3, 132.5, 130.9, 130.8, 128.0, 125.2, 124.9, 121.9, 119.5, 114.8, 113.2, 111.4, 70.2, 44.7.

Example 26

4-{2-[(pyridin-4-ylmethyl)-amino]-benzoylaminooxymethyl}-benzoic acid methyl ester (compound 26)

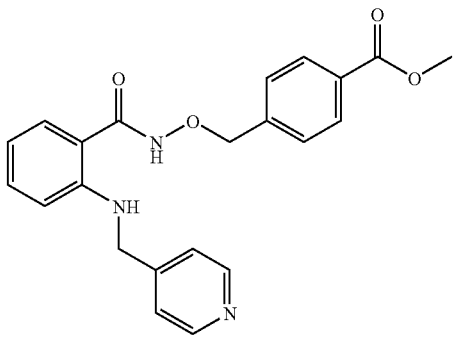

General procedure 1, method 1.

Starting materials: 2-[(Pyridin-4-ylmethyl)-amino]-benzoic acid (see preparation 1) and 4-aminooxymethyl-benzoic acid methyl ester hydrochloride (Bionet research intermediates).

$^{13}$C-NMR (DMSO-$d_6$) δ 167.3, 166.0, 149.5, 148.9, 148.3, 141.5, 132.5, 129.3, 129.1, 128.7, 128.1, 122.0, 114.8, 113.2, 111.5, 76.2, 52.1, 44.8.

Example 27

N-(4-cyano-benzyloxy)-2-[(pyridin-4-ylmethyl)-amino]-benzamide (compound 27)

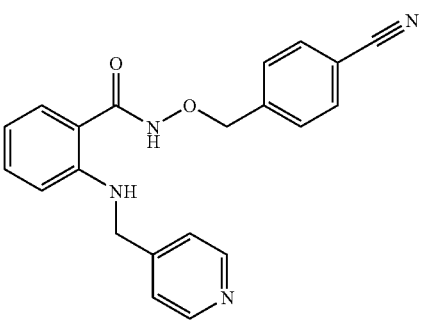

General procedure 1, method 1.

Starting materials: 2-[(Pyridin-4-ylmethyl)-amino]-benzoic acid (see preparation 1) and O-(4-cyanobenzyl)hydroxylamine hydrochloride (see preparation 10).

$^{13}$C-NMR (DMSO-$d_6$) δ 167.4, 149.6, 148.9, 148.3, 141.8, 132.6, 132.2, 129.1, 128.1, 122.0, 118.7, 114.8, 113.1, 111.5, 110.8, 75.9, 44.8.

Example 28

2-[(Pyridin-4-ylmethyl)-amino]-N-(quinolin-2-yl-methoxy)-benzamide (compound 28)

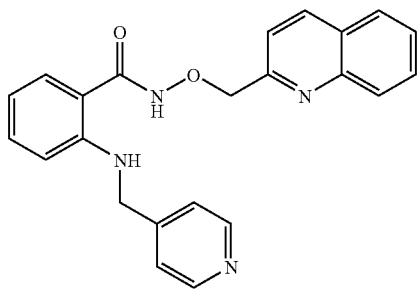

General procedure 1, method 1.
Starting materials: 2-[(Pyridin-4-ylmethyl)-amino]-benzoic acid (see preparation 1) and O-Quinolin-2-ylmethyl-hydroxylamine (see preparation 11).
$^{13}$C-NMR (DMSO-d$_6$) δ 156.9, 149.5, 148.9, 148.2, 146.8, 136.6, 132.5, 129.6, 128.6, 128.1, 127.8, 127.3, 126.6, 121.9, 120.6, 114.8, 113.2, 111.4, 78.3, 44.8.

Example 29

N-Phenoxy-2-[(pyridin-4-ylmethyl)-amino]-benzamide (compound 29)

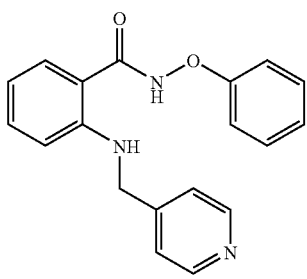

General procedure 1, method 1.
Starting materials: 2-[(Pyridin-4-ylmethyl)-amino]-benzoic acid (see preparation 1) and O-phenylhydroxylamine hydrochloride (Fluka).
$^{13}$C-NMR (DMSO-d$_6$) δ 159.7, 149.6, 148.8, 148.6, 133.1, 129.4, 128.3, 122.2, 122.0, 114.9, 112.9, 112.1, 111.7, 44.8.

Example 30

N-(2-Phenoxy-ethoxy)-2-[(pyridin-4-ylmethyl)-amino]-benzamide (compound 30)

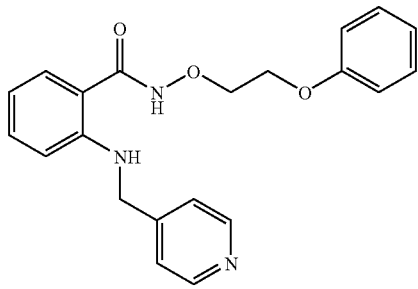

General procedure 1, method 1.
Starting materials: 2-[(Pyridin-4-ylmethyl)-amino]-benzoic acid (see preparation 1) and O-(2-phenoxyethyl)-hydroxylamine hydrochloride (Bionet research intermediates).
$^{13}$C-NMR (DMSO-d$_6$) δ 167.5, 158.5, 149.8, 149.2, 148.6, 132.8, 129.6, 128.3, 122.2, 120.8, 115.0, 114.6, 113.4, 111.7, 74.0, 65.7, 45.0.

Example 31

N-(3-Phenyl-propoxy)-2-[(pyridin-4-ylmethyl)-amino]-benzamide (compound 31)

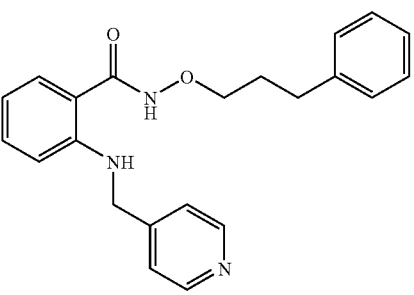

General procedure 1, method 1.
Starting materials: 2-[(Pyridin-4-ylmethyl)-amino]-benzoic acid (see preparation 1) and O-(3-phenylpropyl)hydroxylamine hydrochloride (SPECS).
$^{13}$C-NMR (DMSO-d$_6$) δ 167.1, 149.5, 149.0, 148.3, 141.6, 132.4, 128.3, 128.2, 128.0, 125.7, 122.0, 114.8, 113.5, 111.5, 74.5, 44.8, 31.4, 29.6.

Example 32

N-(2-methyl-thiazol-4 ylmethoxy)-2-[(pyridin-4-ylmethyl)-amino]-benzamide (compound 32)

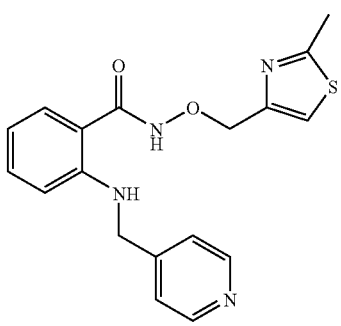

General procedure 1, method 1.
Starting materials: 2-[(Pyridin-4-ylmethyl)-amino]-benzoic acid (see preparation 1) and O-(2-Methyl-thiazol-4-yl-methyl)-hydroxylamine hydrochloride (see preparation 12).
$^{13}$C-NMR (DMSO-d$_6$) δ 167.1, 165.3, 150.5, 149.5, 148.9, 148.3, 132.5, 128.1, 122.0, 119.0, 114.8, 113.4, 111.4, 71.9, 55.9, 44.8, 18.6.

Example 33

N-Benzyloxy-2-2-[(pyridin-4-ylmethyl)-amino]-nicotinamide (compound 33)

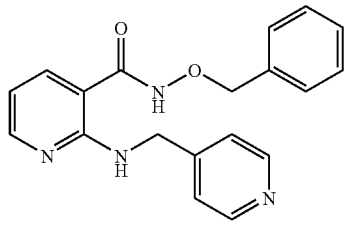

General procedure 1, method 1.
Starting materials: 2-[(Pyridin-4-ylmethyl)-amino]-nicotinic acid (see preparation 2) and O-benzylhydroxylamine hydrochloride (Aldrich).
$^{13}$C-NMR (DMSO-$d_6$) δ 156.7, 151.2, 149.7, 149.4, 136.2, 136.0, 129.0, 128.3, 122.1, 111.2, 108.4, 77.0, 42.8.

Example 34

2-(4-Fluoro-benzylamino)-N-(4-methoxy-benzyloxy)-nicotinamide (compound 34

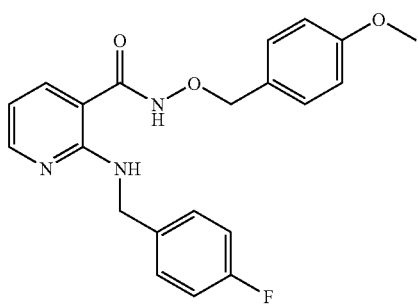

General procedure 1, method 1.
Starting materials: 2-(4-Fluoro-benzylamino)-nicotinic acid (see preparation 3) and O-(4-methoxybenzyl)hydroxylamine hydrochloride (Bionet research intermediates).
$^{13}$C-NMR (DMSO-$d_6$) δ 165.7, 161.0, 159.3, 156.7, 151.2, 136.4, 136.0, 130.6, 129.1, 127.8, 114.9, 113.6, 113.5, 110.8, 108.0, 76.6, 55.0, 43.0.

Example 35

2-(4-Methoxy-benzylamino)-N-(4-methoxy-benzyloxy)-nicotinamide (compound 35)

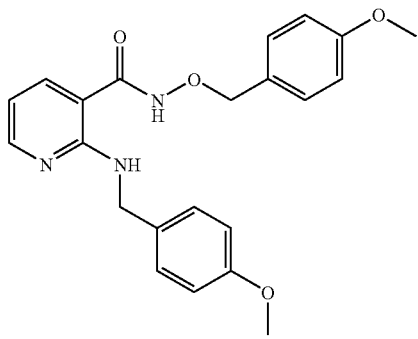

General procedure 1, method 1.
Starting materials: 2-(4-Methoxy-benzylamino)-nicotinic acid (see preparation 4) and O-(4-methoxybenzyl)hydroxylamine hydrochloride (Bionet research intermediates).
$^{13}$C-NMR (DMSO-$d_6$) δ 165.8, 159.3, 158.1, 156.8, 151.2, 135.9, 131.9, 130.6, 128.6, 127.7, 113.7, 113.6, 110.6, 107.7, 76.6, 55.0, 54.9, 43.3.

Example 351

N-(4-Cyano-phenoxy)-2-[(pyridin-4-ylmethyl)-amino]-benzamide (compound 36)

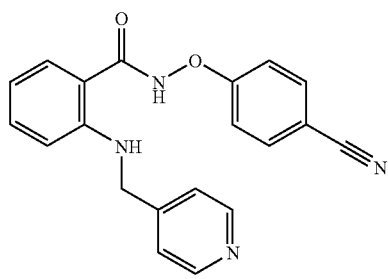

General procedure 1, method 1.
Starting materials: 2-[(Pyridin-4-ylmethyl)-amino]-benzoic acid (see preparation 1) and 4-aminooxy-benzonitrile (prepared using procedures described by Petrassi, H. M. et al. *Organic Letters,* 2001, 3, 139-142)
$^{13}$C-NMR (DMSO-$d_6$) δ 165.5, 154.0, 150.8, 149.6, 148.4, 135.8, 133.9, 131.8, 123.6, 121.9, 118.3, 115.2, 112.1, 108.6, 108.1, 44.6.

Example 352

N-(4-Bromo-phenoxy)-2-[(pyridin-4-ylmethyl)-amino]-benzamide (compound 37)

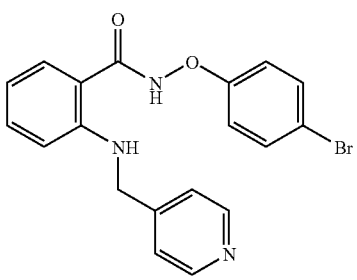

General procedure 1, method 1.
Starting materials: 2-[(Pyridin-4-ylmethyl)-amino]-benzoic acid (see preparation 1) and O-(4-Bromo-phenyl)-hydroxylamine hydrochloride (prepared using procedures described by Petrassi, H. M. et al. *Organic Letters,* 2001, 3, 139-142).
$^{13}$C-NMR (DMSO-$d_6$) δ 165.9, 150.7, 149.7, 149.6, 148.4, 135.6, 132.2, 131.8, 124.5, 121.9, 118.0, 115.2, 112.0, 108.4, 44.6.

Example 353

N-(4-Fluoro-2,6-dimethyl-benzyloxy)-2-[(pyridin-4-ylmethyl)-amino]-benzamide (compound 38)

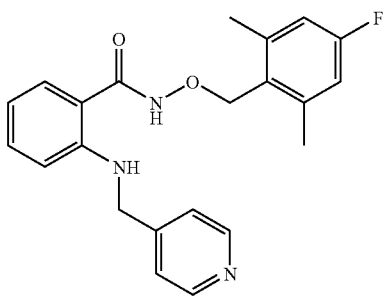

General procedure 1A.

Starting materials: 1-Pyridin-4-ylmethyl-1H-benzo[d][1,3]oxazine-2,4-dione (see preparation 7A) and O-(4-fluoro-2,6-dimethyl-benzyl)-hydroxylamine hydrochloride (see preparation 13)

$^{13}$C-NMR (DMSO-d$_6$) δ 167.3, 161.6 (d), 149.5, 149.0, 148.4, 141.6 (d), 132.5, 128.3 (d), 128.0, 121.9, 114.8, 114.0 (d), 113.3, 111.5, 70.4, 44.7, 19.2.

Example 354

N-(4-Fluoro-2-methoxy-benzyloxy)-2-[(pyridin-4-ylmethyl)-amino]-benzamide (compound 39)

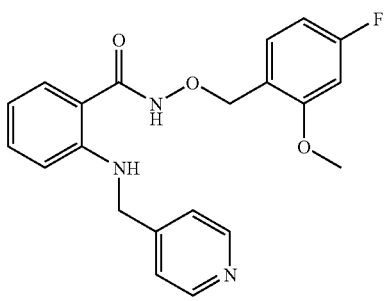

General procedure 1A.

Starting materials: 1-Pyridin-4-ylmethyl-1H-benzo[d][1,3]oxazine-2,4-dione (see preparation 7A) and O-(4-fluoro-2-methoxy-benzyl)-hydroxylamine hydrochloride (see preparation 14)

$^{13}$C-NMR (DMSO-d$_6$) δ 167.1, 163.2 (d), 158.9 (d), 149.5, 149.0, 148.3, 132.4, 132.0 (d), 128.1, 122.0, 120.1, 114.8, 113.5, 111.4, 106.2 (d), 99.3 (d), 71.0, 55.9, 44.8.

Example 355

N-(2,3-Difluoro-4-methyl-benzyloxy)-2-[(pyridin-4-ylmethyl)-amino]-benzamide (compound 40)

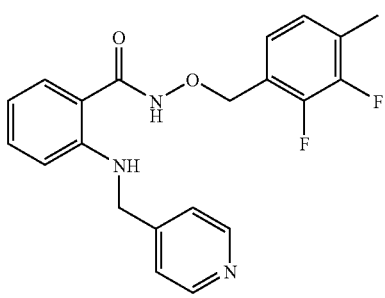

General procedure 1, method 2.

Starting materials: 2-[(Pyridin-4-ylmethyl)-amino]-benzoic acid (see preparation 1) and O-(2,3-difluoro-4-methyl-benzyl)-hydroxylamine (see preparation 15)

$^{13}$C-NMR (CDCl$_3$) δ 169.2, 149.7, 149.6 (dd), 149.1 (dd), 149.1, 148.7, 133.5, 128.1 (d), 127.6, 125.7 (m), 121.9, 115.7, 112.7, 112.0, 71.3, 46.0, 14.4.

Example 356

N-(3-Fluoro-4-methyl-benzyloxy)-2-[(pyridin-4-ylmethyl)-amino]-benzamide (compound 41)

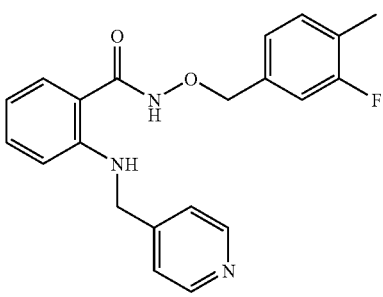

General procedure 1, method 2.

Starting materials: 2-[(Pyridin-4-ylmethyl)-amino]-benzoic acid (see preparation 1) and O-(3-fluoro-4-methyl-benzyl)-hydroxylamine hydrochloride (see preparation 16)

$^{13}$C-NMR (DMSO-d$_6$) δ 167.3, 160.5 (d), 149.5, 149.3, 148.4, 136.1 (d), 132.6, 131.5 (d), 128.2, 124.6 (d), 124.1 (d), 122.1, 115.1 (d), 114.9, 113.5, 111.6, 76.1, 44.9, 14.0.

Example 357

N-(5-Fluoro-2-methyl-benzyloxy)-2-[(pyridin-4-ylmethyl)-amino]-benzamide (compound 42)

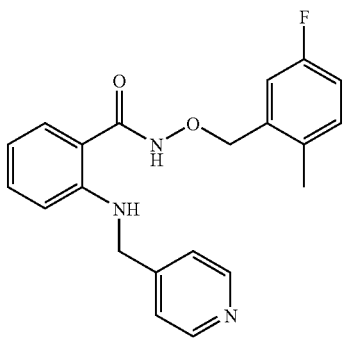

General procedure 1, method 2.

Starting materials: 2-[(Pyridin-4-ylmethyl)-amino]-benzoic acid (see preparation 1) and O-(5-Fluoro-2-methyl-benzyl)-hydroxylamine hydrochloride (see preparation 17)

$^{13}$C-NMR (DMSO-d$_6$) δ 167.3, 160.2 (d), 149.5, 149.0, 148.3, 136.2 (d), 133.2 (d), 132.5, 131.5 (d), 128.1, 121.9, 116.1 (d), 114.8, 114.7 (d), 113.3, 111.5, 74.5, 44.8, 17.7.

Example 358

2-[(Pyridin-4-ylmethyl)-amino]-N-(2,3,5,6-tetrafluoro-4-methoxy-benzyloxy)benzamide (compound 43)

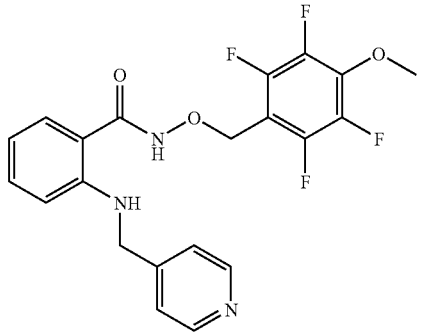

General procedure 1, method 1.
Starting materials: 2-[(Pyridin-4-ylmethyl)-amino]-benzoic acid (see preparation 1) and O-(2,3,5,6-tetrafluoro-4-methoxy-benzyl)-hydroxylamine (see preparation 18).

$^{13}$C-NMR (DMSO-d$_6$) δ 167.3, 149.5, 149.0, 148.3, 145.8 (m), 139.9 (m), 138.4 (m), 132.6, 128.0, 121.9, 114.8, 113.1, 111.5, 107.8 (t), 63.4, 62.2 (t), 44.7.

Example 359

N-(4-Bromo-benzyloxy)-2-[(pyridin-4-ylmethyl)-amino]-benzamide (compound 44)

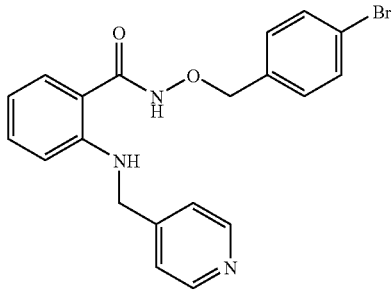

General procedure 1, method 1.
Starting materials: 2-[(Pyridin-4-ylmethyl)-amino]-benzoic acid (see preparation 1) and O-(4-bromo-benzyl)-hydroxylamine hydrochloride (see preparation 19).

$^{13}$C-NMR (DMSO-d$_6$) δ 167.2, 149.5, 148.9, 148.3, 135.4, 132.5, 131.1, 130.9, 128.0, 121.9, 121.4, 114.8, 113.3, 111.5, 76.0, 44.7.

Example 360

N-(2-Iodo-benzyloxy)-2-[(pyridin-4-ylmethyl)-amino]-benzamide (compound 45)

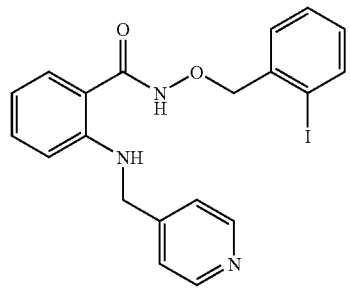

General procedure 1, method 1.
Starting materials: 2-[(Pyridin-4-ylmethyl)-amino]-benzoic acid (see preparation 1) and O-(2-iodo-benzyl)-hydroxylamine hydrochloride (see preparation 20)

$^{13}$C-NMR (DMSO-d$_6$) δ 167.4, 149.5, 148.9, 148.3, 138.9, 138.4, 132.5, 130.2, 130.1, 128.2, 128.2, 121.9, 114.8, 113.2, 111.4, 99.3, 80.2, 44.7.

Example 361

N-(3-Iodo-benzyloxy)-2-[(pyridin-4-ylmethyl)-amino]-benzamide (compound 46)

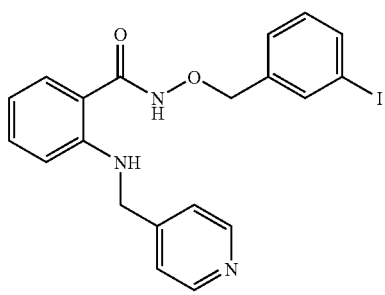

General procedure 1, method 1.
Starting materials: 2-[(Pyridin-4-ylmethyl)-amino]-benzoic acid (see preparation 1) and O-(3-iodo-benzyl)-hydroxylamine hydrochloride (see preparation 21)

$^{13}$C-NMR (DMSO-d$_6$) δ 166.9, 149.5, 148.9, 148.1, 138.7, 137.1, 136.8, 132.4, 130.4, 128.0, 121.9, 114.8, 113.2, 111.4, 94.6, 75.8, 44.7

Example 362

N-(4-Methyl-benzyloxy)-2-[(pyridin-4-ylmethyl)-amino]-benzamide (compound 47)

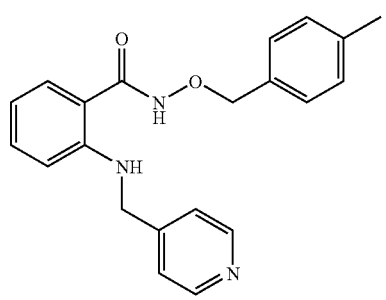

General procedure 1, method 1.
Starting materials: 2-[(Pyridin-4-ylmethyl)-amino]-benzoic acid (see preparation 1) and O-(4-methyl-benzyl)-hydroxylamine hydrochloride (Bionet)

$^{13}$C-NMR (DMSO-d$_6$) δ 167.1, 149.5, 149.0, 148.3, 137.5, 132.9, 132.4, 128.9, 128.8, 128.0, 122.0, 114.8, 113.5, 111.4, 76.7, 44.8, 20.7.

Example 363

N-[2-(3,3-Dimethyl-but-1-enyl)-benzyloxy]-2-[(pyridin-4-ylmethyl)-amino]-benzamide (compound 48)

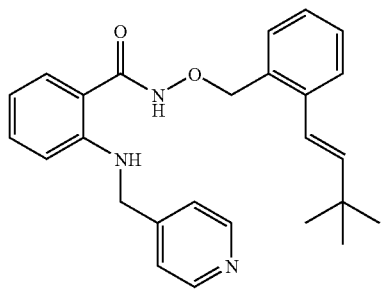

Argon was bobbled through a mixture of N-(2-Iodo-benzyloxy)-2-[(pyridin-4-ylmethyl)-amino]-benzamide (example 360, 151 mg, 0.33 mmol) in toluene (20 ml) for 10 to 15 minutes. Tetrakis(triphenylphosphine) palladium (19 mg) was added and the mixture was stirred for 10 minutes before addition of 3,3-dimethyl-1-butenylboronic acid (Aldrich, 50 mg) and a degassed 2M solution of sodium carbonate (0.329 ml). The reaction flask (screw-cap) was sealed and the reaction mixture was heated to 120° C. for 3 hours. More tetrakis(triphenylphosphine) palladium (0.05 eq.), 2M sodium carbonate (0.329 ml), and 3,3-dimethyl-1-butenylboronic acid (50 mg) was added and stirring was continued at 120° C. over night. The mixture was cooled to room temperature and 25% ammonium acetate was added and stirring was continued for 10 min. The mixture was partitioned between EtOAc and water. The aqueous phase was extracted with EtOAc and the combined organic layers were washed with brine, dried (MgSO$_4$) and evaporated under reduced pressure. The residue was subjected to chromatography on silica gel (elution with 1% methanol in dichloromethane v/v) and gave the title compound (130 mg). $^{13}$C-NMR (CDCl$_3$) δ 168.9, 149.8, 149.1, 148.7, 145.1, 138.8, 133.4, 131.1, 129.2, 127.4, 126.8, 126.2, 122.0, 121.5, 115.7, 112.8, 112.0, 76.2, 46.1, 33.8, 29.6.

Example 364

2-[(Pyridin-4-ylmethyl)-amino]-N-(2-styryl-benzyloxy)-benzamide (compound 49)

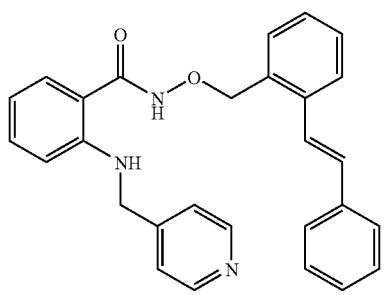

Same procedure as described for the preparation of example 363.

Starting materials: N-(2-Iodo-benzyloxy)-2-[(pyridin-4-ylmethyl)-amino]-benzamide (example 360) and trans-2-phenylvinylboronic acid (Aldrich).

$^{13}$C-NMR (CDCl$_3$) δ 151.2, 148.7, 148.0, 138.1, 137.3, 133.4, 132.5, 131.5, 129.5, 128.6, 127.9, 127.7, 127.6, 126.9, 125.9, 125.5, 122.4, 116.0, 112.7, 111.9, 76.4, 46.1.

Example 365

N-[3-(3-Hydroxy-prop-1-ynyl)-benzyloxy]-2-[(pyridin-4-ylmethyl)-amino]-benzamide (compound 50)

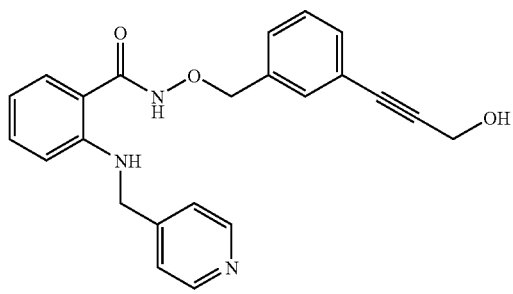

N-(3-Iodo-benzyloxy)-2-[(pyridin-4-ylmethyl)-amino]-benzamide (example 361, 300 mg), propargyl alcohol (69 mg), CuI (19 mg), PdCl$_2$(PPh$_3$)$_2$ (22 mg) and tetrabutylammonium iodide (241 mg) was dissolved in DMF (4 ml) and triethylamine (0.5 ml) was added drop-wise (exothermic reaction). The reaction mixture was stirred at room temperature for 30 minutes and partitioned between EtOAc and water. The aqueous phase was extracted with EtOAc and the combined organic layers were washed with brine, dried (MgSO$_4$) and evaporated under reduced pressure. The residue was purified by chromatography on silica gel (EtOAc as eluent) and gave the title compound. $^{13}$C-NMR (DMSO-d$_6$) δ 167.2, 149.5, 148.9, 148.3, 136.6, 132.5, 131.5, 130.9, 128.7, 128.6, 128.0, 122.3, 114.8, 113.3, 111.5, 90.0, 83.3, 76.3, 49.3, 44.8.

Example 366

N-[3-(5-Cyano-pent-1-ynyl)-benzyloxy]-2-[(pyridin-4-ylmethyl)-amino]-benzamide (compound 51)

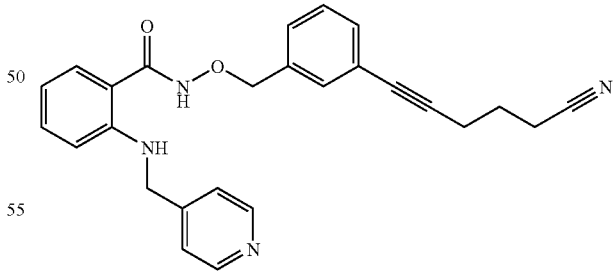

The same procedure was used as described for the preparation of example 365, but without addition of tetrabutylammonium iodide. Starting materials: N-(3-Iodo-benzyloxy)-2-[(pyridin-4-ylmethyl)-amino]-benzamide (see example 361) and 5-cyano-1-pentyne (Aldrich).

$^{13}$C-NMR (DMSO-d$_6$) δ 167.2, 149.5, 148.9, 148.3, 136.4, 132.5, 131.6, 131.0, 128.6, 128.5, 128.0, 122.8, 120.1, 114.8, 113.3, 111.5, 88.7, 81.2, 76.3, 44.8, 24.0, 17.8, 15.5

Example 367

N-[2-(3-Hydroxy-prop-1-ynyl)-benzyloxy]-2-[(pyridin-4-ylmethyl)-amino]-benzamide (compound 52)

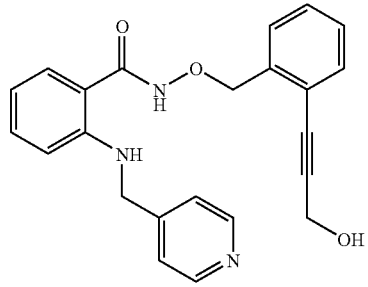

The same procedure was used as described for the preparation of Example 365, but without addition of tetrabutylammonium iodide.

Starting materials: N-(2-Iodo-benzyloxy)-2-[(pyridin-4-ylmethyl)-amino]-benzamide (see example 360) and propargyl alcohol.

$^{13}$C-NMR (DMSO-d$_6$) δ 167.3, 149.5, 149.0, 148.3, 137.4, 132.5, 131.7, 129.0, 128.4, 128.2, 122.0, 121.8, 114.8, 113.2, 111.4, 94.2, 81.0, 74.6, 49.4, 44.7.

Example 368

Acetic acid 2-[3-(2-{2-[(pyridin-4-ylmethyl)-amino]-benzoylaminooxymethyl}-phenyl)-prop-2-ynyloxy]-ethyl ester (compound 53)

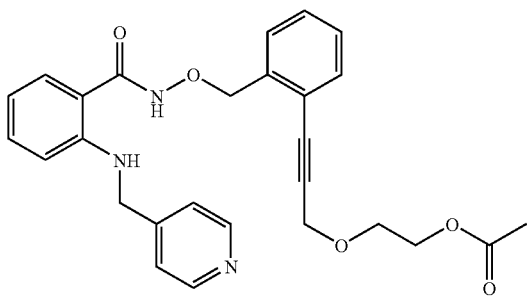

The same procedure was used as described for the preparation of example 365, but without addition of tetrabutylammonium iodide. Starting materials: N-(2-Iodo-benzyloxy)-2-[(pyridin-4-ylmethyl)-amino]-benzamide (see example 360) and 2-(prop-2-ynyloxy)ethyl acetate (Maybridge).

$^{13}$C-NMR (DMSO-d$_6$) δ 170.2, 167.3, 149.5, 148.9, 148.3, 137.6, 132.5, 131.9, 129.4, 128.7, 128.3, 128.1, 121.9, 121.5, 114.8, 113.3, 111.4, 90.0, 83.4, 74.6, 67.1, 62.9, 58.0, 44.8, 20.5.

Example 369

N-[2-(3-Methyl-3H-imidazol-4-ylethynyl)-benzyloxy]-2-[(pyridin-4-ylmethyl)-amino]-benzamide (compound 54)

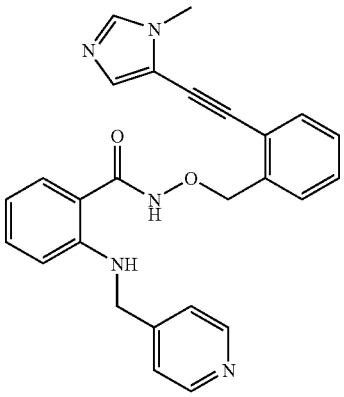

The same procedure was used as described for the preparation of Example 365, but without addition of tetrabutylammonium iodide. The title compound was purified by crystallisation from ethanol.

Starring materials: N-(2-Iodo-benzyloxy)-2-[(pyridin-4-ylmethyl)-amino]-benzamide (see Example 360) and 5-ethynyl-1-methyl-1-H-imidazole (Aldrich).

$^{13}$C-NMR (DMSO-d$_6$) δ 167.3, 149.5, 148.9, 148.2, 139.5, 137.0, 134.0, 132.5, 131.5, 129.8, 128.8, 128.5, 128.1, 121.9, 121.8, 115.0, 114.8, 113.4, 111.4, 93.5, 81.8, 74.7, 44.8, 31.7.

Example 370

N-[3-(3-Methyl-3H-imidazol-4-ylethynyl)-benzyloxy]-2-[(pyridin-4-ylmethyl)-amino]-benzamide (compound 55)

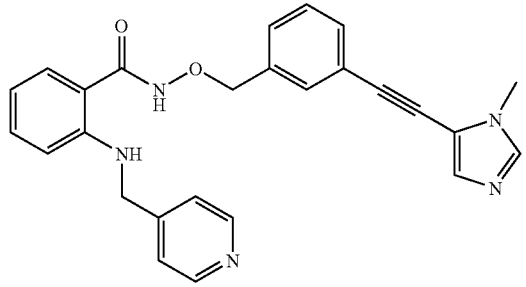

The same procedure was used as described for the preparation of Example 365, but without addition of tetrabutylammonium iodide. The title compound was purified by crystallisation from ethanol.

Starring materials: N-(3-Iodo-benzyloxy)-2-[(pyridin-4-ylmethyl)-amino]-benzamide (see Example 361) and 5-ethynyl-1-methyl-1-H-imidazole (Aldrich).

$^{13}$C-NMR (DMSO-d$_6$) δ 167.2, 149.5, 148.9, 148.2, 139.5, 136.8, 133.9, 132.5, 131.2, 130.7, 129.2, 128.7, 128.0, 121.9, 121.8, 114.8, 113.3, 111.5, 95.5, 77.8, 76.2, 44.8, 31.6.

Example 371

N-(2-Cyanomethyl-benzyloxy)-2-[(pyridin-4-ylmethyl)-amino]-benzamide (compound 56)

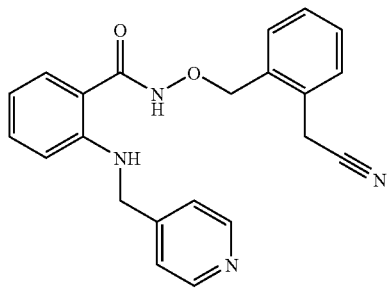

General procedure 1, method 2.
Starting materials: 2-[(Pyridin-4-ylmethyl)-amino]-benzoic acid (see preparation 1) and (2-aminooxymethyl-phenyl)-acetonitrile (see preparation 22).
$^{13}$C-NMR (CDCl$_3$) δ 169.5, 149.8, 149.2, 148.8, 133.7, 132.9, 131.7, 131.0, 130.1, 129.4, 128.3, 127.5, 122.0, 118.3, 115.7, 112.3, 112.2, 76.5, 46.0, 21.2.

Example 372

N-(2-Benzenesulfonylmethyl-benzyloxy)-2-[(pyridin-4-ylmethyl)-amino]-benzamide (compound 57)

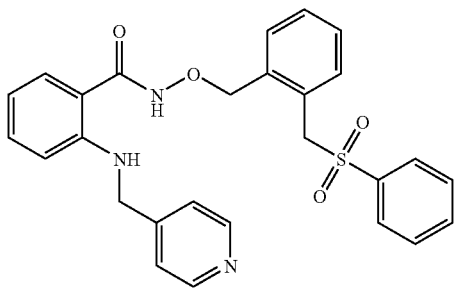

General procedure 1, method 2.
Starting materials: 2-[(Pyridin-4-ylmethyl)-amino]-benzoic acid (see preparation 1) and O-(2-benzenesulfonylmethyl-benzyl)-hydroxylamine (see preparation 23)
$^{13}$C-NMR (CDCl$_3$) δ 168.6, 149.5, 148.9, 148.5, 138.7, 135.2, 133.6, 133.1, 132.3, 131.6, 129.1, 128.8, 128.2, 127.7, 127.3, 121.7, 115.5, 112.3, 111.7, 76.1, 58.8, 45.7.

Example 373

N-(4-Hydroxymethyl-benzyloxy)-2-[(pyridin-4-ylmethyl)-amino]-benzamide (compound 58)

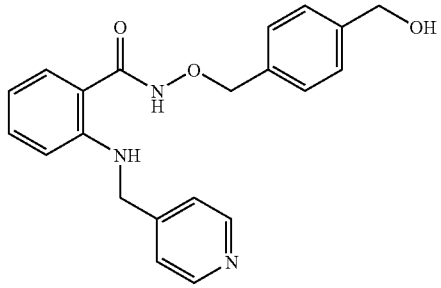

General procedure 1, method 1.
Starting materials: 2-[(Pyridin-4-ylmethyl)-amino]-benzoic acid (see preparation 1) and (4-aminooxymethyl-phenyl)-methanol hydrochloride (see preparation 24)
$^{13}$C-NMR (DMSO-d$_6$) δ 167.1, 149.5, 149.0, 148.3, 142.6, 134.1, 132.4, 128.7, 128.0, 126.2, 122.0, 114.8, 113.5, 111.4, 76.8, 62.6, 44.8.

Example 374

N-(4-Fluoro-2-trifluoromethyl-benzyloxy)-2-[(pyridin-4-ylmethyl)-amino]-benzamide (compound 59)

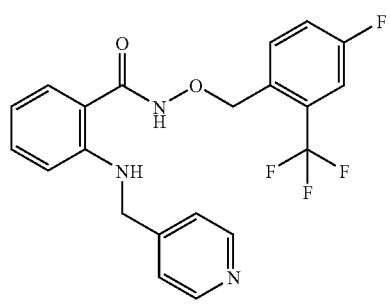

General procedure 1, method 1.
Starting materials: 2-[(Pyridin-4-ylmethyl)-amino]-benzoic acid (see preparation 1) and O-(4-fluoro-2-trifluoromethyl-benzyl)-hydroxylamine hydrochloride (see preparation 25).
$^{13}$C-NMR (DMSO-d$_6$) δ 167.4, 161.3 (d), 149.5, 148.9, 148.3, 134.2 (d), 132.6, 130.7, 129.1 (m), 128.1, 123.2 (m), 121.9, 119.4 (d), 114.8, 113.4 (m), 113.0, 111.5, 72.1, 44.8

Example 375

N-(2-Fluoro-6-trifluoromethyl-benzyloxy)-2-[(pyridin-4-ylmethyl)-amino]-benzamide (compound 60)

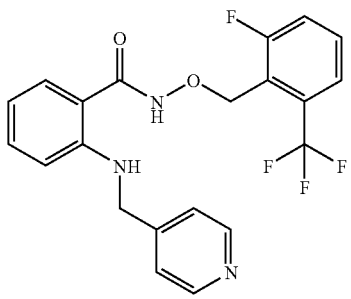

General procedure 1, method 1.
Starting materials: 2-[(Pyridin-4-ylmethyl)-amino]-benzoic acid (see preparation 1) and O-(2-fluoro-6-trifluoromethyl-benzyl)-hydroxylamine hydrochloride (see preparation 26).
$^{13}$C-NMR (DMSO-d$_6$) δ 167.2, 162.2 (d), 149.5, 149.0, 148.3, 132.4, 131.7 (d), 130.3 (m), 128.1, 123.4 (m), 121.9, 121.4, 120.1 (d), 114.7, 113.1, 111.4, 66.1, 44.7.

Example 376

N-(4-Fluoro-3-trifluoromethyl-benzyloxy)-2-[(pyridin-4-ylmethyl)-amino]-benzamide (compound 61)

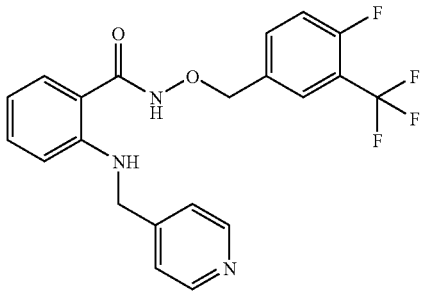

General procedure 1, method 1.

Starting materials: 2-[(Pyridin-4-ylmethyl)-amino]-benzoic acid (see preparation 1) and O-(4-fluoro-3-trifluoromethyl-benzyl)-hydroxylamine hydrochloride (see preparation 27)

$^{13}$C-NMR (DMSO-d$_6$) δ 167.4, 158.7 (d), 149.6, 149.0, 148.4, 135.7 (d), 133.5 (d), 132.7, 128.1, 127.6, 122.6 (q), 122.0, 117.2 (d), 116.5 (m), 114.9, 113.3, 111.6, 75.4, 44.9.

Example 377

N-(4-Methyl-3-trifluoromethyl-benzyloxy)-2-[(pyridin-4-ylmethyl)-amino]-benzamide (compound 62)

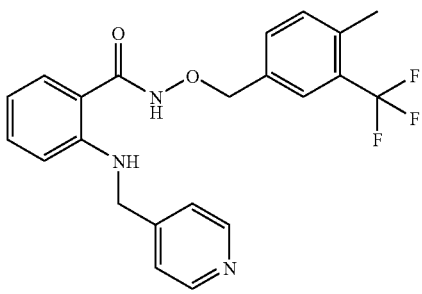

General procedure 1, method 2.

Starting materials: 2-[(Pyridin-4-ylmethyl)-amino]-benzoic acid (see preparation 1) and O-(4-methyl-3-trifluoromethyl-benzyl)-hydroxylamine hydrochloride (see preparation 28)

$^{13}$C-NMR (CDCl$_3$) δ 169.3, 149.6, 149.1, 148.8, 137.2, 133.5, 132.4, 132.2, 129.1 (q), 127.6, 126.6 (q), 124.4 (q), 122.0, 115.6, 112.7, 112.0, 77.5, 46.0, 19.1.

Example 378

N-(4-Methoxy-3-trifluoromethyl-benzyloxy)-2-[(pyridin-4-ylmethyl)-amino]-benzamide (compound 63)

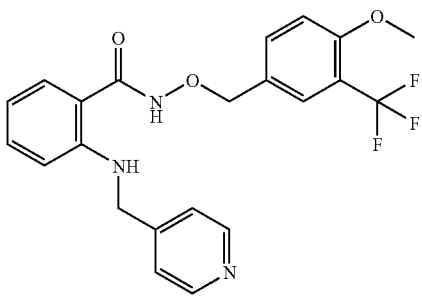

General procedure 1, method 1.

Starting materials: 2-[(Pyridin-4-ylmethyl)-amino]-benzoic acid (see preparation 1) and O-(4-methoxy-3-trifluoromethyl-benzyl)-hydroxylamine (see preparation 29).

$^{13}$C-NMR (DMSO-d$_6$) δ 167.2, 157.0, 149.5, 149.0, 148.2, 135.0, 132.5, 128.0, 127.5 (q), 123.6 (q), 121.9, 116.6 (q), 114.8, 113.4, 112.6, 111.4, 75.7, 56.1, 44.8.

Example 379

N-(2-Methoxy-benzyloxy)-2-[(pyridin-4-ylmethyl)-amino]-benzamide (compound 64)

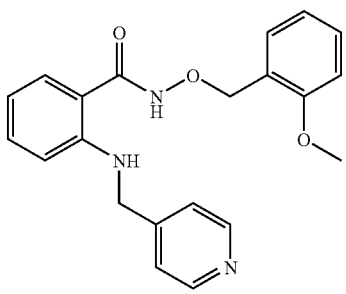

General procedure 1, method 1.

Starting materials: 2-[(Pyridin-4-ylmethyl)-amino]-benzoic acid (see preparation 1) and O-(2-methoxy-benzyl)-hydroxylamine hydrochloride (see preparation 30)

$^{13}$C-NMR (DMSO-d$_6$) δ 167.1, 157.2, 149.5, 149.0, 148.3, 132.4, 130.4, 129.7, 128.1, 123.8, 121.9, 120.0, 114.8, 113.5, 111.4, 110.8, 71.5, 55.3, 44.8.

Example 380

N-(4-Pentyloxy-benzyloxy)-2-[(pyridin-4-ylmethyl)-amino]-benzamide (compound 65)

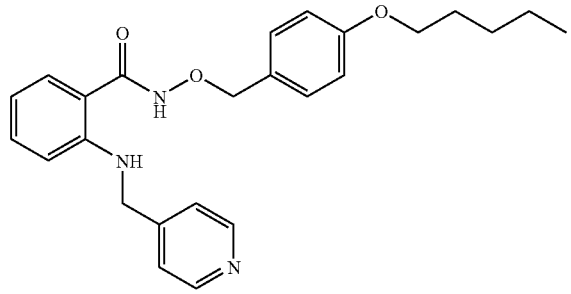

General procedure 1, method 2.

Starting materials: 2-[(Pyridin-4-ylmethyl)-amino]-benzoic acid (see preparation 1) and O-(4-pentyloxy-benzyl)-hydroxylamine (see preparation 31).

$^{13}$C-NMR (CDCl$_3$) δ 168.8, 159.7, 149.7, 149.0, 148.8, 133.3, 131.0, 127.5, 127.3, 122.0, 115.7, 114.6, 113.0, 112.0, 78.1, 68.1, 46.0, 28.9, 28.2, 22.5, 14.0.

Example 381

2-[(Pyridin-4-ylmethyl)-amino]-N-(2-trifluoromethoxy-benzyloxy)-benzamide (compound 66)

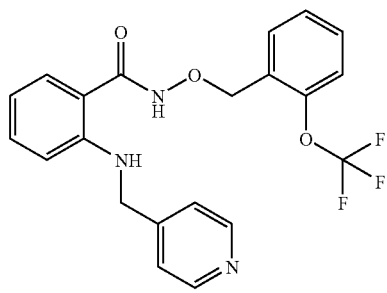

General procedure 1, method 1.
Starting materials: 2-[(Pyridin-4-ylmethyl)-amino]-benzoic acid (see preparation 1) and O-(2-trifluoromethoxy-benzyl)-hydroxylamine hydrochloride (see preparation 32)
$^{13}$C-NMR (DMSO-d$_6$) δ 167.5, 149.6, 149.0, 148.5, 146.8, 132.7, 131.8, 130.4, 128.7, 128.2, 127.5, 122.0, 120.6, 120.2 (q), 114.9, 113.3, 111.6, 70.8, 44.9.

Example 382

2-[(Pyridin-4-ylmethyl)-amino]-N-(3-trifluoromethoxy-benzyloxy)-benzamide (compound 67)

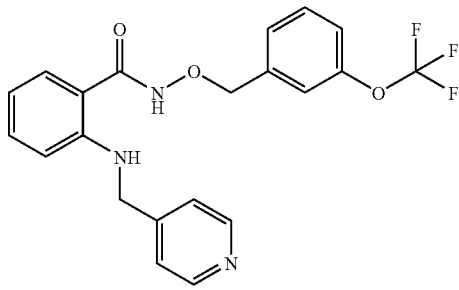

General procedure 1, method 1.
Starting materials: 2-[(Pyridin-4-ylmethyl)-amino]-benzoic acid (see preparation 1) and O-(3-trifluoromethoxy-benzyl)-hydroxylamine hydrochloride (see preparation 33).
$^{13}$C-NMR (DMSO-d$_6$) δ 167.3, 149.5, 148.9, 148.3, 138.9, 132.6, 130.2, 128.0, 127.6, 121.9, 120.8, 120.6, 120.0 (q), 114.8, 113.2, 111.5, 75.9, 44.8.

Example 383

2-[(Pyridin-4-ylmethyl)-amino]-N-(4-trifluoromethoxy-benzyloxy)-benzamide (compound 68)

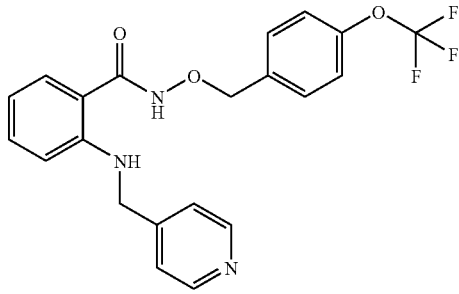

General procedure 1, method 1.
Starting materials: 2-[(Pyridin-4-ylmethyl)-amino]-benzoic acid (see preparation 1) and O-(4-trifluoromethoxy-benzyl)-hydroxylamine hydrochloride (see preparation 34).
$^{13}$C-NMR (DMSO-d$_6$) δ 167.3, 149.6, 149.0, 148.3, 148.2, 135.6, 132.5, 130.7, 128.1, 122.0, 120.8, 120.0 (q), 114.8, 113.3, 111.5, 75.9, 44.8.

Example 384

N-(2-Difluoromethoxy-benzyloxy)-2-[(pyridin-4-ylmethyl)-amino]-benzamide (compound 69)

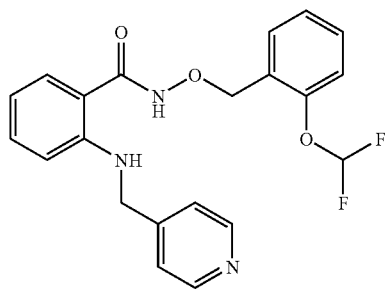

General procedure 1, method 1.
Starting materials: 2-[(Pyridin-4-ylmethyl)-amino]-benzoic acid (see preparation 1) and O-(2-difluoromethoxy-benzyl)-hydroxylamine hydrochloride (see preparation 35).
$^{13}$C-NMR (DMSO-d$_6$) δ 167.4, 149.6, 149.1, 148.4, 132.6, 131.6, 130.2, 128.2, 127.4, 125.4, 122.0, 119.1, 116.9 (t), 114.9, 113.4, 111.5, 71.4, 44.9.

Example 385

2-[(Pyridin-4-ylmethyl)-amino]-N-(2-trifluoromethylsulfanyl-benzyloxy)-benzamide (compound 70)

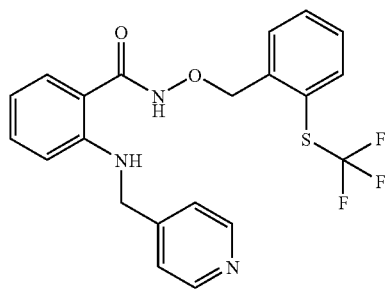

General procedure 1, method 1.
Starting materials: 2-[(Pyridin-4-ylmethyl)-amino]-benzoic acid (see preparation 1) and O-(2-Trifluoromethylsulfanyl-benzyl)-hydroxylamine hydrochloride (see preparation 36).
$^{13}$C-NMR (DMSO-d$_6$) δ 167.3, 149.5, 148.9, 148.3, 140.8, 137.4, 132.6, 131.6, 131.3, 129.7, 129.5 (q), 128.1, 123.2, 121.9, 114.8, 113.2, 111.5, 74.5, 44.8.

Example 386

N-(6-Chloro-benzo[1,3]dioxol-5-ylmethoxy)-2-[(pyridin-4-ylmethyl)amino]-benzamide (compound 71)

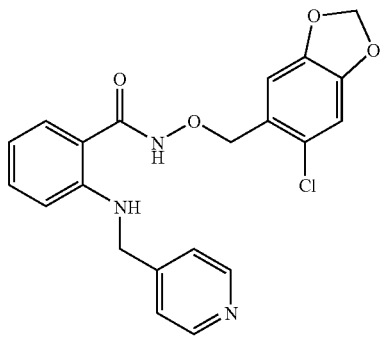

General procedure 1, method 1.
Starting materials: 2-[(Pyridin-4-ylmethyl)-amino]-benzoic acid (see preparation 1) and O-(6-Chloro-benzo[1,3]dioxol-5-ylmethyl)-hydroxylamine hydrochloride (see preparation 37)
$^{13}$C-NMR (DMSO-d$_6$) δ 167.2, 149.5, 149.0, 148.2, 148.1, 146.4, 132.4, 128.1, 126.8, 125.3, 121.9, 114.8, 113.3, 111.4, 110.6, 109.4, 102.1, 73.5, 44.8.

Example 387

N-(Benzo[1,3]-dioxol-5-ylmethoxy)-2-[(pyridin-4-ylmethyl)-amino]-benzamide (compound 72)

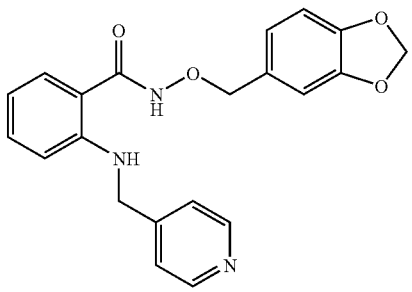

General procedure 1, method 2.
Starting materials: 2-[(Pyridin-4-ylmethyl)-amino]-benzoic acid (see preparation 1) and O-Benzo[1,3]dioxol-5-ylmethyl-hydroxylamine (see preparation 38)
$^{13}$C-NMR (DMSO-d$_6$) δ 166.8, 149.7, 149.6, 149.1, 148.3, 147.3, 147.2, 132.5, 129.9, 128.1, 122.9, 122.1, 122.0, 114.9, 113.6, 111.5, 109.4, 108.0, 101.0, 76.7, 44.9.

Example 388

N-(Indan-5-ylmethoxy)-2-[(pyridin-4-ylmethyl)-amino]-benzamide (compound 73)

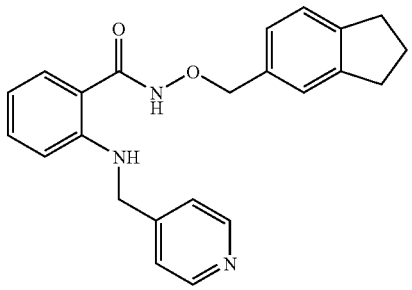

General procedure 1, method 2.
Starting materials: 2-[(Pyridin-4-ylmethyl)-amino]-benzoic acid (see preparation 1) and O-indan-5-ylmethyl-hydroxylamine hydrochloride (see preparation 39).
$^{13}$C-NMR (DMSO-d$_6$) δ 167.2, 150.1, 149.0, 148.3, 143.9, 143.8, 133.7, 132.5, 128.2, 127.1, 125.1, 124.0, 122.3, 115.0, 113.7, 111.5, 77.2, 44.9, 32.2, 32.1, 25.1.

Example 389

N-(3-Cyano-benzyloxy)-2-[(pyridin-4-ylmethyl)-amino]-benzamide (compound 74)

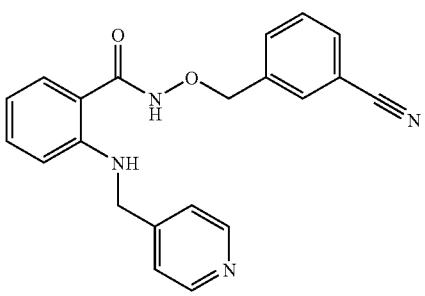

General procedure 1, method 2.
Starting materials: 2-[(Pyridin-4-ylmethyl)-amino]-benzoic acid (see preparation 1) and 3-aminooxymethyl-benzonitrile (see preparation 40).
$^{13}$C-NMR (CDCl$_3$) δ 169.6, 150.3, 149.7, 149.2, 148.8, 137.2, 133.8, 133.3, 132.4, 132.3, 129.5, 127.4, 122.7, 122.0, 118.5, 115.8, 112.8, 112.2, 46.0.

Example 390

N-(2-Cyano-benzyloxy)-2-[(pyridin-4-ylmethyl)-amino]-benzamide (compound 75)

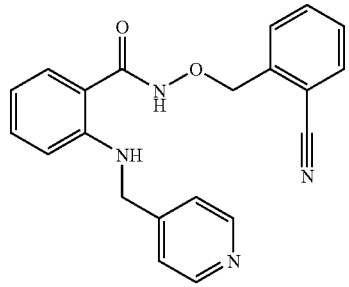

General procedure 1, method 2.
Starting materials: 2-[(Pyridin-4-ylmethyl)-amino]-benzoic acid (see preparation 1) and 2-aminooxymethyl-benzonitrile (see preparation 41).
$^{13}$C-NMR (DMSO-d$_6$) δ 166.9, 149.5, 148.9, 148.2, 139.3, 133.1, 132.8, 132.4, 130.7, 129.2, 128.1, 121.9, 117.2, 114.7, 113.1, 111.9, 111.4, 74.2, 44.7.

Example 391

N-(4-Cyano-2-fluoro-benzyloxy)-2-[(pyridin-4-ylmethyl)-amino]-benzamide (compound 76)

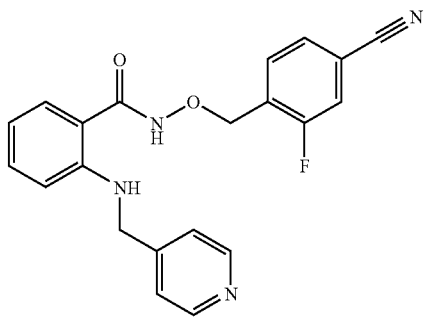

General procedure 1, method 1.
Starting materials: 2-[(Pyridin-4-ylmethyl)-amino]-benzoic acid (see preparation 1) and 4-aminooxymethyl-3-fluoro-benzonitrile hydrochloride (see preparation 42).
$^{13}$C-NMR (DMSO-d$_6$) δ 167.3, 160.1 (d), 149.5, 148.9, 148.2, 132.7, 132.6 (d), 129.2 (d), 128.6 (d), 128.1, 121.9, 119.2 (d), 117.5 (d), 114.8, 113.0, 112.7 (d), 111.4, 69.7, 44.7.

Example 392

N-(3-Bromo-4-cyano-benzyloxy)-2-[(pyridin-4-ylmethyl)-amino]-benzamide (compound 77)

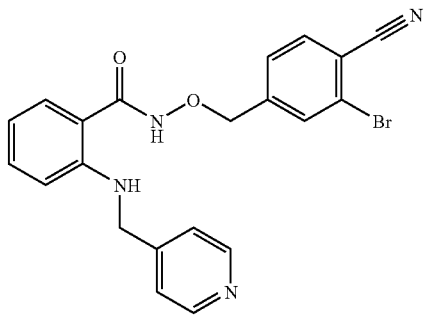

General procedure 1, method 1.
Starting materials: 2-[(Pyridin-4-ylmethyl)-amino]-benzoic acid (see preparation 1) and 4-aminooxymethyl-2-bromo-benzonitrile hydrochloride (see preparation 43)
$^{13}$C-NMR (DMSO-d$_6$) δ 149.5, 148.9, 148.2, 144.2, 134.7, 132.6, 132.3, 128.0, 127.9, 124.2, 121.9, 117.1, 114.8, 113.7, 113.0, 111.5, 75.2, 44.7.

Example 393

N-(2-Chloro-4-cyano-benzyloxy)-2-[(pyridin-4-ylmethyl)-amino]-benzamide (compound 78)

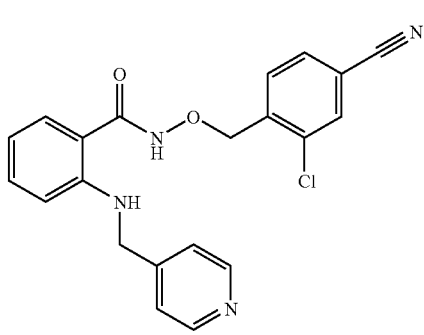

General procedure 1, method 1.
Starting materials: 2-[(Pyridin-4-ylmethyl)-amino]-benzoic acid (see preparation 1) and 4-aminooxymethyl-3-chloro-benzonitrile hydrochloride (see preparation 44).
$^{13}$C-NMR (DMSO-d$_6$) δ 167.4, 149.5, 148.9, 148.2, 139.6, 133.5, 132.5, 131.3, 131.0, 128.1, 121.9, 117.3, 114.8, 112.9, 112.4, 111.5, 73.1, 44.7.

Example 394

N-(4-Cyano-2-methoxy-benzyloxy)-2-[(pyridin-4-ylmethyl)-amino]-benzamide (compound 79)

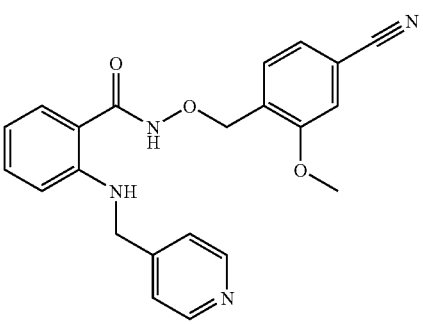

General procedure 1, method 1.
Starting materials: 2-[(Pyridin-4-ylmethyl)-amino]-benzoic acid (see preparation 1) and 4-aminooxymethyl-3-methoxy-benzonitrile hydrochloride (see preparation 45)
$^{13}$C-NMR (DMSO-d$_6$) δ 167.2, 157.1, 154.5, 148.0, 145.9, 132.6, 130.3, 130.0, 128.2, 124.4, 123.2, 118.6, 115.1, 114.1, 113.4, 111.7, 111.4, 71.0, 56.0, 45.0.

Example 395

N-(4-Cyano-2-iodo-benzyloxy)-2-[(pyridin-4-ylmethyl)-amino]-benzamide (compound 80)

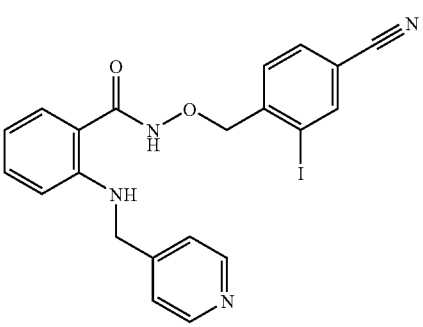

General procedure 1, method 1.
Starting materials: 2-[(Pyridin-4-ylmethyl)-amino]-benzoic acid (see preparation 1) and 4-aminooxymethyl-3-iodo-benzonitrile hydrochloride (see preparation 46).
$^{13}$C-NMR (DMSO-d$_6$) δ 167.4, 149.5, 148.9, 148.3, 144.3, 141.7, 132.6, 131.9, 129.7, 128.2, 121.9, 117.0, 114.8, 112.9, 112.3, 111.5, 98.8, 79.7, 44.8.

Example 396

N-(2-Bromo-5-cyano-benzyloxy)-2-[(pyridin-4-ylmethyl)-amino]-benzamide (compound 81)

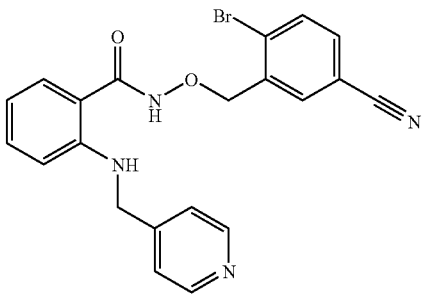

General procedure 1, method 1.
Starting materials: 2-[(Pyridin-4-ylmethyl)-amino]-benzoic acid (see preparation 1) and 3-aminooxymethyl-4-bromo-benzonitrile (see preparation 47).
$^{13}$C-NMR (DMSO-d$_6$) δ 167.5, 149.5, 148.9, 148.3, 137.4, 133.8, 133.2, 132.7, 128.7, 128.1, 121.9, 118.0, 114.8, 113.0, 111.5, 110.7, 75.2, 44.8.

Example 397

N-(4-Cyano-naphthalen-1-ylmethoxy)-2-[(pyridin-4-ylmethyl)-amino]-benzamide (compound 82)

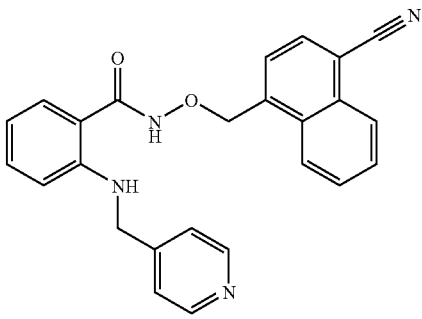

General procedure 1, method 1.
Starting materials: 2-[(Pyridin-4-ylmethyl)-amino]-benzoic acid (see preparation 1) and 4-aminooxymethyl-naphthalene-1-carbonitrile hydrochloride (see preparation 48).
$^{13}$C-NMR (DMSO-d$_6$) δ 167.4, 149.5, 149.0, 148.3, 138.0, 132.7, 132.6, 131.6, 131.3, 128.9, 128.1, 128.0, 127.1, 125.9, 124.6, 121.9, 117.4, 114.8, 113.1, 111.5, 109.7, 74.4, 44.8.

Example 398

N-(4-Morpholin-4-yl-benzyloxy)-2-[(pyridin-4-ylmethyl)-amino]-benzamide (compound 83)

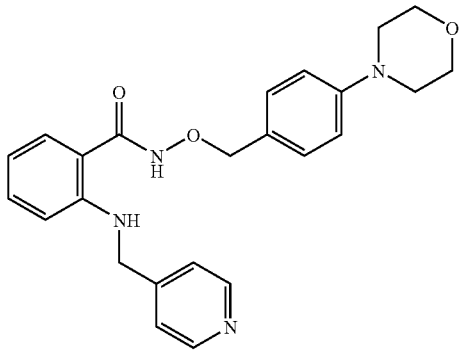

General procedure 1, method 1.
Starting materials: 2-[(Pyridin-4-ylmethyl)-amino]-benzoic acid (see preparation 1) and O-(4-morpholin-4-yl-benzyl)-hydroxylamine hydrochloride (see preparation 49).
$^{13}$C-NMR (DMSO-d$_6$) δ 167.0, 151.0, 149.5, 149.0, 148.2, 132.4, 130.2, 128.0, 126.1, 122.0, 114.8, 114.5, 113.6, 111.4, 76.7, 66.0, 48.1, 44.8.

Example 399

N-(2-Morpholin-4-yl-benzyloxy)-2-[(pyridin-4-ylmethyl)-amino]-benzamide (compound 84)

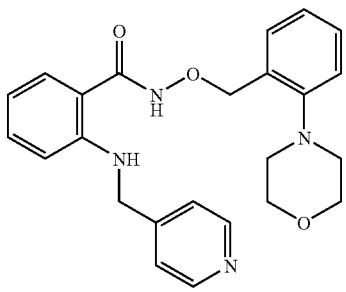

General procedure 1, method 1.
Starting materials: 2-[(Pyridin-4-ylmethyl)-amino]-benzoic acid (see preparation 1) and O-(2-morpholin-4-yl-benzyl)-hydroxylamine hydrochloride (see preparation 50).
$^{13}$C-NMR (DMSO-d$_6$) δ 167.1, 151.9, 149.5, 148.9, 148.3, 132.5, 131.4, 129.7, 129.3, 128.1, 123.0, 121.9, 119.1, 114.8, 113.4, 111.5, 72.9, 66.6, 53.0, 44.8.

Example 400

N-(2-Amino-benzyloxy)-2-[(pyridin-4-ylmethyl)-amino]-benzamide (compound 85)

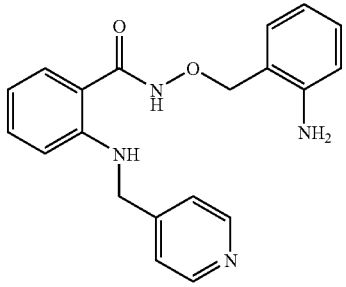

General procedure 1, method 2.
Starting materials: 2-[(Pyridin-4-ylmethyl)-amino]-benzoic acid (see preparation 1) and O-(2-amino-benzyl)-hydroxylamine (see preparation 51).
$^{13}$C-NMR (CDCl$_3$) δ 169.7, 149.8, 149.1, 148.8, 147.8, 133.7, 131.3, 130.7, 127.5, 121.9, 118.4, 117.3, 115.8, 112.3, 112.2, 77.5, 46.0.

Example 401

N-(2-Benzenesulfonylamino-benzyloxy)-2-[(pyridin-4-ylmethyl)-amino]-benzamide (compound 86)

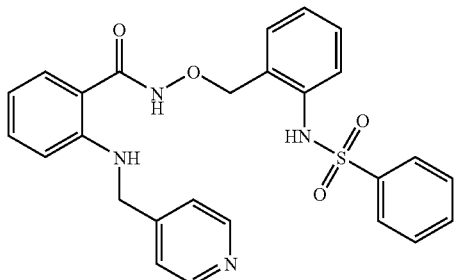

To a stirred solution of N-(2-amino-benzyloxy)-2-[(pyridin-4-ylmethyl)-amino]-benzamide (see example 400) in dichloromethane at 0-5° C. was added triethylamine (1.2 eq.) followed by addition of benzensulfonyl chloride (1.1 eq.). The mixture was allowed to warm to room temperature and stirred for 20 hours. The solvent was evaporated under reduced pressure, and the residue was dissolved in EtOAc and washed with water and brine. The organic layer was dried (MgSO$_4$) and evaporated under reduced pressure. The residue was purified by column chromatography on silica gel (petroleum ether/EtOAc, 2/1, v/v) and gave the title compound. $^{13}$C-NMR (DMSO-d$_6$) δ 170.7, 149.6, 149.4, 149.1, 140.7, 138.3, 134.2, 132.5, 131.0, 130.7, 128.8, 127.4, 126.9, 125.3, 124.5, 123.0, 122.2, 115.7, 112.4, 111.1, 76.6, 46.0.

Example 402

3-{2-[(Pyridin-4-ylmethyl)-amino]-benzoylaminooxymethyl}-benzoic acid methyl ester (compound 87)

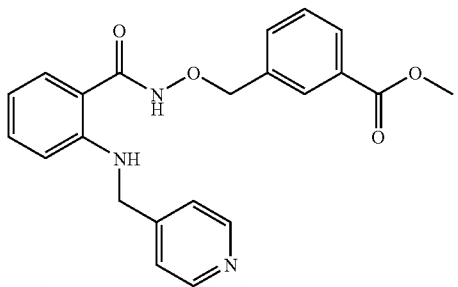

General procedure 1, method 1.

Starting materials: 2-[(Pyridin-4-ylmethyl)-amino]-benzoic acid (see preparation 1) and 3-aminooxymethyl-benzoic acid methyl ester hydrochloride (see preparation 52).

$^{13}$C-NMR (DMSO-d$_6$) δ 167.2, 166.0, 149.5, 148.9, 148.3, 136.7, 133.6, 132.5, 129.6, 129.4, 128.9, 128.7, 128.0, 121.9, 114.8, 113.3, 111.5, 76.2, 52.1, 44.8.

Example 403

3-{2-[(Pyridin-4-ylmethyl)-amino]-benzoylaminooxymethyl}-benzoic acid (compound 88)

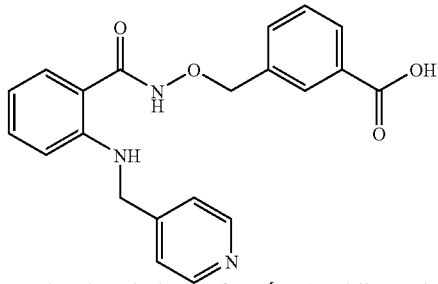

To a stirred solution of 3-{2-[(Pyridin-4-ylmethyl)-amino]-benzoylaminooxymethyl}-benzoic acid methyl ester (see example 402, 89 mg) in methanol (3 ml) was added 2M sodium hydroxide (1 ml). The reaction mixture was stirred at room temperature for 7 hours. The mixture was diluted with water (12 ml) and acidified with 4M HCl aq. The resulting precipitated material was isolated by filtration and dried under vacuum, affording the title compound. $^{13}$C-NMR (DMSO-d$_6$) δ 167.2, 167.1, 149.5, 149.0, 148.3, 136.4, 133.1, 132.5, 130.8, 129.7, 129.1, 128.5, 128.0, 121.9, 114.8, 113.3, 111.4, 76.3, 44.7.

Example 404

4-{2-[(Pyridin-4-ylmethyl)-amino]-benzoylaminooxymethyl}-benzoic acid (compound 89)

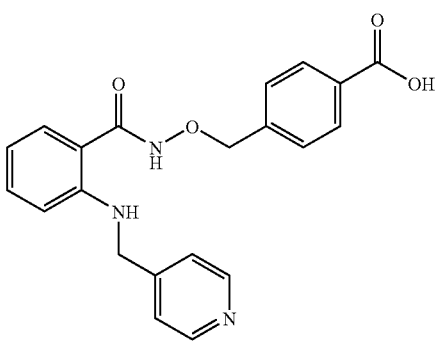

Prepared by the same method as described for preparation of example 403. Starting material: 4-{2-[(Pyridin-4-ylmethyl)-amino]-benzoylaminooxymethyl}-benzoic acid methyl ester (see example 26).

$^{13}$C-NMR (DMSO-d$_6$) δ 167.2, 167.0, 149.5, 149.0, 148.3, 140.9, 132.5, 130.4, 129.2, 128.6, 128.0, 122.0, 114.8, 113.2, 111.5, 76.2, 44.7.

Example 405

N-[4-(Morpholine-4-carbonyl)-benzyloxy]-2-[(pyridin-4-ylmethyl)-amino]-benzamide (compound 90)

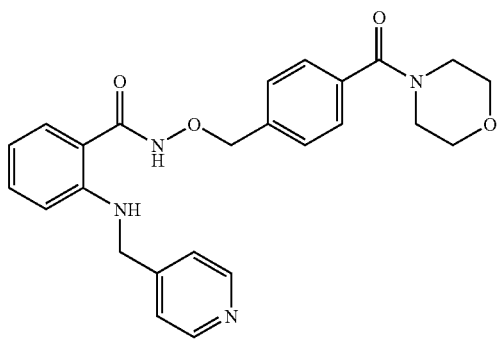

To a stirred mixture of 4-{2-[(pyridin-4-ylmethyl)-amino]-benzoylaminooxymethyl}-benzoic acid (see example 404, 220 mg) in DMF (3 ml) was added N,N'-carbonyldiimidazole (99 mg). The mixture was stirred at room temperature for 45 minutes and morpholine hydrochloride (79 mg) was added. The reaction mixture was stirred at room temperature for 18 hours and poured into water. The product was extracted several times with EtOAc and the combined organic layers were washed with water and brine, dried (Na$_2$SO$_4$) and evaporated under reduced pressure. The residue was purified by column chromatography on silica gel (EtOAc as eluent) and gave the title compound. $^{13}$C-NMR (DMSO-d$_6$) δ 168.7, 167.2, 149.5, 149.0, 148.3, 137.4, 135.3, 132.5, 128.8, 128.1, 127.0, 122.0, 114.8, 113.3, 111.5, 76.4, 66.0, 44.7

Example 406

N-{3-[4-(3-Cyano-pyridin-2-yl)-piperazine-1-carbonyl]-benzyloxy}-2-[(pyridin-4-ylmethyl)-amino]-benzamide (compound 91)

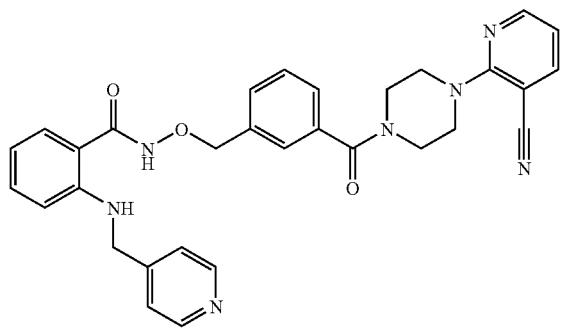

Prepared by a similar procedure as described for preparation of example 405. Starting materials: 3-{2-[(Pyridin-4-ylmethyl)-amino]-benzoylaminooxymethyl}-benzoic acid (see example 403) and 2(1-piperazinyl)-nicotinonitrile (Emka-chemie). $^1$H-NMR (DMSO-d$_6$) δ 11.5 (bs, 1H), 8.48 (m, 2H), 8.43 (dd, 1H), 8.10 (dd, 1H), 7.89 (bt, 1H), 7.60-7.53 (m, 2H), 7.50 (t, 1H), 7.44 (dt, 1H), 7.38 (dd, 1H), 7.30 (m, 2H), 7.16 (m, 1H), 6.97 (dd, 1H), 6.54 (m, 1H), 6.49 (bd, 1H), 5.00 (s, 2H), 4.46 (d, 2H), 4.00-3.36 (m, 8H).

Example 407

N-[3-(4-Methyl-piperazine-1-carbonyl)-benzyloxy]-2-[(pyridin-4-ylmethyl)-amino]-benzamide (compound 92)

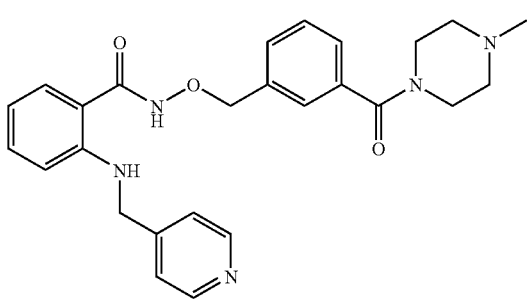

Prepared by a similar procedure as described for preparation of example 405. Starting materials: 3-{2-[(Pyridin-4-ylmethyl)-amino]-benzoylaminooxymethyl}-benzoic acid (see example 403) and 1-methylpiperazine.

$^1$H-NMR (CDCl$_3$) δ 11.6 (bs, 1H), 8.49 (m, 2H), 7.92 (bt, 1H), 7.55 (bd, 1H), 7.50-7.42 (m, 2H), 7.41-7.33 (m, 2H), 7.31 (m, 2H), 7.19 (bt, 1H), 6.60-6.47 (m, 2H), 4.98 (s, 2H), 4.46 (d, 2H), 3.80-3.10 (m, 4H), 2.17 (s, 3H), 2.44-2.00 (m, 4H).

Example 408

N-[3-(Morpholine-4-carbonyl)-benzyloxy]-2-[(pyridin-4-ylmethyl)-amino]-benzamide (compound 93)

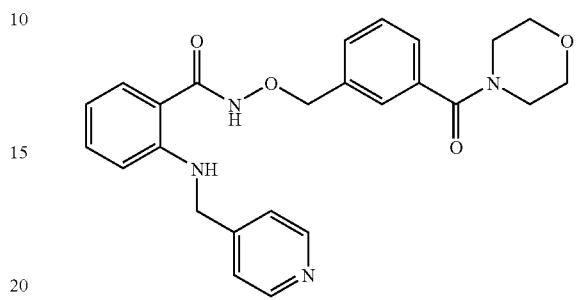

Prepared by a similar procedure as described for preparation of example 405. Starting materials: 3-{2-[(Pyridin-4-ylmethyl)-amino]-benzoylaminooxymethyl}-benzoic acid (see example 403) and morpholine hydrochloride. $^1$H-NMR (DMSO-d$_6$) δ 11.6 (bs, 1H), 8.49 (m, 2H), 7.89 (bt, 1H), 7.56 (m, 1H), 7.52-7.44 (m, 2H), 7.42-7.34 (m, 2H), 7.31 (m, 2H), 7.19 (m, 1H), 6.58-6.49 (m, 2H), 4.98 (s, 2H), 4.47 (d, 2H), 3.80-3.10 (m, 8H).

Example 409

N-[3-(3-Hydroxy-pyrrolidine-1-carbonyl)-benzyloxy]-2-[(pyridin-4-ylmethyl)-amino]-benzamide (compound 94)

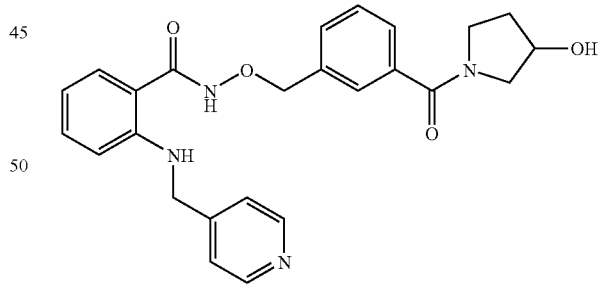

Prepared by a similar procedure as described for preparation of example 405. Starting materials: 3-{2-[(Pyridin-4-ylmethyl)-amino]-benzoylaminooxymethyl}-benzoic acid (see example 403) and 3-pyrrolidinol (Aldrich).

$^1$H-NMR (DMSO-d$_6$) δ (2 rotamers) 11.64 and 11.62 (bs, 1H), 8.49 (m, 2H), 8.00-7.80 (m, 1H), 7.61 (bs, 1H), 7.56 (dt, 1H), 7.53-7.42 (m, 2H), 7.38 (bd, 1H), 7.31 (m, 2H), 7.19 (bt, 1H), 6.60-6.47 (m, 2H), 4.98 (s, 2H), 4.47 (d, 2H), 4.32 and 4.21 (m, 1H), 3.68-3.14 (m, 5H), 2.02-1.62 (m, 2H).

Example 410

N-[4-(4-Methyl-piperazine-1-carbonyl)-benzyloxy]-2-[(pyridin-4-ylmethyl)-amino]-benzamide (compound 95)

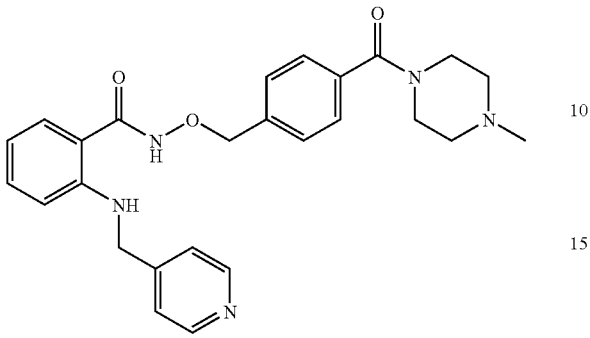

Prepared by a similar procedure as described for preparation of example 405. Starting materials: 4-{2-[(Pyridin-4-ylmethyl)-amino]-benzoylaminooxymethyl}-benzoic acid (see example 404) and 1-methylpiperazine. The title compound was crystallised from toluene. $^{13}$C-NMR (DMSO-$d_6$) δ 168.6, 167.2, 149.5, 148.9, 148.2, 137.3, 135.7, 132.4, 128.7, 128.0, 126.8, 121.9, 114.8, 113.3, 111.4, 76.4, 54.4, 46.8, 45.5, 44.8.

Example 411

N-[3-(2-dimethylaminoethylcarbamoyl)-benzyloxy]-2-[(pyridin-4-ylmethyl)-amino]-benzamide (compound 96)

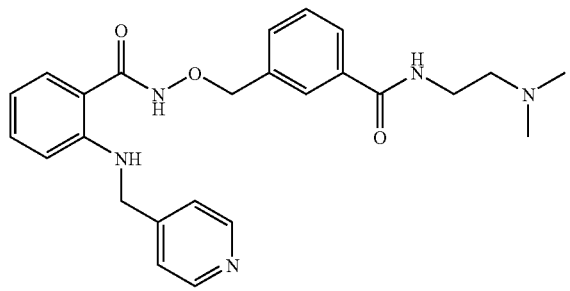

Prepared by a similar procedure as described for preparation of Example 405. Starting materials: 3-{2-[(Pyridin-4-ylmethyl)-amino]-benzoylaminooxymethyl}-benzoic acid (see Example 403) and 2-dimethylaminoethylamine. $^{13}$C-NMR (DMSO-$d_6$) δ 165.8, 149.5, 148.9, 148.2, 136.1, 134.6, 132.4, 131.4, 128.2, 128.0, 127.7, 126.8, 121.9, 114.8, 113.3, 111.4, 76.5, 58.1, 45.2, 44.8, 37.3.

Example 412

N-[3-(2-pyrrolidin-1-yl-ethylcarbamoyl)-benzyloxy]-2-[(pyridin-4-ylmethyl)-amino]-benzamide (compound 97)

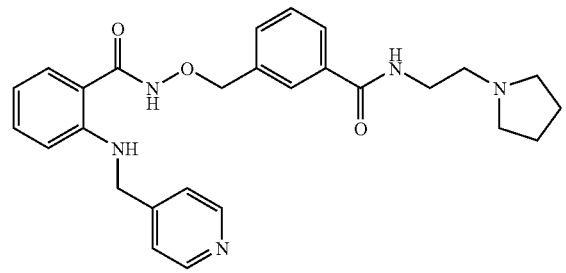

Prepared by a similar procedure as described for preparation of example 405. Starting materials: 3-{2-[(Pyridin-4-ylmethyl)-amino]-benzoylaminooxymethyl}-benzoic acid (see example 403) and N-(2-aminoethyl)pyrrolidine (Aldrich).

$^{13}$C-NMR (DMSO-$d_6$) δ 166.8, 165.8, 149.5, 148.9, 148.2, 136.1, 134.5, 132.4, 131.4, 128.2, 128.0, 127.7, 126.9, 121.9, 114.8, 113.3, 111.4, 76.5, 54.8, 53.6, 44.8, 38.5, 23.0.

Example 413

2-[(Pyridin-4-ylmethyl)-amino]-N-(2-thiophen-2-yl-benzyloxy)-benzamide (compound 98)

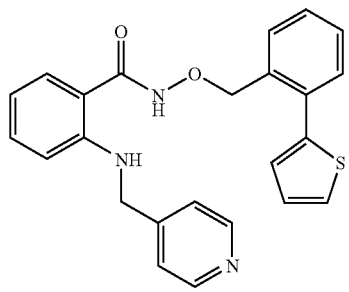

Prepared by a similar procedure as described for preparation of example 363. Starting materials: N-(2-Iodo-benzyloxy)-2-[(pyridin-4-ylmethyl)amino]-benzamide (see example 360) and thiophene-2-boronic acid (Aldrich).

$^1$H-NMR (DMSO-$d_6$) δ 11.60 (bs, 1H), 8.49 (m, 2H), 7.90 (bs, 1H), 7.71-7.62 (m, 2H), 7.52-7.37 (m, 5H), 7.31 (m, 2H), 7.23-7.15 (m, 2H), 6.60-6.47 (m, 2H), 4.99 (s, 2H), 4.46 (bs, 2H).

Example 414

N-(4'-Methoxy-biphenyl-2-ylmethoxy)-2-[(pyridin-4-ylmethyl)-amino]-benzamide (compound 99)

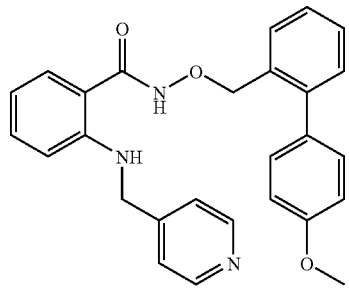

Prepared by a similar procedure as described for preparation of example 363. Starting materials: N-(2-Iodo-benzyloxy)-2-[(pyridin-4-ylmethyl)amino]-benzamide (see example 360) and 4-methoxyphenylboronic acid (Aldrich).

$^{13}$C-NMR (CDCl$_3$) δ 168.8, 159.0, 149.7, 149.1, 148.8, 142.8, 133.5, 132.8, 132.6, 131.0, 130.5, 130.4, 128.8, 127.3, 127.3, 122.0, 115.6, 113.7, 112.7, 112.1, 76.5, 55.3, 46.0

Example 415

N-(Naphthalen-1-ylmethoxy)-2-[(pyridin-4-ylmethyl)-amino]-benzamide (compound 100)

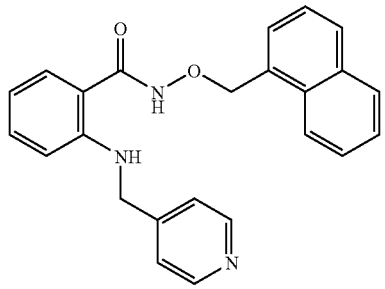

2-[(Pyridin-4-ylmethyl)-amino]-benzoic acid pentafluorophenyl ester (preparation 7C, 150 mg) and O-naphthalen-1-ylmethyl-hydroxylamine (preparation 53, 1.05 eq.) was dissolved in DMF and the stirred mixture was heated to 50° C. The reaction mixture was stirred at this temperature for 15 hours. The mixture was cooled to room temperature and partitioned between EtOAc and water. The organic layer washed with brine, dried (MgSO$_4$) and evaporated under reduced pressure. The residue was purified by column chromatography on silica gel (petroleum ether/EtOAc) and gave the title compound. $^{13}$C-NMR (DMSO-d$_6$) δ 167.3, 149.5, 149.1, 148.4, 133.2, 132.5, 131.9, 131.4, 129.3, 128.4, 128.2, 126.3, 126.1, 125.9, 125.2, 124.8, 121.9, 114.8, 113.4, 111.5, 75.3, 44.8.

Example 416

N-(1-Phenyl-ethoxy)-2-[(pyridin-4-ylmethyl)-amino]-benzamide (compound 101)

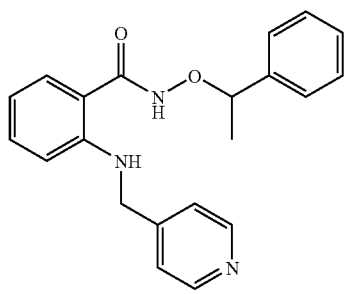

General procedure 1, method 1.

Starting materials: 2-[(Pyridin-4-ylmethyl)-amino]-benzoic acid (see preparation 1) and O-(1-phenyl-ethyl)-hydroxylamine hydrochloride (see preparation 54).

$^{13}$C-NMR (DMSO-d$_6$) δ 167.1, 149.5, 149.0, 148.0, 141.5, 132.3, 128.1, 127.8, 126.7, 122.0, 114.7, 113.8, 111.3, 81.6, 44.7, 20.8.

Example 417

2-[(Pyridin-4-ylmethyl)-amino]-N-[1-(2-trifluoromethyl-phenyl)-ethoxy]-benzamide (compound 102)

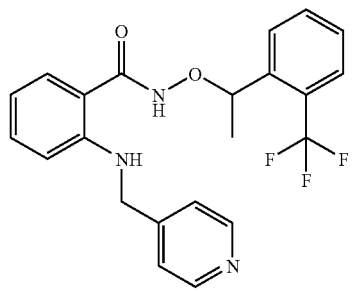

General procedure 1, method 1.

Starting materials: 2-[(Pyridin-4-ylmethyl)-amino]-benzoic acid (see preparation 1) and O-[1-(2-trifluoromethyl-phenyl)-ethyl]-hydroxylamine hydrochloride (see preparation 55). $^{13}$C-NMR (DMSO-d$_6$) δ 167.5, 149.6, 149.0, 148.2, 141.4, 132.9, 132.5, 128.3, 128.2, 128.1, 126.1, 125.0, 124.2, 122.1, 114.8, 113.5, 111.4, 77.1, 44.8, 22.0.

Example 418

N-(Pyridin-2-ylmethoxy)-2-[(pyridin-4-ylmethyl)-amino]-benzamide (compound 103)

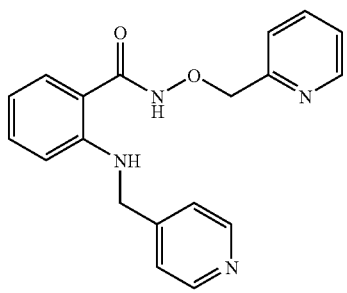

General procedure 1, method 1.

Starting materials: 2-[(Pyridin-4-ylmethyl)-amino]-benzoic acid (see preparation 1) and O-Pyridin-2-ylmethyl-hydroxylamine hydrochloride (see preparation 56)

$^{13}$C-NMR (DMSO-d$_6$) δ 167.3, 155.8, 149.5, 148.9, 148.3, 136.6, 132.5, 128.1, 123.1, 122.7, 121.9, 114.8, 113.3, 111.5, 77.8, 44.8.

Example 419

N-(2,6-Dichloro-pyridin-4-ylmethoxy)-2-[(pyridin-4-ylmethyl)-amino]-benzamide (compound 104)

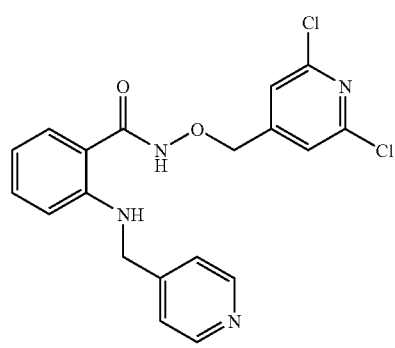

General procedure 1, method 1.

Starting materials: 2-[(Pyridin-4-ylmethyl)-amino]-benzoic acid (see preparation 1) and O-(2,6-dichloro-pyridin-4-ylmethyl)-hydroxylamine hydrochloride (see preparation 57). $^{13}$C-NMR (DMSO-d$_6$) δ 167.6, 153.2, 149.5, 149.1, 148.9, 148.3, 132.8, 128.1, 122.1, 121.9, 114.8, 112.8, 111.6, 74.1, 44.7.

Example 420

2-[(Pyridin-4-ylmethyl)-amino]-N-(thiazol-4-yl-methoxy)-benzamide (compound 105)

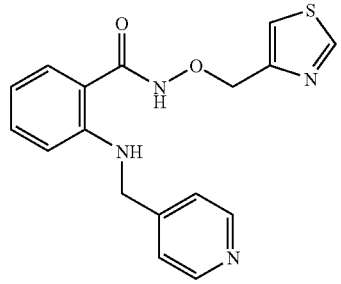

General procedure 1, method 1.

Starting materials: 2-[(Pyridin-4-ylmethyl)-amino]-benzoic acid (see preparation 1) and O-thiazol-4-ylmethyl-hydroxylamine hydrochloride (see preparation 58).

$^{13}$C-NMR (DMSO-d$_6$) δ 167.1, 154.2, 151.8, 149.5, 148.9, 148.2, 132.5, 128.1, 122.0, 119.4, 114.8, 113.4, 111.4, 71.8, 44.8.

Example 421

N-(2-Chloro-thiazol-5-ylmethoxy)-2-[(pyridin-4-ylmethyl)-amino]-benzamide (compound 106)

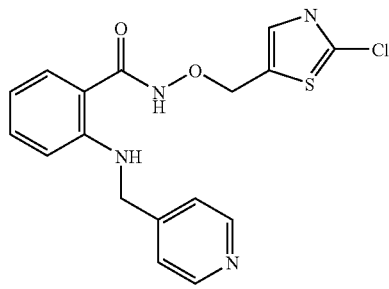

General procedure 1, method 1.

Starting materials: 2-[(Pyridin-4-ylmethyl)-amino]-benzoic acid (see preparation 1) and O-(2-chloro-thiazol-5-ylmethyl)-hydroxylamine hydrochloride (see preparation 59).

$^{13}$C-NMR (DMSO-d$_6$) δ 167.6, 151.4, 149.5, 149.0, 148.3, 142.0, 135.9, 132.7, 128.1, 122.0, 114.8, 113.0, 111.5, 68.2, 44.7.

Example 422

N-(2-Phenyl-thiazol-4-ylmethoxy)-2-[(pyridin-4-ylmethyl)-amino]-benzamide (compound 107)

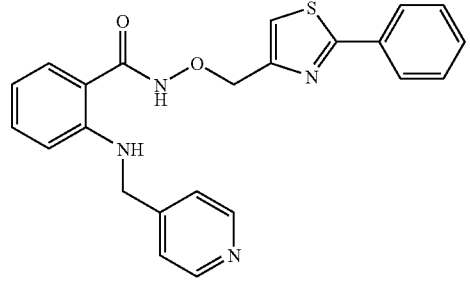

General procedure 1, method 1.

Starting materials: 2-[(Pyridin-4-ylmethyl)-amino]-benzoic acid (see preparation 1) and O-(2-Phenyl-thiazol-4-ylmethyl)-hydroxylamine hydrochloride (see preparation 60).

$^{13}$C-NMR (DMSO-d$_6$) δ 167.0, 152.1, 149.5, 148.9, 148.3, 132.9, 132.5, 130.2, 129.2, 128.2, 126.0, 121.9, 119.9, 114.8, 113.3, 111.4, 71.9, 44.8.

Example 423

N-(5-Methyl-isoxazol-3-ylmethoxy)-2-[(pyridin-4-ylmethyl)-amino]-benzamide (compound 108)

Prepared by the same method as described for example 415. Starting materials: 2-[(Pyridin-4-ylmethyl)-amino]-benzoic acid pentafluorophenyl ester (preparation 7C) and O-(5-Methyl-isoxazol-3-ylmethyl)-hydroxylamine (see preparation 61)

$^{13}$C-NMR (DMSO-d$_6$) δ 169.8, 167.5, 159.7, 149.7, 149.0, 148.5, 132.8, 128.3, 122.1, 114.9, 113.2, 111.6, 102.0, 67.9, 44.9, 11.8.

Example 424

N-(3,5-Dimethyl-isoxazol-4-ylmethoxy)-2-[(pyridin-4-ylmethyl)-amino]-benzamide (compound 109)

General procedure 1, method 1.

Starting materials: 2-[(Pyridin-4-ylmethyl)-amino]-benzoic acid (see preparation 1) and O-(3,5-dimethyl-isoxazol-4-ylmethyl)-hydroxylamine hydrochloride (see preparation 62).

$^{13}$C-NMR (DMSO-d$_6$) δ 168.6, 159.8, 149.5, 149.0, 148.3, 132.5, 128.0, 121.9, 114.8, 113.2, 111.5, 109.7, 65.0, 44.7, 10.5, 9.5.

Example 425

N-(3-Propyl-isoxazol-5-ylmethoxy)-2-[(pyridin-4-ylmethyl)-amino]-benzamide (compound 110)

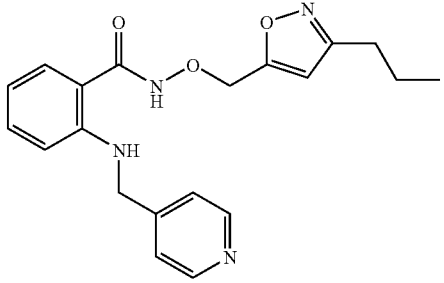

Prepared by the same method as described for example 415. Starting materials: 2-[(Pyridin-4-ylmethyl)-amino]-benzoic acid pentafluorophenyl ester (preparation 7C) and O-(3-Propyl-isoxazol-5-ylmethyl)-hydroxylamine (see preparation 63).

$^{13}$C-NMR (DMSO-d$_6$) δ 167.4, 166.6, 163.4, 149.5, 148.9, 148.4, 132.7, 128.1, 121.9, 114.8, 113.0, 111.5, 104.8, 66.7, 44.8, 27.1, 20.9, 13.4.

Example 426

N-(5-Chloro-thiophen-2-ylmethoxy)-2-[(pyridin-4-ylmethyl)-amino]-benzamide (compound 111)

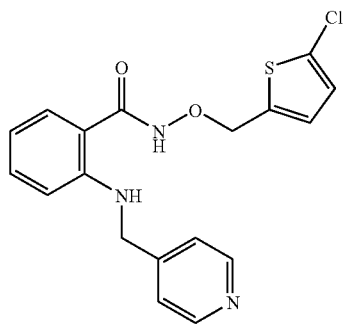

Prepared by the same method as described for example 415. Starting materials: 2-[(Pyridin-4-ylmethyl)-amino]-benzoic acid pentafluorophenyl ester (preparation 7C) and O-(5-chloro-thiophen-2-ylmethyl)-hydroxylamine (see preparation 64).

$^{13}$C-NMR (DMSO-d$_6$) δ 167.4, 149.5, 148.9, 148.4, 137.4, 132.6, 129.3, 128.5, 128.1, 126.4, 122.0, 114.8, 113.2, 111.5, 70.8, 44.8.

Example 427

N-[2-(4-Cyano-phenyl)-ethoxy]-2-[(pyridin-4-ylmethyl)-amino]-benzamide (compound 112)

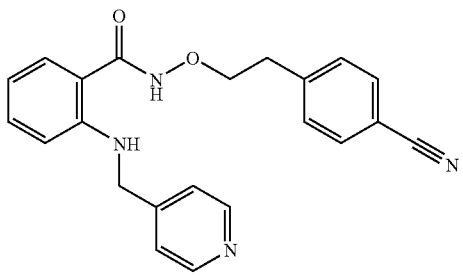

General procedure 1, method 1.

Starting materials: 2-[(Pyridin-4-ylmethyl)-amino]-benzoic acid (see preparation 1) and 4-(2-aminooxy-ethyl)-benzonitrile (see preparation 65).

$^{13}$C-NMR (DMSO-d$_6$) δ 167.2, 149.5, 148.9, 148.3, 144.8, 132.5, 132.0, 129.9, 128.1, 121.9, 118.9, 114.8, 113.3, 111.5, 109.0, 74.8, 44.8, 34.0.

Example 428

N-Cyclopentylmethoxy-2-[(pyridin-4-ylmethyl)-amino]-benzamide (compound 113)

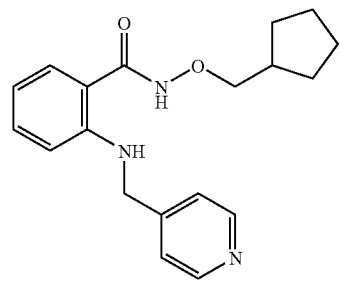

General procedure 1A.

Starting materials: 1-Pyridin-4-ylmethyl-1H-benzo[d][1,3]oxazine-2,4-dione (see preparation 7A) and O-cyclopentylmethyl-hydroxylamine hydrochloride (see preparation 66).

$^{13}$C-NMR (DMSO-d$_6$) δ 166.9, 149.5, 149.0, 148.3, 132.4, 128.0, 122.0, 114.8, 113.5, 111.4, 79.4, 44.8, 37.6, 28.9, 24.9.

Example 429

N-Cyclopropylmethoxy-2-[(pyridin-4-ylmethyl)-amino]-benzamide (compound 114)

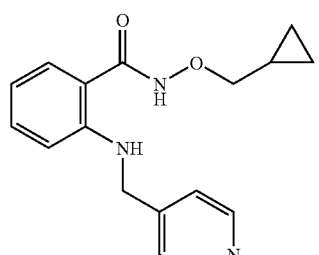

General procedure 1, method 2.

Starting materials: 2-[(Pyridin-4-ylmethyl)-amino]-benzoic acid (see preparation 1) and O-cyclopropylmethyl-hydroxylamine hydrochloride (see preparation 67)

$^{13}$C-NMR (DMSO-d$_6$) δ 166.9, 149.5, 149.0, 148.3, 132.3, 128.0, 122.0, 114.8, 113.6, 111.4, 79.6, 44.8, 9.2, 2.9.

Example 430

N-Methoxy-2-[(pyridin-4-ylmethyl)-amino]-benzamide (compound 115)

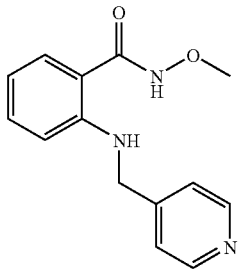

General procedure 1, method 1.
Starting materials: 2-[(Pyridin-4-ylmethyl)-amino]-benzoic acid (see preparation 1) and O-methyl-hydroxylamine hydrochloride.
$^{13}$C-NMR (DMSO-d$_6$) δ 166.7, 149.5, 148.9, 148.3, 132.5, 128.0, 121.9, 114.8, 113.2, 111.5, 63.1, 44.8.

Example 431

N-(2,2-Dimethyl-propoxy)-2-[(pyridin-4-ylmethyl)-amino]-benzamide (compound 116)

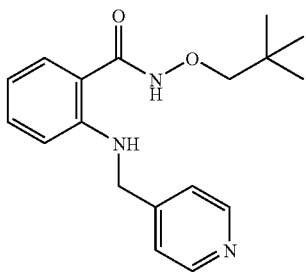

General procedure 1A.
Starting materials: 1-Pyridin-4-ylmethyl-1H-benzo[d][1,3]oxazine-2,4-dione (see preparation 7A) and O-(2,2-dimethyl-propyl)-hydroxylamine hydrochloride (see preparation 68).
$^{13}$C-NMR (DMSO-d$_6$) δ 166.9, 149.5, 149.0, 148.3, 132.3, 128.0, 121.9, 114.8, 113.5, 111.4, 84.9, 44.7, 31.4, 26.5.

Example 432

N-(2-Ethyl-butoxy)-2-[(pyridin-4-ylmethyl)-amino]-benzamide (compound 117)

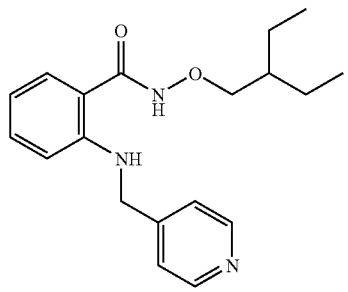

General procedure 1, method 2.
Starting materials: 2-[(Pyridin-4-ylmethyl)-amino]-benzoic acid (see preparation 1) and O-(2-ethyl-butyl)-hydroxylamine hydrochloride (see preparation 69).
$^{13}$C-NMR (DMSO-d$_6$) δ 167.0, 149.6, 149.1, 148.4, 132.5, 128.1, 122.1, 114.9, 113.7, 111.5, 77.5, 44.9, 39.7, 22.9, 11.0.

Example 433

N-(3-Methyl-butoxy)-2-[(pyridin-4-ylmethyl)-amino]-benzamide (compound 118)

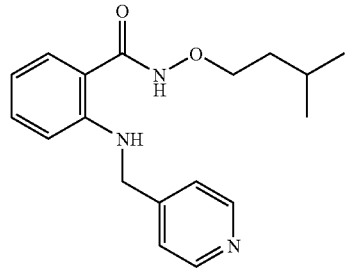

General procedure 1, method 2.
Starting materials: 2-[(Pyridin-4-ylmethyl)-amino]-benzoic acid (see preparation 1) and O-(3-methyl-butyl)-hydroxylamine hydrochloride (see preparation 70).
$^{13}$C-NMR (DMSO-d$_6$) δ 167.1, 149.6, 149.1, 148.4, 132.5, 128.1, 122.1, 114.9, 113.6, 111.6, 73.7, 44.9, 36.6, 24.6, 22.5.

Example 434

N-Cyclobutylmethoxy-2-[(pyridin-4-ylmethyl)-amino]-benzamide (compound 119)

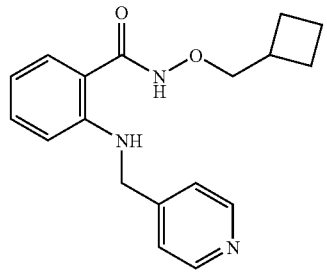

General procedure 1, method 2.
Starting materials: 2-[(Pyridin-4-ylmethyl)-amino]-benzoic acid (see preparation 1) and O-cyclobutylmethyl-hydroxylamine hydrochloride (see preparation 71).
$^{13}$C-NMR (DMSO-d$_6$) δ 166.9, 149.5, 149.0, 148.3, 132.4, 128.0, 122.0, 114.8, 113.5, 111.4, 79.2, 44.8, 33.3, 24.5, 18.2.

Example 435

N-Cyclohexylmethoxy-2-[(pyridin-4-ylmethyl)-amino]-benzamide (compound 120)

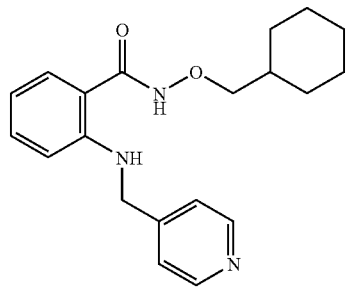

General procedure 1, method 2.

Starting materials: 2-[(Pyridin-4-ylmethyl)-amino]-benzoic acid (see preparation 1) and O-cyclohexylmethyl-hydroxylamine hydrochloride (see preparation 72).

$^{13}$C-NMR (DMSO-$d_6$) δ 166.9, 149.5, 149.0, 148.3, 132.3, 128.0, 122.0, 114.8, 113.5, 111.4, 80.6, 44.8, 36.2, 29.2, 26.0, 25.2.

Example 436

N-Cycloheptylmethoxy-2-[(pyridin-4-ylmethyl)-amino]-benzamide (compound 121)

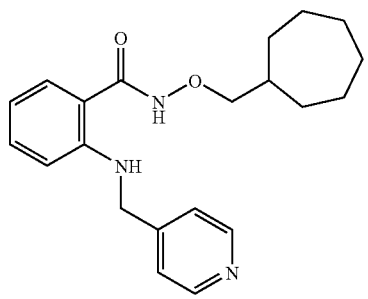

General procedure 1A.

Starting materials: 1-Pyridin-4-ylmethyl-1H-benzo[d][1,3]oxazine-2,4-dione (see preparation 7A) and O-cycloheptylmethyl-hydroxylamine hydrochloride (see preparation 73).

$^{13}$C-NMR (DMSO-$d_6$) δ 166.9, 149.7, 149.5, 149.0, 132.3, 128.0, 122.7, 122.0, 114.8, 111.4, 80.5, 44.9, 37.7, 30.4, 28.0, 25.9.

Example 437

N-Cyclooctylmethoxy-2-[(pyridin-4-ylmethyl)-amino]-benzamide (compound 122)

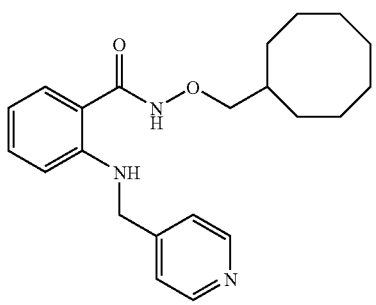

General procedure 1, method 2.

Starting materials: 2-[(Pyridin-4-ylmethyl)-amino]-benzoic acid (see preparation 1) and O-cyclooctylmethyl-hydroxylamine (see preparation 74).

$^{13}$C-NMR (CDCl$_3$) δ 169.0, 149.7, 149.1, 148.8, 133.4, 127.3, 122.0, 115.6, 112.8, 112.1, 82.9, 46.0, 36.5, 29.3, 26.9, 26.4, 25.4.

Example 438

N-(1-Cyclopentyl-ethoxy)-2-[(pyridin-4-ylmethyl)-amino]-benzamide (compound 123)

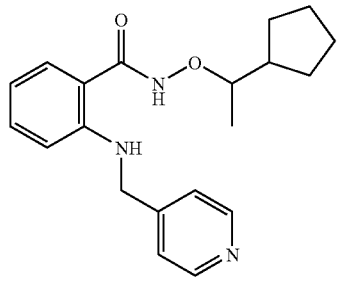

General procedure 1A.

Starting materials: 1-Pyridin-4-ylmethyl-1H-benzo[d][1,3]oxazine-2,4-dione (see preparation 7A) and O-(1-cyclopentyl-ethyl)-hydroxylamine hydrochloride (see preparation 75).

$^{13}$C-NMR (DMSO-$d_6$) δ 167.1, 149.5, 149.1, 148.2, 132.2, 128.2, 122.0, 114.8, 114.0, 111.4, 84.0, 44.8, 43.9, 28.5, 28.4, 25.2, 17.3

Example 439

N-Cyclohexyloxy-2-[(pyridin-4-ylmethyl)-amino]-benzamide (compound 124)

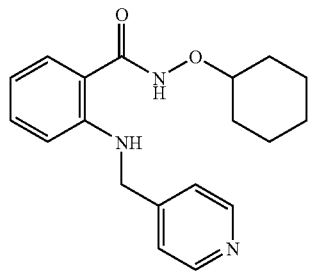

General procedure 1A.

Starting materials: 1-Pyridin-4-ylmethyl-1H-benzo[d][1,3]oxazine-2,4-dione (see preparation 7A) and O-cyclohexyl-hydroxylamine hydrochloride (see preparation 76).

$^{13}$C-NMR (DMSO-$d_6$) δ 167.1, 149.5, 149.0, 148.2, 132.3, 128.1, 122.0, 114.8, 113.8, 111.4, 81.4, 44.8, 30.3, 25.1, 23.0.

Example 440

N-(2-Cyclopropyl-ethoxy)-2-[(pyridin-4-ylmethyl)-amino]-benzamide (compound 125)

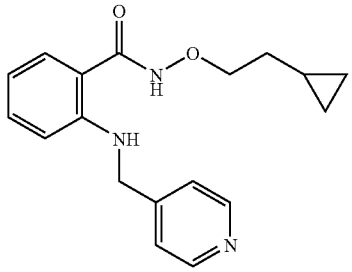

General procedure 1, method 2.

Starting materials: 2-[(Pyridin-4-ylmethyl)-amino]-benzoic acid (see preparation 1) and O-(2-cyclopropyl-ethyl)-hydroxylamine hydrochloride (see preparation 77).

$^{13}$C-NMR (DMSO-d$_6$) δ 167.1, 149.6, 149.1, 148.4, 132.5, 128.1, 122.1, 114.9, 113.6, 111.5, 75.3, 44.9, 32.7, 7.7, 4.2.

Example 441

N-(2-Cyclopentyl-ethoxy)-2-[(pyridin-4-ylmethyl)-amino]-benzamide (compound 126)

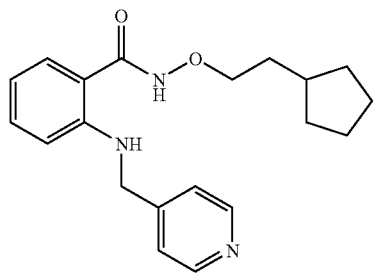

General procedure 1, method 2.

Starting materials: 2-[(Pyridin-4-ylmethyl)-amino]-benzoic acid (see preparation 1) and O-(2-cyclopentyl-ethyl)-hydroxylamine (see preparation 78).

$^{13}$C-NMR (CDCl$_3$) δ 169.1, 149.8, 149.1, 148.7, 133.4, 127.3, 122.0, 115.7, 112.8, 112.1, 46.0, 36.8, 34.3, 32.7, 25.1.

Example 442

N-(3-Cyclopentyl-propoxy)-2-[(pyridin-4-ylmethyl)-amino]-benzamide (compound 127)

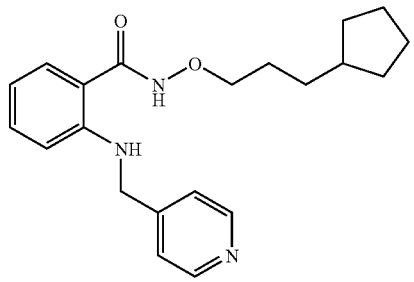

General procedure 1, method 2.

Starting materials: 2-[(Pyridin-4-ylmethyl)-amino]-benzoic acid (see preparation 1) and O-(3-cyclopentyl-propyl)-hydroxylamine (see preparation 79).

$^{13}$C-NMR (CDCl$_3$) δ 168.8, 149.4, 148.7, 133.0, 127.3, 121.8, 115.4, 112.7, 111.7, 77.0, 45.8, 39.7, 32.4, 31.9, 27.2, 24.9.

Example 443

N-(Cyclohex-3-enylmethoxy)-2-[(pyridin-4-ylmethyl)-amino]-benzamide (compound 128)

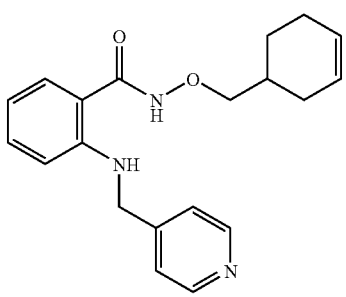

General procedure 1, method 2.

Starting materials: 2-[(Pyridin-4-ylmethyl)-amino]-benzoic acid (see preparation 1) and O-cyclohex-3-enylmethyl-hydroxylamine hydrochloride (see preparation 80).

$^{13}$C-NMR (DMSO-d$_6$) δ 167.0, 149.4, 149.1, 148.3, 132.4, 128.0, 126.7, 125.7, 122.0, 114.8, 113.5, 111.5, 79.7, 44.8, 32.1, 27.7, 24.8, 23.8.

Example 444

N-(6-Methyl-cyclohex-3-enylmethoxy)-2-[(pyridin-4-ylmethyl)-amino]-benzamide (compound 129)

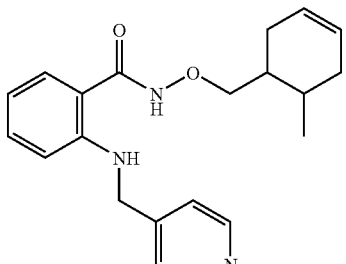

General procedure 1, method 2.

Starting materials: 2-[(Pyridin-4-ylmethyl)-amino]-benzoic acid (see preparation 1) and O-(6-methyl-cyclohex-3-enylmethyl)-hydroxylamine hydrochloride (see preparation 81).

$^{13}$C-NMR (DMSO-d$_6$) δ 167.0, 149.5, 149.0, 148.3, 132.4, 128.0, 125.8, 125.7, 122.0, 114.8, 113.5, 111.5, 77.8, 44.8, 38.0, 32.6, 29.2, 27.4, 19.2.

Example 445

N-(trans-4-Hydroxymethyl-cyclohexylmethoxy)-2-[(pyridin-4-ylmethyl)-amino]-benzamide (compound 130)

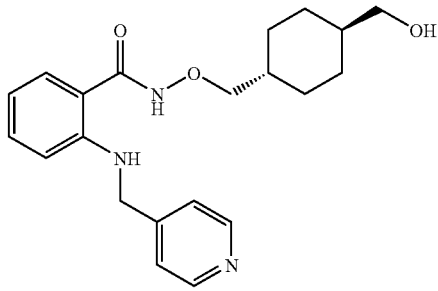

General procedure 1, method 2.

Starting materials: 2-[(Pyridin-4-ylmethyl)-amino]-benzoic acid (see preparation 1) and (trans-4-aminooxymethyl-cyclohexyl)-methanol (see preparation 82).

$^{13}$C-NMR (CDCl$_3$) δ 169.1, 149.7, 149.7, 148.9, 133.4, 127.6, 122.1, 115.6, 112.9, 112.0, 82.3, 68.4, 46.0, 40.5, 37.1, 29.2, 28.8.

Example 446

N-(3-Methoxy-cyclohexylmethoxy)-2-[(pyridin-4-ylmethyl)-amino]-benzamide (compound 131)

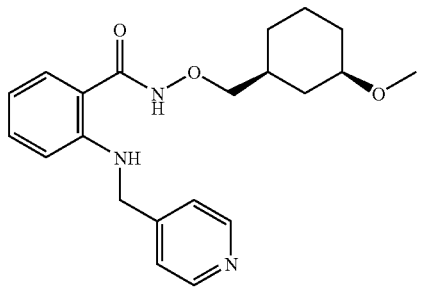

General procedure 1A.

Starting materials: 1-Pyridin-4-ylmethyl-1H-benzo[d][1,3]oxazine-2,4-dione (see preparation 7A) and O-(3-methoxy-cyclohexylmethyl)-hydroxylamine hydrochloride (see preparation 83).

$^{13}$C-NMR (DMSO-d$_6$) δ 167.0, 149.5, 149.0, 148.3, 132.4, 128.0, 122.0, 114.8, 113.5, 111.4, 80.1, 78.1, 54.8, 44.8, 35.1, 34.9, 31.7, 28.5, 23.0.

Example 447

N-(Adamantan-1-ylmethoxy)-2-[(pyridin-4-ylmethyl)-amino]-benzamide (compound 132)

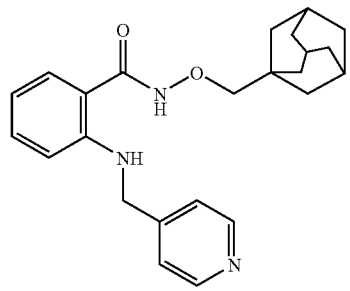

General procedure 1, method 2.

Starting materials: 2-[(Pyridin-4-ylmethyl)-amino]-benzoic acid (see preparation 1) and O-adamantan-1-ylmethyl-hydroxylamine hydrochloride (see preparation 84).

$^{13}$C-NMR (DMSO-d$_6$) δ 166.8, 149.5, 149.0, 148.3, 132.3, 128.0, 122.0, 114.8, 113.6, 111.4, 85.4, 44.7, 36.5, 33.4, 27.4, 27.3.

Example 448

N-(Bicyclo[2.2.1]hept-2-ylmethoxy)-2-[(pyridin-4-ylmethyl)-amino]-benzamide (compound 133)

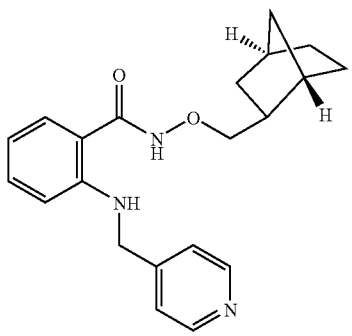

General procedure 1, method 2.

Starting materials: 2-[(Pyridin-4-ylmethyl)-amino]-benzoic acid (see preparation 1) and O-bicyclo[2.2.1]hept-2-ylmethyl-hydroxylamine hydrochloride (see preparation 85).

$^{13}$C-NMR (DMSO-d$_6$) δ 167.0, 149.5, 149.4, 148.4, 132.5, 128.1, 122.1, 114.9, 113.7, 111.6, 79.1, 77.3, 44.9, 39.4, 38.1, 38.0, 37.9, 36.1, 35.6, 35.0, 33.8, 33.5, 29.4, 28.5, 22.5.

Example 449

N-(6,6-Dimethyl-bicyclo[3.1.1]hept-2-ylmethoxy)-2-[(pyridin-4-ylmethyl)-amino]-benzamide) (compound 134)

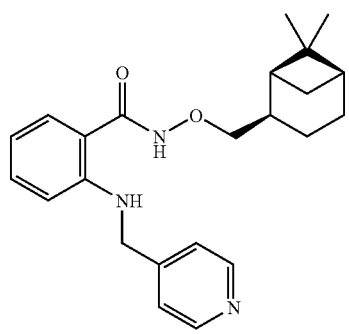

General procedure 1, method 2.

Starting materials: 2-[(Pyridin-4-ylmethyl)-amino]-benzoic acid (see preparation 1) and O-(6,6-dimethyl-bicyclo[3.1.1]hept-2-ylmethyl)-hydroxylamine hydrochloride (see preparation 86).

$^{13}$C-NMR (DMSO-d$_6$) δ 166.9, 149.5, 149.0, 148.3, 132.4, 128.0, 122.0, 114.8, 113.5, 111.5, 80.1, 44.8, 42.7, 39.3, 38.0, 32.3, 27.6, 25.5, 23.0, 18.3.

Example 450

2-[(Pyridin-4-ylmethyl)-amino]-N-(tetrahydro-furan-2-ylmethoxy)-benzamide (compound 135)

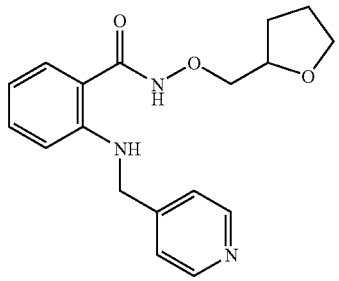

General procedure 1, method 2.

Starting materials: 2-[(Pyridin-4-ylmethyl)-amino]-benzoic acid (see preparation 1) and O-(tetrahydro-furan-2-ylmethyl)-hydroxylamine hydrochloride (see preparation 87).

$^1$H-NMR (DMSO-d$_6$) δ 11.58 (s, 1H), 8.49 (d, 2H), 7.92 (t, 1H), 7.42 (d, 1H), 7.32 (d, 2H), 7.19 (dt, 1H), 6.53 (m, 2H), 4.46 (d, 2H), 4.09 (m, 1H), 3.88 (d, 2H), 3.8-3.6 (m, 2H), 2.0-1.6 (m, 4H).

Example 451

2-[(Pyridin-4-ylmethyl)-amino]-N-(tetrahydro-furan-3-ylmethoxy)-benzamide (compound 136)

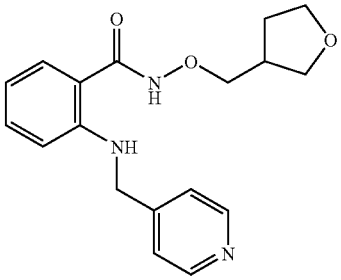

General procedure 1A.

Starting materials: 1-Pyridin-4-ylmethyl-1H-benzo[d][1,3]oxazine-2,4-dione (see preparation 7A) and O-(tetrahydro-furan-3-ylmethyl)-hydroxylamine hydrochloride (see preparation 88).

$^{13}$C-NMR (DMSO-d$_6$) δ 167.1, 149.5, 149.0, 148.3, 132.5, 128.0, 121.9, 114.8, 113.3, 111.5, 77.2, 69.9, 66.7, 44.7, 37.3, 28.4.

Example 452

N-(3-Methyl-4,5-dihydro-isoxazol-5-ylmethoxy)-2-[(pyridin-4-ylmethyl)-amino]-benzamide (compound 137)

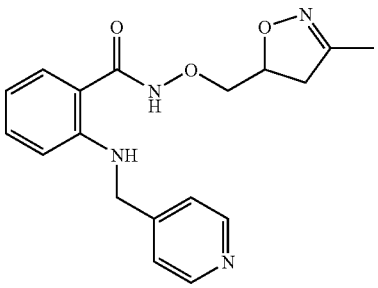

Prepared by a similar method as described for example 415. Starting materials: 2-[(Pyridin-4-ylmethyl)-amino]-benzoic acid pentafluorophenyl ester (preparation 7C) and O-(3-methyl-4,5-dihydro-isoxazol-5-ylmethyl)-hydroxylamine (see preparation 89).

$^{13}$C-NMR (DMSO-d$_6$) δ 167.3, 155.4, 149.6, 149.1, 148.4, 132.6, 128.2, 122.1, 114.9, 113.3, 111.6, 76.9, 76.6, 44.9, 40.5, 12.6.

Example 453

N-(3-Ethyl-4,5-dihydro-isoxazol-5-ylmethoxy)-2-[(pyridin-4-ylmethyl)-amino]-benzamide (compound 138)

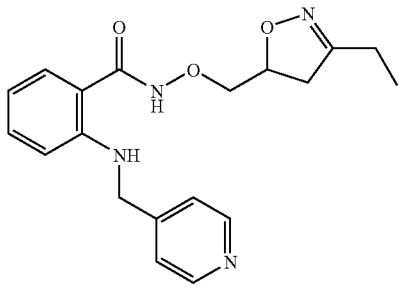

Prepared by a similar method as described for example 415. Starting materials: 2-[(Pyridin-4-ylmethyl)-amino]-benzoic acid pentafluorophenyl ester (preparation 7C) and O-(3-ethyl-4,5-dihydro-isoxazol-5-ylmethyl)-hydroxylamine (see preparation 90).

$^{13}$C-NMR (DMSO-d$_6$) δ 167.2, 159.7, 149.5, 148.9, 148.3, 132.5, 128.1, 122.0, 114.8, 113.2, 111.5, 76.6, 76.4, 44.8, 38.7, 20.4, 10.6.

Example 454

N-(3-Butyl-4,5-dihydro-isoxazol-5-ylmethoxy)-2-[(pyridin-4-ylmethyl)-amino]-benzamide (compound 139)

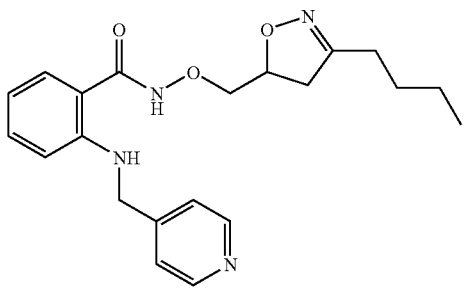

Prepared by a similar method as described for example 415. Starting materials: 2-[(Pyridin-4-ylmethyl)-amino]-benzoic acid pentafluorophenyl ester (preparation 7C) and O-(3-butyl-4,5-dihydro-isoxazol-5-ylmethyl)-hydroxylamine (see preparation 91).

$^{13}$C-NMR (DMSO-d$_6$) δ 167.1, 158.5, 149.4, 148.8, 148.2, 132.4, 128.0, 121.8, 114.7, 113.0, 111.4, 76.4, 76.3, 44.7, 38.5, 27.6, 26.3, 21.5, 13.4.

Example 455

2-[(Pyridin-4-ylmethyl)-amino]-N-(tetrahydro-pyran-2-yloxy)-benzamide (compound 140)

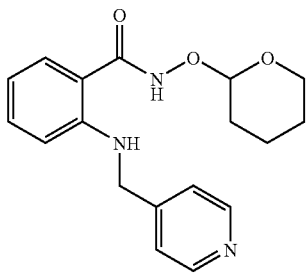

General procedure 1, method 1.
Starting materials: 2-[(Pyridin-4-ylmethyl)-amino]-benzoic acid (see preparation 1) and O-(tetrahydro-2H-pyran-2-yl)hydroxylamine (Aldrich).
$^{13}$C-NMR (DMSO-$d_6$) δ 166.8, 149.5, 148.9, 148.2, 132.4, 128.3, 122.0, 114.8, 113.5, 111.4, 100.8, 61.2, 44.8, 27.8, 24.6, 18.2.

Example 456

2-[(Pyridin-4-ylmethyl)-amino]-N-(tetrahydro-pyran-4-ylmethoxy)-benzamide (compound 141)

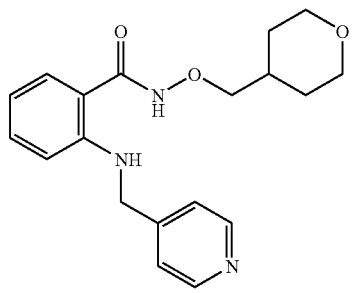

General procedure 1, method 2.
Starting materials: 2-[(Pyridin-4-ylmethyl)-amino]-benzoic acid (see preparation 1) and O-(tetrahydro-pyran-4-ylmethyl)-hydroxylamine hydrochloride (see preparation 92).
$^{13}$C-NMR (DMSO-$d_6$) δ 167.0, 149.5, 149.0, 148.3, 132.4, 128.0, 122.0, 114.8, 113.5, 111.5, 79.9, 66.6, 44.8, 33.6, 29.2.

Example 457

2-[(Pyridin-4-ylmethyl)-amino]-N-(tetrahydro-pyran-2-ylmethoxy)-benzamide (compound 142)

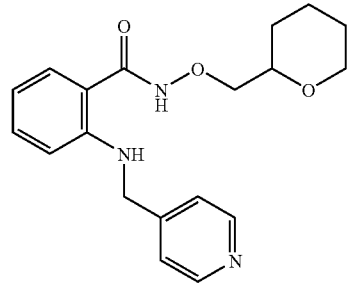

General procedure 1, method 2.
Starting materials: 2-[(Pyridin-4-ylmethyl)-amino]-benzoic acid (see preparation 1) and O-(tetrahydro-pyran-2-ylmethyl)-hydroxylamine hydrochloride (see preparation 93).
$^{13}$C-NMR (DMSO-$d_6$) δ 167.0, 149.5, 148.9, 148.3, 132.4, 128.0, 122.0, 114.8, 113.4, 111.4, 78.5, 74.7, 67.1, 44.8, 27.7, 25.4, 22.5.

Example 458

4-Fluoro-N-(2-methyl-thiazol-4-ylmethoxy)-2-[(pyridin-4-ylmethyl)amino]-benzamide (compound 143)

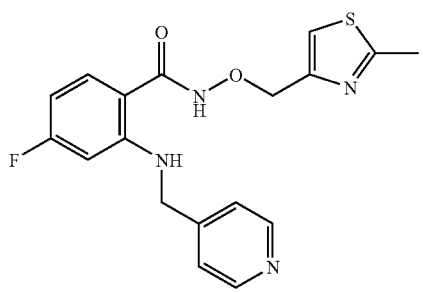

General procedure 1, method 1.
Starting materials: 4-Fluoro-2-[(pyridin-4-ylmethyl)-amino]-benzoic acid (see preparation 1A) and O-(2-methyl-thiazol-4-ylmethyl)-hydroxylamine hydrochloride (see preparation 12).
$^{13}$C-NMR (DMSO-$d_6$) δ 165.3, 165.0, 150.8, 150.6, 149.6, 148.3, 130.6, 122.0, 118.9, 109.9, 101.5, 97.8, 71.8, 44.7, 18.6.

Example 459

2-Fluoro-N-(2-methyl-thiazol-4-ylmethoxy)-6-[(pyridin-4-ylmethyl)-amino]-benzamide (compound 144)

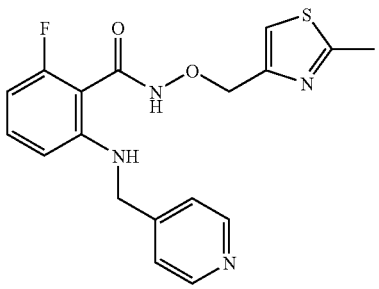

General procedure 1, method 1.
Starting materials: 2-Fluoro-6-[(pyridin-4-ylmethyl)-amino]-benzoic acid (see preparation 1B) and O-(2-methyl-thiazol-4-ylmethyl)-hydroxylamine hydrochloride (see preparation 12).
$^{13}$C-NMR (DMSO-$d_6$) δ 165.4, 160.9, 160.0, 150.4, 149.4, 148.8, 147.9, 131.8, 121.9, 119.0, 106.8, 106.3, 102.4, 71.9, 45.0, 18.6.

Example 460

5-Fluoro-N-(2-methyl-thiazol-4-ylmethoxy)-2-[(pyridin-4-ylmethyl)-amino]-benzamide (compound 145)

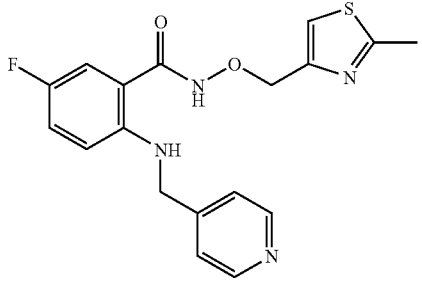

General procedure 1, method 1.

Starting materials: 5-Fluoro-2-[(pyridin-4-ylmethyl)-amino]-benzoic acid (see preparation 1C) and O-(2-methyl-thiazol-4-ylmethyl)-hydroxylamine hydrochloride (see preparation 12).

$^{13}$C-NMR (DMSO-$d_6$) δ 165.4, 154.1, 151.1, 150.5, 149.6, 148.8, 145.0, 122.0, 119.1, 114.2, 113.5, 112.6, 71.8, 45.1, 38.6, 18.6.

Example 461

3-Methoxy-N-(2-methyl-thiazol-4-ylmethoxy)-2-[(pyridin-4-ylmethyl)-amino]-benzamide (compound 146)

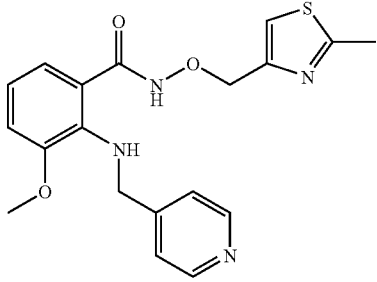

3-Methoxy-2-[(pyridin-4-ylmethyl)-amino]-benzoic acid (200 mg, see preparation 1D) was dissolved in DMF (20 ml) and triethylamine (0.65 ml) at 50-60° C. N,N,N',N'-Tetramethyl-O-(benzotriazole-1-yl)uronium-tetrafluoroborate (250 mg) was added and after 5 minutes O-(2-methyl-thiazol-4-ylmethyl)-hydroxylamine hydrochloride (209 mg, see preparation 12) was added. The reaction mixture was heated to 90° C. and stirred at this temperature for 2 hours. The mixture was cooled to room temperature and water was added. The mixture was extracted several times with EtOAc and the combined organic layers were washed with water, saturated aqueous sodium bicarbonate, water, and brine. The organic layer was dried (MgSO$_4$) and evaporated under reduced pressure. The remaining material was purified by column chromatography on silica gel (elution with 1 to 4% methanol in EtOAc) and gave the title compound as an yellow oil. $^{13}$C-NMR (DMSO-$d_6$) δ 165.3, 150.4, 150.0, 149.8, 149.3, 137.8, 122.2, 120.5, 118.8, 117.9, 114.0, 71.8, 55.7, 48.3, 18.6.

Example 462

N-(4-Chloro-benzyloxy)-3-methoxy-2-[(pyridin-4-ylmethyl)-amino]-benzamide (compound 147)

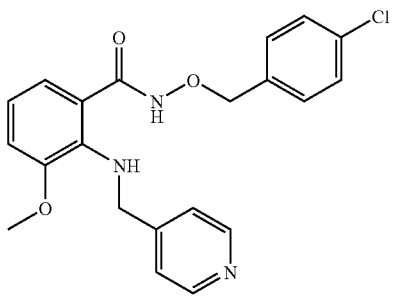

General procedure 1, method 1.

Starting materials: 3-Methoxy-2-[(pyridin-4-ylmethyl)-amino]-benzoic acid (see preparation 1D) and O-(4-chloro-benzyl)-hydroxylamine hydrochloride (see preparation 9).

$^{13}$C-NMR (DMSO-$d_6$) δ 166.6, 150.0, 149.8, 149.2, 137.8, 132.8, 131.3, 130.5, 128.3, 128.2, 122.2, 120.4, 117.9, 114.1, 75.8, 55.7, 48.3.

Example 463

4,5-Dimethoxy-N-(2-methyl-thiazol-4-ylmethoxy)-2-[(pyridin-4-ylmethyl)-amino]-benzamide (compound 148)

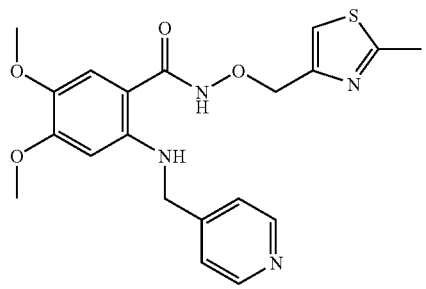

General procedure 1, method 1.

Starting materials: 4,5-Dimethoxy-2-[(pyridin-4-ylmethyl)-amino]-benzoic acid (see preparation 1E) and O-(2-methyl-thiazol-4-ylmethyl)-hydroxylamine hydrochloride (see preparation 12).

$^{13}$C-NMR (DMSO-$d_6$) δ 165.3, 153.3, 150.6, 149.6, 149.1, 145.7, 138.7, 122.2, 118.9, 112.5, 103.0, 96.2, 72.0, 56.4, 55.2, 45.3, 18.6.

Example 464

N-Benzyloxy-4,5-dimethoxy-2-[(pyridin-4-ylmethyl)-amino]-benzamide (compound 149)

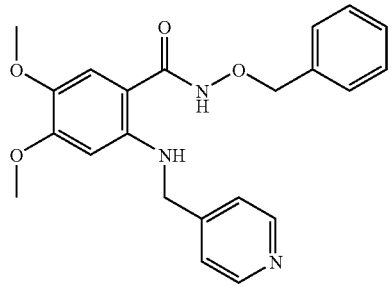

General procedure 1, method 1.

Starting materials: 4,5-Dimethoxy-2-[(pyridin-4-ylmethyl)-amino]-benzoic acid (see preparation 1E) and O-benzyl-hydroxylamine hydrochloride (Aldrich).

$^{13}$C-NMR (DMSO-d$_6$) δ 167.3, 153.3, 149.6, 149.2, 145.7, 138.7, 136.0, 128.8, 128.2, 128.1, 122.2, 112.5, 103.0, 96.2, 77.0, 56.4, 55.2, 45.2.

Example 465

2-Methyl-N-(2-methyl-thiazol-4-ylmethoxy)-6-[pyridin-4-ylmethyl)-amino]-benzamide (compound 150)

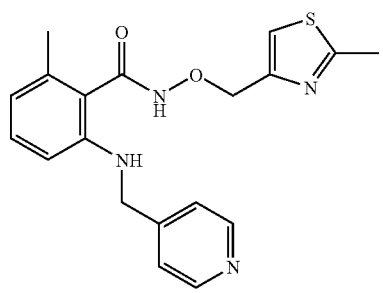

General procedure 1, method 1.

Starting materials: 2-Methyl-6-[(pyridin-4-ylmethyl)-amino]-benzoic acid (see preparation 1F) and O-(2-methyl-thiazol-4-ylmethyl)-hydroxylamine hydrochloride (see preparation 12).

$^{13}$C-NMR (DMSO-d$_6$) δ 165.4, 164.7, 150.7, 149.5, 149.3, 145.0, 135.4, 129.6, 121.9, 120.3, 118.9, 117.8, 108.2, 71.7, 45.0, 19.1, 18.6.

Example 466

N-Benzyloxy-2-methyl-6-[(pyridin-4-ylmethyl)-amino]-benzamide (compound 151)

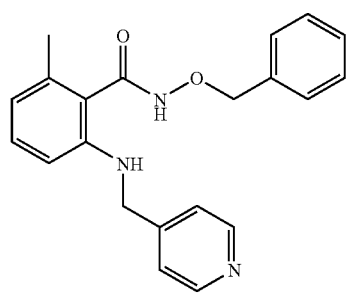

General procedure 1, method 1.

Starting materials: 2-Methyl-6-[(pyridin-4-ylmethyl)-amino]-benzoic acid (see preparation 1F) and O-benzyl-hydroxylamine hydrochloride (Aldrich).

$^{13}$C-NMR (DMSO-d$_6$) δ 164.7, 149.4, 149.3, 145.0, 136.1, 135.3, 129.6, 128.7, 128.2, 121.9, 120.2, 117.8, 108.2, 76.7, 45.0, 19.1.

Example 467

5-Methyl-N-(2-methyl-thiazol-4-ylmethoxy)-2-[(pyridin-4-ylmethyl)-amino]-benzamide (compound 152)

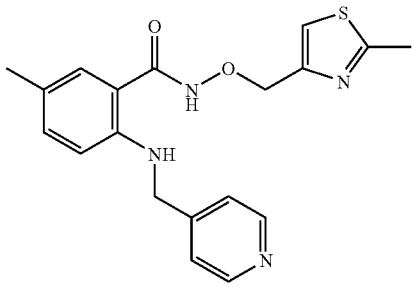

General procedure 1, method 1.

Starting materials: 5-Methyl-2-[(pyridin-4-ylmethyl)-amino]-benzoic acid (see preparation 1G) and O-(2-methyl-thiazol-4-ylmethyl)-hydroxylamine hydrochloride (see preparation 12).

$^{13}$C-NMR (DMSO-d$_6$) δ 165.3, 150.6, 149.5, 149.2, 146.1, 133.0, 128.3, 123.3, 122.0, 118.8, 113.4, 111.6, 71.9, 45.0, 19.7, 18.6.

Example 468

N-Benzyloxy-5-methyl-2-[(pyridin-4-ylmethyl)-amino]-benzamide (compound 153)

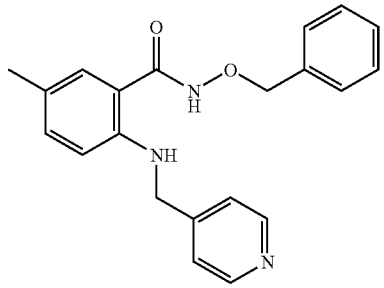

General procedure 1, method 1.

Starting materials: 5-Methyl-2-[(pyridin-4-ylmethyl)-amino]-benzoic acid (see preparation 1G) and O-benzyl-hydroxylamine hydrochloride (Aldrich).

$^{13}$C-NMR (DMSO-d$_6$) δ 167.1, 149.5, 149.2, 146.1, 136.0, 133.0, 128.8, 128.2, 128.2, 123.2, 122.0, 113.4, 111.6, 76.9, 44.9, 19.7.

Example 469

5-Bromo-N-(4-cyano-2-methoxy-benzyloxy)-2-[(pyridin-4-ylmethyl)-amino]-benzamide (compound 154)

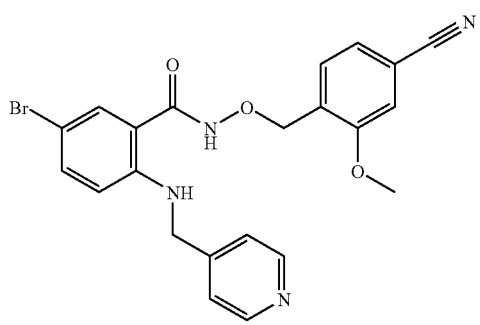

General procedure 1, method 2.

Starting materials: 5-Bromo-2-[(pyridin-4-ylmethyl)-amino]-benzoic acid (see preparation 1H) and 4-aminooxymethyl-3-methoxy-benzonitrile hydrochloride (see preparation 45).

$^{13}$C-NMR (DMSO-d$_6$) δ 165.7, 157.2, 149.6, 148.5, 147.4, 134.8, 130.5, 130.2, 129.9, 124.4, 121.9, 118.6, 115.0, 114.1, 113.7, 111.9, 105.5, 71.0, 56.1, 44.7.

Example 470

N-Benzyloxy-5-bromo-2-[(pyridin-4-ylmethyl)-amino]-benzamide (compound 155)

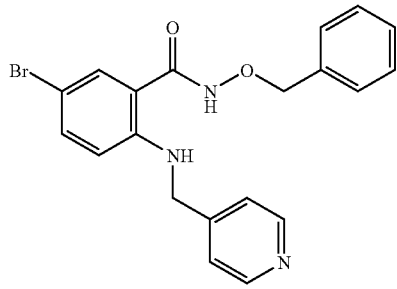

General procedure 1, method 2.

Starting materials: 5-Bromo-2-[(pyridin-4-ylmethyl)-amino]-benzoic acid (see preparation 1H) and O-benzyl-hydroxylamine hydrochloride (Aldrich).

$^{13}$C-NMR (DMSO-d$_6$) δ 165.6, 149.6, 148.5, 147.3, 135.8, 134.7, 130.2, 128.8, 128.2, 121.9, 115.2, 113.7, 105.5, 77.0, 44.7.

Example 471

N-(4-Cyano-benzyloxy)-2-[(pyridin-4-ylmethyl)-amino]-nicotinamide (compound 156)

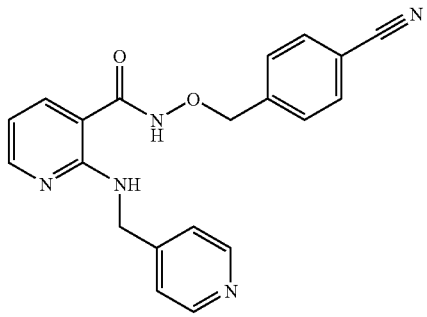

General procedure 1, method 1.

Starting materials: 2-[(Pyridin-4-ylmethyl)-amino]-nicotinic acid (see preparation 2) and O-(4-cyanobenzyl)hydroxylamine hydrochloride (see preparation 10).

$^{13}$C-NMR (DMSO-d$_6$) δ 165.9, 156.5, 151.2, 149.6, 149.3, 141.7, 136.1, 132.2, 129.2, 121.9, 118.6, 111.1, 110.8, 108.0, 76.0, 42.7.

Example 472

N-(2-Chloro-4-cyano-benzyloxy)-2-[(pyridin-4-ylmethyl)-amino]-nicotinamide (compound 157)

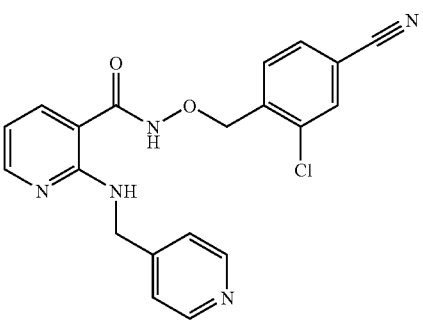

General procedure 1, method 1.

Starting materials: 2-[(Pyridin-4-ylmethyl)-amino]-nicotinic acid (see preparation 2) and 4-aminooxymethyl-3-chloro-benzonitrile hydrochloride (see preparation 44).

$^{13}$C-NMR (DMSO-d$_6$) δ 156.4, 151.2, 149.6, 149.3, 139.4, 136.2, 133.6, 132.6, 131.4, 131.0, 121.9, 117.3, 112.5, 111.1, 107.9, 73.2, 42.7.

Example 473

N-(4-Cyano-2-fluoro-benzyloxy)-2-[(pyridin-4-ylmethyl)-amino]-nicotinamide (compound 158)

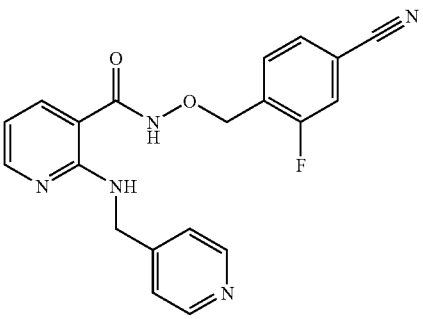

General procedure 1, method 1.

Starting materials: 2-[(Pyridin-4-ylmethyl)-amino]-nicotinic acid (see preparation 2) and 4-aminooxymethyl-3-fluoro-benzonitrile hydrochloride (see preparation 42).

$^{13}$C-NMR (DMSO-d$_6$) δ 160.1, 151.2, 149.6, 149.3, 136.1, 132.7, 128.6, 121.9, 119.3, 117.4, 112.8, 111.1, 107.9, 69.8, 42.7.

Example 474

N-(3-Bromo-4-cyano-benzyloxy)-2-[(pyridin-4-ylmethyl)-amino]-nicotinamide (compound 159)

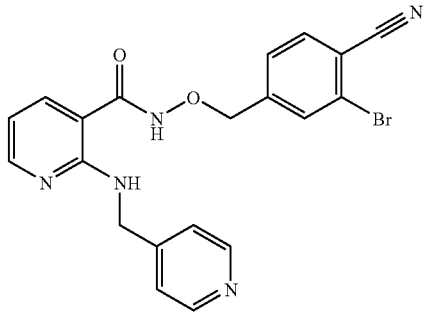

General procedure 1, method 1.
Starting materials: 2-[(Pyridin-4-ylmethyl)-amino]-nicotinic acid (see preparation 2) and 4-aminooxymethyl-2-bromo-benzonitrile hydrochloride (see preparation 43).
$^{13}$C-NMR (DMSO-d$_6$) δ 165.9, 156.5, 151.2, 149.6, 149.3, 136.1, 134.7, 132.4, 128.0, 124.3, 121.9, 117.1, 113.7, 111.1, 107.9, 75.2, 42.7.

Example 475

N-(2-Iodo-benzyloxy)-2-[(pyridin-4-ylmethyl)-amino]-nicotinamide (compound 160)

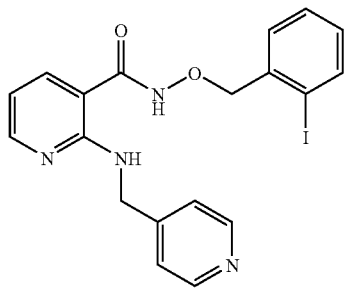

General procedure 1, method 1.
Starting materials: 2-[(Pyridin-4-ylmethyl)-amino]-nicotinic acid (see preparation 2) and O-(2-iodo-benzyl)-hydroxylamine hydrochloride (see preparation 20).
$^{13}$C-NMR (DMSO-d$_6$) δ 156.5, 151.1, 149.6, 149.3, 139.0, 138.3, 136.2, 130.4, 130.2, 128.3, 121.9, 111.1, 108.1, 99.5, 80.2, 42.7.

Example 476

N-(2-Bromo-benzyloxy)-2-[(pyridin-4-ylmethyl)-amino]-nicotinamide (compound 161)

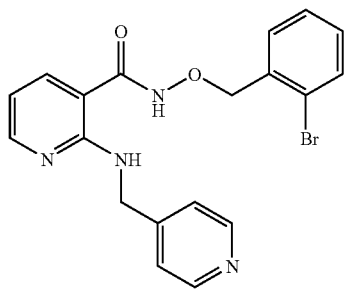

General procedure 1, method 1.
Starting materials: 2-[(Pyridin-4-ylmethyl)-amino]-nicotinic acid (see preparation 2) and O-(2-bromo-benzyl)-hydroxylamine hydrochloride (Bionet).
$^{13}$C-NMR (DMSO-d$_6$) δ 156.6, 151.2, 149.7, 149.4, 136.3, 135.3, 132.6, 131.3, 130.4, 127.8, 123.4, 122.0, 111.2, 108.2, 76.0, 42.8.

Example 477

N-(4-Cyano-2-methoxy-benzyloxy)-2-[(pyridin-4-ylmethyl)-amino]-nicotinamide (compound 162)

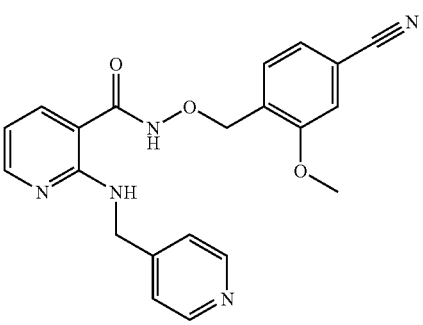

General procedure 1, method 1.
Starting materials: 2-[(Pyridin-4-ylmethyl)-amino]-nicotinic acid (see preparation 2) and 4-aminooxymethyl-3-methoxy-benzonitrile hydrochloride (see preparation 45).
$^{13}$C-NMR (DMSO-d$_6$) δ 165.7, 157.1, 156.5, 151.1, 149.6, 149.3, 136.1, 130.4, 129.9, 124.4, 121.9, 118.6, 114.1, 111.8, 111.1, 108.1, 71.0, 56.0, 42.7.

Example 478

N-(2-Methyl-thiazol-4-ylmethoxy)-2-[(pyridin-4-ylmethyl)-amino]-nicotinamide (compound 163)

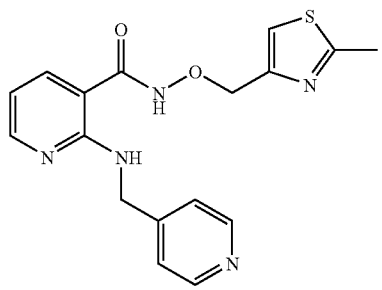

General procedure 1, method 1.
Starting materials: 2-[(Pyridin-4-ylmethyl)-amino]-nicotinic acid (see preparation 2) and O-(2-methyl-thiazol-4-ylmethyl)-hydroxylamine hydrochloride (see preparation 12).
$^{13}$C-NMR (DMSO-d$_6$) δ 165.4, 156.5, 151.0, 150.4, 149.6, 149.3, 136.1, 121.9, 119.1, 111.1, 108.3, 71.8, 42.7, 18.6.

Example 479

N-Cyclopentylmethoxy-2-[(pyridin-4-ylmethyl)-amino]-nicotinamide (compound 164)

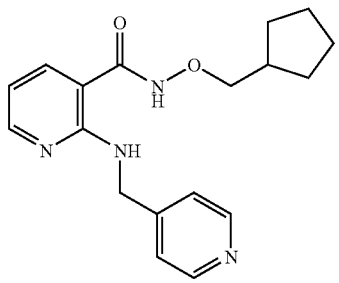

General procedure 1, method 1.
Starting materials: 2-[(Pyridin-4-ylmethyl)-amino]-nicotinic acid (see preparation 2) and o-cyclopentylmethyl-hydroxylamine hydrochloride (see preparation 66).
$^{13}$C-NMR (DMSO-d$_6$) δ 165.5, 156.7, 151.0, 149.6, 149.3, 136.0, 122.0, 111.1, 108.3, 79.5, 42.7, 37.6, 28.9, 24.9.

Example 480

N-Benzyloxy-2-(4-fluoro-benzylamino)-nicotinamide (compound 165)

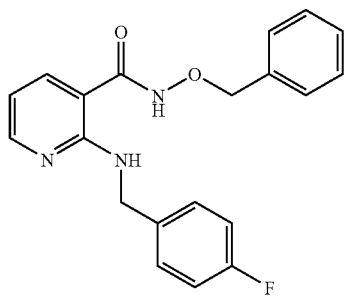

General procedure 1, method 1.
Starting materials: 2-(4-Fluoro-benzylamino)-nicotinic acid (see preparation 3) and O-benzyl-hydroxylamine hydrochloride (Aldrich).
$^{13}$C-NMR (DMSO-d$_6$) δ 165.8, 156.8, 151.2, 140.1, 136.0, 135.8, 128.8, 128.2, 127.1, 126.6, 110.7, 107.7, 76.9, 43.7.

Example 481

N-Benzyloxy-2-(4-chloro-benzylamino)-nicotinamide (compound 166)

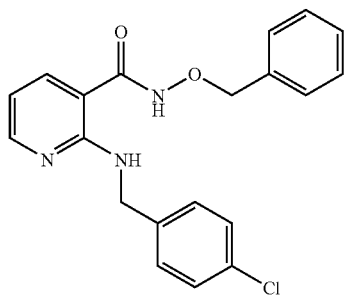

General procedure 1, method 1.
Starting materials: 2-(4-Chloro-benzylamino)-nicotinic acid (see preparation 3A) and O-benzyl-hydroxylamine hydrochloride (Aldrich).
$^{13}$C-NMR (DMSO-d$_6$) δ 165.8, 156.6, 151.2, 139.4, 136.0, 135.8, 131.0, 128.9, 128.8, 128.2, 128.1, 110.9, 107.9, 76.9, 43.0.

Example 482

N-Benzyloxy-2-(4-methoxy-benzylamino)-nicotinamide (compound 167)

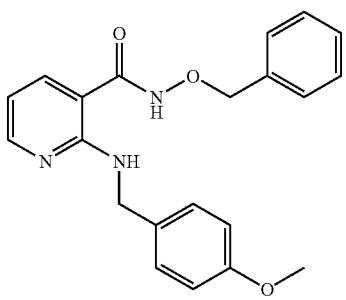

General procedure 1, method 1.
Starting materials: 2-(4-Methoxy-benzylamino)-nicotinic acid (see preparation 4) and O-benzyl-hydroxylamine hydrochloride (Aldrich).
$^{13}$C-NMR (DMSO-d$_6$) δ 158.1, 156.7, 151.3, 135.9, 135.8, 131.8, 128.8, 128.6, 128.2, 113.7, 110.6, 107.6, 76.9, 54.9, 43.3.

Example 483

N-Benzyloxy-2-(isoquinolin-5-ylamino)-nicotinamide (compound 168)

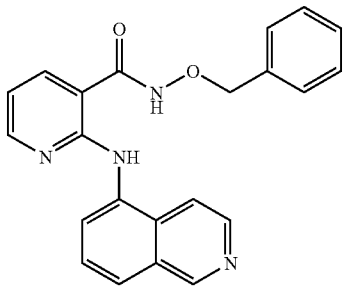

General procedure 1, method 1.
Starting materials: 2-(Isoquinolin-5-ylamino)-nicotinic acid (see preparation 3B) and O-benzyl-hydroxylamine hydrochloride (Aldrich).
$^{13}$C-NMR (DMSO-d$_6$) δ 154.4, 152.8, 150.9, 142.9, 136.7, 135.7, 134.4, 128.9, 128.8, 128.3, 127.5, 121.4, 119.9, 114.1, 113.9, 109.5, 77.1.

Example 484

N-(4-Cyano-2-methoxy-benzyloxy)-3-[(pyridin-4-ylmethyl)-amino]-isonicotinamide (compound 169)

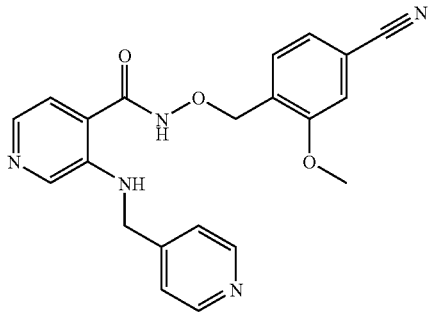

General procedure 1, method 1.
Starting materials: 3-[(Pyridin-4-ylmethyl)-amino]-isonicotinic acid (see preparation 1I) and 4-aminooxymethyl-3-methoxy-benzonitrile hydrochloride (see preparation 45).
$^{13}$C-NMR (DMSO-$d_6$) δ 157.2, 149.6, 148.4, 142.1, 136.3, 135.0, 130.4, 129.9, 124.4, 121.9, 120.6, 118.6, 114.1, 111.9, 71.0, 56.1, 44.5.

Example 485

N-Benzyloxy-3-[(pyridin-4-ylmethyl)-amino]-isonicotinamide (compound 170)

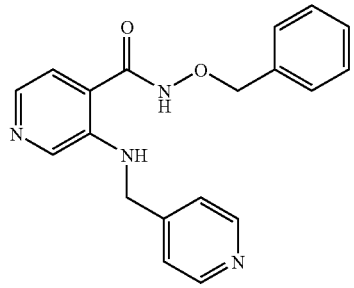

General procedure 1, method 1.
Starting materials: 3-[(Pyridin-4-ylmethyl)-amino]-isonicotinic acid (see preparation 1I) and O-benzyl-hydroxylamine hydrochloride (Aldrich).
$^{13}$C-NMR (DMSO-$d_6$) δ 149.6, 148.5, 142.1, 136.3, 135.8, 135.0, 128.9, 128.2, 122.0, 120.5, 118.9, 76.9, 44.5.

Example 486

N-(2-Methyl-thiazol-4-ylmethoxy)-3-[(pyridin-4-ylmethyl)-amino]-isonicotinamide (compound 171)

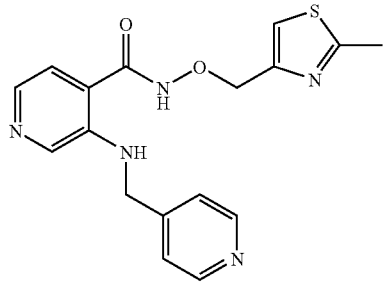

General procedure 1, method 1.
Starting materials: 3-[(Pyridin-4-ylmethyl)-amino]-isonicotinic acid (see preparation 1I) and O-(2-methyl-thiazol-4-ylmethyl)-hydroxylamine hydrochloride (see preparation 12).
$^{13}$C-NMR (DMSO-$d_6$) δ 165.4, 150.4, 149.6, 148.5, 142.0, 136.3, 134.9, 122.0, 120.6, 119.2, 118.9, 71.7, 44.5, 18.6.

Example 487

N-Benzyloxy-2-(4-fluoro-benzylamino)-benzamide (compound 172)

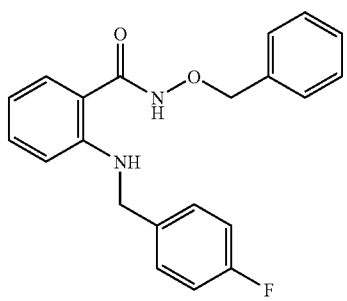

General procedure 1, method 1.
Starting materials: 2-(4-Fluoro-benzylamino)-benzoic acid (see preparation 1J) and O-benzyl-hydroxylamine hydrochloride (Aldrich).
$^{13}$C-NMR (DMSO-$d_6$) δ 167.2, 161.1, 148.6, 135.9, 135.6, 132.5, 128.9, 128.8, 128.2, 128.0, 115.1, 114.5, 113.1, 111.5, 76.9, 45.2.

Example 488

N-(4-Cyano-benzyloxy)-2-(4-fluoro-benzylamino)-benzamide (compound 173)

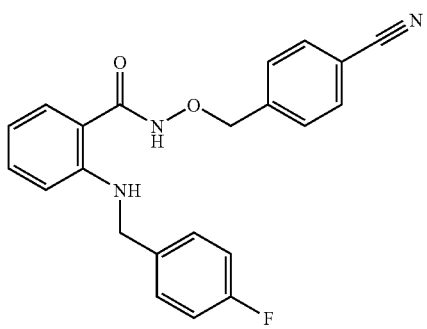

General procedure 1, method 2.
Starting materials: 2-(4-Fluoro-benzylamino)-benzoic acid (see preparation 1J) and O-(4-cyanobenzyl)hydroxylamine hydrochloride (see preparation 10).
$^{13}$C-NMR (DMSO-$d_6$) δ 167.4, 161.1, 148.6, 141.8, 135.5, 132.6, 132.1, 129.1, 128.9, 128.0, 118.7, 115.1, 114.5, 112.8, 111.5, 110.7, 75.9, 45.1.

Example 489

2-(4-Fluoro-benzylamino)-N-(2-methyl-thiazol-4-ylmethoxy)-benzamide (compound 174)

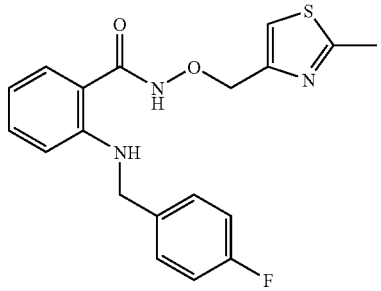

General procedure 1, method 1.

Starting materials: 2-(4-Fluoro-benzylamino)-benzoic acid (see preparation 1J) and O-(2-methyl-thiazol-4-ylmethyl)-hydroxylamine hydrochloride (see preparation 12).

$^{13}$C-NMR (DMSO-d$_6$) δ 167.2, 165.3, 161.1, 150.5, 148.5, 135.5, 132.5, 128.9, 128.0, 118.9, 115.1, 114.5, 113.1, 111.5, 71.9, 45.2, 18.6.

Example 490

N-Benzyloxy-2-(3-cyano-4-fluoro-benzylamino)-benzamide (compound 175)

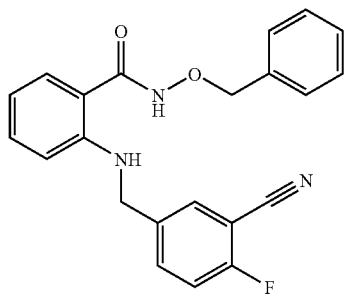

General procedure 1, method 2.

Starting materials: 2-(3-Cyano-4-fluoro-benzylamino)-benzoic acid (see preparation 1K) and O-benzyl-hydroxylamine hydrochloride (Aldrich).

$^{13}$C-NMR (DMSO-d$_6$) δ 167.1, 161.3, 148.0, 137.6, 135.9, 134.6, 132.5, 132.0, 128.8, 128.2, 128.1, 116.6, 114.9, 114.0, 113.6, 111.4, 99.9, 99.7, 76.9, 44.4.

Example 491

N-(2-Bromo-benzyloxy)-2-(3-cyano-4-fluoro-benzylamino)-benzamide (compound 176)

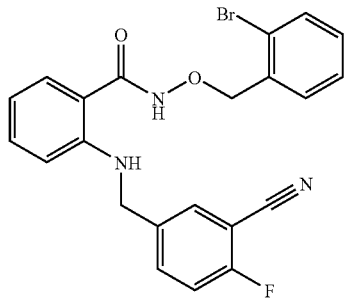

General procedure 1, method 2.

Starting materials: 2-(3-Cyano-4-fluoro-benzylamino)-benzoic acid (see preparation 1K) and 1-[(ammoniooxy)methyl]-2-bromobenzene chloride (Bionet).

$^{13}$C-NMR (DMSO-d$_6$) δ 161.4, 148.1, 137.7, 135.4, 134.7, 132.6, 132.5, 132.1, 131.2, 130.3, 128.3, 127.8, 123.2, 116.7, 115.0, 114.1, 113.5, 111.5, 100.0, 99.8, 75.9, 44.5.

Example 492

5-[(2-Benzyloxycarbamoyl-phenylamino)-methyl]-2-fluoro-benzoic acid methyl ester (compound 177)

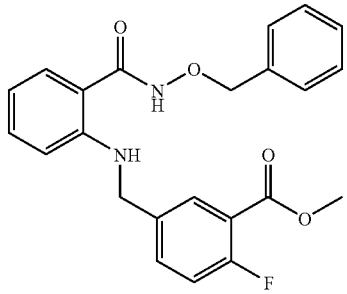

General procedure 1, method 1.

Starting materials: 5-[(2-carboxy-phenylamino)-methyl]-2-fluoro-benzoic acid methyl ester (see preparation 1L) and O-benzyl-hydroxylamine hydrochloride (Aldrich).

$^{13}$C-NMR (DMSO-d$_6$) δ 167.2, 164.0, 159.9, 148.4, 136.2, 135.9, 133.6, 132.5, 130.0, 128.8, 128.7, 128.2, 128.0, 117.9, 117.1, 114.7, 113.3, 111.5, 76.9, 52.3, 44.8.

Example 493

5-[(2-Cyclopentylmethoxycarbamoyl-phenylamino)-methyl]-2-fluoro-benzoic acid methyl ester (compound 178)

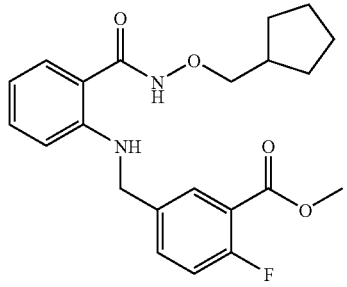

General procedure 1, method 1.

Starting materials: 5-[(2-carboxy-phenylamino)-methyl]-2-fluoro-benzoic acid methyl ester (see preparation 1L) and O-cyclopentylmethyl-hydroxylamine hydrochloride (see preparation 66).

$^1$H-NMR (DMSO-d$_6$) δ 11.45 (s, 1H), 7.87 (m, 2H), 7.62 (m, 1H), 7.40 (d, 1H), 7.31 (dd, 1H), 7.21 (t, 1H), 6.55 (m, 2H), 4.44 (d, 2H), 3.81 (s, 3H), 3.77 (d, 2H), 2.20 (m, 1H), 1.8-1.2 (m, 8H).

Example 494

2-Fluoro-5-{[2-(4-fluoro-benzyloxycarbamoyl)-phenylamino]-methyl}-benzoic acid methyl ester (compound 179)

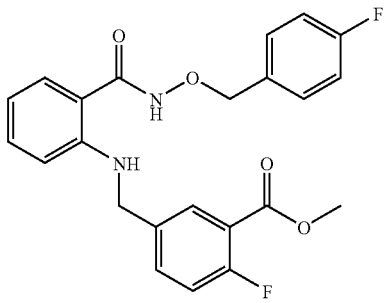

General procedure 1, method 1.

Starting materials: 5-[(2-carboxy-phenylamino)-methyl]-2-fluoro-benzoic acid methyl ester (see preparation 1L) and 1-[(ammoniooxy)methyl]-4-fluorobenzene chloride (Bionet).

$^1$H-NMR (DMSO-d$_6$) δ 11.57 (s, 1H), 7.88 (m, 2H), 7.62 (m, 1H), 7.51 (m, 2H), 7.32 (dd, 1H), 7.27-7.17 (m, 4H), 6.58 (m, 2H), 4.91 (s, 2H), 4.45 (d, 2H), 3.84 (s, 3H).

Example 495

5-{[2-(4-Cyano-benzyloxycarbamoyl)-phenylamino]-methyl}-2-fluoro-benzoic acid methyl ester (compound 180)

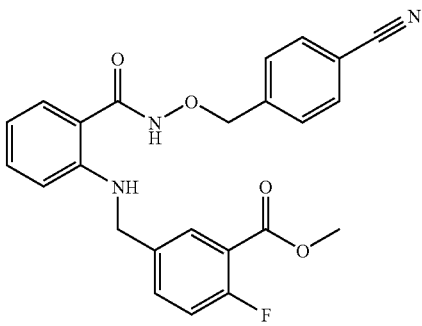

General procedure 1, method 1.

Starting materials: 5-[(2-carboxy-phenylamino)-methyl]-2-fluoro-benzoic acid methyl ester (see preparation 1L) and O-(4-cyanobenzyl)hydroxylamine hydrochloride (see preparation 10).

$^{13}$C-NMR (DMSO-d$_6$) δ 167.4, 164.0, 159.8, 148.4, 141.9, 136.2, 133.5, 132.6, 132.2, 130.0, 129.1, 128.1, 118.7, 117.9, 117.1, 114.7, 113.0, 111.5, 110.8, 75.9, 52.3, 44.8.

Example 496

5-[(2-Cyclopentylmethoxycarbamoyl-phenylamino)-methyl]-2-fluoro-benzoic acid (compound 181)

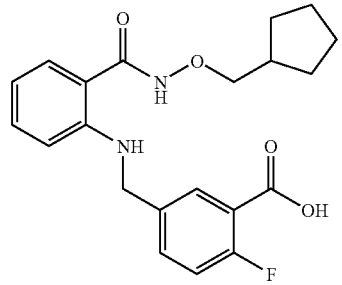

5-[(2-Cyclopentylmethoxycarbamoyl-phenylamino)-methyl]-2-fluoro-benzoic acid methyl ester (Example 493, 511 mg) was dissolved in THF (15 ml) and water (5 ml). Lithium hydroxide (122 mg) was added and the mixture was heated to 60° C. The reaction mixture was stirred at this temperature for 15 hours, cooled to room temperature and concentrated under reduced pressure. The residue was diluted with water and 1M hydrochloric acid was added until a precipitate formed. The solid material was isolated by filtration and washed with water and dried under high vacuum and gave the title compound (380 mg) as a white powder. $^{13}$C-NMR (DMSO-d$_6$) δ 166.9, 165.0, 160.0, 148.4, 135.9, 133.0, 132.4, 130.1, 128.0, 119.1, 116.9, 114.6, 113.4, 111.5, 79.4, 44.8, 37.6, 28.9, 24.9.

Example 497

2-Fluoro-5-{[2-(4-fluoro-benzyloxycarbamoyl)-phenylamino]-methyl}-benzoic acid (compound 182)

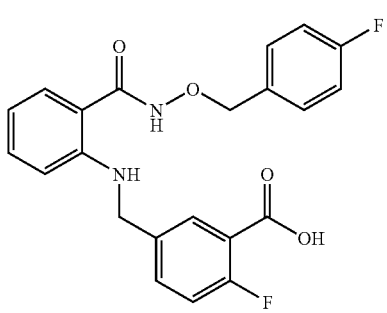

Prepared by a similar procedure as described for preparation of Example 496, starting from 2-Fluoro-5-{[2-(4-fluoro-benzyloxycarbamoyl)-phenylamino]-methyl}-benzoic acid methyl ester (Example 494).

$^{13}$C-NMR (DMSO-d$_6$) δ 167.3, 165.0, 162.0, 160.0, 148.5, 135.9, 133.0, 132.6, 132.3, 131.2, 130.1, 128.1, 119.2, 116.9, 115.1, 114.7, 113.2, 111.5, 76.1, 44.8, 25.1.

Example 498

5-[(2-Benzyloxycarbamoyl-phenylamino)-methyl]-2-fluoro-benzoic acid (compound 183)

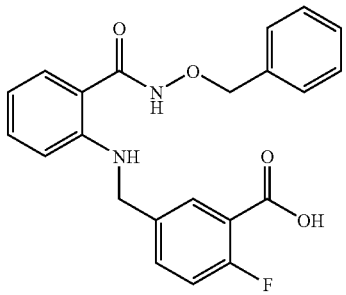

Prepared by a similar procedure as described for preparation of Example 496, starting from 5-[(2-Benzyloxycarbamoyl-phenylamino)-methyl]-2-fluoro-benzoic acid methyl ester (Example 492).

$^{13}$C-NMR (DMSO-d$_6$) δ 167.2, 165.0, 160.0, 148.4, 135.9, 133.0, 132.5, 130.1, 128.8, 128.2, 128.0, 119.1, 116.9, 114.7, 113.2, 111.5, 76.9, 44.8.

Example 499

5-[(2-Benzyloxycarbamoyl-phenylamino)-methyl]-2-fluoro-N-(2-hydroxy-ethyl)-benzamide (compound 184)

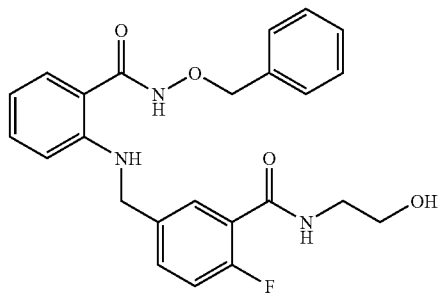

5-[(2-Benzyloxycarbamoyl-phenylamino)methyl]-2-fluoro-benzoic acid (Example 498, 96.5 mg) and 1-hydroxybenzotriazole hydrate (36 mg) was dissolved in DMF (1.0 ml). 2-Amino-ethanol (15 µl), N-methylmorpholine (28 µl), and 1-ethyl-3-(3-dimethylaminopropyl)-carbodiimide hydrochloride (50.1 mg) was added in that order. The reaction mixture was shaken at room temperature for 15 hours. The solvent was evaporated under reduced pressure and the residue was dissolved in dichloromethane and evaporated onto silica gel. Purification by column chromatography on silica gel (elution with 50-100% EtOAc in petroleum ether) gave the title compound.

$^{13}$C-NMR (DMSO-d$_6$) δ 167.2, 163.5, 158.1, 148.5, 135.9, 132.5, 130.7, 129.1, 128.8, 128.6, 128.2, 128.0, 123.7, 116.0, 114.6, 113.2, 111.5, 76.9, 59.5, 45.0, 42.0.

Example 500

5-[(2-Benzyloxycarbamoyl-phenylamino)-methyl]-2-fluoro-N-(3-hydroxy-propyl)benzamide (compound 185)

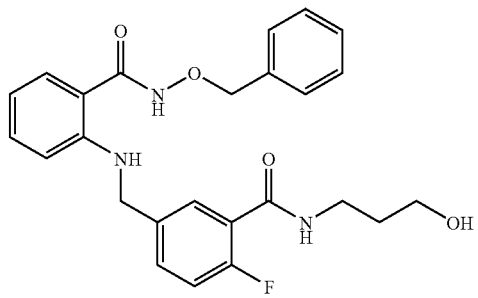

Prepared by a similar procedure as described for the preparation of Example 499, starting from 5-[(2-benzyloxycarbamoyl-phenylamino)methyl]-2-fluoro-benzoic acid (Example 498) and 3-amino-propan-1-ol.

$^{13}$C-NMR (DMSO-d$_6$) δ 167.2, 163.4, 158.0, 148.5, 135.8, 132.5, 130.5, 128.8, 128.5, 128.2, 128.0, 124.0, 116.0, 114.6, 113.2, 111.5, 76.9, 58.5, 45.0, 36.6, 32.1.

Example 501

5-[(2-Benzyloxycarbamoyl-phenylamino)-methyl]-2-fluoro-N-(4-hydroxy-butyl)benzamide (compound 186)

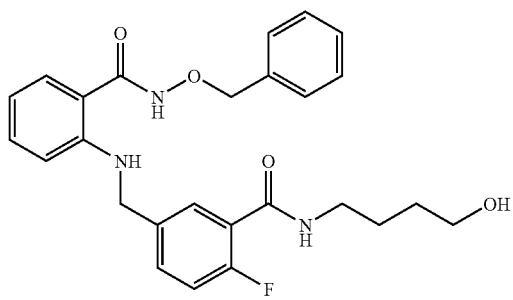

Prepared by a similar procedure as described for the preparation of Example 499, starting from 5-[(2-benzyloxycarbamoyl-phenylamino)methyl]-2-fluoro-benzoic acid (Example 498) and 4-amino-butan-1-ol.

$^{13}$C-NMR (DMSO-d$_6$) δ 167.2, 163.4, 157.9, 148.5, 135.9, 135.8, 132.5, 130.4, 128.8, 128.4, 128.2, 128.0, 124.2, 116.0, 114.6, 113.2, 111.5, 76.9, 60.3, 45.0, 39.0, 29.8, 25.6.

Example 502

5-[(2-Benzyloxycarbamoyl-phenylamino)-methyl]-N-(3-dimethylaminopropyl)-2-fluoro-benzamide (compound 187)

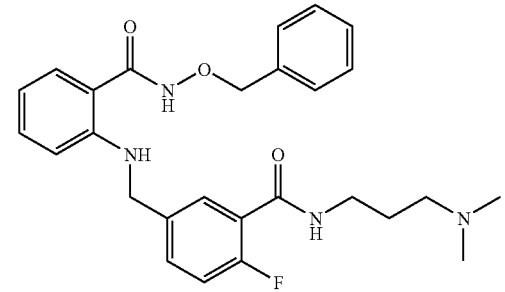

Prepared by a similar procedure as described for the preparation of Example 499, starting from 5-[(2-benzyloxycarbamoyl-phenylamino)methyl]-2-fluoro-benzoic acid (Example 498) and 3-(N,N-dimethylamino)-1-propylamine.

$^{13}$C-NMR (DMSO-d$_6$) δ 166.8, 163.5, 158.0, 148.4, 136.0, 135.9, 132.4, 130.7, 128.8, 128.5, 128.2, 128.0, 123.8, 116.0, 114.6, 113.1, 111.4, 76.8, 55.5, 45.0, 43.4, 37.0, 25.2.

Example 503

5-[(2-Cyclopentylmethoxycarbamoyl-phenylamino)-methyl]-2-fluoro-N-(3-hydroxypropyl)-benzamide (compound 188)

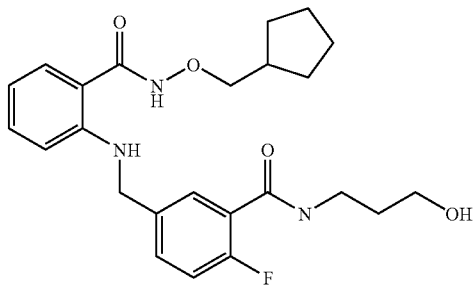

Prepared by a similar procedure as described for the preparation of Example 499, starting from 5-[(2-cyclopentyl-methoxycarbamoyl-phenylamino)-methyl]-2-fluoro-benzoic acid (Example 496) and 3-amino-propan-1-ol.

$^{13}$C-NMR (DMSO-d$_6$) δ 166.9, 163.4, 157.9, 148.4, 135.8, 132.4, 130.5, 128.4, 127.9, 124.0, 116.0, 114.6, 113.3, 111.5, 79.4, 58.5, 44.9, 37.6, 36.6, 32.1, 28.9, 24.9.

Example 504

N-Cyclopentylmethoxy-2-[4-fluoro-3-(4-methyl-piperazine-1-carbonyl)-benzylamino]-benzamide (compound 189)

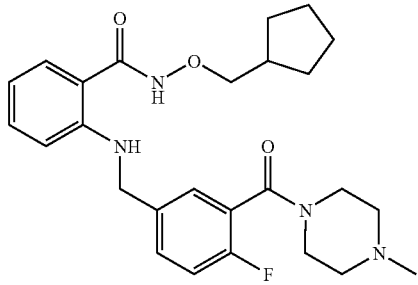

Prepared by a similar procedure as described for the preparation of Example 499, starting from 5-[(2-cyclopentyl-methoxycarbamoyl-phenylamino)-methyl]-2-fluoro-benzoic acid (Example 496) and 1-methyl-piperazine.

$^{13}$C-NMR (DMSO-d$_6$) δ 163.8, 156.4, 148.3, 136.3, 132.3, 129.8, 127.9, 126.9, 123.7, 115.8, 114.6, 113.3, 111.5, 79.4, 54.5, 54.1, 46.3, 45.4, 44.8, 41.1, 37.6, 28.9, 24.9.

Example 505

N-Cyclopentylmethoxy-2-[4-fluoro-3-(morpholine-4-carbonyl)-benzylamino]-benzamide (compound 190)

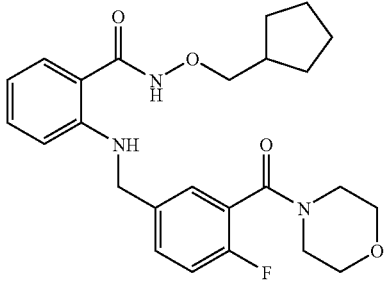

Prepared by a similar procedure as described for the preparation of Example 499, starting from 5-[(2-cyclopentyl-methoxycarbamoyl-phenylamino)methyl]-2-fluoro-benzoic acid (Example 496) and morpholine.

$^{13}$C-NMR (DMSO-d$_6$) δ 166.9, 163.9, 156.5, 148.4, 136.4, 132.3, 129.9, 128.0, 127.1, 123.4, 115.8, 114.6, 113.4, 111.5, 79.4, 66.1, 65.9, 46.9, 44.8, 41.7, 37.6, 28.9, 24.9.

Example 506

N-Benzyloxy-2-(4-methoxy-benzylamino)-benzamide (compound 191)

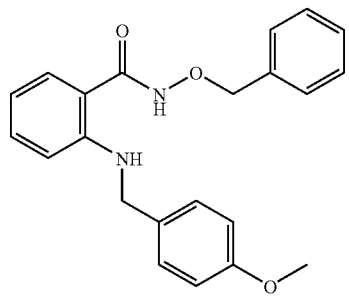

General procedure 1, method 1.

Starting materials: 2-(4-Methoxy-benzylamino)-benzoic acid (see preparation 1M) and O-benzyl-hydroxylamine hydrochloride (Aldrich).

$^{13}$C-NMR (DMSO-d$_6$) δ 167.3, 158.2, 148.7, 135.9, 132.5, 131.1, 128.8, 128.4, 128.2, 127.9, 114.3, 113.8, 112.8, 111.5, 76.8, 54.9, 45.5.

Example 507

2-(4-Methoxy-benzylamino)-N-(2-methyl-thiazol-4-ylmethoxy)-benzamide (compound 192)

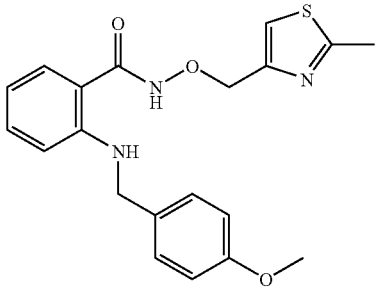

General procedure 1, method 1.

Starting materials: 2-(4-Methoxy-benzylamino)-benzoic acid (see preparation 1M) and O-(2-methyl-thiazol-4-ylmethyl)-hydroxylamine hydrochloride (see preparation 12).

$^{13}$C-NMR (DMSO-d$_6$) δ 167.3, 165.3, 158.2, 150.5, 148.7, 132.5, 131.1, 128.4, 128.0, 118.8, 114.3, 113.8, 112.8, 111.4, 71.8, 54.9, 45.5, 18.6.

Example 508

N-Benzyloxy-2-[(4-methoxy-naphthalen-1-ylmethyl)-amino]-benzamide (compound 193)

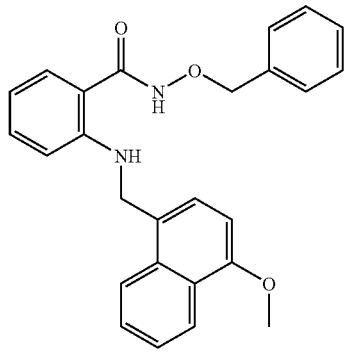

General procedure 1, method 1.

Starting materials: 2-[(4-Methoxy-naphthalen-1-ylmethyl)-amino]-benzoic acid (see preparation 1N) and O-benzyl-hydroxylamine hydrochloride (Aldrich).

$^{13}$C-NMR (DMSO-$d_6$) δ 167.3, 154.4, 148.9, 135.8, 132.7, 131.8, 128.7, 128.1, 127.9, 126.7, 125.8, 125.2, 125.1, 123.4, 122.0, 114.4, 112.7, 111.5, 103.7, 76.8, 55.5, 44.0.

Example 509

N-(4-Cyano-benzyloxy)-2-[(4-methoxy-naphthalen-1-ylmethyl)-amino]-benzamide (compound 194)

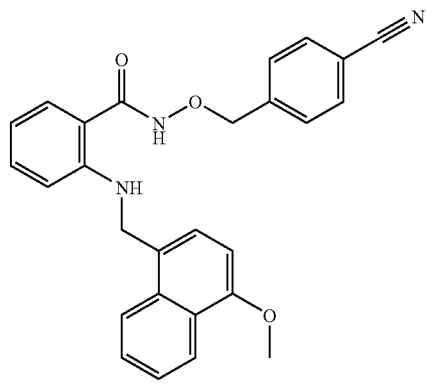

General procedure 1, method 1.

Starting materials: 2-[(4-Methoxy-naphthalen-1-ylmethyl)-amino]-benzoic acid (see preparation 1N) and O-(4-cyanobenzyl)hydroxylamine hydrochloride (see preparation 10).

$^{13}$C-NMR (DMSO-$d_6$) δ 167.5, 154.4, 148.9, 141.7, 132.8, 132.1, 131.8, 129.1, 127.9, 126.7, 125.9, 125.8, 125.2, 125.1, 123.4, 122.0, 118.6, 114.4, 112.4, 111.6, 110.7, 103.6, 75.8, 55.5, 44.0.

Example 510

2-[(2,3-Dihydro-benzofuran-5-ylmethyl)-amino]-N-(4-fluoro-benzyloxy)-benzamide (compound 195)

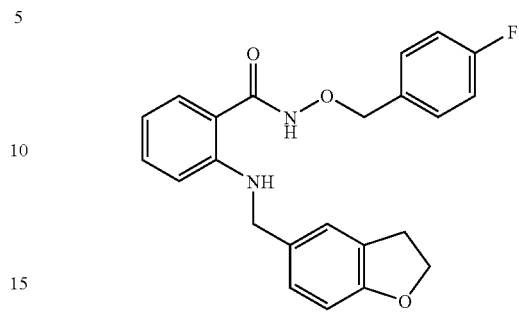

General procedure 1, method 1.

Starting materials: 2-[(2,3-Dihydro-benzofuran-5-ylmethyl)-amino]-benzoic acid (see preparation 10) and 1-[(ammoniooxy)methyl]-4-fluorobenzene chloride (Bionet).

$^{13}$C-NMR (DMSO-$d_6$) δ 167.3, 162.0, 158.7, 148.7, 132.5, 132.3, 131.1, 131.0, 127.7, 125.4, 115.0, 114.3, 112.7, 111.5, 108.6, 76.0, 70.8, 45.8, 29.0.

Example 511

N-(4-Cyano-benzyloxy)-2-[(2,3-dihydro-benzofuran-5-ylmethyl)-amino]-benzamide (compound 196)

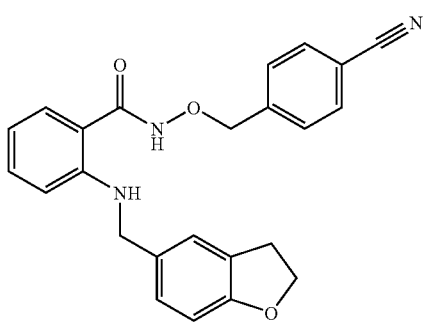

General procedure 1, method 1.

Starting materials: 2-[(2,3-Dihydro-benzofuran-5-ylmethyl)-amino]-benzoic acid (see preparation 10) and O-(4-cyanobenzyl)hydroxylamine hydrochloride (see preparation 10).

$^{13}$C-NMR (DMSO-$d_6$) δ 167.5, 158.7, 148.8, 141.8, 132.7, 132.1, 131.0, 129.1, 127.9, 127.4, 126.8, 124.0, 118.6, 114.3, 112.5, 111.5, 110.7, 108.6, 75.9, 70.8, 45.8, 29.0.

Example 512

2-[(Benzofuran-5-ylmethyl)-amino]-N-(4-cyanobenzyloxy)-benzamide (compound 197)

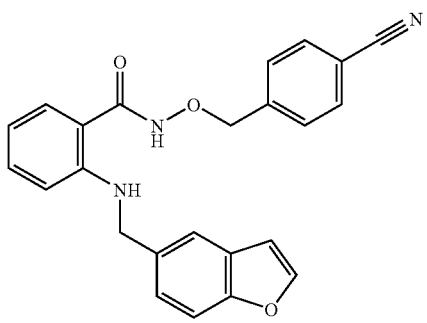

General procedure 1, method 2.

Starting materials: 2-[(Benzofuran-5-ylmethyl)-amino]-benzoic acid (see preparation 1P) and O-(4-cyanobenzyl) hydroxylamine hydrochloride (see preparation 10).

$^{13}$C-NMR (DMSO-d$_6$) δ 167.5, 153.4, 148.7, 146.2, 133.9, 132.1, 132.0, 129.2, 129.1, 127.9, 127.3, 123.6, 119.5, 118.6, 114.4, 111.6, 111.1, 110.7, 106.6, 75.9, 46.0.

Example 513

2-[(Benzofuran-5-ylmethyl)-amino]-N-benzyloxy-benzamide (compound 198)

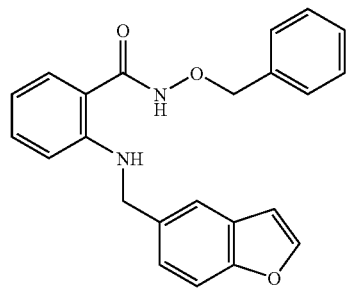

General procedure 1, method 2.

Starting materials: 2-[(Benzofuran-5-ylmethyl)-amino]-benzoic acid (see preparation 1P) and O-benzyl-hydroxylamine hydrochloride (Aldrich).

$^{13}$C-NMR (DMSO-d$_6$) δ 167.3, 153.4, 148.7, 146.2, 135.9, 134.0, 132.5, 128.8, 128.2, 127.9, 127.3, 123.7, 119.5, 114.4, 112.9, 111.5, 111.1, 106.6, 76.9, 46.0.

Example 514

2-[(Benzofuran-5-ylmethyl)-amino]-N-(4-fluoro-benzyloxy)-benzamide (compound 199)

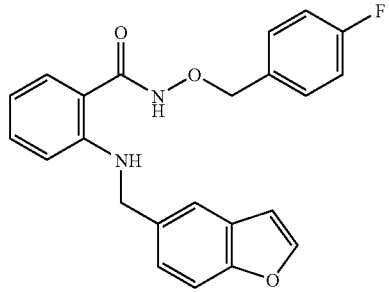

General procedure 1, method 2.

Starting materials: 2-[(Benzofuran-5-ylmethyl)-amino]-benzoic acid (see preparation 1P) and 1-[(ammoniooxy)methyl]-4-fluorobenzene chloride (Bionet).

$^{13}$C-NMR (DMSO-d$_6$) δ 167.3, 162.0, 153.4, 148.7, 146.2, 134.0, 132.5, 132.3, 131.1, 131.0, 127.6, 123.7, 119.5, 115.0, 114.4, 112.9, 111.6, 111.1, 106.6, 76.1, 46.0.

Example 515

N-(4-Cyano-benzyloxy)-2-[(2-oxo-2H-chromen-6-ylmethyl)-amino]-benzamide (compound 200)

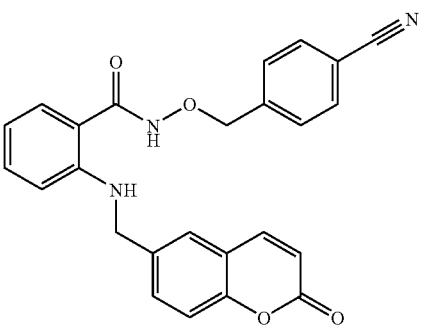

General procedure 1, method 1.

Starting materials: 2-[(2-Oxo-2H-chromen-6-ylmethyl)-amino]-benzoic acid (see preparation 1Q) and O-(4-cyanobenzyl)hydroxylamine hydrochloride (see preparation 10).

$^{13}$C-NMR (DMSO-d$_6$) δ 159.9, 152.5, 148.5, 144.1, 141.8, 135.9, 132.6, 132.1, 130.7, 129.1, 128.0, 126.5, 118.6, 118.6, 116.4, 116.3, 114.7, 112.8, 111.5, 110.7, 75.9, 45.2

Example 516

N-(4-Chloro-benzyloxy)-2-(4-cyano-benzylamino)-benzamide (compound 201)

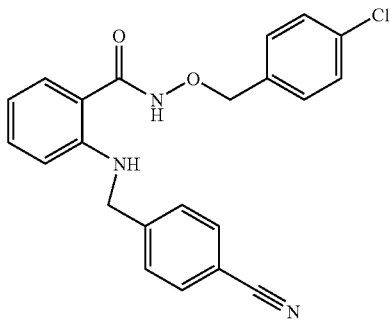

To a stirred mixture of 4-(2,4-dioxo-4H-benzo[d][1,3]oxazin-1-ylmethyl)-benzonitrile (Preparation 7D, 319 mg) and O-(4-chloro-benzyl)-hydroxylamine hydrochloride (preparation 9, 267 mg) in DMF (10 ml) was added N-ethyldiisopropylamine (0.4 ml). The reaction mixture was heated to 100° C. and stirred for 17 hours. The mixture was cooled to room temperature and water was added. The pale brown precipitated material was isolated by filtration and re-crystallised from ethanol and gave the title compound as a white solid material. $^{13}$C-NMR (DMSO-d$_6$) δ 148.2, 145.9, 135.1, 132.8, 132.5, 132.3, 130.6, 128.2, 128.0, 127.7, 118.8, 114.8, 113.2, 111.4, 109.5, 75.9, 45.4.

Example 517

2-[(3,5-Dichloro-pyridin-4-ylmethyl)-amino]-N-(2-methyl-thiazol-4-ylmethoxy)-benzamide (compound 202)

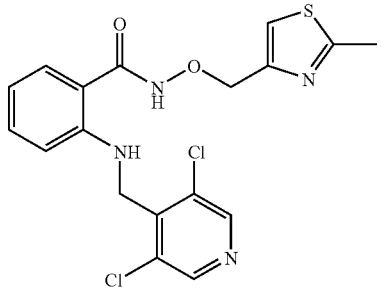

General procedure 1, method 2.

Starting materials: 2-[(3,5-Dichloro-pyridin-4-ylmethyl)-amino]-benzoic acid (see preparation 1R) and O-(2-methyl-thiazol-4-ylmethyl)-hydroxylamine hydrochloride (see preparation 12).

$^{13}$C-NMR (CDCl$_3$) δ 167.1, 150.8, 148.6, 148.0, 142.5, 133.5, 133.1, 127.6, 118.1, 115.9, 113.0, 112.0, 72.9, 41.9, 19.1.

Example 518

N-Benzyloxy-2-[(3,5-dichloro-pyridin-4-ylmethyl)-amino]-benzamide (compound 203)

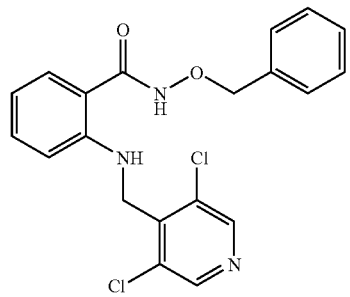

General procedure 1, method 2.

Starting materials: 2-[(3,5-Dichloro-pyridin-4-ylmethyl)-amino]-benzoic acid (see preparation 1R) and O-benzyl-hydroxylamine hydrochloride (Aldrich).

$^{13}$C-NMR (CDCl$_3$) δ 148.5, 148.0, 142.5, 135.5, 133.5, 133.1, 129.2, 128.8, 128.7, 127.4, 115.9, 112.0, 78.3, 41.9.

Example 519

2-[(2-Bromo-pyridin-4-ylmethyl)-amino]-N-(4-fluoro-benzyloxy)benzamide (compound 204)

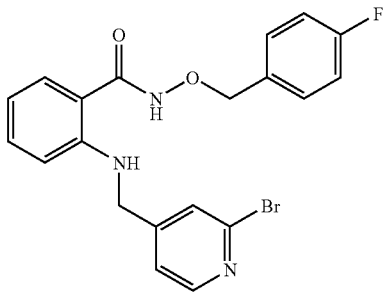

General procedure 1, method 1.

Starting materials: 2-[(2-Bromo-pyridin-4-ylmethyl)-amino]-benzoic acid (see preparation 1S) and 1-[(ammoniooxy)methyl]-4-fluorobenzene chloride (Bionet).

$^{13}$C-NMR (DMSO-d$_6$) δ 167.0, 162.0, 153.5, 150.3, 147.8, 141.5, 132.5, 132.2, 131.1, 128.1, 125.8, 121.7, 115.0, 115.0, 113.6, 111.4, 76.0, 44.3.

Example 520

N-(4-Cyano-2-methoxy-benzyloxy)-2-[(2-hydroxy-pyridin-4-ylmethyl)-amino]-benzamide (compound 205)

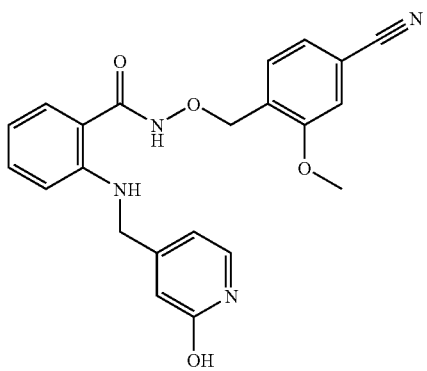

General procedure 1, method 1.

Starting materials: 2-[(2-Hydroxy-pyridin-4-ylmethyl)-amino]-benzoic acid (see preparation 1T) and 4-aminooxymethyl-3-methoxy-benzonitrile hydrochloride (see preparation 45).

$^{13}$C-NMR (DMSO-d$_6$) δ 167.3, 162.4, 157.1, 153.7, 148.2, 135.0, 132.5, 130.3, 130.0, 128.0, 124.4, 118.7, 115.9, 114.7, 114.0, 113.1, 111.7, 111.4, 104.1, 70.9, 56.0, 44.8.

Example 521

2-[(2-Amino-pyridin-4-ylmethyl)-amino]-N-(4-cyano-benzyloxy)-benzamide (compound 206)

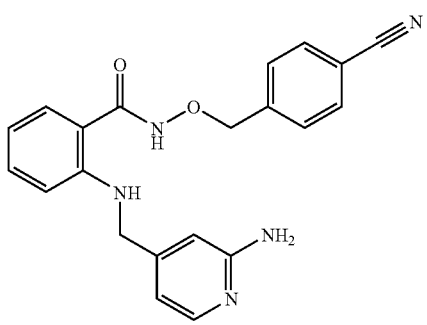

General procedure 1A.

Starting materials: 1-(2-Amino-pyridin-4-ylmethyl)-1H-benzo[d][1,3]oxazine-2,4-dione (see preparation 7B) and O-(4-cyanobenzyl)hydroxylamine hydrochloride (see preparation 10).

$^{13}$C-NMR (DMSO-$d_6$) δ 159.9, 149.4, 148.6, 147.7, 141.9, 132.6, 132.2, 129.1, 127.9, 118.6, 114.5, 112.5, 111.5, 110.7, 110.5, 105.2, 75.9, 45.2,

Example 522

N-(4-Fluoro-benzyloxy)-2-[(2-morpholin-4-yl-pyridin-4-ylmethyl)-amino]-benzamide (compound 207)

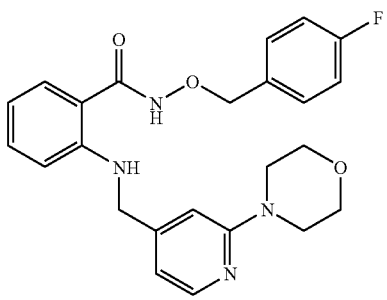

General procedure 1, method 1.

Starting materials: 2-[(2-Morpholin-4-yl-pyridin-4-ylmethyl)-amino]-benzoic acid (see preparation 1U) and 1-[(ammoniooxy)methyl]-4-fluorobenzene chloride (Bionet).

$^{13}$C-NMR (DMSO-$d_6$) δ 167.2, 162.0, 159.4, 150.3, 148.6, 147.6, 132.5, 132.2, 131.1, 128.0, 115.0, 114.7, 113.2, 112.1, 111.6, 104.9, 76.1, 65.8, 45.5, 45.1.

Example 523

N-Cyclopentylmethoxy-2-[(2-methanesulfonylamino-pyridin-4-ylmethyl)-amino]-benzamide (compound 208)

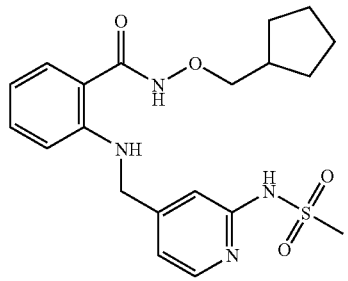

Step 1: To a stirred solution of 1-(2-amino-pyridin-4-ylmethyl)-1H-benzo[d][1,3]oxazine-2,4-dione (600 mg, see preparation 7b) in pyridine (7 ml) was added methanesulfonyl chloride (280 mg) and the reaction mixture was stirred at room temperature for 15 hours. The solvent was evaporated under reduced pressure and the residue was dissolved in EtOAc and washed with water and brine. The organic layer was dried (MgSO$_4$) and evaporated under reduced pressure. The remaining solid yellow material was dissolved in a mixture of hot EtOAc (50 ml) and DMF (4 ml). On cooling a solid material formed, that was isolated by filtration and dried under vacuum, affording N-[4-(2,4-dioxo-4H-benzo[d][1,3]oxazin-1-ylmethyl)-pyridin-2-yl]-methanesulfonamide.
Step 2: This anhydride intermediate was converted into the title compound by reaction with O-cyclopentylmethyl-hydroxylamine hydrochloride (see preparation 66), using general procedure 1A. $^{13}$C-NMR (DMSO-$d_6$) δ 166.8, 152.9, 152.6, 148.3, 132.4, 127.9, 115.2, 114.8, 113.3, 111.4, 110.1, 79.4, 45.0, 41.5, 37.6, 28.9, 24.9.

Example 524

N-(4-Cyano-benzyloxy)-2-[(2-methanesulfonylamino-pyridin-4-ylmethyl)-amino]-benzamide (compound 209)

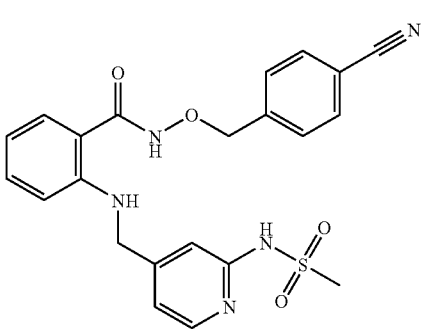

General procedure 1A.

Starting materials: N-[4-(2,4-Dioxo-4H-benzo[d][1,3]oxazin-1-ylmethyl)-pyridin-2-yl]-methanesulfonamide (see example 523 step 1) and O-(4-cyanobenzyl)hydroxylamine hydrochloride (see preparation 10).

$^{13}$C-NMR (DMSO-$d_6$) δ 167.4, 152.9, 152.5, 148.3, 145.6, 141.8, 132.6, 132.2, 129.1, 128.0, 118.7, 115.1, 114.9, 112.9, 111.5, 110.7, 110.2, 75.9, 45.0, 41.6.

Example 525

N-(4-Cyano-benzyloxy)-2-{[2-(3-methyl-ureido)-pyridin-4-ylmethyl]-amino}-benzamide (compound 210)

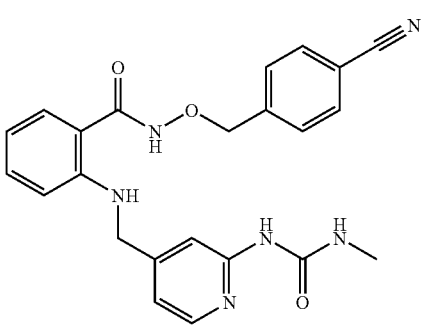

Step 1: To a stirred solution of 1-(2-amino-pyridin-4-ylmethyl)-1H-benzo[d][1,3]oxazine-2,4-dione (7.0 g, see preparation 7b) in pyridine (70 ml) was added isocyanatomethane (5 eq.) over 45 minutes. More isocyanatomethane (in total 20 eq.) was added over time until all starting material had been consumed. The solvent was evaporated under reduced pressure. The remaining solid material washed with EtOAc (50 ml) and gave 1-[4-(2,4-dioxo-4H-benzo[d][1,3]oxazin-1-ylmethyl)-pyridin-2-yl]-3-methyl-urea after drying in vacuo.
Step 2: This anhydride intermediate was converted into the title compound by reaction with O-(4-cyanobenzyl)hydroxylamine hydrochloride (see preparation 10), using general procedure 1A. $^{13}$C-NMR (DMSO-$d_6$) δ 167.4, 155.3, 153.7, 151.2, 148.5, 146.6, 141.8, 132.6, 132.2, 129.2, 128.0, 118.7, 115.1, 114.7, 112.9, 111.5, 110.8, 109.1, 76.0, 45.2, 25.8.

Example 526

N-(4-Cyano-2-methoxy-benzyloxy)-2-{[2-(3-methyl-ureido)-pyridin-4-ylmethyl]-amino}-benzamide (compound 211)

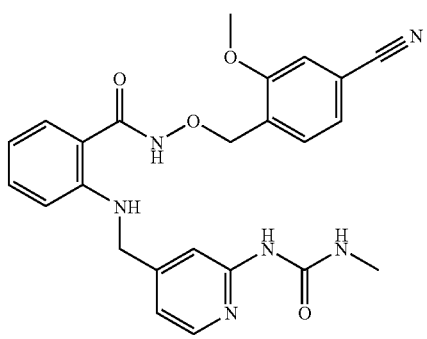

General procedure 1A.

Starting materials: 1-[4-(2,4-Dioxo-4H-benzo[d][1,3]oxazin-1-ylmethyl)-pyridin-2-yl]-3-methyl-urea (see example 525 step 1) and 4-aminooxymethyl-3-methoxy-benzonitrile hydrochloride (see preparation 45).

$^{13}$C-NMR (DMSO-$d_6$) δ 167.3, 157.1, 155.3, 153.7, 151.2, 148.5, 146.6, 132.6, 130.3, 130.0, 128.0, 124.4, 118.7, 115.0, 114.7, 114.0, 112.9, 111.7, 111.5, 109.1, 70.9, 56.0, 45.3, 25.8.

Example 527

N-Cyclopentylmethoxy-2-{[2-(3-methyl-ureido)-pyridin-4-ylmethyl]-amino}-benzamide (compound 212)

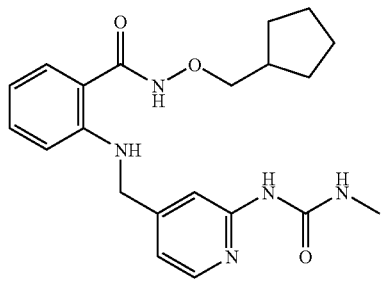

General procedure 1A.

Starting materials: 1-[4-(2,4-Dioxo-4H-benzo[d][1,3]oxazin-1-ylmethyl)-pyridin-2-yl]-3-methyl-urea (see example 525 step 1) and O-cyclopentylmethyl-hydroxylamine hydrochloride (see preparation 66).

$^{13}$C-NMR (DMSO-$d_6$) δ 166.9, 155.3, 153.7, 151.3, 148.5, 146.5, 132.4, 127.9, 115.1, 114.7, 113.3, 111.4, 109.1, 79.4, 45.3, 37.6, 28.9, 25.8, 24.9.

Example 528

N-(2,3-Difluoro-4-methyl-benzyloxy)-2-{[2-(3-methyl-ureido)-pyridin-4-ylmethyl]-amino}-benzamide (compound 213)

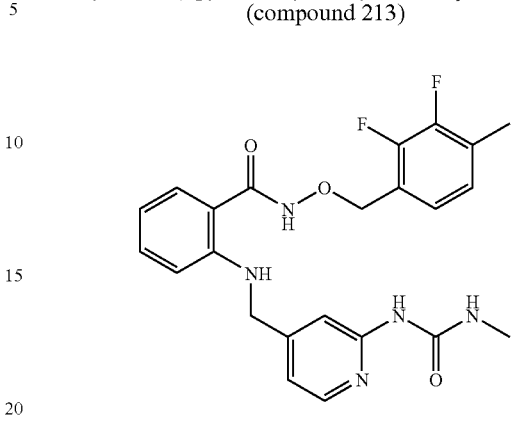

General procedure 1A.

Starting materials: 1-[4-(2,4-Dioxo-4H-benzo[d][1,3]oxazin-1-ylmethyl)-pyridin-2-yl]-3-methyl-urea (see example 525 step 1) and O-(2,3-difluoro-4-methyl-benzyl)hydroxylamine hydrochloride (see preparation 15).

$^{13}$C-NMR (DMSO-$d_6$) δ 167.3, 155.3, 153.8, 151.2, 148.5, 146.6, 132.5, 128.0, 127.2, 126.1, 125.8, 122.6, 115.1, 114.8, 113.1, 111.5, 109.2, 69.8, 45.3, 25.8, 13.8.

Example 529

[3-(4-{[2-(4-Cyano-benzyloxycarbamoyl)-phenylamino]-methyl}-pyridin-2-yl)-ureido]-acetic acid ethyl ester (compound 214)

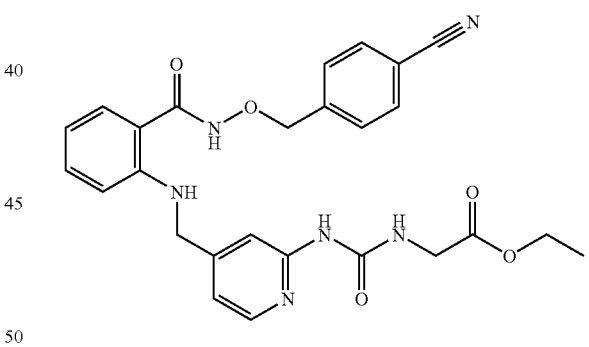

Step 1: To a stirred solution of 1-(2-amino-pyridin-4-ylmethyl)-1H-benzo[d][1,3]oxazine-2,4-dione (600 mg, see preparation 7b) in pyridine (7 ml) was added isocyanatoacetic acid ethyl ester (0.4 ml). The reaction mixture was stirred at room temperature for 3 hours, and the solvent was evaporated under reduced pressure. The residue was dissolved in EtOAc and washed with water and brine. The organic layer was dried (MgSO$_4$) and evaporated under reduced pressure. The resulting oil was treated with EtOAc (3 ml) and gave a precipitate that was isolated by filtration and dried in vacuo, affording {3-[4-(2,4-Dioxo-4H-benzo[d][1,3]oxazin-1-ylmethyl)-pyridin-2-yl]-ureido}-acetic acid ethyl ester (0.53 g). Step 2: This anhydride intermediate was converted into the title compound by reaction with O-(4-cyanobenzyl)hydroxylamine hydrochloride (see preparation 10), using general procedure 1A. $^{13}$C-NMR (DMSO-$d_6$) δ 170.3, 167.4, 154.8, 153.5, 151.4, 148.5, 146.7, 141.8, 132.7, 132.2, 129.1, 128.0, 118.6, 115.4, 114.8, 112.9, 111.5, 110.7, 109.3, 76.0, 60.3, 45.2, 41.2, 14.0.

Example 530

(3-{4-[(2-Cyclopentylmethoxycarbamoyl-phenylamino)-methyl]-pyridin-2-yl}-ureido)acetic acid ethyl ester (compound 215)

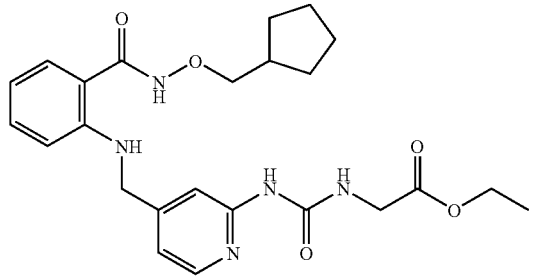

General procedure 1A.

Starting materials: {3-[4-(2,4-Dioxo-4H-benzo[d][1,3]oxazin-1-ylmethyl)-pyridin-2-yl]-ureido}-acetic acid ethyl ester (see example 529 step 1) and O-cyclopentylmethylhydroxyl-amine hydrochloride (see preparation 66).

$^{13}$C-NMR (DMSO-$d_6$) δ 170.3, 166.9, 154.8, 153.5, 151.5, 148.5, 146.6, 132.4, 127.9, 115.4, 114.7, 113.3, 111.4, 109.2, 79.4, 60.3, 45.2, 41.2, 37.6, 28.9, 24.9, 14.0.

Example 531

[3-(4-{[2-(4-Cyano-benzyloxycarbamoyl)-phenylamino]-methyl}-pyridin-2-yl)-ureido]-acetic acid (compound 216)

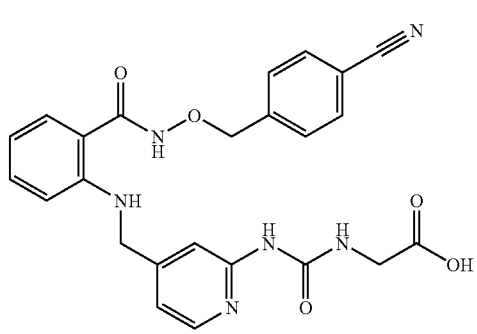

To a stirred suspension of [3-(4-{[2-(4-cyano-benzyloxycarbamoyl)-phenylamino]-methyl}-pyridin-2-yl)-ureido]-acetic acid ethyl ester (Example 529, 188 mg) in methanol (4 ml) was added 2 M aqueous sodium hydroxide (2 ml). The reaction mixture was stirred at room temperature for 15 minutes. Water (6 ml) was added and the pH of the mixture was adjusted to 5 by addition of 4 M hydrochloric acid. The resulting precipitated material was isolated by filtration and dried under high vacuum, affording the title compound. $^{13}$C-NMR (DMSO-$d_6$) δ 171.7, 167.5, 154.7, 153.5, 151.3, 148.4, 146.7, 141.9, 132.6, 132.1, 129.1, 128.0, 118.7, 115.3, 114.8, 112.8, 111.5, 110.7, 109.2, 75.9, 45.3, 41.4

Example 532

(3-{4-[(2-Cyclopentylmethoxycarbamoyl-phenylamino)-methyl]-pyridin-2-yl}-ureido)-acetic acid (compound 217)

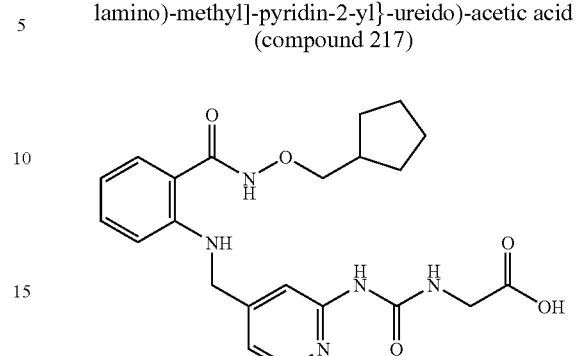

Prepared by a similar procedure as described for preparation of Example 531, starting from: (3-{4-[(2-Cyclopentylmethoxycarbamoyl-phenylamino)-methyl]-pyridin-2-yl}-ureido)-acetic acid ethyl ester (Example 530).

$^{13}$C-NMR (DMSO-$d_6$) δ 171.6, 166.9, 154.8, 153.6, 151.4, 148.5, 146.7, 132.4, 128.0, 115.3, 114.8, 113.4, 111.5, 109.3, 79.5, 45.3, 41.2, 37.6, 29.0, 24.9.

Example 533

2-Methyl-acrylic acid 2-[3-(4-{[2-(4-cyano-benzyloxycarbamoyl)-phenylamino]-methyl}-pyridin-2-yl)-ureido]-ethyl ester (compound 218)

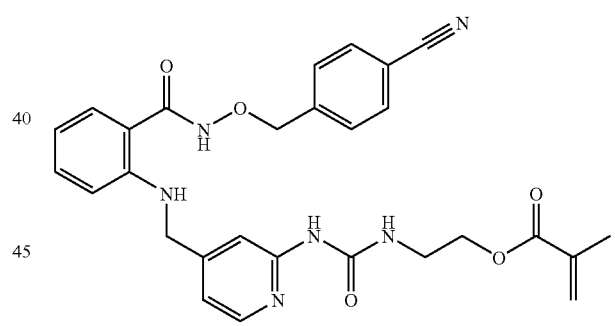

Step 1: To a stirred solution of 1-(2-amino-pyridin-4-ylmethyl)-1H-benzo[d][1,3]oxazine-2,4-dione (1.2 g, see preparation 7b) in pyridine was added isocyanatoethyl methacrylate (0.76 ml). The reaction mixture was heated to 40° C. and stirred for 2 hours. More isocyanatoethyl methacrylate (0.1 ml) was added and stirring was continued for 2 hours. The solvent was evaporated under reduced pressure and EtOAc (10 ml) was added to the residue. On scraping a solid material formed, that was isolated by filtration and dried in vacuo, affording 2-methyl-acrylic acid 2-{3-[4-(2,4-dioxo-4H-benzo[d][1,3]oxazin-1-ylmethyl)-pyridin-2-yl]-ureido}-ethyl ester (1.78 g). Step 2: This anhydride intermediate was converted into the title compound by reaction with O-(4-cyanobenzyl)hydroxylamine hydrochloride (see preparation 10), using general procedure 1A. $^{13}$C-NMR (DMSO-$d_6$) δ 167.5, 166.5, 154.8, 153.7, 151.4, 148.6, 146.6, 141.9, 135.8, 132.8, 132.3, 129.2, 128.1, 125.9, 118.8, 115.4, 114.9, 113.0, 111.6, 110.9, 109.4, 76.1, 63.7, 45.4, 38.0, 18.0.

Example 534

2-Methyl-acrylic acid 2-(3-{4-[(2-cyclopentyl-methoxycarbamoyl-phenylamino)-methyl]-pyridin-2-yl}-ureido)-ethyl ester (compound 219)

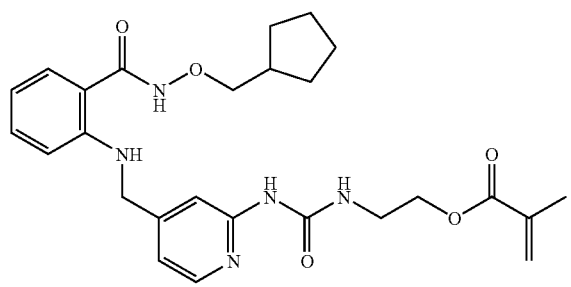

General procedure 1A.

Starting materials: 2-Methyl-acrylic acid 2-{3-[4-(2,4-dioxo-4H-benzo[d][1,3]oxazin-1-ylmethyl)-pyridin-2-yl]-ureido}-ethyl ester (Example 533 step 1) and O-cyclopentylmethylhydroxylamine hydrochloride (see preparation 66).

$^{13}$C-NMR (DMSO-$d_6$) δ 166.9, 166.3, 154.7, 153.6, 151.4, 148.5, 146.5, 135.7, 132.4, 127.9, 125.8, 115.3, 114.7, 113.3, 111.4, 109.2, 79.4, 63.6, 45.3, 37.9, 37.6, 28.9, 24.9, 17.8.

Example 535

N-(4-Cyano-benzyloxy)-2-({2-[3-(2-hydroxy-ethyl)-ureido]-pyridin-4-ylmethyl}-amino)-benzamide (compound 220)

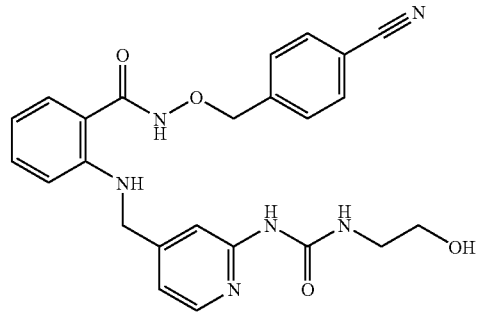

To a stirred suspension of 2-methyl-acrylic acid 2-[3-(4-{[2-(4-cyanobenzyloxy-carbamoyl)-phenylamino]-methyl}-pyridin-2-yl)-ureido]-ethyl ester (Example 533, 500 mg) in methanol (10 ml) was added 2 M aqueous sodium hydroxide (5 ml). The reaction mixture was stirred at room temperature for 20 minutes. The pH of the mixture was adjusted to 5 by addition of 4 M hydrochloric acid and water (15 ml) was added. The resulting precipitated material was isolated by filtration and dried in vacuo, and gave the title compound.
$^{13}$C-NMR (DMSO-$d_6$) δ 167.4, 154.8, 153.8, 151.1, 148.6, 146.7, 141.8, 132.6, 132.1, 129.1, 128.0, 118.6, 115.1, 114.8, 113.0, 111.6, 110.8, 109.3, 76.0, 60.2, 45.3, 41.8.

Example 536

N-Cyclopentylmethoxy-2-({2-[3-(2-hydroxy-ethyl)-ureido]-pyridin-4-ylmethyl}-amino)-benzamide (compound 221)

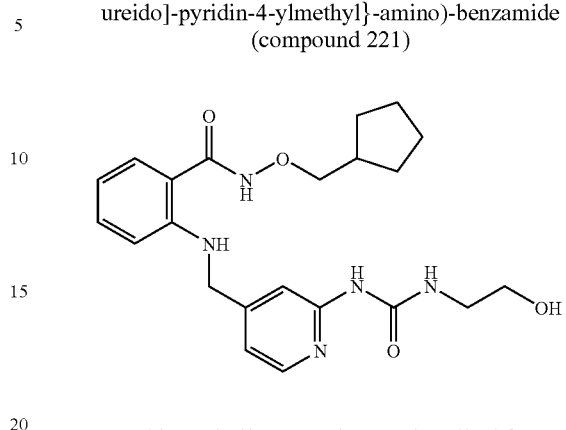

Prepared by a similar procedure as described for preparation of Example 535, starting from 2-methyl-acrylic acid 2-(3-{4-[(2-cyclopentylmethoxycarbamoyl-phenylamino)methyl]-pyridin-2-yl}-ureido)-ethyl ester (Example 534).

$^{13}$C-NMR (DMSO-$d_6$) δ 166.9, 154.8, 153.8, 151.2, 148.5, 146.7, 132.4, 127.9, 115.1, 114.7, 113.4, 111.4, 109.3, 79.5, 60.2, 45.4, 41.8, 37.6, 29.0, 24.9.

Example 537

Acetic acid (4-{[2-(4-cyano-benzyloxycarbamoyl)-phenylamino]-methyl}-pyridin-2-ylcarbamoyl)-methyl ester (compound 222)

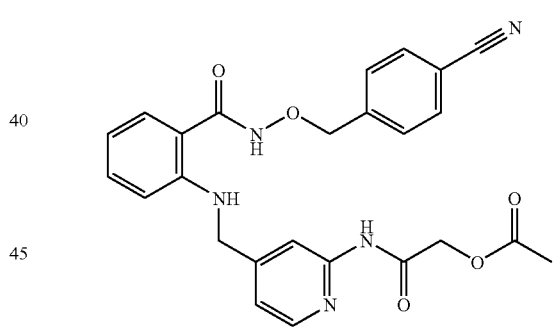

Step 1: To a stirred solution of 1-(2-amino-pyridin-4-ylmethyl)-1H-benzo[d][1,3]oxazine-2,4-dione (600 mg, see preparation 7b) in pyridine (5 ml) was added acetoxyacetyl chloride (0.29 ml). The reaction mixture was stirred at room temperature for 30 minutes. The solvent was evaporated under reduced pressure. The remaining oil was dissolved in EtOAc and washed with water and brine. The organic layer was concentrated to ca. 10 ml under reduced pressure. The resulting solid material was isolated by filtration and dried in vacuo, affording acetic acid [4-(2,4-dioxo-4H-benzo[d][1,3]oxazin-1-ylmethyl)-pyridin-2-ylcarbamoyl]-methyl ester.

Step 2: The obtained anhydride intermediate was converted into the title compound by reaction with O-(4-cyanobenzyl)hydroxylamine hydrochloride (see preparation 10), using general procedure 1A. $^{13}$C-NMR (DMSO-$d_6$) δ 169.9, 167.4, 166.1, 151.7, 151.5, 148.5, 147.9, 141.8, 132.6, 132.2, 129.2, 128.0, 118.7, 117.8, 114.8, 113.0, 111.4, 110.7, 75.9, 62.3, 45.3, 20.3.

Example 538

Acetic acid {4-[(2-cyclopentylmethoxycarbamoyl-phenylamino)-methyl]-pyridin-2-ylcarbamoyl}-methyl ester (compound 223)

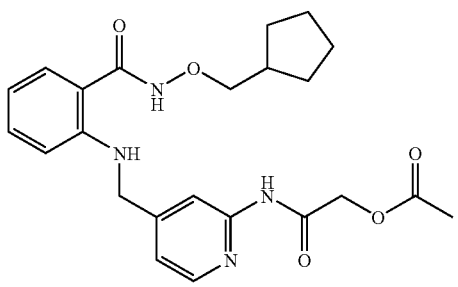

General procedure 1A.

Starting materials: Acetic acid [4-(2,4-dioxo-4H-benzo[d][1,3]oxazin-1-ylmethyl)pyridin-2-ylcarbamoyl]-methyl ester (see Example 537 step 1) and O-cyclopentylmethylhydroxyl-amine hydrochloride (see preparation 66).

$^{13}$C-NMR (DMSO-$d_6$) δ 169.9, 166.9, 166.1, 151.7, 151.6, 148.4, 147.9, 132.4, 128.0, 117.8, 114.7, 113.4, 111.4, 79.4, 62.3, 45.3, 37.6, 28.9, 24.9, 20.3

Example 539

N-(4-Cyano-benzyloxy)-2-{[2-(2-hydroxy-acetylamino)-pyridin-4-ylmethyl]-amino}-benzamide (compound 224)

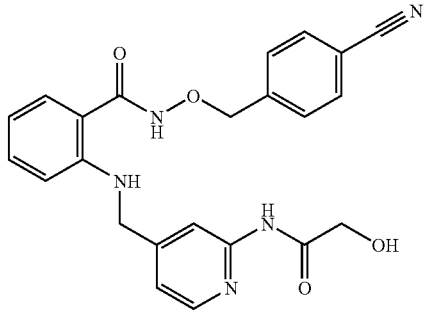

Acetic acid (4-{[2-(4-cyano-benzyloxycarbamoyl)phenylamino]-methyl}-pyridin-2-ylcarbamoyl)-methyl ester (Example 537, 52 mg) was suspended in methanol (2 ml) and 2M aqueous sodium hydroxide (1 ml) was added. The reaction mixture was stirred at room temperature for 10 minutes. The pH of the mixture was adjusted to 7 by addition of 2M hydrochloric acid. The resulting precipitate was isolated by filtration and dried in vacuo, affording the title compound. $^{13}$C-NMR (DMSO-$d_6$) δ 171.2, 167.5, 151.7, 151.3, 148.6, 148.1, 141.9, 132.8, 132.3, 129.3, 128.1, 118.8, 118.1, 114.9, 113.0, 111.6, 111.0, 110.9, 76.1, 61.6, 45.4.

Example 540

4-{[2-(4-Cyano-benzyloxycarbamoyl)-phenylamino]-methyl}-pyridin-2-yl)-carbamic acid ethyl ester (compound 225)

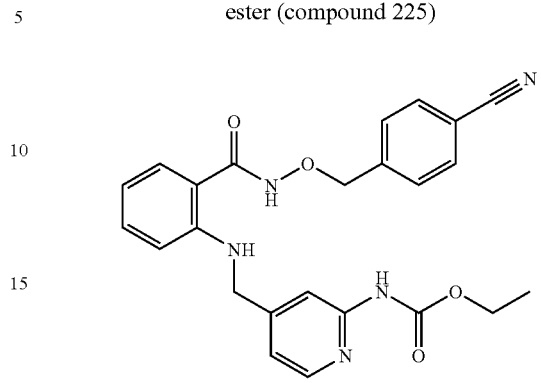

To a stirred solution of 1-(2-amino-pyridin-4-ylmethyl)-1H-benzo[d][1,3]oxazine-2,4-dione (200 mg, see preparation 7b) in pyridine (5 ml) was added chloroformic acid ethyl ester (71 μl). The reaction mixture was stirred at room temperature for 60 minutes. More chloroformic acid ethyl ester (60 μl) was added and stirring continued for 30 minutes. O-(4-Cyanobenzyl)hydroxylamine hydrochloride (1 eq., see preparation 10) was added and the reaction mixture was stirred at room temperature for 15 hours. The solvent was evaporated under reduced pressure. The residue was dissolved in EtOAc and washed with water and brine, dried (MgSO$_4$) and evaporated under reduced pressure. The remaining oil was treated with ethanol (2 ml) and the resulting solid material was isolated by filtration and dried in vacuo, affording the title compound. $^1$H-NMR (DMSO-$d_6$) δ 11.67 (s, 1H), 10.03 (s, 1H), 8.17 (d, 1H), 7.93 (t, 1H), 7.9-7.8 (m, 3H), 7.69 (d, 2H), 7.37 (d, 1H), 7.21 (t, 1H), 6.97 (d, 1H), 6.55 (t, 1H), 6.52 (d, 1H), 5.04 (s, 2H), 4.44 (d, 2H), 4.11 (q, 2H), 1.21 (t, 3H).

Example 541

N-(4-Cyano-benzyloxy)-2-{[2-(cyclopropanecarbonyl-amino)-pyridin-4-ylmethyl]-amino}-benzamide (compound 226)

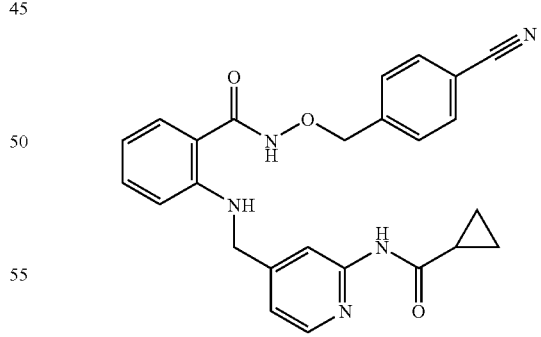

To a stirred solution of 1-(2-amino-pyridin-4-ylmethyl)-1H-benzo[d][1,3]oxazine-2,4-dione (200 mg, see preparation 7b) in pyridine (5 ml) was added cyclopropanecarbonyl chloride (80 μl). The reaction mixture was stirred at room temperature for 20 minutes. More cyclopropanecarbonyl chloride (20 μl) was added and stirring continued for 30 minutes. Cyanobenzyl)hydroxylamine hydrochloride (1 eq., see preparation 10) was added and the reaction mixture was stirred at room temperature for 15 hours. The solvent was evaporated under reduced pressure. The residue was dissolved in EtOAc and washed with water and brine, dried (MgSO$_4$) and evaporated under reduced pressure. The crude product was purified by column chromatography on silica gel (elution with 0 to 100% EtOAc in heptane) and gave the title compound as a foam. $^{13}$C-NMR (DMSO-d$_6$) δ 172.4, 167.4, 152.3, 151.2, 148.5, 147.8, 141.8, 132.7, 132.1, 129.2, 128.0, 118.7, 117.3, 114.8, 112.9, 111.5, 111.3, 110.8, 76.0, 45.4, 14.0, 7.5.

Example 542

N-Cyclopentylmethoxy-2-{[2-(cyclopropanecarbonyl-amino)-pyridin-4-ylmethyl]amino}-benzamide (compound 227)

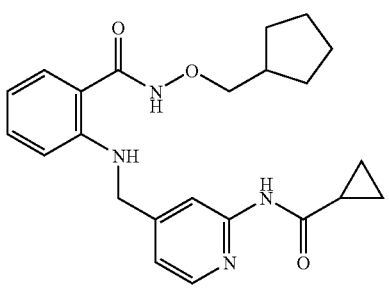

Step 1: To a stirred solution of 1-(2-amino-pyridin-4-ylmethyl)-1H-benzo[d][1,3]oxazine-2,4-dione (1.1 g, see preparation 7b) in pyridine (15 ml) was added cyclopropanecarbonyl chloride (512 mg). The reaction mixture was stirred at room temperature for 30 minutes, and the solvent was evaporated under reduced pressure. The remaining oil was dissolved in EtOAc and washed with water and brine. The organic layer was concentrated under reduced pressure and the resulting solid material was isolated by filtration and dried in vacuo, affording cyclopropanecarboxylic acid [4-(2,4-dioxo-4H-benzo[d][1,3]oxazin-1-ylmethyl)-pyridin-2-yl]-amide. Step 2: The above obtained anhydride intermediate was converted into the title compound by reaction with O-cyclopentyl-methylhydroxyl-amine hydrochloride (see preparation 66), using general procedure 1A. $^{13}$C-NMR (DMSO-d$_6$) δ 172.4, 166.9, 152.3, 151.3, 148.5, 147.8, 132.4, 127.9, 117.3, 114.7, 113.3, 111.4, 111.3, 79.4, 45.4, 37.6, 28.9, 24.9, 14.1, 7.4.

Example 543

N-Cyclopentylmethoxy-2-({2-[2-(2,5-dioxo-imidazolidin-4-yl)-acetylamino]-pyridin-4-ylmethyl}-amino)-benzamide (compound 228)

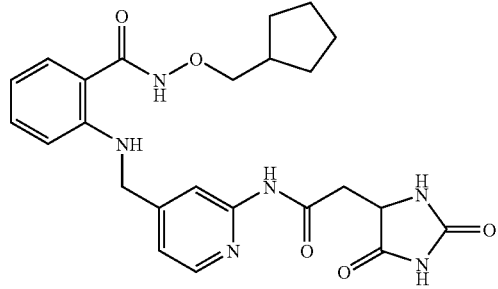

Prepared by a similar procedure as described for preparation of example 541. Starting materials: 1-(2-Amino-pyridin-4-ylmethyl)-1H-benzo[d][1,3]oxazine-2,4-dione (see preparation 7b), hydantoin-5-acetyl chloride (Lancaster), and O-cyclopentyl-methylhydroxylamine hydrochloride (see preparation 66).

$^{13}$C-NMR (DMSO-d$_6$) δ 175.6, 168.2, 166.9, 157.5, 152.0, 151.5, 148.5, 147.8, 132.4, 128.0, 124.2, 117.6, 114.8, 113.3, 111.5, 79.4, 54.3, 45.5, 37.6, 28.9, 24.9.

Example 544

2-[2-Amino-pyridin-4-ylmethyl)-amino]-N-cyclopentylmethoxy-benzamide (compound 229)

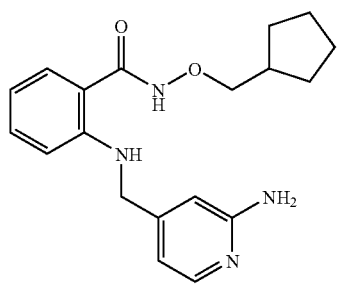

General procedure 1A.

Starting materials: 1-(2-Amino-pyridin-4-ylmethyl)-1H-benzo[d][1,3]oxazine-2,4-dione (see preparation 7B) and O-cyclopentyl-methylhydroxyl-amine hydrochloride (see preparation 66).

$^{13}$C-NMR (DMSO-d$_6$) δ 167.0, 159.9, 149.5, 148.7, 147.7, 132.4, 127.9, 114.5, 113.0, 111.4, 110.5, 105.2, 79.4, 45.2, 37.6, 28.9, 24.9.

Example 545

N-Benzyloxy-2-[(quinolin-4-ylmethyl)-amino]-benzamide (compound 230)

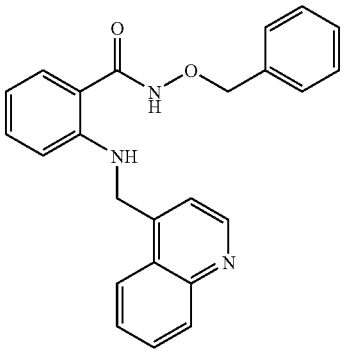

General procedure 1, method 2.

Starting materials: 2-[(Quinolin-4-ylmethyl)-amino]-benzoic acid (see preparation 1V) and O-benzyl-hydroxylamine hydrochloride (Aldrich).

$^{13}$C-NMR (DMSO-d$_6$) δ 167.2, 150.4, 148.5, 147.7, 144.8, 136.0, 132.6, 129.7, 129.3, 128.9, 128.3, 128.1, 126.6, 126.2, 123.6, 118.7, 114.9, 113.4, 111.6, 76.9, 42.9.

Example 546

N-(4-Cyano-benzyloxy)-2-[(quinolin-4-ylmethyl)-amino]-benzamide (compound 231)

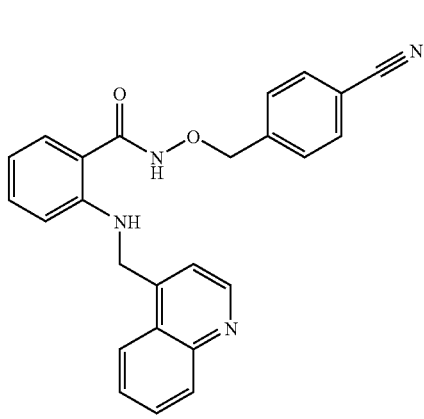

General procedure 1, method 2.

Starting materials: 2-[(Quinolin-4-ylmethyl)-amino]-benzoic acid (see preparation 1V) and O-(4-cyanobenzyl)hydroxylamine (see preparation 10).

$^{13}$C-NMR (DMSO-d$_6$) δ 167.0, 150.2, 148.4, 147.6, 144.7, 141.9, 132.6, 132.1, 129.6, 129.2, 129.1, 128.1, 126.5, 126.1, 123.5, 118.6, 118.6, 114.8, 113.1, 111.5, 110.7, 75.8, 42.8.

Example 547

N-(2-Methyl-thiazol-4-ylmethoxy)-2-[(quinolin-4-ylmethyl)-amino]-benzamide (compound 232)

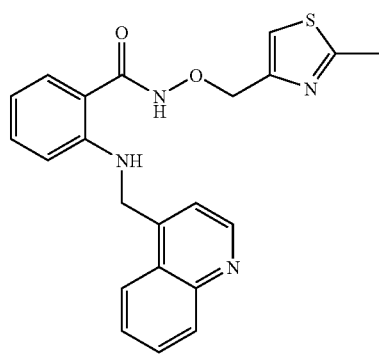

General procedure 1, method 2.

Starting materials: 2-[(Quinolin-4-ylmethyl)-amino]-benzoic acid (see preparation 1V) and O-(2-methyl-thiazol-4-ylmethyl)-hydroxylamine hydrochloride (see preparation 12).

$^{13}$C-NMR (CDCl$_3$) δ 168.9, 167.0, 150.9, 150.4, 149.4, 148.0, 144.1, 133.6, 130.3, 129.3, 127.4, 126.8, 126.5, 122.5, 118.8, 118.2, 115.7, 112.7, 112.1, 73.1, 43.8, 19.2.

Example 548

N-Cyclopentylmethoxy-2-[(quinolin-4-ylmethyl)-amino]-benzamide (compound 233)

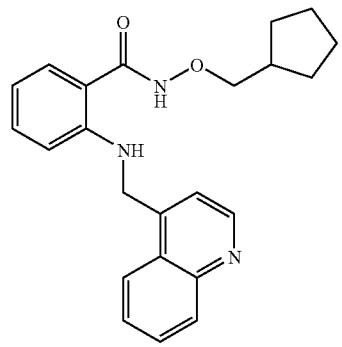

General procedure 1, method 2.

Starting materials: 2-[(Quinolin-4-ylmethyl)-amino]-benzoic acid (see preparation 1V) and O-cyclopentyl-methylhydroxylamine hydrochloride (see preparation 66).

$^1$H-NMR (DMSO-d$_6$) δ 11.48 (br, 1H), 8.81 (d, 1H), 8.23 (d, 1H), 8.06 (d, 1H), 7.98 (t, 1H), 7.79 (t, 1H), 7.67 (t, 1H), 7.44 (d, 1H), 7.39 (d, 1H), 7.19 (t, 1H), 6.59 (d, 1H), 6.59 (t, 1H), 4.97 (d, 2H), 3.76 (d, 2H), 2.19 (m, 1H), 1.72 (m, 2H), 1.54 (m, 4H), 1.30 (m, 2H)

Example 549

2-[(Quinolin-4-ylmethyl)-amino]-N-(tetrahydropyran-4-ylmethoxy)-benzamide (compound 234)

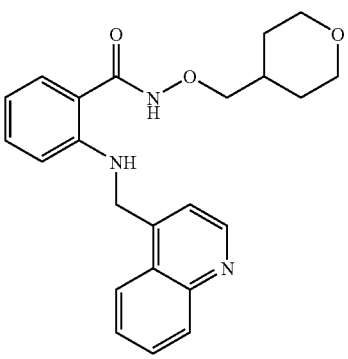

General procedure 1, method 2.

Starting materials: 2-[(Quinolin-4-ylmethyl)-amino]-benzoic acid (see preparation 1V) and O-(tetrahydro-pyran-4-ylmethyl)-hydroxylamine hydrochloride (see preparation 92).

ES$^+$: (M+H)$^+$=392, (M+Na)$^+$=414.

Example 550

N-(4-Cyano-2-methoxy-benzyloxy)-2-[(6-methoxy-pyridin-3-ylmethyl)-amino]-benzamide (compound 235)

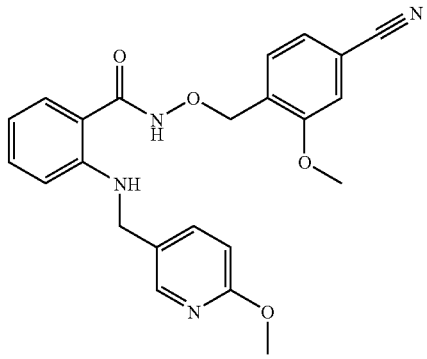

General procedure 1, method 1.

Starting materials: 2-[(6-Methoxy-pyridin-3-ylmethyl)-amino]-benzoic acid (see preparation 1W) and 4-aminooxymethyl-3-methoxy-benzonitrile hydrochloride (see preparation 45).

$^{13}$C-NMR (DMSO-d$_6$) δ 167.3, 162.7, 157.0, 148.4, 145.6, 138.5, 132.6, 130.2, 130.0, 128.0, 127.7, 124.4, 118.7, 114.6, 114.0, 113.0, 111.7, 111.5, 110.3, 70.9, 56.0, 53.0, 42.9.

Example 551

N-Benzyloxy-2-[(6-methoxy-pyridin-3-ylmethyl)-amino]-benzamide compound 236)

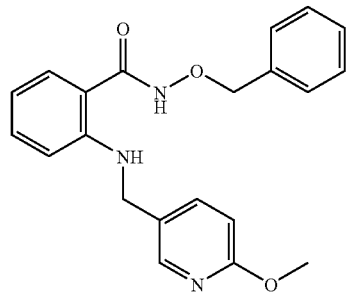

General procedure 1, method 1.

Starting materials: 2-[(6-Methoxy-pyridin-3-ylmethyl)-amino]-benzoic acid (see preparation 1W) and O-benzyl-hydroxylamine hydrochloride (Aldrich).

$^{13}$C-NMR (DMSO-d$_6$) δ 167.2, 162.7, 148.4, 145.6, 138.5, 135.9, 132.5, 128.8, 128.2, 128.0, 127.7, 114.6, 113.2, 111.5, 110.3, 76.9, 53.0, 42.9.

Example 552

N-(4-Cyano-benzyloxy)-2-[(6-methoxy-pyridin-3-ylmethyl)-amino]-benzamide (compound 237)

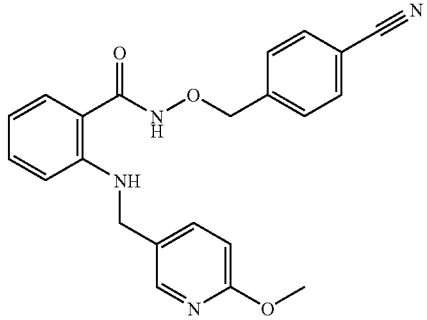

General procedure 1, method 1.

Starting materials: 2-[(6-Methoxy-pyridin-3-ylmethyl)-amino]-benzoic acid (see preparation 1W) and O-(4-cyanobenzyl)hydroxylamine hydrochloride (see preparation 10).

$^{13}$C-NMR (DMSO-d$_6$) δ 167.5, 162.8, 148.5, 145.7, 141.9, 138.6, 132.7, 132.2, 129.2, 128.1, 127.8, 118.8, 114.7, 113.0, 111.7, 110.8, 110.4, 76.0, 56.0, 42.9, 18.6.

Example 553

N-Benzyloxy-2-[(thiazol-5-ylmethyl)-amino]-benzamide (compound 238)

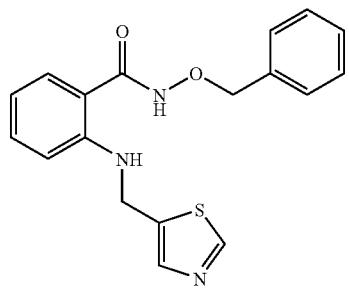

General procedure 1, method 1.

Starting materials: 2-[(Thiazol-5-ylmethyl)-amino]-benzoic acid (see preparation 1X) and O-benzyl-hydroxylamine hydrochloride (Aldrich).

$^{13}$C-NMR (DMSO-d$_6$) δ 167.0, 153.5, 148.0, 140.9, 138.0, 135.9, 132.4, 128.8, 128.2, 128.0, 115.1, 113.5, 111.6, 76.8, 38.5.

Example 554

N-(2,4-Dichloro-benzyloxy)-2-[(thiazol-5-ylmethyl)-amino]-benzamide (compound 239)

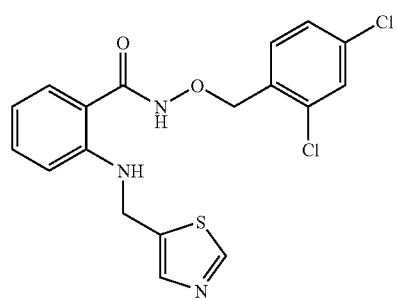

General procedure 1, method 1.

Starting materials: 2-[(Thiazol-5-ylmethyl)-amino]-benzoic acid (see preparation 1x) and 1-[(ammoniooxy)methyl]-2,4-dichlorobenzene chloride (Bionet).

$^{13}$C-NMR (DMSO-d$_6$) δ 153.5, 147.9, 140.9, 138.0, 134.1, 133.7, 132.8, 132.6, 132.5, 128.7, 128.1, 127.3, 115.1, 113.3, 111.6, 72.9, 38.5.

Example 555

N-(2-Methyl-thiazol-4-ylmethoxy)-2-[(5-oxo-4,5-dihydro-1H-[1,2,4]triazol-3-ylmethyl)-amino]-benzamide (compound 240)

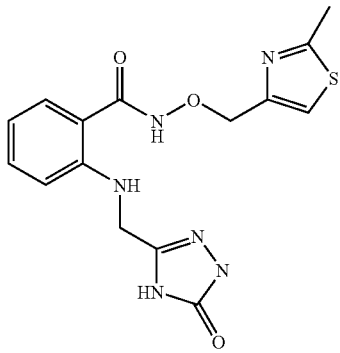

Prepared by a similar procedure as described for preparation of example 516.

Starting materials: 1-(5-Oxo-4,5-dihydro-1H-[1,2,4]triazol-3-ylmethyl)-1H-benzo[d][1,3]oxazine-2,4-dione (see preparation 7E) and O-(2-methyl-thiazol-4-ylmethyl)-hydroxylamine hydrochloride (see preparation 12).

$^{13}$C-NMR (DMSO-d$_6$) δ 165.3, 156.0, 150.5, 148.0, 145.3, 132.5, 128.0, 118.9, 117.1, 115.2, 113.5, 111.3, 71.9, 18.6.

Example 556

N-Benzyloxy-2-[(5-oxo-4,5-dihydro-1H-[1,2,4]triazol-3-ylmethyl)-amino]-benzamide (compound 241)

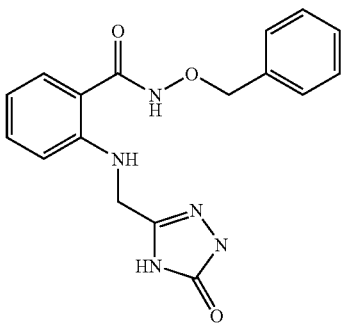

Prepared by a similar procedure as described for preparation of example 516.

Starting materials: 1-(5-Oxo-4,5-dihydro-1H-[1,2,4]triazol-3-ylmethyl)-1H-benzo[d][1,3]oxazine-2,4-dione (see preparation 7E) and O-benzyl-hydroxylamine hydrochloride (Aldrich).

$^1$H-NMR (DMSO-d$_6$) δ 11.56 (br, 1H), 11.35 (br, 1H), 11.25 (s, 1H), 7.71 (t, 1H), 7.5-7.2 (m, 7H), 6.74 (d, 1H), 6.60 (t, 1H), 4.92 (s, 2H), 4.17 (d, 2H)

Example 557

N-Benzyloxy-2-(2-imidazol-1-yl-ethylamino)-benzamide (compound 242)

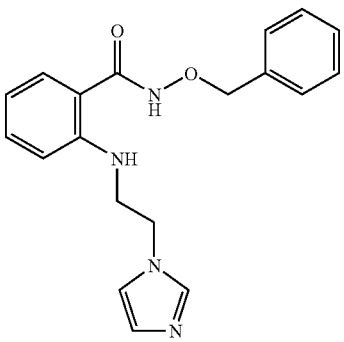

General procedure 1A.

Starting materials: 1-(2-Imidazol-1-yl-ethyl)-1H-benzo[d][1,3]oxazine-2,4-dione (see preparation 7F) and O-benzyl-hydroxylamine hydrochloride (Aldrich).

$^{13}$C-NMR (DMSO-d$_6$) δ 148.5, 137.4, 136.0, 132.7, 129.5, 128.9, 128.4, 128.3, 128.3, 128.1, 119.5, 114.7, 113.0, 111.2, 76.9, 45.3, 43.2.

Example 558

N-Cyclopentylmethoxy-2-(2-imidazol-1-yl-ethylamino)-benzamide (compound 243)

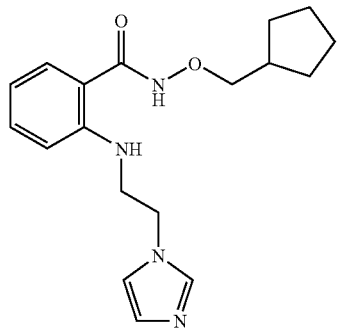

General procedure 1A.

Starting materials: 1-(2-Imidazol-1-yl-ethyl)-1H-benzo[d][1,3]oxazine-2,4-dione (see preparation 7F) and O-cyclopentyl-methylhydroxylamine hydrochloride (see preparation 66).

$^{13}$C-NMR (DMSO-d$_6$) δ 166.8, 148.4, 137.3, 132.5, 128.3, 127.9, 119.4, 114.6, 113.1, 111.0, 79.4, 45.1, 43.1, 37.6, 28.9, 24.9.

Example 559

N-(4-Cyano-benzyloxy)-2-(1-pyridin-4-yl-ethylamino)-benzamide (compound 244)

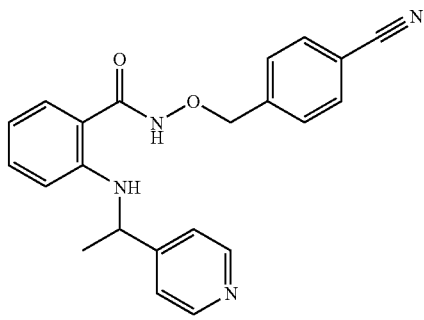

General procedure 1A.

Starting materials: 1-(1-Pyridin-4-yl-ethyl)-1H-benzo[d][1,3]oxazine-2,4-dione (see preparation 7G) and O-(4-cyanobenzyl)hydroxylamine hydrochloride (see preparation 10).

$^{13}$C-NMR (DMSO-$d_6$) δ 167.5, 154.0, 149.7, 147.6, 141.8, 132.5, 132.2, 129.1, 128.0, 121.0, 118.7, 114.9, 112.7, 112.3, 110.7, 75.9, 50.6, 23.8.

Example 560

2-{[2-(3-Methyl-ureido)-pyridin-4-ylmethyl]-amino}-N-(tetrahydro-pyran-2-ylmethoxy)-benzamide (compound 245)

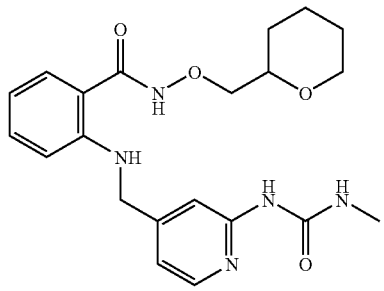

General procedure 1A.

Starting materials: 1-[4-(2,4-Dioxo-4H-benzo[d][1,3]oxazin-1-ylmethyl)-pyridin-2-yl]-3-methyl-urea (see example 525 step 1) and O-(tetrahydro-pyran-2-ylmethyl)hydroxylamine hydrochloride (see preparation 93).

$^{13}$C-NMR (DMSO-$d_6$) δ 167.0, 155.3, 153.7, 151.2, 148.5, 146.6, 132.4, 128.0, 115.1, 114.7, 113.1, 111.4, 109.1, 78.5, 74.7, 67.1, 45.3, 27.7, 25.8, 25.4, 22.5.

Example 561

N-Cyclopentylmethoxy-2-{[2-(2-methoxy-acetylamino)-pyridin-4-ylmethyl]-amino}-benzamide (compound 246)

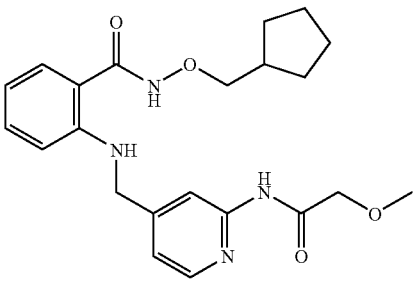

Prepared by a similar procedure as described for preparation 541.

Starting materials: 1-(2-Amino-pyridin-4-ylmethyl)-1H-benzo[d][1,3]oxazine-2,4-dione (see preparation 7b) and methoxyacetyl chloride then O-cyclopentyl-methylhydroxylamine hydrochloride (see preparation 66).

$^{13}$C-NMR (DMSO-$d_6$) δ 168.4, 166.9, 151.6, 151.4, 148.4, 148.0, 132.4, 128.0, 117.9, 114.7, 113.4, 111.4, 111.3, 79.4, 71.1, 58.5, 45.3, 37.6, 28.9, 24.9.

Example 562

N-(4-Cyano-benzyloxy)-2-[(6-oxo-1,6-dihydro-pyridin-3-ylmethyl)-amino]-benzamide (compound 247)

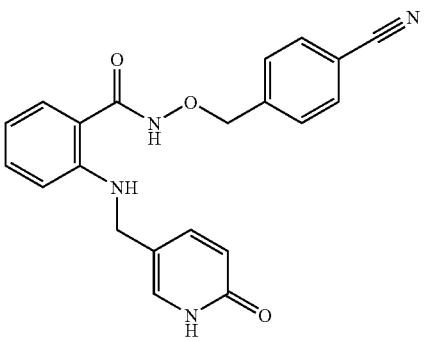

General procedure 1A.

Starting materials: 1-(6-Oxo-1,6-dihydro-pyridin-3-ylmethyl)-1H-benzo[d][1,3]oxazine-2,4-dione (see preparation 7H) and O-(4-cyanobenzyl)hydroxylamine hydrochloride (see preparation 10).

$^{13}$C-NMR (DMSO-$d_6$) δ 167.3, 161.9, 149.5, 148.3, 141.8, 141.2, 133.1, 132.6, 132.1, 129.1, 128.0, 123.8, 120.0, 118.6, 115.6, 114.6, 112.8, 111.5, 110.7, 75.8, 42.2.

Example 563

N-Cyclopentylmethoxy-2-[(tetrahydro-pyran-4-ylmethyl)-amino]-benzamide (compound 248)

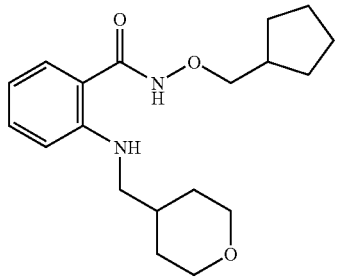

General procedure 1, method 2.

Starting materials: 2-[(Tetrahydro-pyran-4-ylmethyl)-amino]-benzoic acid (see preparation 1Y) and O-cyclopentyl-methylhydroxyl-amine hydrochloride (see preparation 66).

$^{13}$C-NMR (DMSO-d$_6$) δ 167.2, 149.2, 132.6, 127.9, 113.9, 112.5, 111.1, 79.4, 66.7, 48.1, 37.6, 34.0, 30.5, 29.0, 24.9.

Example 564

N-(3-Iodo-4-methyl-benzyloxy)-2-[(pyridin-4-ylmethyl)-amino]-benzamide (compound 250)

Prepared by similar procedures as described above for compounds 1-249.

$^{13}$C-NMR (DMSO-d$_6$) δ 167.1, 149.5, 149.0, 148.2, 140.6, 138.7, 135.6, 132.5, 129.6, 128.8, 128.0, 121.9, 114.8, 113.4, 111.4, 100.9, 75.5, 44.8, 27.1.

Example 565

N-(4-Ethyl-benzyloxy)-2-[(pyridin-4-ylmethyl)-amino]-benzamide (compound 251)

Prepared by similar procedures as described above for compounds 1-249.

$^{13}$C-NMR (DMSO-d$_6$) δ 167.2, 149.8, 149.2, 148.4, 143.9, 133.3, 132.5, 129.1, 128.2, 127.7, 122.2, 114.9, 113.6, 111.5, 76.9, 44.9, 28.0, 15.6.

Example 566

N-(4-Isopropyl-benzyloxy)-2-[(pyridin-4-ylmethyl)-amino]-benzamide (compound 252)

Prepared by similar procedures as described above for compounds 1-249.

$^{13}$C-NMR (DMSO-d$_6$) δ 167.1, 149.5, 149.0, 148.5, 148.3, 133.3, 132.4, 129.0, 128.0, 126.1, 122.0, 114.8, 113.5, 111.4, 76.8, 44.8, 33.1, 23.8.

Example 567

N-(4-tert-Butyl-benzyloxy)-2-[(pyridin-4-ylmethyl)-amino]-benzamide (compound 253)

Prepared by similar procedures as described above for compounds 1-249.

$^{13}$C-NMR (DMSO-d$_6$) δ 167.1, 150.7, 149.5, 149.0, 148.3, 132.9, 132.4, 128.7, 128.0, 125.0, 122.0, 114.8, 113.5, 111.4, 76.7, 44.8, 34.2, 31.0.

Example 568

N-(2-Ethyl-benzyloxy)-2-[(pyridin-4-ylmethyl)-amino]-benzamide (compound 254)

Prepared by similar procedures as described above for compounds 1-249.

$^{13}$C-NMR (DMSO-d$_6$) δ 167.2, 151.7, 148.3, 148.0, 143.7, 133.1, 132.6, 130.7, 128.9, 128.5, 128.3, 125.7, 122.6, 115.0, 113.7, 111.6, 74.9, 45.0, 24.8, 15.7.

Example 569

N-(2-Non-1-enyl-benzyloxy)-2-[(pyridin-4-ylmethyl)-amino]-benzamide (compound 255)

Prepared by similar procedures as described above for compounds 1-249.

$^{13}$C-NMR (CDCl$_3$) δ 168.9, 149.7, 149.1, 148.8, 138.6, 134.5, 133.5, 131.7, 131.1, 129.3, 127.3, 126.8, 126.4, 126.2, 122.0, 115.7, 112.8, 112.1, 76.3, 46.1, 33.4, 31.9, 29.4, 29.2, 29.2, 22.7, 14.1.

Example 570

N-(4-Phenylaminomethyl-benzyloxy)-2-[(pyridin-4-ylmethyl)-amino]-benzamide (compound 256)

Prepared by similar procedures as described above for compounds 1-249.

$^{13}$C-NMR (DMSO-d$_6$) δ 149.5, 149.0, 148.5, 148.2, 140.4, 134.2, 132.4, 128.9, 128.7, 128.0, 126.9, 121.9, 115.6, 114.8, 113.4, 112.2, 111.4, 76.7, 46.1, 44.8.

Example 571

N-(4-Diethylaminomethyl-benzyloxy)-2-[(pyridin-4-ylmethyl)-amino]-benzamide (compound 257)

Prepared by similar procedures as described above for compounds 1-249.

$^{13}$C-NMR (DMSO-d$_6$) δ 166.7, 149.5, 149.0, 148.2, 140.1, 134.2, 132.3, 128.7, 128.3, 128.0, 121.9, 114.8, 113.4, 111.4, 76.7, 56.6, 46.1, 44.8, 11.6.

Example 572

N-(2-Carbamoylmethyl-benzyloxy)-2-[(pyridin-4-ylmethyl)-amino]-benzamide (compound 258)

Prepared by similar procedures as described above for compounds 1-249.

$^1$H-NMR (CD$_3$OD) δ 8.79 (m, 2H), 8.10 (m, 2H), 7.53-7.21 (m, 6H), 6.70 (m, 1H), 6.53 (d, 1H), 5.15 (s, 2H), 4.87 (s, 2H), 3.93 (s, 2H).

Example 573

N-[4-Cyano-2-(2-methoxy-ethoxy)-benzyloxy]-2-[(pyridin-4-ylmethyl)-amino]-benzamide (compound 259)

Prepared by similar procedures as described above for compounds 1-249.

$^{13}$C-NMR (DMSO-d$_6$) δ 167.5, 156.3, 149.7, 149.1, 148.5, 132.7, 130.6, 130.1, 128.2, 124.7, 122.1, 118.8, 115.2, 114.9, 113.2, 111.6, 71.0, 70.2, 68.2, 58.3, 44.9.

Example 574

N-(4-Cyanomethyl-2-methoxy-benzyloxy)-2-[(pyridin-4-ylmethyl)-amino]-benzamide (compound 260)

Prepared by similar procedures as described above for compounds 1-249.

$^{13}$C-NMR (DMSO-d$_6$) δ 167.1, 157.5, 149.5, 149.0, 148.2, 132.9, 132.4, 130.9, 128.1, 123.3, 121.9, 119.7, 119.0, 114.7, 113.4, 111.4, 110.8, 71.1, 55.4, 44.7, 22.4.

Example 575

N-(5-Cyano-2-methoxy-benzyloxy)-2-[(pyridin-4-ylmethyl)-amino]-benzamide (compound 261)

Prepared by similar procedures as described above for compounds 1-249.
$^{13}$C-NMR (DMSO-$d_6$) δ 167.3, 160.6, 149.5, 148.9, 148.3, 134.3, 133.4, 132.5, 128.0, 125.8, 121.9, 119.0, 114.8, 113.3, 111.9, 111.4, 102.4, 70.7, 56.0, 44.8.

Example 576

2-{2-[(Pyridin-4-ylmethyl)-amino]-benzoylaminooxymethyl}-phenyl)-carbamic acid tert-butyl ester (compound 262)

Prepared by similar procedures as described above for compounds 1-249.
$^{13}$C-NMR (CDCl$_3$) δ 170.4, 153.9, 149.8, 149.5, 148.9, 139.7, 133.9, 130.9, 130.4, 127.5, 122.9, 122.4, 121.8, 120.9, 115.7, 112.3, 111.6, 79.7, 76.8, 45.9, 28.4.

Example 577

N-(2-Acetylamino-benzyloxy)-2-[(pyridin-4-ylmethyl)-amino]-benzamide (compound 263)

Prepared by similar procedures as described above for compounds 1-249.
$^{13}$C-NMR (CDCl$_3$) δ 170.3, 170.0, 149.9, 149.4, 148.3, 139.1, 134.2, 130.7, 130.4, 127.5, 123.6, 123.3, 122.7, 122.1, 116.0, 112.3, 111.5, 77.2, 46.2, 24.3.

Example 578

N-(2-Benzoylamino-benzyloxy)-2-[(pyridin-4-ylmethyl)-amino]-benzamide (compound 264)

Prepared by similar procedures as described above for compounds 1-249.
$^{13}$C-NMR (DMSO-$d_6$) δ 168.1, 166.4, 149.6, 148.9, 148.7, 138.0, 135.0, 133.1, 131.5, 130.6, 129.2, 128.1, 128.0, 127.2, 124.6, 124.1, 121.9, 115.0, 112.1, 111.8, 74.7, 44.7.

Example 579

N-(2-Methanesulfonylamino-benzyloxy)-2-[(pyridin-4-ylmethyl)-amino]-benzamide (compound 265)

Prepared by similar procedures as described above for compounds 1-249.
$^{13}$C-NMR (CDCl$_3$) δ 170.7, 149.7, 149.5, 148.6, 138.7, 134.1, 131.3, 130.8, 127.5, 124.5, 124.2, 122.1, 121.5, 115.7, 112.3, 111.2, 76.8, 46.0, 40.1.

Example 580

N-(4-Acetylamino-benzyloxy)-2-[(pyridin-4-ylmethyl)-amino]-benzamide (compound 266)

Prepared by similar procedures as described above for compounds 1-249.
$^{13}$C-NMR (DMSO-$d_6$) δ 168.2, 167.0, 149.5, 149.0, 148.2, 139.3, 132.4, 130.2, 129.6, 128.0, 121.9, 118.5, 114.8, 113.5, 111.4, 76.5, 44.7, 23.9.

Example 581

N-(Biphenyl-4-ylmethoxy)-2-[(pyridin-4-ylmethyl)-amino]-benzamide (compound 267)

Prepared by similar procedures as described above for compounds 1-249.
$^{13}$C-NMR (DMSO-$d_6$) δ 167.3, 149.6, 149.0, 148.4, 140.0, 139.7, 135.1, 132.5, 129.5, 128.9, 128.1, 127.5, 126.6, 126.5, 122.0, 114.8, 113.5, 111.5, 76.6, 44.8.

Example 582

N-(Biphenyl-2-ylmethoxy)-2-[(pyridin-4-ylmethyl)-amino]-benzamide (compound 268)

Prepared by similar procedures as described above for compounds 1-249.
$^{13}$C-NMR (CDCl$_3$) δ 168.7, 149.5, 148.8, 148.5, 142.8, 140.2, 133.1, 132.4, 130.7, 130.1, 129.2, 128.5, 128.0, 127.3, 127.2, 127.1, 121.7, 115.4, 112.6, 111.8, 76.0, 45.8.

Example 583

N-(3'-Methoxy-biphenyl-2-ylmethoxy)-2-[(pyridin-4-ylmethyl)-amino]-benzamide (compound 269)

Prepared by similar procedures as described above for compounds 1-249.
$^{13}$C-NMR (CDCl$_3$) δ 168.8, 159.4, 149.3, 149.0, 142.9, 141.8, 133.4, 132.7, 130.9, 130.1, 129.2, 128.7, 127.6, 127.4, 122.1, 121.9, 118.9, 115.7, 115.1, 112.9, 112.7, 112.0, 76.3, 55.3, 46.0.

Example 584

N-(2'-Methoxy-biphenyl-2-ylmethoxy)-2-[(pyridin-4-ylmethyl)-amino]-benzamide (compound 270)

Prepared by similar procedures as described above for compounds 1-249.
$^{13}$C-NMR (CDCl$_3$) δ 168.4, 156.5, 149.6, 148.9, 138.9, 134.2, 133.3, 131.0, 130.7, 129.6, 129.4, 129.1, 128.4, 127.7, 127.3, 122.0, 120.7, 115.6, 113.0, 111.9, 110.9, 76.3, 55.5, 46.0.

Example 585

N-(3'-Hydroxymethyl-biphenyl-2-ylmethoxy)-2-[(pyridin-4-ylmethyl)-amino]-benzamide (compound 271)

Prepared by similar procedures as described above for compounds 1-249.
$^{13}$C-NMR (CDCl$_3$) δ 168.9, 149.6, 149.0, 143.3, 140.9, 140.6, 133.3, 132.3, 131.7, 130.1, 129.0, 128.4, 128.4, 128.3, 127.7, 127.6, 126.0, 122.0, 115.7, 112.8, 112.0, 76.8, 65.0, 46.0.

Example 586

N-(3-Phenoxy-benzyloxy)-2-[(pyridin-4-ylmethyl)-amino]-benzamide (compound 272)

Prepared by similar procedures as described above for compounds 1-249.
$^{13}$C-NMR (CDCl$_3$) δ 169.0, 157.4, 156.9, 149.6, 148.9, 137.7, 133.3, 129.9, 129.8, 127.8, 123.9, 123.4, 122.0, 119.4, 118.9, 115.6, 112.9, 111.9, 77.8, 46.0.

Example 587

N-(Anthracen-9-ylmethoxy)-2-[(pyridin-4-ylmethyl)-amino]-benzamide (compound 273)

Prepared by similar procedures as described above for compounds 1-249.

¹³C-NMR (DMSO-d₆) δ 167.5, 149.5, 149.1, 148.4, 132.5, 131.0, 130.8, 128.8, 128.7, 128.2, 126.5, 126.2, 125.2, 124.5, 121.9, 114.8, 113.4, 111.5, 68.9, 44.8.

Example 588

N-[4-(2-Methyl-thiazol-4-yl)-benzyloxy]-2-[(pyridin-4-ylmethyl)-amino]-benzamide (compound 274)

Prepared by similar procedures as described above for compounds 1-249.
¹³C-NMR (DMSO-d₆) δ 167.1, 165.5, 153.4, 149.5, 148.9, 148.3, 135.4, 134.0, 132.5, 129.3, 128.0, 125.7, 121.9, 114.8, 113.9, 113.4, 111.4, 76.6, 44.8, 18.8.

Example 589

N-(2-Methanesulfonylamino-1-phenyl-ethoxy)-2-[(pyridin-4-ylmethyl)-amino]-benzamide (compound 275)

Prepared by similar procedures as described above for compounds 1-249.
¹³C-NMR (DMSO-d₆) δ 167.5, 149.5, 148.9, 148.1, 137.8, 132.5, 128.3, 128.1, 127.4, 121.9, 114.8, 113.2, 111.4, 85.3, 46.4, 44.7, 39.6.

Example 590

2-[(Pyridin-4-ylmethyl)-amino]-N-[2-(4-trifluoromethyl-phenyl)-thiazol-4-ylmethoxy]-benzamide (compound 276)

Prepared by similar procedures as described above for compounds 1-249.
¹³C-NMR (DMSO-d₆) δ 167.3, 165.2, 152.7, 149.6, 149.0, 148.4, 136.4, 132.6, 130.0, 128.2, 126.8, 126.2, 123.9, 122.0, 121.4, 114.9, 113.4, 111.5, 71.9, 44.9.

Example 591

2-[(Pyridin-4-ylmethyl)-amino]-N-(3-p-tolyl-isoxazol-5-ylmethoxy)-benzamide (compound 277)

Prepared by similar procedures as described above for compounds 1-249.
¹³C-NMR (DMSO-d₆) δ 167.8, 167.5, 161.7, 149.5, 148.9, 148.3, 139.9, 132.7, 129.6, 128.2, 126.4, 125.5, 121.9, 114.8, 112.9, 111.5, 103.2, 66.6, 44.8, 20.9.

Example 592

N-(3-Methyl-isoxazol-5-ylmethoxy)-2-[(pyridin-4-ylmethyl)-amino]-benzamide (compound 278)

Prepared by similar procedures as described above for compounds 1-249.
¹³C-NMR (DMSO-d₆) δ 167.5, 166.8, 159.6, 149.6, 149.0, 148.5, 132.8, 128.2, 122.0, 114.9, 113.1, 111.6, 105.8, 66.7, 44.9, 10.9.

Example 593

N-(3-Ethyl-isoxazol-5-ylmethoxy)-2-[(pyridin-4-ylmethyl)-amino]-benzamide (compound 279)

Prepared by similar procedures as described above for compounds 1-249.
¹³C-NMR (DMSO-d₆) δ 167.4, 166.7, 164.7, 149.5, 148.9, 148.4, 132.7, 128.1, 121.9, 114.8, 113.0, 111.5, 104.5, 66.7, 44.8, 18.8, 12.4.

Example 594

N-(3-Butyl-isoxazol-5-ylmethoxy)-2-[(pyridin-4-ylmethyl)-amino]-benzamide (compound 280)

Prepared by similar procedures as described above for compounds 1-249.
¹³C-NMR (DMSO-d₆) δ 167.4, 166.6, 163.5, 149.5, 148.9, 148.3, 132.7, 128.1, 121.9, 114.8, 113.0, 111.5, 104.8, 66.6, 44.8, 29.6, 24.8, 21.5, 13.4.

Example 595

N-(3-Pentyl-isoxazol-5-ylmethoxy)-2-[(pyridin-4-ylmethyl)-amino]-benzamide (compound 281)

Prepared by similar procedures as described above for compounds 1-249.
¹³C-NMR (DMSO-d₆) δ 167.4, 166.6, 163.6, 149.5, 148.9, 148.4, 132.7, 128.1, 121.9, 114.8, 113.0, 111.5, 104.8, 66.6, 44.8, 30.6, 27.2, 25.1, 21.6, 13.7.

Example 596

2-[(Pyridin-4-ylmethyl)-amino]-N-[5-(3-trifluoromethyl-phenyl)-[1,2,4]oxadiazol-3-ylmethoxy]-benzamide (compound 282)

Prepared by similar procedures as described above for compounds 1-249.
¹³C-NMR (DMSO-d₆) δ 174.1, 167.4, 166.7, 149.8, 149.5, 148.9, 148.4, 132.7, 131.8, 131.1, 129.8, 128.2, 124.2, 124.2, 123.4, 121.9, 114.8, 113.0, 111.5, 66.8, 44.8.

Example 597

N-(1-Benzyl-1H-[1,2,3]-triazol-4-ylmethoxy)-2-[(pyridin-4-ylmethyl)-amino]-benzamide (compound 283)

Prepared by similar procedures as described above for compounds 1-249.
¹³C-NMR (DMSO-d₆) δ 167.2, 149.6, 149.0, 148.4, 142.1, 136.1, 132.6, 128.7, 128.2, 128.1, 127.8, 125.4, 122.1, 114.9, 113.5, 111.5, 67.8, 52.8, 44.9.

Example 598

N-(1-Cyclopentyl-1H-[1,2,3]-triazol-4-ylmethoxy)-2-[(pyridin-4-ylmethyl)-amino]-benzamide (compound 284)

Prepared by similar procedures as described above for compounds 1-249.
¹³C-NMR (DMSO-d₆) δ 167.2, 149.6, 149.0, 148.4, 141.7, 132.6, 128.2, 123.8, 122.1, 114.9, 113.6, 111.5, 67.9, 61.0, 44.9, 32.9, 23.6.

Example 599

N-(5-Oxo-4,5-dihydro-1H-[1,2,4]triazol-3-ylmethoxy)-2-[(pyridin-4-ylmethyl)-amino]-benzamide (compound 285)

Prepared by similar procedures as described above for compounds 1-249.

$^{13}$C-NMR (DMSO-d$_6$) δ 167.4, 149.5, 148.9, 148.4, 137.4, 132.6, 129.3, 128.5, 128.1, 126.4, 122.0, 114.8, 113.2, 111.5, 70.8, 44.8.

Example 600

N-(3-Phenoxy-propoxy)-2-[(pyridin-4-ylmethyl)-amino]-benzamide (compound 286)

Prepared by similar procedures as described above for compounds 1-249.
$^{13}$C-NMR (CDCl$_3$) δ 169.2, 158.8, 149.7, 149.1, 148.8, 133.4, 129.5, 127.5, 122.0, 120.8, 115.6, 114.5, 112.7, 112.0, 73.6, 64.5, 46.0, 28.3.

Example 601

N-(3-Benzyloxy-propoxy)-2-[(pyridin-4-ylmethyl)-amino]-benzamide (compound 287)

Prepared by similar procedures as described above for compounds 1-249.
$^{13}$C-NMR (CDCl$_3$) δ 168.8, 149.8, 149.1, 148.8, 138.2, 133.3, 128.5, 127.8, 127.8, 127.4, 122.0, 115.6, 112.8, 112.0, 74.2, 73.2, 67.4, 46.0, 28.7.

Example 602

N-(2-Benzyloxy-ethoxy)-2-[(pyridin-4-ylmethyl)-amino]-benzamide (compound 288)

Prepared by similar procedures as described above for compounds 1-249.
$^{13}$C-NMR (CDCl$_3$) δ 168.5, 149.8, 149.2, 148.7, 137.7, 133.4, 128.6, 127.9, 127.3, 122.0, 115.7, 112.5, 112.0, 75.3, 73.6, 69.3, 46.0.

Example 603

N-[2-Hydroxy-3-(4-methoxy-phenoxy)-propoxy]-2-[(pyridin-4-ylmethyl)-amino]-benzamide (compound 289)

Prepared by similar procedures as described above for compounds 1-249.
$^{13}$C-NMR (DMSO-d$_6$) δ 167.3, 153.3, 152.5, 149.5, 148.9, 148.3, 132.5, 128.1, 121.9, 115.4, 114.8, 114.5, 113.1, 111.5, 77.1, 69.9, 66.8, 55.2, 44.8

Example 604

N-(3-Benzoylamino-propoxy)-2-[(pyridin-4-ylmethyl)-amino]-benzamide (compound 290)

Prepared by similar procedures as described above for compounds 1-249.
$^{13}$C-NMR (CDCl$_3$) δ 169.3, 168.0, 149.8, 149.2, 148.8, 134.8, 133.5, 131.2, 128.2, 127.8, 127.4, 121.9, 115.7, 112.2, 112.1, 75.3, 45.9, 37.4, 27.5.

Example 605

N-(4-Benzoylamino-butoxy)-2-[(pyridin-4-ylmethyl)-amino]-benzamide (compound 291)

Prepared by similar procedures as described above for compounds 1-249.
$^{13}$C-NMR (CDCl$_3$) δ 169.2, 168.0, 149.7, 149.1, 148.9, 134.6, 133.3, 131.4, 128.5, 127.8, 127.0, 122.0, 115.7, 112.7, 111.9, 46.0, 39.6, 26.7, 25.3.

Example 606

N-(2-Methanesulfonylamino-ethoxy)-2-[(pyridin-4-ylmethyl)-amino]-benzamide (compound 292)

Prepared by similar procedures as described above for compounds 1-249.
$^{13}$C-NMR (CDCl$_3$) δ 170.6, 149.8, 149.3, 148.8, 134.0, 127.5, 122.0, 115.8, 112.3, 111.6, 75.9, 46.0, 41.6, 40.5

Example 607

N-(4-Benzenesulfonylamino-butoxy)-2-[(pyridin-4-ylmethyl)-amino]-benzamide (compound 293)

Prepared by similar procedures as described above for compounds 1-249.
$^{13}$C-NMR (CDCl$_3$) δ 169.2, 149.6, 149.1, 140.1, 133.4, 132.4, 129.0, 127.7, 127.0, 122.1, 115.6, 112.6, 112.0, 76.3, 46.0, 42.9, 26.1, 25.6.

Example 608

N-(3-Benzenesulfonylamino-propoxy)-2-[(pyridin-4-ylmethyl)-amino]-benzamide (compound 294)

Prepared by similar procedures as described above for compounds 1-249.
$^{13}$C-NMR (CDCl$_3$) δ 169.6, 149.7, 149.2, 148.8, 140.5, 133.7, 132.3, 129.0, 127.6, 127.0, 122.0, 115.7, 112.1, 112.0, 74.7, 46.0, 40.8, 27.6.

Example 609

N-[2-(4-Cyano-benzenesulfonylamino)-ethoxy]-2-[(pyridin-4-ylmethyl)-amino]-benzamide (compound 295)

Prepared by similar procedures as described above for compounds 1-249.
$^{13}$C-NMR (CDCl$_3$) δ 170.9, 149.8, 149.3, 148.7, 144.6, 134.2, 132.8, 127.7, 127.5, 122.0, 117.4, 116.1, 115.8, 112.4, 111.3, 75.5, 45.9, 41.6.

Example 610

N-[3-(4-Cyano-benzenesulfonylamino)-propoxy]-2-[(pyridin-4-ylmethyl)-amino]-benzamide (compound 296)

Prepared by similar procedures as described above for compounds 1-249.
$^{13}$C-NMR (CDCl$_3$) δ 169.9, 149.8, 149.2, 148.7, 145.1, 133.9, 132.8, 127.7, 127.6, 122.1, 117.5, 115.8, 112.2, 111.8, 75.0, 46.0, 41.1, 27.4.

Example 611

N-(3-Phenylmethanesulfonylamino-propoxy)-2-[(pyridin-4-ylmethyl)-amino]-benzamide (compound 297)

Prepared by similar procedures as described above for compounds 1-249.

$^{13}$C-NMR (CDCl$_3$) δ 169.2, 149.6, 149.0, 148.5, 133.5, 130.5, 129.4, 128.4, 128.3, 127.3, 121.7, 115.5, 111.9, 111.8, 74.2, 58.9, 45.8, 40.8, 28.3.

Example 612

N-(2-Phenylmethanesulfonylamino-ethoxy)-2-[(pyridin-4-ylmethyl)-amino]-benzamide (compound 298)

Prepared by similar procedures as described above for compounds 1-249.
$^{13}$C-NMR (CDCl$_3$) δ 170.3, 149.9, 149.3, 148.6, 133.9, 130.8, 129.3, 128.7, 128.7, 127.4, 121.9, 115.8, 112.3, 111.7, 76.2, 59.7, 46.0, 42.0.

Example 613

N-[3-(2-Acetylamino-4-methyl-thiazole-5-sulfonylamino)-propoxy]-2-[(pyridin-4-ylmethyl)-amino]-benzamide (compound 299)

Prepared by similar procedures as described above for compounds 1-249.
$^1$H-NMR (CD$_3$OD) δ 8.45 (d, 2H), 7.44 (d, 2H), 7.40 (d, 1H), 7.22 (dt, 1H), 6.60 (t, 1H), 6.55 (d, 1H), 4.55 (s, 2H), 4.01 (t, 2H), 3.20 (t, 2H), 2.50 (s, 3H), 2.17 (s, 3H), 1.89 (m, 2H).

Example 614

N-[2-(2-Acetylamino-4-methyl-thiazole-5-sulfonylamino)-ethoxy]-2-[(pyridin-4-ylmethyl)-amino]-benzamide (compound 300)

Prepared by similar procedures as described above for compounds 1-249.
$^1$H-NMR (DMSO-d$_6$) δ 12.48 (s, 1H), 11.57 (s, 1H), 8.49 (d, 2H), 7.87 (m, 2H), 7.38 (dd, 1H), 7.31 (d, 2H), 7.21 (dt, 1H), 6.55 (t, 1H), 6.51 (d, 1H), 4.47 (d, 2H), 3.92 (t, 2H), 3.15 (q, 2H), 2.46 (s, 3H), 2.14 (s, 3H).

Example 615

N-(2-Benzylamino-ethoxy)-2-[(pyridin-4-ylmethyl)-amino]-benzamide (compound 301)

Prepared by similar procedures as described above for compounds 1-249.
$^{13}$C-NMR (CDCl$_3$) δ 168.4, 150.0, 149.0, 148.6, 138.9, 133.2, 128.6, 128.4, 127.7, 127.4, 122.0, 115.6, 112.7, 111.9, 74.6, 53.6, 47.9, 46.1.

Example 616

N-(4-Benzylamino-butoxy)-2-[(pyridin-4-ylmethyl)-amino]-benzamide (compound 302)

Prepared by similar procedures as described above for compounds 1-249.
$^{13}$C-NMR (CDCl$_3$) δ 168.2, 150.0, 149.0, 148.6, 139.5, 133.1, 128.5, 128.2, 127.5, 127.2, 122.0, 115.6, 112.9, 111.9, 76.3, 53.8, 48.8, 46.1, 26.3, 25.3.

Example 617

(2-{2-[(Pyridin-4-ylmethyl)-amino]-benzoylaminooxy}-ethyl)-carbamic acid tert-butyl ester (compound 303)

Prepared by similar procedures as described above for compounds 1-249.
$^{13}$C-NMR (CDCl$_3$) δ 169.0, 157.1, 149.8, 149.3, 148.8, 133.5, 127.4, 122.0, 115.8, 112.4, 112.1, 80.0, 75.3, 46.1, 38.5, 28.4.

Example 618

(3-{2-[(Pyridin-4-ylmethyl)-amino]-benzoylaminooxy}-propyl)-carbamic acid tert-butyl ester (compound 304)

Prepared by similar procedures as described above for compounds 1-249.
$^{13}$C-NMR (CDCl$_3$) δ 168.9, 156.6, 149.8, 149.3, 148.8, 133.4, 127.5, 122.0, 115.6, 112.5, 112.1, 79.4, 74.4, 46.0, 37.2, 28.7, 28.4.

Example 619

(4-{2-[(Pyridin-4-ylmethyl)-amino]-benzoylaminooxy}-butyl)-carbamic acid tert-butyl ester (compound 305)

Prepared by similar procedures as described above for compounds 1-249.
$^{13}$C-NMR (CDCl$_3$) δ 169.0, 156.4, 149.8, 149.2, 148.8, 133.3, 127.7, 122.0, 115.6, 112.8, 111.9, 79.3, 76.9, 46.0, 40.2, 28.4, 27.4, 25.0.

Example 620

N-[2-(3-Phenyl-thioureido)-ethoxy]-2-[(pyridin-4-ylmethyl)-amino]-benzamide (compound 306)

Prepared by similar procedures as described above for compounds 1-249.
$^{13}$C-NMR (CDCl$_3$) δ 180.8, 169.9, 149.8, 149.3, 148.7, 136.4, 133.7, 129.8, 127.6, 126.8, 125.4, 122.0, 115.8, 112.1, 111.8, 74.8, 45.9, 43.6.

Example 621

N-[4-(3-Phenyl-thioureido)-butoxy]-2-[(pyridin-4-ylmethyl)-amino]-benzamide (compound 307)

Prepared by similar procedures as described above for compounds 1-249.
$^{13}$C-NMR (CDCl$_3$) δ 180.9, 169.2, 149.7, 149.0, 148.8, 136.9, 133.6, 129.8, 127.6, 126.8, 125.0, 122.0, 115.8, 112.3, 112.1, 46.0, 45.0, 25.8.

Example 622

N-[2-(3-Phenyl-ureido)-ethoxy]-2-[(pyridin-4-ylmethyl)-amino]-benzamide (compound 308)

Prepared by similar procedures as described above for compounds 1-249.
$^{13}$C-NMR (CDCl$_3$) δ 168.9, 157.4, 149.8, 149.3, 148.7, 139.0, 133.7, 129.1, 127.8, 123.1, 122.0, 119.8, 116.1, 112.2, 112.0, 75.4, 46.0, 37.8.

Example 623

N-[3-(3-Phenyl-ureido)-propoxy]-2-[(pyridin-4-ylmethyl)-amino]-benzamide (compound 309)

Prepared by similar procedures as described above for compounds 1-249.

¹³C-NMR (CDCl₃) δ 169.2, 156.8, 149.7, 149.0, 148.9, 139.3, 133.5, 128.9, 128.0, 122.6, 122.0, 119.3, 115.9, 112.3, 112.0, 75.1, 45.9, 37.3, 28.0.

Example 624

N-[4-(3-Phenyl-ureido)-butoxy]-2-[(pyridin-4-ylmethyl)-amino]-benzamide (compound 310)

Prepared by similar procedures as described above for compounds 1-249.
¹³C-NMR (CDCl₃) δ 156.7, 149.6, 149.1, 149.0, 139.6, 133.5, 128.9, 128.2, 122.3, 122.1, 119.0, 116.0, 112.5, 112.0, 76.8, 46.0, 39.7, 27.2, 26.1.

Example 625

N-(2-Amino-ethoxy)-2-[(pyridin-4-ylmethyl)-amino]-benzamide (compound 311)

Prepared by similar procedures as described above for compounds 1-249.
¹³C-NMR (CDCl₃) δ 164.7, 149.5, 142.4, 134.9, 129.5, 126.5, 117.6, 113.9, 113.1, 73.8, 47.1, 39.2.

Example 626

N-(3-Amino-propoxy)-2-[(pyridin-4-ylmethyl)-amino]-benzamide (compound 312)

Prepared by similar procedures as described above for compounds 1-249.
¹³C-NMR (DMSO-d₆) δ 167.5, 149.4, 149.2, 148.4, 132.7, 128.2, 122.0, 114.8, 112.8, 111.5, 73.2, 44.8, 36.8, 25.5.

Example 627

N-(4-Amino-butoxy)-2-[(pyridin-4-ylmethyl)-amino]-benzamide (compound 313)

Prepared by similar procedures as described above for compounds 1-249.
¹³C-NMR (DMSO-d₆) δ 166.6, 149.5, 149.2, 147.7, 130.9, 128.4, 122.0, 116.2, 114.6, 110.8, 73.9, 45.0, 40.5, 28.2, 25.6.

Example 628

N-(2-Morpholin-4-yl-2-oxo-ethoxy)-2-[(pyridin-4-ylmethyl)-amino]-benzamide (compound 314)

Prepared by similar procedures as described above for compounds 1-249.
¹³C-NMR (DMSO-d₆) δ 167.3, 165.5, 149.5, 148.9, 148.3, 132.7, 128.2, 121.9, 114.8, 112.9, 111.5, 73.5, 66.0, 65.9, 45.1, 44.7, 41.5.

Example 629

N-[(2-Methoxy-phenylcarbamoyl)-methoxy]-2-[(pyridin-4-ylmethyl)-amino]-benzamide (compound 315)

Prepared by similar procedures as described above for compounds 1-249.
¹³C-NMR (DMSO-d₆) δ 168.1, 166.5, 149.5, 149.1, 148.7, 148.6, 133.0, 128.2, 126.6, 124.5, 122.0, 120.8, 120.3, 114.9, 112.1, 111.7, 111.2, 75.3, 55.7, 44.8.

Example 630

N-tert-Butoxy-2-[(pyridin-4-ylmethyl)-amino]-benzamide (compound 316)

Prepared by similar procedures as described above for compounds 1-249.
¹³C-NMR (DMSO-d₆) δ 168.6, 149.5, 148.9, 148.1, 132.2, 128.3, 122.0, 114.8, 114.3, 111.3, 80.8, 44.8, 26.5.

Example 631

N-Isobutoxy-2-[(pyridin-4-ylmethyl)-amino]-benzamide (compound 317)

Prepared by similar procedures as described above for compounds 1-249.
¹³C-NMR (DMSO-d₆) δ 167.1, 149.6, 149.1, 148.4, 132.5, 128.1, 122.1, 114.9, 113.6, 111.5, 81.7, 44.9, 27.0, 19.2.

Example 632

N-(2-Methyl-allyloxy)-2-[(pyridin-4-ylmethyl)-amino]-benzamide (compound 318)

Prepared by similar procedures as described above for compounds 1-249.
¹³C-NMR (DMSO-d₆) δ 167.1, 149.6, 149.1, 148.3, 140.8, 132.5, 128.2, 122.1, 114.9, 114.5, 113.7, 111.5, 78.9, 44.9, 19.6.

Example 633

N-(3-Methyl-but-2-enyloxy)-2-[(pyridin-4-ylmethyl)-amino]-benzamide (compound 319)

Prepared by similar procedures as described above for compounds 1-249.
¹³C-NMR (DMSO-d₆) δ 167.0, 149.6, 149.1, 148.4, 139.3, 132.5, 128.1, 122.1, 118.9, 114.9, 113.7, 111.5, 71.2, 44.9, 25.5, 18.0.

Example 634

N-(4-Hydroxy-pent-2-enyloxy)-2-[(pyridin-4-ylmethyl)-amino]-benzamide (compound 320)

Prepared by similar procedures as described above for compounds 1-249.
¹³C-NMR (DMSO-d₆) δ 166.8, 149.5, 148.9, 148.3, 140.7, 132.3, 128.0, 122.2, 122.0, 114.8, 113.6, 111.4, 75.3, 65.8, 44.9, 23.5

Example 635

N-Cyclopentyloxy-2-[(pyridin-4-ylmethyl)-amino]-benzamide (compound 321)

Prepared by similar procedures as described above for compounds 1-249.
¹³C-NMR (DMSO-d₆) δ 167.0, 149.5, 149.0, 148.2, 132.3, 128.0, 122.0, 114.8, 113.7, 111.4, 86.2, 44.8, 30.7, 23.3.

Example 636

N-Cyclooctyloxy-2-[(pyridin-4-ylmethyl)-amino]-benzamide (compound 322)

Prepared by similar procedures as described above for compounds 1-249.

$^{13}$C-NMR (DMSO-d$_6$) δ 167.0, 149.5, 149.0, 148.2, 132.3, 128.0, 122.0, 114.8, 113.8, 111.4, 84.5, 44.8, 29.6, 26.7, 24.9, 22.6.

Example 637

N-(2-Cyclohexyl-ethoxy)-2-[(pyridin-4-ylmethyl)-amino]-benzamide (compound 323)

Prepared by similar procedures as described above for compounds 1-249.
$^{13}$C-NMR (DMSO-d$_6$) δ 167.0, 149.6, 149.1, 148.4, 132.5, 128.1, 122.1, 114.9, 113.6, 111.5, 73.3, 44.9, 35.2, 34.0, 32.8, 26.1, 25.8.

Example 638

N-(2-Methyl-cyclohexylmethoxy)-2-[(pyridin-4-ylmethyl)-amino]-benzamide (compound 324)

Prepared by similar procedures as described above for compounds 1-249.
$^{13}$C-NMR (DMSO-d$_6$) δ 166.9, 149.5, 149.0, 148.3, 132.3, 128.0, 122.0, 114.8, 113.6, 111.4, 78.6, 44.8, 43.1, 35.1, 33.6, 29.7, 25.8, 25.6, 20.1.

Example 639

N-(4-Methyl-cyclohexylmethoxy)-2-[(pyridin-4-ylmethyl)-amino]-benzamide (compound 325)

Prepared by similar procedures as described above for compounds 1-249.
$^{13}$C-NMR (DMSO-d$_6$) δ 166.9, 149.5, 149.0, 148.3, 132.4, 128.0, 122.0, 114.8, 113.5, 111.4, 80.7, 44.8, 36.1, 34.1, 32.1, 29.2, 22.5.

Example 640

N-(4-Methoxy-cyclohexylmethoxy)-2-[(pyridin-4-ylmethyl)-amino]-benzamide (compound 326)

Prepared by similar procedures as described above for compounds 1-249.
$^{13}$C-NMR (DMSO-d$_6$) δ 166.9, 149.5, 149.0, 148.3, 132.4, 128.0, 122.0, 114.8, 113.5, 111.4, 80.0, 78.5, 54.8, 44.8, 35.7, 30.8, 27.1.

Example 641

N-(3-Methyl-bicyclo[2.2.1]hept-2-ylmethoxy)-2-[(pyridin-4-ylmethyl)-amino]-benzamide (compound 327)

Prepared by similar procedures as described above for compounds 1-249.
$^{13}$C-NMR (CDCl$_3$) δ 169.0, 149.8, 149.1, 148.8, 133.4, 127.3, 122.0, 115.7, 112.8, 112.1, 80.5, 78.6, 49.1, 48.3, 46.0, 43.2, 41.7, 41.2, 39.9, 39.1, 39.0, 37.5, 36.5, 30.0, 29.9, 22.0, 21.6, 16.4.

Example 642

N-(Bicyclo[2.2.1]hept-5-en-2-ylmethoxy)-2-[(pyridin-4-ylmethyl)-amino]-benzamide (compound 328)

Prepared by similar procedures as described above for compounds 1-249.
$^{13}$C-NMR (DMSO-d$_6$) δ 167.0, 149.5, 149.3, 148.4, 137.0, 136.6, 136.3, 132.5, 128.1, 122.1, 114.9, 111.6, 79.6, 78.8, 48.9, 44.9, 43.6, 43.3, 41.6, 41.1, 37.2, 37.0, 29.2, 28.8.

Example 643

Benzyl-(2-{2-[(pyridin-4-ylmethyl)-amino]-benzoylaminooxymethyl}-cyclohexyl)carbamic acid tert-butyl ester (compound 329)

Prepared by similar procedures as described above for compounds 1-249.
$^{13}$C-NMR (CDCl$_3$) δ 168.9, 156.0, 149.6, 149.1, 149.1, 140.4, 133.5, 128.3, 127.4, 126.5, 126.2, 122.1, 115.7, 112.6, 112.1, 79.9, 75.8, 58.2, 46.1, 36.9, 28.4, 27.9, 26.4, 20.7.

Example 644

N-(2-Benzylamino-cyclohexylmethoxy)-2-[(pyridin-4-ylmethyl)-amino]-benzamide (compound 330)

Prepared by similar procedures as described above for compounds 1-249.
$^{13}$C-NMR (DMSO-d$_6$) δ 167.4, 149.6, 149.1, 148.3, 132.3, 128.4, 128.3, 128.1, 126.8, 122.0, 114.9, 113.9, 111.5, 76.1, 54.9, 50.0, 44.9, 37.1, 27.4, 25.4, 22.8, 22.2.

Example 645

N-(3-Propyl-4,5-dihydro-isoxazol-5-ylmethoxy)-2-[(pyridin-4-ylmethyl)-amino]-benzamide (compound 331)

Prepared by similar procedures as described above for compounds 1-249.
$^{13}$C-NMR (DMSO-d$_6$) δ 167.6, 158.9, 150.0, 149.4, 148.8, 133.0, 128.5, 122.4, 115.2, 113.6, 111.9, 77.0, 76.9, 45.2, 39.2, 29.1, 19.5, 13.9.

Example 646

N-(3-Pentyl-4,5-dihydro-isoxazol-5-ylmethoxy)-2-[(pyridin-4-ylmethyl)-amino]-benzamide (compound 332)

Prepared by similar procedures as described above for compounds 1-249.
$^{13}$C-NMR (DMSO-d$_6$) δ 167.3, 158.8, 149.6, 149.0, 148.5, 132.6, 128.2, 122.0, 114.9, 113.2, 111.6, 76.6, 76.5, 44.9, 38.8, 30.8, 26.8, 25.4, 21.8, 13.8.

Example 647

4-Methyl-N-(2-methyl-thiazol-4-ylmethoxy)-2-[(pyridin-4-ylmethyl)-amino]-benzamide (compound 333)

Prepared by similar procedures as described above for compounds 1-249.
$^{13}$C-NMR (DMSO-d$_6$) δ 167.4, 165.3, 150.6, 149.6, 149.0, 148.7, 142.5, 128.1, 122.0, 118.8, 115.9, 111.7, 110.4, 71.9, 44.8, 21.4, 18.6.

Example 648

N-(5-Cyano-2-methoxy-benzyloxy)-2-[(pyridin-4-ylmethyl)-amino]-nicotinamide (compound 334)

Prepared by similar procedures as described above for compounds 1-249.

$^{13}$C-NMR (DMSO-d$_6$) δ 165.8, 160.7, 156.6, 151.2, 149.6, 149.3, 136.1, 134.5, 133.6, 125.6, 121.9, 119.0, 112.0, 111.1, 108.1, 102.4, 70.8, 56.0, 42.7.

Example 649

2-Benzylamino-N-benzyloxy-nicotinamide (compound 335)

Prepared by similar procedures as described above for compounds 1-249.
$^{13}$C-NMR (DMSO-d$_6$) δ 165.8, 156.8, 151.2, 140.1, 136.0, 135.8, 128.8, 128.2, 127.1, 126.6, 110.7, 107.7, 76.9, 43.7.

Example 650

2-Benzylamino-N-(4-methoxy-benzyloxy)-nicotinamide (compound 336)

Prepared by similar procedures as described above for compounds 1-249.
$^{13}$C-NMR (DMSO-d$_6$) δ 165.7, 159.3, 156.8, 151.2, 140.1, 135.9, 130.6, 128.2, 127.7, 127.1, 126.6, 113.6, 110.7, 107.8, 76.6, 55.0, 43.7.

Example 651

N-Benzyloxy-2-(2-chloro-benzylamino)-nicotinamide (compound 337)

Prepared by similar procedures as described above for compounds 1-249.
$^{13}$C-NMR (DMSO-d$_6$) δ 165.7, 156.6, 151.2, 137.1, 136.0, 135.8, 132.2, 129.1, 128.8, 128.7, 128.3, 128.2, 127.0, 111.0, 108.1, 76.9, 41.7

Example 652

2-(2-Chloro-benzylamino)-N-(4-methoxy-benzyloxy)-nicotinamide (compound 338)

Prepared by similar procedures as described above for compounds 1-249.
$^{13}$C-NMR (DMSO-d$_6$) δ 165.7, 159.3, 156.6, 151.1, 137.2, 136.0, 132.2, 130.7, 129.1, 128.7, 128.3, 127.7, 127.0, 113.6, 111.0, 108.2, 76.6, 55.0, 41.8.

Example 653

N-Benzyloxy-2-(2,4-dichloro-benzylamino)-nicotinamide (compound 339)

Prepared by similar procedures as described above for compounds 1-249.
$^{13}$C-NMR (DMSO-d$_6$) δ 165.6, 156.4, 151.1, 136.5, 136.1, 135.8, 132.9, 131.8, 129.9, 128.8, 128.5, 128.2, 127.1, 111.2, 108.2, 76.9, 41.4.

Example 654

2-(3,5-Dichloro-benzylamino)-N-(4-methoxy-benzyloxy)-nicotinamide (compound 340)

Prepared by similar procedures as described above for compounds 1-249.
$^{13}$C-NMR (DMSO-d$_6$) δ 165.6, 159.3, 156.5, 151.1, 136.5, 136.0, 132.9, 131.8, 130.7, 129.9, 128.5, 127.8, 127.1, 113.6, 111.2, 108.3, 76.6, 55.0, 41.4.

Example 655

N-Benzyloxy-2-(2-methoxy-benzylamino)-nicotinamide (compound 341)

Prepared by similar procedures as described above for compounds 1-249.
$^{13}$C-NMR (DMSO-d$_6$) δ 165.8, 157.0, 151.3, 135.9, 135.8, 128.8, 128.2, 127.9, 127.8, 127.3, 120.0, 110.5, 107.7, 76.9, 55.2, 39.3.

Example 656

2-(2-Methoxy-benzylamino)-N-(4-methoxy-benzyloxy)-nicotinamide (compound 342)

Prepared by similar procedures as described above for compounds 1-249.
$^{13}$C-NMR (DMSO-d$_6$) δ 165.8, 159.3, 157.0, 151.2, 135.9, 130.6, 129.6, 127.9, 127.8, 127.3, 120.1, 113.6, 113.5, 110.5, 107.8, 76.6, 55.2, 55.0, 39.3.

Example 657

N-Benzyloxy-2-(2-pyridin-4-yl-ethylamino)-nicotinamide (compound 343)

Prepared by similar procedures as described above for compounds 1-249.
$^{13}$C-NMR (DMSO-d$_6$) δ 156.8, 151.3, 149.4, 148.6, 135.9, 128.8, 128.2, 124.1, 110.5, 107.7, 76.9, 40.6, 34.2.

Example 658

N-(2-Bromo-benzyloxy)-2-([1,2,4]triazol-4-ylamino)-nicotinamide (compound 344)

Prepared by similar procedures as described above for compounds 1-249.
$^{13}$C-NMR (DMSO-d$_6$) δ 155.0, 150.6, 144.5, 136.8, 135.0, 132.5, 131.2, 130.4, 127.8, 123.3, 115.7, 110.4, 76.1.

Example 659

4-{[3-(4-Methoxy-benzyloxycarbamoyl)-pyridin-2-ylamino]-methyl}-piperidine-1-carboxylic acid tert-butyl ester (compound 345)

Prepared by similar procedures as described above for compounds 1-249.
$^{13}$C-NMR (DMSO-d$_6$) δ 159.3, 157.1, 153.8, 151.2, 135.9, 130.6, 127.8, 113.6, 110.2, 107.5, 78.3, 76.5, 55.0, 45.5, 43.2, 35.3, 29.5, 28.0.

Example 660

N-Benzyloxy-5-[(2-benzyloxycarbamoyl-phenylamino)-methyl]-2-fluoro-benzamide (compound 346)

Prepared by similar procedures as described above for compounds 1-249.
$^{13}$C-NMR (DMSO-d$_6$) δ 167.2, 161.2, 157.9, 148.4, 136.0, 135.7, 132.5, 131.0, 128.8, 128.2, 128.0, 121.5, 116.1, 114.6, 113.2, 111.5, 77.0, 76.9, 44.9.

Example 661

N-(2-Bromo-benzyloxy)-2-(3-cyano-4-methoxy-benzylamino)-benzamide (compound 347)

Prepared by similar procedures as described above for compounds 1-249.

$^{13}$C-NMR (DMSO-d$_6$) δ 167.4, 159.8, 148.3, 135.3, 133.8, 132.5, 132.4, 132.0, 131.1, 130.2, 128.1, 127.7, 123.1, 116.4, 114.7, 113.2, 112.4, 111.5, 100.0, 75.8, 56.2, 44.5.

Example 662

N-(2-Bromo-benzyloxy)-2-(4-methanesulfonyl-benzylamino)-benzamide (compound 348)

Prepared by similar procedures as described above for compounds 1-249.
$^{13}$C-NMR (DMSO-d$_6$) δ 167.4, 148.4, 146.1, 139.3, 135.3, 132.6, 132.4, 131.1, 130.2, 128.2, 127.7, 127.6, 127.1, 123.2, 114.7, 113.1, 111.5, 75.9, 45.4, 43.5

Example 663

2-[4-(Methoxyimino-methyl)-benzylamino]-N-(2-methyl-thiazol-4-ylmethoxy)-benzamide (compound 349)

Prepared by similar procedures as described above for compounds 1-249.
$^{13}$C-NMR (DMSO-d$_6$) δ 167.2, 165.3, 150.6, 148.5, 148.4, 141.6, 132.4, 130.5, 128.0, 127.3, 126.9, 118.8, 114.6, 113.0, 111.5, 71.8, 61.4, 45.7, 18.6.

Example 664

N-(2-Bromo-benzyloxy)-2-[(2,6-dichloro-pyridin-4-ylmethyl)-amino]-benzamide (compound 350)

Prepared by similar procedures as described above for compounds 1-249.
$^{13}$C-NMR (DMSO-d$_6$) δ 153.0, 149.4, 149.0, 138.7, 134.1, 132.4, 131.5, 130.6, 127.8, 127.8, 123.2, 123.0, 121.3, 116.0, 114.6, 76.0, 45.5.

Example 665

N-Benzyloxy-2-[(pyridin-3-ylmethyl)-amino]-benzamide (compound 351)

Prepared by similar procedures as described above for compounds 1-249.
$^{13}$C-NMR (CDCl$_3$) δ 168.9, 149.2, 148.8, 148.5, 135.4, 134.9, 134.5, 133.5, 129.3, 128.8, 128.7, 127.4, 123.7, 115.6, 112.7, 112.0, 78.5, 44.7.

Example 666

N-(2-Methyl-thiazol-4-ylmethoxy)-2-[(pyridin-3-ylmethyl)-amino]-benzamide (compound 352)

Prepared by similar procedures as described above for compounds 1-249.
$^{13}$C-NMR (CDCl$_3$) δ 168.9, 166.9, 150.9, 149.2, 148.9, 148.5, 134.9, 134.5, 133.4, 127.6, 123.6, 118.3, 115.5, 112.8, 112.0, 73.0, 44.7, 19.1.

Example 667

N-(2-Methyl-thiazol-4-ylmethoxy)-2-[(pyridin-2-ylmethyl)-amino]-benzamide (compound 353)

Prepared by similar procedures as described above for compounds 1-249.
$^{13}$C-NMR (CDCl$_3$) δ 168.9, 166.9, 158.9, 151.0, 149.2, 136.8, 133.3, 127.7, 122.0, 121.1, 118.3, 115.3, 112.9, 112.2, 73.0, 48.8, 19.1.

Example 668

N-Benzyloxy-2-[(pyridin-2-ylmethyl)-amino]-benzamide (compound 354)

Prepared by similar procedures as described above for compounds 1-249.
$^{13}$C-NMR (CDCl$_3$) δ 168.9, 158.8, 149.1, 136.9, 135.6, 133.3, 129.3, 128.7, 128.6, 127.5, 122.0, 121.0, 115.4, 113.0, 112.3, 78.3, 48.7.

Example 669

N-Benzyloxy-2-[(3-bromo-pyridin-2-ylmethyl)-amino]-benzamide (compound 355)

Prepared by similar procedures as described above for compounds 1-249.
$^{13}$C-NMR (CDCl$_3$) δ 161.0, 148.8, 141.6, 139.2, 135.5, 133.5, 129.3, 128.8, 128.7, 127.4, 126.4, 119.6, 115.8, 112.7, 112.3, 78.4, 48.5.

Example 670

2-[(3-Bromo-pyridin-2-ylmethyl)-amino]-N-(2-methyl-thiazol-4-ylmethoxy)-benzamide (compound 356)

Prepared by similar procedures as described above for compounds 1-249.
$^{13}$C-NMR (CDCl$_3$) δ 168.8, 167.0, 161.1, 150.8, 149.0, 141.6, 139.2, 133.4, 127.6, 126.3, 119.6, 118.3, 115.7, 112.8, 112.1, 72.9, 48.4, 19.0

Example 671

N-(2,4-Dichloro-benzyloxy)-2-[(2,6-dimethoxy-pyrimidin-4-ylmethyl)-amino]-benzamide (compound 357)

Prepared by similar procedures as described above for compounds 1-249.
$^{13}$C-NMR (DMSO-d$_6$) δ 168.7, 167.3, 164.2, 156.9, 148.3, 134.1, 133.7, 132.8, 132.6, 128.7, 128.1, 127.3, 114.8, 113.3, 111.9, 111.4, 72.9, 54.3, 53.8, 38.3

Example 672

N-Benzyloxy-2-[(1,3,5-trimethyl-1H-pyrazol-4-ylmethyl)-amino]-benzamide (compound 358)

Prepared by similar procedures as described above for compounds 1-249.
$^{13}$C-NMR (DMSO-d$_6$) δ 167.3, 162.2, 148.9, 144.4, 136.9, 135.8, 132.7, 128.7, 128.2, 127.8, 114.2, 112.5, 111.3, 76.8, 36.4, 35.5, 11.4, 9.0.

Example 673

N-(2,4-Dichloro-benzyl)-2-[(1,3,5-trimethyl-1H-pyrazol-4-ylmethyl)-amino]-benzamide (compound 359)

Prepared by similar procedures as described above for compounds 1-249.
$^{13}$C-NMR (DMSO-d$_6$) δ 167.4, 162.2, 148.8, 144.4, 136.8, 134.0, 133.6, 132.7, 132.5, 128.6, 127.9, 127.3, 114.2, 112.4, 112.2, 111.3, 72.9, 36.4, 35.5, 11.4, 9.0.

Example 674

N-Benzyloxy-2-[(1-methyl-1H-imidazol-2-ylmethyl)-amino]-benzamide (compound 360)

Prepared by similar procedures as described above for compounds 1-249.
$^{13}$C-NMR (CDCl$_3$) δ 148.6, 144.9, 135.7, 133.3, 129.3, 128.7, 128.6, 127.6, 126.7, 121.8, 116.0, 113.4, 112.5, 78.2, 40.4, 33.0

Example 675

2-[(1-Methyl-1H-imidazol-2-ylmethyl)-amino]-N-(2-methyl-thiazol-4-ylmethoxy)-benzamide (compound 361)

Prepared by similar procedures as described above for compounds 1-249.
$^1$H-NMR (CD$_3$OD) δ 7.46 (s, 1H), 7.36 (dd, 1H), 7.29 (dt, 1H), 7.08 (s, 1H), 6.94 (s, 1H), 6.85 (d, 1H), 6.63 (t, 1H), 4.99 (s, 2H), 4.53 (s, 2H), 3.75 (s, 3H), 2.69 (s, 3H).

Example 676

N-Benzyloxy-2-[(3-methyl-3H-imidazol-4-ylmethyl)-amino]-benzamide (compound 362)

Prepared by similar procedures as described above for compounds 1-249.
$^{13}$C-NMR (DMSO-d$_6$) δ 167.2, 148.4, 138.5, 135.9, 132.5, 128.8, 128.6, 128.2, 127.9, 127.5, 114.8, 113.0, 111.6, 76.8, 36.1, 30.9

Example 677

2-[(3-Methyl-3H-imidazol-4-ylmethyl)-amino]-N-(2-methyl-thiazol-4-ylmethoxy)-benzamide (compound 363)

Prepared by similar procedures as described above for compounds 1-249.
$^{13}$C-NMR (DMSO-d$_6$) δ 167.2, 165.3, 150.5, 148.4, 138.5, 132.5, 128.6, 128.0, 127.5, 118.9, 114.8, 113.1, 111.6, 71.8, 36.1, 30.9, 18.6.

Example 678

N-Benzyloxy-2-[(5-methyl-3H-imidazol-4-ylmethyl)-amino]-benzamide (compound 364)

Prepared by similar procedures as described above for compounds 1-249.
$^{13}$C-NMR (DMSO-d$_6$) δ 167.0, 148.7, 136.0, 133.2, 132.5, 130.4, 128.7, 128.2, 128.1, 127.8, 124.4, 114.1, 112.6, 111.3, 76.8, 38.8, 9.7.

Example 679

2-[(5-Methyl-3H-imidazol-4-ylmethyl)-amino]-N-(2-methyl-thiazol-4-ylmethoxy)-benzamide (compound 365)

Prepared by similar procedures as described above for compounds 1-249.
$^{13}$C-NMR (CDCl$_3$) δ 168.5, 166.7, 150.8, 148.8, 133.5, 133.1, 129.2, 128.2, 126.2, 118.4, 115.2, 113.2, 111.6, 72.7, 39.0, 18.9, 10.0.

Example 680

2-[(2-Ethyl-3H-imidazol-4-ylmethyl)-amino]-N-(2-methyl-thiazol-4-ylmethoxy)-benzamide (compound 366)

Prepared by similar procedures as described above for compounds 1-249.
$^{13}$C-NMR (CD$_3$OD) δ 170.1, 168.8, 152.0, 151.4, 150.2, 136.1, 134.2, 129.2, 120.4, 117.0, 116.4, 114.5, 112.9, 73.4, 40.9, 22.3, 18.7, 13.0.

Example 681

N-Benzyloxy-2-[(2-ethyl-3H-imidazol-4-ylmethyl)-amino]-benzamide (compound 367)

Prepared by similar procedures as described above for compounds 1-249.
$^{13}$C-NMR (CD$_3$OD) δ 170.1, 151.5, 150.3, 137.2, 136.5, 134.1, 130.5, 129.6, 129.5, 129.1, 117.1, 116.3, 114.6, 112.9, 79.2, 41.2, 22.5, 13.2.

Example 682

N-(2,5-Dichloro-benzyloxy)-2-[(5-oxo-pyrrolidin-2-ylmethyl)-amino]-benzamide (compound 368)

Prepared by similar procedures as described above for compounds 1-249.
$^{13}$C-NMR (DMSO-d$_6$) δ 176.7, 167.6, 149.1, 134.2, 133.8, 133.0, 132.8, 128.8, 128.7, 128.2, 127.4, 114.5, 112.7, 111.2, 73.1, 52.5, 46.8, 29.6, 24.2.

Example 683

N-Benzyloxy-2-[(3-ethyl-4,5-dihydro-isoxazol-5-ylmethyl)-amino]-benzamide (compound 369)

Prepared by similar procedures as described above for compounds 1-249.
$^{13}$C-NMR (DMSO-d$_6$) δ 167.2, 159.9, 148.9, 135.9, 132.6, 128.8, 128.2, 128.0, 114.5, 112.9, 111.3, 77.5, 76.9, 45.8, 20.5, 10.6.

Example 684

N-Benzyloxy-2-[(3-propyl-4,5-dihydro-isoxazol-5-ylmethyl)-amino]-benzamide (compound 370)

Prepared by similar procedures as described above for compounds 1-249.
$^{13}$C-NMR (DMSO-d$_6$) δ 167.2, 158.7, 148.9, 135.9, 132.6, 128.8, 128.2, 128.0, 114.5, 112.9, 111.3, 77.4, 76.9, 45.7, 28.8, 19.0, 13.5.

Example 685

5-[(2-Benzyloxycarbamoyl-phenylamino)-methyl]-3-methyl-4,5-dihydro-isoxazole-5-carboxylic acid ethyl ester (compound 371)

Prepared by similar procedures as described above for compounds 1-249.

$^{13}$C-NMR (DMSO-d$_6$) δ 170.5, 167.1, 155.5, 148.9, 135.9, 132.5, 128.8, 128.2, 127.9, 114.9, 113.2, 111.8, 87.0, 76.8, 61.3, 47.2, 45.0, 13.8, 12.3.

Example 686

5-[(2-Benzyloxycarbamoyl-phenylamino)-methyl]-3-ethyl-4,5-dihydro-isoxazole-5-carboxylic acid ethyl ester (compound 372)

Prepared by similar procedures as described above for compounds 1-249.
$^{13}$C-NMR (DMSO-d$_6$) δ 170.5, 167.1, 159.9, 148.9, 135.9, 132.5, 128.8, 128.2, 127.9, 114.9, 113.1, 111.7, 86.8, 76.8, 61.4, 47.1, 43.3, 20.2, 13.8, 10.5.

Example 687

5-[(2-Benzyloxycarbamoyl-phenylamino)-methyl]-3-propyl-4,5-dihydro-isoxazole-5-carboxylic acid ethyl ester (compound 373)

Prepared by similar procedures as described above for compounds 1-249.
$^{13}$C-NMR (DMSO-d$_6$) δ 170.5, 167.1, 158.7, 148.9, 135.9, 132.5, 128.8, 128.2, 127.9, 114.9, 113.1, 111.7, 86.7, 76.8, 61.4, 46.9, 43.3, 28.4, 18.9, 13.8, 13.3.

Example 688

N-(4-Cyano-benzyloxy)-2-[(3-methyl-4,5-dihydro-isoxazol-5-ylmethyl)-amino]-benzamide (compound 374)

Prepared by similar procedures as described above for compounds 1-249.
$^{13}$C-NMR (DMSO-d$_6$) δ 167.4, 155.6, 148.9, 141.8, 132.7, 132.1, 129.1, 127.9, 118.7, 114.5, 112.5, 111.3, 110.7, 77.7, 75.9, 45.8, 41.4, 12.6.

Example 689

N-(4-Cyano-benzyloxy)-2-[(3-ethyl-4,5-dihydro-isoxazol-5-ylmethyl)-amino]-benzamide (compound 375)

Prepared by similar procedures as described above for compounds 1-249.
$^{13}$C-NMR (DMSO-d$_6$) δ 167.4, 159.9, 148.9, 141.8, 132.8, 132.2, 129.1, 128.0, 118.7, 114.5, 112.6, 111.3, 110.7, 77.5, 75.9, 45.8, 20.5, 10.6

Example 690

N-(4-Cyano-benzyloxy)-2-[(3-propyl-4,5-dihydro-isoxazol-5-ylmethyl)-amino]-benzamide (compound 376)

Prepared by similar procedures as described above for compounds 1-249.
$^{13}$C-NMR (DMSO-d$_6$) δ 167.4, 158.8, 148.9, 141.8, 132.7, 132.2, 129.1, 128.0, 118.7, 114.5, 111.3, 110.7, 77.4, 75.9, 45.7, 28.8, 19.0, 13.5.

Example 691

5-{[2-(4-Cyano-benzyloxycarbamoyl)-phenylamino]-methyl}-3-methyl-4,5-dihydro-isoxazole-5-carboxylic acid ethyl ester (compound 377)

Prepared by similar procedures as described above for compounds 1-249.
$^{13}$C-NMR (DMSO-d$_6$) δ 170.5, 167.3, 155.6, 148.9, 141.9, 132.6, 132.2, 129.1, 127.9, 118.7, 115.0, 112.8, 111.8, 110.7, 87.0, 75.8, 61.3, 47.2, 45.0, 13.7, 12.3.

Example 692

5-{[2-(4-Cyano-benzyloxycarbamoyl)-phenylamino]-methyl}-3-ethyl-4,5-dihydro-isoxazole-5-carboxylic acid ethyl ester (compound 378)

Prepared by similar procedures as described above for compounds 1-249.
$^{13}$C-NMR (DMSO-d$_6$) δ 170.5, 167.4, 159.9, 148.9, 141.8, 132.6, 132.2, 129.1, 127.9, 118.7, 114.9, 112.8, 111.8, 110.7, 86.8, 75.9, 61.3, 47.1, 43.3, 20.2, 13.8, 10.4.

Example 693

5-{[2-(4-Cyano-benzyloxycarbamoyl)-phenylamino]-methyl}-3-propyl-4,5-dihydro-isoxazole-5-carboxylic acid ethyl ester (compound 379)

Prepared by similar procedures as described above for compounds 1-249.
$^{13}$C-NMR (DMSO-d$_6$) δ 170.5, 167.4, 158.7, 148.9, 141.8, 132.6, 132.2, 129.1, 127.9, 118.6, 114.9, 112.8, 111.7, 110.7, 86.7, 75.9, 61.3, 46.9, 43.3, 28.4, 18.9, 13.7, 13.3.

Example 694

N-(4-Cyano-benzyloxy)-2-[(3-methyl-isoxazol-5-ylmethyl)-amino]-benzamide (compound 380)

Prepared by similar procedures as described above for compounds 1-249.
$^{13}$C-NMR (DMSO-d$_6$) δ 170.3, 167.3, 159.4, 148.1, 141.8, 132.7, 132.2, 129.1, 128.0, 118.7, 115.2, 113.3, 111.5, 110.8, 102.6, 75.9, 38.1, 10.8.

Example 695

N-(4-Cyano-benzyloxy)-2-[(3-ethyl-isoxazol-5-ylmethyl)-amino]-benzamide (compound 381)

Prepared by similar procedures as described above for compounds 1-249.
$^{13}$C-NMR (DMSO-d$_6$) δ 170.3, 167.2, 164.6, 148.1, 141.8, 132.7, 132.2, 129.1, 128.0, 118.6, 115.2, 113.2, 111.4, 110.8, 101.3, 75.9, 38.2, 18.8, 12.3.

Example 696

N-(4-Cyano-benzyloxy)-2-[(3-propyl-isoxazol-5-ylmethyl)-amino]-benzamide (compound 382)

Prepared by similar procedures as described above for compounds 1-249.
$^{13}$C-NMR (DMSO-d$_6$) δ 170.2, 167.3, 163.3, 148.1, 141.8, 132.7, 132.2, 129.1, 128.0, 118.7, 115.2, 113.2, 111.5, 110.8, 101.6, 75.9, 38.2, 27.1, 20.9, 13.4.

Example 697

N-(4-Cyano-benzyloxy)-2-[(3,5-dimethyl-4,5-dihydro-isoxazol-5-ylmethyl)-amino]-benzamide (compound 383)

Prepared by similar procedures as described above for compounds 1-249.

$^{13}$C-NMR (DMSO-d$_6$) δ 167.5, 155.5, 149.3, 141.9, 132.6, 132.2, 129.1, 127.9, 118.7, 114.4, 112.4, 111.5, 110.7, 84.9, 75.8, 49.5, 46.8, 23.4, 12.9.

Example 698

N-(4-Cyano-benzyloxy)-2-[(3-ethyl-5-methyl-4,5-dihydro-isoxazol-5-ylmethyl)-amino]-benzamide (compound 384)

Prepared by similar procedures as described above for compounds 1-249.
$^{13}$C-NMR (DMSO-d$_6$) δ 167.4, 159.9, 149.3, 141.8, 132.7, 132.1, 129.0, 127.9, 118.6, 114.4, 112.4, 111.4, 110.7, 84.6, 75.8, 49.5, 45.0, 23.3, 20.7, 10.6.

Example 699

N-(4-Cyano-benzyloxy)-2-[(5-methyl-3-propyl-4,5-dihydro-isoxazol-5-yl)-amino]-benzamide (compound 385)

Prepared by similar procedures as described above for compounds 1-249.
$^{13}$C-NMR (DMSO-d$_6$) δ 167.5, 158.8, 149.4, 141.8, 132.7, 132.1, 129.1, 127.9, 118.7, 114.4, 112.4, 111.5, 110.7, 84.6, 75.9, 49.4, 45.1, 29.0, 23.4, 19.0, 13.4.

Example 700

N-Benzyloxy-2-[(3-methyl-4,5-dihydro-isoxazol-5-ylmethyl)-amino]-benzamide (compound 386)

Prepared by similar procedures as described above for compounds 1-249.
$^{13}$C-NMR (DMSO-d$_6$) δ 167.3, 155.7, 149.0, 136.0, 132.7, 128.9, 128.3, 128.0, 114.6, 113.0, 111.4, 77.8, 77.0, 45.9, 41.5, 12.7.

Example 701

N-(4-Cyano-benzyloxy)-2-[2-(3-methyl-4,5-dihydro-isoxazol-5-yl)-ethylamino]-benzamide (compound 387)

Prepared by similar procedures as described above for compounds 1-249.
$^{13}$C-NMR (DMSO-d$_6$) δ 167.3, 155.5, 148.8, 141.9, 132.7, 132.1, 129.1, 128.0, 118.7, 114.2, 112.3, 111.0, 110.7, 77.4, 75.8, 43.3, 38.9, 34.2, 12.7.

Example 702

N-Cyclopentylmethoxy-2-[2-(3-methyl-4,5-dihydro-isoxazol-5-yl)-ethylamino]-benzamide (compound 388)

Prepared by similar procedures as described above for compounds 1-249.
$^{13}$C-NMR (DMSO-d$_6$) δ 167.1, 155.4, 148.9, 132.6, 127.9, 114.2, 112.8, 110.9, 79.4, 77.4, 43.3, 38.8, 37.6, 34.2, 29.0, 24.9, 12.7.

Example 703

N-(4-Cyano-benzyloxy)-2-[2-(3-ethyl-4,5-dihydro-isoxazol-5-yl)-ethylamino]-benzamide (compound 389)

Prepared by similar procedures as described above for compounds 1-249.
$^{13}$C-NMR (DMSO-d$_6$) δ 167.3, 159.9, 148.8, 141.9, 132.7, 132.2, 129.1, 128.0, 118.7, 114.2, 112.3, 111.0, 110.7, 77.2, 75.8, 41.6, 38.9, 34.1, 20.6, 10.7.

Example 704

N-Cyclopentylmethoxy-2-[2-(3-ethyl-4,5-dihydro-isoxazol-5-yl)-ethylamino]-benzamide (compound 390)

Prepared by similar procedures as described above for compounds 1-249.
$^{13}$C-NMR (DMSO-d$_6$) δ 167.1, 159.9, 148.9, 132.6, 128.0, 114.2, 112.8, 110.9, 79.4, 77.2, 41.6, 38.9, 37.6, 34.1, 29.0, 24.9, 20.6, 10.7.

Example 705

N-(4-Cyano-benzyloxy)-2-[2-(3-propyl-4,5-dihydro-isoxazol-5-yl)-ethylamino]-benzamide (compound 391)

Prepared by similar procedures as described above for compounds 1-249.
$^{13}$C-NMR (DMSO-d$_6$) δ 167.3, 158.7, 148.8, 142.0, 132.7, 132.2, 129.1, 128.0, 118.7, 114.2, 112.3, 111.0, 110.7, 77.1, 75.8, 41.6, 38.9, 34.2, 28.9, 19.1, 13.5.

Example 706

N-Cyclopentylmethoxy-2-[2-(3-propyl-4,5-dihydro-isoxazol-5-yl)-ethylamino]-benzamide (compound 392)

Prepared by similar procedures as described above for compounds 1-249.
$^{13}$C-NMR (DMSO-d$_6$) δ 167.1, 158.7, 149.0, 132.6, 128.0, 114.2, 112.8, 110.9, 79.4, 77.2, 41.6, 38.9, 37.7, 34.2, 29.0, 28.9, 25.0, 19.1, 13.5.

Example 707

N-Benzyloxy-2-[2-(2,4-dioxo-imidazolidin-1-yl)-ethylamino]-benzamide (compound 393)

Prepared by similar procedures as described above for compounds 1-249.
$^{13}$C-NMR (DMSO-d$_6$) δ 171.9, 167.2, 157.0, 148.7, 136.0, 132.7, 128.9, 128.3, 128.2, 114.6, 113.3, 111.1, 76.9, 51.0, 40.9, 40.3.

Example 709

N-Benzyloxy-2-[(6-chloro-imidazo[2,1-b]thiazol-5-ylmethyl)-amino]-benzamide (compound 395)

Prepared by similar procedures as described above for compounds 1-249.
$^{13}$C-NMR (DMSO-d$_6$) δ 166.8, 147.5, 146.1, 135.8, 132.3, 130.3, 128.8, 128.2, 128.1, 119.1, 118.9, 115.2, 114.1, 113.5, 111.2, 76.9, 35.5.

Example 710

N-Benzyloxy-2-[(2-methyl-imidazo[1,2-a]pyrimidin-3-ylmethyl)-amino]-benzamide (compound 396)

Prepared by similar procedures as described above for compounds 1-249.

$^{13}$C-NMR (DMSO-d$_6$) δ 167.0, 148.7, 146.9, 146.9, 142.2, 135.8, 132.6, 132.4, 128.7, 128.2, 128.0, 115.6, 115.0, 111.7, 108.0, 76.8, 35.2, 13.4.

Example 711

N-Benzyloxy-2-(2-benzyloxy-ethylamino)-benzamide (compound 397)

Prepared by similar procedures as described above for compounds 1-249.
$^{13}$C-NMR (DMSO-d$_6$) δ 167.3, 149.0, 138.3, 135.9, 132.6, 128.8, 128.2, 128.1, 127.9, 127.4, 127.3, 114.2, 112.8, 111.1, 76.9, 71.8, 68.0, 42.0.

Example 712

N-(2-Benzyloxycarbamoyl-phenyl)-isonicotinamide (compound 398)

Prepared by similar procedures as described above for compounds 1-249.
$^{13}$C-NMR (DMSO-d$_6$) δ 165.8, 162.9, 150.7, 141.3, 138.1, 135.6, 132.3, 128.9, 128.3, 128.2, 128.0, 123.8, 121.4, 120.8, 120.1, 77.0.

Example 713

N-Benzyloxy-2-(2-pyridin-4-yl-acetylamino)-benzamide (compound 399)

Prepared by similar procedures as described above for compounds 1-249.
$^{13}$C-NMR (CDCl$_3$) δ 167.9, 149.7, 143.8, 139.2, 135.1, 133.1, 129.3, 129.0, 128.7, 126.8, 124.7, 123.2, 121.5, 117.8, 78.4, 44.5.

Example 714

N-Benzyloxy-N-methyl-2-[(pyridin-4-ylmethyl)-amino]-benzamide (compound 400)

Prepared by similar procedures as described above for compounds 1-249.
$^{13}$C-NMR (CDCl$_3$) δ 170.5, 149.9, 148.8, 147.0, 134.3, 131.9, 129.9, 129.6, 128.9, 128.6, 122.0, 117.2, 116.1, 111.6, 76.4, 46.3, 36.0.

Example 715

N-(5-Oxo-pyrrolidin-2-ylmethoxy)-2-[(pyridin-4-ylmethyl)-amino]-benzamide (compound 402)

Prepared by similar procedures as described above for compounds 1-249.
$^{13}$C-NMR (DMSO-d$_6$) δ 176.7, 167.4, 149.7, 149.1, 148.4, 132.7, 128.2, 122.1, 114.9, 113.1, 111.6, 78.4, 51.7, 44.9, 29.4, 22.8.

Example 716

4-{2-[(Pyridin-4-ylmethyl)-amino]-benzoylaminooxymethyl}-piperidine-1-carboxylic acid tert-butyl ester (compound 403)

Prepared by similar procedures as described above for compounds 1-249.
$^{13}$C-NMR (DMSO-d$_6$) δ 167.1, 153.8, 149.5, 149.0, 148.4, 132.4, 128.1, 122.0, 114.8, 113.4, 111.5, 79.6, 78.4, 44.8, 37.5, 34.5, 28.3, 28.0.

Example 717

N-Cyclopentylmethoxy-2-{[6-(cyclopropanecarbonyl-amino)-pyridin-3-ylmethyl]-amino}-benzamide (compound 404)

Prepared by similar procedures as described above for compounds 1-249.
$^{13}$C-NMR (DMSO-d$_6$) δ 172.4, 166.9, 151.1, 148.4, 146.7, 137.1, 132.4, 130.0, 127.9, 114.7, 113.4, 113.1, 111.5, 79.4, 43.1, 37.6, 28.9, 24.9, 14.0, 7.5.

Example 718

N-Cyclopentylmethoxy-2-[(6-pyrrolidin-1-yl-pyridin-3-ylmethyl)-amino]-benzamide (compound 405)

Prepared by similar procedures as described above for compounds 1-249.
$^{13}$C-NMR (DMSO-d$_6$) δ 167.0, 156.3, 148.6, 147.1, 136.6, 132.4, 127.8, 121.1, 114.4, 113.0, 111.5, 106.1, 79.4, 46.3, 43.4, 37.6, 28.9, 24.9.

Example 719

2-[(6-Amino-pyridin-3-ylmethyl)-amino]-N-(4-cyano-benzyloxy)-benzamide (compound 406)

Prepared by similar procedures as described above for compounds 1-249.
$^{13}$C-NMR (DMSO-d$_6$) δ 167.4, 159.0, 148.6, 146.9, 141.8, 136.7, 132.6, 132.1, 129.1, 127.9, 121.8, 118.7, 114.4, 112.5, 111.5, 110.7, 107.8, 75.8, 43.4.

Example 720

N-(4-Cyano-benzyloxy)-2-[(6-pyrrolidin-1-yl-pyridin-3-ylmethyl)-amino]-benzamide (compound 407)

Prepared by similar procedures as described above for compounds 1-249.
$^{13}$C-NMR (DMSO-d$_6$) δ 167.4, 156.3, 148.6, 147.1, 141.8, 136.6, 132.1, 132.0, 129.1, 127.9, 121.0, 118.7, 114.4, 112.6, 111.6, 110.7, 106.1, 75.8, 46.3, 43.4, 24.9.

Example 721

N-Cyclopentylmethoxy-2-{[2-(cyclopropanecarbonyl-amino)-4-methyl-thiazol-5-ylmethyl]-amino}-benzamide (compound 408)

Prepared by similar procedures as described above for compounds 1-249. $^{13}$C- and $^1$H-NMR data were found to be in full accordance with the structure.

Example 722

2-[(6-Amino-pyridin-3-ylmethyl)-amino]-N-cyclopentylmethoxy-benzamide (compound 409)

Prepared by similar procedures as described above for compounds 1-249.

$^{13}$C-NMR (DMSO-d$_6$) δ 167.0, 159.0, 148.6, 146.8, 136.7, 132.4, 127.8, 121.9, 114.4, 113.0, 111.5, 107.7, 79.4, 43.4, 37.6, 28.9, 24.9

Example 723

N-[3-(2,2-Dibromo-vinyl)-cyclopentylmethoxy]-2-[(pyridin-4-ylmethyl)-amino]-benzamide (compound 410)

Prepared by similar procedures as described above for compounds 1-249. $^{13}$C- and $^1$H-NMR data were found to be in full accordance with the structure.

Example 724

N-(3-Hydroxymethyl-cyclopentylmethoxy)-2-[(pyridin-4-ylmethyl)-amino]-benzamide (compound 411)

Prepared by similar procedures as described above for compounds 1-249. $^{13}$C- and $^1$H-NMR data were found to be in full accordance with the structure.

Example 725

N-(2-Hydroxymethyl-cyclohexylmethoxy)-2-[(pyridin-4-ylmethyl)-amino]-benzamide (compound 412)

Prepared by similar procedures as described above for compounds 1-249. $^{13}$C- and $^1$H-NMR data were found to be in full accordance with the structure.

Example 726

N-[4-(4-Methyl-piperazin-1-ylmethyl)-benzyloxy]-2-[(pyridin-4-ylmethyl)-amino]-benzamide (compound 413)

Prepared by similar procedures as described above for compounds 1-249. $^{13}$C- and $^1$H-NMR data were found to be in full accordance with the structure.

Example 727

N-{-4-[4-(2-Hydroxy-ethyl)-piperazin-1-ylmethyl]-benzyloxy}-2-[(pyridin-4-ylmethyl)-amino]-benzamide (compound 414)

Prepared by similar procedures as described above for compounds 1-249. $^{13}$C- and $^1$H-NMR data were found to be in full accordance with the structure.

Example 728

N-(4-Cyano-benzyloxy)-2-{[2-(3-isopropyl-ureido)-pyridin-4-ylmethyl]-amino}-benzamide (compound 415)

Prepared by similar procedures as described above for compounds 1-249. $^{13}$C- and $^1$H-NMR data were found to be in full accordance with the structure.

Example 729

N-(4-Cyano-benzyloxy)-2-{[2-(3-ethyl-ureido)-pyridin-4-ylmethyl]-amino}-benzamide (compound 416)

Prepared by similar procedures as described above for compounds 1-249. $^{13}$C- and $^1$H-NMR data were found to be in full accordance with the structure.

Example 730

N-Cyclopentylmethoxy-2-{[2-(3-isopropyl-ureido)-pyridin-4-ylmethyl]-amino}-benzamide (compound 417)

Prepared by similar procedures as described above for compounds 1-249. $^{13}$C- and $^1$H-NMR data were found to be in full accordance with the structure.

Example 731

N-Cyclopentylmethoxy-2-[2-(3-propyl-ureido)-pyridin-4-ylmethyl-amino]-benzamide (compound 418)

Prepared by similar procedures as described above for compounds 1-249. $^{13}$C- and $^1$H-NMR data were found to be in full accordance with the structure.

Example 732

N-Cyclopentylmethoxy-2-{[2-(3-ethyl-ureido)-pyridin-4-ylmethyl]-amino}-benzamide (compound 419)

Prepared by similar procedures as described above for compounds 1-249. $^{13}$C- and $^1$H-NMR data were found to be in full accordance with the structure.

Example 733

N-(3-Hydroxy-cyclopentylmethoxy)-2-[(pyridin-4-ylmethyl)-amino]-benzamide (compound 420)

Prepared by similar procedures as described above for compounds 1-249. $^{13}$C- and $^1$H-NMR data were found to be in full accordance with the structure.

Example 734

N-Cyclopentylmethoxy-2-{[2-(3-methyl-thioureido)-pyridin-4-ylmethyl]-amino}-benzamide (compound 421)

Prepared by similar procedures as described above for compounds 1-249. $^{13}$C- and $^1$H-NMR data were found to be in full accordance with the structure.

Example 735

2-{[2-(3-tert-Butyl-ureido)-pyridin-4-ylmethyl]-amino}-N-cyclopentylmethoxy-benzamide (compound 422)

Prepared by similar procedures as described above for compounds 1-249. $^{13}$C- and $^1$H-NMR data were found to be in full accordance with the structure.

Example 736

N-(4-Cyano-benzyloxy)-2-{[2-(3-cyclohexyl-ureido)-pyridin-4-ylmethyl]-amino}-benzamide (compound 423)

Prepared by similar procedures as described above for compounds 1-249. $^{13}$C- and $^1$H-NMR data were found to be in full accordance with the structure.

Example 737

2-{[2-(3-Cyclohexyl-ureido)-pyridin-4-ylmethyl]-amino}-N-cyclopentylmethoxy-benzamide (compound 424)

Prepared by similar procedures as described above for compounds 1-249. $^{13}$C- and $^1$H-NMR data were found to be in full accordance with the structure.

Example 738

N-{4-[(2-Cyclopentylmethoxycarbamoyl-phenylamino)-methyl]-pyridin-2-yl}-isonicotinamide (compound 425)

Prepared by similar procedures as described above for compounds 1-249. $^{13}$C- and $^1$H-NMR data were found to be in full accordance with the structure.

Example 739

1-(2,2,2-Trifluoro-acetyl)-pyrrolidine-2-carboxylic acid {4-[(2-cyclopentylmethoxycarbamoyl-phenylamino)-methyl]-pyridin-2-yl}-amide (compound 426)

Prepared by similar procedures as described above for compounds 1-249. $^{13}$C- and $^1$H-NMR data were found to be in full accordance with the structure.

Example 740

1-(2,2,2-Trifluoro-acetyl)-pyrrolidine-2-carboxylic acid (4-{[2-(4-cyano-benzyloxycarbamoyl)-phenylamino]-methyl}-pyridin-2-yl)-amide (compound 427)

Prepared by similar procedures as described above for compounds 1-249. $^{13}$C- and $^1$H-NMR data were found to be in full accordance with the structure.

Example 741

1-Acetyl-piperidine-4-carboxylic acid {4-[(2-cyclopentyl-methoxycarbamoyl-phenylamino)-methyl]-pyridin-2-yl}-amide (compound 428)

Prepared by similar procedures as described above for compounds 1-249. $^{13}$C- and $^1$H-NMR data were found to be in full accordance with the structure.

Example 742

1-Acetyl-piperidine-4-carboxylic acid (4-{[2-(4-cyano-benzyloxy-carbamoyl)phenylamino]-methyl}-pyridin-2-yl)-amide (compound 429)

Prepared by similar procedures as described above for compounds 1-249. $^{13}$C- and $^1$H-NMR data were found to be in full accordance with the structure.

Example 743

N-Cyclopentylmethoxy-2-[(2,4-dihydroxy-pyrimidin-5-ylmethyl)-amino]-benzamide (compound 430)

Prepared by similar procedures as described above for compounds 1-249. $^{13}$C- and $^1$H-NMR data were found to be in full accordance with the structure.

Example 744

Pyrrolidine-2-carboxylic acid (4-{[2-(4-cyano-benzyloxycarbamoyl)-phenylamino]-methyl}-pyridin-2-yl)-amide (compound 431)

Prepared by similar procedures as described above for compounds 1-249. $^{13}$C- and $^1$H-NMR data were found to be in full accordance with the structure.

Example 745

Pyrrolidine-2-carboxylic acid {4-[(2-cyclopentylmethoxycarbamoyl-phenylamino)methyl]-pyridin-2-yl}-amide (compound 432)

Prepared by similar procedures as described above for compounds 1-249. $^{13}$C- and $^1$H-NMR data were found to be in full accordance with the structure.

Example 746

2-[(Pyridin-4-ylmethyl)-amino]-N-(4-vinylbenzyloxy)benzamide (compound 433)

Prepared by similar procedures as described above for compounds 1-249. $^{13}$C- and $^1$H-NMR data were found to be in full accordance with the structure.

Example 36

In Vitro KDR Kinase Assay

The intracellular domain of the KDR receptor was used in the in vitro KDR assay. This domain contains the tyrosine kinase domain of KDR, and when expressed in Sf9 cells, this domain is constitutively active i.e. the kinase domain is phosphorylated on tyrosine residues. The substrate is the two SH2 domains of PLCγ, which has been shown to be sufficient for physiological interaction with PDGF-R (Ji, Q. S., Chattopadhyay, A., Vecchi, M., and Carpenter, G. *Mol. Cell. Biol.*, 19: 4961-4970, 1999) and TrkA (Angeles, T. S., Steffler, C., Bartlett, B. A., Hudkins, R. L., Stephens, R. M., Kaplan, D. R., and Dionne, C. A. *Anal Biochem*, 236: 49-55, 1996).

Biological Materials:

Antibodies against PLCγ1 (530) (sc-426), Flk-1/KDR (C-20) (sc-315), GST (B-14) (sc-138) were purchased form Santa Cruz Biotechnology Inc., Santa-Cruz-Europe, Heidelberg, Germany. Anti-phospho-Tyrosine (4G10) (cat. no. 05-321) was from Upstate Biotechnology. Anti-phospho-Tyrosine (PY20) (cat. no. P11120) was from Transduction Laboratories, BD Biosciences, Franklin Lakes, N.J., USA. Europium-labelled PY20 anti-phosphotyrosine antibody was from Wallac, Finland. Gluthathione Sepharose 4B (cat. no. 17-0756-01), ECL Western Blotting detection reagent (cat. no. 2106), ECL Hyperfilm (cat. no. RPN 3103H), 14.3-220 kDa rainbow coloured protein molecular markers (cat. no. RPN 756), PD-10 columns, γ-$^{32}$P-ATP (cat. no. AA0068 250 µCi/25 µl), pGEX-4T-1 vector and BL21 *E. Coli* cells (cat. no. 27-1542-01) were purchased from Amersham-Pharmacia Biotech, Europe, Denmark. Pefabloc (cat. no. 1429868), Leupeptin (cat. no. 1017101), Aprotinin (cat. no. 236624) were from Roche Molecular Biochemical, Hvidovre, Denmark. Secondary antibodies were from DAKO, Glostrup, Denmark. Biotin-marker (cat. no. 7726L) was from Cell Signaling Technologies Inc., Beverly, Mass., USA. Non-fat milk (MILEX®240) was from Arla (former MD Foods), Viby, Denmark. Nitro-cellulose membrane 0.2 µm (cat. no. A010A304C) was from Advantec MFC. 3 mM Whatmann filters (cat. no. 3030917) was from Whatmann International, England. TRIzol™, TA-cloning kit, GATEWAY system, pDONR201 Entry vector, pDEST20 vector, Bac-to-Bac system, pCR-3.1-Uni vector, pCR-Blunt II-TOPO, Zero Blunt TOPO cloning kit, Sf9 cell line, Grace's insect Medium Supplemented and CELLFECTIN were from Invitrogen, Carlsbad, Calif., USA. DMSO (D-2650), Gluthathione (G-4251), Lysozyme (L-6876) and 10×PBS were purchased from Sigma, Vallensbaek Str. Denmark. Chemicals for the different buffers were from Merck KGaA, Darmstadt, Germany. Black 96-wells microtiter MaxiSorp plates were from NUNC, Denmark.

RT-PCR Cloning of Human KDR:

Total RNA was isolated from human umbilical vein endothelial (HUVE) cells using TRIzol™ reagent according to the manufacturer's protocol. Two µg of total RNA was reverse transcribed into the first-strand cDNA using oligo(dT)$_{16}$ as a primer. The first-strand cDNA, encoding the complete coding region of human KDR, was then PCR amplified using the oligonucleotides 5'-TCTAGACAGGCGCTGGGA-GAAAGA-3' and 5'-TGCTGGTGGAAAGAACAA-CACTTCA-3'. The design of the oligonucleotides was based on the DNA sequence from GenBank accesssion no. X89776 and X61656. The PCR product was cloned into the pCR-3,1-Uni expression vector using the TA-cloning kit according to the manufacturer's protocol. The plasmid was designated pMWM-78.

Construction of KDR-cyt Baculovirus Bacmid:

The cDNA encoding the intracellular part of KDR (KDR-cyt) including the kinase domain (nucleotide 2683-4455, transcriptional start being +1) was PCR amplified using the oligonucleotides 5'-GGGGACAAGTTTGTACAAAAAAGCAGGCTCCGGAGGG<u>GCGGACTCTGCAC</u> and 5'-GGGGACCACTTTGTACAAGAAAGCTGGGTATTTGCTGGTG. Both oligonucleotides contained attB recombination sequences (underlined) for further cloning by the GATEWAY system. The PCR product was subcloned into the pDONR201 Entry vector using the GATEWAY system according to the manufacturer's protocol. The identity of the sequence was verified by DNA sequencing. The cDNA encoding the KDR-cyt was then transferred from the pDORN201 to the pDEST20 vector thereby placing the KDR-cyt in a cassette for insect cell expression of a GST-KDR-cyt fusion protein under control of the polyhedrin promoter. The GST-KDR-cyt was transferred to a baculovirus bacmid using the Bac-to-Bac system according to the manufacturer's protocol. Briefly, the pDEST20/KDR-cyt was transformed into *E. coli* DH10Bac in which it recombined with the bMON14272 bacmid. The recombined bacmid was purified from the *E. coli* by miniprep.

Sf9 Cells:

The Sf9 cell line originating from the pupal ovarian tissue of the fall army worm, *Spodoptera frugiperda* was grown in Grace's Insect Medium Supplemented, 10% fetal calf serum (FCS), 100 U/ml penicillin and 100 mg/ml streptomycin at 27° C. The cell line was passaged at confluency and typically diluted at 1:6. Cells were dislodged by scraping.

Production of GST-KDR-cyt Baculovirus in Sf9 Cells:

The baculovirus bacmid containing the GST-KDR-cyt expression cassette was transfected into Sf9 insect cells using CELLFECTIN liposome mediated transfection according to the manufacturer's protocol. Three days after transfection the medium was collected and clarified by centrifugation (500× G, 5 minutes, 4° C.) and the supernatant containing the baculovirus particles was placed at 4° C. for short term storage or at −80° C. for long term storage.

Amplification of Recombinant Baculovirus:

In order to amplify the virus, Sf9 cells from a subconfluent culture were seeded in a T-80 culture flask at a density of 1×10$^5$ cells/cm$^2$ and left to adhere for 45-60 min. at 27° C. The medium was aspired from the monolayer and a 300 µl virus stock from the first production was added together with 1700 µl Grace's Insect Medium Supplemented (no antibiotics and no FCS). The cells were incubated for 1 hour at 27° C. before the addition of 15 ml of Grace's Insect Medium Supplemented (100 U/ml penicillin, 100 mg/ml streptomycin and 10% FCS). Following an incubation period of 72 hours, the supernatant containing the baculovirus was harvested as described above.

Production of GST-KDR-cyt Fusion Protein:

For the purification GST coupled KDR-cyt from Sf-9 cells, 2 T-175 culture flasks were seeded with cells from a subconfluent culture at a density of 1×10$^5$ cells/cm$^2$. The cells were left to adhere at 27° C. for 45-60 min. The culture medium was removed and cells were infected with an optimal amount of virus in 20 ml Grace's Insect Medium Supplemented (no antibiotics and no FCS). Following an incubation period of 60 min. at 27° C., 17 ml Grace's Insect Medium Supplemented (10% FCS, 100 U/ml penicillin and 100 mg/ml streptomycin) was added and the cells were harvested at the optimal time after infection. The cells were scraped off into the medium in their culture flask, and the cells and medium was transferred to tubes and centrifuged (500×G, 5 min., 4° C.). The supernatant was aspired and the pellet washed in 2×5 ml ice cold 1× phosphate buffered saline (PBS). The cells were lysed in 4 ml of the following lysis buffer which was prepared just prior to use: 50 mM HEPES pH 7.5, 150 mM NaCl, 10 mM EDTA, 10 mM Na$_4$PO$_7$, 100 mM NaF, 500 µM Pefabloc, 10 µg/l Aprotinin, 10 µg/µl Leupeptin, 2 mM Na$_3$VO$_4$ and 1% Triton X-100. The sample was incubated on ice for 10 min., then centrifuged (10.000×G, 10 min., 4° C.) and the supernatant was transferred to a new centrifuge tube.

Purification of GST-KDR-cyt Fusion Protein:

Gluthathione-Sepharose Beads were prepared by washing 400 µl beads 3 times with a HNT buffer containing 30 mM HEPES pH 7.5, 30 mM NaCl and 0.1% Triton X-100 followed by washing twice in the lysis buffer (50 mM HEPES pH 7.5, 150 mM NaCl, 10 mM EDTA, 10 mM Na$_4$PO$_7$, 100 mM NaF, 500 µM Pefabloc, 10 µg/µl Aprotinin, 10 µg/µl Leupeptin, 2 mM Na$_3$VO$_4$ and 1% Triton X-100. Then 4000 µl supernatant from the lysed cells were added to the Glutathione-Sepharose beads and the sample was left to rotate slowly for 2 hours at 4° C. after which it was centrifuged (1000×G, 30 sec., 4° C.) and the supernatant removed.

To elute the proteins, 400 µl 50 mM Tris/HCl pH 8.0 and 20 mM Gluthathione were added to the sample, which was incubated for 20 min. while rotating slowly at 4° C. The sample was centrifuged (1000×G, 30 sec., 4° C.) and the supernatant was collected. This procedure was repeated 4 times or till no more protein was eluted determined by measuring the absorbance at 280 nm (A$_{280}$). The GST-KDR-cyt was desalted, and the Glutathione/Tris buffer was exchanged to a TBS-Buffer (150 mM NaCl, 10 mM Tris/HCl pH 7.5) using a PD10 column. The PD10 column contains Sephadex G-25 M. Briefly, the GST-KDR-cyt eluate was added to the PD-10 column, and eluted with 2.5 ml TBS-Buffer. The GST-KDR-cyt eluate in the TBS-Buffer was measured by A$_{280}$, and the amount of protein was determined using a BSA standard. The purified GST-protein was analysed by SDS-PAGE followed by Coomasie staining and Western blotting.

RT-PCT Cloning of Human PLCγ cDNA:

Total RNA was isolated from human embryonic kidney HEK293 cells using TRIzol™ reagent. Two µg of total RNA was reverse transcribed into the first-strand cDNA using oligo (dT)$_{16}$ as a primer. The first-strand cDNA encoding a part of human PLCγ (nucleotide 1593-2635, GenBank accession no. M34667) containing the two SH2 domains and 2 tyrosine residues for phosphorylation, was then PCR amplified using the oligonucleotides 5'-TATCCCCACTACTTTGTTCT-GACCA-3' and 5'-CACGGGGTTGACCATCTCTTC-3'.

The PCR product was cloned into the pCR-Blunt II-TOPO vector using the Zero Blunt TOPO cloning kit according to the manufacturer's protocol. The cloned PLCγ was verified by DNA sequencing and the plasmid was designated pCR-Blunt II-TOPO/PLCγ.

Construction of GST-PLCγ Vector for *E. coli* Expression:

For the construction of the vector for *E. coli* expression of GST-PLCγ, the PLCγ part of the pCR-Blunt II-TOPO/PLCγ was PCR amplified using the oligonucleotides: 5'-ACG-GAATTCAGCACAGAGCTGCAGTCCAATG-3' (incorporating an Eco RI site) and 5'-GATGCGGC-CGCTCTTTGACTGCACACTTGAAAGTTGG-3' (incorporating a Not I site). This PCR product was then ligated into the pGEX-4T-1 vector using the Eco RI and Not I sites for expression of a GST-PLCγ fusion protein (see FIG. 1). The construction was verified by DNA sequencing and designated pMWM-79.

Production of GST-PLCγ:

*Escherichia coli* BL21 cells were transformed with pGEX-PLCγ plasmid DNA. The bacteria were cultured to an $OD_{600}$ of approx. 0.5 in a shaking incubator at 37° C., and induced by 1 mM isopropyl-β-D-thiogalactopyranoside (IPTG) for 4 hours. The bacteria were pelleted by centrifugation at 4000 rpm, for 20 min. at 4° C. and the pellet was frozen at −80° C. overnight. The following day, the pellet was resuspended in NETN-buffer (20 mM Tris-HCl pH 8.0, 10 mM NaCl, 1 mM EDTA, 500 μM Pefabloc, 10 μg/μl Leupeptin, 10 μg/μl Aprotinin, 0.5% Triton X-100, 10 mM DTT) on an ice-bath. The bacteria were lysed on ice-bath for 1 hour by the addition of 20 μg/ml lysozyme, prior to centrifugation at 10.000×g, for 30 min. at 4° C., and transfer of the supernatant to new tubes.

Purification of GST-PLCγ:

Glutathione-Sepharose beads were prepared by washing 200 μl beads 3 times with a HNT buffer containing 30 mM HEPES pH 7.5, 30 mM NaCl and 0.1% Triton X-100 followed by washing twice in the NETN-buffer. Then the supernatant from the lysed bacteria was added to the Glutathione-Sepharose beads and the sample was left to rotate slowly for 2 hours at 4° C. The GST-PLCγ fusion protein adsorbed to the Glutathione-Sepharose beads was then washed three times in NETN-buffer and clarified by centrifugation at 1000×g, for 30 sec. at 4° C., to remove non-specifically bound proteins. Afterwards, the GST-PLCγ fusion proteins were separated from the beads by eluting with 200 μl elution-buffer (50 mM Tris-HCl pH 8.0, 20 mM Glutathione). The eluate was examined by an SDS-PAGE followed by Coomassie staining as well as by the Western blot technique using anti-PLCγ (530) (sc-426) (1:1000) and anti-GST (B-14) (sc-138) antibodies (1:2000). The yield of fusion protein was calculated from the absorbance at 280 nm.

The compounds to be tested were dissolved in DMSO at 10 mM, stored at −20° C. and protected from light. The maximum concentration of DMSO in the in vitro assay was 0.1%. Control samples received the same concentration of solvent as the samples treated with the test compounds.

For the kinase assays, black 96 wells MaxiSorp microtiter plates were coated by an overnight incubation with 100 μl/well of a 2.5 μg/ml solution of phospholipase Cγ in TBS buffer (40 mM Tris-HCl, pH 7.4, 20 mM $Mg(C_2H_3O_2)_2$, 0.02% $NaN_3$) at 4° C. The plates were washed 3 times with TBS buffer containing 0.1% Tween-20, and the residual binding sites were masked by incubation with 1% BSA in TBS buffer containing 0.1% Tween-20 for 1 h. The plates were washed again and the test compounds were added at final concentrations up to 10 μM, together with ATP at the final concentration of 100 μM in 50 μl TBS buffer/well. Then, 50 μl of the human intracellular domain of KDR (VEGF Receptor-2) finally diluted 3000-3500 fold were added and were incubated for 30 min at room temperature. The plates were washed and 100 μl of the Europium labelled PY-20 anti-phosphotyrosine antibody (Wallac, FIN) were incubated in each well at the concentration of approximately 114 ng/ml for 2 h. Then, the plates were washed and 100 μl of enhancer solution (Wallac, FIN) were incubated in each well for 5 min in the dark. The plates were read in a Victor 1420 multilabel counter, using a Europium protocol for time-resolved fluorometry (Wallac, FIN): excitation 340 nm, emission 615 nm, sample pulse cycle 400 μs. Fluorescence was measured for 400 μs between flashes after a delay time of 400 μs. The background measured in the absence of enzyme was subtracted from all samples. The molar concentrations that inhibited 50% of the maximal enzymatic activity ($IC_{50}$) were calculated from the dose-response curve, by fitting a straight line between the two concentrations immediately above and below the 50% inhibition point (i.e. by solving the equation y=a+bx).

The in vitro KDR inhibitory activities of compounds of general formula (I) of the present invention are listed in Table 6.

TABLE 6

In vitro KDR inhibition

| Compound No. | $-LogIC_{50}$ (KDR) |
|---|---|
| 1 | 7.1 |
| 2 | 6.9 |
| 3 | 7.0 |
| 4 | 6.7 |
| 5 | 7.5 |
| 6 | 7.2 |
| 7 | 7.4 |
| 8 | 7.5 |
| 9 | 7.0 |
| 10 | 7.3 |
| 11 | 6.9 |
| 12 | 7.8 |
| 13 | 7.8 |
| 14 | 8.2 |
| 15 | 7.3 |
| 16 | 7.6 |
| 17 | 7.2 |
| 18 | 7.7 |
| 19 | 7.2 |
| 20 | 7.5 |
| 21 | 7.6 |
| 22 | 7.6 |
| 23 | 7.6 |
| 24 | 7.7 |
| 25 | 7.3 |
| 26 | 7.1 |
| 27 | 7.9 |
| 28 | 7.0 |
| 29 | 6.9 |
| 30 | 6.0 |
| 31 | 6.9 |
| 32 | 7.7 |
| 33 | 7.0 |
| 34 | 6.1 |
| 35 | 6.0 |
| 38 | 8.0 |
| 39 | 8.2 |
| 40 | 8.0 |
| 41 | 7.7 |
| 42 | 8.0 |
| 43 | 7.7 |
| 44 | 7.3 |
| 45 | 7.5 |
| 46 | 7.2 |
| 47 | 7.8 |
| 50 | 7.2 |
| 52 | 7.2 |
| 56 | 7.3 |
| 58 | 7.2 |
| 59 | 7.5 |
| 60 | 7.7 |
| 61 | 7.8 |

TABLE 6-continued

In vitro KDR inhibition

| Compound No. | −LogIC$_{50}$ (KDR) |
|---|---|
| 62 | 7.2 |
| 63 | 7.2 |
| 64 | 7.3 |
| 66 | 7.2 |
| 67 | 7.3 |
| 68 | 7.1 |
| 69 | 8.2 |
| 70 | 7.5 |
| 71 | 7.6 |
| 72 | 7.4 |
| 73 | 7.8 |
| 74 | 7.2 |
| 75 | 7.2 |
| 76 | 7.6 |
| 77 | 7.4 |
| 78 | 7.8 |
| 79 | 7.4 |
| 80 | 7.4 |
| 81 | 7.3 |
| 82 | 7.8 |
| 85 | 7.3 |
| 87 | 7.0 |
| 96 | 7.1 |
| 98 | 7.4 |
| 100 | 7.2 |
| 104 | 7.2 |
| 106 | 7.3 |
| 107 | 7.0 |
| 110 | 7.1 |
| 111 | 7.1 |
| 113 | 8.6 |
| 114 | 7.0 |
| 116 | 7.4 |
| 117 | 7.9 |
| 118 | 7.8 |
| 119 | 7.8 |
| 120 | 7.4 |
| 121 | 7.3 |
| 122 | 8.1 |
| 123 | 7.5 |
| 124 | 7.2 |
| 125 | 7.4 |
| 126 | 8.1 |
| 127 | 7.8 |
| 128 | 7.8 |
| 129 | 8.0 |
| 130 | 7.3 |
| 131 | 7.4 |
| 132 | 7.0 |
| 133 | 7.7 |
| 134 | 7.6 |
| 135 | 7.1 |
| 141 | 7.3 |
| 142 | 7.4 |
| 143 | 7.0 |
| 156 | 7.2 |
| 157 | 7.3 |
| 158 | 7.1 |
| 160 | 7.2 |
| 161 | 7.2 |
| 162 | 7.2 |
| 164 | 8.1 |
| 188 | 7.1 |
| 195 | 7.1 |
| 196 | 7.1 |
| 198 | 7.2 |
| 199 | 7.3 |
| 204 | 7.2 |
| 206 | 7.4 |
| 207 | 7.1 |
| 208 | 7.1 |
| 210 | 8.1 |
| 211 | 7.7 |
| 212 | 8.0 |
| 213 | 8.1 |
| 214 | 7.3 |
| 215 | 7.2 |
| 216 | 8.0 |
| 217 | 8.1 |
| 219 | 7.4 |
| 220 | 8.1 |
| 221 | 8.1 |
| 222 | 8.2 |
| 223 | 7.5 |
| 224 | 8.2 |
| 225 | 8.1 |
| 226 | 8.2 |
| 227 | 8.3 |
| 228 | 8.2 |
| 229 | 8.1 |
| 230 | 7.6 |
| 231 | 7.4 |
| 232 | 7.7 |
| 233 | 8.0 |
| 234 | 7.2 |
| 235 | 7.2 |
| 236 | 7.1 |
| 237 | 7.1 |
| 244 | 7.2 |
| 245 | 8.1 |
| 246 | 7.7 |
| 247 | 7.3 |

Example 37

Metabolic Stability

Synthesis: The reference compounds 1 and 2 were prepared, using the methods described in WO 00/27819.

Isolation Procedure: Fresh rat (tac SPRD) hepatocytes were isolated by the end lobe technique. The right lateral liver lobe was cut off, placed on a perfusion platform and first perfused with calcium-free buffer, then buffer containing calcium and collagenase. The resulting cell suspension was centrifuged and the cells were washed several times. Cell Viability and Yield: Cell viability and yield were assessed by the Trypan Blue Exclusion method. Only cell suspensions with viability over 80% were used. A suspension of $2 \times 10^6$ cells/mL was prepared and used for the assay.

Assay for Metabolic Stability: The test compounds (10 mM in DMSO) were placed in the liquid handler. A work-solution A (200 µM) was prepared by transferring 10 µL stock solution and 490 µL of a 0.2% solution of bovine serum albumin (BSA) in Krebs-Henseleit Buffer (KHB) to a microtiter plate. A work-solution B (10 µM) was prepared by transferring 25 µL of work-solution A and 475 µL KHB with 0.2% BSA to a microtiter plate. The cells were diluted to $2 \times 10^6$ cells/mL in KHB with 0.2% BSA, then 475 µL suspension was manually transferred to each well on two 24-well plates (Costar, cat. no. 3524). The plated cells were placed in the liquid handler and pre-incubated at 37° C. for 20 minutes in order to activate the metabolic capacity of the cells. After preincubation, 25 µL of work-solution B (10 µM) was added to each well, resulting in a final concentration of 0.5 µM test compound in the cell suspension. After addition of test compound to all wells on the plate, the plate was gently stirred and incubated. After 15, 30, 60, 90, and 120 minutes, 25 µL sample was withdrawn and added to a microtiter plate containing 100 μL methanol with internal standard in order to stop the metabolic reaction. The microtiter plate was centrifuged (30 min, 4500 rpm) and the supernatant was analysed by LC-MS/MS (See Analysis for details). Samples t=0 were made by manually adding 190 μL cell suspension to each well on a 96-well plate (Costar, cat. no. 3594; same material as the 24-well plates). 10 μL of work solution B was added to each well. After every four compounds (4 needles on the liquid handler), the plate was shaken, and 25 μL sample was instantly withdrawn and transferred to a microtiter plate containing 100 μL methanol with internal standard. The samples were analysed as described below.

Analysis: The HPLC system consisted of an Agilent 1100 Pump and Column Oven, and a CTC HTS-PAL AutoSampler. The mass spectrometer was a Sciex API 3000 MS/MS. The chromatographic conditions were as follows: Column: Zorbax Sb—C18, 5 μm, 2.1×50 mm; Injection volume: 10 μL; Eluent A: 5% methanol in MilliQ-water (v/v %), 2 mM ammonium acetate, 20 mM formic acid; Eluent B: 90% methanol in MilliQ-water (v/v %), 2 mM ammonium acetate, 20 mM formic acid; Flow rate: 500 μL/min; Step-gradient-program: 0-2 min, 0% B→100% B; 2-3 min, 100% B; 3-3.1 min, 100% B→0% B; 3.1-5 min, 0% B.

Data were processed using Analyst version 1.2. All compounds were tuned and optimised on the mass spectrometer by infusion.

Calculations: The initial concentration of test compound was defined as 100%, and the amount of intact compound (%) versus time was plotted in a graph. The Area Under the Curve (AUC) was calculated using the linear trapezoidal method:

$$\text{Linear trapezodial rule: } AUC_0^{t=2h} = \sum_{i=0}^{2h} (t_{i+1} - t_i) \times \frac{C_{i+1} - C_i}{2}$$

The AUC values for each compound were normalised to values between 0 and 100, and this number was used as a measurement for metabolic stability. Compounds with AUC values close to 0 have low metabolic stability, whereas compounds with AUC values close to 100 have high metabolic stability.

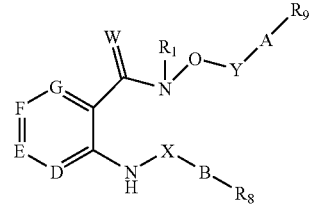

The invention claimed is:

1. A compound of general formula I wherein $R_1$ represents hydrogen or a straight, branched and/or cyclic, saturated or unsaturated hydrocarbon radical, optionally substituted with one or more substituents selected from the group consisting of halogen, hydroxyl, amino, nitro, and cyano;
D represents nitrogen or C—$R_2$;
E represents nitrogen or C—$R_3$;
F represents C—$R_4$;

G represents nitrogen or C—$R_5$;

$R_2$, $R_3$, $R_4$, and $R_5$ are the same or different and individually represent hydrogen, halogen, hydroxyl, amino, nitro, carboxy, cyano, alkoxy, alkylthio, alkoxycarbonyl, alkylcarbonyloxy, alkoxycarbonyloxy, alkylcarbonyl, alkoxysulfonyloxy, formyl, aminocarbonyl, alkylcarbonylamino, or a straight or branched, saturated or unsaturated hydrocarbon radical, optionally substituted with one or more substituents independently selected from the group consisting of halogen, hydroxyl, amino, nitro, carboxy, cyano, alkoxy, alkylthio, alkoxycarbonyl, alkylcarbonyloxy, alkoxycarbonyloxy, alkylcarbonyl, alkoxysulfonyloxy, aminosulfonyl, alkylsulfonylamino, formyl, aminocarbonyl, and alkylcarbonylamino, or $R_2$ and $R_3$, or $R_3$ and $R_4$, or $R_4$ and $R_5$ together with the C atoms to which they are attached form a 5- or 6-membered carbocyclic or heterocyclic ring;

W represents oxygen;

X represents a radical of the formula —$(CH_2)_i$—NH—C(O)—$(CH_2)_j$—, where i, j, p, q, r, s, t, and u are integers from 0-6, and n is an integer from 1-6, wherein said radicals are optionally substituted by one or more substituents independently selected from the group consisting of $R_7$;

Y represents a radical of the formula —$(CH_2)_i$—NH—C(O)—$(CH_2)_j$—, —$(CH_2)_k$—C(O)—$(CH_2)_m$—, —$(CH_2)_n$—, —$(CH_2)_p$—CH=CH—$(CH_2)_q$—, —$(CH_2)_r$—O—$(CH_2)_s$—, —$(CH_2)_t$NH—$(CH_2)_u$—, —$(CH_2)_w$—C(O)—NH—$(CH_2)_z$— where i, j, k, m, n, p, q, r, s, t, u, w, and z are integers from 0-6, wherein said radicals are optionally substituted by one or more substituents independently selected from the group consisting of $R_7$;

$R_7$ represents hydrogen, oxo, thioxo, halogen, hydroxyl, amino, imino, nitro, carboxy, carbamoyl, cyano, cycloalkyl, alkyl, heteroaryl, heterocycloalkyl, heterocycloalkenyl, heterocycloalkyl-heteroaryl, heterocycloalkylcarbonylamino, cycloalkenyl, alkenyl, alkynyl, alkoxy, alkoxyimino, alkylthio, alkoxycarbonyl, alkylcarbonyloxy, alkenylcarbonyloxy, alkoxycarbonyloxy, alkylureido, alkylthioureido, alkylcarbonyl, alkoxysulfonyloxy, aminosulfonyl, alkylsulfonylamino, alkylsulfonyl, arylsulfonyl, formyl, aminocarbonyl, and alkylcarbonylamino, wherein said amino, imino, cycloalkyl, alkyl, heteroaryl, heterocycloalkyl, heterocycloalkenyl, heterocycloalkyl-heteroaryl, heterocycloalkylcarbonylamino, cycloalkenyl, alkenyl, alkynyl, alkoxy, alkoxyimino, alkylthio, alkoxycarbonyl, alkylcarbonyloxy, alkenylcarbonyloxy, alkoxycarbonyloxy, alkylureido, alkylthioureido, alkylcarbonyl, alkoxysulfonyloxy, aminosulfonyl, alkylsulfonylamino, alkylsulfonyl, arylsulfonyl, aminocarbonyl, and alkylcarbonylamino are optionally substituted by one or more substituents independently selected from the group consisting of hydrogen, oxo, thioxo, hydroxyl, amino, imino, nitro, carboxy, cyano, alkoxy, alkylthio, alkoxycarbonyl, alkylcarbonyloxy, alkoxycarbonyloxy, alkylcarbonyl, alkoxysulfonyloxy, aminosulfonyl, alkylsulfonylamino, alkylsulfonyl, arylsulfonyl, aminocarbonyloxy, heteroarylsulfonylamino, formyl, aminocarbonyl, trifluoromethyl, alkylcarbonylamino, heterocycloalkyl, heterocycloalkenyl, aryl, alkylureido, alkylthioureido, heteroaryl, cycloalkyl, alkyl, cycloalkenyl, alkenyl, alkynyl, and alkylaminocarbonyl;

B represents aryl, heteroaryl, heterocycloalkyl, heterocycloalkenyl, cycloalkyl, or cycloalkenyl, all of which are optionally substituted with one or more substituents independently selected from the group consisting of $R_8$;

$R_8$ represents hydrogen, halogen, hydroxyl, amino, imino, oxo, thioxo, nitro, carboxy, cyano, alkoxy, phenoxy, alkylthio, alkoxycarbonyl, alkoxycarbamoyl, alkylcarbonyloxy, alkoxycarbonyloxy, alkylcarbonyl, alkoxysulfonyloxy, aminosulfonyl, arylsulfonyl, alkylsulfonylamino, formyl, aminocarbonyl, alkylureido, alkylthioureido, aminocarbonyloxy, alkylcarbonylamino, heterocycloalkylcarbonylamino, heterocycloalkyl, heterocycloalkenyl, aryl, heteroaryl, alkylaminocarbonyl, and a straight or branched, saturated or unsaturated hydrocarbon radical, wherein said amino, alkoxy, phenoxy, alkylthio, alkoxycarbonyl, alkoxycarbamoyl, alkylcarbonyloxy, alkoxycarbonyloxy, alkylcarbonyl, alkoxysulfonyloxy, aminosulfonyl, arylsulfonyl, alkylsulfonylamino, aminocarbonyl, alkylureido, alkylthioureido, aminocarbonyloxy, alkylcarbonylamino, heterocycloalkylcarbonylamino, heterocycloalkyl, heterocycloalkenyl, aryl, heteroaryl, alkylaminocarbonyl, and straight or branched, saturated or unsaturated hydrocarbon radical are optionally substituted with one or more substituents independently selected from the group consisting of $R_7$;

A represents a straight, branched and/or cyclic, saturated or unsaturated hydrocarbon radical, a heterocycloalkyl, a heterocycloalkenyl, or a heteroaryl, all of which are optionally substituted with one or more substituents independently selected from the group consisting of $R_9$;

$R_9$ represents hydrogen, oxo, halogen, trifluoromethyl, hydroxyl, amino, nitro, carboxy, cyano, alkoxy, alkylthio, alkoxycarbonyl, alkylcarbonyloxy, alkoxycarbonyloxy, alkylureido, alkylthioureido, alkylcarbonyl, alkoxysulfonyloxy, aminosulfonyl, arylsulfonyl, alkylsulfonylamino, arylsulfonylamino, heteroarylsulfonylamino, alkylsulfonyl, formyl, aminocarbonyl, alkylcarbonylamino, alkylaminocarbonyl, aminocarbonyloxy, heterocycloalkyl, heterocycloalkenyl, heteroaryl and a straight or branched, saturated or unsaturated hydrocarbon radical, wherein said amino, alkoxy, alkylthio, alkoxycarbonyl, alkylcarbonyloxy, alkoxycarbonyloxy, alkylureido, alkylthioureido, alkylcarbonyl, alkoxysulfonyloxy, aminosulfonyl, arylsulfonyl, alkylsulfonylamino, arylsulfonylamino, heteroarylsulfonylamino alkylsulfonyl, aminocarbonyl, alkylcarbonylamino, alkylaminocarbonyl, aminocarbonyloxy, heterocycloalkyl, heterocycloalkenyl, heteroaryl and straight or branched, saturated or unsaturated hydrocarbon radical are optionally substituted by one or more substituents independently selected from the group consisting of $R_7$;

and pharmaceutically acceptable salts, hydrates, or solvates thereof.

2. A compound according to claim 1 wherein $R_1$ represents hydrogen.

3. A compound according to claim 1 wherein D is C—$R_2$, E is C—$R_3$, F is C—$R_4$, and G is C—$R_5$.

4. A compound according to claim 3 wherein $R_2$, $R_3$, $R_4$, and $R_5$ are hydrogen, chloro, bromo, fluoro, methoxy, or methyl.

5. A compound according to claim 1 wherein D is nitrogen, E is C—$R_3$, F is C—$R_4$, and G is C—$R_5$.

6. A compound according to claim 5 wherein $R_3$, $R_4$ and $R_5$ are hydrogen.

7. A compound according to claim 1 wherein D is C—$R_2$, E is nitrogen, F is C—$R_4$, and G is C—$R_5$.

8. A compound according to claim 7 wherein $R_2$, $R_4$ and $R_5$ are hydrogen.

9. A compound according to claim 1 wherein B represents phenyl or pyridyl, such as 2-pyridyl, 3-pyridyl, or 4-pyridyl, all of which are optionally substituted with one or more substituents independently selected from the group consisting of $R_8$.

10. A compound according to claim 1 wherein B represents, naphthyl, 2,3-dihydrobenzofuranyl, benzofuranyl, 2H-chromenyl, thiazolyl, 4,5-dihydro-1H-[1,2,4]-triazolyl, tetrahydropyranyl, 1,6-dihydropyridinyl, imidazolyl, imidazolidinyl, imidazo[2,1-b]thiazolyl, imidazo[1,2-a]pyrimidinyl, 1,2,4-triazolyl, piperidinyl, pyrrolidinyl, 4,5-dihydrooxazolyl, isoxazolyl, 4,5-dihydro-isoxazolyl, pyrimidinyl, 1-H-pyrazolyl, 1H-indazol-6-yl, quinolinyl or isoquinolinyl, all of which are optionally substituted with one or more substituents independently selected from the group consisting of $R_8$.

11. A compound according to claim 1 wherein $R_8$ is hydrogen, halogen, alkoxy, phenoxy, alkoxycarbonyl, alkoxycarbamoyl, carboxy, aminocarbonyl, cyano, alkyl, oxo, hydroxy, amino, heterocycloalkyl, heterocycloalkenyl, alkylsulfonylamino, alkylsulfonyl, alkylureido, alkylthioureido, alkylcarbonylamino, heterocycloalkylcarbonylamino, or aminocarbonyloxy, wherein said alkoxy, phenoxy, alkoxycarbonyl, alkoxycarbamoyl, aminocarbonyl, alkyl, amino, heterocycloalkyl, alkylsulfonylamino, alkylsulfonyl, alkylureido, alkylthioureido, alkylcarbonylamino, heterocycloalkylcarbonylamino, or aminocarbonyloxy are optionally substituted with one or more substituents independently selected from the group consisting of $R_7$.

12. A compound according to claim 1 wherein $R_8$ is hydrogen, fluoro, chloro, bromo, cyano, carboxy, oxo, —$NH_2$, hydroxy, methoxy, phenoxy, methoxycarbonyl, ethoxycarbonyl, methoxycarbamoyl, methylaminocarbonyl, pyrrolidinylcarbonylamino, ethylaminocarbonyl, propylaminocarbonyl, butylaminocarbonyl, methyl, ethyl, propyl, morpholine, pyrrolidinyl, methylsulfonylamino, methylsulfonyl, methylureido, ethylureido, tert-butylureido, cyclohexylureido, methylthioureido, isopropylureido, n-propylureido, methylamino, or ethylamino, wherein said methoxy, phenoxy, methoxycarbonyl, ethoxycarbonyl, methoxycarbamoyl, tert-butoxycarbonyl, methylaminocarbonyl, pyrrolidinylcarbonylamino, ethylaminocarbonyl, propylaminocarbonyl, butylaminocarbonyl, methyl, ethyl, propyl, morpholine, pyrrolidinyl, methylsulfonylamino, methylsulfonyl, methylureido, ethylureido, tert-butylureido, cyclohexylureido, methylthioureido, isopropylureido, n-propylureido, methylamino, or ethylamino are optionally substituted with one or more substituents independently selected from the group consisting of $R_7$;
wherein $R_9$ is hydrogen, nitro, fluoro, chloro, bromo, iodo, oxo, cyano, carboxy, ethenyl, ethynyl, propynyl, butynyl, methoxy, aminomethyl, aminoethyl, aminophenyl, morpholine, carbomethoxy, cyano, trifluoromethyl, methyl, tert-butoxy, ethyl, propyl, butyl, pentyl, cyclopentyl, nonenyl, methylsulfanyl, aminocarbonyl-tert-butoxy, methylsulfonylamino, thiazolesulfonylamino, phenylsulfonylamino, —NH—C(S)—$NH_2$, —NH—C(O)—$NH_2$, morpholinyl, ethylaminocarbonyl, thiophene, amino, or phenyl, wherein said ethenyl, ethynyl, propynyl, butynyl, methoxy, ethoxy, aminomethyl, aminoethyl, morpholine, carbomethoxy, cyano, trifluoromethyl, methyl, ethyl, propyl, butyl, pentyl, cyclopentyl, nonenyl, methylsulfanyl, methylsulfonylamino, thiazolesulfonylamino, phenylsulfonylamino, —NH—C(S)—$NH_2$, —NH—C(O)—$NH_2$, morpholinyl, ethylaminocarbonyl, thiophene, amino, or phenyl are optionally substituted by one or more substituents independently selected from the group consisting of $R_7$; and
wherein $R_7$ is hydrogen, hydroxy, amino, —$NH_2$, diethylamino, cyclohexylamino, tert-butylamino, oxo, thioxo, phenyl, pyridyl, acetylamino, fluoro, methyl, ethyl, propyl, butyl, morpholine, methoxy, tert-butoxy, cyclopropyl, hydroxyethyl, methoxyimino, —NH-phenyl, acetyl, ethoxy, 2-acetylamino-4-methyl-thiazole, tert-butyl, methylpiperazine, 2-hydroxyethylpiperazinyl, methylthiazol, hydroxypyrrolidine, dimethylamino, toluoyl, methylamino, pyrrolidine, methoxycarbonyl, ethoxycarbonyl, carboxy, carbamoyl, cyano, methylcarbonyloxy, ethylcarbonyloxy, acryloyloxy, cyclopropyl, or 2,5-dioxoimazolidinyl.

13. A compound according to claim 1 wherein X is —$CH_2$—, —$(CH_2)_2$—, —$CH(CH_3)$—, —$(CH_2)_2$—O—$CH_2$—, or —CH=CH—.

14. A compound according to claim 1 wherein Y is radical of the formula —$(CH_2)_i$—NH—C(O)—$(CH_2)_j$—, where i is an integer from 1-4 and j is 0; or Y is radical of the formula —$(CH_2)_n$—, where n is an integer from 0-6; or Y is radical of the formula —$(CH_2)_p$—C(O)—NH—$(CH_2)_q$, where p is an integer from 0-6 and q is 0; or Y is radical of the formula —$(CH_2)_r$—O—$(CH_2)_s$, where r is an integer from 0-6 and s is an integer from 0-1; or Y is radical of the formula —$(CH_2)_t$—NH—$(CH_2)_u$—, where t is an integer from 0-4 and u is an integer from 0-1; wherein said radicals are optionally substituted by one or more substituents independently selected from the group consisting of $R_7$.

15. A compound according to claim 1 wherein Y is a bond, —$CH_2$—, —$CH_2$—$CH_2$—, —$CH(CH_3)$—, —$CH_2$—$CH_2$—O—, —$(CH_2)_2$—O—$CH_2$—, —$(CH_2)_3$—O—$CH_2$—, —$(CH_2)_3$—NH—C(O)—, —$(CH_2)_4$—NH—C(O)—, —$CH_2$—CH(OH)—$CH_2$—O—, —$(CH_2)_2$—NH—$CH_2$—, —$(CH_2)_4$—NH—$CH_2$—, —$CH_2$—$CH_2$—$CH_2$—, —$CH_2$—C(O)—, —$CH_2$—C(O)—NH—, or —CH($CH_2NHSO_2CH_3$)—.

16. A compound according to claim 1 wherein A represents ($C_6$-$C_{10}$)aryl, ($C_{3-10}$)heterocycloalkyl, ($C_3$-$C_{10}$)cycloalkyl, ($C_3$-$C_6$)cycloalkenyl, ($C_2$-$C_5$)alkenyl, ($C_1$-$C_6$)alkyl, ($C_2$-$C_{10}$)heteroaryl, heterocycloalkenyl, or toluoyl, all of which are optionally substituted with one or more substituents independently selected from the group consisting of $R_9$.

17. A compound according claim 1 wherein A represents methyl, ethyl, ($C_6$)aryl, ($C_9$)aryl, ($C_{10}$)aryl, ($C_{1-4}$)aryl, ($C_3$)alkyl, ($C_4$)alkyl, ($C_5$)alkyl, ($C_2$)alkenyl, ($C_3$)alkenyl, ($C_4$)alkenyl, ($C_5$)alkenyl, ($C_3$)cycloalkyl, ($C_4$)cycloalkyl, ($C_5$)cycloalkyl, ($C_6$)cycloalkyl, ($C_7$)cycloalkyl, ($C_8$)cycloalkyl, ($C_{10}$)cycloalkyl, ($C_6$)cycloalkenyl, ($C_3$)heteroaryl, ($C_4$)heteroaryl, ($C_5$)heteroaryl, ($C_6$)heteroaryl, ($C_7$)heteroaryl, ($C_9$)heteroaryl, ($C_4$)heterocycloalkyl, ($C_5$)heterocycloalkyl, ($C_3$)heterocycloalkenyl, ($C_4$)heterocycloalkenyl, ($C_5$)heterocycloalkenyl, or toluoyl, all of which are optionally substituted with one or more substituents independently selected from the group consisting of $R_9$.

18. A compound according to claim 1 wherein A represents methyl, ethyl, allyl, butenyl, phenyl, thiazolyl, pyridyl, tert-butyl, propyl, pentyl, isobutyl, benzo[1,3]dioxolyl, indanyl, naphthyl, anthracenyl, thiazolyl, thiophenyl, oxadiazolyl, isoxazolyl, cyclopropyl, cyclobutyl, [1,2,3]triazolyl, cyclopentyl, cyclohexyl, cyclohexenyl, adamantyl, bicyclo[2.2.1]heptenyl, bicyclo[2.2.1]heptyl, bicyclo[4.1.0]heptenyl, cycloheptyl, cyclooctyl, quinolinyl, tetrahydrofuranyl, 4,5-dihydrooxazolyl, or tetrahydropyranyl, all of which are optionally substituted with one or more substituents independently selected from the group consisting of $R_9$.

19. A compound according to claim 1 wherein $R_9$ is hydrogen, nitro, halogen, oxo, cyano, trifluoromethyl, carboxy, alkoxy, alkoxycarbonyl, alkyl, cycloalkyl, alkenyl, alkynyl, alkylthio, heterocycloalkyl, heterocycloalkenyl, heteroaryl, amino, arylsulfonylamino, alkylthioureido, alkylureido, heteroarylsulfonylamino, alkylsulfonylamino, aminocarbonyl, aminocarbonyloxy, aryl, wherein said alkoxycarbonyl, alkyl, cycloalkyl, alkenyl, alkynyl, alkylthio, heterocycloalkyl, heteroaryl, amino, arylsulfonylamino, alkylthioureido, alkylureido, heteroarylsulfonylamino, alkylsulfonylamino, aminocarbonyl, aminocarbonyloxy, or aryl, are optionally substituted by one or more substituents independently selected from the group consisting of $R_7$.

20. A compound according to claim 1 wherein $R_7$ is hydrogen, halogen, hydroxy, carboxy, carbamoyl, cyano, oxo, thioxo, alkyl, alkoxy, arylsulfonyl, aminocarbonyl, heterocycloalkyl-heteroaryl, heterocycloalkyl, heteroaryl, heterocycloalkenyl, alkoxycarbonyl, imino, alkoxyimino, alkylcarbonyloxy, alkenylcarbonyloxy, cycloalkyl, or amino, wherein said alkyl, alkoxy, alkoxyimino, arylsulfonyl, aminocarbonyl, heterocycloalkyl-heteroaryl, heterocycloalkyl, heteroaryl, heterocycloalkenyl, alkoxycarbonyl, imino, alkylcarbonyloxy, alkenylcarbonyloxy, cycloalkyl, or amino are optionally substituted by one or more substituents independently selected from the group consisting of halogen, alkenyloxy, hydroxy, cyano, amino, alkylcarbonyloxy, alkylcarbonylamino, alkyl, alkoxy, aryl, or oxo.

21. A compound according to claim 1 wherein B represents 4-pyridyl optionally substituted in the 2-position with $R_8$ or B represents phenyl optionally substituted with up to two $R_8$, same or different.

22. A compound according to claim 1 selected from the group consisting of
- N-Benzyloxy-2-[(pyridin-4-ylmethyl)-amino]-benzamide (compound 1),
- N-(4-Nitro-benzyloxy)-2-[(pyridin-4-ylmethyl)-amino]-benzamide (compound 2),
- N-(2-Nitro-benzyloxy)-2-[(pyridin-4-ylmethyl)-amino]-benzamide (compound 3),
- 2-[(Pyridin-4-ylmethyl)-amino]-N-(3-trifluoromethyl-benzyloxy)-benzamide (compound 4),
- 2-[(Pyridin-4-ylmethyl)-amino]-N-(2-trifluoromethyl-benzyloxy)-benzamide (compound 5),
- N2-[(Pyridin-4-ylmethyl)-amino]-N-(4-trifluoromethyl-benzyloxy)-benzamide (compound 6),
- N-(4-Methoxy-benzyloxy)-2-[(pyridin-4-ylmethyl)-amino]-benzamide (compound 7),
- N-(3-Methoxy-benzyloxy)-2-[(pyridin-4-ylmethyl)-amino]-benzamide (compound 8),
- 2-[(pyridin-4-ylmethyl)-amino]-N-(3,4,5-trimethoxy-benzyloxy)-benzamide (compound 9),
- N-(4-Chloro-benzyloxy)-2-[(pyridin-4-ylmethyl)-amino]-benzamide (compound 10),
- N-(3-Chloro-benzyloxy)-2-[(pyridin-4-ylmethyl)-amino]-benzamide (compound 11),
- N-(2-Chloro-benzyloxy)-2-[(pyridin-4-ylmethyl)-amino] benzamide (compound 12),
- N-(2-Bromo-benzyloxy)-2-[(pyridin-4-ylmethyl)-amino]-benzamide (compound 13),
- N-(2,4-Dichloro-benzyloxy)-2-[(pyridin-4-ylmethyl)-amino]-benzamide (compound 14),
- N-(3,4-Dichloro-benzyloxy)-2-[(pyridine-4-ylmethyl)-amino]-benzamide (compound 15),
- N-(2,6-Dichloro-benzyloxy)-2-[(pyridin-4-ylmethyl)-amino]-benzamide (compound 16),
- N-(3,5-Dichloro-benzyloxy)-2-[(pyridin-4-ylmethyl)-amino]-benzamide (compound 17),
- N-(2,3-Dichloro-benzyloxy)-2-[(pyridin-4-ylmethyl)-amino]-benzamide (compound 18),
- N-(2,5-Dichloro-benzyloxy)-2-[(pyridin-4-ylmethyl)-amino]-benzamide (compound 19),
- N-(2-Fluoro-benzyloxy)-2-[(pyridin-4-ylmethyl)-amino]-benzamide (compound 20),
- N-(3-Fluoro-benzyloxy)-2-[(pyridin-4-ylmethyl)-amino]-benzamide (compound 21),
- N-(4-Fluoro-benzyloxy)-2-[(pyridin-4-ylmethyl)-amino] benzamide (compound 22),
- N-(2-Chloro-6-fluoro-benzyloxy)-2-[(pyridin-4-ylmethyl)-amino]-benzamide (compound 23),
- N-(2-Chloro-4-fluoro-benzyloxy)-2-[(pyridin-4-ylmethyl)-amino]-benzamide (compound 24),
- N-(3-Chloro-2-fluoro-benzyloxy)-2-[(pyridin-4-ylmethyl)-amino]-benzamide (compound 25),
- 4-{2-[(pyridin-4-ylmethyl)-amino]-benzoylaminooxymethyl}-benzoic acid methyl ester (compound 26),
- N-(4-cyano-benzyloxy)-2-[(pyridin-4-ylmethyl)-amino]-benzamide (compound 27),
- 2-[(Pyridin-4-ylmethyl)-amino]-N-(quinolin-2-ylmethoxy)-benzamide (compound 28),
- N-Phenoxy-2-[(pyridin-4-ylmethyl)-amino]-benzamide (compound 29),
- N-(2-Phenoxy-ethoxy)-2-[(pyridin-4-ylmethyl)-amino]-benzamide (compound 30),
- N-(3-Phenyl-propoxy)-2-[(pyridin-4-ylmethyl)-amino]-benzamide (compound 31),
- N-(2-methyl-thiazol-4 ylmethoxy)-2-[(pyridin-4-ylmethyl)-amino]-benzamide (compound 32),
- N-Benzyloxy-2-2-[(pyridin-4-ylmethyl)-amino]-nicotinamide (compound 33),
- 2-(4-Fluoro-benzylamino)-N-(4-methoxy-benzyloxy)-nicotinamide (compound 34),
- 2-(4-methoxy-benzylamino)-N-(4-methoxy-benzyloxy)-nicotinamide (compound 35),
- N-(4-Cyano-phenoxy)-2-[(pyridin-4-ylmethyl)-amino]-benzamide (compound 36),
- N-(4-Bromo-phenoxy)-2-[(pyridin-4-ylmethyl)-amino]-benzamide (compound 37),
- N-(4-Fluoro-2,6-dimethyl-benzyloxy)-2-[(pyridin-4-ylmethyl)-amino]-benzamide (compound 38),
- N-(4-Fluoro-2-methoxy-benzyloxy)-2-[(pyridin-4-ylmethyl)-amino]-benzamide (compound 39),
- N-(2,3-Difluoro-4-methyl-benzyloxy)-2-[(pyridin-4-ylmethyl)-amino]-benzamide (compound 40)
- N-(3-Fluoro-4-methyl-benzyloxy)-2-[(pyridin-4-ylmethyl)-amino]-benzamide (compound 41),
- N-(5-Fluoro-2-methyl-benzyloxy)-2-[(pyridin-4-ylmethyl)-amino]-benzamide (compound 42),
- 2-[(Pyridin-4-ylmethyl)-amino]-N-(2,3,5,6-tetrafluoro-4-methoxy-benzyloxy)-benzamide (compound 43),
- N-(4-Bromo-benzyloxy)-2-[(pyridin-4-ylmethyl)-amino]-benzamide (compound 44),
- N-(2-Iodo-benzyloxy)-2-[(pyridin-4-ylmethyl)-amino]-benzamide (compound 45),
- N-(3-Iodo-benzyloxy)-2-[(pyridin-4-ylmethyl)-amino]-benzamide (compound 46),
- N-(4-Methyl-benzyloxy)-2-[(pyridin-4-ylmethyl)-amino]-benzamide (compound 47)
- N-[2-(3,3-Dimethyl-but-1-enyl)-benzyloxy]-2-[(pyridin-4-ylmethyl)-amino]-benzamide (compound 48),
- 2-[(Pyridin-4-ylmethyl)-amino]-N-(2-styryl-benzyloxy)-benzamide (compound 49),
- N-[3-(3-Hydroxy-prop-1-ynyl)-benzyloxy]-2-[(pyridin-4-ylmethyl)-amino]-benzamide (compound 50),
- N-[3-(5-Cyano-pent-1-ynyl)-benzyloxy]-2-[(pyridin-4-ylmethyl)-amino]-benzamide (compound 51),
- N-[2-(3-Hydroxy-prop-1-ynyl)-benzyloxy]-2-[(pyridin-4-ylmethyl)-amino]-benzamide (compound 52),
- Acetic acid 2-[3-(2-{2-[(pyridin-4-ylmethyl)-amino]-benzoylaminooxymethyl}-phenyl)-prop-2-ynyloxy]-ethyl ester (compound 53),
- N-[2-(3-Methyl-3H-imidazol-4-ylethynyl)-benzyloxy]-2-[(pyridin-4-ylmethyl)-amino]-benzamide (compound 54),
- N-[3-(3-Methyl-3H-imidazol-4-ylethynyl)-benzyloxy]-2-[(pyridin-4-ylmethyl)-amino]-benzamide (compound 55),
- N-(2-Cyanomethyl-benzyloxy)-2-[(pyridin-4-ylmethyl)-amino]-benzamide (compound 56),
- N-(4-Hydroxymethyl-benzyloxy)-2-[(pyridin-4-ylmethyl)-amino]-benzamide (compound 58),
- N-(4-Fluoro-2-trifluoromethyl-benzyloxy)-2-[(pyridin-4-ylmethyl)-amino]-benzamide (compound 59), N-(2-Fluoro-6-trifluoromethyl-benzyloxy)-2-[(pyridin-4-ylmethyl)-amino]-benzamide (compound 60),
N-(4-Fluoro-3-trifluoromethyl-benzyloxy)-2-[(pyridin-4-ylmethyl)-amino]-benzamide (compound 61),
N-(4-Methyl-3-trifluoromethyl-benzyloxy)-2-[(pyridin-4-ylmethyl)-amino]-benzamide (compound 62),
N-(4-Methoxy-3-trifluoromethyl-benzyloxy)-2-[(pyridin-4-ylmethyl)-amino]-benzamide (compound 63),
N-(2-Methoxy-benzyloxy)-2-[(pyridin-4-ylmethyl)-amino]-benzamide (compound 64),
N-(4-Pentyloxy-benzyloxy)-2-[(pyridin-4-ylmethyl)-amino]-benzamide (compound 65),
2-[(Pyridin-4-ylmethyl)-amino]-N-(2-trifluoromethoxy-benzyloxy)-benzamide (compound 66),
2-[(Pyridin-4-ylmethyl)-amino]-N-(3-trifluoromethoxy-benzyloxy)-benzamide (compound 67),
2-[(Pyridin-4-ylmethyl)-amino]-N-(4-trifluoromethoxy-benzyloxy)-benzamide (compound 68),
N-(2-Difluoromethoxy-benzyloxy)-2-[(pyridin-4-ylmethyl)-amino]-benzamide (compound 69),
2-[(Pyridin-4-ylmethyl)-amino]-N-(2-trifluoromethylsulfanyl-benzyloxy)-benzamide (compound 70),
N-(6-Chloro-benzo[1,3]dioxol-5-ylmethoxy)-2-[(pyridin-4-ylmethyl)-amino]-benzamide (compound 71),
N-(Benzo[1,3]dioxol-5-ylmethoxy)-2-[(pyridin-4-ylmethyl)-amino]-benzamide (compound 72),
N-(Indan-5-ylmethoxy)-2-[(pyridin-4-ylmethyl)-amino]-benzamide (compound 73),
N-(3-Cyano-benzyloxy)-2-[(pyridin-4-ylmethyl)-amino]-benzamide (compound 74),
N-(2-Cyano-benzyloxy)-2-[(pyridin-4-ylmethyl)-amino]-benzamide (compound 75),
N-(4-Cyano-2-fluoro-benzyloxy)-2-[(pyridin-4-ylmethyl)-amino]-benzamide (compound 76),
N-(3-Bromo-4-cyano-benzyloxy)-2-[(pyridin-4-ylmethyl)-amino]-benzamide (compound 77),
N-(2-Chloro-4-cyano-benzyloxy)-2-[(pyridin-4-ylmethyl)-amino]-benzamide (compound 78),
N-(4-Cyano-2-methoxy-benzyloxy)-2-[(pyridin-4-ylmethyl)-amino]-benzamide (compound 79),
N-(4-Cyano-2-iodo-benzyloxy)-2-[(pyridin-4-ylmethyl)-amino]-benzamide (compound 80),
N-(2-Bromo-5-cyano-benzyloxy)-2-[(pyridin-4-ylmethyl)-amino]-benzamide (compound 81),
N-(4-Cyano-naphthalen-1-ylmethoxy)-2-[(pyridin-4-ylmethyl)-amino]-benzamide (compound 82),
N-(4-Morpholin-4-yl-benzyloxy)-2-[(pyridin-4-ylmethyl)-amino]-benzamide (compound 83),
N-(2-Morpholin-4-yl-benzyloxy)-2-[(pyridin-4-ylmethyl)-amino]-benzamide (compound 84),
N-(2-Amino-benzyloxy)-2-[(pyridin-4-ylmethyl)-amino]-benzamide (compound 85),
N-(2-Benzenesulfonylamino-benzyloxy)-2-[(pyridin-4-ylmethyl)-amino]-benzamide (compound 86),
3-{2-[(Pyridin-4-ylmethyl)-amino-benzoylaminooxymethyl}-benzoic acid methyl ester (compound 87),
3-{2-[(Pyridin-4-ylmethyl)-amino]-benzoylaminooxymethyl}-benzoic acid (compound 88),
4-{2-[(Pyridin-4-ylmethyl)-amino]-benzoylaminooxymethyl}-benzoic acid (compound 89),
N-[4-(Morpholine-4-carbonyl)-benzyloxy]-2-[(pyridin-4-ylmethyl)-amino]-benzamide (compound 90),
N-{3-[4-(3-Cyano-pyridin-2-yl)-piperazine-1-carbonyl]-benzyloxy}-2-[(pyridin-4-ylmethyl)-amino]-benzamide (compound 91),
N-[3-(4-Methyl-piperazine-1-carbonyl)-benzyloxy]-2-[(pyridin-4-ylmethyl)-amino]-benzamide (compound 92),
N-[3-(Morpholine-4-carbonyl)-benzyloxy]-2-[(pyridin-4-ylmethyl)-amino]-benzamide (compound 93),
N-[3-(3-Hydroxy-pyrrolidine-1-carbonyl)-benzyloxy]-2-[(pyridin-4-ylmethyl)-amino]-benzamide (compound 94),
N-[4-(4-Methyl-piperazine-1-carbonyl)-benzyloxy]-2-[(pyridin-4-ylmethyl)-amino]-benzamide (compound 95),
N-[3-(2-dimethylaminoethylcarbamoyl)-benzyloxy]-2-[(pyridin-4-ylmethyl)-amino]-benzamide (compound 96),
N-[3-(2-pyrrolidin-1-yl-ethylcarbamoyl)-benzyloxy]-2-[(pyridin-4-ylmethyl)-amino]-benzamide (compound 97),
2-[(Pyridin-4-ylmethyl)-amino]-N-(2-thiophen-2-yl-benzyloxy)-benzamide (compound 98),
N-(4'-Methoxy-biphenyl-2-ylmethoxy)-2-[(pyridin-4-ylmethyl)-amino]-benzamide (compound 99),
N-(Naphthalen-1-ylmethoxy)-2-[(pyridin-4-ylmethyl)-amino]-benzamide (compound 100),
N-(1-Phenyl-ethoxy)-2-[(pyridin-4-ylmethyl)-amino]-benzamide (compound 101),
2-[(Pyridin-4-ylmethyl)-amino]-N-[1-(2-trifluoromethyl-phenyl)-ethoxy]-benzamide (compound 102),
N-(Pyridin-2-ylmethoxy)-2-[(pyridin-4-ylmethyl)-amino]-benzamide (compound 103),
N-(2,6-Dichloro-pyridin-4-ylmethoxy)-2-[(pyridin-4-ylmethyl)-amino]-benzamide (compound 104),
2-[(Pyridin-4-ylmethyl)-amino]-N-(thiazol-4-ylmethoxy)-benzamide (compound 105),
N-(2-Chloro-thiazol-5-ylmethoxy)-2-[(pyridin-4-ylmethyl)-amino]-benzamide (compound 106),
N-(2-Phenyl-thiazol-4-ylmethoxy)-2-[(pyridin-4-ylmethyl)-amino]-benzamide (compound 107),
N-(5-Methyl-isoxazol-3-ylmethoxy)-2-[(pyridin-4-ylmethyl)-amino]-benzamide (compound 108),
N-(3,5-Dimethyl-isoxazol-4-ylmethoxy)-2-[(pyridin-4-ylmethyl)-amino]-benzamide (compound 109),
N-(3-Propyl-isoxazol-5-ylmethoxy)-2-[(pyridin-4-ylmethyl)-amino]-benzamide (compound 110),
N-(5-Chloro-thiophen-2-ylmethoxy)-2-[(pyridin-4-ylmethyl)-amino]-benzamide (compound 111),
N-[2-(4-Cyano-phenyl)-ethoxy]-2-[(pyridin-4-ylmethyl)-amino]-benzamide (compound 112),
N-Cyclopentylmethoxy-2-[(pyridin-4-ylmethyl)-amino]-benzamide (compound 113),
N-Cyclopropylmethoxy-2-[(pyridin-4-ylmethyl)-amino]-benzamide (compound 114),
N-Methoxy-2-[(pyridin-4-ylmethyl)-amino]-benzamide (compound 115),
N-(2,2-Dimethyl-propoxy)-2-[(pyridin-4-ylmethyl)-amino]-benzamide (compound 116),
N-(2-Ethyl-butoxy)-2-[(pyridin-4-ylmethyl)-amino]-benzamide (compound 117),
N-(3-Methyl-butoxy)-2-[(pyridin-4-ylmethyl)-amino]-benzamide (compound 118),
N-Cyclobutylmethoxy-2-[(pyridin-4-ylmethyl)-amino]-benzamide (compound 119),
N-Cyclohexylmethoxy-2-[(pyridin-4-ylmethyl)-amino]-benzamide (compound 120),
N-Cycloheptylmethoxy-2-[(pyridin-4-ylmethyl)-amino]-benzamide (compound 121),
N-Cyclooctylmethoxy-2-[(pyridin-4-ylmethyl)-amino]-benzamide (compound 122),
N-(1-Cyclopentyl-ethoxy)-2-[(pyridin-4-ylmethyl)-amino]-benzamide (compound 123),
N-Cyclohexyloxy-2-[(pyridin-4-ylmethyl)-amino]-benzamide (compound 124),
N-(2-Cyclopropyl-ethoxy)-2-[(pyridin-4-ylmethyl)-amino]-benzamide (compound 125),
N-(2-Cyclopentyl-ethoxy)-2-[(pyridin-4-ylmethyl)-amino]-benzamide (compound 126), N-(3-Cyclopentyl-propoxy)-2-[(pyridin-4-ylmethyl)-amino]-benzamide (compound 127),
N-(Cyclohex-3-enylmethoxy)-2-[(pyridin-4-ylmethyl)-amino]-benzamide (compound 128),
N-(6-Methyl-cyclohex-3-enylmethoxy)-2-[(pyridin-4-ylmethyl)-amino]-benzamide (compound 129),
N-(trans-4-Hydroxymethyl-cyclohexylmethoxy)-2-[(pyridin-4-ylmethyl)-amino]-benzamide (compound 130),
N-(3-Methoxy-cyclohexylmethoxy)-2-[(pyridin-4-ylmethyl)-amino]-benzamide (compound 131),
N-(Adamantan-1-ylmethoxy)-2-[(pyridin-4-ylmethyl)-amino]-benzamide (compound 132)
N-(Bicyclo[2.2.1]hept-2-ylmethoxy)-2-[(pyridin-4-ylmethyl)-amino]-benzamide (compound 133),
N-(6,6-Dimethyl-bicyclo[3.1.1]hept-2-ylmethoxy)-2-[(pyridin-4-ylmethyl)-amino]-benzamide (compound 134),
2-[(Pyridin-4-ylmethyl)-amino]-N-(tetrahydro-furan-2-ylmethoxy)-benzamide (compound 135),
2-[(Pyridin-4-ylmethyl)-amino]-N-(tetrahydro-furan-3-ylmethoxy)-benzamide (compound 136)
N-(3-Methyl-4,5-dihydro-isoxazol-5-ylmethoxy)-2-[(pyridin-4-ylmethyl)-amino]-benzamide (compound 137),
N-(3-Ethyl-4,5-dihydro-isoxazol-5-ylmethoxy)-2-[(pyridin-4-ylmethyl)-amino]-benzamide (compound 138),
N-(3-Butyl-4,5-dihydro-isoxazol-5-ylmethoxy)-2-[(pyridin-4-ylmethyl)-amino]-benzamide (compound 139),
2-[(Pyridin-4-ylmethyl)-amino]-N-(tetrahydro-pyran-2-yloxy)-benzamide (compound 140),
2-[(Pyridin-4-ylmethyl)-amino]-N-(tetrahydro-pyran-4-ylmethoxy)-benzamide (compound 141),
2-[(Pyridin-4-ylmethyl)-amino]-N-(tetrahydro-pyran-2-ylmethoxy)-benzamide (compound 142),
4-Fluoro-N-(2-methyl-thiazol-4-ylmethoxy)-2-[(pyridin-4-ylmethyl)-amino]-benzamide (compound 143),
2-Fluoro-N-(2-methyl-thiazol-4-ylmethoxy)-6-[(pyridin-4-ylmethyl)-amino]-benzamide (compound 144),
5-Fluoro-N-(2-methyl-thiazol-4-ylmethoxy)-2-[(pyridin-4-ylmethyl)-amino]-benzamide (compound 145),
3-Methoxy-N-(2-methyl-thiazol-4-ylmethoxy)-2-[(pyridin-4-ylmethyl)-amino]-benzamide (compound 146),
N-(4-Chloro-benzyloxy)-3-methoxy-2-[(pyridin-4-ylmethyl)-amino]-benzamide (compound 147),
4,5-Dimethoxy-N-(2-methyl-thiazol-4-ylmethoxy)-2-[(pyridin-4-ylmethyl)-amino]-benzamide (compound 148),
N-Benzyloxy-4,5-dimethoxy-2-[(pyridin-4-ylmethyl)-amino]-benzamide (compound 149),
2-Methyl-N-(2-methyl-thiazol-4-ylmethoxy)-6-[(pyridin-4-ylmethyl)-amino]-benzamide (compound 150),
N-Benzyloxy-2-methyl-6-[(pyridin-4-ylmethyl)-amino]benzamide (compound 151),
5-Methyl-N-(2-methyl-thiazol-4-ylmethoxy)-2-[(pyridin-4-ylmethyl)-amino]-benzamide (compound 152),
N-Benzyloxy-5-methyl-2-[(pyridin-4-ylmethyl)-amino]-benzamide (compound 153),
5-Bromo-N-(4-cyano-2-methoxy-benzyloxy)-2-[(pyridin-4-ylmethyl)-amino]-benzamide (compound 154),
N-Benzyloxy-5-bromo-2-[(pyridin-4-ylmethyl)-amino]-benzamide (compound 155),
N-(4-Cyano-benzyloxy)-2-[(pyridin-4-ylmethyl)-amino]-nicotinamide (compound 156),
N-(2-Chloro-4-cyano-benzyloxy)-2-[(pyridin-4-ylmethyl)-amino]-nicotinamide (compound 157),
N-(4-Cyano-2-fluoro-benzyloxy)-2-[(pyridin-4-ylmethyl)-amino]-nicotinamide (compound 158),
N-(3-Bromo-4-cyano-benzyloxy)-2-[(pyridin-4-ylmethyl)-amino]-nicotinamide (compound 159),
N-(2-Iodo-benzyloxy)-2-[(pyridin-4-ylmethyl)-amino]-nicotinamide (compound 160),
N-(2-Bromo-benzyloxy)-2-[(pyridin-4-ylmethyl)-amino]-nicotinamide (compound 161),
N-(4-Cyano-2-methoxy-benzyloxy)-2-[(pyridin-4-ylmethyl)-amino]-nicotinamide (compound 162),
N-(2-Methyl-thiazol-4-ylmethoxy)-2-[(pyridin-4-ylmethyl)-amino]-nicotinamide (compound 163),
N-Cyclopentylmethoxy-2-[(pyridin-4-ylmethyl)-amino]-nicotinamide (compound 164),
N-Benzyloxy-2-(4-fluoro-benzylamino)-nicotinamide (compound 165),
N-Benzyloxy-2-(4-chloro-benzylamino)-nicotinamide (compound 166),
N-Benzyloxy-2-(4-methoxy-benzylamino)-nicotinamide (compound 167),
N-(4-Cyano-2-methoxy-benzyloxy)-3-[(pyridin-4-ylmethyl)-amino]-isonicotinamide (compound 169),
N-Benzyloxy-3-[(pyridin-4-ylmethyl)-amino]sonicotinamide (compound 170),
N-(2-Methyl-thiazol-4-ylmethoxy)-3-[(pyridin-4-ylmethyl)-amino]-isonicotinamide (compound 171),
N-Benzyloxy-2-(4-fluoro-benzylamino)-benzamide (compound 172),
N-(4-Cyano-benzyloxy)-2-(4-fluoro-benzylamino)-benzamide (compound 173),
2-(4-Fluoro-benzylamino)-N-(2-methyl-thiazol-4-ylmethoxy)-benzamide (compound 174),
N-Benzyloxy-2-(3-cyano-4-fluoro-benzylamino)-benzamide (compound 175),
N-(2-Bromo-benzyloxy)-2-(3-cyano-4-fluoro-benzylamino)-benzamide (compound 176),
5-[(2-Benzyloxycarbamoyl-phenylamino)-methyl]-2-fluoro-benzoic acid methyl ester (compound 177),
5-[(2-Cyclopentylmethoxycarbamoyl-phenylamino)-methyl]-2-fluoro-benzoic acid methyl ester (compound 178),
2-Fluoro-5-{[2-(4-fluoro-benzyloxycarbamoyl)-phenylamino]-methyl}-benzoic acid methyl ester (compound 179),
5-{[2-(4-Cyano-benzyloxycarbamoyl)-phenylamino]-methyl}-2-fluoro-benzoic acid methyl ester (compound 180),
5-[(2-Cyclopentylmethoxycarbamoyl-phenylamino)-methyl]-2-fluoro-benzoic acid (compound 181),
2-Fluoro-5-{[2-(4-fluoro-benzyloxycarbamoyl)-phenylamino]-methyl}-benzoic acid (compound 182),
5-[(2-Benzyloxycarbamoyl-phenylamino)-methyl]-2-fluoro-benzoic acid (compound 183),
5-[(2-Benzyloxycarbamoyl-phenylamino)-methyl]-2-fluoro-N-(2-hydroxy-ethyl)-benzamide (compound 184),
5-[(2-Benzyloxycarbamoyl-phenylamino)-methyl]-2-fluoro-N-(3-hydroxy-propyl)-benzamide (compound 185),
5-[(2-Benzyloxycarbamoyl-phenylamino)-methyl]-2-fluoro-N-(4-hydroxy-butyl)-benzamide (compound 186),
5-[(2-Benzyloxycarbamoyl-phenylamino)-methyl]-N-(3-dimethylamino-propyl)-2-fluoro-benzamide (compound 187),
5-[(2-Cyclopentylmethoxycarbamoyl-phenylamino)-methyl]-2-fluoro-N-(3-hydroxy-propyl)-benzamide (compound 188),
N-Cyclopentylmethoxy-2-[4-fluoro-3-(4-methyl-piperazine-1-carbonyl)-benzylamino]-benzamide (compound 189),
N-Cyclopentylmethoxy-2-[4-fluoro-3-(morpholine-4-carbonyl)-benzylamino]-benzamide (compound 190),
N-Benzyloxy-2-(4-methoxy-benzylamino)-benzamide (compound 191), 2-(4-Methoxy-benzylamino)-N-(2-methyl-thiazol-4-yl-methoxy)-benzamide (compound 192),
N-Benzyloxy-2-[(4-methoxy-naphthalen-1-ylmethyl)-amino]-benzamide (compound 193),
N-(4-Cyano-benzyloxy)-2-[(4-methoxy-naphthalen-1-yl-methyl)-amino]-benzamide (compound 194),
2-[(2,3-Dihydro-benzofuran-5-ylmethyl)-amino]-N-(4-fluoro-benzyloxy)-benzamide (compound 195),
N-(4-Cyano-benzyloxy)-2-[(2,3-dihydro-benzofuran-5-ylmethyl)-amino]-benzamide (compound 196),
2-[(Benzofuran-5-ylmethyl)-amino]-N-(4-cyano-benzyloxy)-benzamide (compound 197),
2-[(Benzofuran-5-ylmethyl)-amino]-N-benzyloxy-benzamide (compound 198),
2-[(Benzofuran-5-ylmethyl)-amino]-N-(4-fluoro-benzyloxy)-benzamide (compound 199),
N-(4-Cyano-benzyloxy)-2-[(2-oxo-2H-chromen-6-ylmethyl)-amino]-benzamide (compound 200),
N-(4-Chloro-benzyloxy)-2-(4-cyano-benzylamino)-benzamide (compound 201),
2-[(3,5-Dichloro-pyridin-4-ylmethyl)-amino]-N-(2-methyl-thiazol-4-ylmethoxy)-benzamide (compound 202),
N-Benzyloxy-2-[(3,5-dichloro-pyridin-4-ylmethyl)-amino]-benzamide (compound 203),
2-[(2-Bromo-pyridin-4-ylmethyl)-amino]-N-(4-fluoro-benzyloxy)-benzamide (compound 204),
N-(4-Cyano-2-methoxy-benzyloxy)-2-[(2-hydroxy-pyridin-4-ylmethyl)-amino]-benzamide (compound 205),
2-[(2-Amino-pyridin-4-ylmethyl)-amino]-N-(4-cyano-benzyloxy)-benzamide (compound 206),
N-(4-Fluoro-benzyloxy)-2-[(2-morpholin-4-yl-pyridin-4-ylmethyl)-amino]-benzamide (compound 207),
N-Cyclopentylmethoxy-2-[(2-methanesulfonylamino-pyridin-4-ylmethyl)-amino]-benzamide (compound 208),
N-(4-Cyano-benzyloxy)-2-[(2-methanesulfonylamino-pyridin-4-ylmethyl)-amino]-benzamide (compound 209),
N-(4-Cyano-benzyloxy)-2-{[2-(3-methyl-ureido)-pyridin-4-ylmethyl]-amino}-benzamide (compound 210),
N-(4-Cyano-2-methoxy-benzyloxy)-2-{[2-(3-methyl-ureido)-pyridin-4-ylmethyl]-amino}-benzamide (compound 211),
N-Cyclopentylmethoxy-2-{[2-(3-methyl-ureido)-pyridin-4-ylmethyl]-amino}-benzamide (compound 212),
N-(2,3-Difluoro-4-methyl-benzyloxy)-2-{[2-(3-methyl-ureido)-pyridin-4-ylmethyl]-amino}-benzamide (compound 213)
[3-(4-{[2-(4-Cyano-benzyloxycarbamoyl)-phenylamino]-methyl}-pyridin-2-yl)-ureido]-acetic acid ethyl ester (compound 214),
(3-{4-[(2-Cyclopentylmethoxycarbamoyl-phenylamino)-methyl]-pyridin-2-yl}-ureido)-acetic acid ethyl ester (compound 215),
[3-(4-{[2-(4-Cyano-benzyloxycarbamoyl)-phenylamino]-methyl}-pyridin-2-yl)-ureido]-acetic acid (compound 216),
(3-{4-[(2-Cyclopentylmethoxycarbamoyl-phenylamino)-methyl]-pyridin-2-yl}-ureido)-acetic acid (compound 217),
2-Methyl-acrylic acid 2-[3-(4-{[2-(4-cyano-benzyloxycarbamoyl)-phenylamino]-methyl}-pyridin-2-yl)-ureido]-ethyl ester (compound 218),
2-Methyl-acrylic acid 2-(3-{4-[(2-cyclopentylmethoxycarbamoyl-phenylamino)-methyl]-pyridin-2-yl}-ureido)-ethyl ester (compound 219),
N-(4-Cyano-benzyloxy)-2-({2-[3-(2-hydroxy-ethyl)-ureido]-pyridin-4-ylmethyl}-amino)-benzamide (compound 220),
N-Cyclopentylmethoxy-2-({2-[3-(2-hydroxy-ethyl)-ureido]-pyridin-4-ylmethyl}-amino)-benzamide (compound 221),
Acetic acid (4-{[2-(4-cyano-benzyloxycarbamoyl)-phenylamino]-methyl}-pyridin-2-ylcarbamoyl)-methyl ester (compound 222),
Acetic acid {4-[(2-cyclopentylmethoxycarbamoyl-phenylamino)-methyl]-pyridin-2-ylcarbamoyl}-methyl ester (compound 223),
N-(4-Cyano-benzyloxy)-2-{[2-(2-hydroxy-acetylamino)-pyridin-4-ylmethyl]-amino}-benzamide (compound 224),
4-{[2-(4-Cyano-benzyloxycarbamoyl)-phenylamino]-methyl}-pyridin-2-yl)-carbamic acid ethyl ester (compound 225),
N-(4-Cyano-benzyloxy)-2-{[2-(cyclopropanecarbonyl-amino)-pyridin-4-ylmethyl]-amino}-benzamide (compound 226),
N-Cyclopentylmethoxy-2-{[2-(cyclopropanecarbonyl-amino)-pyridin-4-ylmethyl]-amino}-benzamide (compound 227),
N-Cyclopentylmethoxy-2-({2-[2-(2,5-dioxo-imidazolidin-4-yl)-acetylamino]-pyridin-4-ylmethyl}-amino)-benzamide (compound 228),
2-[(2-Amino-pyridin-4-ylmethyl)-amino]-N-cyclopentylmethoxy-benzamide (compound 229),
N-Benzyloxy-2-[(quinolin-4-ylmethyl)-amino]-benzamide (compound 230),
N-(4-Cyano-benzyloxy)-2-[(quinolin-4-ylmethyl)-amino]benzamide (compound 231),
N-(2-Methyl-thiazol-4-ylmethoxy)-2-[(quinolin-4-ylmethyl)-amino]-benzamide (compound 232),
N-Cyclopentylmethoxy-2-[(quinolin-4-ylmethyl)-amino]-benzamide (compound 233),
2-[(Quinolin-4-ylmethyl)-amino]-N-(tetrahydro-pyran-4-ylmethoxy)-benzamide (compound 234),
N-(4-Cyano-2-methoxy-benzyloxy)-2-[(6-methoxy-pyridin-3-ylmethyl)-amino]-benzamide (compound 235),
N-Benzyloxy-2-[(6-methoxy-pyridin-3-ylmethyl)-amino]benzamide (compound 236),
N-(4-Cyano-benzyloxy)-2-[(6-methoxy-pyridin-3-ylmethyl)-amino]-benzamide (compound 237),
N-Benzyloxy-2-[(thiazol-5-ylmethyl)-amino]-benzamide (compound 238),
N-(2,4-Dichloro-benzyloxy)-2-[(thiazol-5-ylmethyl)-amino]-benzamide (compound 239),
N-(2-Methyl-thiazol-4-ylmethoxy)-2-[(5-oxo-4,5-dihydro-1H-[1,2,4]triazol-3-ylmethyl)-amino]-benzamide (compound 240),
N-Benzyloxy-2-[(5-oxo-4,5-dihydro-1H-[1,2,4]triazol-3-ylmethyl)-amino]-benzamide (compound 241),
N-Benzyloxy-2-(2-imidazol-1-yl-ethylamino)-benzamide (compound 242),
N-Cyclopentylmethoxy-2-(2-imidazol-1-yl-ethylamino)-benzamide (compound 243),
N-(4-Cyano-benzyloxy)-2-(1-pyridin-4-yl-ethylamino)-benzamide (compound 244),
2-{[2-(3-Methyl-ureido)-pyridin-4-ylmethyl]-amino}-N-(tetrahydro-pyran-2-ylmethoxy)-benzamide (compound 245),
N-Cyclopentylmethoxy-2-{[2-(2-methoxy-acetylamino)-pyridin-4-ylmethyl]-amino}-benzamide (compound 246),
N-(4-Cyano-benzyloxy)-2-[(6-oxo-1,6-dihydro-pyridin-3-ylmethyl)-amino]-benzamide (compound 247),
N-Cyclopentylmethoxy-2-[(tetrahydro-pyran-4-ylmethyl)-amino]-benzamide (compound 248),
N-(3-Iodo-4-methyl-benzyloxy)-2-[(pyridin-4-ylmethyl)-amino]-benzamide (compound 250), N-(4-Ethyl-benzyloxy)-2-[(pyridin-4-ylmethyl)-amino]-benzamide (compound 251),
N-(4-Isopropyl-benzyloxy)-2-[(pyridin-4-ylmethyl)-amino]-benzamide (compound 252),
N-(4-tert-Butyl-benzyloxy)-2-[(pyridin-4-ylmethyl)-amino]-benzamide (compound 253),
N-(2-Ethyl-benzyloxy)-2-[(pyridin-4-ylmethyl)-amino]-benzamide (compound 254),
N-(2-Non-1-enyl-benzyloxy)-2-[(pyridin-4-ylmethyl)-amino]-benzamide (compound 255),
N-(4-Phenylaminomethyl-benzyloxy)-2-[(pyridin-4-ylmethyl)-amino]-benzamide (compound 256),
N-(4-Diethylaminomethyl-benzyloxy)-2-[(pyridin-4-ylmethyl)-amino]-benzamide (compound 257),
N-(2-Carbamoylmethyl-benzyloxy)-2-[(pyridin-4-ylmethyl)-amino]-benzamide (compound 258),
N-[4-Cyano-2-(2-methoxy-ethoxy)-benzyloxy]-2-[(pyridin-4-ylmethyl)-amino]-benzamide (compound 259),
N-(4-Cyanomethyl-2-methoxy-benzyloxy)-2-[(pyridin-4-ylmethyl)-amino]-benzamide (compound 260),
N-(5-Cyano-2-methoxy-benzyloxy)-2-[(pyridin-4-ylmethyl)-amino]-benzamide (compound 261),
2-{2-[(Pyridin-4-ylmethyl)-amino]-benzoylaminooxymethyl}-phenyl)-carbamic acid tert-butyl ester (compound 262),
N-(2-Acetylamino-benzyloxy)-2-[(pyridin-4-ylmethyl)-amino]-benzamide (compound 263),
N-(2-Benzoylamino-benzyloxy)-2-[(pyridin-4-ylmethyl)-amino]-benzamide (compound 264),
N-(2-Methanesulfonylamino-benzyloxy)-2-[(pyridin-4-ylmethyl)-amino]-benzamide (compound 265),
N-(4-Acetylamino-benzyloxy)-2-[(pyridin-4-ylmethyl)-amino]-benzamide (compound 266),
N-(Biphenyl-4-ylmethoxy)-2-[(pyridin-4-ylmethyl)-amino]-benzamide (compound 267),
N-(Biphenyl-2-ylmethoxy)-2-[(pyridin-4-ylmethyl)-amino]-benzamide (compound 268),
N-(3'-Methoxy-biphenyl-2-ylmethoxy)-2-[(pyridin-4-ylmethyl)-amino]-benzamide (compound 269),
N-(2'-Methoxy-biphenyl-2-ylmethoxy)-2-[(pyridin-4-ylmethyl)-amino]-benzamide (compound 270),
N-(3'-Hydroxymethyl-biphenyl-2-ylmethoxy)-2-[(pyridin-4-ylmethyl)-amino]-benzamide (compound 271),
N-(Anthracen-9-ylmethoxy)-2-[(pyridin-4-ylmethyl)-amino]-benzamide (compound 273),
N-[4-(2-Methyl-thiazol-4-yl)-benzyloxy]-2-[(pyridin-4-ylmethyl)-amino]-benzamide (compound 274),
N-(2-Methanesulfonylamino-1-phenyl-ethoxy)-2-[(pyridin-4-ylmethyl)-amino]-benzamide (compound 275),
2-[(Pyridin-4-ylmethyl)-amino]-N-(3-p-tolyl-isoxazol-5-ylmethoxy)-benzamide (compound 277),
N-(3-Methyl-isoxazol-5-ylmethoxy)-2-[(pyridin-4-ylmethyl)-amino]-benzamide (compound 278),
N-(3-Ethyl-isoxazol-5-ylmethoxy)-2-[(pyridin-4-ylmethyl)-amino]-benzamide (compound 279),
N-(3-Butyl-isoxazol-5-ylmethoxy)-2-[(pyridin-4-ylmethyl)-amino]-benzamide (compound 280),
N-(3-Pentyl-isoxazol-5-ylmethoxy)-2-[(pyridin-4-ylmethyl)-amino]-benzamide (compound 281),
N-(1-Cyclopentyl-1H-[1,2,3]triazol-4-ylmethoxy)-2-[(pyridin-4-ylmethyl)-amino]-benzamide (compound 284),
N-(5-Oxo-4,5-dihydro-1H-[1,2,4]triazol-3-ylmethoxy)-2-[(pyridin-4-ylmethyl)-amino]-benzamide (compound 285),
N-(3-Phenoxy-propoxy)-2-[(pyridin-4-ylmethyl)-amino]-benzamide (compound 286),
N-(3-Benzyloxy-propoxy)-2-[(pyridin-4-ylmethyl)-amino]-benzamide (compound 287),
N-(2-Benzyloxy-ethoxy)-2-[(pyridin-4-ylmethyl)-amino]-benzamide (compound 288),
N-(3-Benzoylamino-propoxy)-2-[(pyridin-4-ylmethyl)-amino]-benzamide (compound 290),
N-(4-Benzoylamino-butoxy)-2-[(pyridin-4-ylmethyl)-amino]-benzamide (compound 291),
N-(2-Methanesulfonylamino-ethoxy)-2-[(pyridin-4-ylmethyl)-amino]-benzamide (compound 292),
N-(4-Benzenesulfonylamino-butoxy)-2-[(pyridin-4-ylmethyl)-amino]-benzamide (compound 293),
N-(3-Benzenesulfonylamino-propoxy)-2-[(pyridin-4-ylmethyl)-amino]-benzamide (compound 294),
N-[2-(4-Cyano-benzenesulfonylamino)-ethoxy]-2-[(pyridin-4-ylmethyl)-amino]-benzamide (compound 295),
N-[3-(4-Cyano-benzenesulfonylamino)-propoxy]-2-[(pyridin-4-ylmethyl)-amino]-benzamide (compound 296),
N-(3-Phenylmethanesulfonylamino-propoxy)-2-[(pyridin-4-ylmethyl)-amino]-benzamide (compound 297),
N-(2-Phenylmethanesulfonylamino-ethoxy)-2-[(pyridin-4-ylmethyl)-amino]-benzamide (compound 298),
N-[3-(2-Acetylamino-4-methyl-thiazole-5-sulfonylamino)-propoxy]-2-[(pyridin-4-ylmethyl)-amino]-benzamide (compound 299),
N-[2-(2-Acetylamino-4-methyl-thiazole-5-sulfonylamino)-ethoxy]-2-[(pyridin-4-ylmethyl)-amino]-benzamide (compound 300),
N-(2-Benzylamino-ethoxy)-2-[(pyridin-4-ylmethyl)-amino]-benzamide (compound 301),
N-(4-Benzylamino-butoxy)-2-[(pyridin-4-ylmethyl)-amino]-benzamide (compound 302),
(2-{2-[(Pyridin-4-ylmethyl)-amino]-benzoylaminooxy}-ethyl)-carbamic acid tert-butyl ester (compound 303),
(3-{2-[(Pyridin-4-ylmethyl)-amino]-benzoylaminooxy}-propyl)-carbamic acid tert-butyl ester (compound 304),
(4-{2-[(Pyridin-4-ylmethyl)-amino]-benzoylaminooxy}-butyl)-carbamic acid tert-butyl ester (compound 305),
N-[2-(3-Phenyl-ureido)-ethoxy]-2-[(pyridin-4-ylmethyl)-amino]-benzamide (compound 308),
N-[3-(3-Phenyl-ureido)-propoxy]-2-[(pyridin-4-ylmethyl)-amino]-benzamide (compound 309),
N-[4-(3-Phenyl-ureido)-butoxy]-2-[(pyridin-4-ylmethyl)-amino]-benzamide (compound 310),
N-(2-Amino-ethoxy)-2-[(pyridin-4-ylmethyl)-amino]-benzamide (compound 311),
N-(3-Amino-propoxy)-2-[(pyridin-4-ylmethyl)-amino]-benzamide (compound 312),
N-(4-Amino-butoxy)-2-[(pyridin-4-ylmethyl)-amino]-benzamide (compound 313),
N-(2-Morpholin-4-yl-2-oxo-ethoxy)-2-[(pyridin-4-ylmethyl)-amino]-benzamide (compound 314),
N-tert-Butoxy-2-[(pyridin-4-ylmethyl)-amino]-benzamide (compound 316),
N-Isobutoxy-2-[(pyridin-4-ylmethyl)-amino]-benzamide (compound 317),
N-(2-Methyl-allyloxy)-2-[(pyridin-4-ylmethyl)-amino]-benzamide (compound 318),
N-(3-Methyl-but-2-enyloxy)-2-[(pyridin-4-ylmethyl)-amino]-benzamide (compound 319),
N-(4-Hydroxy-pent-2-enyloxy)-2-[(pyridin-4-ylmethyl)-amino]-benzamide (compound 320),
N-Cyclopentyloxy-2-[(pyridin-4-ylmethyl)-amino]-benzamide (compound 321),
N-Cyclooctyloxy-2-[(pyridin-4-ylmethyl)-amino]-benzamide (compound 322),
N-(2-Cyclohexyl-ethoxy)-2-[(pyridin-4-ylmethyl)-amino]-benzamide (compound 323),
N-(2-Methyl-cyclohexylmethoxy)-2-[(pyridin-4-ylmethyl)-amino]-benzamide (compound 324),
N-(4-Methyl-cyclohexylmethoxy)-2-[(pyridin-4-ylmethyl)-amino]-benzamide (compound 325), N-(4-Methoxy-cyclohexylmethoxy)-2-[(pyridin-4-ylmethyl)-amino]-benzamide (compound 326),
N-(3-Methyl-bicyclo[2.2.1]hept-2-ylmethoxy)-2-[(pyridin-4-ylmethyl)-amino]-benzamide (compound 327),
N-(Bicyclo[2.2.1]hept-5-en-2-ylmethoxy)-2-[(pyridin-4-ylmethyl)-amino]-benzamide (compound 328),
Benzyl-(2-{2-[(pyridin-4-ylmethyl)-amino]-benzoylaminooxymethyl}-cyclohexyl)-carbamic acid tert-butyl ester (compound 329),
N-(2-Benzylamino-cyclohexylmethoxy)-2-[(pyridin-4-ylmethyl)-amino]-benzamide (compound 330),
N-(3-Propyl-4,5-dihydro-isoxazol-5-ylmethoxy)-2-[(pyridin-4-ylmethyl)-amino]-benzamide (compound 331),
N-(3-Pentyl-4,5-dihydro-isoxazol-5-ylmethoxy)-2-[(pyridin-4-ylmethyl)-amino]-benzamide (compound 332),
4-Methyl-N-(2-methyl-thiazol-4-ylmethoxy)-2-[(pyridin-4-ylmethyl)-amino]-benzamide (compound 333),
N-(5-Cyano-2-methoxy-benzyloxy)-2-[(pyridin-4-ylmethyl)-amino]-nicotinamide (compound 334),
2-Benzylamino-N-benzyloxy-nicotinamide (compound 335),
2-Benzylamino-N-(4-methoxy-benzyloxy)-nicotinamide (compound 336),
N-Benzyloxy-2-(2-chloro-benzylamino)-nicotinamide (compound 337),
2-(2-Chloro-benzylamino)-N-(4-methoxy-benzyloxy)-nicotinamide (compound 338),
N-Benzyloxy-2-(2,4-dichloro-benzylamino)-nicotinamide (compound 339),
2-(3,5-Dichloro-benzylamino)-N-(4-methoxy-benzyloxy)-nicotinamide (compound 340),
N-Benzyloxy-2-(2-methoxy-benzylamino)-nicotinamide (compound 341),
2-(2-Methoxy-benzylamino)-N-(4-methoxy-benzyloxy)-nicotinamide (compound 342),
N-Benzyloxy-2-(2-pyridin-4-yl-ethylamino)-nicotinamide (compound 343),
4-{[3-(4-Methoxy-benzyloxycarbamoyl)-pyridin-2-ylamino]-methyl}-piperidine-1-carboxylic acid tert-butyl ester (compound 345),
N-Benzyloxy-5-[(2-benzyloxycarbamoyl-phenylamino)-methyl]-2-fluoro-benzamide (compound 346),
N-(2-Bromo-benzyloxy)-2-(3-cyano-4-methoxy-benzylamino)-benzamide (compound 347),
N-(2-Bromo-benzyloxy)-2-(4-methanesulfonyl-benzylamino)-benzamide (compound 348),
2-[4-(Methoxyimino-methyl)-benzylamino]-N-(2-methyl-thiazol-4-ylmethoxy)-benzamide (compound 349),
N-(2-Bromo-benzyloxy)-2-[(2,6-dichloro-pyridin-4-ylmethyl)-amino]-benzamide (compound 350),
N-Benzyloxy-2-[(pyridin-3-ylmethyl)-amino]benzamide (compound 351),
N-(2-Methyl-thiazol-4-ylmethoxy)-2-[(pyridin-3-ylmethyl)-amino]-benzamide (compound 352),
N-(2-Methyl-thiazol-4-ylmethoxy)-2-[(pyridin-2-ylmethyl)-amino]-benzamide (compound 353),
N-Benzyloxy-2-[(pyridin-2-ylmethyl)-amino]-benzamide (compound 354),
N-Benzyloxy-2-[(3-bromo-pyridin-2-ylmethyl)-amino]benzamide (compound 355),
2-[(3-Bromo-pyridin-2-ylmethyl)-amino]-N-(2-methyl-thiazol-4-ylmethoxy)-benzamide (compound 356),
N-(2,4-Dichloro-benzyloxy)-2-[(2,6-dimethoxy-pyrimidin-4-ylmethyl)-amino]-benzamide (compound 357),
N-Benzyloxy-2-[(1,3,5-trimethyl-1H-pyrazol-4-ylmethyl)-amino]-benzamide (compound 358),
N-(2,4-Dichloro-benzyl)-2-[(1,3,5-trimethyl-1H-pyrazol-4-ylmethyl)-amino]-benzamide (compound 359),
N-Benzyloxy-2-[(1-methyl-1H-imidazol-2-ylmethyl)-amino]-benzamide (compound 360),
2-[(1-Methyl-1H-imidazol-2-ylmethyl)-amino]-N-(2-methyl-thiazol-4-ylmethoxy)-benzamide (compound 361),
N-Benzyloxy-2-[(3-methyl-3H-imidazol-4-ylmethyl)-amino]-benzamide (compound 362),
2-[(3-Methyl-3H-imidazol-4-ylmethyl)-amino]-N-(2-methyl-thiazol-4-ylmethoxy)-benzamide (compound 363),
N-Benzyloxy-2-[(5-methyl-3H-imidazol-4-ylmethyl)-amino]-benzamide (compound 364),
2-[(5-Methyl-3H-imidazol-4-ylmethyl)-amino]-N-(2-methyl-thiazol-4-ylmethoxy)-benzamide (compound 365),
2-[(2-Ethyl-3H-imidazol-4-ylmethyl)-amino]-N-(2-methyl-thiazol-4-ylmethoxy)-benzamide (compound 366),
N-Benzyloxy-2-[(2-ethyl-3H-imidazol-4-ylmethyl)-amino]-benzamide (compound 367),
N-(2,5-Dichloro-benzyloxy)-2-[(5-oxo-pyrrolidin-2-ylmethyl)-amino]-benzamide (compound 368),
N-Benzyloxy-2-[(3-ethyl-4,5-dihydro-isoxazol-5-ylmethyl)-amino]-benzamide (compound 369),
N-Benzyloxy-2-[(3-propyl-4,5-dihydro-isoxazol-5-ylmethyl)-amino]-benzamide (compound 370),
5-[(2-Benzyloxycarbamoyl-phenylamino)-methyl]-3-methyl-4,5-dihydro-isoxazole-5-carboxylic acid ethyl ester (compound 371),
5-[(2-Benzyloxycarbamoyl-phenylamino)-methyl]-3-ethyl-4,5-dihydro-isoxazole-5-carboxylic acid ethyl ester (compound 372),
5-[(2-Benzyloxycarbamoyl-phenylamino)-methyl]-3-propyl-4,5-dihydro-isoxazole-5-carboxylic acid ethyl ester (compound 373),
N-(4-Cyano-benzyloxy)-2-[(3-methyl-4,5-dihydro-isoxazol-5-ylmethyl)-amino]-benzamide (compound 374),
N-(4-Cyano-benzyloxy)-2-[(3-ethyl-4,5-dihydro-isoxazol-5-ylmethyl)-amino]-benzamide (compound 375),
N-(4-Cyano-benzyloxy)-2-[(3-propyl-4,5-dihydro-isoxazol-5-ylmethyl)-amino]-benzamide (compound 376),
5-{[2-(4-Cyano-benzyloxycarbamoyl)-phenylamino]-methyl}-3-methyl-4,5-dihydro-isoxazole-5-carboxylic acid ethyl ester (compound 377),
5-{[2-(4-Cyano-benzyloxycarbamoyl)-phenylamino]-methyl}-3-ethyl-4,5-dihydro-isoxazole-5-carboxylic acid ethyl ester (compound 378),
5-{[2-(4-Cyano-benzyloxycarbamoyl)-phenylamino]-methyl}-3-propyl-4,5-dihydro-isoxazole-5-carboxylic acid ethyl ester (compound 379),
N-(4-Cyano-benzyloxy)-2-[(3-methyl-isoxazol-5-ylmethyl)-amino]-benzamide (compound 380),
N-(4-Cyano-benzyloxy)-2-[(3-ethyl-isoxazol-5-ylmethyl)-amino]-benzamide (compound 381),
N-(4-Cyano-benzyloxy)-2-[(3-propyl-isoxazol-5-ylmethyl)-amino]-benzamide (compound 382),
N-(4-Cyano-benzyloxy)-2-[(3,5-dimethyl-4,5-dihydro-isoxazol-5-ylmethyl)-amino]-benzamide (compound 383),
N-(4-Cyano-benzyloxy)-2-[(3-ethyl-5-methyl-4,5-dihydro-isoxazol-5-ylmethyl)-amino]-benzamide (compound 384),
N-(4-Cyano-benzyloxy)-2-[(5-methyl-3-propyl-4,5-dihydro-isoxazol-5-ylmethyl)-amino]-benzamide (compound 385),
N-Benzyloxy-2-[(3-methyl-4,5-dihydro-isoxazol-5-ylmethyl)-amino]-benzamide (compound 386),
N-(4-Cyano-benzyloxy)-2-[2-(3-methyl-4,5-dihydro-isoxazol-5-yl)-ethylamino]-benzamide (compound 387),
N-Cyclopentylmethoxy-2-[2-(3-methyl-4,5-dihydro-isoxazol-5-yl)-ethylamino]-benzamide (compound 388),
N-(4-Cyano-benzyloxy)-2-[2-(3-ethyl-4,5-dihydro-isoxazol-5-yl)-ethylamino]-benzamide (compound 389), N-Cyclopentylmethoxy-2-[2-(3-ethyl-4,5-dihydro-isoxazol-5-yl)-ethylamino]-benzamide (compound 390),
N-(4-Cyano-benzyloxy)-2-[2-(3-propyl-4,5-dihydro-isoxazol-5-yl)-ethylamino]-benzamide (compound 391),
N-Cyclopentylmethoxy-2-[2-(3-propyl-4,5-dihydro-isoxazol-5-yl)-ethylamino]-benzamide (compound 392),
N-Benzyloxy-2-[2-(2,4-dioxo-imidazolidin-1-yl)-ethylamino]-benzamide (compound 393),
N-Benzyloxy-2-[(6-chloro-imidazo[2,1-b]thiazol-5-ylmethyl)-amino]-benzamide (compound 395),
N-Benzyloxy-2-[(2-methyl-imidazo[1,2-a]pyrimidin-3-ylmethyl)-amino]-benzamide (compound 396),
N-Benzyloxy-2-(2-benzyloxy-ethylamino)-benzamide (compound 397),
N-Benzyloxy-N-methyl-2-[(pyridin-4-ylmethyl)-amino]-benzamide (compound 400),
N-(5-oxo-pyrrolidin-2-ylmethoxy)-2-[(pyridin-4-ylmethyl)-amino]-benzamide (compound 402),
4-{2-[(Pyridin-4-ylmethyl)-amino]-benzoylaminooxymethyl}-piperidine-1-carboxylic acid tert-butyl ester (compound 403),
N-Cyclopentylmethoxy-2-{[6-(cyclopropanecarbonylamino)-pyridin-3-ylmethyl]amino}-benzamide (compound 404),
N-Cyclopentylmethoxy-2-[(6-pyrrolidin-1-yl-pyridin-3-ylmethyl)-amino]-benzamide (compound 405),
2-[(6-Amino-pyridin-3-ylmethyl)-amino]-N-(4-cyano-benzyloxy)-benzamide (compound 406),
N-(4-Cyano-benzyloxy)-2-[(6-pyrrolidin-1-yl-pyridin-3-ylmethyl)-amino]-benzamide (compound 407),
N-Cyclopentylmethoxy-2-{[2-(cyclopropanecarbonylamino)-4-methyl-thiazol-5-ylmethyl]-amino}-benzamide (compound 408),
2-[(6-Amino-pyridin-3-ylmethyl)-amino]-N-cyclopentylmethoxy-benzamide (compound 409),
N-[3-(2,2-Dibromo-vinyl)-cyclopentylmethoxy]-2-[(pyridin-4-ylmethyl)-amino]-benzamide (compound 410),
N-(3-Hydroxymethyl-cyclopentylmethoxy)-2-[(pyridin-4-ylmethyl)-amino]-benzamide (compound 411),
N-(2-Hydroxymethyl-cyclohexylmethoxy)-2-[(pyridin-4-ylmethyl)-amino]-benzamide (compound 412),
N-[4-(4-Methyl-piperazin-1-ylmethyl)-benzyloxy]-2-[(pyridin-4-ylmethyl)-amino]-benzamide (compound 413),
N-{4-[4-(2-Hydroxy-ethyl)-piperazin-1-ylmethyl]-benzyloxy}-2-[(pyridin-4-ylmethyl)-amino]-benzamide (compound 414),
N-(4-Cyano-benzyloxy)-2-{[2-(3-isopropyl-ureido)-pyridin-4-ylmethyl]-amino}-benzamide (compound 415),
N-(4-Cyano-benzyloxy)-2-{[2-(3-ethyl-ureido)-pyridin-4-ylmethyl]-amino}-benzamide (compound 416),
N-Cyclopentylmethoxy-2-{[2-(3-isopropyl-ureido)-pyridin-4-ylmethyl]-amino}-benzamide (compound 417),
N-Cyclopentylmethoxy-2-{[2-(3-propyl-ureido)-pyridin-4-ylmethyl]-amino}-benzamide (compound 418),
N-Cyclopentylmethoxy-2-{[2-(3-ethyl-ureido)-pyridin-4-ylmethyl]-amino}-benzamide (compound 419),
N-(3-Hydroxy-cyclopentylmethoxy)-2-[(pyridin-4-ylmethyl)-amino]-benzamide (compound 420),
N-Cyclopentylmethoxy-2-{[2-(3-methyl-thioureido)-pyridin-4-ylmethyl]-amino}-benzamide (compound 421),
2-{[2-(3-tert-Butyl-ureido)-pyridin-4-ylmethyl]-amino}-N-cyclopentylmethoxy-benzamide (compound 422),
N-(4-Cyano-benzyloxy)-2-{[2-(3-cyclohexyl-ureido)-pyridin-4-ylmethyl]-amino}-benzamide (compound 423),
2-{[2-(3-Cyclohexyl-ureido)-pyridin-4-ylmethyl]-amino}-N-cyclopentylmethoxy-benzamide (compound 424),
N-{4-[(2-Cyclopentylmethoxycarbamoyl-phenylamino)-methyl]-pyridin-2-yl}sonicotinamide (compound 425),
1-Acetyl-piperidine-4-carboxylic acid {4-[(2-cyclopentylmethoxycarbamoyl-phenylamino)-methyl]-pyridin-2-yl}-amide (compound 428),
1-Acetyl-piperidine-4-carboxylic acid (4-{[2-(4-cyano-benzyloxycarbamoyl)-phenylamino]-methyl}-pyridin-2-yl)-amide (compound 429),
N-Cyclopentylmethoxy-2-[(2,4-dihydroxy-pyrimidin-5-ylmethyl)-amino]-benzamide (compound 430),
Pyrrolidine-2-carboxylic acid (4-{[2-(4-cyano-benzyloxycarbamoyl)-phenylamino]-methyl}-pyridin-2-yl)-amide (compound 431),
Pyrrolidine-2-carboxylic acid {4-[(2-cyclopentylmethoxycarbamoyl-phenylamino)-methyl]-pyridin-2-yl}-amide (compound 432), and
2-[(Pyridin-4-ylmethyl)-amino]-N-(4-vinylbenzyloxy)benzamide (compound 433).

23. A pharmaceutical composition comprising a compound according to claim 1 or a pharmaceutically acceptable salt, hydrate, or solvate thereof together with a pharmaceutically acceptable vehicle or excipient.

24. A method of treating a disease or condition characterized by abnormal angiogenesis comprising administering to a patient in need thereof an effective amount of a compound of claim 1.

* * * * *